(12) United States Patent
Jones et al.

(10) Patent No.: US 8,933,083 B2
(45) Date of Patent: *Jan. 13, 2015

(54) 1,2,3-TRISUBSTITUTED ARYL AND HETEROARYL DERIVATIVES AS MODULATORS OF METABOLISM AND THE PROPHYLAXIS AND TREATMENT OF DISORDERS RELATED THERETO SUCH AS DIABETES AND HYPERGLYCEMIA

(75) Inventors: Robert M. Jones, San Diego, CA (US); Graeme Semple, San Diego, CA (US); Beatriz Fioravanti, Tucson, AZ (US); Guilherme Pereira, San Diego, CA (US); Imelda Calderon, San Diego, CA (US); Jane Laguerta Uy, Monrovia, CA (US); Kameshwari Duvvuri, Lexington, KY (US); Jin Sun Karoline Choi, San Diego, CA (US); Yifeng Xiong, San Diego, CA (US); Vibha Dave, San Diego, CA (US); Mihai D. Azimioara, La Jolla, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 41 days.

This patent is subject to a terminal disclaimer.

(21) Appl. No.: 13/618,592

(22) Filed: Sep. 14, 2012

(65) Prior Publication Data

US 2013/0023527 A1 Jan. 24, 2013

Related U.S. Application Data

(63) Continuation of application No. 10/541,657, filed as application No. PCT/US2004/001267 on Jan. 14, 2004, now Pat. No. 8,293,751.

(60) Provisional application No. 60/470,875, filed on May 14, 2003, provisional application No. 60/453,390, filed on Mar. 6, 2003, provisional application No. 60/449,829, filed on Feb. 24, 2003, provisional application No. 60/440,394, filed on Jan. 14, 2003.

(51) Int. Cl.
| | | |
|---|---|---|
| *C07D 239/48* | (2006.01) | |
| *C07D 401/14* | (2006.01) | |
| *C07D 403/12* | (2006.01) | |
| *C07D 403/14* | (2006.01) | |
| *C07D 401/04* | (2006.01) | |
| *C07D 401/12* | (2006.01) | |
| *C07D 417/14* | (2006.01) | |
| *C07D 409/14* | (2006.01) | |
| *C07D 405/04* | (2006.01) | |
| *C07D 419/14* | (2006.01) | |
| *C07D 405/14* | (2006.01) | |
| *C07D 213/79* | (2006.01) | |
| *C07D 239/50* | (2006.01) | |
| *C07D 213/68* | (2006.01) | |
| *C07D 239/34* | (2006.01) | |
| *C07D 411/14* | (2006.01) | |
| *C07D 413/14* | (2006.01) | |
| *C07D 295/096* | (2006.01) | |

(52) U.S. Cl.
CPC ............ *C07D 213/68* (2013.01); *C07D 401/14* (2013.01); *C07D 403/12* (2013.01); *C07D 403/14* (2013.01); *C07D 401/04* (2013.01); *C07D 401/12* (2013.01); *C07D 417/14* (2013.01); *C07D 409/14* (2013.01); *C07D 405/04* (2013.01); *C07D 419/14* (2013.01); *C07D 405/14* (2013.01); *C07D 213/79* (2013.01); *C07D 239/50* (2013.01); *C07D 239/34* (2013.01); *C07D 411/14* (2013.01); *C07D 413/14* (2013.01); *C07D 295/096* (2013.01)
USPC ......................................................... 514/256

(58) Field of Classification Search
None
See application file for complete search history.

(56) References Cited

U.S. PATENT DOCUMENTS

| | | | |
|---|---|---|---|
| 3,503,963 | A | 3/1970 | Schweizer et al. |
| 3,592,932 | A | 7/1971 | Duerr et al. |

(Continued)

FOREIGN PATENT DOCUMENTS

| | | |
|---|---|---|
| AT | 327605 | 6/2006 |
| AU | 492126 | 11/1975 |

(Continued)

OTHER PUBLICATIONS

"Obesity: Prevention", http://www.mayoclinic.com/health/obesity/ds00314/dsection=prevention, accessed May 19, 2010.*

(Continued)

*Primary Examiner* — Noble Jarrell
(74) *Attorney, Agent, or Firm* — Fish & Richardson P.C.; Lyle W. Spruce

(57) ABSTRACT

The present invention relates to certain 1,2,3-trisubstituted aryl and heteroaryl derivatives of Formula (Ia) that are modulators of metabolism.

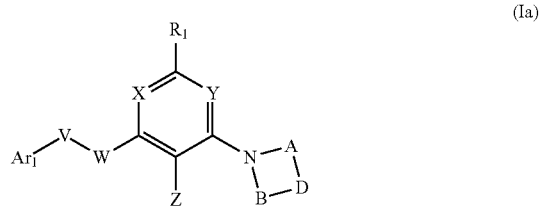

Accordingly, compounds of the present invention are useful in the prophylaxis or treatment of metabolic disorders and complications thereof, such as, diabetes and obesity.

37 Claims, 10 Drawing Sheets

(56) References Cited

U.S. PATENT DOCUMENTS

| | | |
|---|---|---|
| 3,598,801 A | 8/1971 | Beffa et al. |
| 3,608,087 A | 9/1971 | Patchett et al. |
| 3,686,238 A | 8/1972 | Zaffaroni et al. |
| 3,690,834 A | 9/1972 | Goldstein et al. |
| 3,849,420 A | 11/1974 | Tong |
| 3,852,434 A | 12/1974 | Kahan et al. |
| 3,862,117 A | 1/1975 | Leverenz |
| 3,887,329 A | 6/1975 | Hegar et al. |
| 3,948,914 A | 4/1976 | Fischer |
| 3,966,744 A | 6/1976 | Goldstein et al. |
| 3,966,764 A | 6/1976 | Goldstein et al. |
| 3,975,384 A | 8/1976 | Narr et al. |
| 3,984,411 A | 10/1976 | Claverie et al. |
| 4,101,541 A | 7/1978 | Petipierre et al. |
| 4,139,705 A | 2/1979 | Dunbar et al. |
| 4,189,427 A | 2/1980 | Komorowski |
| 4,189,579 A | 2/1980 | Dunbar et al. |
| 4,242,507 A | 12/1980 | Itoh et al. |
| 4,267,174 A | 5/1981 | Berger et al. |
| 4,273,870 A | 6/1981 | Endo et al. |
| 4,275,148 A | 6/1981 | Endo et al. |
| 4,343,804 A | 8/1982 | Munison et al. |
| 4,397,848 A | 8/1983 | Bosies et al. |
| 4,493,726 A | 1/1985 | Burdeska et al. |
| 4,517,183 A | 5/1985 | Bosies et al. |
| 4,643,995 A | 2/1987 | Engel et al. |
| 4,766,213 A | 8/1988 | Juraszyk et al. |
| 4,880,932 A | 11/1989 | Moriya et al. |
| 5,571,815 A | 11/1996 | Schaper et al. |
| 5,624,941 A | 4/1997 | Barth et al. |
| 5,691,364 A | 11/1997 | Buckman et al. |
| 5,849,759 A | 12/1998 | Arnaiz et al. |
| 5,948,786 A | 9/1999 | Fujwara et al. |
| 5,952,504 A | 9/1999 | Yoo et al. |
| 5,962,479 A | 10/1999 | Chen |
| 6,008,234 A | 12/1999 | Kochanny et al. |
| 6,060,478 A | 5/2000 | Gilligan |
| 6,107,301 A | 8/2000 | Aldrich et al. |
| 6,187,777 B1 | 2/2001 | Norman et al. |
| 6,191,149 B1 | 2/2001 | Chokai et al. |
| 6,218,431 B1 | 4/2001 | Schoen et al. |
| 6,239,126 B1 | 5/2001 | Kelly et al. |
| 6,267,985 B1 | 7/2001 | Chen et al. |
| 6,294,671 B1 | 9/2001 | Frietze |
| 6,350,750 B1 | 2/2002 | Den Hartog et al. |
| 6,414,002 B1 | 7/2002 | Cheng et al. |
| 6,506,762 B1 | 1/2003 | Horvath et al. |
| 6,525,064 B1 | 2/2003 | Dellaria et al. |
| 6,545,016 B1 | 4/2003 | Dellaria et al. |
| 6,545,017 B1 | 4/2003 | Dellaria et al. |
| 6,552,192 B1 | 4/2003 | Hanus et al. |
| 6,569,879 B2 | 5/2003 | Liu et al. |
| 6,583,154 B1 | 6/2003 | Norman et al. |
| 6,620,821 B2 | 9/2003 | Robl et al. |
| 6,660,744 B1 | 12/2003 | Hirst et al. |
| 6,713,508 B2 | 3/2004 | Sahoo et al. |
| 6,787,542 B2 | 9/2004 | Wang et al. |
| 6,844,351 B1 | 1/2005 | Chen et al. |
| 6,849,636 B2 | 2/2005 | Waddell et al. |
| 6,956,047 B1 | 10/2005 | Chen et al. |
| 7,056,942 B2 | 6/2006 | Hildeasheim et al. |
| 7,057,046 B2 | 6/2006 | Sher et al. |
| 7,083,933 B1 | 8/2006 | Griffin |
| 7,276,249 B2 | 10/2007 | Ryde et al. |
| 7,417,039 B2 | 8/2008 | Davis |
| 7,425,630 B2 | 9/2008 | Gharbaoui et al. |
| 7,470,699 B2 | 12/2008 | Jones et al. |
| 7,625,906 B2 | 12/2009 | Jones et al. |
| 7,763,278 B2 | 7/2010 | Cooper et al. |
| 7,812,159 B2 | 10/2010 | Gharbaoui et al. |
| 7,838,525 B2 | 11/2010 | Jones et al. |
| 8,293,751 B2 * | 10/2012 | Jones et al. ............... 514/256 |
| 8,362,248 B2 | 1/2013 | Jones et al. |
| 8,410,119 B2 | 4/2013 | Jones et al. |
| 2002/0058026 A1 | 5/2002 | Hammerly |
| 2002/0137755 A1 | 9/2002 | Bilodeau et al. |
| 2002/0156081 A1 | 10/2002 | Hirst et al. |
| 2003/0224058 A1 | 12/2003 | Ryde et al. |
| 2004/0110241 A1 | 6/2004 | Segal |
| 2005/0043327 A1 | 2/2005 | Coe et al. |
| 2005/0070562 A1 | 3/2005 | Jones et al. |
| 2005/0182067 A1 | 8/2005 | Balan et al. |
| 2005/0197353 A1 | 9/2005 | Ritzeler et al. |
| 2005/0209251 A1 | 9/2005 | Linker et al. |
| 2006/0154866 A1 | 7/2006 | Chu et al. |
| 2006/0155128 A1 | 7/2006 | Jones et al. |
| 2006/0217379 A1 | 9/2006 | Jones et al. |
| 2007/0066590 A1 | 3/2007 | Jones et al. |
| 2007/0072844 A1 | 3/2007 | Jones et al. |
| 2007/0078150 A1 | 4/2007 | Jones et al. |
| 2007/0082874 A1 | 4/2007 | Jones et al. |
| 2007/0167413 A1 | 7/2007 | Srinivas et al. |
| 2007/0167473 A1 | 7/2007 | Jones et al. |
| 2007/0225351 A1 | 9/2007 | Lippa et al. |
| 2009/0036434 A1 | 2/2009 | Jones et al. |
| 2009/0270409 A1 | 10/2009 | Alper et al. |
| 2009/0286816 A1 | 11/2009 | Jones et al. |
| 2010/0004272 A1 | 1/2010 | Jones et al. |
| 2010/0160359 A1 | 6/2010 | Jones et al. |
| 2011/0082134 A1 | 4/2011 | Jones et al. |
| 2011/0112060 A1 | 5/2011 | Jones et al. |
| 2013/0023494 A1 | 1/2013 | Jones et al. |
| 2013/0023527 A1 | 1/2013 | Jones et al. |

FOREIGN PATENT DOCUMENTS

| | | |
|---|---|---|
| BE | 829845 | 12/1975 |
| BE | 868796 | 1/1979 |
| CA | 2499497 | 4/2004 |
| CH | 560197 | 3/1975 |
| CN | 1212117 | 7/2005 |
| CN | 1823056 A | 8/2006 |
| CN | 101657471 | 2/2010 |
| DE | 2048375 | 4/1971 |
| DE | 2223644 | 11/1972 |
| DE | 2356644 | 5/1974 |
| DE | 2341925 | 3/1975 |
| DE | 2460238 | 7/1975 |
| DE | 2503136 | 7/1975 |
| DE | 2831850 | 2/1980 |
| DE | 3334455 | 9/1984 |
| DE | 3406329 | 8/1985 |
| DE | 3601196 | 7/1987 |
| DE | 19602095 | 7/1997 |
| DE | 19737723 | 2/1999 |
| DE | 19962936 | 6/2001 |
| EP | 0 014 976 | 9/1980 |
| EP | 0053678 | 10/1981 |
| EP | 0050671 | 5/1982 |
| EP | 0 055 693 | 7/1982 |
| EP | 0123402 | 10/1984 |
| EP | 0149088 | 12/1984 |
| EP | 0154190 | 9/1985 |
| EP | 0191603 | 8/1986 |
| EP | 0193249 | 9/1986 |
| EP | 0283261 | 9/1988 |
| EP | 0324426 | 7/1989 |
| EP | 0518675 | 12/1992 |
| EP | 0526004 | 2/1993 |
| EP | 0556 889 | 8/1993 |
| EP | 0565488 | 10/1993 |
| EP | 0604800 | 7/1994 |
| EP | 0667343 | 8/1995 |
| EP | 0772087 | 7/1997 |
| EP | 0801059 | 10/1997 |
| EP | 0857483 | 8/1998 |
| EP | 0940 387 | 9/1999 |
| EP | 1074 549 | 2/2001 |
| EP | 1097709 | 5/2001 |
| EP | 1287133 | 3/2003 |
| EP | 1040831 | 5/2003 |
| EP | 1338651 | 8/2003 |
| EP | 1340749 | 9/2003 |
| EP | 1475094 | 11/2004 |

(56) References Cited

FOREIGN PATENT DOCUMENTS

| | | |
|---|---|---|
| EP | 1902730 | 3/2008 |
| FR | 1551400 | 12/1968 |
| GB | 935595 | 8/1963 |
| GB | 1250624 | 10/1971 |
| GB | 1311956 | 3/1973 |
| GB | 1393993 | 5/1975 |
| GB | 1493380 | 11/1977 |
| GB | 1495665 | 12/1977 |
| JP | 55-17382 | 2/1980 |
| JP | 61-057587 | 3/1986 |
| JP | 05-33359 | 12/1993 |
| JP | 07-53546 | 2/1995 |
| JP | 11-193277 | 7/1999 |
| JP | 2000-038350 | 2/2000 |
| JP | 2001-089452 | 4/2001 |
| JP | 2004-269468 | 9/2004 |
| JP | 2004-269469 | 9/2004 |
| JP | 2005292786 | 10/2005 |
| NL | 6614961 | 4/1967 |
| NL | 6814810 | 4/1969 |
| RU | 2067978 | 10/1996 |
| RU | 2119917 | 10/1998 |
| RU | 2153495 | 7/2000 |
| RU | 2158258 | 10/2000 |
| RU | 2198879 | 2/2003 |
| RU | 2200734 | 3/2003 |
| SU | 938 559 | 11/1993 |
| WO | WO 81/03174 | 11/1981 |
| WO | WO 92/01697 | 2/1992 |
| WO | WO 92/12976 | 8/1992 |
| WO | WO 94/07858 | 4/1994 |
| WO | WO94/13677 | 6/1994 |
| WO | WO 95/33750 | 12/1995 |
| WO | WO 96/28427 | 9/1996 |
| WO | WO 96/32383 | 10/1996 |
| WO | WO 96/33980 | 10/1996 |
| WO | WO96/33994 | 10/1996 |
| WO | WO 96/35689 | 11/1996 |
| WO | WO96/36613 | 11/1996 |
| WO | WO97/08152 | 3/1997 |
| WO | WO97/26252 | 7/1997 |
| WO | WO 97/28137 | 8/1997 |
| WO | WO97/29109 | 8/1997 |
| WO | WO97/40832 | 11/1997 |
| WO | WO 97/48696 | 12/1997 |
| WO | WO97/49706 | 12/1997 |
| WO | WO98/04528 | 2/1998 |
| WO | WO98/08846 | 3/1998 |
| WO | WO98/08847 | 3/1998 |
| WO | WO98/11094 | 3/1998 |
| WO | WO 98/13354 | 4/1998 |
| WO | WO98/19998 | 5/1998 |
| WO | WO 98/27081 | 6/1998 |
| WO | WO 98/35967 | 8/1998 |
| WO | WO98/47874 | 10/1998 |
| WO | WO98/47903 | 10/1998 |
| WO | WO99/09026 | 2/1999 |
| WO | WO99/51599 | 10/1999 |
| WO | WO00/11003 | 3/2000 |
| WO | WO00/27825 | 5/2000 |
| WO | WO00/31068 | 6/2000 |
| WO | WO 00/31258 | 6/2000 |
| WO | WO00/34241 | 6/2000 |
| WO | WO00/35875 | 6/2000 |
| WO | WO00/35886 | 6/2000 |
| WO | WO 00/55153 | 9/2000 |
| WO | WO 01/60807 | 2/2001 |
| WO | WO01/22938 | 4/2001 |
| WO | WO01/23387 | 4/2001 |
| WO | WO01/23388 | 4/2001 |
| WO | WO01/25210 | 4/2001 |
| WO | WO01/27107 | 4/2001 |
| WO | WO 01/37831 | 5/2001 |
| WO | WO 01/46204 | 6/2001 |
| WO | WO01/47887 | 7/2001 |
| WO | WO01/49677 | 7/2001 |
| WO | WO01/53263 | 7/2001 |
| WO | WO01/58900 | 8/2001 |
| WO | WO 01/60870 | 8/2001 |
| WO | WO01/62233 | 8/2001 |
| WO | WO 01/76573 | 10/2001 |
| WO | WO01/85699 | 11/2001 |
| WO | WO 01/87829 | 11/2001 |
| WO | WO 01/87892 | 11/2001 |
| WO | WO 01/90082 | 11/2001 |
| WO | WO 02/02539 | 1/2002 |
| WO | WO02/02549 | 1/2002 |
| WO | WO02/06237 | 1/2002 |
| WO | WO02/06274 | 1/2002 |
| WO | WO 02/08188 | 1/2002 |
| WO | WO02/19975 | 3/2002 |
| WO | WO 02/24169 | 3/2002 |
| WO | WO 02/32408 | 4/2002 |
| WO | WO02/32893 | 4/2002 |
| WO | WO 02/60388 | 4/2002 |
| WO | WO02/40451 | 5/2002 |
| WO | WO02/40456 | 5/2002 |
| WO | WO02/40458 | 5/2002 |
| WO | WO02/40480 | 5/2002 |
| WO | WO 02/40480 | 5/2002 |
| WO | WO02/44362 | 6/2002 |
| WO | WO02/45652 | 6/2002 |
| WO | WO 02/50071 | 6/2002 |
| WO | WO02/059083 | 8/2002 |
| WO | WO 02/064094 | 8/2002 |
| WO | WO02/070485 | 9/2002 |
| WO | WO02/072101 | 9/2002 |
| WO | WO 02/081454 | 10/2002 |
| WO | WO 02/085892 | 10/2002 |
| WO | WO02/098864 | 12/2002 |
| WO | WO02/098878 | 12/2002 |
| WO | WO 02/102313 | 12/2002 |
| WO | WO03/000666 | 1/2003 |
| WO | WO03/002544 | 1/2003 |
| WO | WO03/004498 | 1/2003 |
| WO | WO 03/018556 | 3/2003 |
| WO | WO03/026661 | 4/2003 |
| WO | WO03/032989 | 4/2003 |
| WO | WO03/050117 | 6/2003 |
| WO | WO 03/051822 | 6/2003 |
| WO | WO03/057689 | 7/2003 |
| WO | WO 03/059378 | 7/2003 |
| WO | WO 03/061663 | 7/2003 |
| WO | WO 03/076418 | 9/2003 |
| WO | WO03/077656 | 9/2003 |
| WO | WO 03/080070 | 10/2003 |
| WO | WO03/087064 | 10/2003 |
| WO | WO 03/088962 | 10/2003 |
| WO | WO 03/093269 | 11/2003 |
| WO | WO03/094845 | 11/2003 |
| WO | WO 03/103632 | 12/2003 |
| WO | WO 03/103633 | 12/2003 |
| WO | WO 03/103640 | 12/2003 |
| WO | WO 03/104208 | 12/2003 |
| WO | WO 03/105763 | 12/2003 |
| WO | WO 03/106450 | 12/2003 |
| WO | WO 2004/000762 | 12/2003 |
| WO | WO2004/000819 | 12/2003 |
| WO | WO 2004/000843 | 12/2003 |
| WO | WO2004/000843 | 12/2003 |
| WO | WO 2004/002495 | 1/2004 |
| WO | WO 2004/004777 | 1/2004 |
| WO | WO 2004/004778 | 1/2004 |
| WO | WO2004/009596 | 1/2004 |
| WO | WO2004/009597 | 1/2004 |
| WO | WO2004/009602 | 1/2004 |
| WO | WO 2004/010936 | 2/2004 |
| WO | WO 2004/010992 | 2/2004 |
| WO | WO 2004/013633 | 2/2004 |
| WO | WO 2004/014871 | 2/2004 |
| WO | WO 2004/017896 | 3/2004 |
| WO | WO 2004/019869 | 3/2004 |
| WO | WO 2004/020408 | 3/2004 |
| WO | WO 2004/020409 | 3/2004 |

(56) References Cited

FOREIGN PATENT DOCUMENTS

| | | |
|---|---|---|
| WO | WO2004/024943 | 3/2004 |
| WO | WO2004/029204 | 4/2004 |
| WO | WO2004/031189 | 4/2004 |
| WO | WO 2004/033431 | 4/2004 |
| WO | WO 2004/033710 | 4/2004 |
| WO | WO2004/035588 | 4/2004 |
| WO | WO2004/037823 | 5/2004 |
| WO | WO2004/041164 | 5/2004 |
| WO | WO 2004/056748 | 7/2004 |
| WO | WO2004/056825 | 7/2004 |
| WO | WO2004/056829 | 7/2004 |
| WO | WO 2004/058174 | 7/2004 |
| WO | WO 2004/058727 | 7/2004 |
| WO | WO2004/062665 | 7/2004 |
| WO | WO2004/065380 | 8/2004 |
| WO | WO 2004/066963 | 8/2004 |
| WO | WO2004/074218 | 9/2004 |
| WO | WO2004/076413 | 9/2004 |
| WO | WO 2004/085401 | 10/2004 |
| WO | WO 2004/098583 | 11/2004 |
| WO | WO 2004/099144 | 11/2004 |
| WO | WO 2004/000819 | 12/2004 |
| WO | WO 2004/103997 | 12/2004 |
| WO | WO 2004/110368 | 12/2004 |
| WO | WO2004/111000 | 12/2004 |
| WO | WO2005/007647 | 1/2005 |
| WO | WO 2005/007658 | 1/2005 |
| WO | WO2005/016894 | 2/2005 |
| WO | WO2005/020920 | 3/2005 |
| WO | WO2005/025554 | 3/2005 |
| WO | WO2005/026148 | 3/2005 |
| WO | WO2005/030127 | 4/2005 |
| WO | WO2005/030129 | 4/2005 |
| WO | WO2005/030751 | 4/2005 |
| WO | WO2005/033099 | 4/2005 |
| WO | WO2005/035525 | 4/2005 |
| WO | WO2005/037215 | 4/2005 |
| WO | WO2005/023762 | 5/2005 |
| WO | WO2005/040095 | 5/2005 |
| WO | WO2005/042488 | 5/2005 |
| WO | WO2005/046603 | 5/2005 |
| WO | WO2005/047297 | 5/2005 |
| WO | WO2005/049033 | 6/2005 |
| WO | WO2005/058315 | 6/2005 |
| WO | WO2005/058849 | 6/2005 |
| WO | WO2005/061489 | 7/2005 |
| WO | WO2005/063750 | 7/2005 |
| WO | WO2005/072530 | 8/2005 |
| WO | WO2005/075426 | 8/2005 |
| WO | WO 2005/080330 | 9/2005 |
| WO | WO2005/090348 | 9/2005 |
| WO | WO2005/100365 | 10/2005 |
| WO | WO2005/117909 | 12/2005 |
| WO | WO2005/121121 | 12/2005 |
| WO | WO 2006/034446 | 3/2006 |
| WO | WO 2006/039325 | 4/2006 |
| WO | WO2006/040966 | 4/2006 |
| WO | WO2006/043490 | 4/2006 |
| WO | WO 2006/047516 | 5/2006 |
| WO | WO 2006/050946 | 5/2006 |
| WO | WO 2006/052566 | 5/2006 |
| WO | WO2006/067531 | 6/2006 |
| WO | WO2006/067532 | 6/2006 |
| WO | WO2006/070208 | 7/2006 |
| WO | WO 2006/076231 | 7/2006 |
| WO | WO 2006/076243 | 7/2006 |
| WO | WO 2006/076455 | 7/2006 |
| WO | WO 2006/078992 | 7/2006 |
| WO | WO 2006/083491 | 8/2006 |
| WO | WO 2007/003964 | 1/2007 |
| WO | WO 2007/005673 | 1/2007 |
| WO | WO 2007/035355 | 3/2007 |
| WO | WO 2007/039470 | 4/2007 |
| WO | WO 2007/089335 | 8/2007 |
| WO | WO 2007/120689 | 10/2007 |
| WO | WO 2007/120702 | 10/2007 |
| WO | WO 2008/005569 | 1/2008 |
| WO | WO 2008/005576 | 1/2008 |
| WO | WO 2008/025798 | 3/2008 |
| WO | WO 2008/070692 | 6/2008 |
| WO | WO 2008/076243 | 6/2008 |
| WO | WO 2009/038974 | 3/2009 |
| WO | WO 2009/126245 | 10/2009 |
| WO | WO 2009/126535 | 10/2009 |
| WO | WO 2010/074271 | 7/2010 |
| WO | WO 2010/075271 | 7/2010 |
| WO | WO 2010/075273 | 7/2010 |
| WO | WO 2011/005929 | 1/2011 |
| WO | WO 2011/008663 | 1/2011 |
| WO | WO 2011/030139 | 3/2011 |
| WO | WO 2011/127051 | 10/2011 |
| WO | WO 2012/040279 | 3/2012 |
| WO | WO 2012/135570 | 10/2012 |
| WO | WO 2012/145361 | 10/2012 |
| WO | WO 2012/145603 | 10/2012 |
| WO | WO 2012/145604 | 10/2012 |
| WO | WO 2012/170702 | 12/2012 |
| WO | WO 2013/055910 | 4/2013 |

OTHER PUBLICATIONS

"Obesity: Prevention", http://www.mayoclinic.com/health/obesity/ds00314/dsection=prevention, accessed Jul. 1, 2011.*

"NDEP", http://ndep.nih.gov/diabetes/prev/prevention.htm, accessed Jul. 1, 2011.*

"Insulin resistance and Pre-Diabetes", http://diabetes.niddk.nih.gov/dm/pubs/insulinresistance/, accessed Jul. 1, 2011.*

"High blood sugar", http://www.emedicinehealth.com/high_blood_sugar_hyperglycemia/page9_em.htm, accessed Jul. 1, 2011.*

"Familial hypercholesterolemia", http://www.umm.edu/ency/article/000392prv.htm, accessed Jul. 1, 2011.*

Shah. Vitamins and Hormones, 2010, 84, 415-448.*

Rayasam. Expert Opinion on Therapeutic Targets, 2007, 11(5), 661-671.*

Han. Journal of Endocrinology, 2009, 201, 219-230.*

"Dyslipidemia", http://www.nlm.nih.gov/cgi/mesh/2013/MB_cgi, accessed Jul. 18, 2013.*

"Metabolic syndrome", http://www.mayoclinic.com/health/metabolic%20syndrome/DS00522, accessed Jul. 18, 2013.*

Abdalla et al., "Synthesis and reaction of 3-cyano 2-(1H)-pyridones," *Pakistan Journal of Scientific and Industrial Research* (1977) 30(3):139-149.

Abramovitch et al., "Solution and flash vacuum pyrolysis of some 2.6-disubstituted B-phenethyslulfonyl azides and of (B-styrenesulfonyl azide," *j Org Chem* (1985) 50-2066-2073.

American Diabetes Association, "Hyperglycemia (High blood glucose)," downloaded from http://www.diabetes org/living-with-diabetes/treatment-and-care/blood-glucose-control/hyperglycemia.html?print=t on Jan. 28, 2011, 2 pgs.

Appukkuttan et al, "Translation-Metal-Free Sonogashira-Type Coupling Reactions in Water," *European Journal of Organic Chemistry* (2003) 24-4713-4716.

Arvanitis et al., "Non-peptide corticotropin-releasing hormone antagonists; syntheses and structure-activity relationships of 2-anilinopyrimidines and triaznes," *J Med Chem.* (1999) 42(5):805-18.

Arvanitis et al., "Non-peptide corticotropin-releasing hormone antagonists; syntheses and structure-activity relationships of 2-anilnopyrimidines and triaznes," *J Med Chem.* (1999) Supporting Material, pp. 1-10.

Arvanitis et al., "CRF Ligands via Suzuki and negishi couplings of 3-pyridyl boronic acids or halides with 2-benzyloxy-4-chloro-3-nitropyridione," *Bioorganic & Medicinal Chemistry Letters* (2003) 13(2)-289-291.

Arvanitis et al., "Imidazo[4,5-b]ppyridines as corticotropin releasing factor receptor ligands," *Bioorganic & Medicinal Chemistry Letters* (2003) 12(1):125-128.

(56) References Cited

OTHER PUBLICATIONS

Arvela et al., "Rapid, Easy Cyanation of Aryl Bromides and Chlorides Using Nickel Salts in Conjunction with Microwave Prmotion," *J. Org. Chem.* (2003) 68:9122-9125.
Arvela et al., "Rapid cyanation of aryl iodides in water using microwave promotion," *Org. Biomo, Chem.* (2003) 1:1119-1121).
Baindur et al., "Solution-Phase Synthesis of a Library of 3,5,7-Trisubstituted 3H-[1,2,3]triazolo[4,5-Id]pyrimidines," *J. Comb. Chem.* (2003) 5:653-659.
Bakkestuen et al., "Regioselective N-9 arylation of purines employing arylboronic acids in presence of Cu(III)," *Tetrahedron Leters* (2003) 44-3359-3362.
Baraldi et al., "An efficient one-pot synthesis of 6-alkoxy-8,9-dialkylpurines via reaction of 5-amino-4-chloro-6-alkylaminopyrimidines with N,N-dimethylakanearrides and alkoxide ions," *Tetrahedron* (2002) 58:7607-7611.
Barta et al, Synthesis and activity of selective MMP inhibitors with an aryl backbone,: *Bioorg & Med Chem Ltrs* (2000) 10(24); 2815-2817.
Baskin et al., "A mild, convenient synthesis of sulfinic acid salts and sulfonamides from alkyl and aeyl haledes," *Tetrahedron Letters* (2002) 43.8479-8483.
Baskin et al., "An Efficient Copper Catalyst for the Formation of Sulfones from Sulfinic Acid Salts and Aryl Iodids," *Org. Ltt.* (2002) 4(25); 4423-4425.
Baskin et al., "An Efficient Cooper Catalyst for the Formation of Sulfones from Sulfinic Acid Salts and Aryl Iodides," *Org. Lett.* (2002) 4(25;4423-4425, Supporting Material #1.
Baskin et al., "An Efficient Cooper Catalyst for the Formation of Sulfones from Sulfinic Acid Salts and Aryl Iodides," *Org. Lett.* (2002) 4(25;4423-4425, Supporting Material #2.
Bedford et al., "Nonquaternary cholinesterase reactivators. 3.3(5)-Substituted 1,2,4-oxadiazol-5(3)-aldoximes and 1,2,4-oxadiazole-5(3)-thiocarbohydroximates as reactivators of organophsphonate-inhibited eel and hunan acetylcholinesterase in vitro," *J Med Chem* (1986) 29(11);2174-2183.
Beller et al., Based-catalyzed amination of olefins; an example of an environmentally friendly synthesis of amines, *Chemosphere* (2001) 43(1);21-26.
Berge et al., "Pharmaceutical Salts," Journal of Pharmaceutical Sciences (1977) 66(1):1-19.
Blagi et al, "5,5,6-trisubstituted 2-phenylpyrimidines and their affinity towards A1 adenosine receptors," *Farnaco* (1997) 52(I); 61-65.
Betti, et al., "Novel 3-Aralkyl-7 (amino-substituted)-1,2,3-triazole[4,5-djprimidines with High Affinity toward A1 Adensoide Receptors," *J. Med. Chem* (1998) 41:668-673.
Boldt et al, "Synthesis of 2,4-diaminopyridines," *Angewandie Chemie International Edition* (1970) 9(5); 377.
Bomika et al, Translation of "Certain reactions of nucleophilic substitution in the 2-chloro-3-cyanopyridine series," Khimiya Geterotsiklicheskikh Soedinenii (1976) (8)1085-1088 (Translated pp. 896-899).
Boschelli et al, "1,3,4-Oxadiazole, 134-thiadiazole, and 1,2,4-triazole analogs of the fenamates: in vitro inhibition of cyclooxygenase activities," *J Med Chem* (1953) 36-1802-1810.
Boswell et al, "Synthesis of Some N-carboxylic acid derivatives of phenoxypyrrolidines, 4-phenoxypiperidines, and 3-phpenoxynortropanes with muscle relaxant and anticonvulsant activities," *J Med Chem* (1974) 17(9); 100-1008.
Brancati et al., "Body Weight Patterns From 20 to 49 Years of Age and Subsequent Risk for Diebetes Mellitus: The Johns Hopkins Precursors Study," *Arch Intern Med.* (1999) 159:957-963.
Bromidge et al., "Design of [R-(Z)-]-(+)-alpha-(methoxylmino)-1azabicyclo[2.2.2]octane-3-acetonitri le (SB 202026), a functionally selective azabicyclic muscarinic M1 against incorporating the N-methoxy imidoyl nitrile group as a novel ester bioisostere," *J Med Chem* (1997) 40(26)-4265-4280.
Buehler et al, "Physiologically active compounds. VI. Cyclic amino thiolesters of substituted chloracetic, benzilic and glycolic acids," *J Med Chem* (1965) 8:643-647.

Bulger et al., "An investigation inot the alkylation of 1,2,4-triazole," *Tetrahedron Letters* (2000) 41:1297-1301.
Chan et al., "Isoquinoline-6-Carboxamides as Potent and Selective Anti-Human Cytomegalovirus (HCMV)Inhibitors," *Bioorganic & Medicinal Chemistryletters* (1999) 9:2583-2586.
Chen et al., "Optimization of 3-phyenylprazolo[1,5-alpha]pyrimidines as potent corticotrophin-releasing factor-I antagonists with adequate lipophilicity and water solubility," *Bioorganic & Medicinal Chemistry Letters* 2004 14-3669-3673.
Chen et al., "Design and Synthesis of a Series of Non-Peptide High Affinity Human Corticotropin-Releasing Factor 1 Receptor Antagonists," *J Med. Chem.* (1996) 39.4358-4360.
Chen et al., "Free Radical Method for the Synthesis of Spiro-Piperidinyl Heterocycles," *Tetrahedron Letters* (1996) 37(3);5233-5234.
Chorvat et al,, "Synthesis, Corticotropin-Releasing Factor Receptor Binding Affinity, and Pharmacokinetic Properties of Triazolo-, Imidazo-, and Pyrrolopyrimidines and—pyridines," *J. Med. Chem.* (1999) 42:833-848.
Chu et al., 'A Role for Intestinal Endocrine Cell-expressed GPR119 in Glycemic Control by Enhancing GLP-1 and GIP Release,' Arena Pharmaceuticals, Endocrinology 149(5), pp. 2038-2047 (2008) [retrieved Jun. 9, 2009]. Retrieved from the Internet: http://endo.endojournals.org/cgi/reprint/149/5/2038.pdf.
Chu et al., "A role for β-cell-expressed G protein-coupled receptor 119 in glycemic control by enhancing glucose-dependent insulin release," Endocrinology (2007) 148:2601-2609.
Clark et al., "Synthesis and Analgesic Activity of 1,3-Dihydro-3-(Substituted phenyl)imidazo(4,5-b]pyridine-2-ones and 3-(Substituted phenyl)-1,2,3-triazolo(4,5bpyridines," *J. Med. Chem.* (1978) 21(9):965-978.
Cocco et al., "Transformation of 6-Methylthiopyrimidines," Journal of Heterocyclic Chemistry (2000), 37(4), 707-710.
Cocuzza et al, "Use of the Suzuki Reaction for the Synthesis of Aryl-Substituted Heterocycles as Corticotropin-Releasing Hormone (CRH) Antagonists," *Bioorganic & Medicinal Chemistry Letters* (1999) 9:1063-1066.
Cohen et al., "The Preparation and Properties of 6-Halomethylpurines," *Div. of Nucleoprotein Chemistry, Sloan-Kettering Institute for Cancer Research, and Sloan Kettering Div. Grad. School of Med. Sci., Cornell Univ. Med. College* (1962) 27:3545-3549.
Colandrea et al., "Synthesis and regioselective alkylation of 1,6-and 1,7-naphythridines," *Tetrahedron Letters* (2000) 41:8053-8057.
Collier et al, "Radiosynthesis and in-vivo evaluation of the pseudopeptide δ-opioid antagonist [$^{125}$I]ITIPP(Ψ),"*j. Labeled Comp. Radiopharm.*, (1999) 42(Suppl.1):S264-S266.
Cossey et al, "Amide-acid chloride adducts. VI. Pyridines and pyridinium salts from cyanoacetamides," *Australian Journal of Chemistry* (1976) 29(5):1039-1050.
Cryan et al, "Behavioral characterization of the novel GABAB receptor-postive modulator GS539783 (N,N'-dicyclopentyl-2-methylsulfanyl-5nitropyrmidine-4,6 diamine): Anxiolytic-like activity without side effects associated with baclofen or benzodiazepines," *Journal of Pharmacology and Experimental Therapeutics* (2004) 310(3):952-963.
Dai et al., "The first general method for palladium-catalyzed Negishi cross-coupling of anyl and vinyl chlorides: use of commercially available Pd(P(i-Bu)$_3$)$_2$ as a catalyst,"*J M Chem Soc* (2001) 123(12):2179-2724.
Desimoni et al, "Polynuclear Isoxazole Types-I-Isoxazolo[4,5-d]Pyrimidines," *Tetrahedron* (1967) 23:675-680.
Devita et al, "Identification and initial structure-activity relationships of a novel non-peptide quinolone GnRH receptor antagonist," *Bioorg & Med Chem Ltrs* (1999) 9(17):2615-2620.
Di Braccio et al., "Synthesis and preliminary pharmacological examination of 2,4-disubstituted N,N-dialkyl-1,8-napthyridine-3-carboxamides," *Farmaco* (1989) 44(9):865-881.
Dorwald, A Guide to Successful Snythesis Design, Side Reactions in Organic Synthesis, 2005, Wiley: VCH, Weinheim, p. IX of Preface.
Dzierba et al., "Synthesis, Structure-Activity Relationships, and in Vivo Properties of 3,4-Dihydo-1H-pyrido[2,3$_b$]pyrazin-2-ones as

(56) References Cited

OTHER PUBLICATIONS orticotropin-Releasing Factor-1 Receptor Antagonists," *Journal of Medicinal Chemistry* (2004) 47(23):5783-5790.

Eicher et al., "Reaction of trialfulvenes with isonitriles. A simple synthesis of diphenyl-substituted functionalized cyclobutene derivatives and related products," *Synthesis* (1987)(7):619-626.

emedicinehealth.com, "High Blood Sugar", http://www.emedicinehealth.com/high_blood_sugar_hyperglycemia/page9_em.htm, accessed Jul. 1, 2011, 3 pgs.

Escher et al, "Cyclopentylamine Substituted Triazoko[4,5-D]Pyrimidine: Implications for Binding to the Adenosine Receptor," *Tetrahedron Leters* (1991) 32(29):3583-3584.

Fyfe et al., Diabetes (2007) 56(Supplement 1):A142 (Abstract #532-P).

Fyfe et al. "GPR119 agonists as potential new oral agents for the treatment of type 2 diabetes and obesity," Expert Opinion on Drug Discovery, 2008, 3(4), 403-413, 11 pgs.

Gangloff et al., "Synthesis of 3,5-disubstituted-1,2,4-oxadiazoles using tetrautylammonium fluoride a mild and efficient catalyst," *Tetrahedron Letters* (2001) 42:1441-1443.

Gilligan et al., "Corticotropin-releasing factor antagonists: Recent advances and exciting prospects for the treatment of human diseases," *Current Opinion in Drug Discovery & Development* (2004) 7(4):487-497.

Gilligan, et al., "Corticotropin Releasing Factor (CRF) Receptor Modulators Progress and Opportunities for New Therapeutic Agents," *J. Med. Chem*, (2000) 43(9):1641-1660.

Goldner et al., "Die Darstellung 2,9-; 2,6,9- and 6,9-substituierter Purine," *Journal fuer Praktische Chemie (Leipzig)* (1961) 12:242-252.

Giner-Sorolla et al., "The Synthesis and Properties of 6-Mercaptomethylpurine and Derivatives," *Cornell University Medical College* (1965) 8:667-672.

"Glucose Metabolism Disorders" http://www.nlm.nih.gov/cgi/mesh/2011/MB_cgi?mode=&term=Glucose+Metabolism+Disorders&field=entry, accessed Jan. 11, 2011, 3 pgs.

Gomtsyan et al., "Design, synthesis, and structure-activity relationship of 6-alkynylpyrimidines as potent adenosine kinase inhibitors," *J Med Chem*. (2002) 45(17):3639-3648.

Gottlieb et al., "NMR Chemical Shifts of Common Laboratory Solvents as Trace Impurities" J. Org. Chem., 1997, 62,7512-7515.

Greene et al., Protective Groups in Organic Synthesis, 3$^{rd}$ Ed., John Wiley & Sons, New York (1999).

Guillory, "Generation of Polymorphs, Hydrates, Solvates, and Amorphous Solids," in: Polymorphism in Pharmaceuticals Solids, ed. Harry G. Brittan, vol. 95, Marcell Dekker, Inc., New York, 1999, pp. 202-209.

Hamada et al., "An improved synthesis of arylsulfonyl chlorides from arylhalides," Synthesis (1986) pp. 852-854.

H Lan, "GPR119 is Required for Physiological Regulation of Glucagon-line Peptide-1 Secretion but not for Metabolic Homeostasis," Journal of Endocrinology, 2009, 201, 219-230.

He et al., "4-(1,3-Dimethozyprop-2-ylamino)-2,7-dimethyl-8-(2,4-dichlorophenyl)-pyrazolo[1,5-al-1,3,5-triazine: A Potent, Orally Bioavailable CRF1 Receptor Antagonist," *J. Med. Chem.* (2000) 43:449-456.

Hecht et al., On the "activation" of cytokins, *J of Biological Chemistry* (1975) 250(18):7343-7351.

Hersperger et al., "Palladium-Catalyzed Cross-Coupling Rtions for the Synthesis of 6,8- Disubstituted 1,7-Naphthyridines: A Novel Class of Potent and Selective Phosphodiesterase Type 4D Inhibitors," *J. Med. Chem.* (2000) 43:675-682.

Higuchi et aL, "Pro-drugs as novel delivery systems," A.C.S. *Symposium* Series, vol. 14 (1987).

Hill et al., "Environmental contributions to the obesity epidemic," *Science* (1998) 280(5368):1371-4.

Hocek et al., "An Efficient Synthesis of 2-Substituted 6-Methylpurine Bases and Nucleosides by Fe- or Pd-Catalyzed Cross-Coupling Reactions of 2,6-Dichloropurines," *J. Org. Chem.* (2003) 68:5773-5776.

Huang et at., "Synthesis and Antiplatelet Activity of Phenyl Quinolones," *Bioorganic & Medicinal Chemistry* (1998) 6:1657-1662.

Jia, et al., "Design, Synthesis and Biological Activity of Novel Non-Amidine Factor Xa Inhibitors. Part 1: P1 Structure-Activity Relationships of the Substituted 1-(2-Naphtyl)-1H-pyrazole-5-carboxylamides," *Bioorganic & Medicinal Chemistry Letters* (2002)12:1651-1655.

Jogie et al., "Unusual protein-binding specificity and capacity of aza-arenophilic gels," *Journal of Molecular Recognition* (1998) 11:261-262.

Kawase et al., "a-trifluoromethylated acyloins induce apoptosis in human oral tumor cell lines," *Bioorg & Med Chem Ltrs* (1999) 9(21):3113-3118.

Kelly et at., "A Synthesis of Aaptamine," *Tetrahedron* (1985) 41(15):3033-3066.

Kelley et al., "Benzodiazepine receptor binding activity of 8-substituted-9-(3-substituted-benzyl)-6 diamethylamino)-9H-purines," *Med Chem* (1990) 33(1):196-202.

Kempson et al., "Fused pyrimidine based inhibitors of phosphodiesterase 7 (PDE7): synthesis and initial structure-activity relationships," *Bioorganic & Medicinal Chemstry Letters* (2005) 15:1829-1833.

Khattab et al., "Quinolines with heteroatom substituents in position 2 and 4. Nucleophilic substitution of 2,4-dichloro-3-phenylquinolines," *ACH—Models in Chemistry* (1994) 131(3-4):521-527.

Kloetzer et al., "Chlorierende formylierungsreaktionen an pyrimidinen," Monatshefte *fuer Chemie*, (1965) 96(5):1567-1572.

Kotian et al., "Synthesis, ligand binding, and quantitative structure-activity relationship study of 3β-(4'- substituted phenyl)-2β-heterocyclic tropanes: evidence for an electrostatic interaction at the 2β-position," *I Med Chem* (1996) 39(14):2753-2763.

Krauze et al., "Derivatives of 3-cyano-6-phenyl-4-(3'-pyridyl)-pyridine-2(1H)-thione and their neurotropic activity," *European Journal of Medicinal Chemistry* (1999) 34(4):301-310.

Krauze et al., "Synthesis of 3-oxoisothiazolo[5,4-b]pyridines," Khimiya *Geterotsiklicheskikh* Soedinenii (1982) (4):508-512.

Kreisberg et al., Hyperlipidemia (High Blood Fat), The Journal of Clinical Endocrinology & Metabolism, (2005), 90:0, 2 pgs.

Kumegai et al., "Synthesis, SAR and biological activities of CRH1 Receptor: Novel 3- or 4-carbamoyl-1,2,5,6- tetrahydropyridinopyrrolopyrimidine derivative," 4$^{th}$ ACS National Meeting, Aug. 18-22, 2002, Boston, MA. Poster #259.

Lanier et al., "Small molecule corticotrophin-releasing factor antagonists," *Expert Opinion* (2002) 12(11):1619-1630.

Leadbeater et al., "First Examples of Transition-Metal Free Sonogashira-Type Couplings," Organic *Letters* (2003) 5(21):3919-3922.

Leadbeater et al., 'Transition-metal Free Sonogashira-type Couplings,' Department of Chemistry, King's College London, Supplemental Information for Leadbeater et al., First Examples of Transition-Metal Free Sonogashira-Type Couplings, Organic Letters 5(21) pp. 3919-3922 (2003).

Lee et al., "Synthesis and biological evaluation of clitocine analogues as adenosine kinase inhibitors," *Bioorg & Med Chem Ltrs* (2001) 11(18):2419-2422.

Leese et al., "Potential antipurines. H. Synthesis of 6- and 9-substituted purines and 8-azapurines," *Journal of the Chemical Society* (1958) 4107-4110.

Le Bas et al., "Radioiodinated analogs of EP 00652218 for the exploration of the tachykinin NK1 receptor by spect," *J. Labeled Compd. Radiopharm.* (2001) 44:S280-S282.

Le Stunff et al., "Early changes in postprandial insulin secretion, not in insulin sensitivity, characterize juvenile obesity," Diabetes (1989) 43:696-702.

Lin, et al., "Synthesis and Antitumor Activity of Halogen-Substituted 4-(3,3-Dimethyl-l-triazeno)15uinolones," *J. Med. Chem.* (1978) 21(3):268-272.

(56) References Cited

OTHER PUBLICATIONS

Litvak et al., "Polynucleotides and Their Components in the Processes of Aromatic Nucleophilic Substitution: 11.1 Nucleophilic Modification of 3',5'-Bis-O-(a,(β,a',(β-tetrafluoropyrid-yl)thymidine," *Russian Journal of Bioorganic Chemistry* (2004) 30(4):337-343.

Litvinov et at., "Naphythyridines. Structure, physicochemical properties and general methods of synthesis," *Russian Chemical Reviews* (2000) 69(3):201-220.

Loupy et al., "Easy and efficient SNAr Reactions on halopyridines in solvent free conditions," *Heterocycles* (1991) 32(10):1947-1952.

Luo et al., "Microwave-assisted synthesis of aminopyrimidines," *Tetrahedron Letters* (2002) 43:5739-5742.

Groger "Moderne methoden der Suzuki-kreuzkupplung: die langerwarteten universellen synthesevarianten mit arylchloriden," *J Prakt Chem* (2000) 342(4):334-339.

Ma, et at. "Mild Method for Ullmann Coupling Reaction of Amines and Aryl Halides," *Organic Letters* (2003) 5(14):2453-2455.

Macchia et al., "New N-n-propyl-substituted 3-aryl- and 3-cyclohexylpiperidines as partial agonists at the D4 dopamine receptor," *J Med Chem* (2003) 46(1):161-168.

Mackman et al., "2-(2-Hydroxy-3-alkoxyphenyl)-IH-benzimidazole-5-carboxamidine derivatives as potent and selective urokinase-type plasminogen activator inhibitors," *Bioorganic & Medicinal Chemistry Letters* (2002) 12(15):2019-2022.

Majeed, et at, "Stannylation Reactions and Cross-Couplings in Pyrimidines," *Tetrahedron* (1989) 45(4):993-1006.

Matsui et al., "Highly potent inhibitors of TNF-a production. Part II: metabolic stabilization of a newly found chemical lead and conformational analysis of an active diastereoisomer," *Bioorg Med Chem.* (2002) 10(12):3787-805.

Matsuno et al., "Potent and selective inhibitors of platelet-derived growth factor receptor phosphorylation 3. Replacement of quinazoline moiety and improvement of metabolic polymorphism of 4-[-N-substituted (thio) caramoyl)-1-piperazinyl]- 6,7-diamethoxyquinazoline derivatives," *J Med Chem* (2003) 46(23:4910-4925.

MayoClinic.com "Obesity: Prevention", http://www.mayoclinic.com/health/obesity/ds00314/dsection-prevention, accessed Jul. 1, 2011, 4 pgs.

MayoClinic.com "Obesity: Prevention", http://www.mayoclinic.com/health/obesity/ds00314/dsection-prevention, accessed May 19, 2010, 4 pgs.

MayoClinic.com "Type 2 diabetes," downloaded from http://www.mayoclinic.com/health/type-2-diabetes/DS00585/METHOD=print on Jan. 28, 2011, 14 pgs.

Mesguiche et al., "4-Alkoxy-2,6-diaminopyrimidine derivatives: inhibitors of cyclin dependent kinases 1 and 2," *Bioorganic & Medicinal Chemistry Letters* (2003) 13(2):217-222.

Metzger et al., "Einstufensynthese von 2,4-Bis(sec-alkylamino-6-halogen-3-pyridincarbonitrilen," *Liebigs Annalen der Chemie* (1980) (6):946-953.

Mittelbach et al., "Syntheses with nitriles. 60. Preparation of 4-amino-5-cyano-6-phenylpyrimidines from 2-amino-1,1-dicyano-2-phenylethene," *Journal of Heterocyclic Chemistry* (1980) 17(7):1385-1387.

Miyashita et al., "Preparation of Heterarenecarbonitriles by Reaction of Haloheteroarenes with Potassium Cyanide Atalyzied by Sodium p-Toluenesulfinate;" *Heterocycles* (1994) 39(1):345-350.

Mohan et al., "Solid-phase synthesis of N-substituted amidinophenoxy pyridines as factor Xa inhibitors," *Bioorganic & Medicinal Chemistry Letters* (1998) 8(14):1877-1882.

Mombereau et al., "Genetic and Pharmacological Evidence of a Role for GABAB Receptors in the Modulation of Anxiety- and Antidepressant-Like Behavior," *Neuropsychopharmacology* (2004) 29(6):1050-1062.

Mongin et al., "Advances in the directed metallation of azines and diazines (pyridines, pyrimidines, pyrazines, pyridazines, 17uinolones, benzodiazines and carbolines). Part 1: Metallation of pyridines, 17uinolones and carbolines," *Tetrahedron* (2001) 57(19):4059-4090.

Montgomery et al., "Isonucleosides. I. Preparation of methyl 2-deoxy-2-(purin-9-yl)arabinofuranosides and methyl 3-deoxy-3-(purin-9-yl) arabinofuranosides and methyl 3-deoxy-3-(purin-9-yl)xylofuranosides," *Journal of Organic Chemistry* (1975) 40(13)-1923-1927.

Morimoto et al., "Potent and selective ET-A antagonists. 1. Syntheses and structure-activity relationships of N-(6-(2-(aryloxy)ethoxy)-4-pyrimidinyl)sulfonamide derivatives," *J Med Chem*, (2001) 44 (21):3355-3368.

Morissette et al., High-throughput crystallization: polymorphs, salts, co-crystals and solvates of pharmaceutical solids, Adv. Drug Delivery reviews, 2004, 56, 275-300.

Moschitskii et al., Translation of "Reaction of 2,3,5,6-tetrachloro-4-pyridyl-vinyl sulfone with nuleophilic agents," *Khimiya Geterotsiklicheskikh Soedinenii* (1972) pp. 1634-1637, (Translated pp. 1482-1485).

Muci et al. "Practical Palladium Catalysts for C-N and C-O Bond Formation," Topics in Current Chemistry (2002) 219;131-209.

Muller et al., "7-Deaza-2-phenyladenines: Structure-Activity Relationships of Potent A1 Selective adenosine Receptor Antagonists," *J. Med, Chem.* (1990) 33:2822-2828.

Nakazato et al., "Synthesis, SAR and biological activities of CRH1 Receptor: Novel 3- or 4-carbamoyl-1,2,5,6-tetrahydropyridinoquinoline derivative," 24th ACS National Meeting, Aug. 18-22, 2002, Boston, MA. Poster #258.

Nakazato et al., "Design, synthesis and structure-affinity relationships of 4-methylidenepiperidine and 4-aryl-1,2,3,6-tetrahydropyridine derivatives as corticotropin-releasing factors receptor antagonists," *Bioorganic & Medicinal Chemistry* (2000)8(5):1183-1193.

National Diabetes Information Clearinghouse, "Insulin resistance and Pre-Diabetes," http://diabetes.niddk.nih.gov/dm/pubs/insulinresistance/, accessed Jul. 1, 2011, 6 pgs.

ndep.nih.gov, "Diabetes Prevention" (May 26, 2009) http://ndep.nih.gov/diabetes/prev/prevention.htm, accessed Jul. 1, 2011, 7 pgs.

Nesi et al., "New Difunctionalized 4-Nitroisoxazoles from Alpha-Nitroacetophenone Oxime," *Heterocycles* (1985) 23(6):1465-1469.

Nicewonger et al., "Microwave-assisted acylation of 7-amino-5-aryl-6-cyanopyrido[2,3-d]pyrimidines," *Molecular Diversity* (2003) 7(2-4):247-252.

Norman et al., "Structure—activity relationships of a series of pyrrolo(3,2-d) pyrimidine derivatives and related compounds as neuropeptide Y5 receptor antagonists" *J. Med. Chem.* (2000) 43(22):4288-4312.

Norman et al., "Structure—activity relationships of a series of pyrrolo(3,2-d) pyrimidine derivatives and related compounds as neuropeptideY5 receptor antagonists" J. Med. Chem. (2000) 43(22):4288-4312, JM000269T, Supplemental Material, pp. 1-11.

Oae, Organic Chemistry of Sulfur, Ed., Plenum Press: New York (1977).

Olesen et al., "The use of bioisosteric groups in lead optimization," *Current Opinion in Drug Discovery & Development* (2001) 4(4):471-478.

Overton et al., "Deorphanization of a G protein-coupled receptor for oleoylethanolamide and its use in the discovery of small-molecule hypophagic agents," Cell Metabolism (2006) 3:167-175.

Parlow et al., "Design, synthesis, and crystal structure of selective 2-pyridone tissue factor VIIa inhibitors," *J Med Chem* (2003) 46(22):4696-4701.

Paulsen et al., "Darstellung von Bausteinen zur Synthese carbocyclischer furanose-analoga," *Chemische Berichte* (1981)114(1):346-358.

Pederson, "The impact of obesity on the pathogenesis of non-insulin-dependent diabetes mellitus: a review of current hypotheses," *Diab. Metab. Rev.*, (1989) 5(6):495-509.

Perry et al., "Prospective study of risk factors for development of non-insulin dependent diabetes in middle aged British men," *BMJ* (1995) 310(6979):560-4.

(56) References Cited

OTHER PUBLICATIONS

Phillips et al., "Discovery of N-[2[5-[Amino(imino)methyl]-2-hydroxyphenoxyl]-3,5-difluoro-6-[3-(4,5-dihydro-1-methyl-1H-imidazol-2-yl)phenoxy]pyridine-4-yl)-N-methylglycine(ZK-807834): A Potent, Selective, and Orally Active Inhibitor of the Blood Coagulation Enzyme Factor Xa," *J. Med. Chem.* (1998) 41(19):3557-3562.
Pomorski "Synthesis of Acids, Derivatives of 4-Hydroxy-1,5-Naphthyridine," *Roczniki Chemii Ann. Soc. Chim. Polonorum* (1974) 48:321-325.
Potenza et al., "A rapid quantitative bioassay for evaluating the effects of ligands upon receptors that modulate cAMP levels in a melanophore cell line," *Pigment Cell Res.* (1992) 5(6):372-8.
Prasad, et al., "Convenient Methods for the Reduction of Amides, Nitriles, Carboxylic Esters, Acids and Hydroboration of Alkenes Using $NaBH+/I_2 System$," *Tetrahedron* (1992) 48(22):4623-4628.
Press et al, "Synthesis and SAR of 6-Substituted Purine Derivatives as Novel Selective Positive Inotropes," *J. Med. Chem* (1992) 35(24):4509-4515.
Quesada et al., 2-Amino-5-nitro-4,6-dipperidionpyrimidinium hydrogensulfate monohydrate, Acta Cryst, 2003, C59, 102-104 (Abstract; 1 page).
Quintela et al., "6-Dimethylamino 1H-Pyrazolo[3,4-d]pyrimidine Derivatives as New Inhibitors of Inflammatory Mediators in Intact Cells," *Bioorganic &Medicinal Chemistry* (2003) 11:863-868.
Quintela et al., "Pyrazolopyrimidines: synthesis, effect on histamine release from rat peritoneal mast cells and cytotoxic activity," *Eur. J. Med. Chem.* (2001) 36:321-332.
Ram et al., "Chemotherapeutic agents. Part XXII. Synthesis of n-deficient pyrimidines as leishmanicides," *Indian Journal of Chemistry*, Section B (1991) 30B(10):962-965.
Reed et al., "In-vivo and in-vitro models of type 2 diabetes in pharmaceutical drug discovery," *Diabetes Obes Metab*, (1999) 1(2):75-86.
Rehwald et al, "Syntheses of thieno[2,3-d]pyrimidines and aminopyrimidines from 2-alkoxy-5-cyano-4-thioxopyrimidine intermediates," *Heterocycles* (1998) 48(6):1157-1167.
Remington's Pharmaceutical Sciences, 17th Ed., (1985), Mack Publishing Company, Easton, PA, p. 1418-1419.
Remington's *Pharnuaceutieal Sciences*, 16[th] Ed., (1980), Mack Publishing Company, Easton, PA.
Remington, The Science and Practice of Pharmacy, 20[th] Ed.; Lippincott Williams & Wilkins (2000).
Rewcastle, et al., "Tyrosine Kinase Inhibitors. 10. Isomeric 4-[(3-Bromophenyl)amino]pyrido[d]pyrimidines are Potent ATP Binding Site Inhibitors of the Tyrosine Kinase Function of the Epidermal Growth Factor Receptor," *J. Med. Chem.* (1996) 39:1823-1835.
Raffel et al., "Diabetes Mellitus," *Principles and Practice of Medical Genetics*, 3b Ed. 1:1401-1440 (1996).
Rao et al., "Impaired Glucose Tolerance and Impaired Fasting Glucose," 1962 American Family Physician, vol. 69, No. 8 (Apr. 15, 2004), 8 pgs.
Rayasam et al., "Fatty Acid Receptors as New Therapeutic Targets for Diabetes," Expert Opinion on Therapeutic Targets, 2007, 11(5), 661-671.
Roberts et al., "Peroxy-acid oxidation of N,N-disubstituted aminotetrafluoro-, amino-3-chlorotrifluoro-, and amino-3,5-dichlorodifluoro-pyridines," *Journal of the Chemical Society [Section] C: Organic* (1969) (11):1485-1491.
Roberts et at., "Polychloroaromatic compounds. L Oxidation of pentachloropyridine and its N,N-disubstituted amino derivatives with peroxyacids," *Journal of the Chemical Society* (Section) C: Organic (1968) (12):1537-1541.
Robins, et al., "Potential Purine Antagonists. W. Synthesis of Some 9-Methyl-6-substituted purines," (1957) 79:490-494.
Robev et al., "4-Cyclopropylamino- and 4-cyclobutylamino derivatives of some aryl-substituted 5- cyanopyrimidines," *Doktady Bolgarskoi Akademii Nauk* (1981) 34(12):1677-1680.
Roche, Bioreversible Carriers in Drug Design, ed., American Pharmaceutical Association and Pergamon Press (1987).
Rodriquez-Spong et al., General Principles of Pharmaceutical Solid state Polymorphism: A Supramolecular Perspective, Adv. Drug Delivery Rev., 2004, 56, 241-274 (available online Dec. 19, 2003).
Rotwein et al., "Polymorphism in the 5' flanking region of the human insulin gene: a genetic marker for non-insulin-dependent diabetes," N Engl *I Med.* (1983) 308(2):65-71.
Sigma-Aldrich, catalog entry for 4,6-diamino-2-mercaptopyrimidine hydrate (catalog No. 125830); 1 page; retrieval date Mar. 16, 2010.
Sigma-Aldrich, catalog entry for 2-amino-6-chloro-4-pyrimidinol hydrate (catalog No. 07460); 1 page; retrieval date Mar. 16, 2010.
Sigma-Aldrich, catalog entry for 2-amino-6-hydroxy-2-mercaptopyrimidine monohydrate (catalog No. A57406); 1 page; retrieval date Mar. 16, 2010.
Sigma-Aldrich, catalog entry for 4,5-diamino-6-hydroxy-2-mercaptopyrimidine hemisulfate salt hydrate (392464); 1 page; retrieval date Mar. 16, 2010.
Shah et al., "GPR119 Agonists for the Potential Treatment of Type 2 Diabetes and Related Metabolic Disorders," Vitamins and Hormones, 2010, 84, 415-448.
Showell et al., "Tetrahydropyridyloxadiazoles: semirigid muscarinic ligands," *J Med Chem* (1991) 34(3):1086-1094.
Silhar et al., "Facile and Efficient Synthesis of 6-(Hydroxymethyl)purines," *Org. Lett.* (2004) 6(19):3225-3228.
Smith et at., "Effects of positive allosteric modulators of the GABAB receptor on cocaine self administration in rats," *Psychopharmacology* (2004)173 (1-2):105-111.
Silvestri et at,, "Novel indolyl aryl sulfones active against HIV-1 carrying NNRTI resistance mutations: synthesis and SAR studies," *J Med Chem* (2003) 46(12):2482-2493.
Soga et al., "Lysophosphatidylcholine enhances glucose-dependent insulin secretion via an orphan G-protein-coupled receptor," Biochem Biophys Res Commun. (2005) 326:744-751.
Steensma et al., "A novel method for the synthesis of aryl sulfones," *Tetrahedron Ltrs* (2001) 42:2281-2283.
Sternfeld et al., "Synthesis and serotonergic activity of 3-[2-(pyrrolidin-1-yl)ethyl]indoles: potent agonists for the h5-HT1D receptor with high selectivity over the h5-HTIB receptor," *J Med Chem* (1999) 42(4):677-690.
Strupczewski et al., "Synthesis and neuroleptic activity of 3-(1-substituted-4-piperidinyl)-1,2-benzisoxazoles," *J Med Chem* (1985) 28(6):761-769.
Suami et al., "Nucleoside analogs. I. Synthesis of 1,3-dihydroxy-2-(6-substituted-9-purinyl)cyclohexane," *Journal of Heterocyclic Chemistry* (1969) 6(5):663-665.
Sugimoto et al., "Preparation of Nitrogen-Containing n-Deficient Heteroaromatic Grignard Reagents: Oxidative Magnesiation of Nitrogen-Containing n-Deficient Halgenoheteroaromatics Using Active Magnesium," *J. Org. Chem.* (2003) 68:2054-2057.
Sugimoto et al., "Lithiation of 1H-Pyrazolo[3,4-d]pyrimidine Derivative Using Lithium. Alkanetellurolate," *Tetrahedron* Letters (1999) 40:2139-2140.
Terashima et al., "Inhibition of human 06-alkylguanine-DNA alkyltransferase and potentiation of the cytotoxicity of chloroethylni. trosourea by 4(6)-(benzyloxy)-2,6(4)-diamino-5-(nitro or nitroso)pyrimidine derivatives and analogues," *J Med* Chem (1998) 41(4):503-508.
Thompson et al., "$N_6$,9-Disubstituted Adenines: Potent, Selective Antagonists at the A1 Adenosine Receptor," *J. Med. Chem.* (1991) 34:2877-2882.
Thompson et al., "Synthesis and evaluation of 6-(dibromomethyl)-5-nitropyrimidines as potential antitumor agents," J Med Chem (1997) 40(5):766-770.
Turck et al., "Advances in the directed metallation of azines and diazines (pyridines, pyrimidines, pyrazines, pyridazines, 22uinolones, benzodiazines and carbolines). Part 2: Metallation of pyrimidines, pyrazines, pyridazines and benzodiazines," *Tetrahedron* (2001) 57(21):4489-4505.
University of Maryland Medical Center, "Familial hypercholesterolemia", http://www.umm.edu/ency/article/000392prv.htm, accessed Jul. 1, 2011, 4 pgs.

(56) References Cited

OTHER PUBLICATIONS

Urgaonkar et al., "Pd/P(i-BuNCH$_2$CH$_2$)$_3$N: an efficient catalyst for Suzuki cross-coupling of aryl bromides and chlorides with arylboronic adds," *Tetrahedron Letters* (2002) 43(49):8921-8924.
Urwyler et al., "N,N'-Dicydopentyl-2-methylsulfanyl-5-nitro-pyrimidine-4,6-diamine (GS39783) and structurally related compounds: Novel allosteric enhancers of y-aminobutyric adds receptor function," *Journal of Pharmacolo and Experimental Therapeutics* (2003) 307(1):322-330.
Vascular Web, "Hyperlipidemia," downloaded from https://www.vascularweb.org/vascularhealth/Pages/Hyperlipidemia.aspx on Jan. 28, 2011, 4 pgs.
Vaughan et al., "The Reformatsky Reaction. I. Zinc and Ethyl Alpha-Bromoisobutyrate," *Dept. of Chem., The Univ. of Michigan, Ann Arbor, MI.*, (1964) 30:1790-1795.
Vippagunta et al., "Crystalline Solids," *Advanced Drug Delivery Reviews*, 28 (2001) 3-26.
Vice,et al., "Concise Formation of 4-Benzyl Piperidines and Related Derivatives Using a Suzuki Protocol," J. *Org. Chem.* (2001) 66:2487-2492.
Vice,et al., "Concise Formation of 4-Benzyl Piperidines and Related Derivatives Using a Suzuki Protocol," *J. Org. Chem.* (2001) 66:2487-2492, Supporting Information, pp. S1-S32.
Wang et al., "Improving the oral efficacy of CNS drug candidates: discovery of highly orally efficacious piperidinyl piperidine M2 muscarinic receptor antagonists," *J Med Chem* (2002). 45(25):5415-5418.
Webmd.com, "Type I Diabetes Prevention," http://diabetes.webmd.com/tc/type-1-diabetes-prevention, accessed May 26, 2009, 3 pgs.
Wei et al., "Association between Obesity and Hyperlipidemia Among Children," Yale Journal of Biology and Medicine 74 (2001), pp. 205-210.
Wells et al., Regioselective nucleophilic substitutions of fluorobenzene derivatives, *Tetrahedron Letters* (1996) 37(36):6439-6442.
Werbel et al., "Synthesis and antimalarial effects of 5,6-dichioro-2-[(4-[[ [4-(diethylamino)1-methylbutyl]amino [[-6-methyl-2-pyrimidinyl)amino] benzimidazole and related benzimidazoles and I,H-Imidazo[4,5-b] pyridines," J. *Het. Chem* (1973) vol. 10, 363-382.
Wilson et al., "Microwave-assisted synthesis of 2-aminoquinolines," *Tetrahedron Letters* (2002) 43(4):581-583.
Wolfe et al., "Scope and limitations of the Pd/BINAP-catalyzed amination of aryl bromides," *J Org Chem* (2000) 65(4):1144-1157.
Wolfe et al., "Simple, efficient catalyst system for the palladium-catalyzed amination of aryl chlorides, bromides, and triflates," *J Org Chem* (2000) 65(4):1158-1174.
Wolter et al., "Copper-Catalyzed Coupling of Aryl Iodides with Aliphatic Alcohols," *Organic Letters* (2002) 4(6):973-976.
Wolter et al., "Copper-Catalyzed Coupling of Aryl Iodides with Aliphatic Alcohols," *Organic Letters* (2002) 4(6):973-976, Supporting Information, pp. S1-S16.
Wu et al., "One-Pot Two-Step Microwave-Assisted Reaction in Constructing 4,5-Disubstituted Pyrazolopyrimidines," *Org. Lett.*, (2003) 5(20):3587-3590.
Yarovenko et al., "New method for the preparation of 5-amino-1,2,4-oxadiazoles," *Bull Acad Sci, USSR Div Chem Sci*, (1991) 40:1924.
Yoon et al., "Reaction of Diisobutylaluminum Hydride with Selected Organic Compounds Containing Representative Functional Groups," *J. Org. Chem.* (1985) 50:2443-2450.
Zamponi et al., "Unique structure-activity relationship for 4-isoxazolyl-1,4-dihydropyridines," *J Med Chem* (2003) 46:87-96.
Zamponi et al., "Unique structure-activity relationship for 4-isoxazolyl-1,4-dihydropyridines," *J Med Chem* (2003), Supporting Information., pp. 1-31.
Zhang, et al., "Preparation of 1-(Tri-n-Butylstannyl) Furanoid Glycals and Their Use in Palladium-Mediated Coupling Reactions," *Tetrahedron Letters* (1993) 34(10):1571-1574.
Zhu et al., Synthesis and mode of action of (125)1- and (3)H-labeled thieno[2,3-c]pyridine antagonists of cell adhesion molecule expression, *J Org Chem.* (2002) 67(3):943-8.

Accession No. 2003:2415108 CHEMCATS, Interbioscreen Compound Library, Chemical Name: 1H-Pyrazolo[3,4-d]pyrimidine-4-amine, N-cyclohexyl-N-methyl-1-(3-methylphenyl)-, XP-002311326, 2003, CAS Registry No. 393844-90-1.
Accession No. 2003:2415906 CHEMCATS, Interbioscreen Compound Library, Chemical Name: 1H-Pyrazolo [3,4-d]pyrimidine-4-amine, N-cyclohexyl-1-1-(4-methylphenyl)-, XP-002311325, 2003, CAS Registry No. 393844-89-8.
Accession No. 2003:2416398 CHEMCATS, Interbioscreen Compound Library, Chemical Name: 1H-Pyrazolo[3,4-d]pyrimidine-4-amine, N-cyclohexyl-1-1-(2,4-dimethylphenyl)-N-methyl-, XP-002311324, 2003, CAS Registry No. 393844-91-2.
Accession No. 2003:2417080 CHEMCATS, Interbioscreen Compound Library, Chemical Name: 1H-Pyrazolo[3,4-d]pyrimidine-4-amine, N-cyclohexyl-N-methyl-1-phenyl)-, XP-002311323, 2003, CAS Registry No. 393844-87-6.
Cover Sheet and 18 Compounds, CAS Registry, 9 pp., (various dates—Aug. 1, 2004-Jan. 13, 2005).
Cover Sheet and 23 Compounds, ChemCats file, 11 pp., (2006).
Cover Sheet and 54 Compounds, CAS Registry and ChemCats files, 23 pp., (various dates—Jan. 15, 1998-Jun. 16, 2004).
Cover Sheet and 1185 Compounds, CAS Registry and ChemCats files, 391 pp., (various dates—Jan. 12, 2005-Nov. 10, 2006).
Cover Sheet and 2534 Compounds, CAS Registry and ChemCats files, 817 pp., (various dates—Feb. 7, 2006-Nov. 6, 2006).
Abstract #107, p. 56, *Toward Understanding Islet Biology*, Jan. 21, 2003-Jan. 26, 2003, Keystone, Colorado.
Abstract #112, p. 42, *Diabetes Mellitus: Molecular Mechanisms, Genetics and New Therapies*, Jan. 27, 2005-Feb. 2, 2005, Keystone, Colorado.
Abstract #228, p. 54, *Diabetes Mellitus: Molecular Mechanisms, Genetics and New Therapies*, Jan. 27, 2005-Feb. 2, 2005, Keystone, Colorado.
Abstract #117 & Poster, *Diabetes: Molecular Genetics, Signaling Pathways and Integrated Physiology*, Jan. 14, 2007-Jan. 19, 2007, Keystone, Colorado.
Abstract #230 & Poster, *Diabetes: Molecular Genetics, Signaling Pathways and Integrated Physiology*, Jan. 14, 2007-Jan. 19, 2007, Keystone, Colorado.
U.S. Appl. No. 12/945,712, filed Nov. 1, 2010, Jones et al.
"Hyperglycemia (High blood glucose)," American Diabetes Association, retrieved on Mar. 29, 2010, http://www.diabetes.org/living-with-diabetes/treatment-and-care/blood-glucose-control/hyperglycemia.html, 2 pages.
"Type I Diabetes Prevention", http://diabetes.webmd.com/tc/type-1-diabetes-prevention, accessed May 26, 2009.
"Obesity: Prevention" http://www.mayoclinic.com/health/obesity/ds00314/dsection=prevention, accessed May 19, 2010.
Abbott et al, "Blockade of the neuropeptide Y Y2 receptor with the specific antagonist BIIE0246 attenuates the effect of endogenous and exogenous peptide YY $_{(3-36)}$ on food intake," *Brain Res*, 2005, 1043:139-144.
Abe et al., "First Synthesis and Determination of the Absolute Configuration of Sulphostin, a Novel Inhibitor of Dipeptidyl Peptidase IV," J. Nat. Prod., 2004, 67:999-1004.
Accession No. 2003:2246299 Chemicals, IH-Pyrazolo [3,4-d] pyrimidin-4-amine, N-cyclohexyl-N-methyl-1-(3 -methylphenyl)- (2003).
Accession No. 2003:2246300 Chemicals, 1H-Pyrazolo [3,4-d] pyrimidin-4-amine, N-cyclohexyl-1-(2,4-dimethlphenyl)-N-methyl- (2003).
Adrian et al., "Human Distribution and Release of a Putative New Gut Hormone, Peptide YY," *Gastroenterol.*, 1985, 89(5):1070-1077.
Ahren et al., "Inhibition of Dipeptidyl Peptidase-4 Augments Insulin Secretion in Response to Exogenously Administered Glucagon-Like Peptide-1, Glucose-Dependent Insulinotropic Polypeptide, Pituitary Adenylate Cyclase-Activating Polypeptide, and Gastrin-Releasing Peptide in Mice," *Endocrinology*, 2005, 146:2055-2059.
Ahren et al., "Inhibition of Dipeptidyl Peptidase-4 Reduces Glycemia, Sustains Insulin Levels, and Reduces Glucagon Levels in Type 2 Diabetes," *J. Clin. Endocrinol. Metab.*, 2004, 89:2078-2084.

(56) References Cited

OTHER PUBLICATIONS

Ahren et al., "Inhibition of Dipeptidyl Peptidease IV Improves Metabolic Control Over a 4-week Study Period in Type 2 Diabetes," *Diabetes Care*, 2002, 25:869-875.

Arehart et al, "Acceleration of Cardiovascular Disease by a Dysfunctional Prostacyclin Receptor Mutation—Potential Implications for Cyclooxygenase-2 Inhibition," *Circ Res*, 2008, 102:986-993.

Atik et al., "Burden of Osteoporosis," *Clin Orthop Relat Res*, 2006, 443:19-24.

Atwal, et al.; Synthesis and Biological Activity of 5-aryl-4-(5-methyl-1H-imidazol-4-yl)piperidin-1-yl)pyrimidine Analogs as Potent, Highly Selective, and Orally Bioavailable NHE-1 Inhibitors; Bioorganic & Medicinal Chemistry Letters (2006), 16(18), 4796-4799.

Augustyns, et al., "Inhibitors of proline-specific dipeptidyl peptidases: DPP-IV inhibitors as a novel approach for the treatment of type 2 diabetes," *Expert Opin. Ther. Patents*, 2005, 15:1387-1407.

Bailey, et al.; Interactions Between Grapefruit Juice and Cardiovascular Drugs; American Journal of Cardiovascular Drug; 4(5), 281-297 (2004).

Balasubramaniam et al, "Neuropeptide Y (NPY) $Y_2$ receptor-selective agonist inhibits food intake and promotes fat metabolism in mice: Combined anorectic effects of $Y_2$ and $Y_4$ receptor-selective agonists," *Peptides*, 2007, 28:235-240.

Balasubramaniam et al, "Structure-Activity Studies Including a (CH-NH) Scan of Peptide YY (PYY) Active Site, PYY(22-36), for Interaction with Rat Intestinal PYY Receptors: Development of Analogues with Potent in Vivo Activity in the Intestine," *J. Med. Chem.*, 2000, 43:3420-3427.

Batterham et al, "Gut hormone $PYY_{3-36}$ physiologically inhibits food intake," *Nature*, 2002, 418:650-654.

Bayes, et al.; Apolipoprotein E alleles, Dyslipemia, and Kidney Transplantation; Transplantation Proceedings, 34(1), 373 (2002).

Becalski et al., "Synthesis of carbolines by the graebe-ullmann method," Acta Pol Pharm. (1984)41:601-606.

Berge et al., "Pharmaceutical Salts," *Journal of Pharmaceutical Sciences*, 1977, 66:1-19.

Bhatt et al., "Preparation and study of a nickel(II) ion selective electrode," Indian ]. Chem (1994) 33B:436-437.

Bilchik et al, "Peptide YY is a Physiological Regulator of Water and Electrolyte Absorption in the Canine Small Bowel in Vivo," *Gastroenterol.*, 1993, 105:1441-1448.

Boey et al, "Peptide YY ablation in mice leads to the development of hyperinsulinaemia and obesity," *Diabetologia*, 2006, 49:1360-1370.

Boey et al, "PYY transgenic mice are protected against diet-induced and genetic obesity," *Neuropeptides*, 2008, 42:19-30.

Bol'but, et al., "A new synthetic approach to fused pyrimidin-4-ones", Institute of Organic Chemistry, National Academy of Sciences of Ukraine, Murmanskaya str. 5, Kiev, 02094, Ukraine; Abstract only http://conf.iflab.kiev.ua/eng/reports/show/?id=348., 2 pages (2003).

Bol'v, et al., "A new synthetic approach to fused pyrimidin-4-ones", Institute of Organic Chemistry, National Academy of Sciences of Ukraine, Murmanskaya str. 5, Kiev, 02094, Ukraine; Abstract only http://conf.iflab.kiev.ua/eng/reports/show/?id=348.

Bollag et al., "Glucose-dependent insulinotropic peptide is an integrative hormone with osteotropic effects," *Mol Cell Endocrinol*, 2001, 177:35-41.

Bollag et al., "Osteoblast-Derived Cells Express Functional Glucose-Dependent Insulinotropic Peptide Receptors," *Endocrinology*, 2000, 141:1228-1235.

Bradley, "TNF-mediated inflammatory disease," J Pathol, 2008, 214:149-160.

Breuer; Hypertriglyceridemia: A Review of Clinical Relevance and Treatment Options: Focus on Cerivastatin; Current Medical Research and Opinion, 17(1), 60-73 (2001).

Brewer; Benefit-Risk Assessment of Rosuvastatin 10 to 40 Milligrams; American Journal of Cardioloty, 92(4B), 23K-29K (2003).

Caldwell et al., "Fluoropyrrolidine amides as dipeptidyl peptidase IV inhibitors," *Bioorg. Med.Chem. Lett.*, 2004, 14:1265-1268.

Capuzzi, et al.; Beneficial Effects of Rosuvastatin Alone and in Combination with a Combined Hyperlipidemia and Low High-Density Lipoprotein Cholesterol Levels; American Journal of Cardiology, 91(11), 1304-1310 (2003).

Capuzzi, et al.; Rosuvastatin Alone or With Extended-Release Niacin: A New Therapeutic Option for Patients with Combined Hyperlipidemia; Preventive Cardiology, 7(4), 176-181 (2004).

Carswell, et al.; Rosuvastatin; Drugs, 62(14), 2075-2085 (2002).

Chapman, et al.; Non-High-Density Lipoprotein Cholesterol as a Risk Factor: Addressing Risk Associated with Apolipoprotein B-Containing Lipoproteins; European Heart Journal Supplements, 6(Suppl. A), A43-A48 (2004).

Chapoulaud et al., "Synthesis of 4,8-Diarylcinnolines and Quinazolines with Potential Applications in Nonlinear Optics. Diazines. Part 28," Tetrahedron (2000) 56:5499.

Chaudhri et al, "Gastrointestinal Satiety Signals," *Annu Rev Physiol*, 2008, 70:239-255.

Chen et al., "Synthesis and Oral Efficacy of a 4-(Bulylethylamino)pyrrolo[2,3-d]pyrimidine: A Centrally Active Corticotropin-Releasing Factor: Receptor Antagonist," J. Med. Chem. (1997) 40:1749-1754.

Chen, et al.; Inhibitory Effect of Candesartan and Rousuvastatin on CD40 and MPs Expression in Apo-E Knockout Mice: Novel Insights into the Role of RAS and Dyslipidemia in Atherogenesis; Journal of Cardiovascular Pharmacology; 44(4), 446-452 (2004).

Cheng et al., "Potential purin antagonists. VI. Synthesis of 1-alkyl and 1-aryl-4-substituted pyrazolo[3,4-d]pyrimidines," J. Org Chem, 1956, 21:1240-1256.

Cheng, et al., "Potential purine antagonists. XII. Synthesis of 1-alkyl(aryl)-4,6-disubstituted pyrazolo[3,4-d]pyrimidines", J. Org. Chem. (1957), 23:852-61.

Cheng; Rosuvastatin in the Management of Hyperlipidemia; Clinical Therapeutics; 26(9), 1368-1387 (2004).

Cheng-Lai, Cerivastatin, Heart Disease (2):93-99 (2000).

Cheng-Lai; Rosuvastatin: A New HMG-CoA Reductase Inhibitor for the Treatment of Hypercholesterolemia; Heart Disease, 5(1), 72-78 (2003).

Chu et al., "A Role for Intestinal Endocrine Cell-Expressed GPR119 in Glycemic Control by Enhancing GLP-1 and Glucose-Dependent Insulinotropic Peptide Release," Endocrinology 149(5):2038-2047 (2008).

Clark et al., "Synthsis and analgesic activity of 1,3-dihydro-3-(substituted phenyl)midazol[4,5-b]pyridine-2-ones and 3-(substituted phenyl)-1,2,3-triazolo[4,5-b]pyridines" Journal of Medicinal Chemistry (1978) 21(9):665-978.

Clark; Treating Dyslipidemia with Statins: The Risk-Benefit Profile; American Heart Journal, 145(3), 387-396 (2003).

Cox, "Peptide YY: A neuroendocrine neighbor of note," *Peptides*, 2007, 28:345-351.

Crouse, et al.; Measuring Effects on Intima Media Thickness: An Evaluation of Rosuvastatin in Subclinical Atherosclerosis—The Rationale and Methodology of the METEOR Study; Cardiovascular Drugs and Therapy, 18(3), 231-238 (2004).

Cruze et al, "The $Y_2$ receptor mediates increases in collateral-dependent blood flow in a model of peripheral arterial insufficiency," *Peptides*, 2007, 28:269-280.

Davidson; Rosuvastatin: A Highly Efficacious Statin for the Treatment of Dyslipidemia, Expert Opinion on Investigational Drugs, 11(3), 455 (2002).

De Denus, et al.; Dyslipidemias and HMG-CoA Reductase Inhibitor Prescription in Heart Transplant Recipients; Annals of Pharmacotherapy, 28 (7/8), 1136-1141 (2004).

Deacon et al, "Degradation of Endogenous and Exogenous Gastric Inhibitory Polypeptide in Healthy and in Type 2 Diabetic Subjects as Revealed Using a New Assay for the Intact Peptide," *J Clin Endocrinol Metab*, 2000, 85:3575-3581.

Deacon, "What do we know about the secretion and degradation of incretin hormones?" *Regul Pept*, 2005, 128:117-124

Deighan, et al.; Comparative Effects of Cerivastatin and Fenofibrate on the Atherogenic Lipoprotein Phenotype in Proteinuric Renal Disease; Journal of the American Society of Nephrology, 12(2), 341-348 (2001).

(56) References Cited

OTHER PUBLICATIONS

Demuth et al., "Type 2 diabetes-therapy with dipeptidyl peptidase IV inhibitors," *Biochim. Biophys. Acta*, 2005, 1751: 33-44.
Ding et al., "A Combinatorial Scaffold Approach toward Kinase-Directed Heterocycle Libraries" J. Am. Chem. Soc. (2002) 124:1594-1596.
Drucker, "The biology of incretin hormones," *Cell Metab*, 2006, 3:153-165.
Dubau-Assibat et al., "Lawesson's Reagent: An Efficient 1,3-Dipole Trapping Agent", J. Org. Chem. 1995, 60(12), 3904-3906 CAS: 123:8809.
Dugue, et al., Detection and Incidence of Muscular Adverse Drug Reactions: A prospective Analysis from Laboratory Signals; European Journal of clinical Pharmacology, 60(4), 285-292 (2004).
During et al., "Glucagon-like peptide-1 receptor is involved in learning and neuroprotection," *Nat. Med.*, 2003, 9:1173-1179.
Eberlein et al, "A New Molecular Form of PYY: Structural Characterization of Human PYY (3-36) and PYY(1-36)," *Peptides*, 1989, 10:797-803.
Edmondson et al., "Potent and selective proline derived dipeptidyl peptidase IV inhibitors," *Bioorg. Med. Chem. Lett.*, 2004, 14:5151-5155.
Ekblad et al, "Distribution of pancreatic polypeptide and peptide YY," *Peptides*, 2002, 23:251-261.
Ekstrand et al, "Deletion of neuropeptide Y (NPY) 2 receptor in mice results in blockage of NPY-induced angiogenesis and delayed wound healing," *PNAS USA*, 2003, 100:6033-6038.
El Bahh et al, "The anti-epileptic actions of neuropeptide Y in the hippocampus are mediated by $Y_2$ and not $Y_5$ receptors," *Eur. J. Neurosci.*, 2005, 22:1417-1430.
Estel et al., "Synthesis of ortho-substiluted aminopyridines. Metalation of pivaloylamino derivatives," J. Heterocyclic Chem. (1989) 26:105-112.
Fellstrom, et al; Why Do We Need a Statin Trial in Hemodialysis Patients?; Kidney International Supplement, 84, S204-S206 (2003).
Garcia, et al.; Effects of Cerivastatin in Dyslipemia and Other Cardiovascular Risk Factors after Renal Transplantation; Transplantation Proceedings, 34(1), 401-402 (2002).
Gewald et al., "Synthese und Raektionen von 4-aminosothizolen," Leibigs Ann. Chim (1979) 10:1534-1546.
Gomez et al, "Intestinal peptide YY: ontogeny of gene expression in rat bowel and trophic actions on rat and mouse bowel," *Am. J. Physiol.*, 1995, 268:G71-G81.
Gonon et al, "Adiponectin protects against myocardial ischaemia-reperfusion injury via AMP-activated protein kinase, Akt, and nitric oxid," *Cardiovasc Res.*, 2008, 78:116-122.
Grandt et al, "Two molecular forms of Peptide YY (PYY) are abundant in human blood: characterization of a radioimmunoassay recognizing PYY 1-36 and PYY 3-36," Regul. Pept., 1994, 51:151-159.
Greig et al., "New Therapeutic Strategies and Drug Candidates for Neurodegenerative Diseases," *Ann N Y Acad Sci*, 2004, 1035:290-315.
Grise et al, "Peptide YY Inhibits Growth of Human Breast Cancer in Vitro and in Vivo," *J. Surg. Res.*, 1999, 82:151-155.
Guerre-Millo, "Adiponectin: An Update," *Diabetes & Metabolism*, 2008, 34:12-18.
Gundersen "Synthesis of purinecarbonitriles by Pd(0)-catalysed coupling of halopurines with zinc cyanide," Acia Chemica Scandinavia (1996) 50:58-63.
Hansmann et al, "Pulmonary Arterial Hypertension is Linked to Insulin Resistance and Reversed by Peroxisome Proliferator-Activated Receptor-γ Activation," *Circulation*, 2007, 115:1275-1284.
Hara et al, "Measurement of the High-Molecular Weight Form a Adiponectin in Plasma is Useful for the Prediction of Insulin Resistance and Metabolic Syndrome," *Diabetes Care*, 2006, 29:1357-1362.
Hay et al, "Inflammatory Bowel Disease: Costs-of-Illness," *J Clin Gastroenterol*, 1992, 14:309-317.
Higuchi and Stella, "Pro-drugs as Novel Delivery Systems," vol. 14 of the A.C.S. Symposium Series; and in *Bioreversible Carriers in Drug Design*, ed. Edward B. Roche, American Pharmaceutical Association and Pergamon Press, 1975 too large to provide.
Higuchi et al., "On the 'activation' of cytokins," J. of Biological Chemistry, 1975, 250(18):7343-7351.
Higuchi et al., Bioreversible Carries in Drug Design, ed. Edward B. Roche, American Pharmaceutical Association and Pergamon Press (1987).
Holdgate, et al., Molecular Mechanism for Inhibition of 3-hydroxy-3-methyglutaryl CoA (HMG-CoA) Reductase by Rosuvastatin; Biochemical Society Transactions, 31(3), 528-531 (2003).
Jones and Leonard, "The Emergence of GPR119 Agonists as Anti-Diabetic Agents," *Ann. Rep. Med. Chem.*, 2009, 44:149-170.
Jones et. al. "GPR119 agonists for the treatment of type 2 diabetes," *Expert Opin. Ther. Patents*, 2009, 19(10): 1339-1359.
Kametani et al. "Benzyene reactions of o-halobenzenes with acetonitrile or phenylacetonitrile in organic solvents," J. Org. Chem., 1972, 36(2):327-330.
Kanstrup, et al., Quality of Lipid-Lowering Therapy in Patients with Ischaemic Heart disease: A Register-Based Study in 3477 Patients; Journal of Internal Medicine, 255(3), 367-372 (2004).
Kawakita et al., CAPLUS Abstract 115:136096 (1991).
Keane et al.; The CHORUS (Cerivastatin in Heart Outcomes in Renal Disease: Understanding Survival) Protocol: A Double-Blind, Placebo-Controlled Trial in Patients with ESRD; American Journal of Kidney Diseases, 37(1, Suppl. 2), S48-S53 (2001).
Keighley and Stockbrugger, "Inflammatory bowel disease," *Ailment Pharmacol Ther*, 2003, 18:66-70.
Keire et al., "Primary structures of PYY, [Pro$^{34}$]PYY, and PYY-(3-36) confer different conformations and receptor selectivity," *Am. J. Physiol. Gastrointest. Liver Physiol.*, 2000, 279:G126-G131.
Kolosov et al., "The interaction between 4-phenyl-5-acetyl-6-methyl-3,4-dihydropyrimidin-2-one and 4-brombenzaldehide", Institute of Organic Chemistry, Kharkiv, National V.N.Karazin University, Ukraine, 61077, Kharkiv-077, Svobody sq., 4; (2003) Abstract only at http://conf.iflab.kiev.ua/eng/reports/show/?id=926 2 pages.
Lai et al., "A one-pot method for the efficient conversion of aryl-and acyl-substituted methyl alcohols into chlorides," Synthetic Communications (2003) 33(10):1727-1732.
Lechleitner; Dyslipidaemia and Renal Disease—Pathophysiology and Lipid Lowering Therapy in Patients with Impaired Renal Function; Journal of Clinical and Basic Cardiology, 3(1), 3-6 (2000).
Lee et al, "Neuropeptide Y induces ischemia angiogenesis and restores function of ischemic skeletal muscles," *J. Clin. Invest.*, 2003, 111:1853-1862.
Lee et al., "Impaired angiogenesis in neuropeptide Y (NPY)-Y2 receptor knockout mice," *Peptides*, 2003, 24:99-106.
Liu et al, "Human Pancreatic Cancer Growth is inhibited by Peptide YY and BIM-43004-1," *J. Surg. Res.*, 1995, 58:707-712.
Liu et al, "Pancreatic Peptide YY mRNA Levels Increase during Adaptation after Small Intestinal Resection," *J. Surg. Res.*, 1995, 58:6-11.
Liu et al, "Peptide YY: A Potential Proabsorptive Hormone for the Treatment of Malabsorptive Disorders," *Am Surg.*, 1996, 62:232-236.
Liu et al, "Y2 receptors decrease human pancreatic cancer growth and intracellular cyclic adenosine monophosphate levels," *Surgery*, 1995, 118:229-236.
Lundberg et al., "Localization of peptide YY (PYY) in gastrointestinal endocrine cells and effects on intestinal blood flow and motility," PNAS USA, 1982, 79:4471-4475.
Maeda et al., "Diet-induced insulin resistance in mice lacking adiponectin/ACRP30," Nat. Med., 2002, 8:731-737.
Markwalder, et al., "Synthesis and biological evaluation of 1-aryl-4,5-dihydro-1H-pyrazolo[3,4-d]pyrimidin-4-one inhibitors of cyclin-dependent kinases", J. Med. Chem., (2004), 47:5894-5911.
Marso et al., "Low Adiponectin Levels are Associated with Atherogenic Dyslipidemia and Lipid-Rich Plaque in Nondiabetic Coronary Arteries," *Diabetes Care*, 2008, 31:989-944.
Martin, et al.; A Double-Blind, Randomized, Incomplete Crossover Trial to Assess the Dose Proportionality of Rosuvastatin in Healthy Volunteers; Clinical Therapeutics, 25(8), 2215-2224 (2003).

(56) References Cited

OTHER PUBLICATIONS

Martin, et al.; Absolute Oral Bioavailability of Rosuvastatin in Healthy White Adult Male Volunteers; Clinical Therapeutics, 25(10), 2553-2563 (2003).
Martin, et al.; An Open-Label, Randomized, Three-Way Crossover Trial of the Effects of Coadministration of Rosuvastatin and Fenofibrate on the Pharmacokinetic Properties of Rosuvastatin and Fenofibric Acid in Healthy Male Volunteers; Clinical Therapeutics, 25(2), 459-471 (2003).
Martin, et al.; Metabolism, Excretion, and Pharmacokinetics of Rosuvastatin in Healthy Adult Male Volunteers; Clinical Therapeutics, 25(11), 2822-2835 (2003).
Matsuda et al., "Role of Adiponectin in Preventing Vascular Stenosis," *J Biol Chem*, 2002, 277:37487-37491.
McFadden et al., "Peptide YY inhibits the growth of Barrett's esophageal adenocarcinoma in vitro," *Am. J. Surg.*, 2004, 188:516-519.
McIntosh et al., "Dipeptidyl peptidase IV inhibitors: How do they work as new antidiabetic agents," *Regul Pept*, 2005, 128:159-165.
Mentlein, "Therapeutic assessment of glucagon-like peptide-1 agonists compared with dipeptidyl peptidase IV inhibitors as potential antidiabetic drugs," *Expert Opin Investig Drugs*, 2005, 14:57-64.
Mitsunobu, "The use of diethyl azodicarboxylate and triphenylphosphine in synthesis and transformation of natural products", Synthesis, (1981), 1-28.
Mosti et al. Arzneimittel-Forschung 2000, 50(11), 963-972.
Mosti et al., Farmaco 1990, 45(4), 415-29.
Muck, et al.; Lack of Pharmacolinetic Drud-Drug Interaction Between Orlistat and Cerivastatin; Clinical Drug Investigation, 19(1), 71-73 (2000).
Nakamura, et al.; Effect of Cerivastatin on Endothelial Dysfunction and Aortic CD36 Expression in Diabetic Hyperlipidemic Rats; Hypertension Research; 27(8) 589-598; (2004).
Nauck et al., "Gastric Inhibitory Polypeptide and Glucagon-Like Peptide-1 in the Pathogenesis of Type 2 Diabetes," *Diabetes*, 2004, 53(Suppl 3):S190-196.
Nauck et al., "Incretins and Their Analogues as New Antidiabetic Drugs," *Drug News Perspect*, 2003, 16:413-422.
Nezasa, et al.; Uptake of Rosuvastatin by Isolated Rat Hepatocytes: Comparison with Pravastatin; Xenobiotica, 33(4), 379-388 (2003).
Niementowski, J. Praktika Chem., [2] "Synthesen von Chinazolinverbindugen" (1895), 51, 564-572.
Nightingale et al., "Gastrointestinal hormones in short bowel syndrome. Peptide YY may be the "colonic brake" to gastric emptying," *Gut*, 1996, 39:267-272.
Nishimura et al., "Adiponectin Prevents Cerebral Ischemic Injury Through Endothelial Nitric Oxide Synthase-Dependent Mechanisms," *Circulation*, 2008, 117:216-223.
Novinson et al., "Novel heterocyclic nitrofurfural hydrazones. In vivo antitrypanosomal activity," J. Med. Chem. (1976) 19(4):512-516.
Okada et al., "Peripherally not centrally administered peptide YY(PYY) Decreases High Fat Diet Intake," *Endocrinology Society*, 1993, 520 B:180.
Oku et al., "Adiponectin deficiency suppresses ABCA1 expression and ApoA-I synthesis in the liver," *FEBS Letters*, 2007, 581:5029-5033.
Olsson, et al.; Rosuvastatin: A Highly Effective New HMG-CoA Reductase Inhibitor; Cardiovascular Drug Reviews, 20(4), 303-328 (2002).
Olsson, Statins: how far have we come? A review of rosuvastatin, International Journal of Clinical Practice, Supplement, 137, 15-25 (2003).
Ortiz et al., "A Novel Long-Acting Selective Neuropeptide Y2 Receptor Polyethylene Glycol-Conjugated Peptide Agonist Reduces Food Intake and Body Weight and Improves Glucose Metabolism in Rodents," *JPET*, 2007, 323:692-700.
Ouchi and Walsh, "Adiponectin as an anti-inflammatory factor," *Clin Chim Acta*, 2007, 380:24-30.
Ouchi et al, "Novel Modulator for Endothelial Adhesion Molecules: Adipocyte-Derived Plasma Protein Adiponectin," *Circulation*, 1999, 100:2473-2476.
Ozeki el al., "[Studies on antiallergy agent. I. Synthesis of 1,4-dihydro-4-oxo-3quinolinecarboxylic acids]" Yakugaku Zasshi (1987) 107(2):123-134.
Parker and Balasubramaniam, "Neuropeptide YY2 receptor in health and disease," *Br. J. Pharmacol.*, 2008, 153:420-431.
Pearson, "Inflammatory bowel disease," *Nursing Times*, 2004, 100:86-90.
Peat, et al., "Novel pyrazolopyrimidine derivatives as GSK-3 inhibitors", Bioorganic & Medicinal Chemistry Letters (2004), 14:2121-2125.
Pei, et al.; Discovery and Structure-Adctivity Relationships of Piperidinone- and Pipe Constrained Phenethylamines as Novel, Potent, and Selective Dipeptidyl Peptidase IV Inhibitors; Journal of Medical Chemistry; 50; 1983-1987 (2007).
Pelat, et al.; Rosuvastatin Decreases Caveolin-1 and Improves Nitric Oxide-Dependent Heart Rate and Blood Pressure Variability in Apolipoprotein E-/- Mice in Vivo; Circulation, 107(19), 2480-2486 (2003).
Peters et al., "Aminomethylpyrimidines as novel DPP-IV inhibitors: A $10^5$-fold activity increase by optimization of aromatic substituents," *Bioorg. Med. Chem. Lett.*, 2004, 14:1491-1493.
Pittner et al, "Effects of PYY[3-36] in rodent models of diabetes and obesity," Int. J. Obes. Relat. Metab. Disord., 2004, 28:963-971.
Raisz, "Pathogenesis of osteoporosis: concepts, conflicts, and prospects," *J Clin Invest*, 2005, 115:3318-3325.
Remington, The Science and Practice of Pharmacy, 20th Edition, 2000, Lippincott Williams & Wilkins too large to provide.
Renshaw and Batterham, "Peptide YY: A Potential Therapy for Obesity," Current Drug Targets, 2005, 6:171-179.
Rimoin et al., Emery and Rimoin's Principles and Practice of Medical Genetics, 3rd Ed. 1:1401-1402 (1996).
Roberts; Two More Drugs for Dyslipidemia; American Journal of Cardiology; 93(6), 8martin09-811 (2004).
Rondinone, Expert Opin. Ther. Targets, 2005, 9(2):415-418.
Rosenson, Rosuvastatin: a new inhibitor of HMG-CoA reductase for the treatment of dyslipidemia, Expert Review of Cardiovascular Therapy, 1(4):495-505 (2003).
Ruggeri, "Platelets in atherothrombosis," *Nat Med.*, 2002, 8:1227-1234.
Sage, Carleton R., Document regarding search, (Feb. 2003) (1 p.).
Sarosotnikov et al., Russian Chemical Bulletin 2003, 52(8), 1782-1809.
Schafer et al., "Zur synthese von 4-aminochinolinen durch intramolekulare Friedel-Cfafts-Reaktion," Montash fur Chemie (1978) 109:527-535.
Schuster; Rosuvastatin—A Highly Effective New 3-hydroxy-3-methylglutaryl Coenzyme A Reductase Inhibitor: Review of clinical Trial Data at 10-40 mg doses in Dyslipidemic Patients; Cardiology, 99(3), 126-139 (2003).
Schwartz and Holst, "An Enteroendocrine Full Package Solution," *Cell Metabolism*, 2010, 11:445-447.
Scott, et al.; Rosuvastatin: A Review of Its Use in the Management of Dyslipidemia; American Journal of Cardiovascular Drugs, 4(2), 117-138 (2004).
Semple et al., "Discovery of a second generation of the orphan G-protein coupled receptor GPR119 with an improved profile," Bioogancic & Medicinal Chemistry Letters, 2012, 22:1750-1755.
Shah, "GPR119 agonists: A promising new approach for the treatment of type 2 diabetes and related metabolic disorders," *Current Opin Drug Discov Develop.*, 2009, 12:519-532.
Shepherd, et al., Safety of rosuvastatin, Dept. of Vascular Biochemistry, University of Glasgow, Glasgow, UK, American Journal of Cardiology, 94(7):882-888 (2004), ISSN: 0002-9419.
Shibata et al., "Adiponectin protects against myocardial ischemia-reperfusion injury through AMPK- and COX-2-dependent mechanisms," *Nat Med*, 2005, 11:1096-1103.
Shibata et al., "Adiponectin Stimulates Angiogenesis in Response to Tissue Ischemia through Stimulation of AMP-activated Protein Kinase Signaling," *J. Biol. Chem.*, 2004, 279:28670-28674.

(56) References Cited

OTHER PUBLICATIONS

Shibata et al., "Adiponection protects against the development of systolic dysfunction following myocardial infarction," *J. Mol. Cell Cardiol.*, 2007, 42:1065-1074.
Shore et al., "Adiponectin attenuates allergen-induced airway inflammation and hyperresponsiveness in mice," *J. Allergy Clin. Immunol*, 2006, 118:389-395.
Spruce, Lyle W., Document regarding search, (2004) (1 p.).
Stein; Management of Dyslipidemia in the High-Risk Patient; American Heart Journal, 144(6, Suppl.), S43-S50 (2002).
Summer et al., "Alveolar macrophage activation and an emphysema-like phenotype in adiponectin-deficient mice," *Am J. Physiol. Lung Cell Mol. Physiol*, 2008, 294:L1035-L1042.
Takei et al., "A new synthetic method for some pyrazolo[4m3-d]pyrimidines" Bull Chem Soc. Japan (19:79) 52:208-211.
Tao et al., "Adiponectin Cardioprotection After Myocardial Ischemia/Reperfusion Involves the Reduction of Oxidative/Nitrative Stress," *Circulation*, 2007, 115:1408-1416.
Tatemoto and Mutt, "Isolation of two novel candidate hormones using a chemical method for finding naturally occurring polypeptides," *Nature*, 1980, 285:417-418.
Tilg and Moschen, "Adipocytokines: mediators linking adipose tissue, inflammation and immunity," *Nat. Rev. Immunol.*, 2006, 2006, 6:772-783.
Trejo et al., "Design and Synthesis of 4-Azaindoles as Inhibitors of p38 MAP Kinase," J. Med. Chem. (2003) 46:4702-4713.
Tseng and Liu, "Peptide YY and cancer: current findings and potential clinical applications," *Peptides*, 2002, 23:389-395.
Tsukiyama et al., "Gastric Inhibitory Polypeptide as an Endogenous Factor Promoting New Bone Formation after Food Ingestion," *Mol Endocrinol.*, 2006, 20:1644-1651.
Tuomilehto, et al.; A Review of the Efficacy of Rosuvastatin in Patients with Type 2 Diabetes; International Journal of Clinical Practice, Supplement, 143, 30-40 (2004).
Ueno et al., "The role of PYY in feeding regulation," *Regul Pept.*, 2008, 145:12-16.
Ulrich, "Crystallization," *Kirk-Othmer Enclyclopedia of the Chemical Technology*, 2002, Chapter 4, 8:95-147.
Ural, et al.; Treatment with Cervistatin in Primary Mixed Hyperlipidemia Induces Changes in Platelet Aggregation and Coagulation System Components; International Journal of Hematology, 76(3) 279-283 (2002).
Villhauer et al., "1-[[(3-Hydroxy-1-adamantyl)amino]acetyl]-2-cyano-(S)-pyrrolidine: A Potent, Selective, and Orally Bioavailable Dipeptidyl Peptidase IV Inhibitor with Antihyperglycemic Properties," *J. Med. Chem.*, 2003, 46:2774-2789.
Villhauer et al., "1-[2-[(5-Cyanopyridin-2-yl)amino]-ethylamino]acetyl-2-(S)-pyrrolidine-carbonitrile: A Potent, Selective, and Orally Bioavailable Dipeptidyl Peptidase IV Inhibitor with Antihyperglycemic Properties," *J. Med. Chem.*, 2002, 45:2362-2365.
Vinogradov et al., Mendeleev Communications 2002, (5), 198-200.
Vona-Davis and McFadden, "PYY and the pancreas. Inhibition of tumor growth and inflammation," *Peptides*, 2007, 28:334-338.
Wang, et al.; Amino-Substituted Heterocycles as Isosteres of Trans-Cinnamides: Design and Synthesis of Heterocyclic Biaryl Sulfides as Potent Antagonists of LFA-1/ICAM-1 Binding; Bioorganic & Medicinal Chemistry Letters, 15(1), 195-201 (2005).
Weber et al., "Microbic Superinfection in Relapse of Inflammatory Bowel Disease," *J Clin Gastroenterol.*, 1992, 14(4):302-308.
West, Solid State Chemistry and its application, New York, 1988, pp. 358 & 365.
Winkelmann, et al.; Haplotypes of the Cholesteryl Ester Transfer Protein Gene Predict Lipid-Modifying Response to Statin Therapy; Germany Pharmacogenomics Journal, 3(5), 284-296 (2003).
Woldbye et al., "Differential suppression of seizures via Y2 and Y5 neuropeptide Y receptors," *Neurobiology of Disease*, 2005, 20:760-772.
World Health Organization Technical Report Series 921, "Prevention and Management of Osteopoosis," 2003, 206 pages.
Wortley et al., "Peptide YY Regulates Bone Turnover in Rodents," *Gastroenterol.*, 2007, 133:1534-1543.
Wuts, Protective Groups in Organic Synthesis. 3rd edition. John Wiley & Sons, New York (1999).
Xia et al., "Discovery of a nortropanol derivative as a potent and orally active GPR119 agonist for type 2 diabetes," *Bioorganic Med. Chem. Lett.*, 2011, 21:3290-3296.
Xie et al., "Glucose-dependent insulinotropic polypeptide receptor knockout mice have altered bone turnover," *Bone*, 2005 37:759-769.
Yamamoto et al., "Correlation of the adipocyte-derived protein adiponectin with insulin resistance index and serum high-density lipoprotein-cholesterol, independent of body mass index, in the Japanese population," *Clinical Science*, 2002, 103:137-142.
Yokota et al., "Adiponectin, a new member of the family of soluble defense collagens, negatively regulates the growth of myelomonocytic progenitors and the functions of macrophages," Blood, 2000, 96:1723-1732.
Yuan et al., "3-Aryl pyrazolo[4,3-d]pyrimidine derivatives nonpeptide CRF-1 antagonists," Bioorganic Medicinal Chemistry Lett. (2002) 2133-2136.
Zander et al., "Effect of 6-week course of glucagon-like peptide 1 on glycaemic control, insulin sensitivity, and β-cell function in type 2 diabetes: a parallel-group study," Lancet, 2002, 359:824-830.
Zhong et al., "Effects of glucose-dependent insulinotropic peptide on osteoclast function," Am J Physiol Endocrinol Metab, 2007, 292:E543-E548.

\* cited by examiner

SEQUENCE LISTING

```
<160> NUMBER OF SEQ ID NOS: 6

<210> SEQ ID NO 1
<211> LENGTH: 1191
<212> TYPE: DNA
```

<213> ORGANISM: Homo Sapien

<400> SEQUENCE: 1

| | | | | | |
|---|---|---|---|---|---|
| atgtacccat | acgacgtccc | agactacgct | ggaagcttgg | aatcatcttt | ctcatttgga | 60
| gtgatccttg | ctgtcctggc | ctccctcatc | attgctacta | acacactagt | ggctgtggct | 120
| gtgctgctgt | tgatccacaa | gaatgatggt | gtcagtctct | gcttcacctt | gaatctggct | 180
| gtggctgaca | ccttgattgg | tgtggccatc | tctggcctac | tcacagacca | gctctccagc | 240
| ccttctcggc | ccacacagaa | gaccctgtgc | agcctgcgga | tggcatttgt | cacttcctcc | 300
| gcagctgcct | ctgtcctcac | ggtcatgctg | atcacctttg | acaggtacct | tgccatcaag | 360
| cagcccttcc | gctacttgaa | gatcatgagt | gggttcgtgg | ccggggcctg | cattgccggg | 420
| ctgtggttag | tgtcttacct | cattggcttc | ctcccactcg | gaatccccat | gttccagcag | 480
| actgcctaca | aagggcagtg | cagcttcttt | gctgtatttc | accctcactt | cgtgctgacc | 540
| ctctcctgcg | ttggcttctt | cccagccatg | ctcctctttg | tcttcttcta | ctgcgacatg | 600
| ctcaagattg | cctccatgca | cagccagcag | attcgaaaga | tggaacatgc | aggagccatg | 660
| gctggaggtt | atcgatcccc | acggactccc | agcgacttca | agctctccg | tactgtgtct | 720
| gttctcattg | ggagctttgc | tctatcctgg | accccttcc | ttatcactgg | cattgtgcag | 780
| gtggcctgcc | aggagtgtca | cctctaccta | gtgctggaac | ggtacctgtg | gctgctcggc | 840
| gtgggcaact | ccctgctcaa | cccactcatc | tatgcctatt | ggcagaagga | ggtgcgactg | 900
| cagctctacc | acatggccct | aggagtgaag | aaggtgctca | cctcattcct | cctctttctc | 960
| tcggccagga | attgtggccc | agagaggccc | agggaaagtt | cctgtcacat | cgtcactatc | 1020
| tccagctcag | agtttgatgg | cgaattcgga | tccaagggca | attctgcaga | tatccagcac | 1080
| agtggcggcc | gctcgagtct | agagggcccg | cggttcgaag | gtaagcctat | ccctaaccct | 1140
| ctcctcggtc | tcgattctac | gcgtaccggt | catcatcacc | atcaccattg | a | 1191

<210> SEQ ID NO 2
<211> LENGTH: 396
<212> TYPE: PRT
<213> ORGANISM: Homo Sapien

<400> SEQUENCE: 2

Met Tyr Pro Tyr Asp Val Pro Asp Tyr Ala Gly Ser Leu Glu Ser Ser
1               5                   10                  15

Phe Ser Phe Gly Val Ile Leu Ala Val Leu Ala Ser Leu Ile Ile Ala
            20                  25                  30

Thr Asn Thr Leu Val Ala Val Ala Val Leu Leu Leu Ile His Lys Asn
        35                  40                  45

Asp Gly Val Ser Leu Cys Phe Thr Leu Asn Leu Ala Val Ala Asp Thr
    50                  55                  60

Leu Ile Gly Val Ala Ile Ser Gly Leu Leu Thr Asp Gln Leu Ser Ser
65                  70                  75                  80

Pro Ser Arg Pro Thr Gln Lys Thr Leu Cys Ser Leu Arg Met Ala Phe
                85                  90                  95

Val Thr Ser Ser Ala Ala Ala Ser Val Leu Thr Val Met Leu Ile Thr
            100                 105                 110

Phe Asp Arg Tyr Leu Ala Ile Lys Gln Pro Phe Arg Tyr Leu Lys Ile
        115                 120                 125

Met Ser Gly Phe Val Ala Gly Ala Cys Ile Ala Gly Leu Trp Leu Val
    130                 135                 140

Ser Tyr Leu Ile Gly Phe Leu Pro Leu Gly Ile Pro Met Phe Gln Gln
145                 150                 155                 160

Thr Ala Tyr Lys Gly Gln Cys Ser Phe Ala Val Phe His Pro His
            165                 170                 175

Phe Val Leu Thr Leu Ser Cys Val Gly Phe Pro Ala Met Leu Leu
                180                 185                 190

Phe Val Phe Tyr Cys Asp Met Leu Lys Ile Ala Ser Met His Ser
            195                 200                 205

Gln Gln Ile Arg Lys Met Glu His Ala Gly Ala Met Ala Gly Tyr
210                 215                 220

Arg Ser Pro Arg Thr Pro Ser Asp Phe Lys Ala Leu Arg Thr Val Ser
225                 230                 235                 240

Val Leu Ile Gly Ser Phe Ala Leu Ser Trp Thr Pro Phe Leu Ile Thr
                245                 250                 255

Gly Ile Val Gln Val Ala Cys Gln Glu Cys His Leu Tyr Leu Val Leu
                260                 265                 270

Glu Arg Tyr Leu Trp Leu Leu Gly Val Gly Asn Ser Leu Leu Asn Pro
            275                 280                 285

Leu Ile Tyr Ala Tyr Trp Gln Lys Glu Val Arg Leu Gln Leu Tyr His
            290                 295                 300

Met Ala Leu Gly Val Lys Lys Val Leu Thr Ser Phe Leu Leu Phe Leu
305                 310                 315                 320

Ser Ala Arg Asn Cys Gly Pro Glu Arg Pro Arg Glu Ser Ser Cys His
                325                 330                 335

Ile Val Thr Ile Ser Ser Ser Glu Phe Asp Gly Glu Phe Gly Ser Lys
                340                 345                 350

Gly Asn Ser Ala Asp Ile Gln His Ser Gly Gly Arg Ser Ser Leu Glu
            355                 360                 365

Gly Pro Arg Phe Glu Gly Lys Pro Ile Pro Asn Pro Leu Leu Gly Leu
            370                 375                 380

Asp Ser Thr Arg Thr Gly His His His His His
385                 390                 395

<210> SEQ ID NO 3
<211> LENGTH: 24
<212> TYPE: DNA
<213> ORGANISM: Artificial
<220> FEATURE:
<223> OTHER INFORMATION: Homo Sapien Primer

<400> SEQUENCE: 3
cattgccggg ctgtggttag tgtc                                          24

<210> SEQ ID NO 4
<211> LENGTH: 24
<212> TYPE: DNA
<213> ORGANISM: Artificial
<220> FEATURE:
<223> OTHER INFORMATION: Homo Sapien Primer

<400> SEQUENCE: 4
ggcatagatg agtgggttga gcag                                          24

<210> SEQ ID NO 5
<211> LENGTH: 22
<212> TYPE: DNA
<213> ORGANISM: Artificial
<220> FEATURE:
<223> OTHER INFORMATION: Rat Primer

```
<400> SEQUENCE: 5
catgggccct gcaccttctt tg                22

<210> SEQ ID NO 6
<211> LENGTH: 24
<212> TYPE: DNA
<213> ORGANISM: Artificial
<220> FEATURE:
<223> OTHER INFORMATION: Rat Primer

<400> SEQUENCE: 6
gctccggatg gctgatgata gtga              24
```

1,2,3-TRISUBSTITUTED ARYL AND HETEROARYL DERIVATIVES AS MODULATORS OF METABOLISM AND THE PROPHYLAXIS AND TREATMENT OF DISORDERS RELATED THERETO SUCH AS DIABETES AND HYPERGLYCEMIA

RELATED APPLICATIONS

This application is a continuation of U.S. Application Ser. No. 10/541,657, now U.S. Pat. No. 8,293,751, which is the national phase under 35 U.S.C. §371 of PCT/US2004/001267, which was filed on Jan. 14, 2004, and which claims the benefit of U.S. Provisional Applications 60/440,394, filed Jan. 14, 2003, 60/449,829, filed Feb. 24, 2003, 60/453,390, filed Mar. 6, 2003 and 60/470,875 filed May 14, 2003. The entire content of U.S. Application Ser. No. 10/541,657 is hereby incorporated by reference.

FIELD OF THE INVENTION

The present invention relates to certain 1,2,3-trisubstituted aryl and heteroaryl derivatives that are modulators of glucose metabolism. Accordingly, compounds of the present invention are useful in the prophylaxis or treatment of metabolic disorders and complications thereof, such as, diabetes and obesity.

BACKGROUND OF THE INVENTION

Diabetes mellitus is a serious disease afflicting over 100 million people worldwide. In the United States, there are more than 12 million diabetics, with 600,000 new cases diagnosed each year.

Diabetes mellitus is a diagnostic term for a group of disorders characterized by abnormal glucose homeostasis resulting in elevated blood sugar. There are many types of diabetes, but the two most common are Type I (also referred to as insulin-dependent diabetes mellitus or IDDM) and Type II (also referred to as non-insulin-dependent diabetes mellitus or NIDDM).

The etiology of the different types of diabetes is not the same; however, everyone with diabetes has two things in common: overproduction of glucose by the liver and little or no ability to move glucose out of the blood into the cells where it becomes the body's primary fuel.

People who do not have diabetes rely on insulin, a hormone made in the pancreas, to move glucose from the blood into the cells of the body. However, people who have diabetes either don't produce insulin or can't efficiently use the insulin they produce; therefore, they can't move glucose into their cells. Glucose accumulates in the blood creating a condition called hyperglycemia, and over time, can cause serious health problems.

Diabetes is a syndrome with interrelated metabolic, vascular, and neuropathic components. The metabolic syndrome, generally characterized by hyperglycemia, comprises alterations in carbohydrate, fat and protein metabolism caused by absent or markedly reduced insulin secretion and/or ineffective insulin action. The vascular syndrome consists of abnormalities in the blood vessels leading to cardiovascular, retinal and renal complications. Abnormalities in the peripheral and autonomic nervous systems are also part of the diabetic syndrome.

People with IDDM, which accounts for about 5% to 10% of those who have diabetes, don't produce insulin and therefore must inject insulin to keep their blood glucose levels normal. IDDM is characterized by low or undetectable levels of endogenous insulin production caused by destruction of the insulin-producing β cells of the pancreas, the characteristic that most readily distinguishes IDDM from NIDDM. IDDM, once termed juvenile-onset diabetes, strikes young and older adults alike.

Approximately 90 to 95% of people with diabetes have Type II (or NIDDM). NIDDM subjects produce insulin, but the cells in their bodies are insulin resistant: the cells don't respond properly to the hormone, so glucose accumulates in their blood. NIDDM is characterized by a relative disparity between endogenous insulin production and insulin requirements, leading to elevated blood glucose levels. In contrast to IDDM, there is always some endogenous insulin production in NIDDM; many NIDDM patients have normal or even elevated blood insulin levels, while other NIDDM patients have inadequate insulin production (Rotwein, R. et al. *N. Engl. J. Med.* 308, 65-71 (1983)). Most people diagnosed with NIDDM are age 30 or older, and half of all new cases are age 55 and older. Compared with whites and Asians, NIDDM is more common among Native Americans, African-Americans, Latinos, and Hispanics. In addition, the onset can be insidious or even clinically inapparent, making diagnosis difficult.

The primary pathogenic lesion on NIDDM has remained elusive. Many have suggested that primary insulin resistance of the peripheral tissues is the initial event. Genetic epidemiological studies have supported this view. Similarly, insulin secretion abnormalities have been argued as the primary defect in NIDDM. It is likely that both phenomena are important contributors to the disease process (Rimoin, D. L., et. al. Emery and Rimoin's Principles and Practice of Medical Genetics $3^{rd}$ Ed. 1:1401-1402 (1996)).

Many people with NIDDM have sedentery lifestyles and are obese; they weigh approximately 20% more than the recommended weight for their height and build. Furthermore, obesity is characterized by hyperinsulinemia and insulin resistance, a feature shared with NIDDM, hypertension and atherosclerosis.

Obesity and diabetes are among the most common human health problems in industrialized societies. In industrialized countries a third of the population is at least 20% overweight. In the United States, the percentage of obese people has increased from 25% at the end of the 1970s, to 33% at the beginning the 1990s. Obesity is one of the most important risk factors for NIDDM. Definitions of obesity differ, but in general, a subject weighing at least 20% more than the recommended weight for his/her height and build is considered obese. The risk of developing NIDDM is tripled in subjects 30% overweight, and three-quarters with NIDDM are overweight.

Obesity, which is the result of an imbalance between caloric intake and energy expenditure, is highly correlated with insulin resistance and diabetes in experimental animals and human. However, the molecular mechanisms that are involved in obesity-diabetes syndromes are not clear. During early development of obesity, increase insulin secretion balances insulin resistance and protects patients from hyperglycemia (Le Stunff, et al. *Diabetes* 43, 696-702 (1989)). However, after several decades, β cell function deteriorates and non-insulin-dependent diabetes develops in about 20% of the obese population (Pederson, P. *Diab. Metab. Rev.* 5, 505-509 (1989)) and (Brancati, F. L., et al., *Arch. Intern. Med.* 159, 957-963 (1999)). Given its high prevalence in modern societies, obesity has thus become the leading risk factor for NIDDM (Hill, J. O., et al., *Science* 280, 1371-1374 (1998)).

However, the factors which predispose a fraction of patients to alteration of insulin secretion in response to fat accumulation remain unknown.

Whether someone is classified as overweight or obese is generally determined on the basis of their body mass index (BMI) which is calculated by dividing body weight (kg) by height squared ($m^2$). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$ (see TABLE below). There are problems with this definition in that it does not take into account the proportion of body mass that is muscle in relation to fat (adipose tissue). To account for this, obesity can also be defined on the basis of body fat content: greater than 25% and 30% in males and females, respectively.

Classification of Weight by Body Mass Index (BMI)

| BMI | CLASSIFICATION |
| --- | --- |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that is independent of other risk factors. The most common diseases with obesity are cardiovascular disease (particularly hypertension), diabetes (obesity aggravates the development of diabetes), gall bladder disease (particularly cancer) and diseases of reproduction. Research has shown that even a modest reduction in body weight can correspond to a significant reduction in the risk of developing coronary heart disease.

Compounds marketed as anti-obesity agents include Orlistat (XENICAL™) and Sibutramine. Orlistat (a lipase inhibitor) inhibits fat absorption directly and tends to produce a high incidence of unpleasant (though relatively harmless) side-effects such as diarrhea. Sibutramine (a mixed 5-HT/noradrenaline reuptake inhibitor) can increase blood pressure and heart rate in some patients. The serotonin releaser/reuptake inhibitors fenfluramine (Pondimin™) and dexfenfluramine (Redux™) have been reported to decrease food intake and body weight over a prolonged period (greater than 6 months). However, both products were withdrawn after reports of preliminary evidence of heart valve abnormalities associated with their use. Accordingly, there is a need for the development of a safer anti-obesity agent.

Obesity considerably increases the risk of developing cardiovascular diseases as well. Coronary insufficiency, atheromatous disease, and cardiac insufficiency are at the forefront of the cardiovascular complication induced by obesity. It is estimated that if the entire population had an ideal weight, the risk of coronary insufficiency would decrease by 25% and the risk of cardiac insufficiency and of cerebral vascular accidents by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for NIDDM and coronary heart disease and the potential value of an integrated approach to the prevention of these conditions based on the prevention of these conditions based on the prevention of obesity (Perry, I. J., et al., *BMJ* 310, 560-564 (1995)).

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

SUMMARY OF THE INVENTION

The present invention is drawn to compounds, which bind to and modulate the activity of a GPCR referred to herein as RUP3, and uses thereof. The term RUP3, as used herein, includes the human sequences found in GeneBank accession number XM_066873, naturally-occurring allelic variants, mammalian orthologs, and recombinant mutants thereof. A preferred human RUP3 for use in screening and testing of the compounds of the invention is provided in the nucleotide sequence of Seq. ID.No:1 and the corresponding amino acid sequence in Seq. ID.No:2.

One aspect of the present invention encompasses 1,2,3-trisubstituted aryl and heteroaryl derivatives as shown in Formula (Ia):

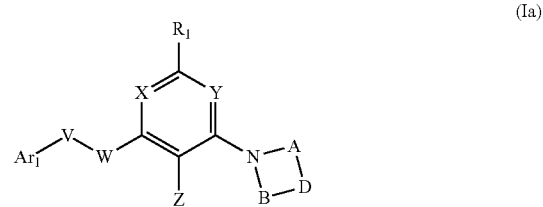

or a pharmaceutically acceptable salt, hydrate or solvate thereof, wherein:

A and B are independently $C_{1-3}$ alkylene optionally substituted with 1 to 4 methyl groups;

D is O, S, S(O), S(O)$_2$, $CR_2R_3$ or N—$R_2$;

V is selected from the group consisting of $C_{1-3}$ alkylene, ethynylene and $C_{1-2}$ heteroalkylene wherein each are optionally substituted with 1 to 4 substituents selected from the group consisting of $C_{1-3}$ alkyl, $C_{1-4}$ alkoxy, carboxy, cyano, $C_{1-3}$ haloalkyl and halogen; or V is absent;

W is $NR_4$, O, S, S(O) or S(O)$_2$; or W is absent;

X is N or $CR_5$;

Y is N or $CR_6$;

Z is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, $C_{1-2}$ alkylamino, $C_{2-4}$ dialkylamino, carbo-$C_{1-6}$-alkoxy, carboxamide, carboxy, cyano, $C_{4-8}$ diacylamino, $C_{2-6}$ dialkylcarboxamide, $C_{1-4}$ dialkylthiocarboxamide, $C_{2-6}$ dialkylsulfonamide, $C_{1-4}$ dialkylsulfonylamino, formyl, $C_{1-4}$ haloalkoxy, $C_{1-4}$ haloalkyl, $C_{1-4}$ haloalkylcarboxamide, $C_{1-4}$ haloalkylsulfinyl, $C_{1-4}$ haloalkylsulfonyl, $C_{1-4}$ haloalkylthio, halogen, aryl, heterocyclic, heteroaryl, hydroxyl, hydroxylamino, nitro and tetrazolyl, wherein $C_{1-8}$ alkyl and $C_{1-5}$ acyl are each optionally substituted with 1, 2, 3 or 4 groups selected from the group consisting of $C_{1-5}$ acyl, $C_{1-5}$ acyloxy, $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-2}$ alkylamino, $C_{2-4}$ dialkylamino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro; or Z is a group of Formula (A):

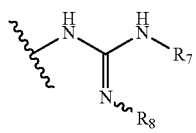

(A)

wherein:

$R_7$ is H, $C_{1-8}$ alkyl or $C_{3-6}$ cycloalkyl; and $R_8$ is H, nitro or nitrile;

$Ar_1$ is aryl or heteroaryl wherein each are optionally substituted with $R_9$-$R_{13}$;

$R_1$ is selected from the group consisting of H, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, $C_{1-4}$ alkylamino, $C_{2-8}$ dialkylamino, carboxamide, cyano, $C_{3-6}$ cycloalkyl, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio and hydroxyl;

$R_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, heteroaryl, hydroxyl and phenyl; and wherein $C_{1-8}$ alkyl, heteroaryl and phenyl are each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{3-6}$-cycloalkyl-$C_{1-3}$-alkylene, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$-$Ar_3$ wherein $Ar_2$ and $Ar_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

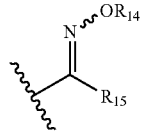

(B)

wherein:

$R_{14}$ is $C_{1-8}$ alkyl or $C_{3-6}$ cycloalkyl; and $R_{15}$ is F, Cl, Br or CN; or $R_2$ is a group of Formula (C):

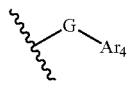

(C)

wherein:

G is C=O, $CR_{16}R_{17}$, O, S, S(O), S(O)$_2$; where $R_{16}$ and $R_{17}$ are independently H or $C_{1-8}$ alkyl; and $Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy, halogen or hydroxyl;

$R_4$ is H or $C_{1-8}$ alkyl;

$R_5$ and $R_6$ are independently H, $C_{1-8}$ alkyl or halogen;

$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (D):

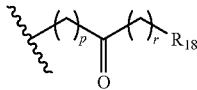

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{14}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and
$R_{10}$-$R_{13}$ are independently selected form the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{10}$-$R_{11}$ groups together with $Ar_1$ form a 5, 6 or 7 membered cycloalkyl, cycloalkenyl or heterocyclic group wherein the 5, 6 or 7 membered group is optionally substituted with halogen.

Some embodiments of the present invention include pharmaceutical compositions comprising at least one compound of the present invention and a pharmaceutically acceptable carrier.

Some embodiments of the present invention include methods for prophylaxis or treatment of a metabolic disorder in an individual comprising administering to the individual a therapeutically effective amount of a compound of the present invention or a pharmaceutical composition thereof.

Some embodiments of the present invention include methods of controlling or decreasing weight gain of an individual comprising administering to the individual a therapeutically effective amount of a compound of the present invention or pharmaceutical composition thereof.

Some embodiments of the present invention include methods of modulating a RUP3 receptor comprising contacting the receptor with a compound of the present invention.

Some embodiments of the present invention include methods of modulating a RUP3 receptor in an individual comprising contacting the receptor with a compound of the present invention. In some embodiments, the compound is an agonist. In some embodiments, the compound is an inverse agonist.

Some embodiments of the present invention include methods of modulating a RUP3 receptor in an individual comprising contacting the receptor with a compound of the present invention wherein the modulation of the RUP3 receptor is prophylaxis or treatment of a metabolic disorder.

Some embodiments of the present invention include methods of modulating a RUP3 receptor in an individual comprising contacting the receptor with a compound of the present invention wherein the modulation of the RUP3 receptor controls or reduces weight gain of the individual.

Some embodiments of the present invention include the use of compounds of the present invention for production of a medicament for use in prophylaxis or treatment of a metabolic disorder.

Some embodiments of the present invention include the use of compounds of the present invention for production of a medicament for use in controlling or decreasing weight gain in an individual.

One aspect of the present invention pertains to compounds of the present invention, as described herein, for use in methods of treatment of the human or animal body by therapy.

One aspect of the present invention pertains to compounds of the present invention, as described herein, for use in methods of prophylaxis or treatment of a metabolic disorder of the human or animal body by therapy.

In some embodiments, the metabolic disorder is type I, type II diabetes, inadequate glucose tolerance, insulin resistance, hyperglycemia, hyperlipidemia, hypertriglyceridemia, hypercholesterolemia, dyslipidemia, syndrome X or metabolic syndrome.

One aspect of the present invention pertains to methods of producing a pharmaceutical compositions comprising admixing at least one compound of the present invention and a pharmaceutically acceptable carrier.

BRIEF DESCRIPTION OF THE DRAWINGS

FIG. 5B shows Compound B70 and Ex-4 significantly reduces glucose levels compared to vehicle control.

DEFINITIONS

Figure 1:
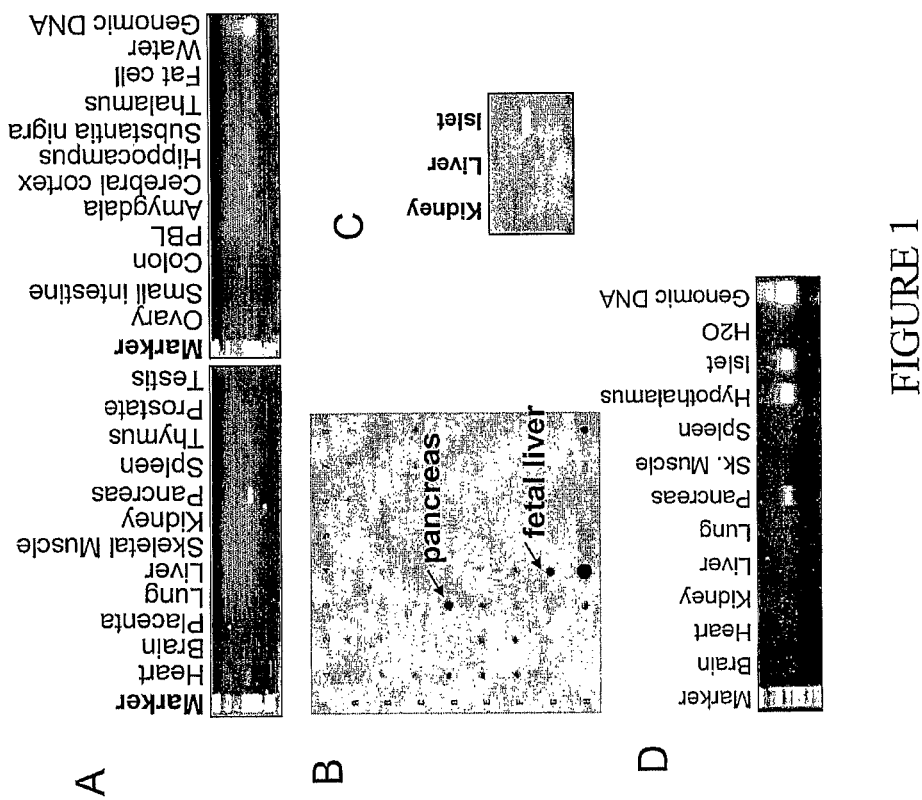
FIG. 1A shows RT-PCR analysis of RUP3 expression in human tissues. A total of twenty-two (22) human tissues were analyzed.
FIG. 1B shows the cDNA Dot-Blot analysis of RUP 3 expression in human tissues.
FIG. 1C shows analysis of RUP3 by RT-PCR with isolated huyman pancreatic islets of Langerhans.
FIG. 1D shows analysis of RUP3 expression with cDNAs of rat origin by RT-PCR.

The scientific literature that has evolved around receptors has adopted a number of terms to refer to ligands having various effects on receptors. For clarity and consistency, the following definitions will be used throughout this patent document.

AGONISTS shall mean moieties that activate the intracellular response when they bind to the receptor, or enhance GTP binding to membranes.

AMINO ACID ABBREVIATIONS used herein are set out in Table 1:

TABLE 1

| ALANINE | ALA | A |
| ARGININE | ARG | R |
| ASPARAGINE | ASN | N |
| ASPARTIC ACID | ASP | D |
| CYSTEINE | CYS | C |
| GLUTAMIC ACID | GLU | E |
| GLUTAMINE | GLN | Q |
| GLYCINE | GLY | G |
| HISTIDINE | HIS | H |
| ISOLEUCINE | ILE | I |
| LEUCINE | LEU | L |
| LYSINE | LYS | K |
| METHIONINE | MET | M |
| PHENYLALANINE | PHE | F |
| PROLINE | PRO | P |
| SERINE | SER | S |
| THREONINE | THR | T |
| TRYPTOPHAN | TRP | W |
| TYROSINE | TYR | Y |
| VALINE | VAL | V |

Chemical Group, Moiety or Radical:

The term "$C_{1-5}$ acyl" denotes an alkyl radical attached to a carbonyl wherein the definition of alkyl has the same definition as described herein; some examples include formyl, acetyl, propionyl, butanoyl, iso-butanoyl, pentanoyl, hexanoyl, heptanoyl, and the like.

The term "$C_{1-5}$ acyloxy" denotes an acyl radical attached to an oxygen atom wherein acyl has the same definition has described herein; some examples include acetyloxy, propionyloxy, butanoyloxy, iso-butanoyloxy and the like.

The term "$C_{2-6}$ alkenyl" denotes a radical containing 2 to 6 carbons wherein at least one carbon-carbon double bond is present, some embodiments are 2 to 4 carbons, some embodiments are 2 to 3 carbons, and some embodiments have 2 carbons. Both E and Z isomers are embraced by the term "alkenyl." Furthermore, the term "alkenyl" includes di- and tri-alkenyls. Accordingly, if more than one double bond is present then the bonds may be all E or Z or a mixtures of E and Z. Examples of an alkenyl include vinyl, allyl, 2-butenyl, 3-butenyl, 2-pentenyl, 3-pentenyl, 4-pentenyl, 2-hexenyl, 3-hexenyl, 4-hexenyl, 5-hexenyl, 2,4-hexadienyl and the like.

The term "$C_{1-4}$ alkoxy" as used herein denotes a radical alkyl, as defined herein, attached directly to an oxygen atom. Example include methoxy, ethoxy, n-propoxy, iso-propoxy, n-butoxy, t-butoxy, iso-butoxy and the like.

The term "$C_{1-8}$ alkyl" denotes a straight or branched carbon radical containing 1 to 8 carbons, some embodiments are 1 to 6 carbons, some embodiments are 1 to 3 carbons, and some embodiments are 1 or 2 carbons. Examples of an alkyl include methyl, ethyl, n-propyl, iso-propyl, n-butyl, sec-butyl, t-butyl, amyl, t-amyl, n-pentyl and the like.

The term "$C_{1-4}$ alkylcarboxamido" denotes a single alkyl group attached to an amide, wherein alkyl has the same definition as found herein. The $C_{1-5}$ alkylcarboxamido may be represented by the following:

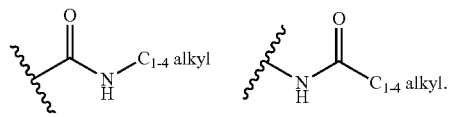

Examples include N-methylcarboxamide, N-ethylcarboxamide, N-(iso-propyl)carboxamide and the like.

The term "$C_1$-$C_3$ alkylene" refers to a divalent straight carbon group, such as, —$CH_2$—, —$CH_2CH_2$—, —$CH_2CH_2CH_2$—.

The term "$C_{1-4}$ alkylsulfinyl" denotes an alkyl radical attached to a sulfoxide radical of the formula: —S(O)— wherein the alkyl radical has the same definition as described herein. Examples include methylsulfinyl, ethylsulfinyl and the like.

The term "$C_{1-4}$ alkylsulfonamide" refers to the groups

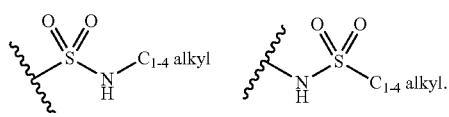

The term "$C_{1-4}$ alkylsulfonyl" denotes an alkyl radical attached to a sulfone radical of the formula: —S(O)$_2$— wherein the alkyl radical has the same definition as described herein. Examples include methylsulfonyl, ethylsulfonyl and the like.

The term "$C_{1-4}$ alkylthio" denotes an alkyl radical attached to a sulfide of the formula: —S— wherein the alkyl radical has the same definition as described herein. Examples include methylsulfanyl (i.e., $CH_3S$—), ethylsulfanyl, isopropylsulfanyl and the like.

The term "$C_{1-4}$ alkylthiocarboxamide" denotes a thioamide of the following formulae:

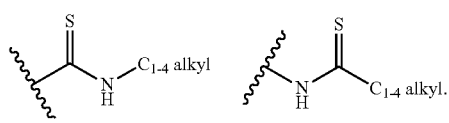

The term "$C_{1-4}$ alkylthioureyl" denotes the group of the formula: —NC(S)N— wherein one are both of the nitrogens are substituted with the same or different alkyl group and alkyl has the same definition as described herein. Examples of an alkylthioureyl include, $CH_3NHC(O)NH$—, $NH_2C(O)NCH_3$—, $(CH_3)_2N(O)NH$—, $(CH_3)_2N(O)NH$—, $(CH_3)_2N(O)NCH_3$—, $CH_3CH_2NHC(O)NH$—, $CH_3CH_2NHC(O)NCH_3$—, and the like.

The term "$C_{1-4}$ alkylureyl" denotes the group of the formula: —NC(O)N— wherein one are both of the nitrogens are substituted with the same or different alkyl group wherein alkyl has the same definition as described herein. Examples of an alkylureyl include, $CH_3NHC(O)NH$—, $NH_2C(O)NCH_3$—, $(CH_3)_2N(O)NH$—, $(CH_3)_2N(O)NH$—, $(CH_3)_2N(O)NCH_3$—, $CH_3CH_2NHC(O)NH$—, $CH_3CH_2NHC(O)NCH_3$—, and the like.

The term "$C_{2-6}$ alkynyl" denotes a radical containing 2 to 6 carbons and at least one carbon-carbon triple bond, some embodiments are 2 to 4 carbons, some embodiments are 2 to 3 carbons, and some embodiments have 2 carbons.

Examples of an alkynyl include ethynyl, ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like. The term "alkynyl" includes di- and tri-ynes.

The term "amino" denotes the group —NH$_2$.

The term "$C_{1-4}$ alkylamino" denotes one alkyl radical attached to an amino radical wherein the alkyl radical has the same meaning as described herein. Some examples include methylamino, ethylamino, propylamino and the like.

The term "aryl" denotes an aromatic ring radical containing 6 to 10 ring carbons. Examples include phenyl and naphthyl.

The term "arylalkyl" defines a $C_1$-$C_4$ alkylene, such as —CH$_2$—, —CH$_2$CH$_2$— and the like, which is further substituted with an aryl group. Examples of an "arylalkyl" include benzyl, phenethylene and the like.

The term "arylcarboxamido" denotes a single aryl group attached to the amine of an amide, wherein aryl has the same definition as found herein. The example is N-phenylcarboxamide.

The term "arylureyl" denotes the group —NC(O)N— where one of the nitrogens are substituted with an aryl.

The term "benzyl" denotes the group —CH$_2$C$_6$H$_5$.

The term "carbo-$C_{1-6}$-alkoxy" refers to an alkyl ester of a carboxylic acid, wherein the alkyl group is $C_{1-6}$. Examples include carbomethoxy, carboethoxy, carboisopropoxy and the like.

The term "carboxamide" refers to the group —CONH$_2$.

The term "carboxy" or "carboxyl" denotes the group —CO$_2$H; also referred to as a carboxylic acid.

The term "cyano" denotes the group —CN.

The term "$C_{3-7}$ cycloalkenyl" denotes a non-aromatic ring radical containing 3 to 6 ring carbons and at least one double bond; some embodiments contain 3 to 5 carbons; some embodiments contain 3 to 4 carbons. Examples include cyclopropenyl, cyclobutenyl, cyclopentenyl, cyclopentenyl, cyclohexenyl, and the like.

The term "$C_{3-7}$ cycloalkyl" denotes a saturated ring radical containing 3 to 6 carbons; some embodiments contain 3 to 5 carbons; some embodiments contain 3 to 4 carbons. Examples include cyclopropyl, cyclobutyl, cyclopentyl, cyclohexyl, and the like.

The term "$C_{3-6}$ cycloalkyl-$C_{1-3}$-alkylene" denotes a saturated ring radical containing 3 to 6 carbons bonded to a $C_{1-3}$-alkylene as described herein; some embodiments contain 3 to 5 carbons; some embodiments contain 3 to 4 carbons. Examples include cyclopropyl-CH$_2$—, cyclopropyl-CH$_2$CH$_2$—, cyclobutyl-CH$_2$—, cyclopentyl-CH$_2$—, cyclohexyl-CH$_2$—, and the like.

The term "$C_{4-8}$ diacylamino" denotes an amino group bonded with two acyl groups defined herein wherein the acyl groups may be the same or different, such as:

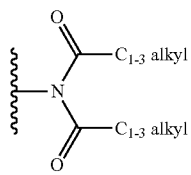

Represented dialkylamino groups include diacetylamino, dipropionylamino, acetylpropionylamino and the like.

The term "$C_{2-6}$ dialkylamino" denotes an amino substituted with two of the same or different alkyl radicals wherein alkyl radical has the same definition as described herein. Some embodiments are $C_{2-4}$ dialkylamino groups. Some examples include dimethylamino, methylethylamino, diethylamino and the like.

The term "$C_{1-4}$ dialkylcarboxamido" or "$C_{1-4}$ dialkylcarboxamide" denotes two alkyl radicals, that are the same or different, attached to an amide group, wherein alkyl has the same definition as described herein. A $C_{1-4}$ dialkylcarboxamido may be represented by the following groups:

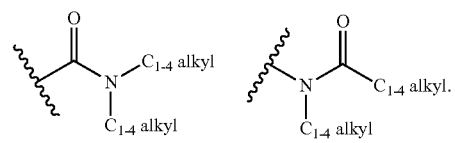

Examples of a dialkylcarboxamide include N,N-dimethylcarboxamide, N-methyl-N-ethylcarboxamide and the like.

The term "$C_{2-6}$ dialkylsulfonamide" refers to one of the following groups shown below:

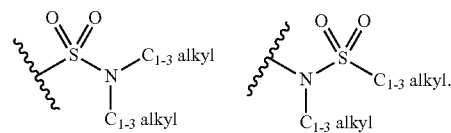

The term "$C_{1-4}$ dialkylthiocarboxamido" or "$C_{1-4}$ dialkylthiocarboxamide" denotes two alkyl radicals, that are the same or different, attached to a thioamide group, wherein alkyl has the same definition as described herein. A $C_{1-4}$ dialkylthiocarboxamido may be represented by the following groups:

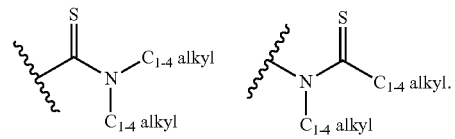

Examples of a dialkylthiocarboxamide include N,N-dimethylthiocarboxamide, N-methyl-N-ethylthiocarboxamide and the like.

The term "$C_{1-4}$ dialkylsulfonylamino" refers to an amino group bonded with two $C_{1-4}$ alkylsulfonyl groups as defined herein.

The term "ethynylene" refers to the carbon-carbon triple bond group as represented below:

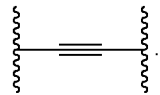 [SMILES: *C#C*]

The term "formyl" refers to the group —CHO.

The term "$C_{1-4}$ haloalkoxy" denotes a haloalkyl, as defined herein, that is directly attached to an oxygen to form a difluoromethoxy, trifluoromethoxy, 2,2,2-trifluoroethoxy, pentafluoroethoxy and the like.

The term "$C_{1-4}$ haloalkyl" denotes an alkyl group, defined herein, wherein the alkyl is substituted with one halogen up to fully substituted represented by the formula $C_nF_{2n+1}$; when more than one halogen is present they may be the same or different and selected from F, Cl, Br or I. Some embodiments are 1 to 3 carbons. Examples include fluoromethyl, difluoromethyl, trifluoromethyl, chlorodifluoromethyl, 2,2,2-trifluoroethyl, pentafluoroethyl and the like.

The term "$C_{1-4}$ haloalkylcarboxamide" denotes an alkylcarboxamide group, defined herein, wherein the alkyl is substituted with one halogen up to fully substituted represented by the formula $C_nF_{2n+1}$ and "n" is 1, 2, 3 or 4. When more than one halogen is present they may be the same or different and selected from F, Cl, Br or I. Examples include 2-fluoroacetyl, 2,2-difluoroacetyl, 2,2,2-trifluoroacetyl, 2-chloro-2,2-difluoroacetyl, 3,3,3-trifluoropropionyl, 2,2,3,3,3-pentafluoropropionyl and the like.

The term "$C_{1-4}$ haloalkylsulfinyl" denotes a haloalkyl radical attached to a sulfoxide of the formula: —S(O)— wherein the alkyl radical has the same definition as described herein. Examples include trifluoromethylsulfinyl, 2,2,2-trifluoroethylsulfinyl, 2,2-difluoroethylsulfinyl and the like.

The term "$C_{1-4}$ haloalkylsulfonyl" denotes a haloalkyl attached to a sulfone of the formula: —S(O)$_2$— wherein haloalkyl has the same definition as described herein. Examples include trifluoromethylsulfonyl, 2,2,2-trifluoroethylsulfonyl, 2,2-difluoroethylsulfonyl and the like.

The term "$C_{1-4}$ haloalkylthio" denotes an alkylthio radical substituted with one or more halogens. Examples include trifluoromethylthio, 1,1-difluoroethylthio, 2,2,2-trifluoroethylthio and the like.

The term "halogen" or "halo" denotes to a fluoro, chloro, bromo or iodo group.

The term "$C_{1-2}$ heteroalkylene" refers to a $C_{1-2}$ alkylene bonded to a heteroatom selected from O, S, S(O), S(O)$_2$ and NH. Some represented examples include the groups of the following formulae:

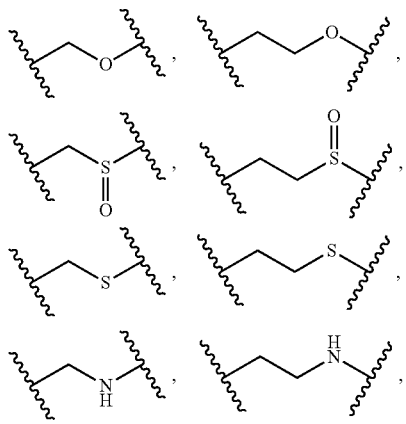

and the like

The term "heteroaryl" denotes an aromatic ring system that may be a single ring, two fused rings or three fused rings containing carbons and at least one ring heteroatom selected from O, S and N. Examples of heteroaryl groups include, but not limited to, pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline, 1H-imidazolyl, [1,2,4]triazolyl, [1,2,3]triazolyl, [1,2,4]triazolyl, pyrrolyl, pyrazolyl, 1H-pyrazolyl, imidazolyl, oxazolyl, oxazolyl, [1,3,4]oxadiazolyl, [1,3,4]thiadiazolyl, [1,2,4]oxadiazolyl, [1,2,4]thiadiazolyl, tetrazolyl, 1,3-dioxo-1,3-dihydro-isoindolyl, [1,2,3]thiadiazol-4-yl and the like.

The term "heterocyclic" denotes a non-aromatic carbon ring (i.e., cycloalkyl or cycloalkenyl as defined herein) wherein one, two or three ring carbons are replaced a heteroatom, such as, O, S, N, wherein the N can be optionally substituted with H, $C_{1-4}$ acyl or $C_{1-4}$ alkyl, and ring carbon atoms optionally substituted with oxo or a thiooxo thus forming a carbonyl or thiocarbonyl group. The heterocyclic group is a 3-, 4-, 5-, 6- or 7-membered containing ring. Examples of a heterocyclic group include but not limited to aziridin-1-yl, aziridin-2-yl, azetidin-1-yl, azetidin-2-yl, azetidin-3-yl, piperidin-1-yl, piperidin-4-yl, morpholin-4-yl, piperzin-1-yl, piperzin-4-yl, pyrrolidin-1-yl, pyrrolidin-3-yl, [1,3]-dioxolan-2-yl and the like. Additional examples of heterocyclic groups are shown in Tables 2B, 2C, 2D, 2E, 2F and 2G, infra.

The term "heterocycliccarboxamido" denotes a heterocyclic group with a ring nitrogen where the ring nitrogen is bonded directly to the carbonyl forming an amide. Examples include:

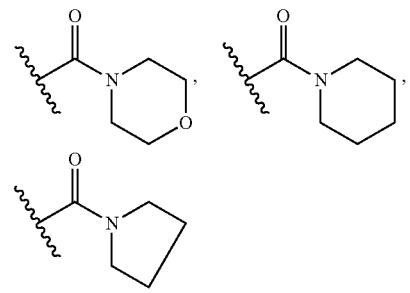

and the like.

The term "heterocyclicsulfonyl" denotes a heterocyclic group with a ring nitrogen where the ring nitrogen is bonded directly to an SO$_2$ group forming an sulfonamide. Examples include:

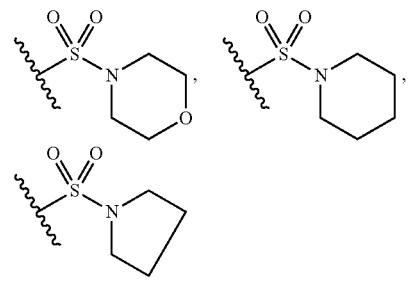

and the like.

The term "hydroxyl" refers to the group —OH.
The term "hydroxylamino" refers to the group —NHOH.

The term "nitro" refers to the group —NO$_2$.

The term "C$_{4-7}$ oxo-cycloalkyl" refers to a C$_{4-7}$ cycloalkyl, as defined herein, wherein one of the ring carbons is replaced with a carbonyl. Examples of C$_{4-7}$ oxo-cycloalkyl include but are not limited to: 2-oxo-cyclobutyl, 3-oxo-cyclobutyl, 3-oxo-cyclopentyl, 4-oxo-cyclohexyl, and the like and represented the following structures respectively:

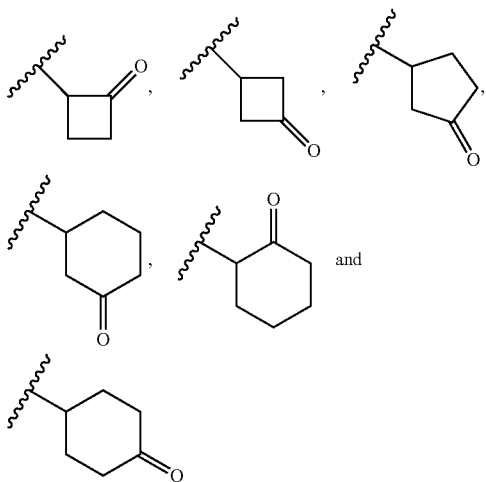

The term "perfluoroalkyl" denotes the group of the formula —C$_n$F$_{2n+1}$; stated differently, a perfluoroalkyl is an alkyl as defined herein wherein the alkyl is fully substituted with fluorine atoms and is therefore considered a subset of haloalkyl. Examples of perfluoroalkyls include CF$_3$, CF$_2$CF$_3$, CF$_2$CF$_2$CF$_3$, CF(CF$_3$)$_2$, CF$_2$CF$_2$CF$_2$CF$_3$, CF$_2$CF(CF$_3$)$_2$, CF(CF$_3$)CF$_2$CF$_3$ and the like.

The term "phenoxy" refers to the group C$_6$H$_5$O—.

The term "phenyl" refers to the group C$_6$H$_5$—.

The term "sulfonic acid" refers to the group —SO$_3$H.

The term "tetrazolyl" refers to the five membered heteroaryl of the following formulae:

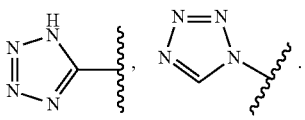

In some embodiments, the tetrazolyl group is further substituted at either the 1 or 5 position respectively.

The term "thiol" denotes the group —SH.

CODON shall mean a grouping of three nucleotides (or equivalents to nucleotides) which generally comprise a nucleoside (adenosine (A), guanosine (G), cytidine (C), uridine (U) and thymidine (T)) coupled to a phosphate group and which, when translated, encodes an amino acid.

COMPOSITION shall mean a material comprising at least two compounds or two components; for example, and not limitation, a Pharmaceutical Composition is a Composition.

COMPOUND EFFICACY shall mean a measurement of the ability of a compound to inhibit or stimulate receptor functionality, as opposed to receptor binding affinity.

CONSTITUTIVELY ACTIVATED RECEPTOR shall mean a receptor subject to constitutive receptor activation.

CONSTITUTIVE RECEPTOR ACTIVATION shall mean stabilization of a receptor in the active state by means other than binding of the receptor with its endogenous ligand or a chemical equivalent thereof.

CONTACT or CONTACTING shall mean bringing at least two moieties together, whether in an in vitro system or an in vivo system.

ENDOGENOUS shall mean a material that a mammal naturally produces. ENDOGENOUS in reference to, for example and not limitation, the term "receptor" shall mean that which is naturally produced by a mammal (for example, and not limitation, a human) or a virus.

In contrast, the term NON-ENDOGENOUS in this context shall mean that which is not naturally produced by a mammal (for example, and not limitation, a human) or a virus. For example, and not limitation, a receptor which is not constitutively active in its endogenous form, but when manipulated becomes constitutively active, is most preferably referred to herein as a "non-endogenous, constitutively activated receptor." Both terms can be utilized to describe both "in vivo" and "in vitro" systems. For example, and not a limitation, in a screening approach, the endogenous or non-endogenous receptor may be in reference to an in vitro screening system. As a further example and not limitation, where the genome of a mammal has been manipulated to include a non-endogenous constitutively activated receptor, screening of a candidate compound by means of an in vivo system is viable.

INDIVIDUAL as used herein refers to any animal, including mammals, preferably mice, rats, other rodents, rabbits, dogs, cats, swine, cattle, sheep, horses, or primates, and most preferably humans.

INHIBIT or INHIBITING, in relationship to the term "response" shall mean that a response is decreased or prevented in the presence of a compound as opposed to in the absence of the compound.

INVERSE AGONISTS shall mean moieties that bind the endogenous form of the receptor or to the constitutively activated form of the receptor, and which inhibit the baseline intracellular response initiated by the active form of the receptor below the normal base level of activity which is observed in the absence of agonists or partial agonists, or decrease GTP binding to membranes. Preferably, the baseline intracellular response is inhibited in the presence of the inverse agonist by at least 30%, more preferably by at least 50%, and most preferably by at least 75%, as compared with the baseline response in the absence of the inverse agonist.

LIGAND shall mean an endogenous, naturally occurring molecule specific for an endogenous, naturally occurring receptor.

As used herein, the terms MODULATE or MODULATING shall mean to refer to an increase or decrease in the amount, quality, response or effect of a particular activity, function or molecule.

PHARMACEUTICAL COMPOSITION shall mean a composition comprising at least one active ingredient, whereby the composition is amenable to investigation for a specified, efficacious outcome in a mammal (for example, and not limitation, a human). Those of ordinary skill in the art will understand and appreciate the techniques appropriate for determining whether an active ingredient has a desired efficacious outcome based upon the needs of the artisan.

DETAILED DESCRIPTION

Compound of the Present Invention

One aspect of the present invention pertains to certain 1,2,3-trisubstituted aryl and heteroaryl derivatives as shown in Formula (Ia):

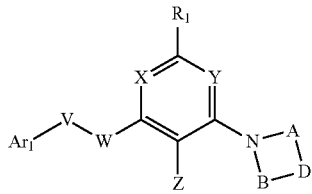

(Ia)

or a pharmaceutically acceptable salt, hydrate or solvate thereof, wherein A, B, D, V, W, X, Y, Z Ar$_1$, and R$_1$ are as described herein, supra and infra.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable subcombination.

One aspect of the present invention encompasses N-oxides of 1,2,3-trisubstituted aryl and heteroaryl derivatives of Formula (Ia).

One aspect of the present invention encompasses 1,2,3-trisubstituted aryl and heteroaryl derivatives as shown in Formula (Ia) wherein W is NR$_4$ and compounds may be represented by Formula (Ib) as shown below:

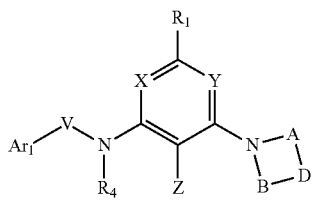

(Ib)

wherein each variable in Formula (Ib) has the same meaning as described herein. In some embodiments, R$_4$ is H. In some embodiments, R$_4$ is CH$_3$ or CH$_2$CH$_3$.

One aspect of the present invention encompasses 1,2,3-trisubstituted aryl and heteroaryl derivatives as shown in Formula (Ia) wherein W is O, (i.e., an oxygen atom) and compounds may be represented by Formula (Ic) as shown below:

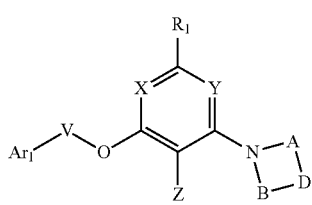

(Ic)

wherein each variable in Formula (Ic) has the same meaning as described herein.

One aspect of the present invention encompasses 1,2,3-trisubstituted aryl and heteroaryl derivatives as shown in Formula (Ia) wherein W is S, S(O) or S(O)$_2$ and compounds may be represented by Formulae (Id), (Ie) and (If) respectively as shown below:

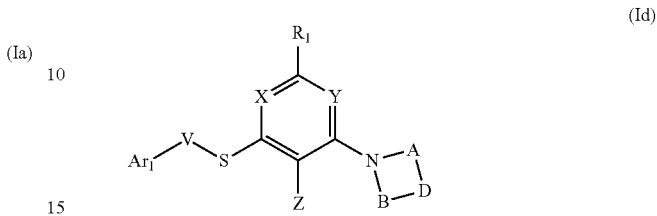

(Id)

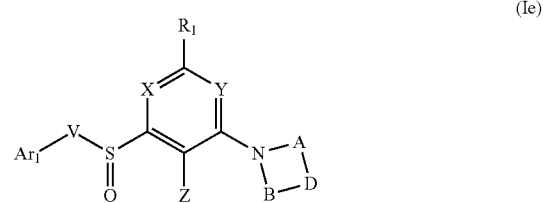

(Ie)

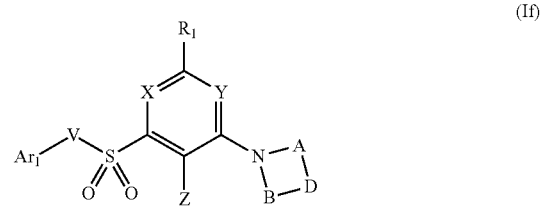

(If)

wherein each variable in Formulae (Id), (Ie) and (If) has the same meaning as described herein.

One aspect of the present invention encompasses 1,2,3-trisubstituted aryl and heteroaryl derivatives as shown in Formula (Ia) wherein W is absent and compounds may be represented by Formula (Ig) as shown below:

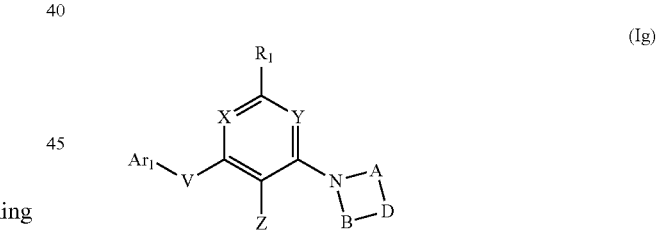

(Ig)

wherein each variable in Formula (Ig) has the same meaning as described herein. In some embodiments, compounds of the present invention are of Formula (Ig) wherein V is absent and accordingly these compounds may be represented by Formula (Ih) as shown below:

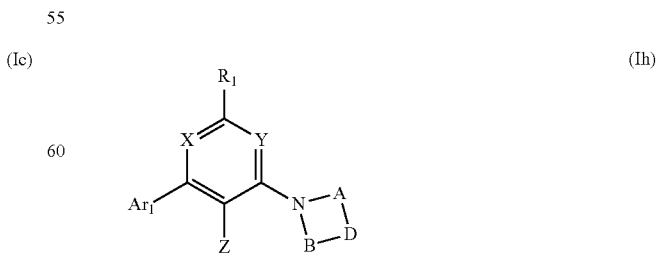

(Ih)

wherein each variable in Formula (Ih) has the same meaning as described herein.

One aspect of the present invention encompasses 1,2,3-trisubstituted aryl and heteroaryl derivatives as shown in Formula (Ia) wherein W is absent and V is ethynylene. Compounds may be represented by Formula (Ii) as shown below:

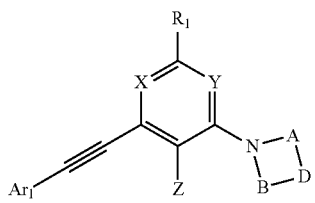

(Ii)

wherein each variable in Formula (Ii) has the same meaning as described herein.

In some embodiments, V is $C_{1-3}$ alkylene optionally substituted with 1 to 4 substituents selected from the group consisting of $C_{1-3}$ alkyl, $C_{1-4}$ alkoxy and halogen. In some embodiments, V is a methylene group (i.e., —CH$_2$—). In some embodiments, V is an ethylene group (i.e., —CH$_2$CH$_2$—). In some embodiments, V is a methylene and W is an oxygen atom. In some embodiments, V is methylene and W is a NR$_4$ group. In some embodiments, V is methylene and W is a NH group. In some embodiments, V is ethylene and W is an oxygen atom. In some embodiments, V is ethylene and W is a NR$_4$ group. In some embodiments, V is ethylene and W is a NH group.

In some embodiments, V is $C_{1-2}$ heteroalkylene optionally substituted with 1 to 4 substituents selected from the group consisting of $C_{1-3}$ alkyl, $C_{1-4}$ alkoxy and halogen. In some embodiments, V is —OCH$_2$CH$_2$—. In some embodiments, V is —OCH$_2$CH$_2$— and W is an oxygen atom and may be represented by the formula: —OCH$_2$CH$_2$O—. In some embodiments, V is —OCH$_2$CH$_2$— and W is a NH group and may be represented by the formula:—OCH$_2$CH$_2$NH—.

In some embodiments, V is absent and may be represented by Formula (Ij) as shown below:

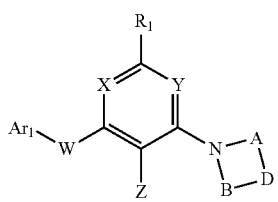

(Ij)

wherein each variable in Formula (Ij) has the same meaning as described herein.

In some embodiments, A and B are both methylene wherein A and B are optionally substituted with 1 to 2 methyl groups and therefore form a four-membered nitrogen containing ring. In some embodiments, compounds of the invention may be represented by Formula (Ik) as shown below:

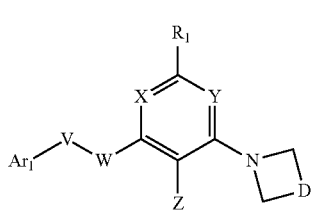

(Ik)

wherein each variable in Formula (Ik) has the same meaning as described herein. In some embodiments, D is —CHR$_2$—.

In some embodiments, A is ethylene and B is methylene wherein A is optionally substituted with 1 to 4 methyl groups and B is optionally substituted with 1 to 2 methyl groups. In some embodiments, compounds of the invention may be represented by Formula (Im) as shown below:

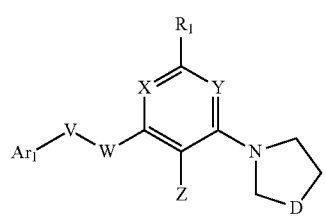

(Im)

wherein each variable in Formula (Im) has the same meaning as described herein. In some embodiments, D is —CHR$_2$—. In some embodiments, R$_2$ is $C_{1-4}$ alkylsulfonyl.

In some embodiments, A is propylene and B is methylene wherein A is optionally substituted with 1 to 4 methyl groups and B is optionally substituted with 1 to 2 methyl groups. In some embodiments, compounds of the invention may be represented by Formula (In) as shown below:

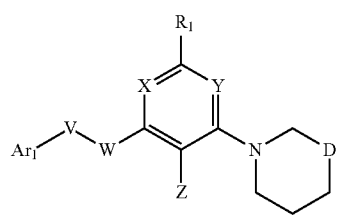

(In)

wherein each variable in Formula (In) has the same meaning as described herein. In some embodiments, D is —CHR$_2$—.

In some embodiments, A and B are both ethylene wherein A and B are optionally substituted with 1 to 4 methyl groups. In some embodiments, compounds of the invention may be represented by Formula (Io) as shown below:

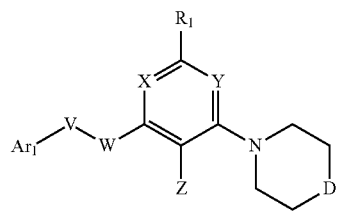

(Io)

wherein each variable in Formula (Io) has the same meaning as described herein. In some embodiments, D is —CHR$_2$—.

In some embodiments, A is propylene and B is ethylene wherein A and B are optionally substituted with 1 to 4 methyl groups. In some embodiments, compounds of the invention may be represented by Formula (Ip) as shown below:

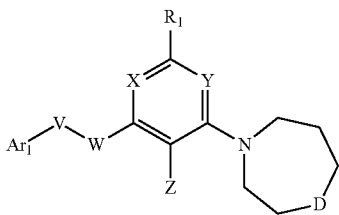

(Ip)

wherein each variable in Formula (Ip) has the same meaning as described herein. In some embodiments, D is —$CHR_2$—.

In some embodiments, A and B are both propylene wherein A and B are optionally substituted with 1 to 4 methyl groups. In some embodiments, compounds of the invention may be represented by Formula (Iq) as shown below:

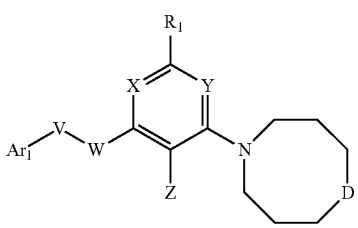

(Iq)

wherein each variable in Formula (Iq) has the same meaning as described herein. In some embodiments, D is —$CHR_2$—.

In some embodiments, D is O, S, S(O) or $S(O)_2$. In some embodiments, D is S, S(O) or $S(O)_2$; and A and B are independently optionally substituted with 1 or 2 methyl groups. In some embodiments, A and B are ethylene groups. In some embodiments, A and B are ethylene groups substituted with 2 methyl groups and D is an oxygen atom (i.e., forming a 2,6-dimethyl-morpholin-4-yl group).

In some embodiments, D is $CR_2R_3$.

In some embodiments, $R_2$ is selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-5}$-alkoxy, carboxamide, carboxyl, $C_{3-6}$ cycloalkyl, $C_{1-4}$ haloalkoxy, $C_{1-4}$ haloalkyl, halogen and hydroxyl.

In some embodiments, $R_2$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OC(O)CH_3$, $OC(O)CH_2CH_3$, $OC(O)CH_2CH_2CH_3$, $OCH_3$, $OCH_2CH_3$, $OCH_2CH_2CH_3$, $OCH(CH_3)_2$, $OCH_2(CH_2)_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, $CO_2CH_3$, $CO_2CH_2CH_3$, $CO_2CH_2CH_2CH_3$, $CO_2CH(CH_3)_2$ and $CO_2CH_2(CH_2)_2CH_3$.

In some embodiments, $R_2$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OC(O)CH_3$, $OC(O)CH_2CH_3$, $OC(O)CH_2CH_2CH_3$, $OCH_3$, $OCH_2CH_3$, $OCH_2CH_2CH_3$, $OCH(CH_3)_2$, $OCH_2(CH_2)_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $C(O)NH_2$, $CO_2CH_3$, $CO_2CH_2CH_3$, $CO_2CH_2CH_2CH_3$, $CO_2CH(CH_3)_2$, $CO_2CH_2(CH_2)_2CH_3$, and $CO_2H$.

In some embodiments, $R_2$ is selected from the group consisting of $SCH_3$, $SCH_2CH_3$, $SCH_2CH_2CH_3$, $SCH(CH_3)_2$, $SCH_2(CH_2)_2CH_3$, $S(O)CH_3$, $S(O)CH_2CH_3$, $S(O)CH_2CH_2CH_3$, $S(O)CH(CH_3)_2$, $S(O)CH_2(CH_2)_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, cyclopropyl, cyclobutyl, cyclopentyl, cyclohexyl, $OCF_3$, $OCHF_2$, $CF_3$, $CHF_2$ and F.

In some embodiments, $R_2$ is selected from the group consisting of $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, cyclopropyl, cyclobutyl, cyclopentyl, cyclohexyl, hydroxyl, and F.

In some embodiments, $R_2$ is $C_{1-8}$ alkyl, or heteroaryl each optionally substituted with 1 to 5 substituents selected from the group consisting of $C_{1-5}$ acyloxy, $C_{1-4}$ alkoxy, $C_{1-8}$ alkyl, $C_{1-4}$ alkylsulfonyl, carbo-$C_{1-6}$-alkoxy, carboxamide, carboxy, $C_{3-6}$-cycloalkyl, $C_{3-6}$-cycloalkyl-$C_{1-3}$-alkylene, $C_{3-6}$-cycloalkyl-$C_{1-3}$-heteroalkylene, and hydroxyl.

In some embodiments, $R_2$ is selected from the group consisting of $CH_2OCH_3$, $CH_2CH_2OCH_3$, $CH_2OCH_2CH_3$, $CH_2OCH_2CH_2CH_3$, $CH_2CH_2OCH_2CH_3$, $CH_2CH_2OCH_2CH_2CH_3$, $CH_2OCH(CH_3)_2$, $CH_2OCH_2CH(CH_3)_2$, $CH_2CO_2H$, $CH_2CH_2CO_2H$, $CH_2OH$, $CH_2CH_2OH$ and $CH_2CH_2CH_2OH$.

In some embodiments, $R_2$ is $C_{1-8}$ alkyl, heteroaryl or phenyl each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{8-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

In some embodiments, $R_2$ is selected from the group consisting of $CH_2OCH_3$, $CH_2CH_2OCH_3$, $CH_2OCH_2CH_3$, $CH_2OCH_2CH_2CH_3$, $CH_2CH_2OCH_2CH_3$, $CH_2CH_2OCH_2CH_2CH_3$, $CH_2OCH(CH_3)_2$, $CH_2OCH_2CH(CH_3)_2$, $CH_2CO_2H$, $CH_2CH_2CO_2H$, $CH_2OH$, $CH_2CH_2OH$ and $CH_2CH_2CH_2OH$.

In some embodiments, $R_2$ is selected from the group consisting of $CH_2SCH_3$, $CH_2SCH_2CH_3$, $CH_2SCH_2CH_2CH_3$, $CH_2SCH(CH_3)_2$, $CH_2SCH_2(CH_2)_2CH_3$, $CH_2CH_2SCH_3$, $CH_2CH_2SCH_2CH_3$, $CH_2CH_2SCH_2CH_2CH_3$, $CH_2CH_2SCH$ $(CH_3)_2$, $CH_2CH_2SCH_2(CH_2)_2CH_3$, $CH_2S(O)CH_3$, $CH_2S(O)CH_2CH_3$, $CH_2S(O)CH_2CH_2CH_3$, $CH_2S(O)CH(CH_3)_2$, $CH_2S(O)CH_2(CH_2)_2CH_3$, $CH_2CH_2S(O)CH_3$, $CH_2CH_2S(O)CH_2CH_3$, $CH_2CH_2S(O)CH_2CH_2CH_3$, $CH_2CH_2S(O)CH(CH_3)_2$, $CH_2CH_2S(O)CH_2(CH_2)_2CH_3$, $CH_2S(O)_2CH_3$, $CH_2S(O)_2CH_2CH_3$, $CH_2S(O)_2CH_2CH_2CH_3$, $CH_2S(O)_2CH(CH_3)_2$, $CH_2S(O)_2CH_2(CH_2)_2CH_3$, $CH_2CH_2S(O)_2CH_3$, $CH_2CH_2S(O)_2CH_2CH_3$, $CH_2CH_2S(O)_2CH_2CH_2CH_3$, $CH_2CH_2S(O)_2CH(CH_3)_2$ and $CH_2CH_2S(O)_2CH_2(CH_2)_2CH_3$.

In some embodiments, $R_2$ is selected from the group consisting of $CH_2OCH_2$-cyclopropyl, $CH_2OCH_2$-cyclobutyl, $CH_2OCH_2$-cyclopentyl, $CH_2OCH_2$-cyclohexyl, $CH_2OCH_2CH_2$-cyclopropyl, $CH_2OCH_2CH_2$-cyclobutyl, $CH_2OCH_2CH_2$-cyclopentyl, $CH_2OCH_2CH_2$-cyclohexyl, $CH_2CH_2OCH_2$-cyclopropyl, $CH_2CH_2OCH_2$-cyclobutyl, $CH_2CH_2OCH_2$-cyclopentyl, $CH_2CH_2OCH_2$-cyclohexyl, $CH_2CH_2OCH_2CH_2$-cyclopropyl, $CH_2CH_2OCH_2CH_2$-cyclobutyl, $CH_2CH_2OCH_2CH_2$-cyclopentyl and $CH_2CH_2OCH_2CH_2$-cyclohexyl.

In some embodiments, $R_2$ is selected from the group consisting of 1,2,4-oxadiazol-3-yl, 1,2,4-oxadiazol-5-yl, 1,3,4- oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 5-ethyl-1,2,4-oxadiazol-3-yl, 5-methyl-1,3,4-oxadiazol-2-yl, 5-ethyl-1,3,4-oxadiazol-2-yl, 3-methyl-1,2,4-triazol-5-yl, 3-ethyl-1,2,446 azol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments, $R_2$ is selected from the group consisting of 1,2,4-oxadiazol-3-yl, 1,2,4-oxadiazol-5-yl, 1,3,4-oxadiazol-2-yl, 3-methyl-1,2,4-oxadiazol-5-yl, 3-ethyl-1,2,4-oxadiazol-5-yl, 3-isopropyl-1,2,4-oxadiazol-5-yl, 3-propyl-1,2,4-oxadiazol-5-yl, 3-1-butyl-1,2,4-oxadiazol-5-yl, and 3-cyclopropyl-1,2,4-oxadiazol-5-yl.

In some embodiments, $R_2$ is selected from the group consisting of 3-methyl-1,2,4-oxadiazol-5-yl, 3-ethyl-1,2,4-oxadiazol-5-yl, 3-propyl-1,2,4-oxadiazol-5-yl, 3-isopropyl-1,2,4-oxadiazol-5-yl, 3-butyl-1,2,4-oxadiazol-5-yl, and 3-(t-butyl)-1,2,4-oxadiazol-5-yl.

In some embodiments, $R_2$ is a heteroaryl comprising 5-atoms in the aromatic ring and are represented by the following formulae:

TABLE 2A

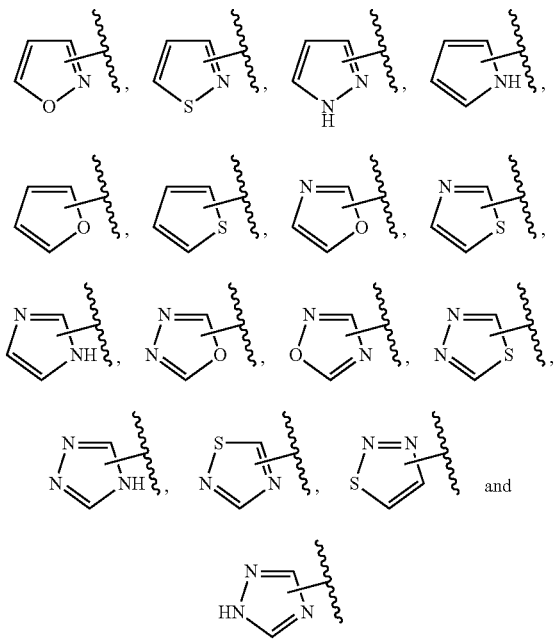

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imiadazol-5-yl group).

In some embodiments, $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

In some embodiments, compounds of the present invention are of the following formula:

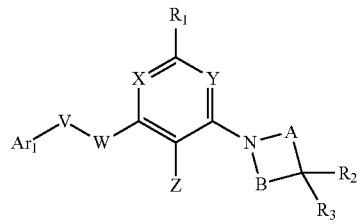

wherein $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-5}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; and $R_3$ is hydrogen or $C_{1-4}$ alkyl.

In some embodiments, $R_2$ is a 5-membered heteroaryl optionally substituted with 1 or 2 substituents selected from the group consisting of $C_{1-8}$ alkyl, $C_{1-4}$ haloalkyl and halogen; and $R_3$ is hydrogen.

In some embodiments, $R_2$ is a 5-membered heteroaryl optionally substituted with 1or 2 $C_{1-8}$ alkyl substituents; and $R_3$ is hydrogen.

In some embodiments, $R_2$ is a 5-membered heteroaryl optionally substituted with $CH_3$, $CH_2CH_3$, $CH(CH_3)_2$, $CH_2CH_2CH_3$, $C(CH_3)_3$; and $R_3$ is hydrogen.

In some embodiments, $R_2$ is a fused heteroaryl group containing to aromatic rings wherein at least one is a heteroaryl ring, such as, benzofuranyl, benzimidazole, benzoxazole, benzothiazole, indole, benzothiophenyl. In some embodiments, $R_2$ is a benzofuran-2-yl group.

In some embodiments, $R_2$ is a heterocyclic represented, for example, by the formulae in TABLE 2B.

TABLE 2B

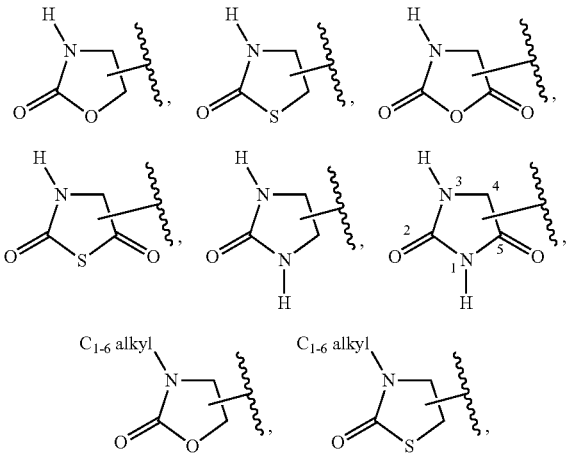

TABLE 2B-continued

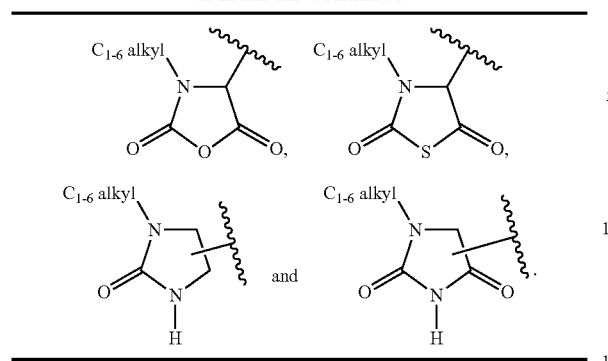

It is understood that any one of the heterocyclic groups shown in TABLES 2B to 2E may be bonded at any available ring carbon or ring nitrogen as allowed by the respective formula. For example, a 2,5-dioxo-imidazolidinyl group may be bonded at the ring carbon or at either of the two ring nitrogens to give the following formulae respectively:

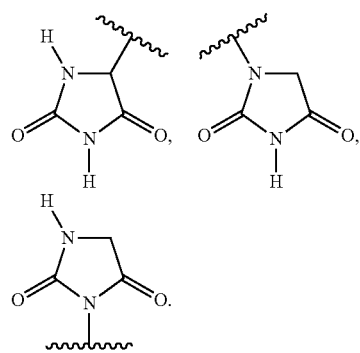

In some embodiments, $R_2$ is a heterocyclic represented, for example, by the formulae in TABLE 2C.

TABLE 2C

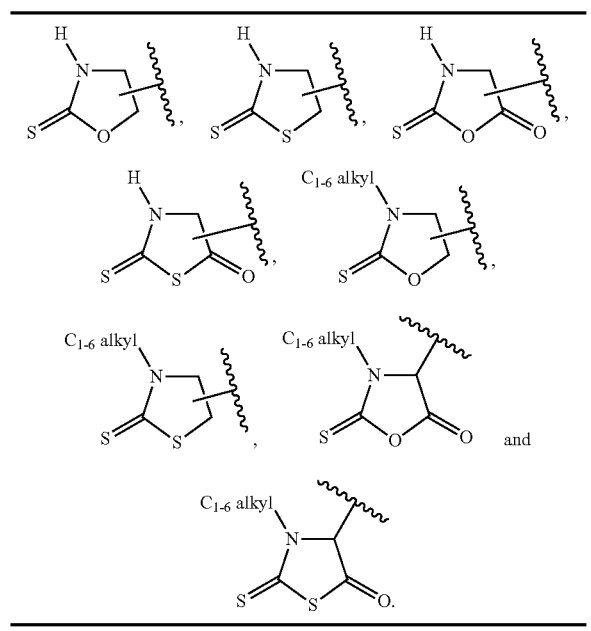

In some embodiments, $R_2$ is a heterocyclic represented, for example, by the formulae in TABLE 2D.

TABLE 2D

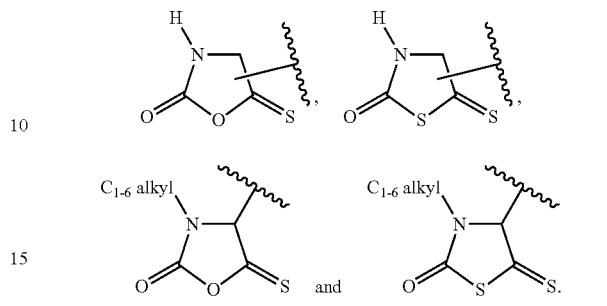

In some embodiments, $R_2$ is a heterocyclic represented, for example, by the formulae in TABLE 2E.

TABLE 2E

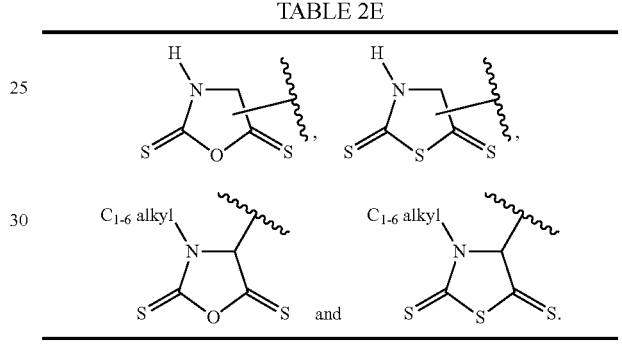

In some embodiments, $R_2$ is a heterocyclic represented, for example, by the formulae in TABLE 2F wherein the $C_{1-6}$ alkyl group on the respective ring nitrogen atoms may be the same or different.

TABLE 2F

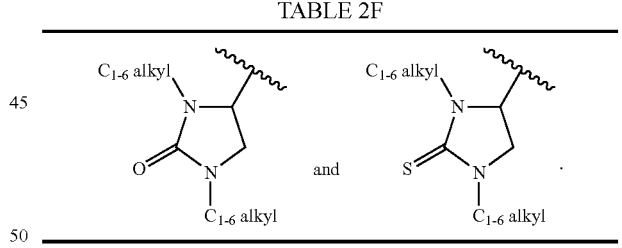

In some embodiments, $R_2$ is a heterocyclic represented, for example, by the formulae in TABLE 2G wherein the $C_{1-6}$ alkyl group on the respective ring nitrogen atoms may be the same or different.

TABLE 2G

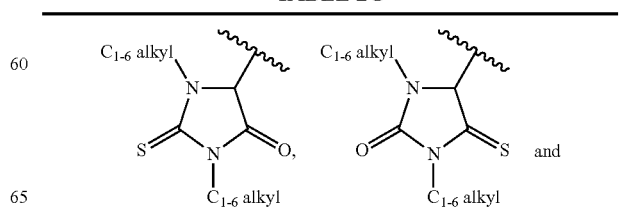

TABLE 2G-continued

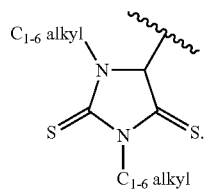

In some embodiments, D is $CR_2R_3$ and $R_2$ is —$Ar_2$-$Ar_3$ wherein $Ar_2$ and $Ar_3$ are independently aryl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro. In some embodiments, $Ar_2$ is a heteroaryl and $Ar_3$ is phenyl. In some embodiments, compounds of the present invention are represented by Formula (Ir) as shown below:

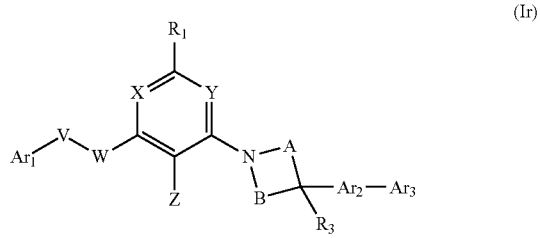

(Ir)

wherein each variable in Formula (Ir) has the same meaning as described herein. In some embodiments, compounds of the present invention are of Formula (Ir) wherein $R_3$ is H.

In some embodiments, $Ar_2$ is a heteroaryl comprising 5-atoms in the aromatic ring and are represented by the following formulae:

TABLE 3

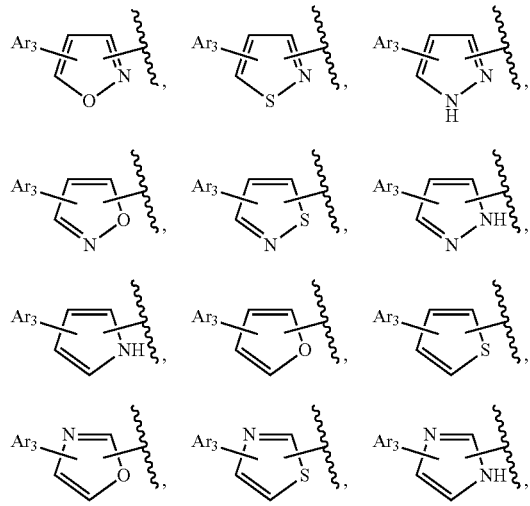

TABLE 3-continued

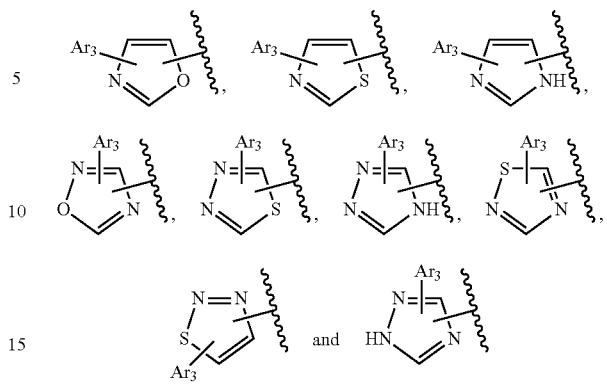

wherein the 5-membered heteroaryl is bonded at any available position of the ring, for example, a imidazolyl ring can be bonded at one of the ring nitrogens (i.e., imidazol-1-yl group) or at one of the ring carbons (i.e., imidazol-2-yl, imidazol-4-yl or imidazol-5-yl group) and $Ar_3$ is bonded to any remaining available ring atom.

In some embodiments, $Ar_2$ is a heteroaryl and $Ar_3$ is phenyl. In some embodiments, the heteroaryl and phenyl are optionally substituted with 1 to 5 substituents selected from the group consisting of H, $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, halogen, hydroxyl and nitro.

In some embodiments, D is $CR_2R_3$ and $R_2$ is Formula (B):

(B)

wherein:
$R_{14}$ is $C_{1-8}$ alkyl or $C_{3-6}$ cycloalkyl; and $R_{15}$ is F, Cl, Br or CN. In some embodiments, $R_{14}$ is $C_{1-8}$ alkyl and $R_{15}$ is F, Cl or CN.

In some embodiments, D is $CR_2R_3$ and $R_2$ is Formula (C):

(C)

wherein:
G is C=O, $CR_{16}R_{17}$, O, S, S(O), $S(O)_2$; where $R_{16}$ and $R_{17}$ are independently H or $C_{1-8}$ alkyl; and $Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro.

In some embodiments, $R_2$ is Formula (C) wherein G is C=O, $CR_{16}R_{17}$, O, S, S(O), S(O)$_2$; wherein $R_{16}$ and $R_{17}$ are independently H or $C_{1-2}$ alkyl; and $Ar_4$ is phenyl or heteroaryl optionally substituted with 1 to 5 substituents selected from the group consisting of $C_{1-4}$ alkoxy, $C_{1-8}$ alkyl, $C_{1-4}$ haloalkoxy, $C_{1-4}$ haloalkyl, and halogen.

In some embodiments, G is C=O, $CH_2$ or O. In some embodiments, G is S, S(O) or S(O)$_2$.

In some embodiments, $Ar_4$ is selected from the group consisting of pyridinyl, pyridazinyl, pyrimidinyl and pyrazinyl. In some embodiments, $Ar_4$ is 2-pyridyl.

In some embodiments, compounds of the present invention are represented by Formula (Is) as shown below:

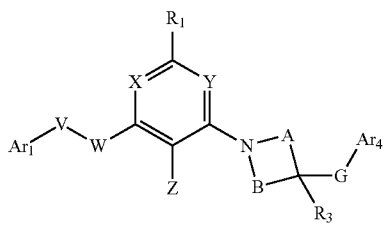

wherein each variable in Formula (Is) has the same meaning as described herein.

In some embodiments, D is $CR_2R_3$, $R_2$ is Formula (C) and G is C=O, $CR_{16}R_{17}$ or O. In some embodiments, $Ar_4$ is phenyl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro.

In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl.

In some embodiments, $Ar_4$ is heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro.

In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl.

In some embodiments, $Ar_4$ is a 5-membered heteroaryl, for example, as shown in TABLE 2A supra. In some embodiments, $Ar_4$ is a 6-membered heteroaryl, for example, the 6-membered heteroaryls as shown in TABLE 4:

TABLE 4

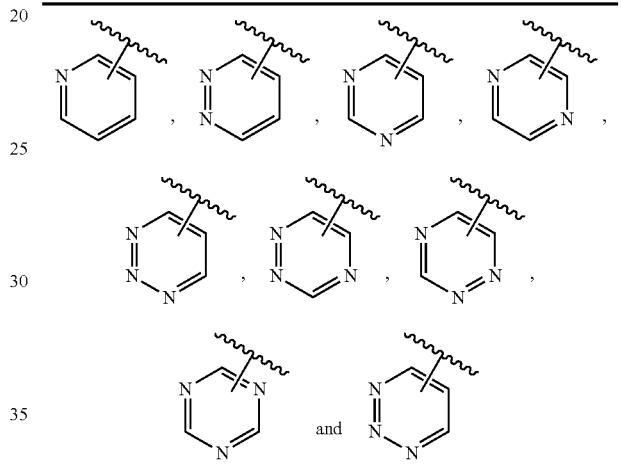

wherein the heteroaryl group is bonded at any ring carbon. In some embodiments, $Ar_4$ is selected from the group consisting of pyridinyl, pyridazinyl, pyrimidinyl and pyrazinyl. In some embodiments, $Ar_4$ is 2-pyridyl. In some embodiments, D is $CR_2R_3$, $R_2$ is Formula (C), G is $CR_{16}R_{17}$ and $R_{16}$ and $R_{17}$ are independently H or $C_{1-2}$ alkyl.

In some embodiments, D is $CR_2R_3$, $R_2$ is Formula (C) and G is S, S(O) or S(O)$_2$.

In some embodiments, $Ar_4$ is phenyl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro.

In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, haloalkyl, $C_{1-4}$ haloalkyl, halogen and hydroxyl.

In some embodiments, $Ar_4$ is heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro.

In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl.

In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl. In some embodiments, $Ar_4$ is a 5-membered heteroaryl, for example, as shown in TABLE 2A, supra.

In some embodiments, $Ar_4$ is a 6-membered heteroaryl, for example, as shown in TABLE 4, supra.

In some embodiments, $Ar_4$ is selected from the group consisting of pyridinyl, pyridazinyl, pyrimidinyl and pyrazinyl. In some embodiments, $Ar_4$ is 2-pyridyl.

In some embodiments, $R_3$ is H.

In some embodiments, D is $N-R_2$. In some embodiments, $R_2$ is selected from the group consisting of H, $C_{1-5}$ acyl, $C_{1-8}$ alkyl, $C_{1-4}$ alkylcarboxamide, $C_{1-4}$ alkylsulfonyl, carbo-$C_{1-6}$-alkoxy, carboxamide, $C_{3-6}$-cycloalkyl and $C_{1-4}$ haloalkyl. In some embodiments, $R_2$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, $CO_2CH_3$, $CO_2CH_2CH_3$, $CO_2CH_2CH_2CH_3$, $CO_2CH(CH_3)_2$ and $CO_2CH_2(CH_2)_2CH_3$. In some embodiments, $R_2$ is selected from the group consisting of $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, cyclopropyl, cyclobutyl, cyclopentyl, cyclohexyl, $CH_2CF_3$, $CF_3$ and $CHF_2$.

In some embodiments, D is $N-R_2$ and $R_2$ is H, or carbo-$C_{1-6}$-alkoxy. In some embodiments, $R_2$ is selected from the group consisting of $CO_2CH_3$, $CO_2CH_2CH_3$, $CO_2CH_2CH_2CH_3$, $CO_2CH(CH_3)_2$ and $CO_2CH_2(CH_2)_2CH_3$. In some embodiments, $R_2$ is $C_{1-8}$ alkyl optionally substituted with 1 to 5 substituents selected from the group consisting of $C_{1-4}$ alkylsulfonyl, carbo-$C_{1-6}$-alkoxy, and carboxy. In some embodiments, $R_2$ is $CH_2CO_2Et$, or $CH_2CH_2CO_2H$. In some embodiments, $R_2$ is selected from the group consisting of $CH_2CH_2S(O)_2CH_3$, $CH_2CH_2S(O)_2CH_2CH_3$, $CH_2CH_2S(O)_2CH_2CH_2CH_3$, $CH_2CH_2S(O)_2CH(CH_3)_2$ and $CH_2CH_2S(O)_2CH_2(CH_2)_2CH_3$.

In some embodiments, D is $N-R_2$ wherein $R_2$ is $C_{1-8}$ alkyl, heteroaryl or phenyl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro. In some embodiments, $R_2$ is selected from the group consisting of $CH_2CH_2OCH_3$, $CH_2CH_2OCH_2CH_3$, $CH_2CH_2OCH_2CH_2CH_3$, $CH_2CO_2H$, $CH_2CH_2CO_2H$, $CH_2CH_2OH$ and $CH_2CH_2CH_2OH$. In some embodiments, $R_2$ is selected from the group consisting of $CH_2CH_2SCH_3$, $CH_2CH_2SCH_2CH_3$, $CH_2CH_2SCH_2CH_2CH_3$, $CH_2CH_2SCH(CH_3)_2$, $CH_2CH_2SCH_2(CH_2)_2CH_3$, $CH_2CH_2S(O)CH_3$, $CH_2CH_2S(O)CH_2CH_3$, $CH_2CH_2S(O)CH_2CH_2CH_3$, $CH_2CH_2S(O)CH(CH_3)_2$, $CH_2CH_2S(O)CH_2(CH_2)_2CH_3$, $CH_2CH_2S(O)_2CH_3$, $CH_2CH_2S(O)_2CH_2CH_3$, $CH_2CH_2S(O)_2CH_2CH_2CH_3$, $CH_2CH_2S(O)_2CH(CH_3)_2$ and $CH_2CH_2S(O)_2CH_2(CH_2)_2CH_3$. In some embodiments, $R_2$ is selected from the group consisting of 1,2,4-oxadiazol-3-yl, 1,2,4-oxadiazol-5-yl, 1,3,4-oxadiazol-2-yl, 1,2,4-triazol-5-yl and 1,2,4-triazol-1-yl, 3-methyl-1,2,4-oxadiazol-5-yl, 3-methyl-1,2,4-oxadiazol-5-yl, 3-ethyl-1,2,4-oxadiazol-5-yl, 3-ethyl-1,2,4-oxadiazol-5-yl, 5-methyl-1,3,4-oxadiazol-2-yl, 5-ethyl-1,3,4-oxadiazol-2-yl, 3-methyl-1,2,4-triazol-5-yl, 3-ethyl-1,2,4-triazol-5-yl, 3-methyl-1,2,4-triazol-1-yl, 3-ethyl-1,2,4-triazol-1-yl, 5-methyl-1,2,4-triazol-1-yl and 5-ethyl-1,2,4-triazol-1-yl.

In some embodiments, D is $N-R_2$ and $R_2$ is $-Ar_2-Ar_3$ wherein $Ar_2$ and $Ar_3$ are independently aryl or heteroaryl optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro. In some embodiments, compounds of the present invention are represented by Formula (It) as shown below:

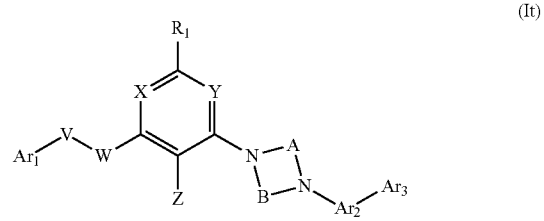

(It)

wherein each variable in Formula (It) has the same meaning as described herein. In some embodiments, $Ar_2$ is a heteroaryl and $Ar_3$ is phenyl. In some embodiments, the heteroaryl and phenyl are optionally substituted with 1 to 5 substituents selected from the group consisting of H, $C_{1-4}$ alkoxy, $C_{1-8}$ alkyl, $C_{1-4}$ alkylcarboxamide, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, halogen, hydroxyl and nitro.

In some embodiments, D is $N-R_2$ wherein $R_2$ is Formula (C):

(C)

wherein:

G is C=O or $CR_{16}R_{17}$; where $R_{16}$ and $R_{17}$ are independently H or $C_{1-8}$ alkyl; and $Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-4}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro. In some embodiments, compounds of the present invention are represented by Formula (Iu) as shown below:

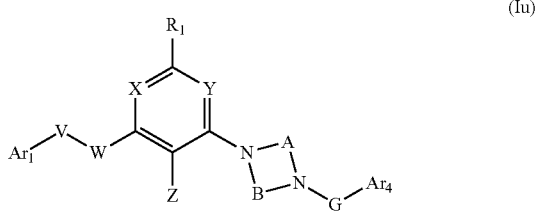

(Iu)

wherein each variable in Formula (Iu) has the same meaning as described herein.

In some embodiments, D is N—$R_2$, $R_2$ is Formula (C) and G is C=O. In some embodiments, $Ar_4$ is phenyl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-4}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro. In some embodiments, $Ar_4$ is phenyl optionally substituted with 1 to 5 substituents selected from the group consisting of $C_{1-5}$ acyl, $C_{1-4}$ alkoxy, $C_{1-4}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $Ar_4$ is phenyl optionally substituted with 1 to 5 substituents selected from the group consisting of $C_{1-5}$ acyl, $C_{1-4}$ alkoxy, $C_{1-4}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl. In some embodiments, $Ar_4$ is heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro. In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl. In some embodiments, $Ar_4$ is a 5-membered heteroaryl, for example, as shown in TABLE 2A, supra. In some embodiments, $Ar_4$ is a 6-membered heteroaryl, for example, as shown in TABLE 4, supra. In some embodiments, $Ar_4$ is selected from the group consisting of pyridinyl, pyridazinyl, pyrimidinyl and pyrazinyl. In some embodiments, $Ar_4$ is 2-pyridyl.

In some embodiments, D is N—$R_2$ wherein $R_2$ is Formula (C) and G is $CR_{16}R_{17}$. In some embodiments, $Ar_4$ is phenyl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro. In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $Ar_4$ is phenyl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl. In some embodiments, $Ar_4$ is heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$ heteroalkylene, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro. In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carboxamide, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, halogen and hydroxyl. In some embodiments, $Ar_4$ is heteroaryl optionally substituted with 1 to 5 substituents selected from the group consisting of $C_{1-5}$ acyl, $C_{1-4}$ alkoxy, $C_{1-8}$ alkyl, $C_{1-4}$ alkylsulfinyl, $C_{1-4}$ alkylsulfonyl, $C_{1-4}$ alkylthio, $C_{1-4}$ haloalkoxy, $C_{1-4}$ haloalkyl, $C_{1-4}$ haloalkyl, halogen and hydroxyl. In some embodiments, $Ar_4$ is a 5-membered heteroaryl, for example, as shown in TABLE 2A, supra. In some embodiments, $Ar_4$ is a 6-membered heteroaryl, for example, as shown in TABLE 4, supra. In some embodiments, $Ar_4$ is selected from the group consisting of pyridinyl, pyridazinyl, pyrimidinyl and pyrazinyl. In some embodiments, $Ar_4$ is 2-pyridyl. In some embodiments, D is $N-R_2$ wherein $R_2$ is Formula (C), G is $CR_{16}R_{17}$ and $R_{16}$ and $R_{17}$ are independently H or $C_{1-2}$ alkyl.

In some embodiments, Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1, or 2 groups selected from the group consisting of $C_{2-4}$ dialkylmino, hydroxy, and halogen.

In some embodiments, Z is selected from the group consisting of nitro, amino, formyl, $NHC(O)CF_3$, Br, $NHC(O)CH_3$, $N(C(O)CH_3)_2$, $N(S(O)_2CH_3)_2$, $CH_3$, [1,3]dioxolan-2-yl, $CH_2OH$, $CH_2N(CH_3)_2$, and $C(O)CH_3$.

In some embodiments, Z is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, carboxamide, carboxy, cyano, aryl, $C_{1-4}$ haloalkyl, $C_{1-4}$ haloalkylcarboxamide, heteroaryl, hydroxyl, hydroxylamino, nitro and tetrazolyl, wherein $C_{1-8}$ alkyl is optionally substituted with 1, 2, 3 or 4 groups selected from the group consisting of $C_{1-5}$ acyl, $C_{1-5}$ acyloxy, $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, carbo-$C_{1-6}$-alkoxy, carboxamide, carboxy, cyano, formyl, $C_{1-4}$ haloalkoxy, $C_{1-4}$ haloalkylsulfinyl, $C_{1-4}$ haloalkylsulfonyl, $C_{1-4}$ haloalkylthio, halogen, hydroxyl, hydroxylamino and nitro.

In some embodiments, Z is selected from the group consisting of $C_{1-5}$ acyl, $C_{1-4}$ alkoxy, $C_{1-8}$ alkyl, $C_{1-4}$ alkylcarboxamide, $C_{1-4}$ alkylthiocarboxamide, $C_{1-4}$ alkylthioureyl, $C_{1-4}$ alkylureyl, carboxamide, carboxy, cyano, aryl, $C_{1-4}$ haloalkyl, $C_{1-4}$ haloalkylcarboxamide, heteroaryl, hydroxyl, hydroxylamino, nitro and tetrazolyl.

In some embodiments, Z is a heterocyclic group. In some embodiments, Z is a 5-membered heterocyclic group containing two oxygen atoms.

In some embodiments, Z is an alkyl group optionally substituted $C_{2-4}$-dialkylamino or hydroxy.

In some embodiments, Z is selected from the group consisting of formyl, $NHC(O)CH_3$, $NHC(O)CH_2CH_3$, $NHC(O)CH(CH_3)_2$, $CH_3$, $CH_2CH_3$, $CH(CH_3)_{25}CH_2CH_2CH_2CH_3$, $NHC(O)CF_3$, carboxy, $CF_3$, $CF_2CF_3$, nitro and 1H-tetrazol-5-yl.

In some embodiments, Z is selected from the group consisting of carboxy, $CF_3$, nitro and 1H-tetrazol-5-yl.

In some embodiments, Z is [1,3]-dioxolan-2-yl.
In some embodiments, Z is a formyl group.
In some embodiments, Z is a carboxy group.
In some embodiments, Z is a —$CH_2OH$ group.
In some embodiments, Z is a —$CH_2N(CH_3)_2$ group.
In some embodiments, Z is Formula (A):

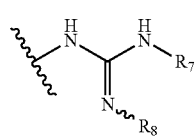

(A)

wherein:
$R_7$ is H, $C_{1-8}$ alkyl or $C_{3-6}$ cycloalkyl; and $R_9$ is H, nitro or nitrile. In some embodiments, $R_7$ is H or $C_{1-8}$ alkyl.

In some embodiments, $R_1$ is selected from the group consisting of H, $C_{1-4}$ alkoxy, $C_{1-8}$ alkyl, $C_{2-6}$ alkynyl, amino, $C_{3-6}$ cycloalkyl and $C_{1-4}$ haloalkyl. In some embodiments, $R_1$ is H or amino.

In some embodiments, $R_1$ is selected from the group consisting of H, $C_{1-8}$ alkyl, and amino.

In some embodiments, $Ar_1$ is aryl optionally substituted with $R_9$-$R_{13}$. In some embodiments, $Ar_1$ is phenyl.

In some embodiments, $Ar_1$ is heteroaryl. In some embodiments, $Ar_1$ is heteroaryl optionally substituted with $R_9$-$R_{13}$. In some embodiments, $Ar_1$ is a heteroaryl selected from TABLE 2A. In some embodiments, $Ar_1$ is a heteroaryl selected from TABLE 4 or an N-oxide thereof. In some embodiments, compounds of the invention are of Formula (Iv):

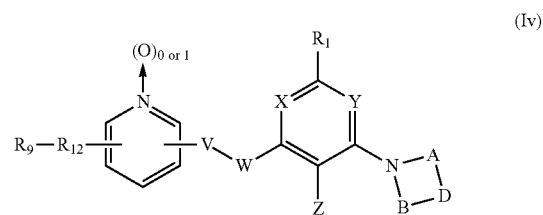

(Iv)

wherein A, B, D, V, W, X, Y, Z, $R_1$, $R_9$, $R_{10}$, $R_{11}$ and $R_{12}$ have the same meaning as described herein, supra and infra.

In some embodiments, $Ar_1$ is heteroaryl and $R_9$ is selected from the group consisting of H, $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide and sulfonamide.

In some embodiments, $R_9$ is selected from the group consisting of $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{2-6}$ dialkylsulfonamide, $C_{1-4}$ alkylsulfinyl, $C_{1-4}$ alkylsulfonyl, $C_{1-4}$ alkylthio, amino, arylsulfonyl, $C_{2-6}$ dialkylamino, $C_{2-6}$ dialkylsulfonamide, and carboxamide.

In some embodiments, $R_9$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4$—$CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, C≡CH, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$, $S(O)_2NHCH(CH_3)CH_2CH_3$, $S(O)_2N(CH_3)_2$, $S(O)_2N(Et)(CH_3)$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$, $SCH_2(CH_2)_2CH_3$, amino, $S(O)_2Ph$, $N(CH_3)_2$, $N(CH_3)(Et)$, $N(Et)_2$ and $C(O)NH_2$.

In some embodiments, $R_9$ is selected from the group consisting of cyano, $C_{3-6}$ cycloalkyl, halogen, $C_{1-4}$ haloalkoxy, $C_{1-4}$ haloalkyl, $C_{1-4}$ haloalkylsulfonyl, and $C_{1-4}$ haloalkylthio.

In some embodiments, $R_9$ is selected from the group consisting of cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$.

In some embodiments, $R_9$ is selected from the group consisting of CN, $CO_2Me$, $CO_2Et$, $S(O)_2CH_3$, $S(O)_2CF_3$, $N(CH_3)_2$, $N(Et)_2$, $C(O)NHCH_3$, $C(O)NHEt$, $C(O)N(CH_3)_2$, OH, $OCH_3$, and OEt.

In some embodiments, $R_9$ is selected from the group consisting of heterocyclic, heterocyclicsulfonyl, heteroaryl, hydroxy, $C_{4-7}$ oxo-cycloalkyl, phenoxy and phenyl.

In some embodiments, $R_9$ is selected from the group consisting of $C_{1-5}$ acyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, carboxamide, halogen and sulfonamide.

In some embodiments, $R_9$ is selected from the group consisting of $C(O)CH_3$, $C(O)CH_2CH_3$, $C(O)CH_2CH_2CH_3$, $C(O)CH(CH_3)_2$, $C(O)CH_2CH_2CH_2CH_3$, $OCH_3$, $OCH_2CH_3$, $OCH_2CH_2CH_3$, $OCH(CH_3)_2$, $OCH_2CH_2CH_2CH_3$, $CH_3$, $CH_2CH_3$, $CH_2CH_2CH_3$, $CH(CH_3)_2$, $CH(CH_3)(CH_2CH_3)$, $CH_2(CH_2)_2CH_3$, $CH_2(CH_2)_3CH_3$, $CH_2(CH_2)_4CH_3$, $CH_2(CH_2)_5CH_3$, $C(O)NHCH_3$, $C(O)NHCH_2CH_3$, $C(O)NHCH_2CH_2CH_3$, $C(O)NHCH(CH_3)_2$, $C(O)NHCH_2(CH_2)_2CH_3$, CCH, $S(O)_2NHCH_3$, $S(O)_2NHCH_2CH_3$, $S(O)_2NHCH_2CH_2CH_3$, $S(O)_2NHCH(CH_3)_2$, $S(O)_2NHCH_2(CH_2)_2CH_3$, $S(O)_2NHCH(CH_3)CH_2CH_3$, $S(O)CH_3$, $S(O)CH_2CH_3$, $S(O)CH_2CH_2CH_3$, $S(O)CH(CH_3)_2$, $S(O)CH_2(CH_2)_2CH_3$, $S(O)CH(CH_3)CH_2CH_3$, $S(O)_2CH_3$, $S(O)_2CH_2CH_3$, $S(O)_2CH_2CH_2CH_3$, $S(O)_2CH(CH_3)_2$, $S(O)_2CH_2(CH_2)_2CH_3$, $S(O)_2CH(CH_3)CH_2CH_3$, $SCH_3$, $SCH_2CH_3$, $SCH_2CH_2CH_3$, $SCH(CH_3)_2$ and $SCH_2(CH_2)_2CH_3$.

In some embodiments, $R_9$ is selected from the group consisting of amino, arylsulfonyl, carboxy, cyano, $C_{3-6}$ cycloalkyl, halogen, $C_{1-4}$ haloalkoxy, $C_{1-4}$ haloalkyl and $C_{1-4}$ haloalkylthio.

In some embodiments, $R_9$ is selected from the group consisting of phenylsulfonyl, cyclopropyl, cyclobutyl, cyclopentyl, cyclohexyl, Cl, F, Br, $OCF_3$, $OCHF_2$, $OCH_2CF_3$, $CF_3$, $CHF_2$, $CH_2CF_3$, $SCF_3$, $SCHF_2$ and $SCH_2CF_3$.

In some embodiments, $R_9$ is selected from the group consisting of heterocyclic, heteroaryl, $C_{4-7}$ oxo-cycloalkyl, phenoxy and phenyl. In some embodiments, $R_9$ is selected from the group consisting of morpholin-4-yl, thiomorpholin-4-yl, 1-oxo-1λ⁴-thiomorpholin-4-yl, 1,1-Dioxo-1λ⁶-thiomorpholin-4-yl, piperazin-1-yl, 4-methyl-piperazin-1-yl, 4-ethyl-piperazin-1-yl, 4-propyl-piperazin-1-yl, piperidin-1-yl, pyrrolidin-1-yl, 2,5-dioxo-imidazolidin-4-yl, 2,4-dioxo-thiazolidin-5-yl, 4-oxo-2-thioxo-thiazolidin-5-yl, 3-methyl-2,5-dioxo-imidazolidin-4-yl, 3-methyl-2,4-dioxo-thiazolidin-5-yl, 3-methyl-4-oxo-2-thioxo-thiazolidin-5-yl, 3-ethyl-2,5-dioxo-imidazolidin-4-yl, 3-ethyl-2,4-dioxo-thiazolidin-5-yl, and 3-ethyl-4-oxo-2-thioxo-thiazolidin-5-yl.

In some embodiments, $R_9$ is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl.

In some embodiments, $R_9$ is $C_{1-8}$ alkyl or $C_{1-4}$ alkoxy optionally substituted with 1 to 5 substituents selected independently from the group consisting of $C_{1-4}$ alkoxy, $C_{1-4}$ alkylcarboxamide, $C_{1-4}$ alkylsulfonamide, $C_{1-4}$ alkylsulfinyl, $C_{1-4}$ alkylsulfonyl, $C_{1-4}$ alkylthio, carbo-$C_{1-6}$-alkoxy, carboxamide, carboxy, cyano, heterocyclic, hydroxyl and phenyl.

In some embodiments, $R_9$ is $C_{1-4}$ alkylsulfonyl optionally substituted with 1 to 5 substituents selected independently from the group consisting of $C_{1-4}$ alkoxy, carboxamide, heteroaryl, heterocyclic and phenyl.

In some embodiments, $R_9$ is $C_{1-4}$ alkylsulfonyl substituted with the heteroaryl group. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl.

In some embodiments, $R_9$ is arylsulfonyl, heteroaryl, phenoxy or phenyl optionally substituted with 1 to 5 substituents selected independently from the group consisting of $C_{1-5}$ acyl, $C_{1-4}$ alkoxy, $C_{1-8}$ alkyl, $C_{1-4}$ alkylsulfonamide, $C_{1-4}$ alkylsulfinyl, $C_{1-4}$ alkylsulfonyl, $C_{1-4}$ alkylthio, carboxamide, carboxy, cyano, halogen, $C_{1-4}$ haloalkoxy, $C_{1-4}$ haloalkyl, $C_{1-4}$ haloalkylthio and hydroxyl.

In some embodiments, $R_9$ is arylsulfonyl, heteroaryl, phenoxy or phenyl each optionally substituted with 1 to 5 substituents selected independently from the group consisting of $C_{1-4}$ alkoxy, $C_{1-8}$ alkyl, cyano, halogen, $C_{1-4}$ haloalkoxy, $C_{1-4}$ haloalkyl and hydroxyl.

In some embodiments, $R_9$ is a heterocyclic group as described herein.

In some embodiments, $R_9$ is a heterocyclic group represented by the formulae shown in Table 2B, supra. In some embodiments, $R_9$ is a heterocyclic group represented by the formulae shown in Table 2C, supra. In some embodiments, $R_9$ is a heterocyclic group represented by the formulae shown in Table 2D, supra. In some embodiments, $R_9$ is a heterocyclic group represented by the formulae shown in Table 2E, supra. In some embodiments, $R_9$ is a heterocyclic group represented by the formulae shown in Table 2F, supra. In some embodiments, $R_9$ is a heterocyclic group represented by the formulae shown in Table 2G, supra.

In some embodiments, $R_9$ is of Formula (D):

(D)

wherein:

"p" and "r" are independently 0, 1, 2 or 3; and $R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl or phenyl may be optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl.

In some embodiments, $R_9$ is of Formula (D) wherein "p" and "r" are independently 0, or 1; and $R_{18}$ is H, carbo-$C_{1-6}$-alkoxy, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl.

In some embodiments, p=0 and r=0.

In some embodiments, $R_{18}$ is phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl.

In some embodiments, p=0 and r=1.

In some embodiments, $R_{18}$ is carbo-$C_{1-6}$-alkoxy or carboxy.

In some embodiments, p=0 and r=0.

In some embodiments, $R_{18}$ is heteroaryl or phenyl optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl. In some embodiments, the heteroaryl is selected from the group consisting of 1H-imidazol-4-yl, [1,2,4]triazol-1-yl, [1,2,3]triazol-1-yl, [1,2,4]triazol-4-yl, pyrrol-1-yl, pyrazol-1-yl, 1H-pyrazol-3-yl, imidazol-1-yl, oxazol-5-yl, oxazol-2-yl, [1,3,4]oxadiazol-2-yl, [1,3,4]thiadiazol-2-yl, [1,2,4]oxadiazol-3-yl, [1,2,4]thiadiazol-3-yl, tetrazol-1-yl, pyrimidin-5-yl, pyrimidin-2-yl, pyrimidin-4-yl, pyridazin-3-yl, pyridazin-4-yl, pyrazin-2-yl, 1,3-dioxo-1,3-dihydro-isoindol-2-yl and [1,2,3]thiadiazol-4-yl.

In some embodiments, p=2 and r=1. In some embodiments, $R_{18}$ is H, $C_{1-5}$ acyl or $C_{1-8}$ alkyl.

In some embodiments, $R_{10}$-$R_{13}$ are independently $C_{1-5}$ acyl, $C_{1-4}$ alkoxy, $C_{1-8}$ alkyl, $C_{1-4}$ alkylcarboxamide, $C_{1-4}$ alkylureyl, carbo-$C_{1-6}$-alkoxy, carboxamide, carboxy, cyano, $C_{3-6}$ cycloalkyl, halogen, $C_{1-4}$ haloalkoxy and $C_{1-4}$ haloalkyl.

In some embodiments, one or two $R_{10}$-$R_{13}$ groups are independently halogen. In some embodiments, one $R_{10}$-$R_{13}$ group is a halogen.

In some embodiments, $Ar_1$ is phenyl and $R_9$ is substituted at the para position on the phenyl.

In some embodiments, $Ar_1$ is phenyl optionally substituted with $R_9$, $R_{10}$ and $R_{11}$. In some embodiments, the compounds of the invention are of Formula (Iw):

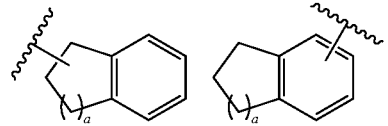

wherein A, B, D, V, W, X, Y, Z, $R_1$ have the same meaning as described herein, supra and infra, and $R_9$ is cyano, carbo-$C_{1-5}$-alkoxy, carboxy, $C_{2-6}$ dialkylamino, $C_{1-4}$ alkylcarboxamide, dialkylsulfonamide, $C_{1-4}$ alkylsulfonyl, hydroxyl, $C_{1-4}$ alkoxy, 5-membered heteroaryl, 6-membered heteroaryl, or heterocyclic, wherein the 6-membered heteroaryl is optionally an N-oxide; and $R_{10}$ and $R_{11}$ are independently H or halogen. In some embodiments, $R_9$ is cyano, carbomethoxy, carboethoxy, carboisopropoxy, carboxy, dimethylamino, diethylamino, methylethylamino, C(O)NHCH$_3$, C(O)NHCH$_2$CH$_3$, C(O)NH(CH$_3$)$_2$, S(O)$_2$CH$_3$, S(O)$_2$CH$_2$CH$_3$, hydroxyl, OCH$_3$, [1,2,4]triazol-4-yl, thiazol-2-yl, 3H-imidazol-4-yl, 1H-imidazol-2-yl, 1H-imidazol-4-yl, pyridin-2-yl, pyridin-3-yl, pyridin-4-yl, 1-oxy-pyridin-2-yl, 1-oxy-pyridin-3-yl, 1-oxy-pyridin-4-yl, or 2-oxo-oxazolidin-4-yl. In some embodiments, $R_{10}$ is H and $R_{11}$ is F.

In some embodiments, $Ar_1$ is phenyl and two adjacent $R_{10}$-$R_{11}$ groups form a 5, 6 or 7 membered cycloalkyl, cycloalkenyl or heterocyclic group with the phenyl group wherein the 5, 6 or 7 membered group is optionally substituted with halogen.

In some embodiments, $Ar_1$ is phenyl and two adjacent $R_{10}$-$R_{11}$ groups form a 5, 6 or 7 membered cycloalkyl group with the phenyl group and is of the formulae shown below:

TABLE 5

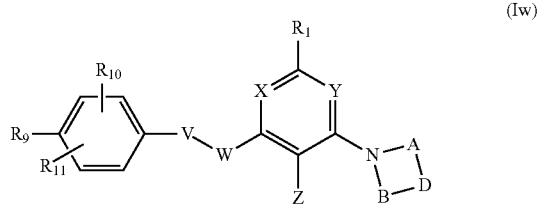

wherein "a" is 1, 2 or 3 to give a 5, 6 or 7 membered cycloalkyl fused together with the phenyl group where two of the ring carbons are shared between the cycloalkyl and phenyl group. In some embodiments, the cycloalkyl is optionally substituted with halogen. In some embodiments, the halogen is fluorine.

In some embodiments, $Ar_1$ is phenyl and two adjacent $R_{10}$-$R_{11}$ groups form a 5, 6 or 7 membered cycloalkenyl group with the phenyl group and is of the formulae shown in TABLE 5 and has at least one carbon-carbon ring double bond present that is not part of the phenyl group (i.e., cycloalkenyl), for example, 1H-Indenyl and dihydro-naphthyl. In some embodiments, the cycloalkenyl is optionally substituted with halogen. In some embodiments, the halogen is fluorine.

In some embodiments, $Ar_1$ is phenyl and two adjacent $R_{10}$-$R_{11}$ groups form a 5, 6 or 7 heterocyclic group with the phenyl group and is of the formulae in TABLE 5 wherein one or more ring cycloalkyl carbons are replaced by a O, S, S(O), S(O)$_2$, NH or N—$C_{1-4}$-alkyl group. In some embodiments, the heterocyclic group is optionally substituted with halogen. In some embodiments, the halogen is fluorine.

In some embodiments, $Ar_1$ is phenyl and two adjacent $R_{10}$-$R_{11}$ groups form a 5 membered heterocyclic group with the phenyl group. In some embodiments, the 5 membered heterocyclic group with the phenyl group together form a 2,3-dihydro-benzofuran-5-yl or benzo[1,3]dioxol-5-yl group. In some embodiments, the two adjacent groups form a 6 membered heterocyclic group with the phenyl group. In some embodiments, the 6 membered heterocyclic group with the phenyl group together form a 2,3-dihydro-benzo[1,4]dioxin-6-yl or 2,3-dihydro-benzo[1,4]dioxin-2-yl group. In some embodiments, the two adjacent groups form a 7 membered heterocyclic group with the phenyl group. In some embodiments, the 7 membered heterocyclic group with the phenyl group together form a 3,4-dihydro-2H-benzo[b][1,4]dioxepin-7-yl group.

In some embodiments, $Ar_1$ is heteroaryl and two adjacent $R_{10}$-$R_{11}$ groups form a 5, 6 or 7 membered cycloalkyl, cycloalkenyl or heterocyclic group with the heteroaryl group wherein the 5, 6 or 7 membered group is optionally substituted with halogen. In some embodiments, An is a heteroaryl selected from TABLE 2A. In some embodiments, $Ar_1$ is a heteroaryl selected from TABLE 4. In some embodiments, the two adjacent groups form a 5 membered heterocyclic group with the heteroaryl group. In some embodiments, the two adjacent groups form a 6 membered heterocyclic group with the heteroaryl group. In some embodiments, the two adjacent groups form a 7 membered heterocyclic group with the heteroaryl group.

In some embodiments, $R_5$ is H, $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, hydroxyl, nitro, $C_{4-7}$ oxo-cycloalkyl, sulfonamide and nitro.

In some embodiments, $R_5$ and $R_6$ are independently H or F.
In some embodiments, X is N and Y is CH.
In some embodiments, X is N and Y is CF.
In some embodiments, X is CH and Y is N.
In some embodiments, X and Y are N.
In some embodiments, X and Y are CH.
In some embodiments, X is CH and Y is CF.

Some embodiments of the present invention include compounds illustrated in TABLES A, B, C, D and E; these TABLES are shown below.

TABLE A

| Cmpd# | Structure | Chemical Name |
|---|---|---|
| A1 | 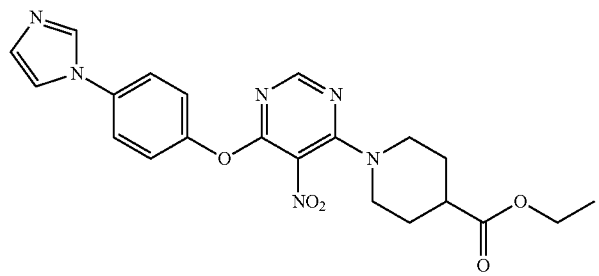 [SMILES: CCOC(=O)C1CCN(c2ncnc(Oc3ccc(-n4ccnc4)cc3)c2[N+](=O)[O-])CC1] | 1-[6-(4-Imidazol-1-yl-phenoxy)-5-nitro-pyrimidin-1-yl]-piperidine-4-carboxylic acid ethyl ester |
| A2 | 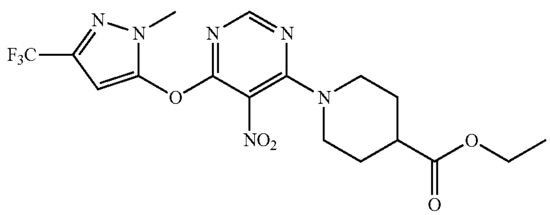 [SMILES: CCOC(=O)C1CCN(c2ncnc(Oc3cc(C(F)(F)F)nn3C)c2[N+](=O)[O-])CC1] | 1-[6-(2-Methyl-5-trifluoromethyl-2H-pyrazol-3-yloxy)-5-nitro-pyrimidin-4-yl]-piperidine-4-carboxylic acid ethyl ester |
| A3 | 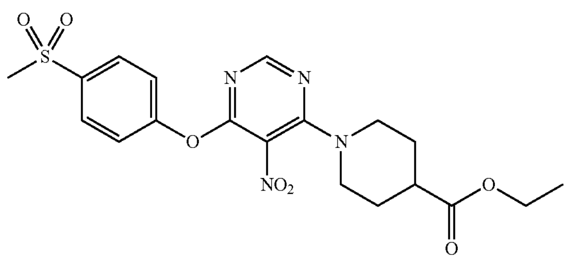 [SMILES: CCOC(=O)C1CCN(c2ncnc(Oc3ccc(S(C)(=O)=O)cc3)c2[N+](=O)[O-])CC1] | 1-[6-(4-Methanesulfonyl-phenoxy)-5-nitro-pyrimidin-4-yl]-piperidine-4-carboxylic acid ethyl ester |
| A4 | 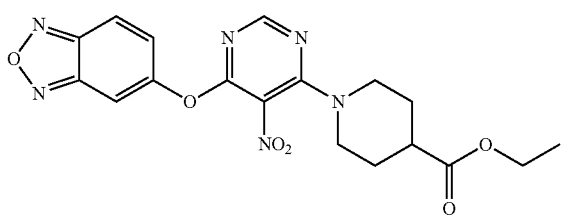 [SMILES: CCOC(=O)C1CCN(c2ncnc(Oc3ccc4nonc4c3)c2[N+](=O)[O-])CC1] | 1-[6-(Benzo[1,2,5]oxadiazol-5-yloxy)-5-nitro-pyrimidin-4-yl]-piperidine-4-carboxylic acid ethyl ester |
| A5 | 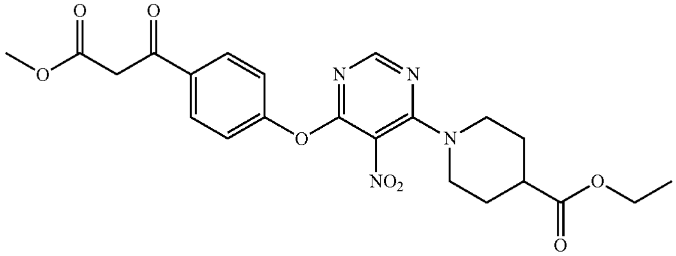 [SMILES: CCOC(=O)C1CCN(c2ncnc(Oc3ccc(C(=O)CC(=O)OC)cc3)c2[N+](=O)[O-])CC1] | 1-{6-[4-(2-Methoxycarbonyl-acetyl)-phenoxy]-5-nitro-pyrimidin-4-yl}-piperidine-4-carboxylic acid ethyl ester |

TABLE A-continued

| Cmpd# | Structure | Chemical Name |
|---|---|---|
| A6 | 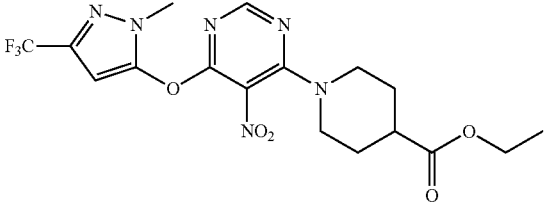 [SMILES: CCOC(=O)C1CCN(c2ncnc(Oc3cc(C(F)(F)F)nn3C)c2[N+](=O)[O-])CC1] | 1-[5-Amino-6-(2-methyl-5-trifluoromethyl-2H-pyrazol-3-yloxy)-pyrimidin-4-yl]-piperidine-4-carboxylic acid ethyl ester |
| A7 | 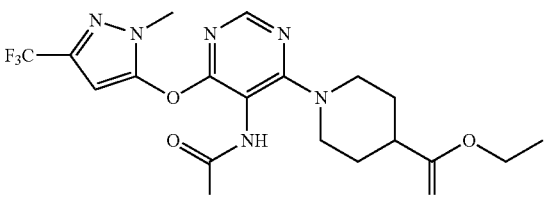 | 1-[6-(2-Methyl-5-trifluoromethyl-2H-pyrazol-3-yloxy)-5-(2,2,2-trifluoro-acetylamino)-pyrimidin-4-yl]-piperidine-4-carboxylic acid ethyl ester |
| A8 | 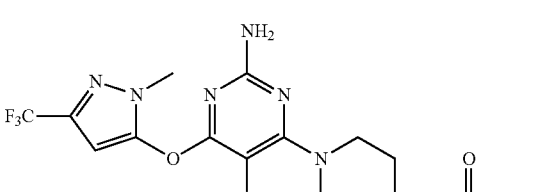 | Propionic acid 1-[2-amino-5-formyl-6-(2-methyl-5-trifluoromethyl-2H-pyrazol-3-yloxy)-pyrimidin-4-yl]-piperidin-4-yl ester |
| A9 | 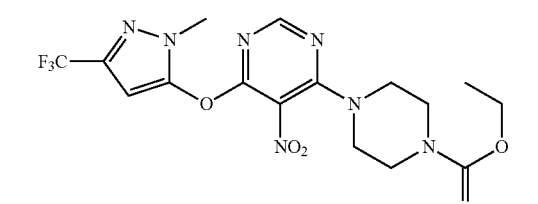 | 4-[6-(2-Methyl-5-trifluoromethyl-2H-pyrazol-3-yloxy)-5-nitro-pyrimidin-4-yl]-piperazine-1-carboxylic acid ethyl ester |
| A10 | 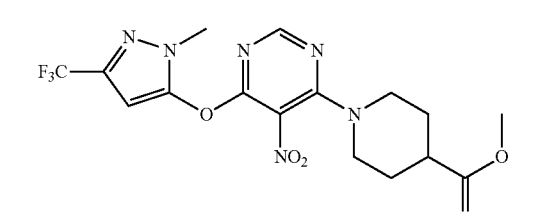 | 1-[6-(2-Methyl-S-trifluoromethyl-2H-pyrazol-3-yloxy)-5-nitro-pyrimidin-4-yl]-piperidine-4-carboxylic acid methyl ester |
| A11 | 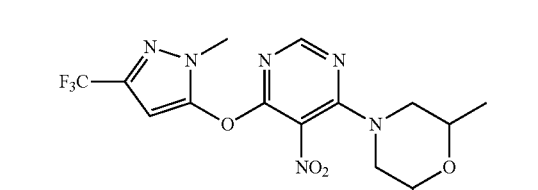 | 2,6-Dimethyl-4-[6-(2-methyl-5-trifluoromethyl-2H-pyrazol-3-yloxy)-5-nitro-pyrimidin-4-yl]-morpholine |
| A12 | 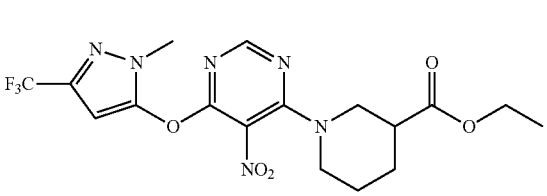 [SMILES: CCOC(=O)C1CCCN(c2ncnc(Oc3cc(C(F)(F)F)nn3C)c2[N+](=O)[O-])C1] | 1-[6-(2-Methyl-5-trifluoromethyl-2H-pyrazol-3-yloxy)-5-nitro-pyrimidin-4-yl]-piperidine-3-carboxylic acid ethyl ester |

TABLE A-continued

| Cmpd# | Structure | Chemical Name |
|---|---|---|
| A13 | 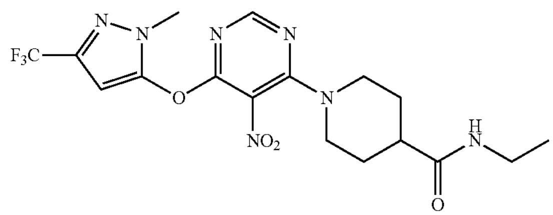 [SMILES: CCNC(=O)C1CCN(c2ncnc(Oc3cc(C(F)(F)F)nn3C)c2[N+](=O)[O-])CC1] | 1-[6-(2-Methyl-5-trifluoromethyl-2H-pyrazol-3-yloxy)-5-nitro-pyrimidin-4-yl]-piperidine-4-carboxylic acid ethylamide |
| A14 | 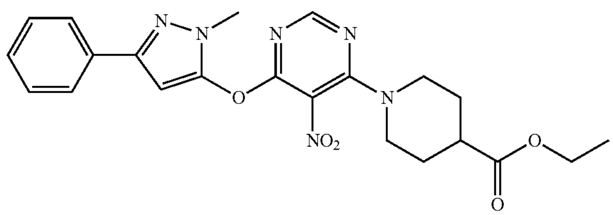 [SMILES: CCOC(=O)C1CCN(c2ncnc(Oc3cc(-c4ccccc4)nn3C)c2[N+](=O)[O-])CC1] | 1-[6-(2-Methyl-5-phenyl-2H-pyrazol-3-yloxy)-5-nitro-pyrimidin-4-yl]-piperidine-4-carboxylic acid ethyl ester |
| A15 | 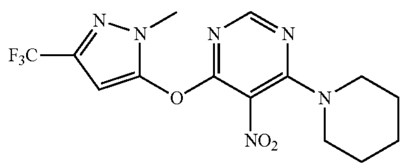 [SMILES: Cn1nc(C(F)(F)F)cc1Oc1ncnc(N2CCCCC2)c1[N+](=O)[O-]] | 4-(2-Methyl-5-trifluoromethyl-2H-pyrazol-3-yloxy)-5-nitro-6-piperidin-1-yl-pyrimidine |
| A16 | 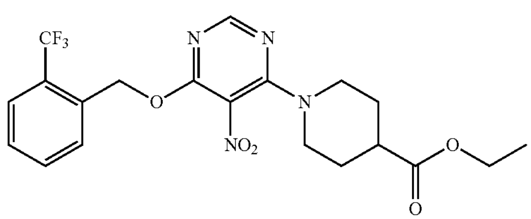 [SMILES: CCOC(=O)C1CCN(c2ncnc(OCc3ccccc3C(F)(F)F)c2[N+](=O)[O-])CC1] | 1-[5-Nitro-6-(2-trifluoromethyl-benzyloxy)-pyrimidin-4-yl]-piperidine-4-carboxylic acid ethyl ester |
| A17 | 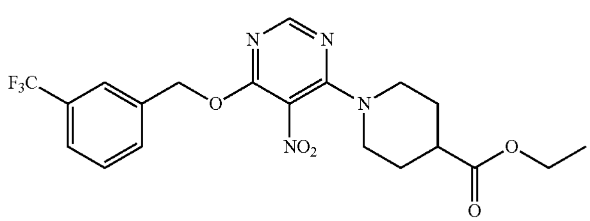 [SMILES: CCOC(=O)C1CCN(c2ncnc(OCc3cccc(C(F)(F)F)c3)c2[N+](=O)[O-])CC1] | 1-[5-Nitro-6-(3-trifluoromethyl-benzyloxy)-pyrimidin-4-yl]-piperidine-4-carboxylic acid ethyl ester |
| A18 | 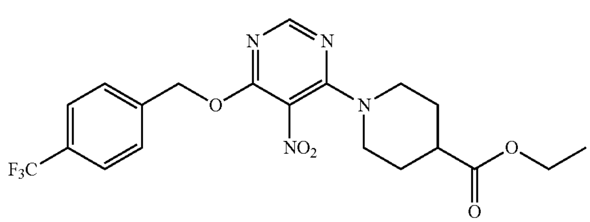 [SMILES: CCOC(=O)C1CCN(c2ncnc(OCc3ccc(C(F)(F)F)cc3)c2[N+](=O)[O-])CC1] | 1-[5-Nitro-6-(4-trifluoromethyl-benzyloxy)-pyrimidin-4-yl]-piperidine-4-carboxylic acid ethyl ester |
| A19 | 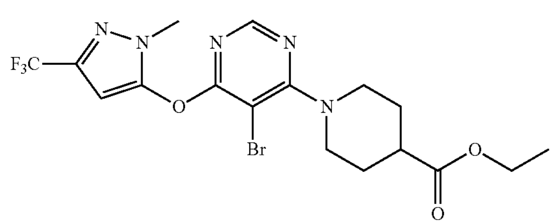 | 1-[5-Bromo-6-(2-methyl-5-trifluoromethyl-2H-pyrazol-3-yloxy)-pyrimidin-4-yl]-piperidine-4-carboxylic acid ethyl ester |

TABLE A-continued

| Cmpd# | Structure | Chemical Name |
|---|---|---|
| A20 | 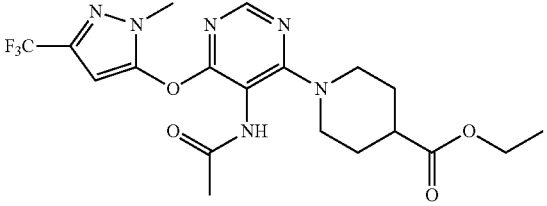 [SMILES: CCOC(=O)C1CCN(c2ncnc(Oc3cc(C(F)(F)F)nn3C)c2NC(C)=O)CC1] | 1-[5-Acetylamino-6-(2-methyl-5-trifluoromethyl-2H-pyrazol-3-yloxy)-pyrimidin-4-yl]-piperidine-4-carboxylic acid ethyl ester |
| A21 | 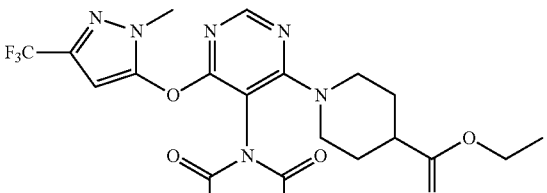 | 1-[5-Diacetylamino-6-(2-methyl-5-trifluoromethyl-2H-pyrazol-3-yloxy)-pyrimidin-4-yl]-piperidine-4-carboxylic acid ethyl ester |
| A22 | 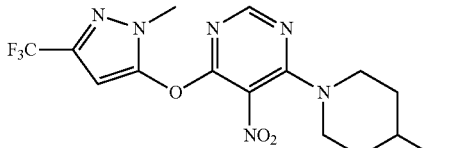 | 1-[6-(2-Methyl-5-trifluoromethyl-2H-pyrazol-3-yloxy)-5-nitro-pyrimidin-4-yl]-piperidine-4-carboxylic acid |
| A23 | 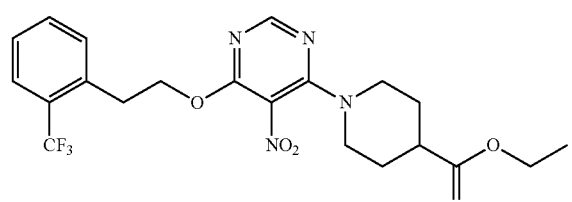 | 1-{5-Nitro-6-[2-(2-trifluoromethyl-phenyl)-ethoxy]-pyrimidin-4-yl}-piperidine-4-carboxylic acid ethyl ester |
| A24 | 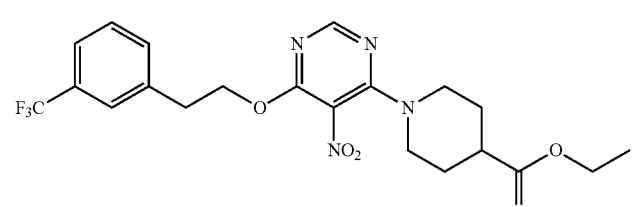 | 1-{5-Nitro-6-[2-(3-trifluoromethyl-phenyl)-ethoxy]-pyrimidin-4-yl}-piperidine-4-carboxylic acid ethyl ester |
| A25 | 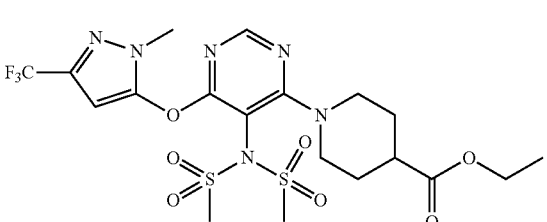 | 1-[5-Di-(methanesulfonyl)amino-6-(2-methyl-5-trifluoromethyl-2H-pyrazol-3-yloxy)-pyrimidin-4-yl]-piperidine-4-carboxylic acid ethyl ester |
| A26 | 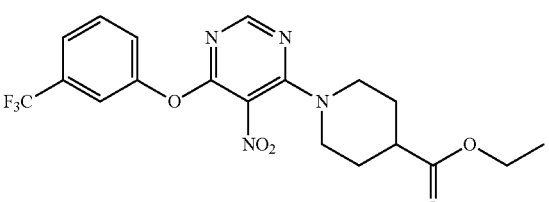 | 1-[5-Nitro-6-(3-trifluoromethyl-phenoxy)-pyrimidin-4-yl]-piperidine-4-carboxylic acid ethyl ester |

TABLE A-continued

| Cmpd# | Structure | Chemical Name |
|---|---|---|
| A27 | 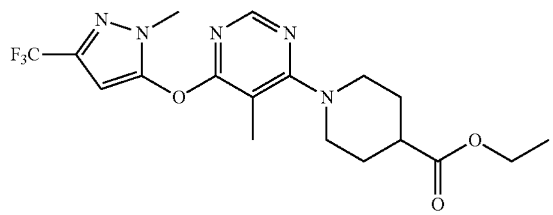 [SMILES: CCOC(=O)C1CCN(c2ncnc(Oc3cc(C(F)(F)F)nn3C)c2C)CC1] | 1-[5-Methyl-6-(2-methyl-5-trifluoromethyl-2H-pyrazol-3-yloxy)-pyrimidin-4-yl]-piperidine-4-carboxylic acid ethyl ester |
| A28 | 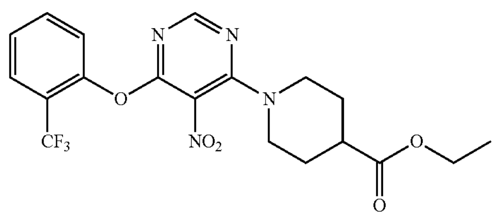 [SMILES: CCOC(=O)C1CCN(c2ncnc(Oc3ccccc3C(F)(F)F)c2[N+](=O)[O-])CC1] | 1-[5-Nitro-6-(2-trifluoromethyl-phenoxy)-pyrimidin-4-yl]-piperidine-4-carboxylic acid ethyl ester |
| A29 | 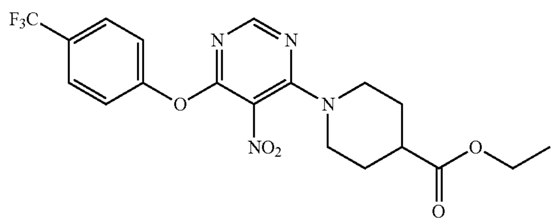 [SMILES: CCOC(=O)C1CCN(c2ncnc(Oc3ccc(C(F)(F)F)cc3)c2[N+](=O)[O-])CC1] | 1-[5-Nitro-6-(4-trifluoromethyl-phenoxy)-pyrimidin-4-yl]-piperidine-4-carboxylic acid ethyl ester |
| A30 | 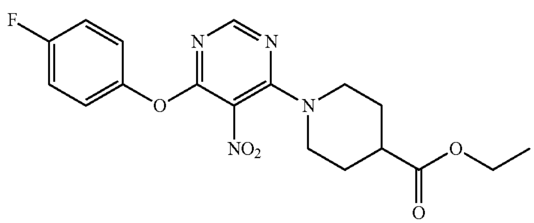 [SMILES: CCOC(=O)C1CCN(c2ncnc(Oc3ccc(F)cc3)c2[N+](=O)[O-])CC1] | 1-[6-(4-Fluoro-phenoxy)-5-nitro-pyrimidin-4-yl]-piperidine-4-carboxylic acid ethyl ester |
| A31 | 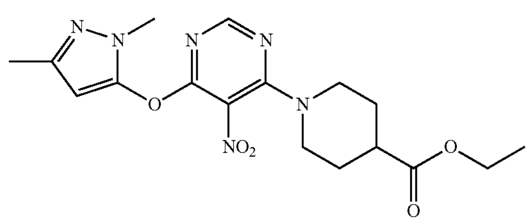 [SMILES: CCOC(=O)C1CCN(c2ncnc(Oc3cc(C)nn3C)c2[N+](=O)[O-])CC1] | 1-[6-(2,5-Dimethyl-2H-pyrazol-3-yloxy)-5-nitro-pyrimidin-4-yl]-piperidine-4-carboxylic acid ethyl ester |
| A32 | 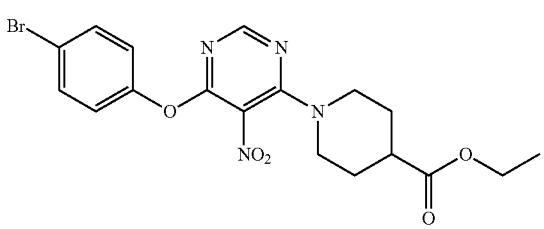 [SMILES: CCOC(=O)C1CCN(c2ncnc(Oc3ccc(Cl)cc3)c2[N+](=O)[O-])CC1] | 1-[6-(4-Bromo-phenoxy)-5-nitro-pyrimidin-4-yl]-piperidine-4-carboxylic acid ethyl ester |
| A33 | 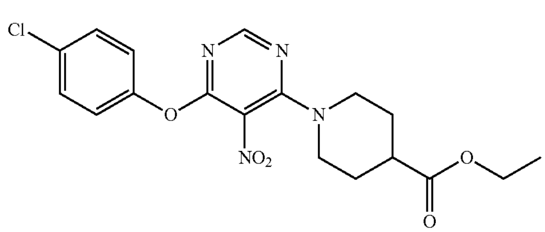 | 1-[6-(4-Chloro-phenoxy)-5-nitro-pyrimidin-4-yl]-piperidine-4-carboxylic acid ethyl ester |

TABLE A-continued

| Cmpd# | Structure | Chemical Name |
|---|---|---|
| A34 | 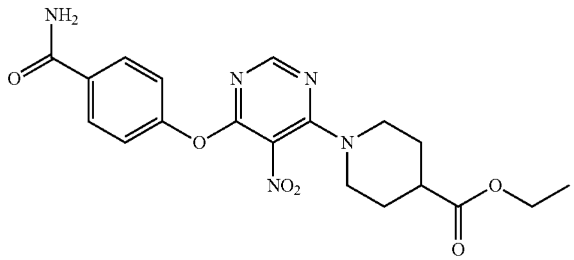 [SMILES: CCOC(=O)C1CCN(c2ncnc(Oc3ccc(C(N)=O)cc3)c2[N+](=O)[O-])CC1] | 1-[6-(4-Carbamoyl-phenoxy)-5-nitro-pyrimidin-4-yl]-piperidine-4-carboxylic acid ethyl ester |
| A35 | 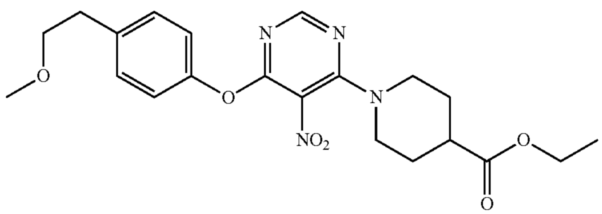 [SMILES: CCOC(=O)C1CCN(c2ncnc(Oc3ccc(CCOC)cc3)c2[N+](=O)[O-])CC1] | 1-{6-[4-(2-Methoxy-ethyl)-phenoxy]-5-nitro-pyrimidin-4-yl}-piperidine-4-carboxylic acid ethyl ester |
| A36 | 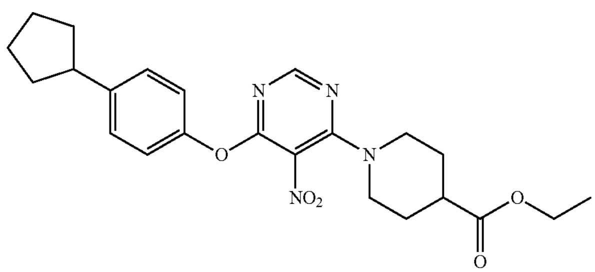 [SMILES: CCOC(=O)C1CCN(c2ncnc(Oc3ccc(C4CCCC4)cc3)c2[N+](=O)[O-])CC1] | 1-[6-(4-Cyclopentyl-phenoxy)-5-nitro-pyrimidin-4-yl]-piperidine-4-carboxylic acid ethyl ester |
| A37 | 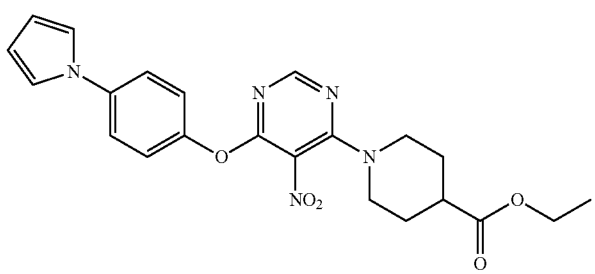 [SMILES: CCOC(=O)C1CCN(c2ncnc(Oc3ccc(-n4cccc4)cc3)c2[N+](=O)[O-])CC1] | 1-[5-Nitro-6-(4-pyrrol-1-yl-phenoxy)-pyrimidin-4-yl]-piperidine-4-carboxylic acid ethyl ester |
| A38 | 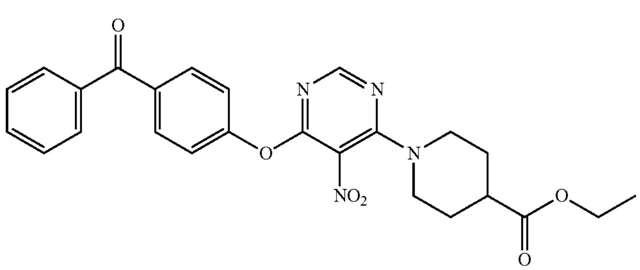 [SMILES: CCOC(=O)C1CCN(c2ncnc(Oc3ccc(C(=O)c4ccccc4)cc3)c2[N+](=O)[O-])CC1] | 1-[6-(4-Benzoyl-phenoxy)-5-nitro-pyrimidin-4-yl]-piperidine-4-carboxylic acid ethyl ester |
| A39 | 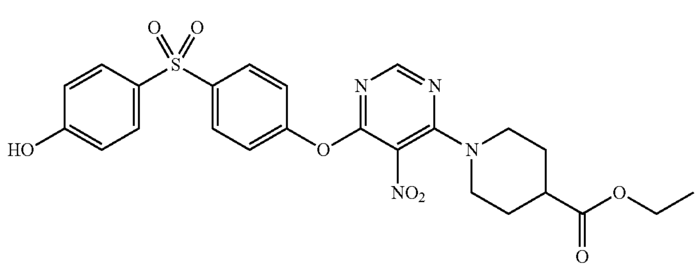 [SMILES: CCOC(=O)C1CCN(c2ncnc(Oc3ccc(S(=O)(=O)c4ccc(O)cc4)cc3)c2[N+](=O)[O-])CC1] | 1-{6-[4-(4-Hydroxy-benzenesulfonyl)-phenoxy]-5-nitro-pyrimidin-4-yl}-piperidine-4-carboxylic acid ethyl ester |

TABLE A-continued

| Cmpd# | Structure | Chemical Name |
| --- | --- | --- |
| A40 | 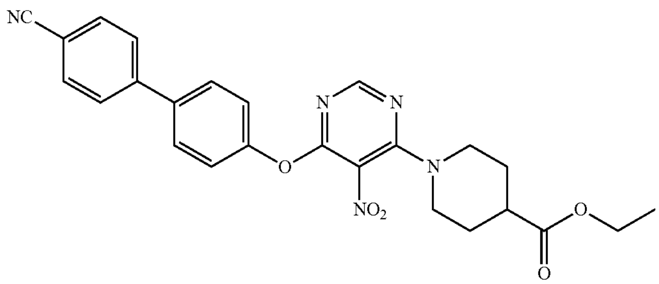 [SMILES: CCOC(=O)C1CCN(c2ncnc(Oc3ccc(-c4ccc(C#N)cc4)cc3)c2[N+](=O)[O-])CC1] | 1-[6-(4'-Cyano-biphenyl-4-yloxy)-5-nitro-pyrimidin-4-yl]-piperidine-4-carboxylic acid ethyl ester |
| A41 | 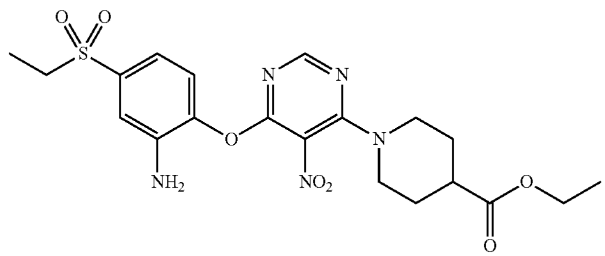 [SMILES: CCOC(=O)C1CCN(c2ncnc(Oc3ccc(S(=O)(=O)CC)cc3N)c2[N+](=O)[O-])CC1] | 1-[6-(2-Amino-4-ethanesulfonyl-phenoxy)-5-nitro-pyrimidin-4-yl]-piperidine-4-carboxylic acid ethyl ester |
| A42 | 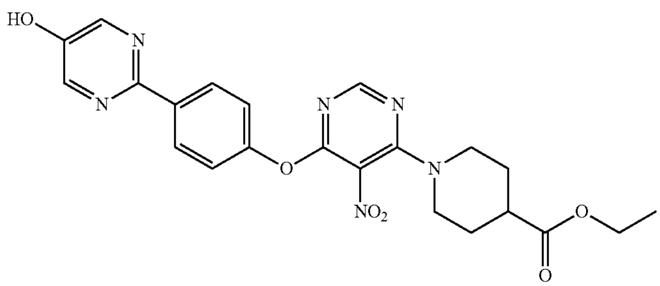 [SMILES: CCOC(=O)C1CCN(c2ncnc(Oc3ccc(-c4ncc(O)cn4)cc3)c2[N+](=O)[O-])CC1] | 1-{6-[4-(5-Hydroxy-pyrimidin-2-yl)-phenoxy]-5-nitro-pyrimidin-4-yl}-piperidine-4-carboxylic acid ethyl ester |
| A43 | 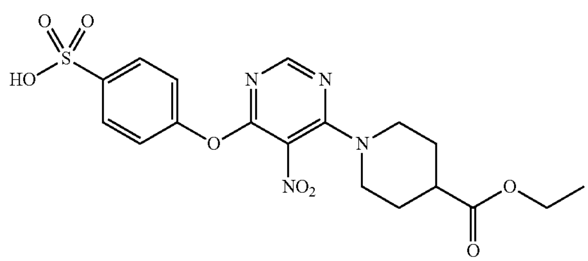 [SMILES: CCOC(=O)C1CCN(c2ncnc(Oc3ccc(S(=O)(=O)O)cc3)c2[N+](=O)[O-])CC1] | 1-[5-Nitro-6-(4-sulfo-phenoxy)-pyrimidin-4-yl]-piperidine-4-carboxylic acid ethyl ester |
| A44 | 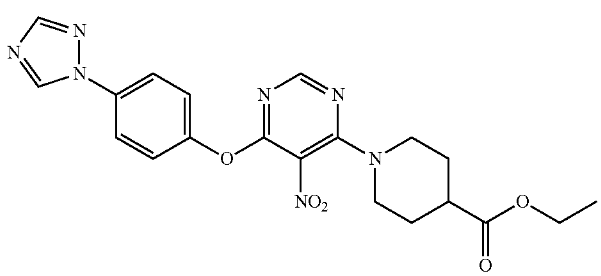 [SMILES: CCOC(=O)C1CCN(c2ncnc(Oc3ccc(-n4cncn4)cc3)c2[N+](=O)[O-])CC1] | 1-[5-Nitro-6-(4-[1,2,4]triazol-1-yl-phenoxy)-pyrimidin-4-yl]-piperidine-4-carboxylic acid ethyl ester |
| A45 | 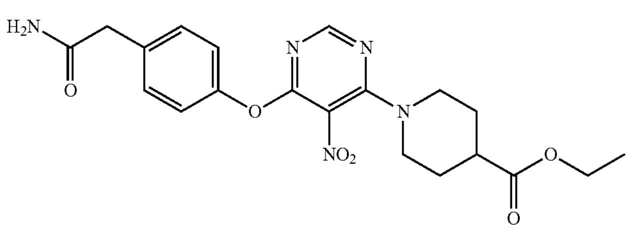 [SMILES: CCOC(=O)C1CCN(c2ncnc(Oc3ccc(CC(N)=O)cc3)c2[N+](=O)[O-])CC1] | 1-[6-(4-Carbamoylmethyl-phenoxy)-5-nitro-pyrimidin-4-yl]-piperidine-4-carboxylic acid ethyl ester |

TABLE A-continued

| Cmpd# | Structure | Chemical Name |
|---|---|---|
| A46 | 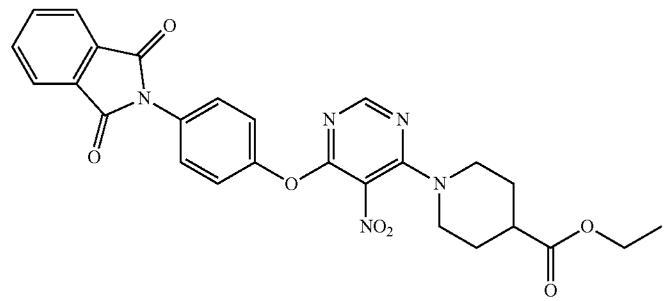 [SMILES: CCOC(=O)C1CCN(c2ncnc(Oc3ccc(N4C(=O)c5ccccc5C4=O)cc3)c2[N+](=O)[O-])CC1] | 1-{6-[4-(1,3-Dioxo-1,3-dihydro-isoindol-2-yl)-phenoxy]-5-nitro-pyrimidin-4-yl}-piperidine-4-carboxylic acid ethyl ester |
| A47 | 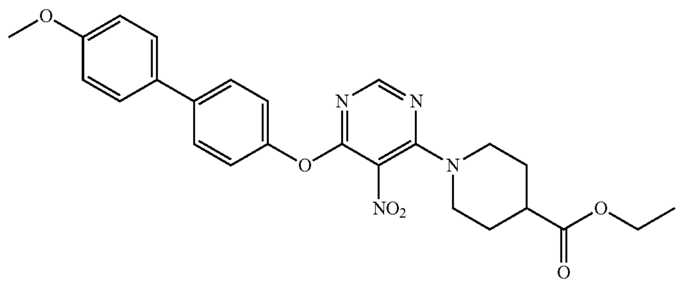 [SMILES: CCOC(=O)C1CCN(c2ncnc(Oc3ccc(-c4ccc(OC)cc4)cc3)c2[N+](=O)[O-])CC1] | 1-[6-(4'-Methoxy-biphenyl-4-yloxy)-5-nitro-pyrimidin-4-yl]-piperidine-4-carboxylic acid ethyl ester |
| A48 | 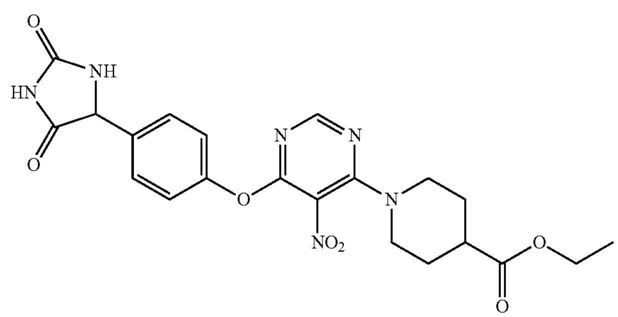 [SMILES: CCOC(=O)C1CCN(c2ncnc(Oc3ccc(C4NC(=O)NC4=O)cc3)c2[N+](=O)[O-])CC1] | 1-{6-[4-(2,5-Dioxo-imidazolidin-4-yl)-phenoxy]-5-nitro-pyrimidin-4-yl}-piperidine-4-carboxylic acid ethyl ester |
| A49 | 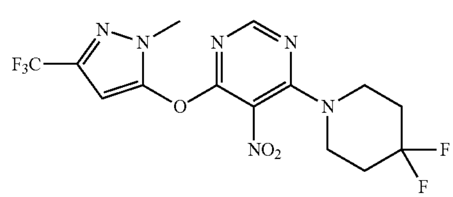 [SMILES: Cn1nc(C(F)(F)F)cc1Oc1ncnc(N2CCC(F)(F)CC2)c1[N+](=O)[O-]] | 4-(4,4-Difluoro-piperidin-1-yl)-6-(2-methyl-5-trifluoromethyl-2H-pyrazol-3-yloxy)-5-nitro-pyrimidine |
| A50 | 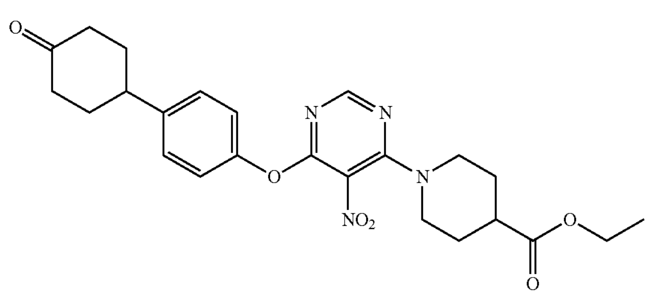 [SMILES: CCOC(=O)C1CCN(c2ncnc(Oc3ccc(C4CCC(=O)CC4)cc3)c2[N+](=O)[O-])CC1] | 1-{5-Nitro-6-[4-(4-oxo-cyclohexyl)-phenoxy]-pyrimidin-4-yl}-piperidine-4-carboxylic acid ethyl ester |

TABLE A-continued

| Cmpd# | Structure | Chemical Name |
|---|---|---|
| A51 | 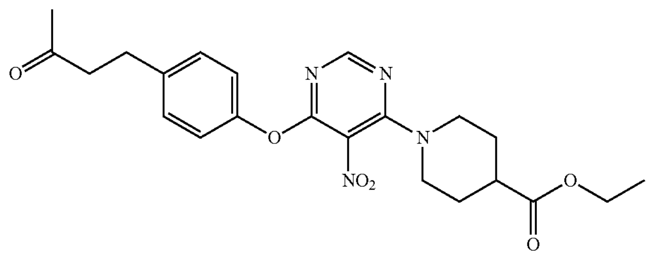 [SMILES: CCOC(=O)C1CCN(c2ncnc(Oc3ccc(CCC(C)=O)cc3)c2[N+](=O)[O-])CC1] | 1-{5-Nitro-6-[4-(3-oxo-butyl)-phenoxy]-pyrimidin-4-yl}-piperidine-4-carboxylic acid ethyl ester |
| A52 | 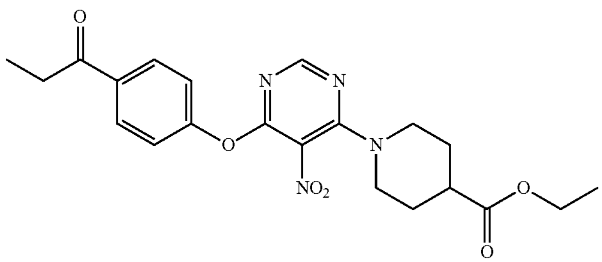 [SMILES: CCOC(=O)C1CCN(c2ncnc(Oc3ccc(C(=O)CC)cc3)c2[N+](=O)[O-])CC1] | 1-[5-Nitro-6-(4-propionyl-phenoxy)-pyrimidin-4-yl]-piperidine-4-carboxylic acid ethyl ester |
| A53 | 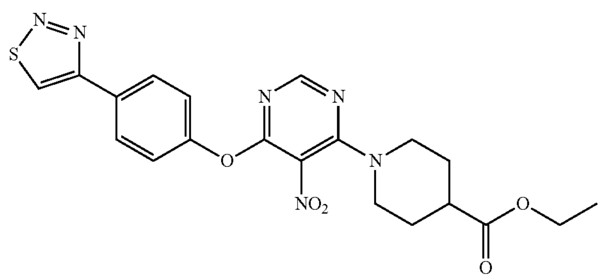 [SMILES: CCOC(=O)C1CCN(c2ncnc(Oc3ccc(-c4csnn4)cc3)c2[N+](=O)[O-])CC1] | 1-[5-Nitro-6-(4-[1,2,3]thiadiazol-4-yl-phenoxy)-pyrimidin-4-yl]-piperidine-4-carboxylic acid ethyl ester |
| A54 | 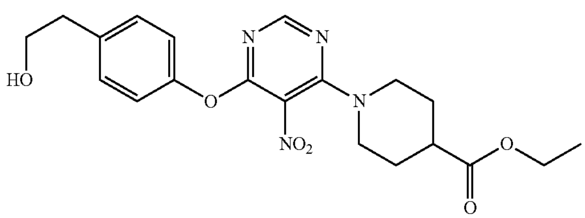 [SMILES: CCOC(=O)C1CCN(c2ncnc(Oc3ccc(CCO)cc3)c2[N+](=O)[O-])CC1] | 1-{6-[4-(2-Hydroxy-ethyl)-phenoxy]-5-nitro-pyrimidin-4-yl}-piperidine-4-carboxylic acid ethyl ester |
| A55 | 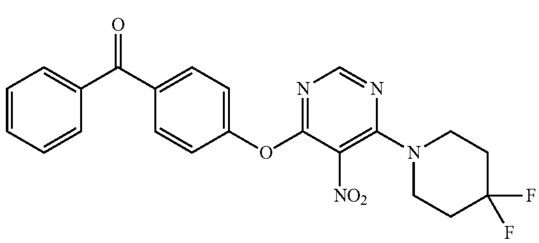 [SMILES: O=C(c1ccccc1)c1ccc(Oc2ncnc(N3CCC(F)(F)CC3)c2[N+](=O)[O-])cc1] | {4-[6-(4,4-Difluoro-piperidin-1-yl)-5-nitro-pyrimidin-4-yloxy]-phenyl}-phenyl-methanone |
| A56 | 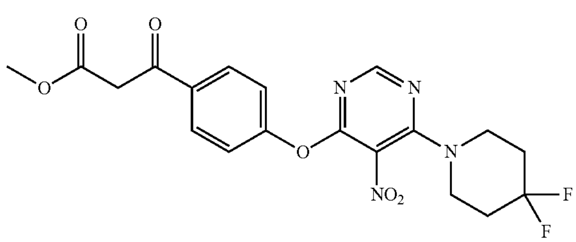 [SMILES: COC(=O)CC(=O)c1ccc(Oc2ncnc(N3CCC(F)(F)CC3)c2[N+](=O)[O-])cc1] | 3-{4-[6-(4,4-Difluoro-piperidin-1-yl)-5-nitro-pyrimidin-4-yloxy]-phenyl}-3-oxo-propionic acid methyl ester |

TABLE A-continued

| Cmpd# | Structure | Chemical Name |
|---|---|---|
| A57 | 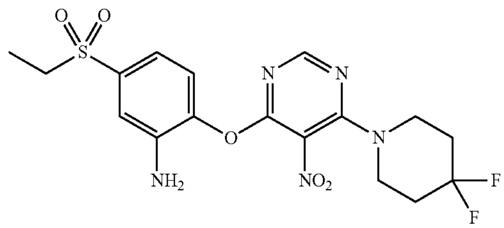 [SMILES: CCS(=O)(=O)c1ccc(Oc2ncnc(N3CCC(F)(F)CC3)c2[N+](=O)[O-])c(N)c1] | 2-[6-(4,4-Difluoro-piperidin-1-yl)-5-nitro-pyrimidin-4-yloxy]-5-ethanesulfonyl-phenylamine |
| A58 | 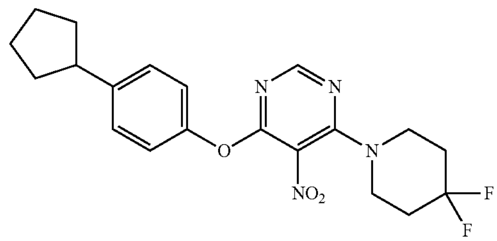 [SMILES: O=[N+]([O-])c1c(Oc2ccc(C3CCCC3)cc2)ncnc1N1CCC(F)(F)CC1] | 4-(4-Cyclopentyl-phenoxy)-6-(4,4-difluoro-piperidin-1-yl)-5-nitro-pyrimidine |
| A59 | 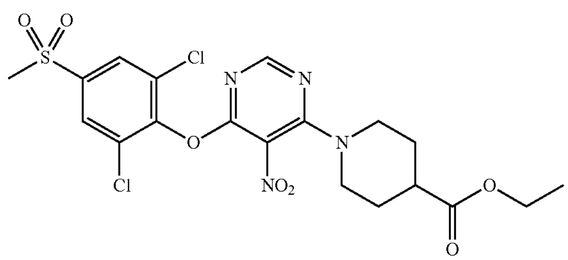 [SMILES: CCOC(=O)C1CCN(c2ncnc(Oc3c(Cl)cc(S(C)(=O)=O)cc3Cl)c2[N+](=O)[O-])CC1] | 1-[6-(2,6-Dichloro-4-methanesulfonyl-phenoxy)-5-nitro-pyrimidin-4-yl]-piperidine-4-carboxylic acid ethyl ester |
| A60 | 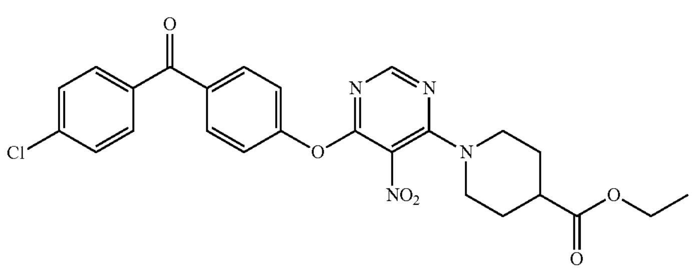 [SMILES: CCOC(=O)C1CCN(c2ncnc(Oc3ccc(C(=O)c4ccc(Cl)cc4)cc3)c2[N+](=O)[O-])CC1] | 1-{6-[4-(4-Chloro-benzoyl)-phenoxy]-5-nitro-pyrimidin-4-yl}-piperidine-4-carboxylic acid ethyl ester |
| A61 | 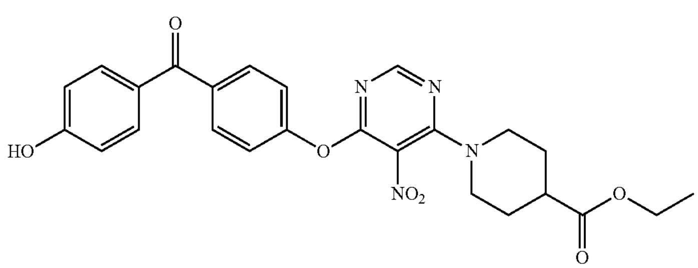 [SMILES: CCOC(=O)C1CCN(c2ncnc(Oc3ccc(C(=O)c4ccc(O)cc4)cc3)c2[N+](=O)[O-])CC1] | 1-{6-[4-(4-Hydroxy-benzoyl)-phenoxy]-5-nitro-pyrimidin-4-yl}-piperidine-4-carboxylic acid ethyl ester |
| A62 | 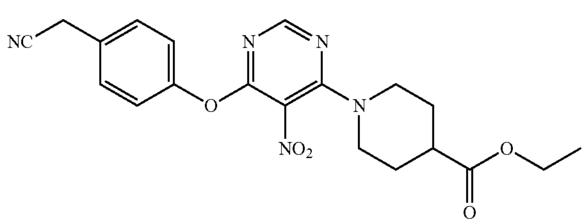 [SMILES: CCOC(=O)C1CCN(c2ncnc(Oc3ccc(CC#N)cc3)c2[N+](=O)[O-])CC1] | 1-[6-(4-Cyanomethyl-phenoxy)-5-nitro-pyrimidin-4-yl]-piperidine-4-carboxylic acid ethyl ester |

TABLE A-continued

| Cmpd# | Structure | Chemical Name |
|---|---|---|
| A63 | 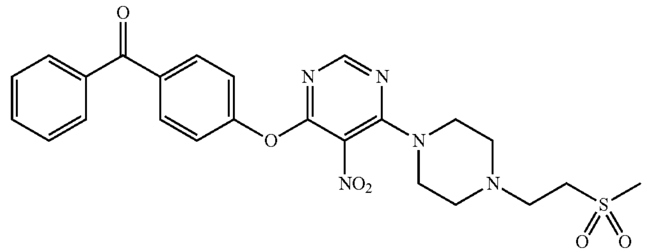 [SMILES: CS(=O)(=O)CCN1CCN(c2ncnc(Oc3ccc(C(=O)c4ccccc4)cc3)c2[N+](=O)[O-])CC1] | (4-{6-[4-(2-Methanesulfonyl-ethyl)-piperazin-1-yl]-5-nitro-pyrimidin-4-yloxy}-phenyl)-phenyl-methanone |
| A64 | 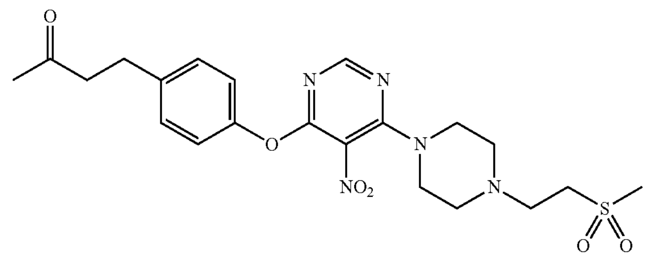 [SMILES: CC(=O)CCc1ccc(Oc2ncnc(N3CCN(CCS(C)(=O)=O)CC3)c2[N+](=O)[O-])cc1] | 4-(4-{6-[4-(2-Methanesulfonyl-ethyl)-piperazin-1-yl]-5-nitro-pyrimidin-4-yloxy}-phenyl)-butan-2-one |
| A65 | 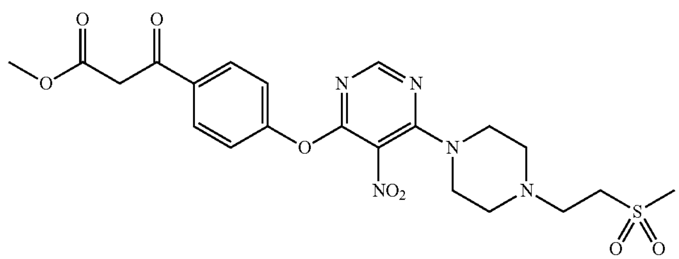 | 3-(4-{6-[4-(2-Methanesulfonyl-ethyl)-piperazin-1-yl]-5-nitro-pyrimidin-4-yloxy}-phenyl)-3-oxo-propionic acid methyl ester |
| A66 | 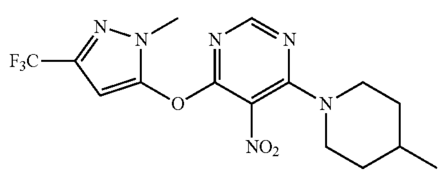 [SMILES: CC1CCN(c2ncnc(Oc3cc(C(F)(F)F)nn3C)c2[N+](=O)[O-])CC1] | 4-(4-Methyl-piperidin-1-yl)-6-(2-methyl-5-trifluoromethyl-2H-pyrazol-3-yloxy)-5-nitro-pyrimidine |
| A67 | 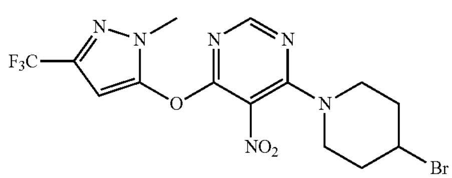 [SMILES: Cn1nc(C(F)(F)F)cc1Oc1ncnc(N2CCC(Br)CC2)c1[N+](=O)[O-]] | 4-(4-Bromo-piperidin-1-yl)-6-(2-methyl-5-trifluoromethyl-2H-pyrazol-3-yloxy)-5-nitro-pyrimidine |
| A68 | 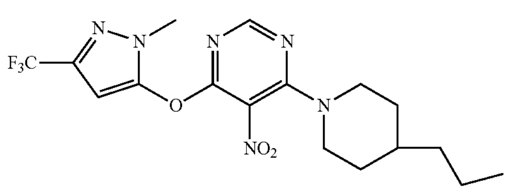 [SMILES: CCCC1CCN(c2ncnc(Oc3cc(C(F)(F)F)nn3C)c2[N+](=O)[O-])CC1] | 4-(2-Methyl-5-trifluoromethyl-2H-pyrazol-3-yloxy)-5-nitro-6-(4-propyl-piperidin-1-yl)-pyrimidine |
| A69 | 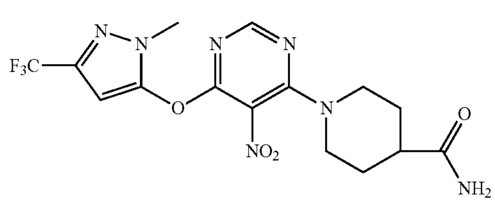 [SMILES: Cn1nc(C(F)(F)F)cc1Oc1ncnc(N2CCC(C(N)=O)CC2)c1[N+](=O)[O-]] | 1-(6-(2-Methyl-5-trifluoromethyl-2H-pyrazol-3-yloxy)-5-nitro-pyrimidin-4-yl]-piperidine-4-carboxylic acid amide |

TABLE A-continued

| Cmpd# | Structure | Chemical Name |
|---|---|---|
| A70 | 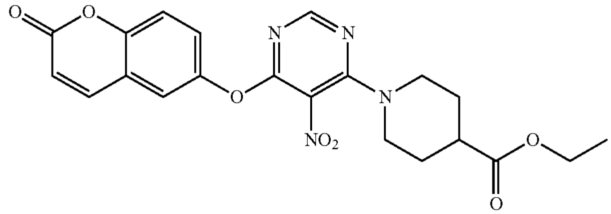 [SMILES: CCOC(=O)C1CCN(c2ncnc(Oc3ccc4oc(=O)ccc4c3)c2[N+](=O)[O-])CC1] | 1-[5-Nitro-6-(2-oxo-2H-chromen-6-yloxy)-pyrimidin-4-yl]-piperidine-4-carboxylic acid ethyl ester |
| A71 | 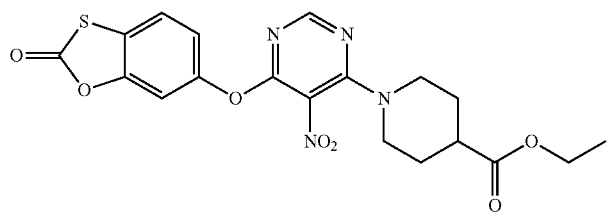 [SMILES: CCOC(=O)C1CCN(c2ncnc(Oc3ccc4sc(=O)oc4c3)c2[N+](=O)[O-])CC1] | 1-[5-Nitro-6-(2-oxo-benzo[1,3]oxathiol-6-yloxy)-pyrimidin-4-yl]-piperidine-4-carboxylic acid ethyl ester |
| A72 | 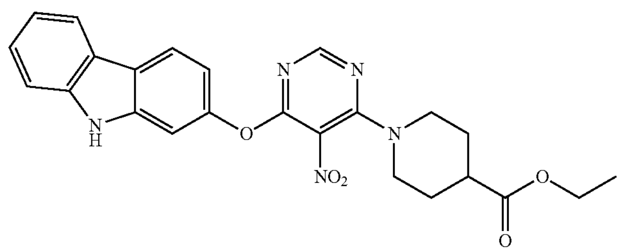 [SMILES: CCOC(=O)C1CCN(c2ncnc(Oc3ccc4c(c3)[nH]c3ccccc34)c2[N+](=O)[O-])CC1] | 1-[6-(9H-Carbazol-2-yloxy)-5-nitro-pyrimidin-4-yl]-piperidine-4-carboxylic acid ethyl ester |
| A73 | 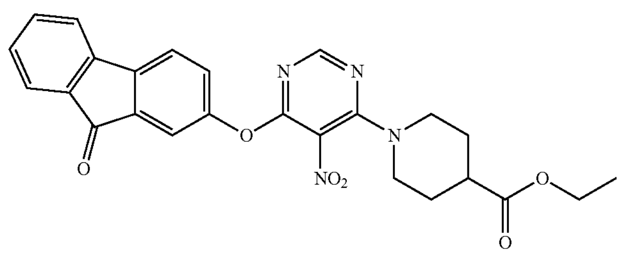 [SMILES: CCOC(=O)C1CCN(c2ncnc(Oc3ccc4c(c3)C(=O)c3ccccc3-4)c2[N+](=O)[O-])CC1] | 1-[5-Nitro-6-(9-oxo-9H-(fluoren-2-yloxy)-pyrimidin-4-yl]-piperidine-4-carboxylic acid ethyl ester |
| A74 | 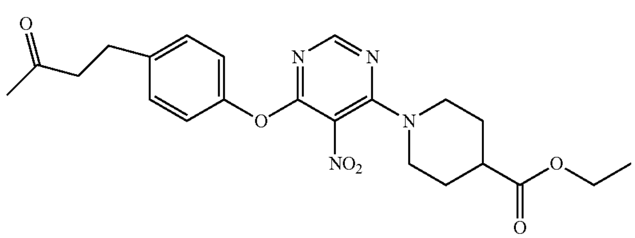 [SMILES: CCOC(=O)C1CCN(c2ncnc(Oc3ccc(CCC(C)=O)cc3)c2[N+](=O)[O-])CC1] | 1-{5-Amino-6-[4-(3-oxo-butyl)-phenoxy]-pyrimidin-4-yl}-piperidine-4-carboxylic acid ethyl ester |
| A75 | 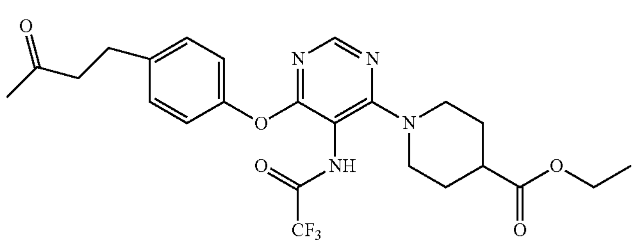 [SMILES: CCOC(=O)C1CCN(c2ncnc(Oc3ccc(CCC(C)=O)cc3)c2NC(=O)C(F)(F)F)CC1] | 1-[6-[4-(3-Oxo-butyl)-phenoxy]-5-(2,2,2-trifluoro-acetylamino)-pyrimidin-4-yl]-piperidine-4-carboxylic acid ethyl ester |

TABLE A-continued

| Cmpd# | Structure | Chemical Name |
|---|---|---|
| A76 | 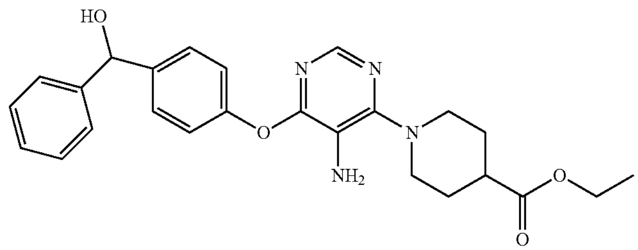 [SMILES: CCOC(=O)C1CCN(c2ncnc(Oc3ccc(C(O)c4ccccc4)cc3)c2N)CC1] | 1-{5-Amino-6-[4-(hydroxy-phenyl-methyl)-phenoxy]-pyrimidin-4-yl}-piperidine-4-carboxylic acid ethyl ester |
| A77 | 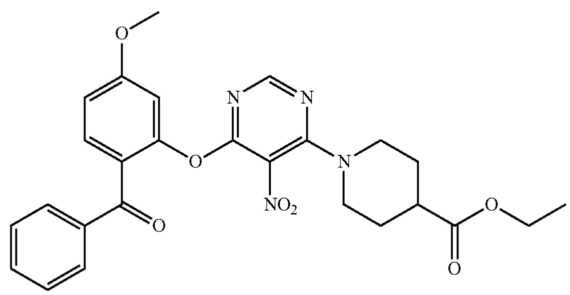 [SMILES: CCOC(=O)C1CCN(c2ncnc(Oc3cc(OC)ccc3C(=O)c3ccccc3)c2[N+](=O)[O-])CC1] | 1-[6-(2-Benzoyl-5-methoxy-phenoxy)-5-nitro-pyrimidin-4-yl]-piperidine-4-carboxylic acid ethyl ester |
| A78 | 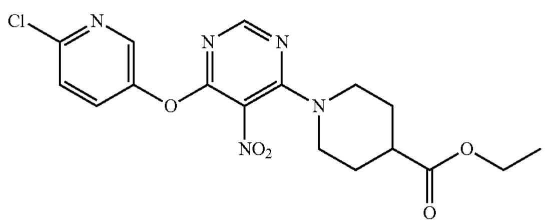 [SMILES: CCOC(=O)C1CCN(c2ncnc(Oc3ccc(Cl)nc3)c2[N+](=O)[O-])CC1] | 1-[6-(6-Chloro-pyridin-3-yloxy)-5-nitro-pyrimidin-4-yl]-piperidine-4-carboxylic acid ethyl ester |
| A79 | 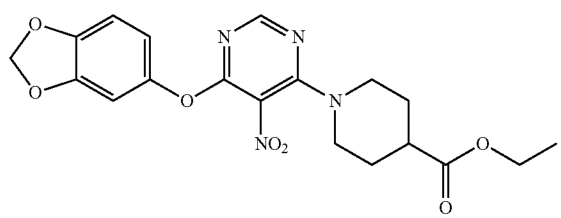 [SMILES: CCOC(=O)C1CCN(c2ncnc(Oc3ccc4c(c3)OCO4)c2[N+](=O)[O-])CC1] | 1-[6-(Benzo[1,3]dioxol-5-yloxy)-5-nitro-pyrimidin-4-yl]-piperidine-4-carboxylic acid ethyl ester |
| A80 | 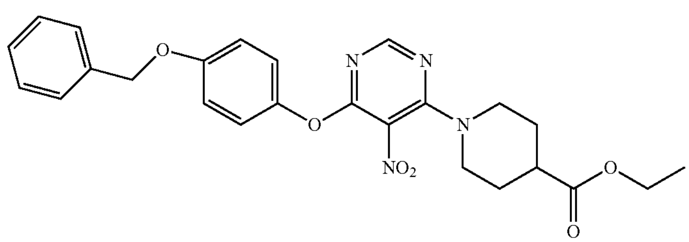 [SMILES: CCOC(=O)C1CCN(c2ncnc(Oc3ccc(OCc4ccccc4)cc3)c2[N+](=O)[O-])CC1] | 1-[6-(4-Benzyloxy-phenoxy)-5-nitro-pyrimidin-4-yl]-piperidine-4-carboxylic acid ethyl ester |
| A81 | 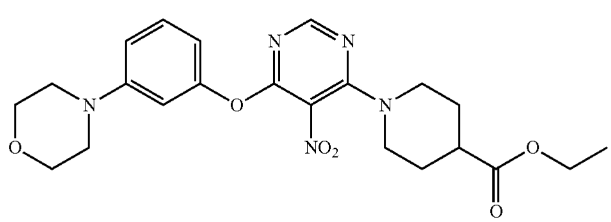 [SMILES: CCOC(=O)C1CCN(c2ncnc(Oc3cccc(N4CCOCC4)c3)c2[N+](=O)[O-])CC1] | 1-[6-(3-Morpholin-4-yl-phenoxy)-5-nitro-pyrimidin-4-yl]-piperidine-4-carboxylic acid ethyl ester |

TABLE A-continued

| Cmpd# | Structure | Chemical Name |
|---|---|---|
| A82 | 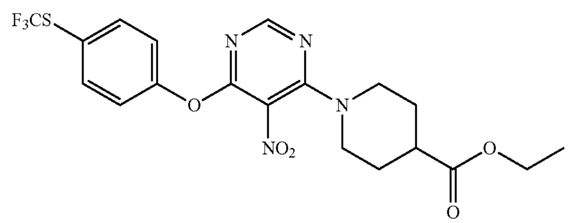 | 1-[5-Nitro-6-(4-trifluoromethylsulfanyl-phenoxy)-pyrimidin-4-yl]-piperidine-4-carboxylic acid ethyl ester |
| A83 | 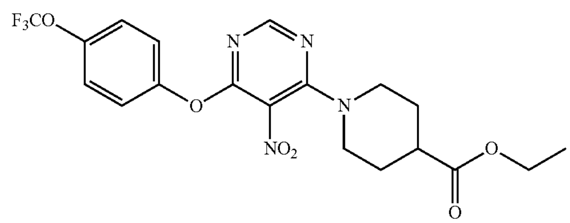 | 1-[5-Nitro-6-(4-trifluoromethoxy-phenoxy)-pyrimidin-4-yl]-piperidine-4-carboxylic acid ethyl ester |
| A84 | 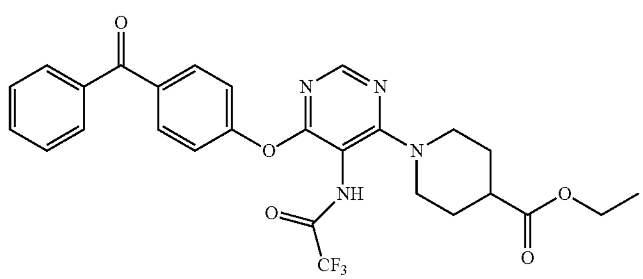 [SMILES: CCOC(=O)C1CCN(c2ncnc(Oc3ccc(C(=O)c4ccccc4)cc3)c2NC(=O)C(F)(F)F)CC1] | 1-[6-(4-Benzoyl-phenoxy)-5-(2,2,2-trifluoro-acetylamino)-pyrimidin-4-yl]-piperidine-4-carboxylic acid ethyl ester |
| A85 | 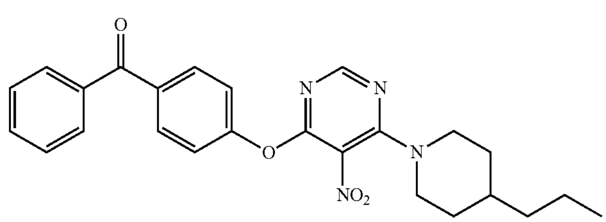 [SMILES: CCCC1CCN(c2ncnc(Oc3ccc(C(=O)c4ccccc4)cc3)c2[N+](=O)[O-])CC1] | {4-[5-Nitro-6-(4-propyl-piperidin-1-yl)-pyrimidin-4-yloxy]-phenyl}-phenyl-methanone |
| A86 | 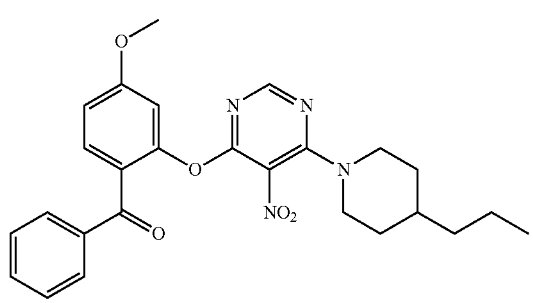 [SMILES: CCCC1CCN(c2ncnc(Oc3cc(OC)ccc3C(=O)c3ccccc3)c2[N+](=O)[O-])CC1] | {4-Methoxy-2-[5-nitro-6-(4-propyl-piperidin-1-yl)-pyrimidin-4-yloxy]-phenyl}-phenyl-methanone |
| A87 | 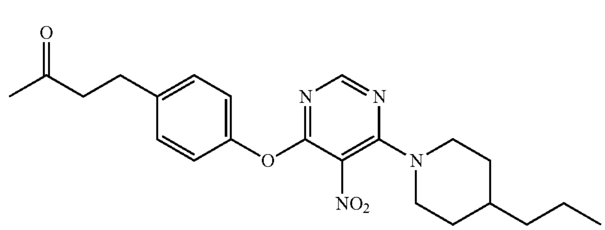 [SMILES: CCCC1CCN(c2ncnc(Oc3ccc(CCC(C)=O)cc3)c2[N+](=O)[O-])CC1] | 4-{4-[5-Nitro-6-(4-propyl-piperidin-1-yl)-pyrimidin-4-yloxy]-phenyl}-butan-2-one |

TABLE A-continued

| Cmpd# | Structure | Chemical Name |
|---|---|---|
| A88 | 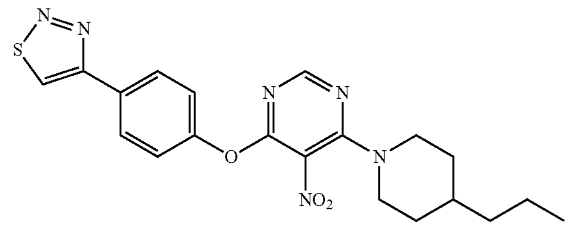 [SMILES: CCCC1CCN(c2ncnc(Oc3ccc(-c4csnn4)cc3)c2[N+](=O)[O-])CC1] | 5-Nitro-4-(4-propyl-piperidin-1-yl)-6-(4-[1,2,3]thiadiazol-4-yl-phenoxy)-pyrimidine |
| A89 | 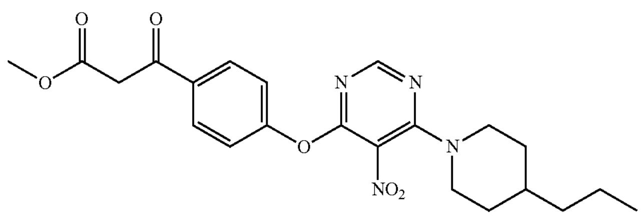 [SMILES: CCCC1CCN(c2ncnc(Oc3ccc(C(=O)CC(=O)OC)cc3)c2[N+](=O)[O-])CC1] | 3-{4-[5-Nitro-6-(4-propyl-piperidin-1-yl)-pyrimidin-4-yloxy]-phenyl}-3-oxo-propionic acid methyl ester |
| A90 | 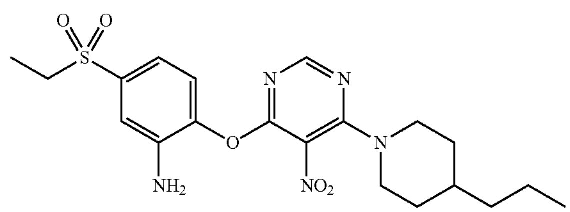 [SMILES: CCCC1CCN(c2ncnc(Oc3ccc(S(=O)(=O)CC)cc3N)c2[N+](=O)[O-])CC1] | 5-Ethanesulfonyl-2-[5-nitro-6-(4-propyl-piperidin-1-yl)-pyrimidin-4-yloxy]-phenylamine |
| A91 | 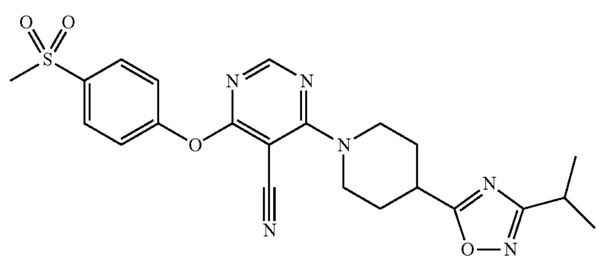 [SMILES: CC(C)c1noc(C2CCN(c3ncnc(Oc4ccc(S(C)(=O)=O)cc4)c3C#N)CC2)n1] | 4-[4-(3-Isopropyl-[1,2,4]oxadiazol-5-yl)-piperidin-1-yl]-6-(4-methanesulfonyl-phenoxy)-pyrimidine-5-carbonitrile |
| A92 | 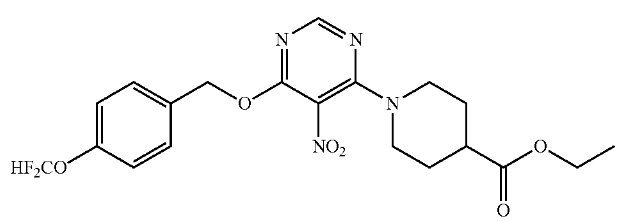 | 1-[6-(4-Difluoromethoxy-benzyloxy)-5-nitro-pyrimidin-4-yl]-piperidine-4-carboxylic acid ethyl ester |
| A93 | 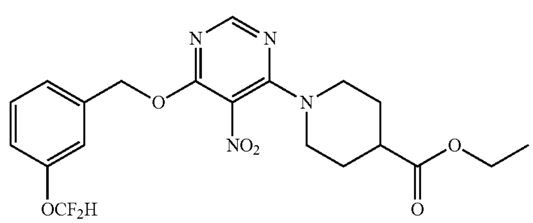 | 1-[6-(3-Difluoromethoxy-benzyloxy)-5-nitro-pyrimidin-4-yl]-piperidine-4-carboxylic acid ethyl ester |
| A94 | 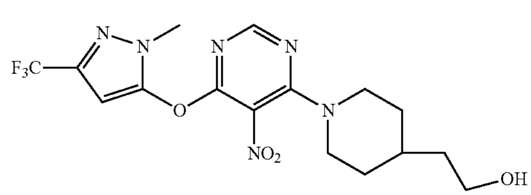 [SMILES: Cn1nc(C(F)(F)F)cc1Oc1ncnc(N2CCC(CCO)CC2)c1[N+](=O)[O-]] | 2-{1-[6-(2-Methyl-5-trifluoromethyl-2H-pyrazol-3-yloxy)-5-nitro-pyrimidin-4-yl]-piperidin-4-yl}-ethanol |

TABLE A-continued

| Cmpd# | Structure | Chemical Name |
|---|---|---|
| A95 | 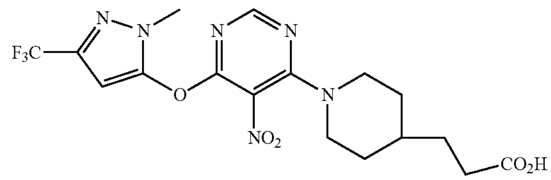 [SMILES: Cn1nc(C(F)(F)F)cc1Oc1ncnc(N2CCC(CCC(=O)O)CC2)c1[N+](=O)[O-]] | 3-{1-[6-(2-Methyl-5-trifluoromethyl-2H-pyrazol-3-yloxy)-5-nitro-pyrimidin-4-yl]-piperidin-4-yl}-propionic acid |
| A96 | 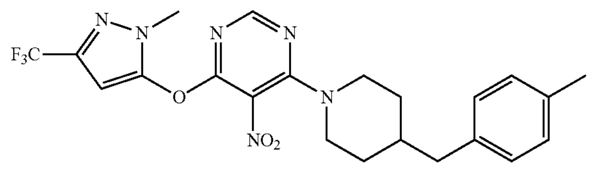 [SMILES: Cc1ccc(CC2CCN(c3ncnc(Oc4cc(C(F)(F)F)nn4C)c3[N+](=O)[O-])CC2)cc1] | 4-[4-(4-Methyl-benzyl)-piperidin-1-yl]-6-(2-methyl-5-trifluoromethyl-2H-pyrazol-3-yloxy)-5-nitro-pyrimidine |
| A97 | 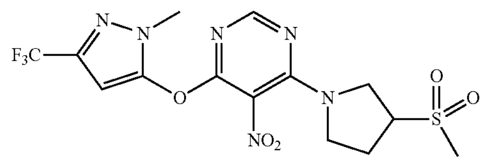 [SMILES: Cn1nc(C(F)(F)F)cc1Oc1ncnc(N2CCC(S(C)(=O)=O)C2)c1[N+](=O)[O-]] | 4-(3-Methanesulfonyl-pyrrolidin-1-yl)-6-(2-methyl-5-trifluoromethyl-2H-pyrazol-3-yloxy)-5-nitro-pyrimidine |
| A98 | 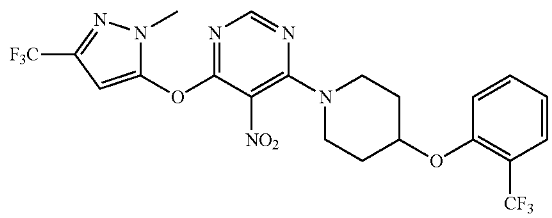 [SMILES: Cn1nc(C(F)(F)F)cc1Oc1ncnc(N2CCC(Oc3ccccc3C(F)(F)F)CC2)c1[N+](=O)[O-]] | 4-(2-Methyl-5-trifluoromethyl-2H-pyrazol-3-yloxy)-5-nitro-6-[4-(2-trifluoromethyl-phenoxy)-piperidin-1-yl]-pyrimidine |
| A99 | 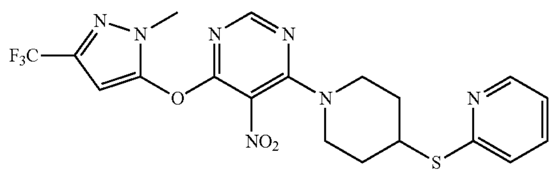 [SMILES: Cn1nc(C(F)(F)F)cc1Oc1ncnc(N2CCC(Sc3ccccn3)CC2)c1[N+](=O)[O-]] | 4-(2-Methyl-5-trifluoromethyl-2H-pyrazol-3-yloxy)-5-nitro-6-[4-(pyridin-2-ylsulfanyl)-piperidin-1-yl]-pyrimidine |
| A100 | 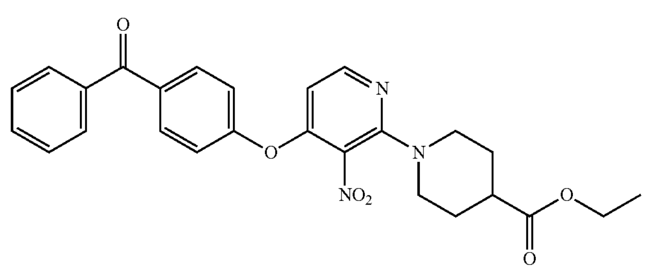 [SMILES: CCOC(=O)C1CCN(c2nccc(Oc3ccc(C(=O)c4ccccc4)cc3)c2[N+](=O)[O-])CC1] | 4'-(4-Benzoyl-phenoxy)-3'-nitro-3,4,5,6-tetrahydro-2H-[1,2']bipyridinyl-4-carboxylic acid ethyl ester |
| A101 | 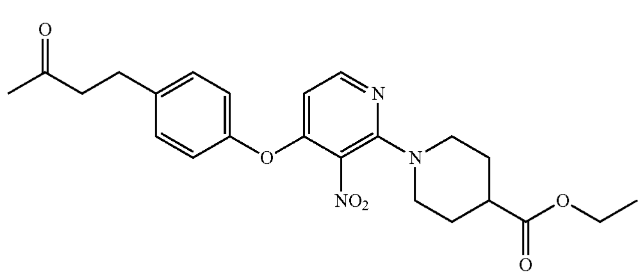 [SMILES: CCOC(=O)C1CCN(c2nccc(Oc3ccc(CCC(C)=O)cc3)c2[N+](=O)[O-])CC1] | 3'-Nitro-4'-[4-(3-oxo-butyl)-phenoxy]-3,4,5,6-tetrahydro-2H-[1,2']bipyridinyl-4-carboxylic acid ethyl ester |

TABLE A-continued

| Cmpd# | Structure | Chemical Name |
|---|---|---|
| A102 | 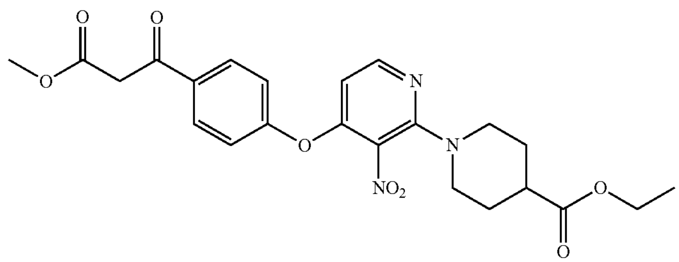 [SMILES: CCOC(=O)C1CCN(c2nccc(Oc3ccc(C(=O)CC(=O)OC)cc3)c2[N+](=O)[O-])CC1] | 4'-[4-(2-Methoxycarbonyl-acetyl)-phenoxy]-3'-nitro-3,4,5,6-tetrahydro-2H-[1,2']bipyridinyl-4-carboxylic acid ethyl ester |
| A103 | 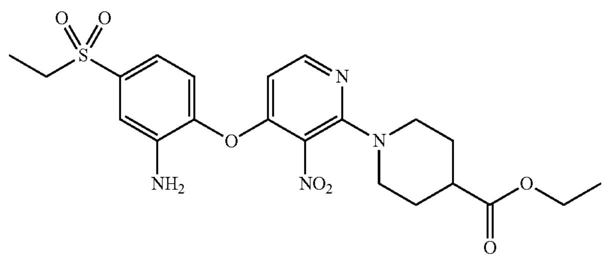 [SMILES: CCOC(=O)C1CCN(c2nccc(Oc3ccc(S(=O)(=O)CC)cc3N)c2[N+](=O)[O-])CC1] | 4'-(2-Amino-4-ethanesulfonyl-phenoxy)-3'-nitro-3,4,5,6-tetrahydro-2H-[1,2']bipyridinyl-4-carboxylic acid ethyl ester |
| A104 | 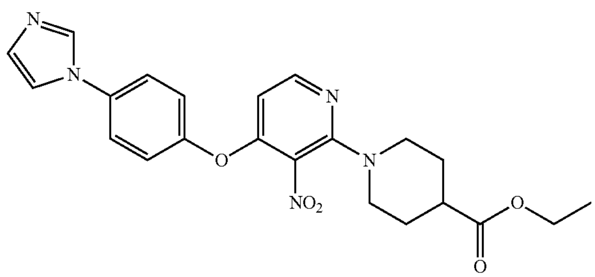 [SMILES: CCOC(=O)C1CCN(c2nccc(Oc3ccc(-n4ccnc4)cc3)c2[N+](=O)[O-])CC1] | 4'-(4-Imidazol-1-yl-phenoxy)-3'-nitro-3,4,5,6-tetrahydro-2H-[1,2']bipyridinyl-4-carboxylic acid ethyl ester |
| A105 | 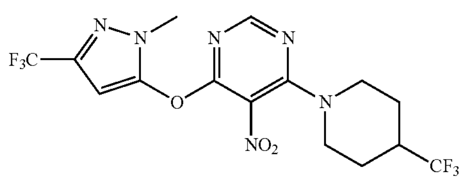 [SMILES: Cn1nc(C(F)(F)F)cc1Oc1ncnc(N2CCC(C(F)(F)F)CC2)c1[N+](=O)[O-]] | 4-(2-Methyl-5-trifluoromethyl-2H-pyrazol-3-yloxy)-5-nitro-6-(4-trifluoromethyl-piperidin-1-yl)-pyrimidine |
| A106 | 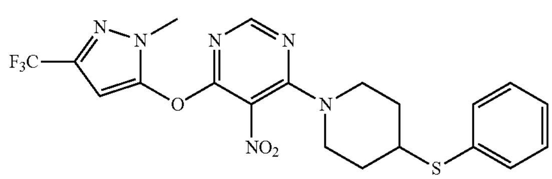 [SMILES: Cn1nc(C(F)(F)F)cc1Oc1ncnc(N2CCC(Sc3ccccc3)CC2)c1[N+](=O)[O-]] | 4-(2-Methyl-5-trifluoromethyl-2H-pyrazol-3-yloxy)-5-nitro-6-(4-phenylsulfanyl-piperidin-1-yl)-pyrimidine |
| A107 | 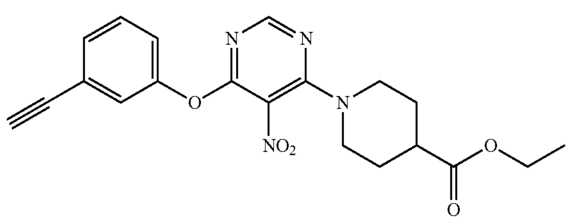 [SMILES: C#Cc1cccc(Oc2ncnc(N3CCC(C(=O)OCC)CC3)c2[N+](=O)[O-])c1] | 1-[6-(3-Ethynyl-phenoxy)-5-nitro-pyrimidin-4-yl]-piperidine-4-carboxylic acid ethyl ester |
| A108 | 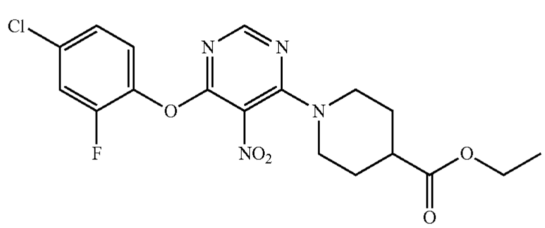 [SMILES: CCOC(=O)C1CCN(c2ncnc(Oc3ccc(Cl)cc3F)c2[N+](=O)[O-])CC1] | 1-[6-(4-Chloro-2-fluoro-phenoxy)-5-nitro-pyrimidin-4-yl]-piperidine-4-carboxylic acid ethyl ester |

TABLE A-continued

| Cmpd# | Structure | Chemical Name |
| --- | --- | --- |
| A109 | 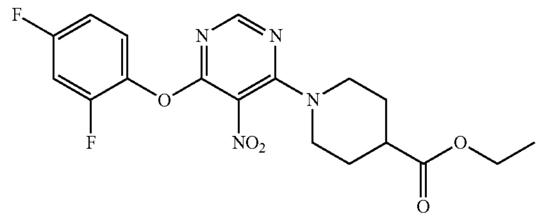 [SMILES: CCOC(=O)C1CCN(c2ncnc(Oc3ccc(F)cc3F)c2[N+](=O)[O-])CC1] | 1-[6-(2,4-Difluoro-phenoxy)-5-nitro-pyrimidin-4-yl]-piperidine-4-carboxylic acid ethyl ester |
| A110 | 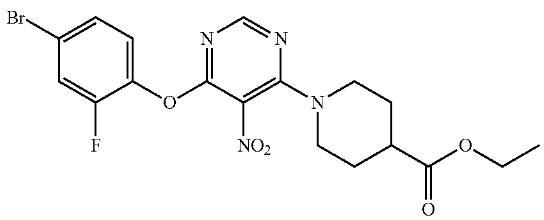 | 1-[6-(4-Bromo-2-fluoro-phenoxy)-5-nitro-pyrimidin-4-yl]-piperidine-4-carboxylic acid ethyl ester |
| A111 | 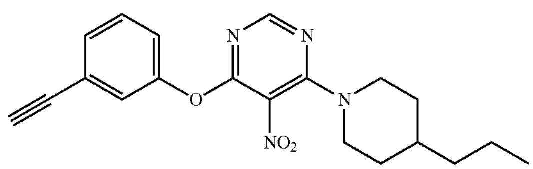 [SMILES: C#Cc1cccc(Oc2ncnc(N3CCC(CCC)CC3)c2[N+](=O)[O-])c1] | 4-(3-Ethynyl-phenoxy)-5-nitro-6-(4-propyl-piperidin-1-yl)-pyrimidine |
| A112 | 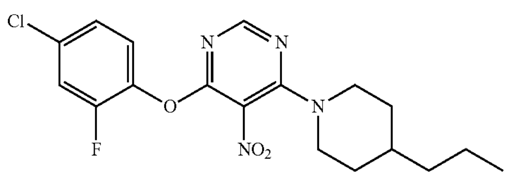 [SMILES: CCCC1CCN(c2ncnc(Oc3ccc(Cl)cc3F)c2[N+](=O)[O-])CC1] | 4-(4-Chloro-2-fluoro-phenoxy)-5-nitro-6-(4-propyl-piperidin-1-yl)-pyrimidine |
| A113 | 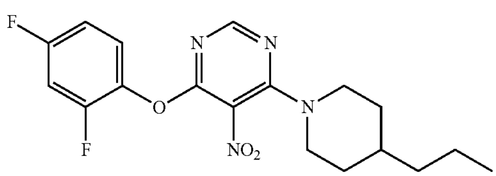 [SMILES: CCCC1CCN(c2ncnc(Oc3ccc(F)cc3F)c2[N+](=O)[O-])CC1] | 4-(2,4-Difluoro-phenoxy)-5-nitro-6-(4-propyl-piperidin-1-yl)-pyrimidine |
| A114 | 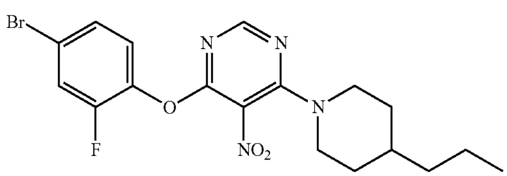 [SMILES: CCCC1CCN(c2ncnc(Oc3ccc(Br)cc3F)c2[N+](=O)[O-])CC1] | 4-(4-Bromo-2-fluoro-phenoxy)-5-nitro-6-(4-propyl-piperidin-1-yl)-pyrimidine |
| A115 | 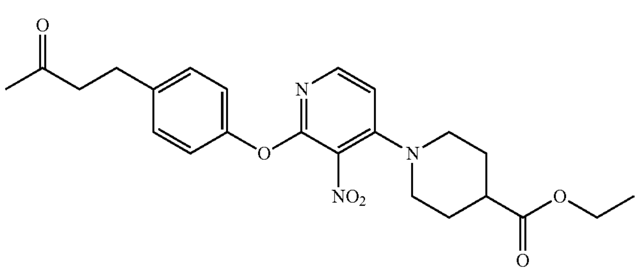 [SMILES: CCOC(=O)C1CCN(c2ccnc(Oc3ccc(CCC(C)=O)cc3)c2[N+](=O)[O-])CC1] | 3'-Nitro-2'-[4-(3-oxo-butyl)-phenoxy]-3,4,5,6-tetrahydro-2H-[1,4']bipyridinyl-4-carboxylic acid ethyl ester |

TABLE A-continued

| Cmpd# | Structure | Chemical Name |
|---|---|---|
| A116 | 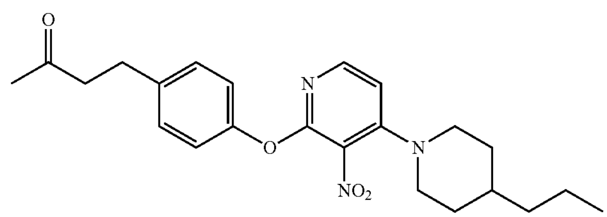 | 4-[4-(3'-Nitro-4-propyl-3,4,5,6-tetrahydro-2H-[1,4']bipyridinyl-2'-yloxy)-phenyl]-butan-2-one |
| A117 | 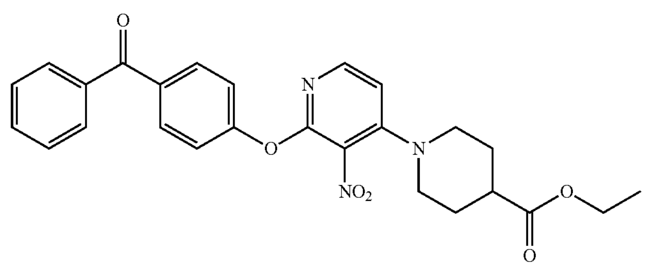 [SMILES: CCOC(=O)C1CCN(c2ccnc(Oc3ccc(C(=O)c4ccccc4)cc3)c2[N+](=O)[O-])CC1] | 2'-(4-Benzoyl-phenoxy)-3'-nitro-3,4,5,6-tetrahydro-2H-[1,4']bipyridinyl-4-carboxylic acid ethyl ester |
| A118 | 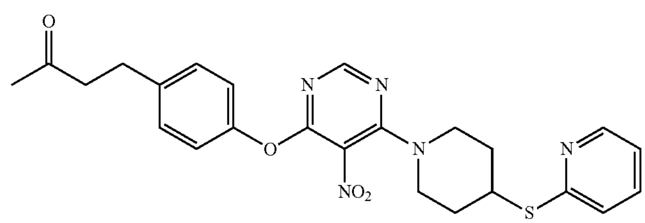 [SMILES: CC(=O)CCc1ccc(Oc2ncnc(N3CCC(Sc4ccccn4)CC3)c2[N+](=O)[O-])cc1] | 4-(4-{5-Nitro-6-[4-(pyridin-2-ylsulfanyl)-piperidin-1-yl]-pyrimidin-4-yloxy}-phenyl)-butan-2-one |
| A119 | 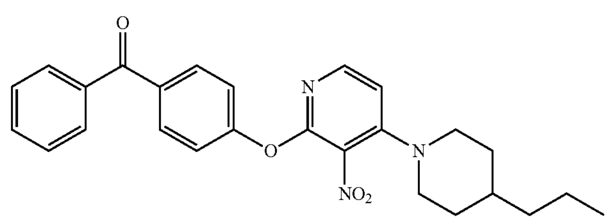 [SMILES: CCCC1CCN(c2ccnc(Oc3ccc(C(=O)c4ccccc4)cc3)c2[N+](=O)[O-])CC1] | [4-(3'-Nitro-4-propyl-3,4,5,6-tetrahydro-2H-[1,4']bipyridinyl-2'-yloxy)-phenyl]-phenyl-methanone |
| A120 | 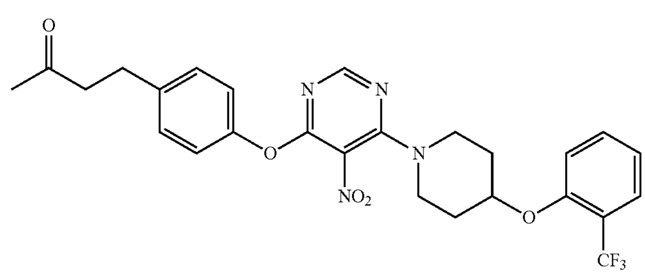 [SMILES: CC(=O)CCc1ccc(Oc2ncnc(N3CCC(Oc4ccccc4C(F)(F)F)CC3)c2[N+](=O)[O-])cc1] | 4-(4-{5-Nitro-6-[4-(2-trifluoromethyl-phenoxy)-piperidin-1-yl]-pyrimidin-4-yloxy}-phenyl)-butan-2-one |
| A121 | 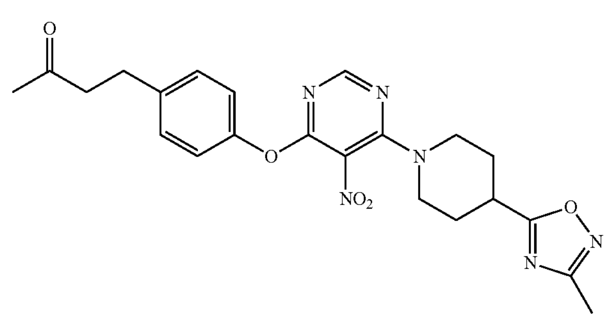 [SMILES: CC(=O)CCc1ccc(Oc2ncnc(N3CCC(c4nc(C)no4)CC3)c2[N+](=O)[O-])cc1] | 4-(4-{6-[4-(3-Methyl-[1,2,4]oxadiazol-5-yl)-piperidin-1-yl]-5-nitro-pyrimidin-4-yloxy}-phenyl)-butan-2-one |

TABLE A-continued

| Cmpd# | Structure | Chemical Name |
| --- | --- | --- |
| A122 | 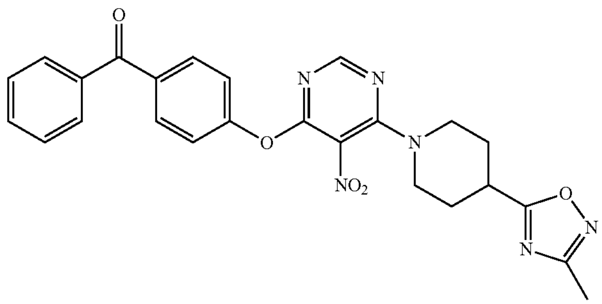 [SMILES: Cc1noc(C2CCN(c3ncnc(Oc4ccc(C(=O)c5ccccc5)cc4)c3[N+](=O)[O-])CC2)n1] | (4-{6-[4-(3-Methyl-[1,2,4]oxadiazol-5-yl)-piperidin-1-yl]-5-nitro-pyrimidin-4-yloxy}-phenyl)-phenyl-methanone |
| A123 | 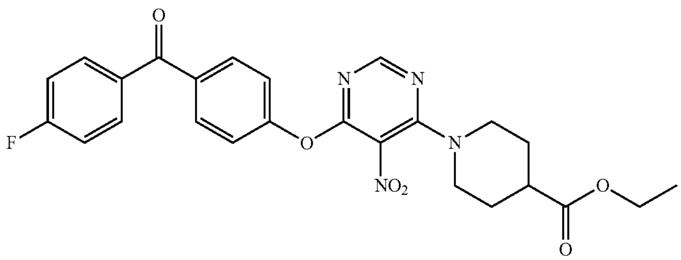 [SMILES: CCOC(=O)C1CCN(c2ncnc(Oc3ccc(C(=O)c4ccc(F)cc4)cc3)c2[N+](=O)[O-])CC1] | 1-{6-[4-(4-Fluoro-benzoyl)-phenoxy]-5-nitro-pyrimidin-4-yl}-piperidine-4-carboxylic acid ethyl ester |
| A124 | 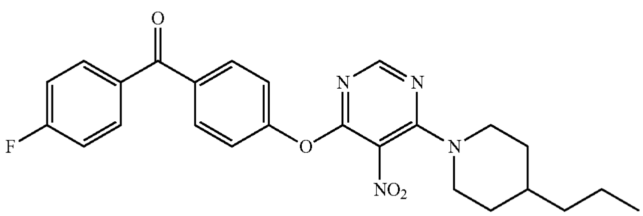 [SMILES: CCCC1CCN(c2ncnc(Oc3ccc(C(=O)c4ccc(F)cc4)cc3)c2[N+](=O)[O-])CC1] | (4-Fluoro-phenyl)-{4-[5-nitro-6-(4-propyl-piperidin-1-yl)-pyrimidin-4-yloxy]-phenyl}-methanone |
| A125 | 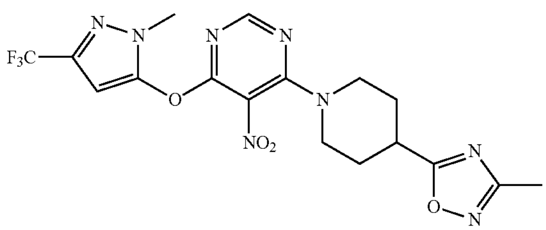 [SMILES: Cc1noc(C2CCN(c3ncnc(Oc4cc(C(F)(F)F)nn4C)c3[N+](=O)[O-])CC2)n1] | 4-[4-(3-Methyl-[1,2,4]oxadiazol-5-yl)-piperidin-1-yl]-6-(2-methyl-5-trifluoromethyl-2H-pyrazol-3-yloxy)-5-nitro-pyrimidine |
| A126 | 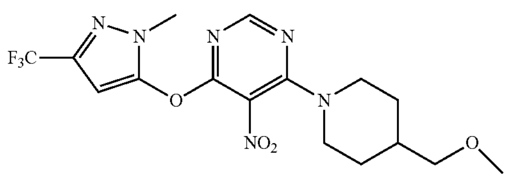 [SMILES: COCC1CCN(c2ncnc(Oc3cc(C(F)(F)F)nn3C)c2[N+](=O)[O-])CC1] | 4-(4-Methoxymethyl-piperidin-1-yl)-6-(2-methyl-5-trifluoromethyl-2H-pyrazol-3-yloxy)-5-nitro-pyrimidine |
| A127 | 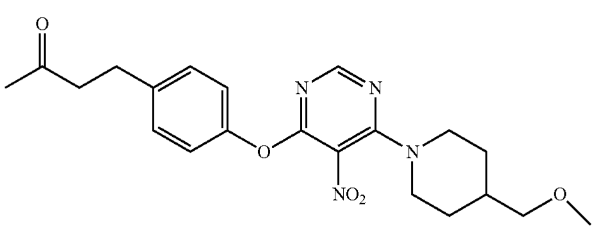 [SMILES: COCC1CCN(c2ncnc(Oc3ccc(CCC(C)=O)cc3)c2[N+](=O)[O-])CC1] | 4-{4-[6-(4-Methoxymethyl-piperidin-1-yl)-5-nitro-pyrimidin-4-yloxy]-phenyl}-butan-2-one |
| A128 | 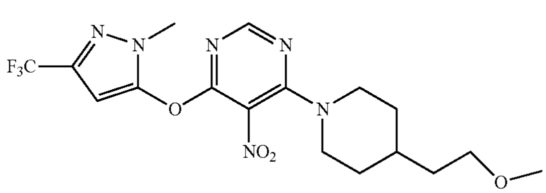 [SMILES: COCCC1CCN(c2ncnc(Oc3cc(C(F)(F)F)nn3C)c2[N+](=O)[O-])CC1] | 4-[4-(2-Methoxy-ethyl)-piperidin-1-yl]-6-(2-methyl-5-trifluoromethyl-2H-pyrazol-3-yloxy)-5-nitro-pyrimidine |

TABLE A-continued

| Cmpd# | Structure | Chemical Name |
|---|---|---|
| A129 | 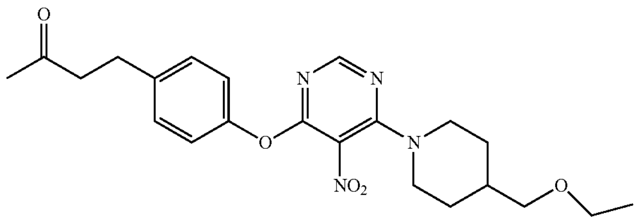 [SMILES: CCOCC1CCN(c2ncnc(Oc3ccc(CCC(C)=O)cc3)c2[N+](=O)[O-])CC1] | 4-{4-[6-(4-Ethoxymethyl-piperidin-1-yl)-5-nitro-pyrimidin-4-yloxy]-phenyl}-butan-2-one |
| A130 | 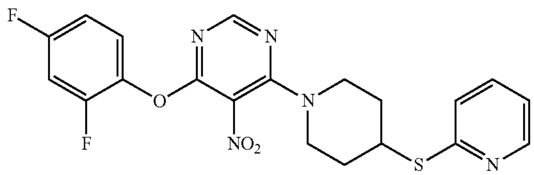 [SMILES: O=[N+]([O-])c1c(Oc2ccc(F)cc2F)ncnc1N1CCC(Sc2ccccn2)CC1] | 4-(2,4-Difluoro-phenoxy)-5-nitro-6-[4-(pyridin-2-ylsulfanyl)-piperidin-1-yl]-pyrimidine |
| A131 | 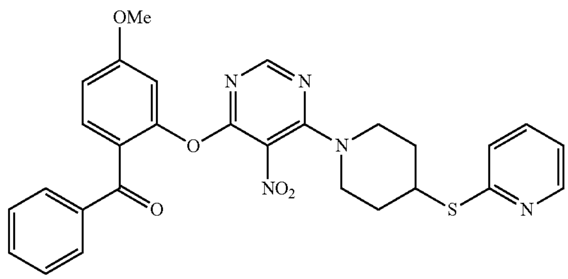 [SMILES: COc1ccc(C(=O)c2ccccc2)c(Oc2ncnc(N3CCC(Sc4ccccn4)CC3)c2[N+](=O)[O-])c1] | (4-Methoxy-2-{5-nitro-6-[4-(pyridin-2-ylsulfanyl)-piperidin-1-yl]-pyrimidin-4-yloxy}-phenyl)-phenyl-methanone |
| A132 | 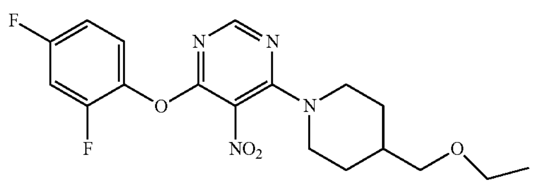 [SMILES: CCOCC1CCN(c2ncnc(Oc3ccc(F)cc3F)c2[N+](=O)[O-])CC1] | 4-(2,4-Difluoro-phenoxy)-6-(4-ethoxymethyl-piperidin-1-yl)-5-nitro-pyrimidine |
| A133 | 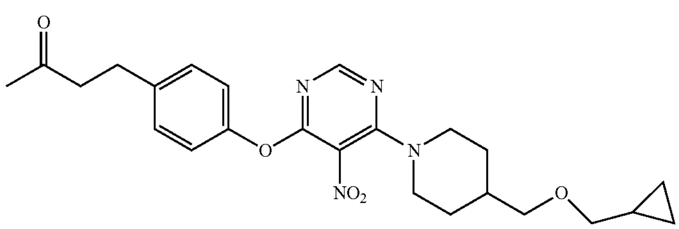 [SMILES: CC(=O)CCc1ccc(Oc2ncnc(N3CCC(COCC4CC4)CC3)c2[N+](=O)[O-])cc1] | 4-{4-[6-(4-Cyclopropylmethoxymethyl-piperidin-1-yl)-5-nitro-pyrimidin-4-yloxy]-phenyl}-butan-2-one |
| A134 | 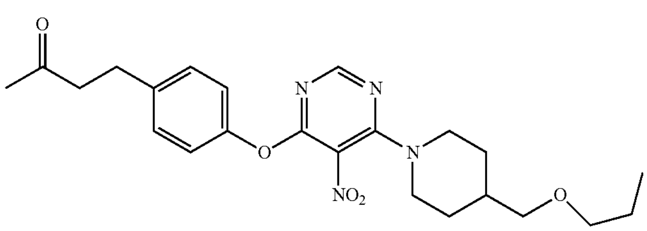 [SMILES: CCCOCC1CCN(c2ncnc(Oc3ccc(CCC(C)=O)cc3)c2[N+](=O)[O-])CC1] | 4-{4-[5-Nitro-6-(4-propoxymethyl-piperidin-1-yl)-pyrimidin-4-yloxy]-phenyl}-butan-2-one |
| A135 | 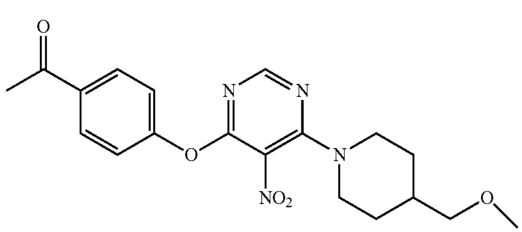 [SMILES: COCC1CCN(c2ncnc(Oc3ccc(C(C)=O)cc3)c2[N+](=O)[O-])CC1] | 1-{4-[6-(4-Methoxymethyl-piperidin-1-yl)-5-nitro-pyrimidin-4-yloxy]-phenyl}-ethanone |

TABLE A-continued

| Cmpd# | Structure | Chemical Name |
|---|---|---|
| A136 | 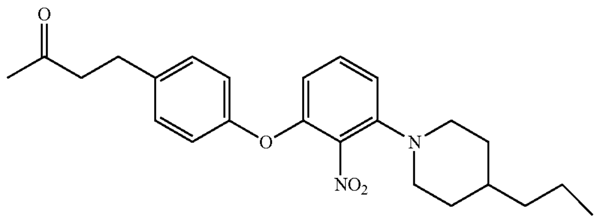 [SMILES: CCCC1CCN(c2cccc(Oc3ccc(CCC(C)=O)cc3)c2[N+](=O)[O-])CC1] | 4-{4-[2-Nitro-3-(4-propyl-piperidin-1-yl)-phenoxy)-phenyl}-butan-2-one |
| A137 | 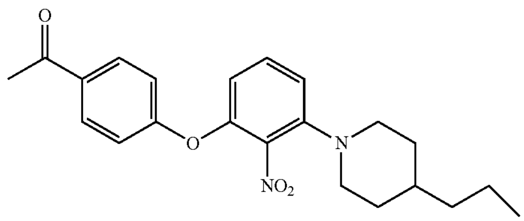 [SMILES: CCCC1CCN(c2cccc(Oc3ccc(C(C)=O)cc3)c2[N+](=O)[O-])CC1] | 1-{4-[2-Nitro-3-(4-propyl-piperidin-1-yl)-phenoxy]-phenyl}-ethanone |
| A138 | 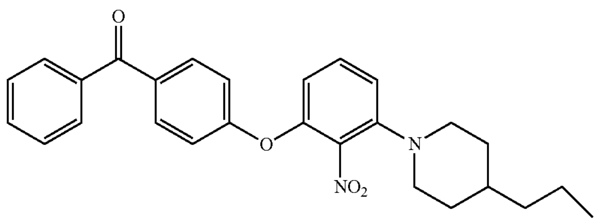 [SMILES: CCCC1CCN(c2cccc(Oc3ccc(C(=O)c4ccccc4)cc3)c2[N+](=O)[O-])CC1] | {4-[2-Nitro-3-(4-propyl-piperidin-1-yl)-phenoxy]-phenyl}-phenyl-methanone |
| A139 | 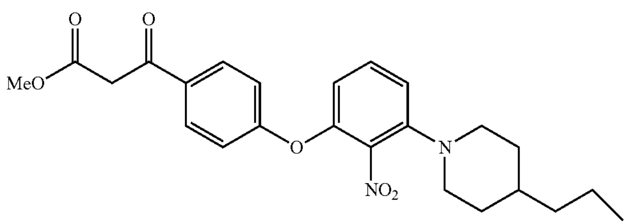 [SMILES: CCCC1CCN(c2cccc(Oc3ccc(C(=O)CC(=O)OC)cc3)c2[N+](=O)[O-])CC1] | 3-{4-[2-Nitro-3-(4-propyl-piperidin-1-yl)-phenoxy]-phenyl}-3-oxo-propionic acid methyl ester |
| A140 | 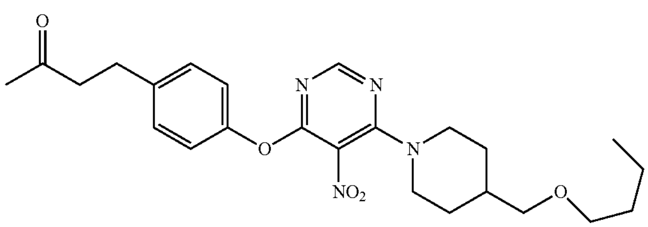 [SMILES: CCCCOCC1CCN(c2ncnc(Oc3ccc(CCC(C)=O)cc3)c2[N+](=O)[O-])CC1] | 4-{4-[6-(4-Butoxymethyl-piperidin-1-yl)-5-nitro-pyrimidin-4-yloxy]-phenyl}-butan-2-one |
| A141 | 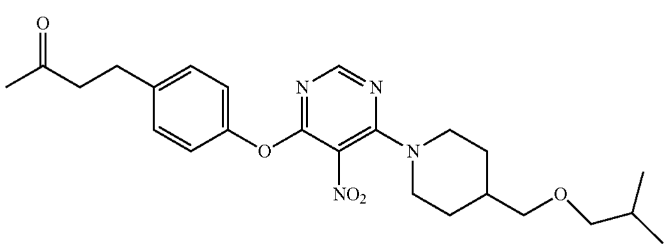 [SMILES: CC(=O)CCc1ccc(Oc2ncnc(N3CCC(COCC(C)C)CC3)c2[N+](=O)[O-])cc1] | 4-{4-[6-(4-Isobutoxymethyl-piperidin-1-yl)-5-nitro-pyrimidin-4-yloxy]-phenyl}-butan-2-one |
| A142 | 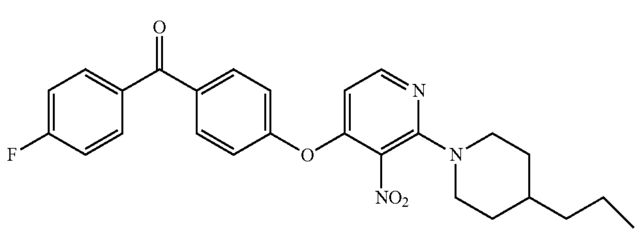 [SMILES: CCCC1CCN(c2nccc(Oc3ccc(C(=O)c4ccc(F)cc4)cc3)c2[N+](=O)[O-])CC1] | (4-Fluoro-phenyl)-[4-(3'-nitro-4-propyl-3,4,5,6-tetrahydro-2H-[1,2']bipyridinyl-4'-yloxy)-phenyl]-methanone |

TABLE A-continued

| Cmpd# | Structure | Chemical Name |
|---|---|---|
| A143 | 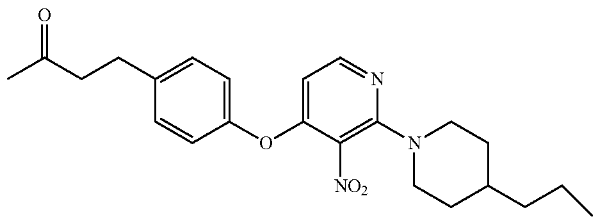 [SMILES: CCCC1CCN(c2nccc(Oc3ccc(CCC(C)=O)cc3)c2[N+](=O)[O-])CC1] | 4-[4-(3'-Nitro-4-propyl-3,4,5,6-tetrahydro-2H-[1,2']bipyridinyl-4'-yloxy)-phenyl]-butan-2-one |
| A144 | 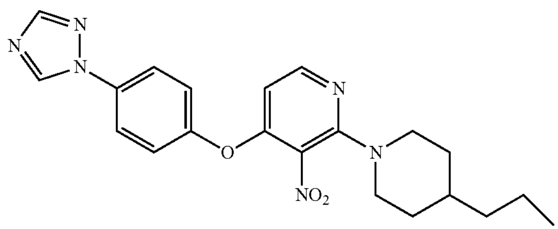 [SMILES: CCCC1CCN(c2nccc(Oc3ccc(-n4cncn4)cc3)c2[N+](=O)[O-])CC1] | 3'-Nitro-4-propyl-4'-(4-[1,2,4]triazol-1-yl-phenoxy)-3,4,5,6-tetrahydro-2H-[1,2']bipyridinyl |
| A145 | 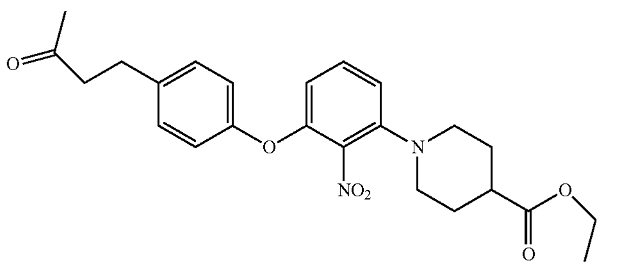 [SMILES: CCOC(=O)C1CCN(c2cccc(Oc3ccc(CCC(C)=O)cc3)c2[N+](=O)[O-])CC1] | 1-{2-Nitro-3-[4-(3-oxo-butyl)-phenoxy]-phenyl}-piperidine-4-carboxylic acid ethyl ester |
| A146 | 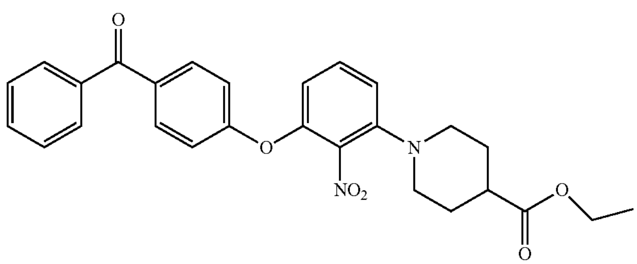 [SMILES: CCOC(=O)C1CCN(c2cccc(Oc3ccc(C(=O)c4ccccc4)cc3)c2[N+](=O)[O-])CC1] | 1-[3-(4-Benzoyl-phenoxy)-2-nitro-phenyl]-piperidine-4-carboxylic acid ethyl ester |
| A147 | 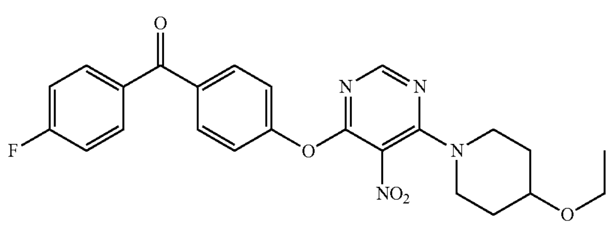 [SMILES: CCOC1CCN(c2ncnc(Oc3ccc(C(=O)c4ccc(F)cc4)cc3)c2[N+](=O)[O-])CC1] | {4-[6-(4-Ethoxy-piperidin-1-yl)-5-nitro-pyrimidin-4-yloxy]-phenyl}-(4-fluoro-phenyl)-methanone |
| A148 | 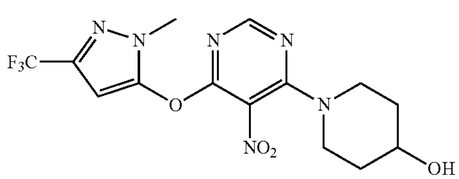 [SMILES: Cn1nc(C(F)(F)F)cc1Oc1ncnc(N2CCC(O)CC2)c1[N+](=O)[O-]] | 1-[6-(2-Methyl-5-trifluoromethyl-2H-pyrazol-3-yloxy)-5-nitro-pyrimidin-4-yl]-piperidin-4-ol |

TABLE A-continued

| Cmpd# | Structure | Chemical Name |
| --- | --- | --- |
| A149 | 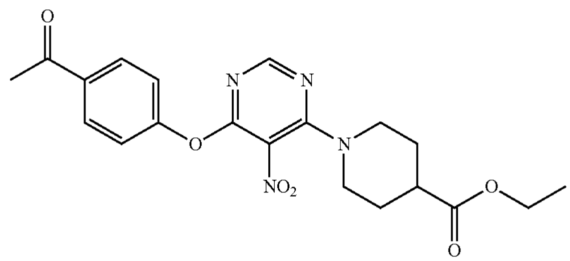 [SMILES: CCOC(=O)C1CCN(c2ncnc(Oc3ccc(C(C)=O)cc3)c2[N+](=O)[O-])CC1] | 1-[6-(4-Acetyl-phenoxy)-5-nitro-pyrimidin-4-yl]-piperidine-4-carboxylic acid ethyl ester |
| A150 | 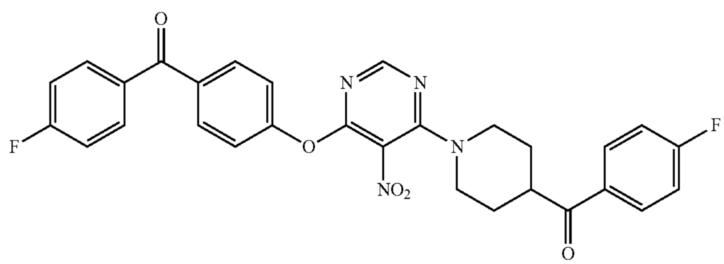 [SMILES: O=C(c1ccc(F)cc1)c1ccc(Oc2ncnc(N3CCC(C(=O)c4ccc(F)cc4)CC3)c2[N+](=O)[O-])cc1] | (1-{6-[4-(4-Fluoro-benzoyl)-phenoxy]-5-nitro-pyrimidin-4-yl}-piperidin-4-yl)-(4-fluoro-phenyl)-methanone |
| A151 | 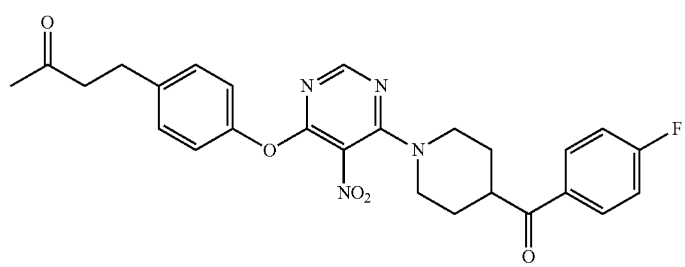 [SMILES: CC(=O)CCc1ccc(Oc2ncnc(N3CCC(C(=O)c4ccc(F)cc4)CC3)c2[N+](=O)[O-])cc1] | 4-(4-{6-[4-(4-Fluoro-benzoyl)-piperidin-1-yl]-5-nitro-pyrimidin-4-yloxy}-phenyl)-butan-2-one |
| A152 | 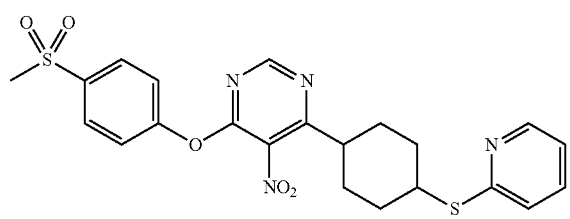 [SMILES: CS(=O)(=O)c1ccc(Oc2ncnc(C3CCC(Sc4ccccn4)CC3)c2[N+](=O)[O-])cc1] | 4-(4-Methanesulfonyl-phenoxy)-5-nitro-6-[4-(pyridin-2-ylsulfanyl)-cyclohexyl]-pyrimidine |
| A153 | 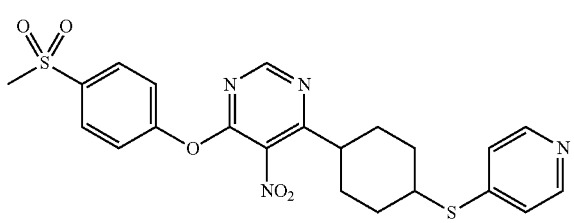 [SMILES: CS(=O)(=O)c1ccc(Oc2ncnc(C3CCC(Sc4ccncc4)CC3)c2[N+](=O)[O-])cc1] | 4-(4-Methanesulfonyl-phenoxy)-5-nitro-6-[4-(pyridin-4-ylsulfanyl)-cyclohexyl]-pyrimidine |
| A154 | 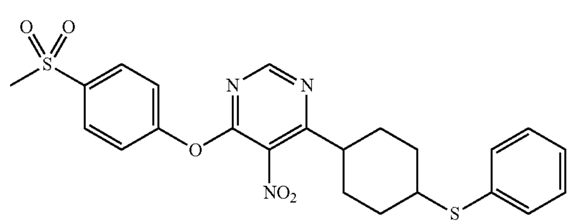 [SMILES: CS(=O)(=O)c1ccc(Oc2ncnc(C3CCC(Sc4ccccc4)CC3)c2[N+](=O)[O-])cc1] | 4-(4-Methanesulfonyl-phenoxy)-5-nitro-6-(4-phenylsulfanyl-cyclohexyl)-pyrimidine |

TABLE A-continued

| Cmpd# | Structure | Chemical Name |
|---|---|---|
| A155 | 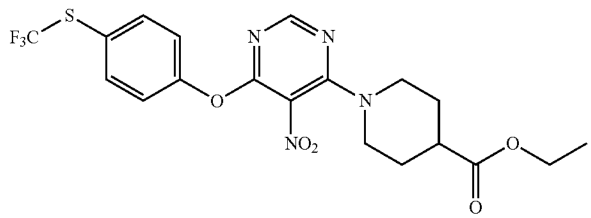 [SMILES: CCOC(=O)C1CCN(c2ncnc(Oc3ccc(SC(F)(F)F)cc3)c2[N+](=O)[O-])CC1] | 1-[5-Nitro-6-(4-trifluoromethylsulfanyl-phenoxy)-pyrimidin-4-yl]-piperidine-4-carboxylic acid ethyl ester |
| A156 | 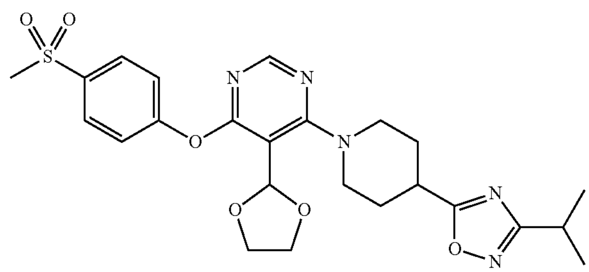 [SMILES: CC(C)c1noc(C2CCN(c3ncnc(Oc4ccc(S(C)(=O)=O)cc4)c3C3OCCO3)CC2)n1] | 5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine |
| A157 | 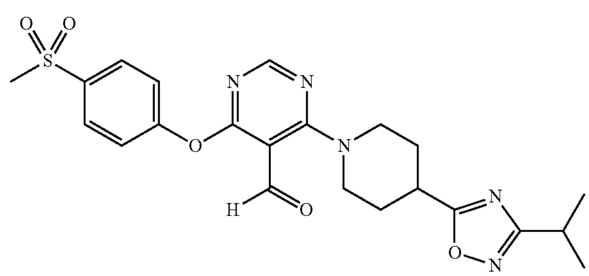 [SMILES: CC(C)c1noc(C2CCN(c3ncnc(Oc4ccc(S(C)(=O)=O)cc4)c3C=O)CC2)n1] | 4-[4-(3-Isopropyl-[1,2,4]oxadiazol-5-yl)-piperidin-1-yl]-6-(4-methanesulfonyl-phenoxy)-pyrimidine-5-carbaldehyde |
| A158 | 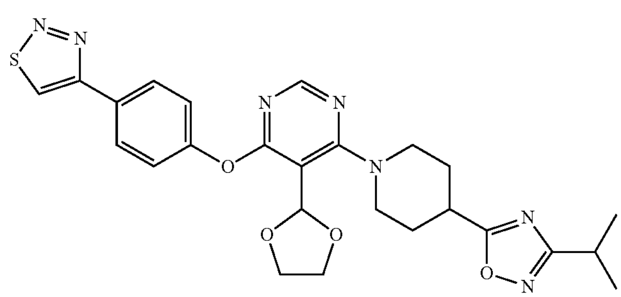 [SMILES: CC(C)c1noc(C2CCN(c3ncnc(Oc4ccc(-c5csnn5)cc4)c3C3OCCO3)CC2)n1] | 5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine |
| A159 | 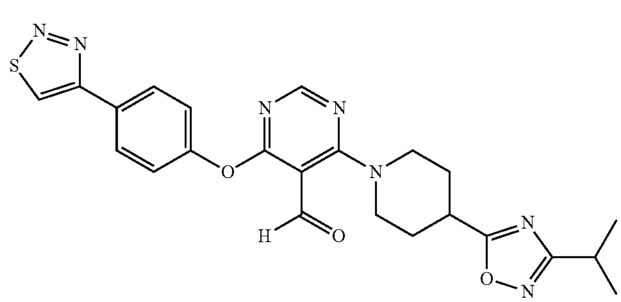 [SMILES: CC(C)c1noc(C2CCN(c3ncnc(Oc4ccc(-c5csnn5)cc4)c3C=O)CC2)n1] | 4-[4-(3-Isopropyl-[1,2,4]oxadiazol-5-yl)-piperidin-1-yl]-6-(4-[1,2,3]thiadiazol-4-yl-phenoxy)-pyrimidine-5-carbaldehyde |

TABLE A-continued

| Cmpd# | Structure | Chemical Name |
|---|---|---|
| A160 | 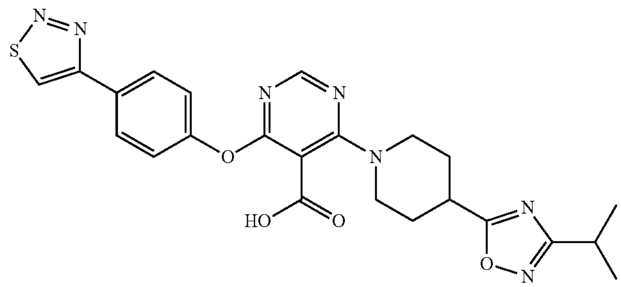 [SMILES: CC(C)c1noc(C2CCN(c3ncnc(Oc4ccc(-c5csnn5)cc4)c3C(=O)O)CC2)n1] | 4-[4-(3-Isopropyl-[1,2,4]oxadiazol-5-yl)-piperidin-1-yl]-6-(4-[1,2,3]thiadiazol-4-yl-phenoxy)-pyrimidine-5-carboxylic acid |
| A161 | 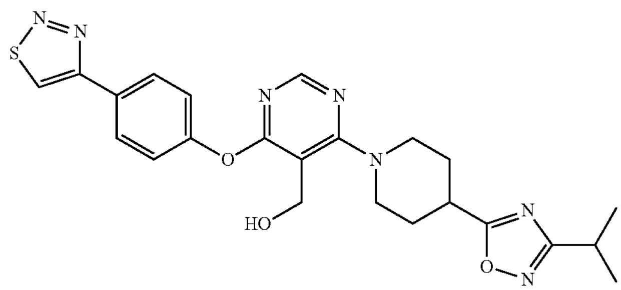 [SMILES: CC(C)c1noc(C2CCN(c3ncnc(Oc4ccc(-c5csnn5)cc4)c3CO)CC2)n1] | [4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol |
| A162 | 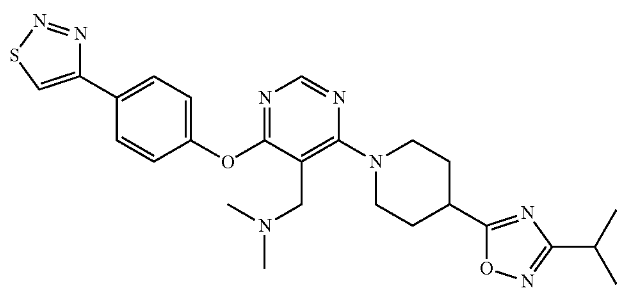 [SMILES: CC(C)c1noc(C2CCN(c3ncnc(Oc4ccc(-c5csnn5)cc4)c3CN(C)C)CC2)n1] | [4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine |
| A163 | 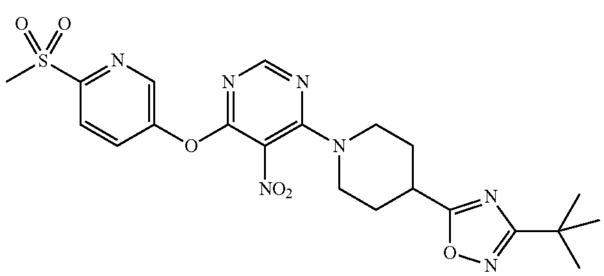 [SMILES: CC(C)(C)c1noc(C2CCN(c3ncnc(Oc4ccc(S(C)(=O)=O)nc4)c3[N+](=O)[O-])CC2)n1] | 4-[4-(3-tert-Butyl-[1,2,4]oxadiazol-5-yl)-piperidin-1-yl]-6-(6-methanesulfonyl-pyridin-3-yloxy)-5-nitro-pyrimidine |
| A164 | 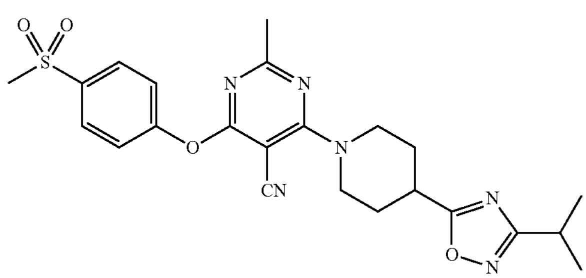 [SMILES: Cc1nc(Oc2ccc(S(C)(=O)=O)cc2)c(C#N)c(N2CCC(c3nc(C(C)C)no3)CC2)n1] | 4-[4-(3-Isopropyl-[1,2,4]oxadiazol-5-yl)-piperidin-1-yl]-6-(4-methanesulfonyl-phenoxy)-2-methyl-pyrimidine-5-carbonitrile |

TABLE A-continued

| Cmpd# | Structure | Chemical Name |
|---|---|---|
| A165 | 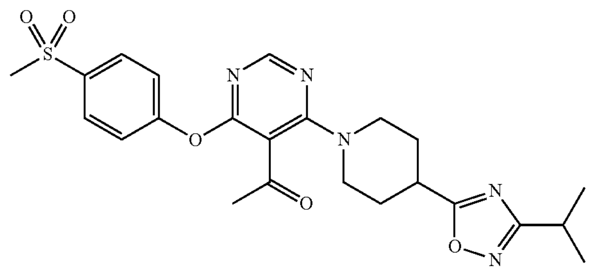 [SMILES: CC(=O)c1c(Oc2ccc(S(C)(=O)=O)cc2)ncnc1N1CCC(c2nc(C(C)C)no2)CC1] | 1-[4-[4-(3-Isopropyl-[1,2,4]oxadiazol-5-yl)-piperidin-1-yl]-6-(4-methanesulfonyl-phenoxy)-pyrimidin-5-yl]-ethanone |

TABLE B

| Cmpd # | Structure | Chemical Name |
|---|---|---|
| B1 | 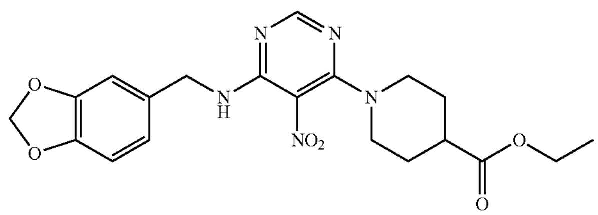 [SMILES: CCOC(=O)C1CCN(c2ncnc(NCc3ccc4c(c3)OCO4)c2[N+](=O)[O-])CC1] | 1-{6-[(Benzo[1,3]dioxol-5-ylmethyl)-amino]-5-nitro-pyrimidin-4-yl}-piperidine-4-carboxylic acid ethyl ester |
| B2 | 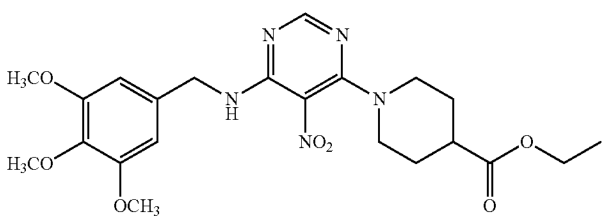 [SMILES: CCOC(=O)C1CCN(c2ncnc(NCc3cc(OC)c(OC)c(OC)c3)c2[N+](=O)[O-])CC1] | 1-[5-Nitro-6-(3,4,5-trimethoxy-benzylamino)-pyrimidin-4-yl]-piperidine-4-carboxylic acid ethyl ester |
| B3 | 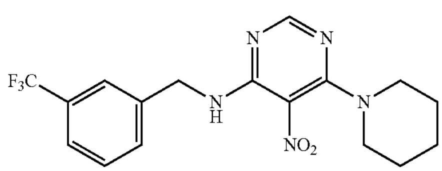 [SMILES: O=[N+]([O-])c1c(NCc2cccc(C(F)(F)F)c2)ncnc1N1CCCCC1] | (5-Nitro-6-piperidin-1-yl-pyrimidin-4-yl)-(3-trifluoromethyl-benzyl)-amine |
| B4 | 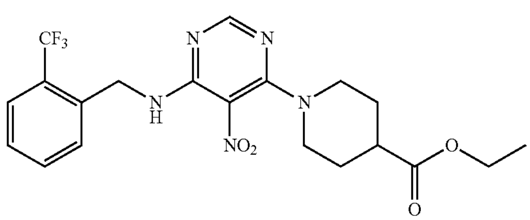 [SMILES: CCOC(=O)C1CCN(c2ncnc(NCc3ccccc3C(F)(F)F)c2[N+](=O)[O-])CC1] | 1-[5-Nitro-6-(2-trifluoromethyl-benzylamino)-pyrimidin-4-yl]-piperidine-4-carboxylic acid ethyl ester |
| B5 | 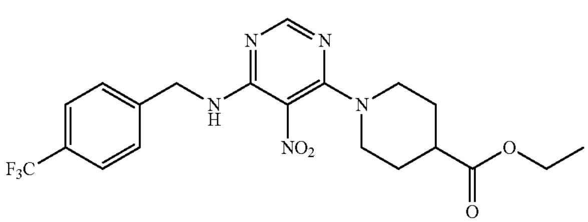 [SMILES: CCOC(=O)C1CCN(c2ncnc(NCc3ccc(C(F)(F)F)cc3)c2[N+](=O)[O-])CC1] | 1-[5-Nitro-6-(4-trifluoromethyl-benzylamino)-pyrimidin-4-yl]-piperidine-4-carboxylic acid ethyl ester |

TABLE B-continued

| Cmpd # | Structure | Chemical Name |
|---|---|---|
| B6 | 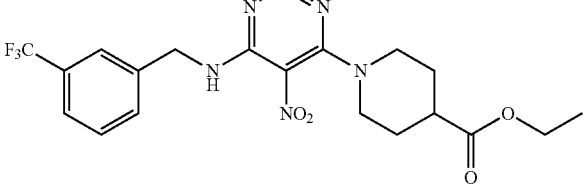 | 1-[5-Nitro-6-(3-trifluoromethyl-benzylamino)-pyrimidin-4-yl]-piperidine-4-carboxylic acid ethyl ester |
| B7 | 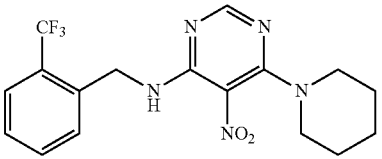 [SMILES: O=[N+]([O-])c1c(NCc2ccccc2C(F)(F)F)ncnc1N1CCCCC1] | (5-Nitro-6-piperidin-1-yl-pyrimidin-4-yl)-(2-trifluoromethyl-benzyl)-amine |
| B8 | 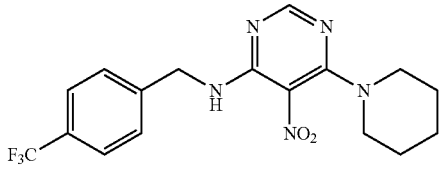 [SMILES: O=[N+]([O-])c1c(NCc2ccc(C(F)(F)F)cc2)ncnc1N1CCCCC1] | (5-Nitro-6-piperidin-1-yl-pyrimidin-4-yl)-(4-trifluoromethyl-benzyl)-amine |
| B9 | 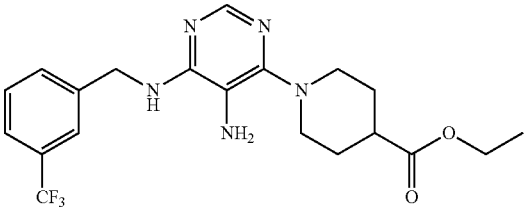 [SMILES: CCOC(=O)C1CCN(c2ncnc(NCc3cccc(C(F)(F)F)c3)c2N)CC1] | 1-[5-Amino-6-(3-trifluoromethyl-benzylamino)-pyrimidin-4-yl]-piperidine-4-carboxylic acid ethyl ester |
| B10 | 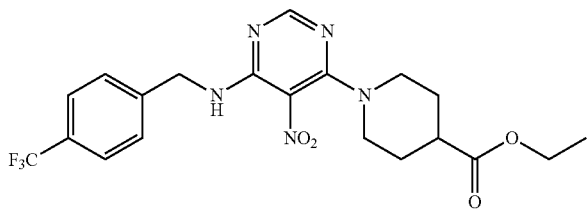 [SMILES: CCOC(=O)C1CCN(c2ncnc(NCc3ccc(C(F)(F)F)cc3)c2[N+](=O)[O-])CC1] | 1-[5-Amino-6-(4-trifluoromethyl-benzylamino)-pyrimidin-4-yl]-piperidine-4-carboxylic acid ethyl ester |
| B11 | 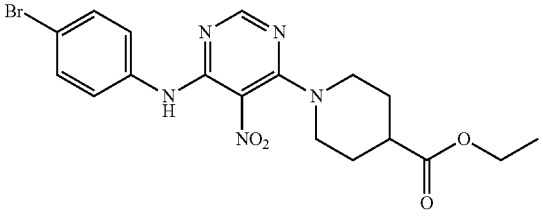 | 1-[6-(4-Bromo-phenylamino)-5-nitro-pyrimidin-4-yl]-piperidine-4-carboxylic acid ethyl ester |
| B12 | 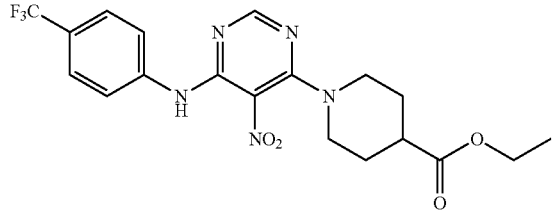 [SMILES: CCOC(=O)C1CCN(c2ncnc(Nc3ccc(C(F)(F)F)cc3)c2[N+](=O)[O-])CC1] | 1-[5-Nitro-6-(4-trifluoromethyl-phenylamino)-pyrimidin-4-yl]-piperidine-4-carboxylic acid ethyl ester |

TABLE B-continued

| Cmpd # | Structure | Chemical Name |
| --- | --- | --- |
| B13 | 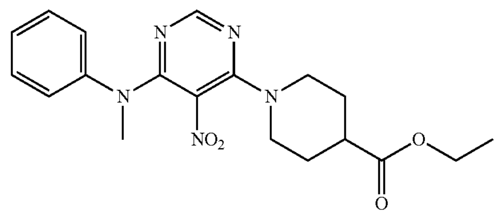 [SMILES: CCOC(=O)C1CCN(c2ncnc(N(C)c3ccccc3)c2[N+](=O)[O-])CC1] | 1-[6-(Methyl-phenyl-amino)-5-nitro-pyrimidin-4-yl]-piperidine-4-carboxylic acid ethyl ester |
| B14 | 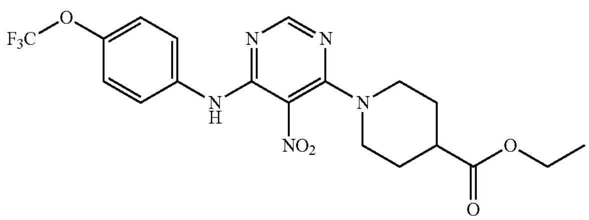 [SMILES: CCOC(=O)C1CCN(c2ncnc(Nc3ccc(OC(F)(F)F)cc3)c2[N+](=O)[O-])CC1] | 1-[5-Nitro-6-(4-trifluoromethoxy-phenylamino)-pyrimidin-4-yl]-piperidine-4-carboxylic acid ethyl ester |
| B15 | 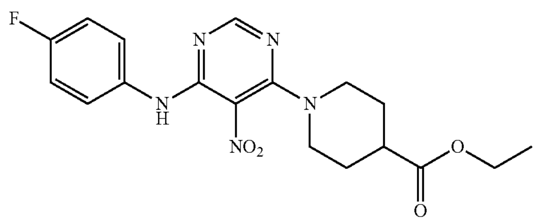 [SMILES: CCOC(=O)C1CCN(c2ncnc(Nc3ccc(F)cc3)c2[N+](=O)[O-])CC1] | 1-[6-(4-Fluoro-phenylamino)-5-nitro-pyrimidin-4-yl]-piperidine-4-carboxylic acid ethyl ester |
| B16 | 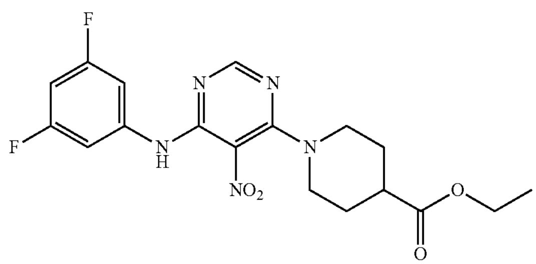 [SMILES: CCOC(=O)C1CCN(c2ncnc(Nc3cc(F)cc(F)c3)c2[N+](=O)[O-])CC1] | 1-[6-(3,5-Difluoro-phenylamino)-5-nitro-pyrimidin-4-yl]-piperidine-4-carboxylic acid ethyl ester |
| B17 | 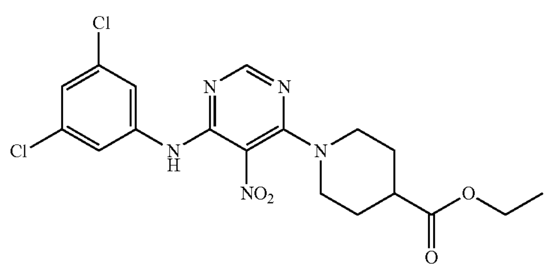 [SMILES: CCOC(=O)C1CCN(c2ncnc(Nc3cc(Cl)cc(Cl)c3)c2[N+](=O)[O-])CC1] | 1-[6-(3,5-Dichloro-phenylamino)-5-nitro-pyrimidin-4-yl]-piperidine-4-carboxylic acid ethyl ester |
| B18 | 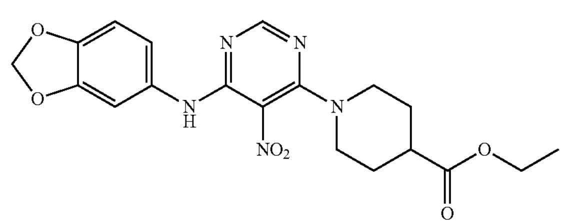 [SMILES: CCOC(=O)C1CCN(c2ncnc(Nc3ccc4c(c3)OCO4)c2[N+](=O)[O-])CC1] | 1-[6-(Benzo[1,3]dioxol-5-ylamino)-5-nitro-pyrimidin-4-yl]-piperidine-4-carboxylic acid ethyl ester |

TABLE B-continued

| Cmpd # | Structure | Chemical Name |
|---|---|---|
| B19 | 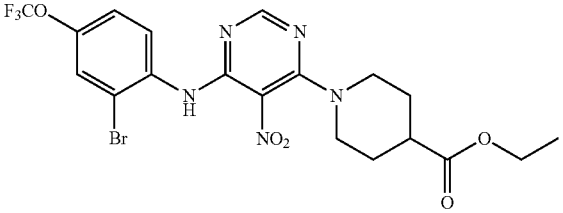 [SMILES: CCOC(=O)C1CCN(c2ncnc(Nc3ccc(OC(F)(F)F)cc3Br)c2[N+](=O)[O-])CC1] | 1-[6-(2-Bromo-4-trifluoromethoxy-phenylamino)-5-nitro-pyrimidin-4-yl]-piperidine-4-carboxylic acid ethyl ester |
| B20 | 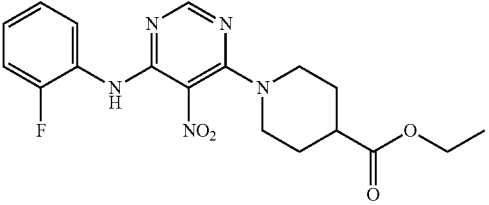 [SMILES: CCOC(=O)C1CCN(c2ncnc(Nc3ccccc3F)c2[N+](=O)[O-])CC1] | 1-[6-(2-Fluoro-phenylamino)-5-nitro-pyrimidin-4-yl]-piperidine-4-carboxylic acid ethyl ester |
| B21 | 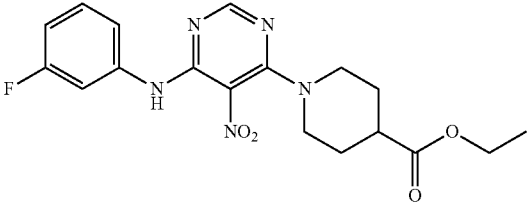 [SMILES: CCOC(=O)C1CCN(c2ncnc(Nc3cccc(F)c3)c2[N+](=O)[O-])CC1] | 1-[6-(3-Fluoro-phenylamino)-5-nitro-pyrimidin-4-yl]-piperidine-4-carboxylic acid ethyl ester |
| B22 | 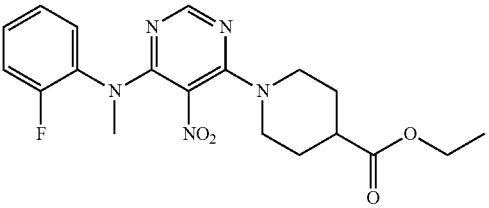 [SMILES: CCOC(=O)C1CCN(c2ncnc(N(C)c3ccccc3F)c2[N+](=O)[O-])CC1] | 1-{6-[(2-Fluoro-phenyl)-methyl-amino]-5-nitro-pyrimidin-4-yl}-piperidine-4-carboxylic acid ethyl ester |
| B23 | 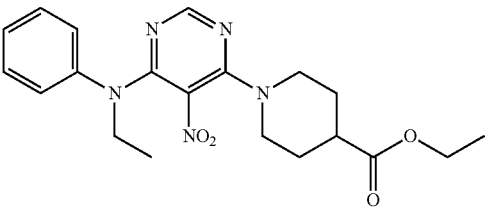 [SMILES: CCOC(=O)C1CCN(c2ncnc(N(CC)c3ccccc3)c2[N+](=O)[O-])CC1] | 1-[6-(Ethyl-phenyl-amino)-5-nitro-pyrimidin-4-yl]-piperidine-4-carboxylic acid ethyl ester |
| B24 | 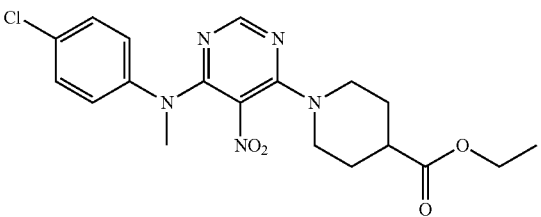 [SMILES: CCOC(=O)C1CCN(c2ncnc(N(C)c3ccc(Cl)cc3)c2[N+](=O)[O-])CC1] | 1-{6-[(4-Chloro-phenyl)-methyl-amino]-5-nitro-pyrimidin-4-yl}-piperidine-4-carboxylic acid ethyl ester |
| B25 | 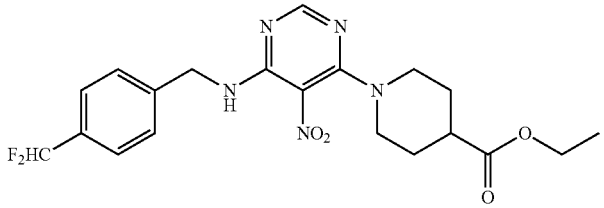 [SMILES: CCOC(=O)C1CCN(c2ncnc(NCc3ccc(C(F)F)cc3)c2[N+](=O)[O-])CC1] | 1-[6-(4-Difluoromethyl-benzylamino)-5-nitro-pyrimidin-4-yl]-piperidine-4-carboxylic acid ethyl ester |

TABLE B-continued

| Cmpd # | Structure | Chemical Name |
|---|---|---|
| B26 | 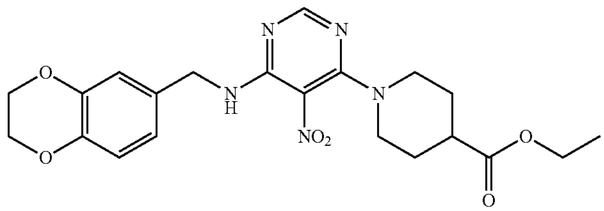 [SMILES: CCOC(=O)C1CCN(c2ncnc(NCc3ccc4c(c3)OCCO4)c2[N+](=O)[O-])CC1] | 1-{6-[(2,3-Dihydro-benzo[1,4]dioxin-6-ylmethyl)-amino]-5-nitro-pyrimidin-4-yl}-piperidine-4-carboxylic acid ethyl ester |
| B27 | 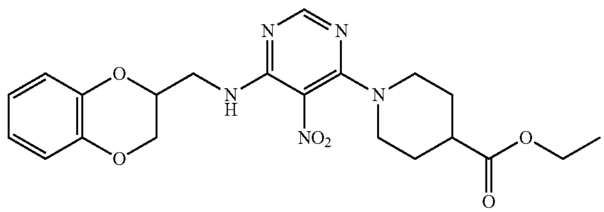 [SMILES: CCOC(=O)C1CCN(c2ncnc(NCC3COc4ccccc4O3)c2[N+](=O)[O-])CC1] | 1-{6-[(2,3-Dihydro-benzo[1,4]dioxin-2-ylmethyl)-amino]-5-nitro-pyrimidin-4-yl}-piperidine-4-carboxylic acid ethyl ester |
| B28 | 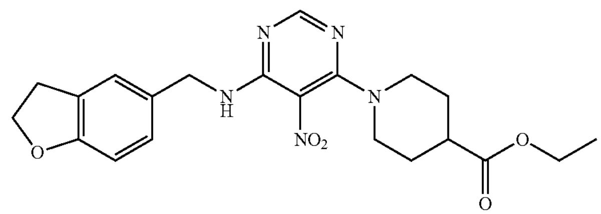 [SMILES: CCOC(=O)C1CCN(c2ncnc(NCc3ccc4c(c3)CCO4)c2[N+](=O)[O-])CC1] | 1-{6-[(2,3-Dihydro-benzofuran-5-ylmethyl)-amino]-5-nitro-pyrimidin-4-yl}-piperidine-4-carboxylic acid ethyl ester |
| B29 | 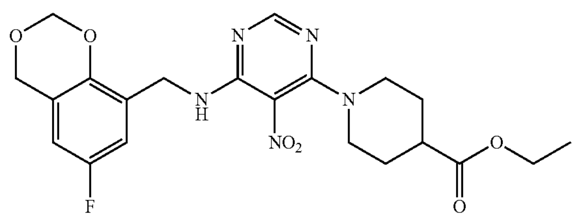 [SMILES: CCOC(=O)C1CCN(c2ncnc(NCc3cc(F)cc4c3OCOC4)c2[N+](=O)[O-])CC1] | 1-{6-[(6-Fluoro-4H-benzo[1,3]dioxin-8-ylmethyl)-amino]-5-nitro-pyrimidin-4-yl}-piperidine-4-carboxylic acid ethyl ester |
| B30 | 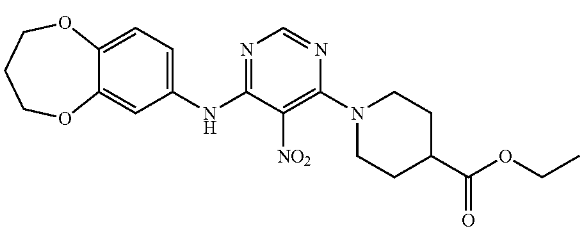 [SMILES: CCOC(=O)C1CCN(c2ncnc(Nc3ccc4c(c3)OCCCO4)c2[N+](=O)[O-])CC1] | 1-[6-(3,4-Dihydro-2H-benzo[b][1,4]dioxepin-7-ylamino)-5-nitro-pyrimidin-4-yl]-piperidine-4-carboxylic acid ethyl ester |
| B31 | 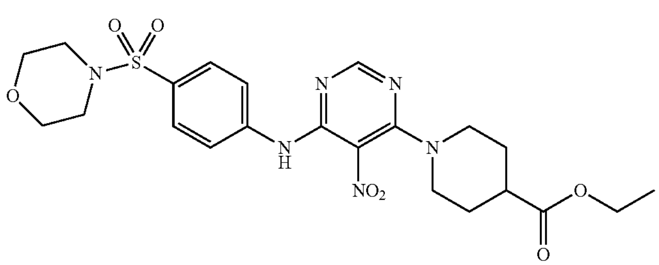 [SMILES: CCOC(=O)C1CCN(c2ncnc(Nc3ccc(S(=O)(=O)N4CCOCC4)cc3)c2[N+](=O)[O-])CC1] | 1-{6-[4-(Morpholine-4-sulfonyl)-phenylamino]-5-nitro-pyrimidin-4-yl}-piperidine-4-carboxylic acid ethyl ester |
| B32 | 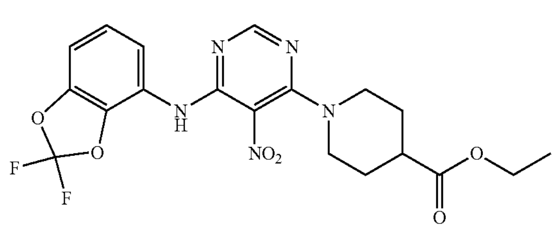 [SMILES: CCOC(=O)C1CCN(c2ncnc(Nc3cccc4c3OC(F)(F)O4)c2[N+](=O)[O-])CC1] | 1-[6-(2,2-Difluoro-benzo[1,3]dioxol-4-ylamino)-5-nitro-pyrimidin-4-yl]-piperidine-4-carboxylic acid ethyl ester |

TABLE B-continued

| Cmpd # | Structure | Chemical Name |
|---|---|---|
| B33 | 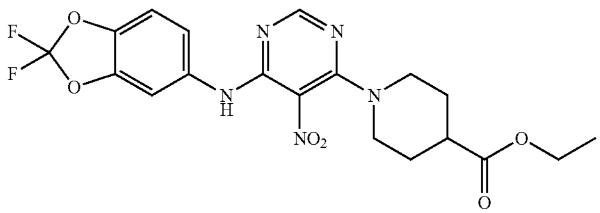 [SMILES: CCOC(=O)C1CCN(c2ncnc(Nc3ccc4c(c3)OC(F)(F)O4)c2[N+](=O)[O-])CC1] | 1-[6-(2,2-Difluoro-benzo[1,3]dioxol-5-ylamino)-5-nitro-pyrimidin-4-yl]-piperidine-4-carboxylic acid ethyl ester |
| B34 | 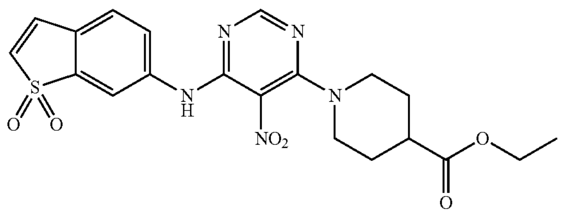 [SMILES: CCOC(=O)C1CCN(c2ncnc(Nc3ccc4c(c3)S(=O)(=O)C=C4)c2[N+](=O)[O-])CC1] | 1-[6-(1,1-Dioxo-1H-1$\lambda^6$-benzo[b]thiophen-6-ylamino)-5-nitro-pyrimidin-4-yl]-piperidine-4-carboxylic acid ethyl ester |
| B35 | 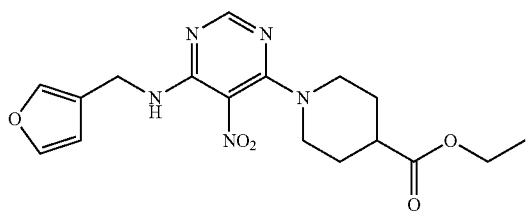 [SMILES: CCOC(=O)C1CCN(c2ncnc(NCc3ccoc3)c2[N+](=O)[O-])CC1] | 1-{6-[(Furan-3-ylmethyl)-amino]-5-nitro-pyrimidin-4-yl}-piperidine-4-carboxylic acid ethyl ester |
| B36 | 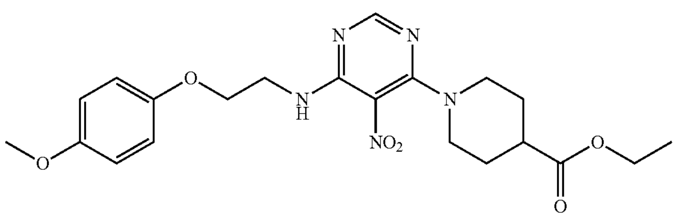 [SMILES: CCOC(=O)C1CCN(c2ncnc(NCCOc3ccc(OC)cc3)c2[N+](=O)[O-])CC1] | 1-{6-[2-(4-Methoxy-phenoxy)-ethylamino]-5-nitro-pyrimidin-4-yl}-piperidine-4-carboxylic acid ethyl ester |
| B37 | 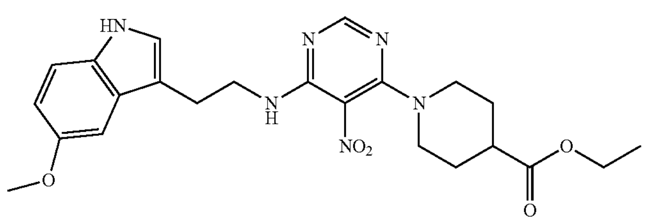 [SMILES: CCOC(=O)C1CCN(c2ncnc(NCCc3c[nH]c4ccc(OC)cc34)c2[N+](=O)[O-])CC1] | 1-{6-[2-(5-Methoxy-1H-indol-3-yl)-ethylamino]-5-nitro-pyrimidin-4-yl}-piperidine-4-carboxylic acid ethyl ester |
| B38 | 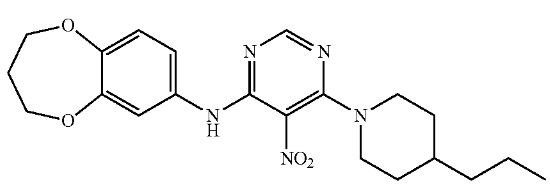 [SMILES: CCCC1CCN(c2ncnc(Nc3ccc4c(c3)OCCCO4)c2[N+](=O)[O-])CC1] | (3,4-Dihydro-2H-benzo[b][1,4]dioxepin-7-yl)-[5-nitro-6-(4-propyl-piperidin-1-yl)-pyrimidin-4-yl]-amine |
| B39 | 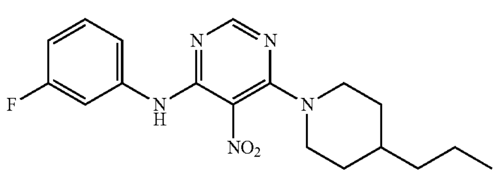 [SMILES: CCCC1CCN(c2ncnc(Nc3cccc(F)c3)c2[N+](=O)[O-])CC1] | (3-Fluoro-phenyl)-[5-nitro-6-(4-propyl-piperidin-1-yl)-pyrimidin-4-yl]-amine |

TABLE B-continued

| Cmpd # | Structure | Chemical Name |
|---|---|---|
| B40 | 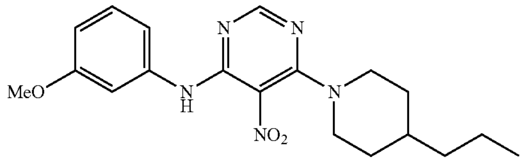 [SMILES: CCCC1CCN(c2ncnc(Nc3cccc(OC)c3)c2[N+](=O)[O-])CC1] | (3-Methoxy-phenyl)-[5-nitro-6-(4-propyl-piperidin-1-yl)-pyrimidin-4-yl]-amine |
| B41 | 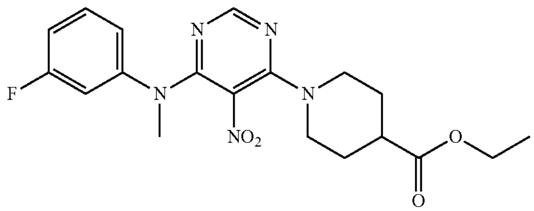 [SMILES: CCOC(=O)C1CCN(c2ncnc(N(C)c3cccc(F)c3)c2[N+](=O)[O-])CC1] | 1-{6-[(3-Fluoro-phenyl)-methyl-amino]-5-nitro-pyrimidin-4-yl}-piperidine-4-carboxylic acid ethyl ester |
| B42 | 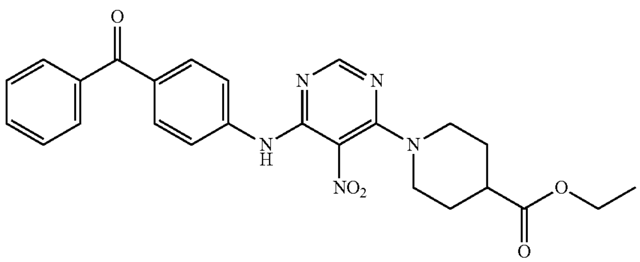 [SMILES: CCOC(=O)C1CCN(c2ncnc(Nc3ccc(C(=O)c4ccccc4)cc3)c2[N+](=O)[O-])CC1] | 1-[6-(4-Benzoyl-phenylamino)-5-nitro-pyrimidin-4-yl]-piperidine-4-carboxylic acid ethyl ester |
| B43 | 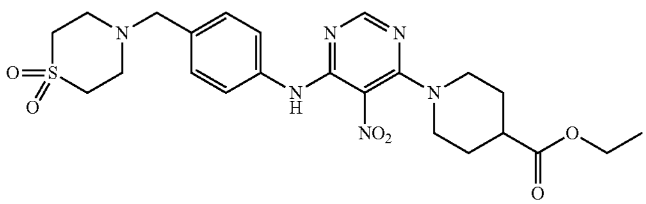 [SMILES: CCOC(=O)C1CCN(c2ncnc(Nc3ccc(CN4CCS(=O)(=O)CC4)cc3)c2[N+](=O)[O-])CC1] | 1-{6-[4-(1,1-Dioxo-1$\lambda^6$-thiomorpholin-4-ylmethyl)-phenylamino]-5-nitro-pyrimidin-4-yl}-piperidine-4-carboxylic acid ethyl ester |
| B44 | 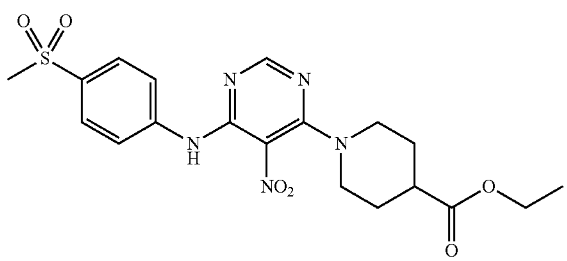 [SMILES: CCOC(=O)C1CCN(c2ncnc(Nc3ccc(S(C)(=O)=O)cc3)c2[N+](=O)[O-])CC1] | 1-[6-(4-Methanesulfonyl-phenylamino)-5-nitro-pyrimidin-4-yl]-piperidine-4-carboxylic acid ethyl ester |
| B45 | 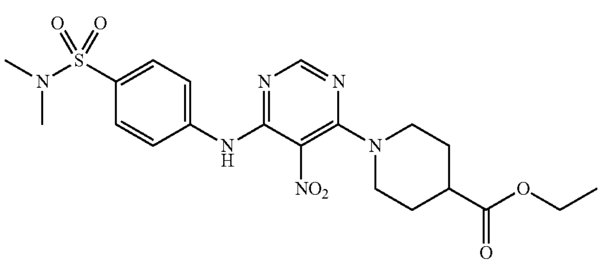 [SMILES: CCOC(=O)C1CCN(c2ncnc(Nc3ccc(S(=O)(=O)N(C)C)cc3)c2[N+](=O)[O-])CC1] | 1-[6-(4-Dimethylsulfamoyl-phenylamine)-5-nitro-pyrimidin-4-yl]-piperidine-4-carboxylic acid ethyl ester |
| B46 | 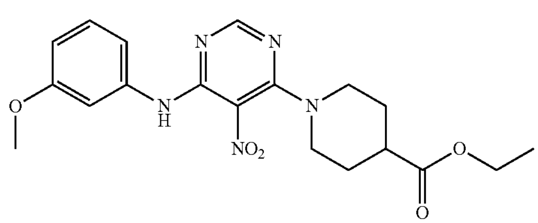 [SMILES: CCOC(=O)C1CCN(c2ncnc(Nc3cccc(OC)c3)c2[N+](=O)[O-])CC1] | 1-[6-(3-Methoxy-phenylamino)-5-nitro-pyrimidin-4-yl]-piperidine-4-carboxylic acid ethyl ester |

TABLE B-continued

| Cmpd # | Structure | Chemical Name |
| --- | --- | --- |
| B47 | 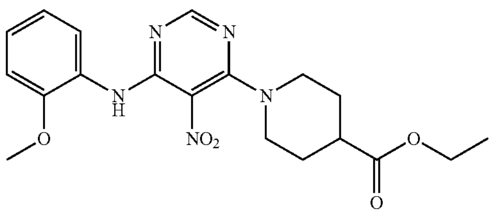 [SMILES: CCOC(=O)C1CCN(c2ncnc(Nc3ccccc3OC)c2[N+](=O)[O-])CC1] | 1-[6-(2-Methoxy-phenylamino)-5-nitro-pyrimidin-4-yl]-piperidine-4-carboxylic acid ethyl ester |
| B48 | 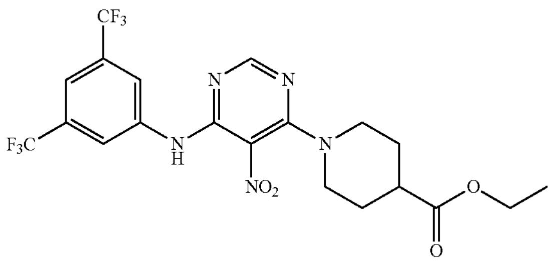 [SMILES: CCOC(=O)C1CCN(c2ncnc(Nc3cc(C(F)(F)F)cc(C(F)(F)F)c3)c2[N+](=O)[O-])CC1] | 1-[6-(3,5-Bis-trifluoromethyl-phenylamino)-5-nitro-pyrimidin-4-yl]-piperidine-4-carboxylic acid ethyl ester |
| B49 | 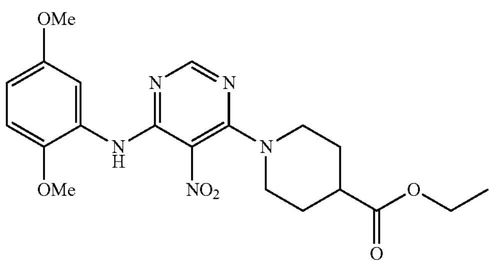 [SMILES: CCOC(=O)C1CCN(c2ncnc(Nc3cc(OC)ccc3OC)c2[N+](=O)[O-])CC1] | 1-[6-(2,5-Dimethoxy-phenylamino)-5-nitro-pyrimidin-4-yl]-piperidine-4-carboxylic acid ethyl ester |
| B50 | 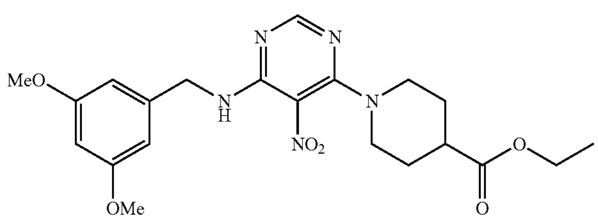 [SMILES: CCOC(=O)C1CCN(c2ncnc(NCc3cc(OC)cc(OC)c3)c2[N+](=O)[O-])CC1] | 1-[6-(3,5-Dimethoxy-benzylamino)-5-nitro-pyrimidin-4-yl]-piperidine-4-carboxylic acid ethyl ester |
| B51 | 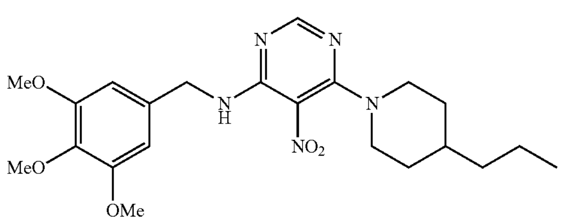 [SMILES: CCCC1CCN(c2ncnc(NCc3cc(OC)c(OC)c(OC)c3)c2[N+](=O)[O-])CC1] | [5-Nitro-6-(4-propyl-piperidin-1-yl)-pyrimidin-4-yl]-(3,4,5-trimethoxy-benzyl)-amine |
| B52 | 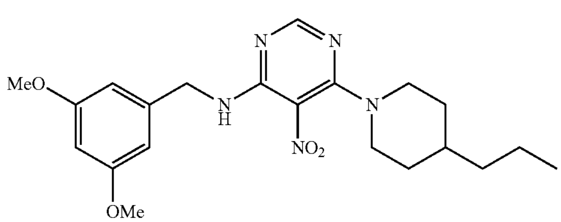 [SMILES: CCCC1CCN(c2ncnc(NCc3cc(OC)cc(OC)c3)c2[N+](=O)[O-])CC1] | (3,5-Dimethoxy-benzyl)-[5-nitro-6-(4-propyl-piperidin-1-yl)-pyrimidin-4-yl]-amine |

TABLE B-continued

| Cmpd # | Structure | Chemical Name |
|---|---|---|
| B53 | 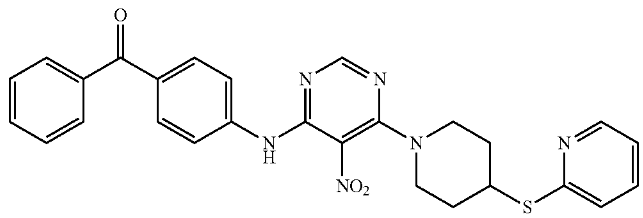 [SMILES: O=C(c1ccccc1)c1ccc(Nc2ncnc(N3CCC(Sc4ccccn4)CC3)c2[N+](=O)[O-])cc1] | (4-{5-Nitro-6-[4-(pyridin-2-ylsulfanyl)-piperidin-1-yl]-pyrimidin-4-ylamino}-phenyl)-phenyl-methanone |
| B54 | 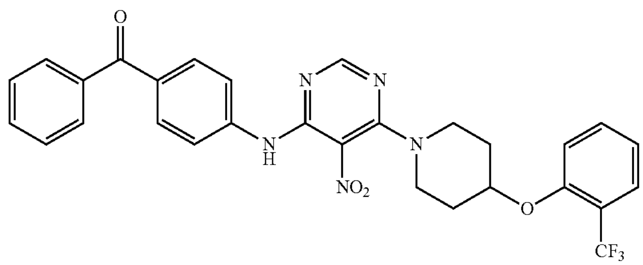 [SMILES: O=C(c1ccccc1)c1ccc(Nc2ncnc(N3CCC(Oc4ccccc4C(F)(F)F)CC3)c2[N+](=O)[O-])cc1] | (4-{5-Nitro-6-[4-(2-trifluoromethyl-phenoxy)-piperidin-1-yl]-pyrimidin-4-ylamino}-phenyl)-phenyl-methanone |
| B55 | 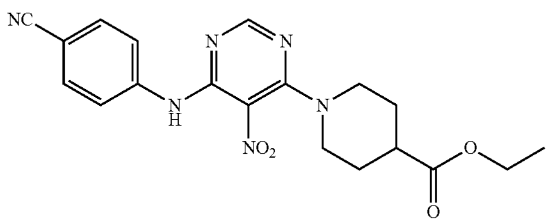 [SMILES: CCOC(=O)C1CCN(c2ncnc(Nc3ccc(C#N)cc3)c2[N+](=O)[O-])CC1] | 1-[6-(4-Cyano-phenylamino)-5-nitro-pyrimidin-4-yl]-piperidine-4-carboxylic acid ethyl ester |
| B56 | 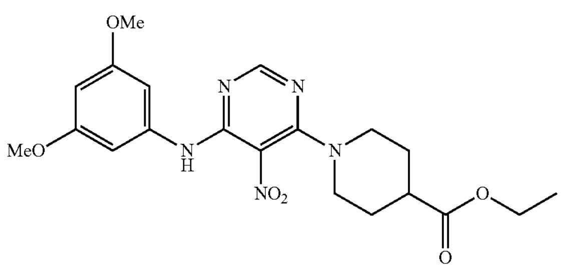 [SMILES: CCOC(=O)C1CCN(c2ncnc(Nc3cc(OC)cc(OC)c3)c2[N+](=O)[O-])CC1] | 1-[6-(3,5-Dimethoxy-phenylamino)-5-nitro-pyrimidin-4-yl]-piperidine-4-carboxylic acid ethyl ester |
| B57 | 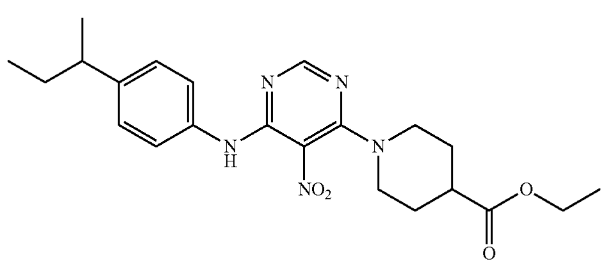 [SMILES: CCOC(=O)C1CCN(c2ncnc(Nc3ccc(C(C)CC)cc3)c2[N+](=O)[O-])CC1] | 1-[6-(4-sec-Butyl-phenylamino)-5-nitro-pyrimidin-4-yl]-piperidine-4-carboxylic acid ethyl ester |
| B58 | 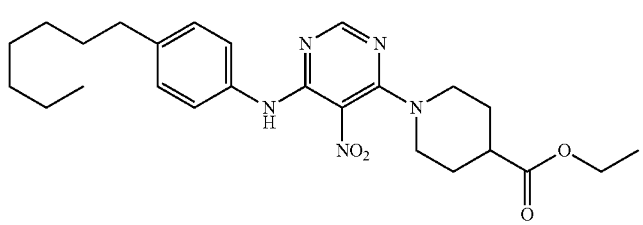 [SMILES: CCCCCCCc1ccc(Nc2ncnc(N3CCC(C(=O)OCC)CC3)c2[N+](=O)[O-])cc1] | 1-[6-(4-Heptyl-phenylamino)-5-nitro-pyrimidin-4-yl]-piperidine-4-carboxylic acid ethyl ester |

TABLE B-continued

| Cmpd # | Structure | Chemical Name |
|---|---|---|
| B59 | 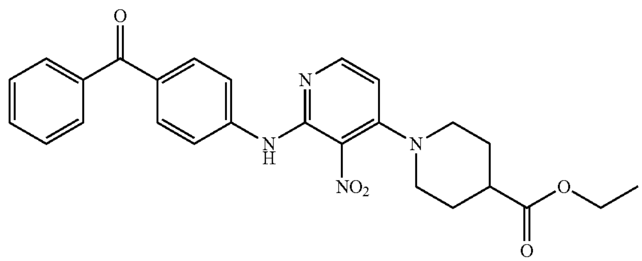 [SMILES: CCOC(=O)C1CCN(c2ccnc(Nc3ccc(C(=O)c4ccccc4)cc3)c2[N+](=O)[O-])CC1] | 2'-(4-Benzoyl-phenylamino)-3'-nitro-3,4,5,6-tetrahydro-2H-[1,4']bipyridinyl-4-carboxylic acid ethyl ester |
| B60 | 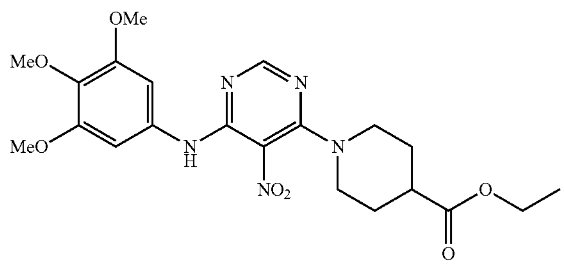 [SMILES: CCOC(=O)C1CCN(c2ncnc(Nc3cc(OC)c(OC)c(OC)c3)c2[N+](=O)[O-])CC1] | 1-[5-Nitro-6-(3,4,5-trimethoxy-phenylamino)-pyrimidin-4-yl]-piperidine-4-carboxylic acid ethyl ester |
| B61 | 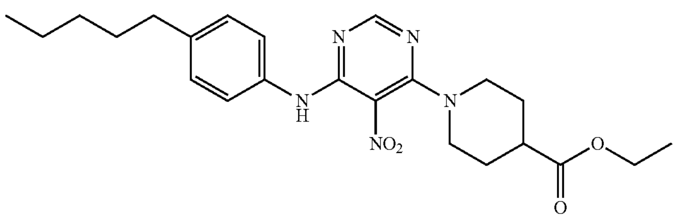 [SMILES: CCCCCc1ccc(Nc2ncnc(N3CCC(C(=O)OCC)CC3)c2[N+](=O)[O-])cc1] | 1-[5-Nitro-6-(4-pentyl-phenylamino)-pyrimidin-4-yl]-piperidine-4-carboxylic acid ethyl ester |
| B62 | 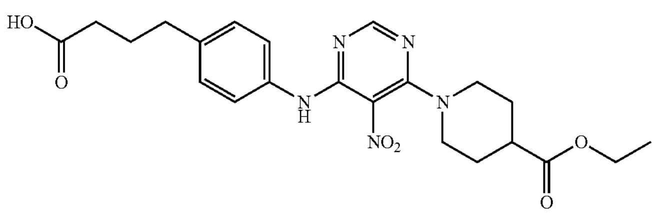 [SMILES: CCOC(=O)C1CCN(c2ncnc(Nc3ccc(CCCC(=O)O)cc3)c2[N+](=O)[O-])CC1] | 1-{6-[4-(3-Carboxy-propyl)-phenylamino]-5-nitro-pyrimidin-4-yl}-piperidine-4-carboxylic acid ethyl ester |
| B63 | 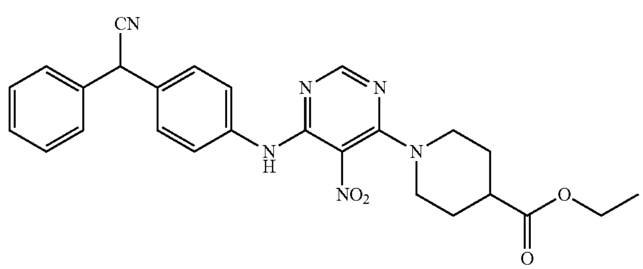 [SMILES: CCOC(=O)C1CCN(c2ncnc(Nc3ccc(C(C#N)c4ccccc4)cc3)c2[N+](=O)[O-])CC1] | 1-{6-[4-(Cyano-phenyl-methyl)-phenylamino]-5-nitro-pyrimidin-4-yl}-piperidine-4-carboxylic acid ethyl ester |
| B64 | 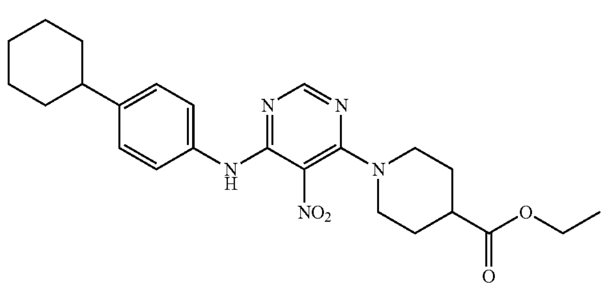 [SMILES: CCOC(=O)C1CCN(c2ncnc(Nc3ccc(C4CCCCC4)cc3)c2[N+](=O)[O-])CC1] | 1-[6-(4-Cyclohexyl-phenylamino)-5-nitro-pyrimidin-4-yl]-piperidine-4-carboxylic acid ethyl ester |

TABLE B-continued

| Cmpd # | Structure | Chemical Name |
|---|---|---|
| B65 | 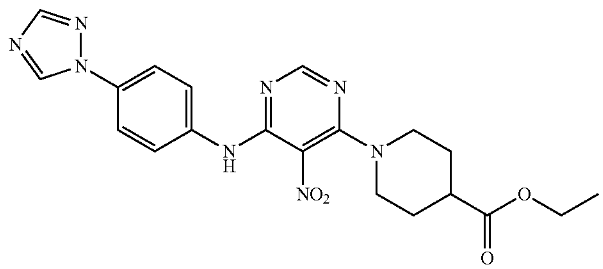 [SMILES: CCOC(=O)C1CCN(c2ncnc(Nc3ccc(-n4cncn4)cc3)c2[N+](=O)[O-])CC1] | 1-[5-Nitro-6-(4-[1,2,4]triazol-1-yl-phenylamino)-pyrimidin-4-yl]-piperidine-4-carboxylic acid ethyl ester |
| B66 | 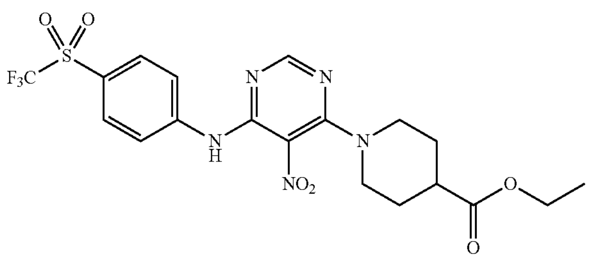 [SMILES: CCOC(=O)C1CCN(c2ncnc(Nc3ccc(S(=O)(=O)C(F)(F)F)cc3)c2[N+](=O)[O-])CC1] | 1-[5-Nitro-6-(4-trifluoromethanesulfonyl-phenylamino)-pyrimidin-4-yl]-piperidine-4-carboxylic acid ethyl ester |
| B67 | 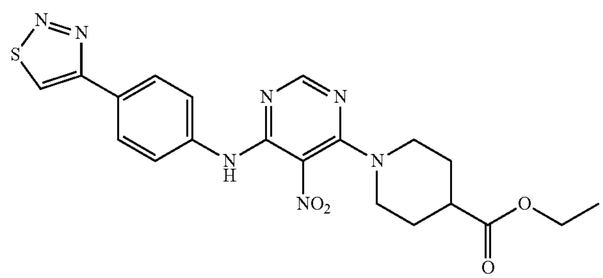 [SMILES: CCOC(=O)C1CCN(c2ncnc(Nc3ccc(-c4csnn4)cc3)c2[N+](=O)[O-])CC1] | 1-[5-Nitro-6-(4-[1,2,3]thiadiazol-4-yl-phenylamino)-pyrimidin-4-yl]-piperidine-4-carboxylic acid ethyl ester |
| B68 | 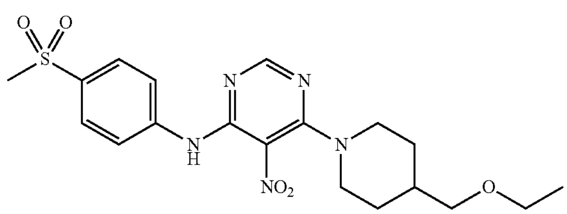 [SMILES: CCOCC1CCN(c2ncnc(Nc3ccc(S(C)(=O)=O)cc3)c2[N+](=O)[O-])CC1] | [6-(4-Ethoxymethyl-piperidin-1-yl)-5-nitro-pyrimidin-4-yl]-(4-methanesulfonyl-phenyl)-amine |
| B69 | 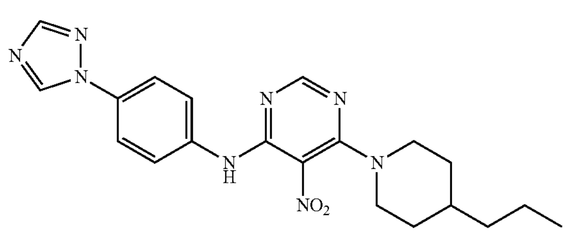 [SMILES: CCCC1CCN(c2ncnc(Nc3ccc(-n4cncn4)cc3)c2[N+](=O)[O-])CC1] | [5-Nitro-6-(4-propyl-piperidin-1-yl)-pyrimidin-4-yl]-(4-[1,2,4]triazol-1-yl-phenyl)-amine |
| B70 | 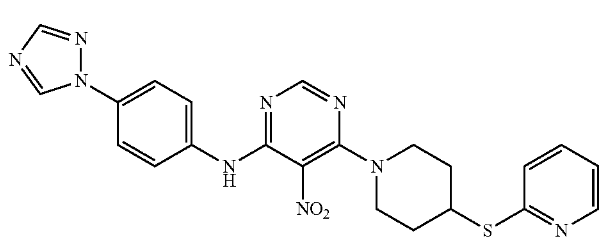 [SMILES: O=[N+]([O-])c1c(Nc2ccc(-n3cncn3)cc2)ncnc1N1CCC(Sc2ccccn2)CC1] | {5-Nitro-6-[4-[4-(pyridin-2-ylsulfanyl)-piperidin-1-yl]-pyrimidin-4-yl}-(4-[1,2,4]triazol-1-yl-phenyl)-amine |

TABLE B-continued

| Cmpd # | Structure | Chemical Name |
|---|---|---|
| B71 | 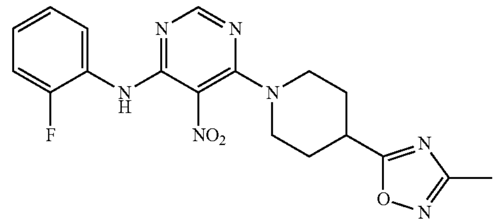 [SMILES: Cc1noc(C2CCN(c3ncnc(Nc4ccccc4F)c3[N+](=O)[O-])CC2)n1] | (2-Fluoro-phenyl)-{6-[4-(3-methyl-[1,2,4]oxadiazol-5-yl)-piperidin-1-yl]-5-nitro-pyrimidin-4-yl}-amine |
| B72 | 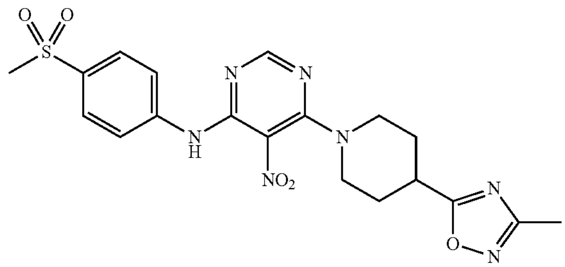 | (4-Methanesulfonyl-phenyl)-{6-[4-(3-methyl-[1,2,4]oxadiazol-5-yl)-piperidin-1-yl]-5-nitro-pyrimidin-4-yl}-amine |
| B73 | 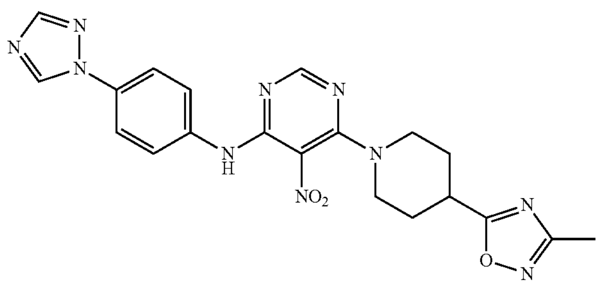 [SMILES: Cc1noc(C2CCN(c3ncnc(Nc4ccc(-n5cncn5)cc4)c3[N+](=O)[O-])CC2)n1] | {6-[4-(3-Methyl-[1,2,4]oxadiazol-5-yl)-piperidin-1-yl]-5-nitro-pyrimidin-4-yl}-(4-[1,2,4]triazol-1-yl-phenyl)-amine |
| B74 | 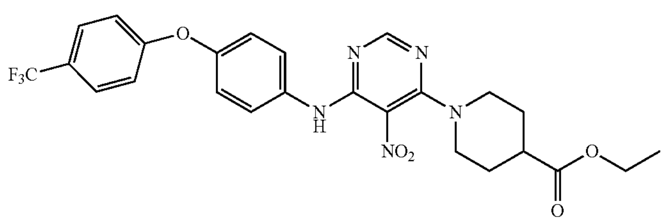 [SMILES: CCOC(=O)C1CCN(c2ncnc(Nc3ccc(Oc4ccc(C(F)(F)F)cc4)cc3)c2[N+](=O)[O-])CC1] | 1-{5-Nitro-6-[4-(4-trifluoromethyl-phenoxy)-phenylamino]-pyrimidin-4-yl}-piperidine-4-carboxylic acid ethyl ester |
| B75 | 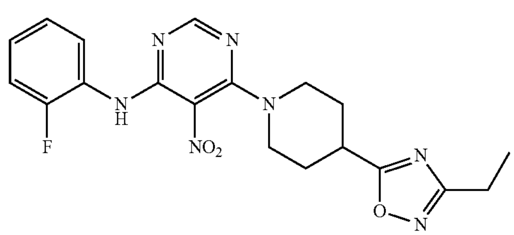 [SMILES: CCc1noc(C2CCN(c3ncnc(Nc4ccccc4F)c3[N+](=O)[O-])CC2)n1] | {6-[4-(3-Ethyl-[1,2,4]oxadiazol-5-yl)-piperidin-1-yl]-5-nitro-pyrimidin-4-yl}-(2-fluoro-phenyl)-amine |
| B76 | 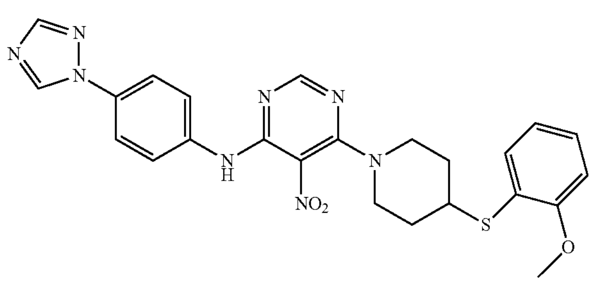 [SMILES: COc1ccccc1SC1CCN(c2ncnc(Nc3ccc(-n4cncn4)cc3)c2[N+](=O)[O-])CC1] | {6-[4-(2-Methoxy-phenylsulfanyl)-piperidin-1-yl]-5-nitro-pyrimidin-4-yl}-(4-[1,2,4]triazol-1-yl-phenyl)-amine |

TABLE B-continued

| Cmpd # | Structure | Chemical Name |
|---|---|---|
| B77 | 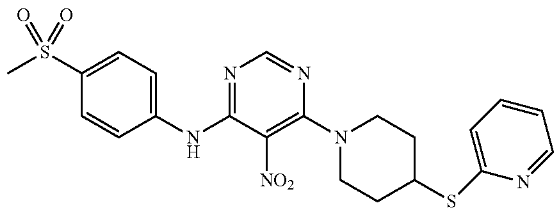 [SMILES: CS(=O)(=O)c1ccc(Nc2ncnc(N3CCC(Sc4ccccn4)CC3)c2[N+](=O)[O-])cc1] | (4-Methanesulfonyl-phenyl)-{5-nitro-6-[4-(pyridin-2-ylsulfanyl)-piperidin-1-yl]-pyrimidin-4-yl}-amine |
| B78 | 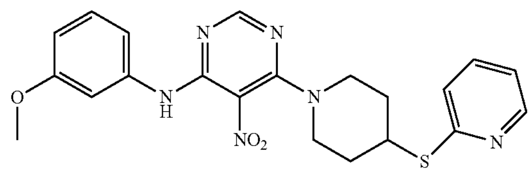 [SMILES: COc1cccc(Nc2ncnc(N3CCC(Sc4ccccn4)CC3)c2[N+](=O)[O-])c1] | (3-Methoxy-phenyl)-{5-nitro-6-[4-(pyridin-2-ylsulfanyl)-piperidin-1-yl]-pyrimidin-4-yl}-amine |
| B79 | 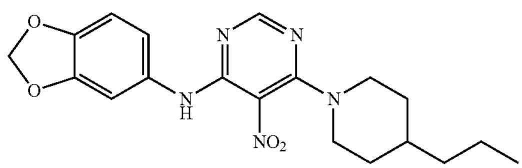 [SMILES: CCCC1CCN(c2ncnc(Nc3ccc4c(c3)OCO4)c2[N+](=O)[O-])CC1] | Benzo[1,3]dioxol-5-yl-[5-nitro-6-(4-propyl-piperidin-1-yl)-pyrimidin-4-yl]-amine |
| B80 | 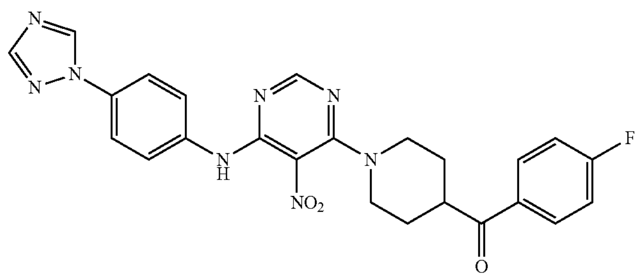 [SMILES: O=C(c1ccc(F)cc1)C1CCN(c2ncnc(Nc3ccc(-n4cncn4)cc3)c2[N+](=O)[O-])CC1] | (4-Fluoro-phenyl)-{1-[5-nitro-6-(4-[1,2,4]triazol-1-yl-phenylamino)-pyrimidin-4-yl]-piperidin-4-yl}-methanone |
| B81 | 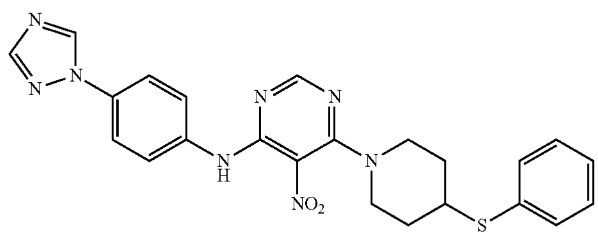 [SMILES: O=[N+]([O-])c1c(Nc2ccc(-n3cncn3)cc2)ncnc1N1CCC(Sc2ccccc2)CC1] | [5-Nitro-6-(4-phenylsulfanyl-piperidin-1-yl)-pyrimidin-4-yl]-(4-[1,2,4]triazol-1-yl-phenyl)-amine |
| B82 | 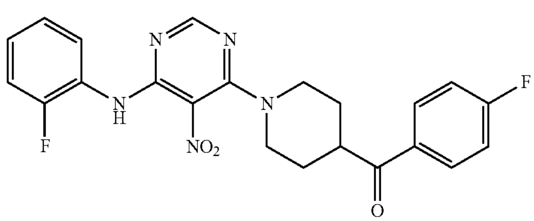 [SMILES: O=C(c1ccc(F)cc1)C1CCN(c2ncnc(Nc3ccccc3F)c2[N+](=O)[O-])CC1] | (4-Fluoro-phenyl)-{1-[6-(2-fluoro-phenylamino)-5-nitro-pyrimidin-4-yl]-piperidin-4-yl}-methanone |
| B83 | 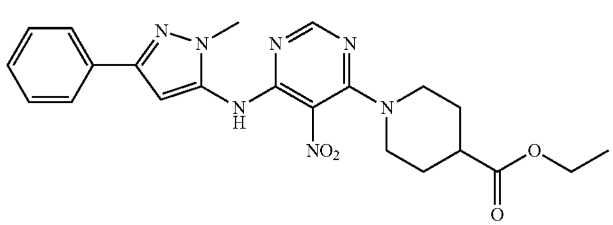 [SMILES: CCOC(=O)C1CCN(c2ncnc(Nc3cc(-c4ccccc4)nn3C)c2[N+](=O)[O-])CC1] | 1-[6-(2-Methyl-5-phenyl-2H-pyrazol-3-ylamino)-5-nitro-pyrimidin-4-yl]-piperidine-4-carboxylic acid ethyl ester |

TABLE B-continued

| Cmpd # | Structure | Chemical Name |
| --- | --- | --- |
| B84 | 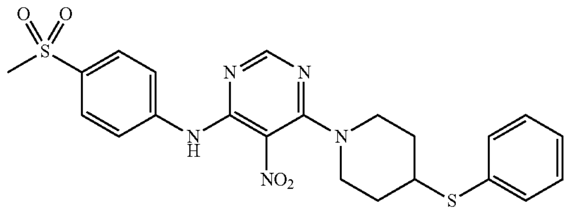 [SMILES: CS(=O)(=O)c1ccc(Nc2ncnc(N3CCC(Sc4ccccc4)CC3)c2[N+](=O)[O-])cc1] | (4-Methanesulfonyl-phenyl)-[5-nitro-6-(4-phenylsulfanyl-piperidin-1-yl)-pyrimidin-4-yl]-amine |
| B85 | 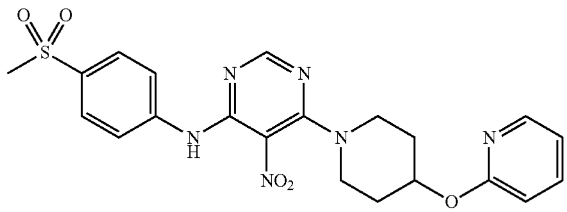 [SMILES: CS(=O)(=O)c1ccc(Nc2ncnc(N3CCC(Oc4ccccn4)CC3)c2[N+](=O)[O-])cc1] | (4-Methanesulfonyl-phenyl)-{5-nitro-6-[4-(pyridin-2-yloxy)-piperidin-1-yl]-pyrimidin-4-yl}-amine |
| B86 | 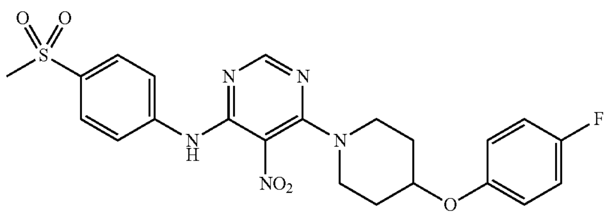 [SMILES: CS(=O)(=O)c1ccc(Nc2ncnc(N3CCC(Oc4ccc(F)cc4)CC3)c2[N+](=O)[O-])cc1] | {6-[4-(4-Fluoro-phenoxy)-piperidin-1-yl]-5-nitro-pyrimidin-4-yl}-(4-methanesulfonyl-phenyl)-amine |
| B87 | 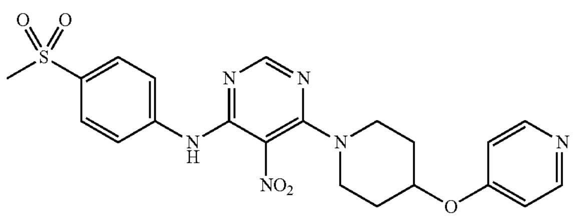 [SMILES: CS(=O)(=O)c1ccc(Nc2ncnc(N3CCC(Oc4ccncc4)CC3)c2[N+](=O)[O-])cc1] | (4-Methanesulfonyl-phenyl)-{5-nitro-6-[4-(pyridin-4-yloxy)-piperidin-1-yl]-pyrimidin-4-yl}-amine |
| B88 | 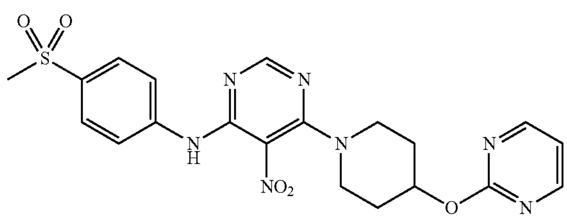 | (4-Methanesulfonyl-phenyl)-{5-nitro-6-[4-(pyrimidin-2-yloxy)-piperidin-1-yl]-pyrimidin-4-yl}-amine |
| B89 | 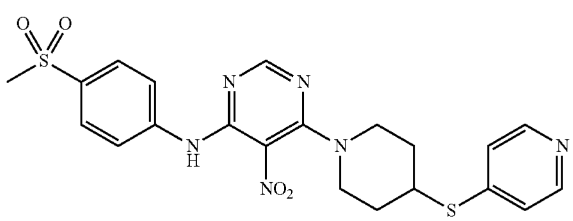 | (4-Methanesulfonyl-phenyl)-{5-nitro-6-[4-(pyridin-4-ylsulfanyl)-piperidin-1-yl]-pyrimidin-4-yl}-amine |
| B90 | 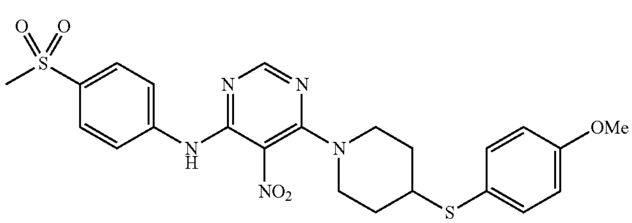 [SMILES: COc1ccc(SC2CCN(c3ncnc(Nc4ccc(S(C)(=O)=O)cc4)c3[N+](=O)[O-])CC2)cc1] | (4-Methanesulfonyl-phenyl)-{6-[4-(4-methoxy-phenylsulfanyl)-piperidin-1-yl]-5-nitro-pyrimidin-4-yl}-amine |

TABLE B-continued

| Cmpd # | Structure | Chemical Name |
| --- | --- | --- |
| B91 | 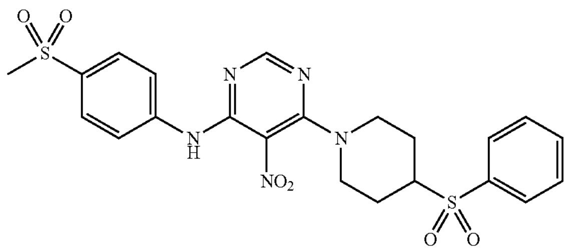 [SMILES: CS(=O)(=O)c1ccc(Nc2ncnc(N3CCC(S(=O)(=O)c4ccccc4)CC3)c2[N+](=O)[O-])cc1] | [6-(4-Benzenesulfonyl-piperidin-1-yl)-5-nitro-pyrimidin-4-yl]-(4-methanesulfonyl-phenyl)-amine |
| B92 | 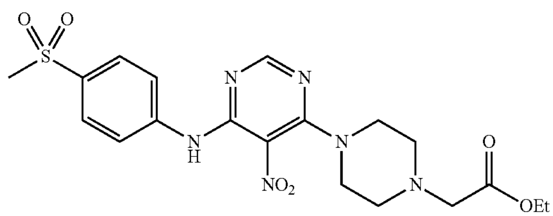 [SMILES: CCOC(=O)CN1CCN(c2ncnc(Nc3ccc(S(C)(=O)=O)cc3)c2[N+](=O)[O-])CC1] | {4-[6-(4-Methanesulfonyl-phenylamino)-5-nitro-pyrimidin-4-yl]-piperazin-1-yl}-acetic acid ethyl ester |
| B93 | 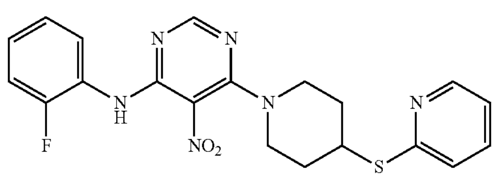 [SMILES: O=[N+]([O-])c1c(Nc2ccccc2F)ncnc1N1CCC(Sc2ccccn2)CC1] | (2-Fluoro-phenyl)-{5-nitro-6-[4-(pyridin-2-ylsulfanyl)-piperidin-1-yl]-pyrimidin-4-yl}-amine |
| B94 | 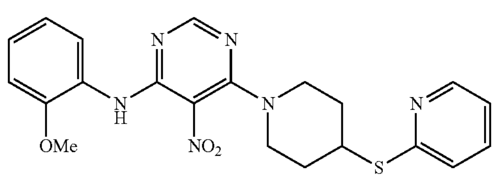 [SMILES: COc1ccccc1Nc1ncnc(N2CCC(Sc3ccccn3)CC2)c1[N+](=O)[O-]] | 2-Methoxy-phenyl)-{5-nitro-6-[4-(pyridin-2-ylsulfanyl)-piperidin-1-yl]-pyrimidin-4-yl}-amine |
| B95 | 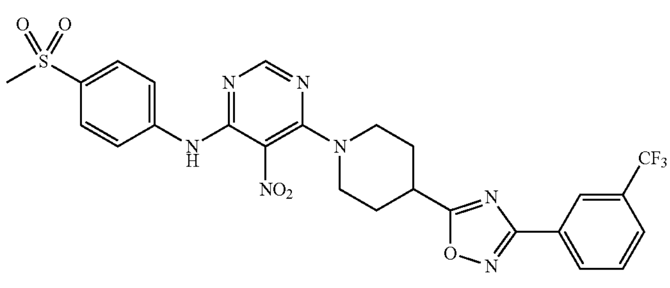 [SMILES: CS(=O)(=O)c1ccc(Nc2ncnc(N3CCC(c4nc(-c5cccc(C(F)(F)F)c5)no4)CC3)c2[N+](=O)[O-])cc1] | (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine |
| B96 | 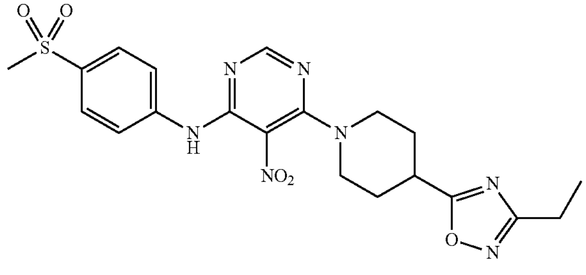 [SMILES: CCc1noc(C2CCN(c3ncnc(Nc4ccc(S(C)(=O)=O)cc4)c3[N+](=O)[O-])CC2)n1] | {6-[4-(3-Ethyl-[1,2,4]oxadiazol-5-yl)-piperidin-1-yl]-5-nitro-pyrimidin-4-yl}-(4-methanesulfonyl-phenyl)-amine |

TABLE B-continued

| Cmpd # | Structure | Chemical Name |
|---|---|---|
| B97 | 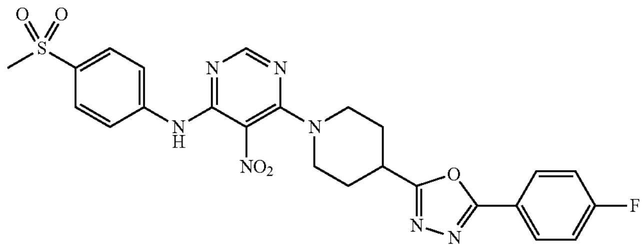 [SMILES: CS(=O)(=O)c1ccc(Nc2ncnc(N3CCC(c4nnc(-c5ccc(F)cc5)o4)CC3)c2[N+](=O)[O-])cc1] | (6-{4-[5-(4-Fluoro-phenyl)-[1,3,4]oxadiazol-2-yl]-piperidin-1-yl}-5-nitro-pyrimidin-4-yl)-(4-methanesulfonyl-phenyl)-amine |
| B98 | 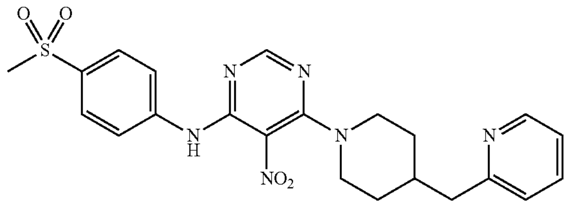 [SMILES: CS(=O)(=O)c1ccc(Nc2ncnc(N3CCC(Cc4ccccn4)CC3)c2[N+](=O)[O-])cc1] | (4-Methanesulfonyl-phenyl)-[5-nitro-6-(4-pyridin-2-ylmethyl-piperidin-1-yl)-pyrimidin-4-yl]-amine |
| B99 | 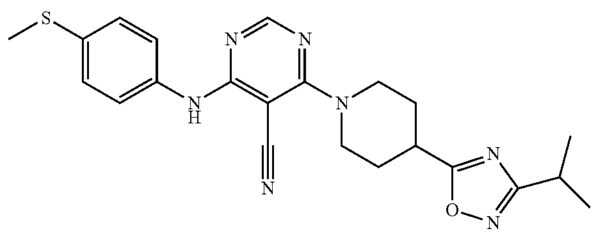 [SMILES: CSc1ccc(Nc2ncnc(N3CCC(c4nc(C(C)C)no4)CC3)c2C#N)cc1] | 4-[4-(3-Isopropyl-[1,2,4]oxadiazol-5-yl)-piperidin-1-yl]-6-(4-methylsulfanyl-phenylamino)-pyrimidine-5-carbonitrile |
| B100 | 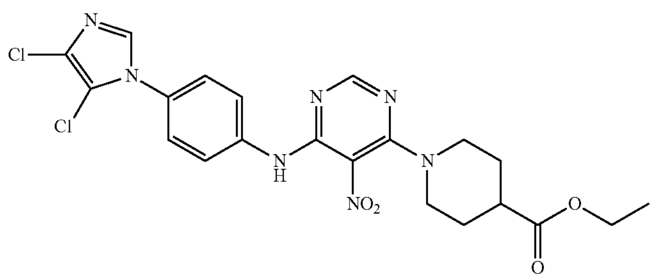 [SMILES: CCOC(=O)C1CCN(c2ncnc(Nc3ccc(-n4cnc(Cl)c4Cl)cc3)c2[N+](=O)[O-])CC1] | 1-{6-[4-(4,5-Dichloro-imidazol-1-yl)-phenylamino]-5-nitro-pyrimidin-4-yl}-piperidine-4-carboxylic acid ethyl ester |
| B101 | 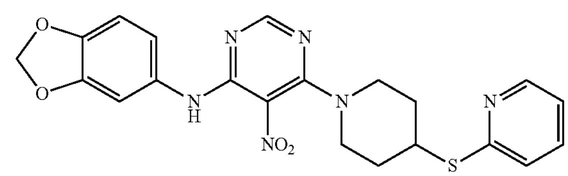 [SMILES: O=[N+]([O-])c1c(Nc2ccc3c(c2)OCO3)ncnc1N1CCC(Sc2ccccn2)CC1] | Benzo[1,3]dioxol-5-yl-{5-nitro-6-[4-(pyridin-2-ylsulfanyl)-piperidin-1-yl]-pyrimidin-4-yl}-amine |
| B102 | 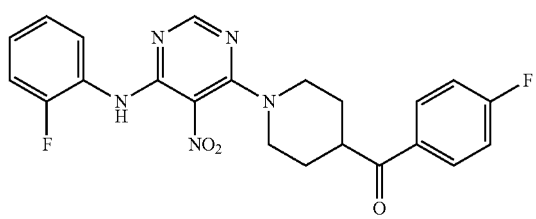 [SMILES: O=C(c1ccc(F)cc1)C1CCN(c2ncnc(Nc3ccccc3F)c2[N+](=O)[O-])CC1] | (4-Fluoro-phenyl)-{1-[6-(2-fluoro-phenylamino)-5-nitro-pyrimidin-4-yl]-piperidin-4-yl}-methanone |
| B103 | 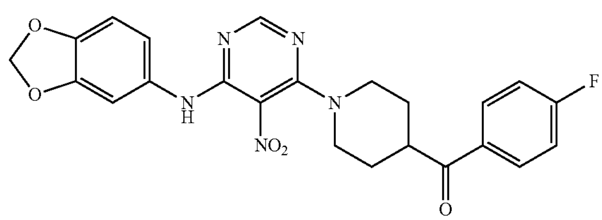 [SMILES: O=C(c1ccc(F)cc1)C1CCN(c2ncnc(Nc3ccc4c(c3)OCO4)c2[N+](=O)[O-])CC1] | {1-[6-(Benzo[1,3]dioxol-5-ylamino)-5-nitro-pyrimidin-4-yl]-piperidin-4-yl}-(4-fluoro-phenyl)-methanone |

TABLE B-continued

| Cmpd # | Structure | Chemical Name |
| --- | --- | --- |
| B104 | 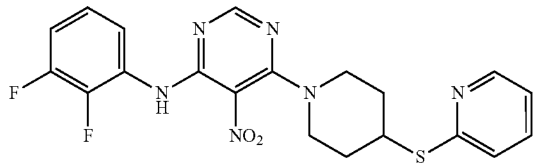 [SMILES: O=[N+]([O-])c1c(Nc2cccc(F)c2F)ncnc1N1CCC(Sc2ccccn2)CC1] | (2,3-Difluoro-phenyl)-{5-nitro-6-[4-(pyridin-2-ylsulfanyl)-piperidin-1-yl]-pyrimidin-4-yl}-amine |
| B105 | 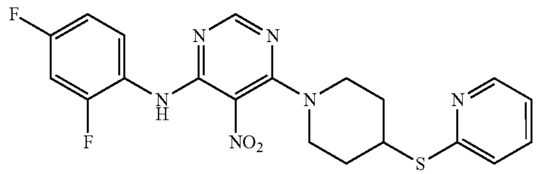 [SMILES: O=[N+]([O-])c1c(Nc2ccc(F)cc2F)ncnc1N1CCC(Sc2ccccn2)CC1] | (2,4-Difluoro-phenyl)-{5-nitro-6-[4-(pyridin-2-ylsulfanyl)-piperidin-1-yl]-pyrimidin-4-yl}-amine |
| B106 | 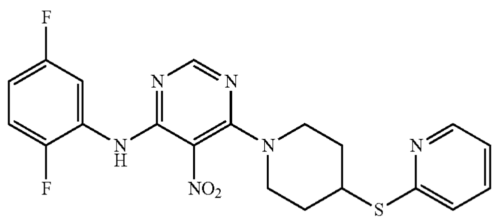 [SMILES: O=[N+]([O-])c1c(Nc2cc(F)ccc2F)ncnc1N1CCC(Sc2ccccn2)CC1] | (2,5-Difluoro-phenyl)-{5-nitro-6-[4-(pyridin-2-ylsulfanyl)-piperidin-1-yl]-pyrimidin-4-yl}-amine |
| B107 | 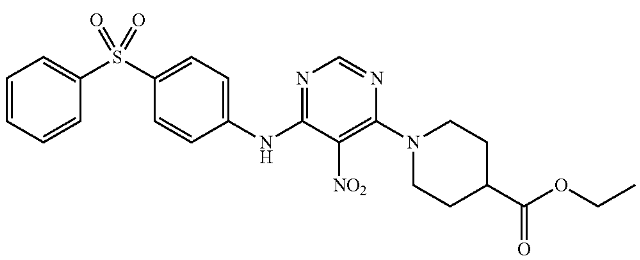 [SMILES: CCOC(=O)C1CCN(c2ncnc(Nc3ccc(S(=O)(=O)c4ccccc4)cc3)c2[N+](=O)[O-])CC1] | 1-[6-(4-Benzenesulfonyl-phenylamino)-5-nitro-pyrimidin-4-yl]-piperidine-4-carboxylic acid ethyl ester |
| B108 | 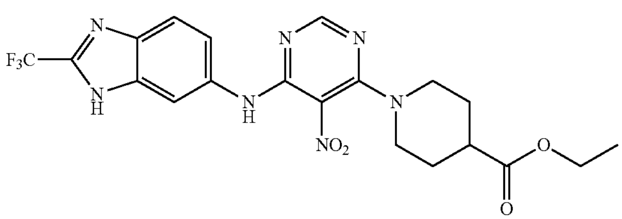 [SMILES: CCOC(=O)C1CCN(c2ncnc(Nc3ccc4nc(C(F)(F)F)[nH]c4c3)c2[N+](=O)[O-])CC1] | 1-[5-Nitro-6-(2-trifluoromethyl-3H-benzoimidazol-5-ylamino)-pyrimidin-4-yl]-piperidine-4-carboxylic acid ethyl ester |
| B109 | 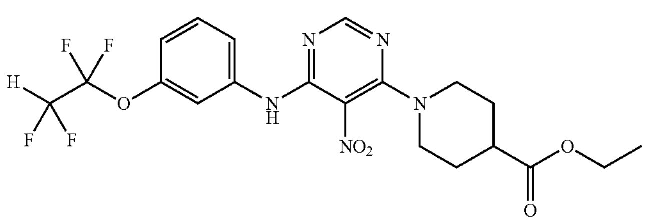 [SMILES: CCOC(=O)C1CCN(c2ncnc(Nc3cccc(OC(F)(F)C(F)F)c3)c2[N+](=O)[O-])CC1] | 1-{5-Nitro-6-[3-(1,1,2,2-tetrafluoro-ethoxy)-phenylamino]-pyrimidin-4-yl}-piperidine-4-carboxylie acid ethyl ester |
| B110 | 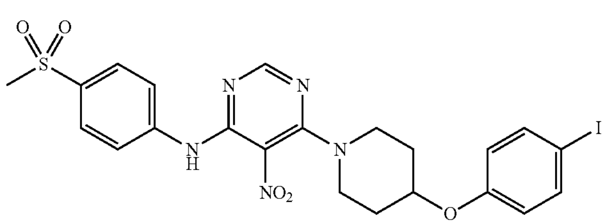 [SMILES: CS(=O)(=O)c1ccc(Nc2ncnc(N3CCC(Oc4ccc(I)cc4)CC3)c2[N+](=O)[O-])cc1] | {6-[4-(4-Iodo-phenoxy)-piperidin-1-yl]-5-nitro-pyrimidin-4-yl}-(4-methanesulfonyl-phenyl)-amine |

TABLE B-continued

| Cmpd # | Structure | Chemical Name |
| --- | --- | --- |
| B111 | 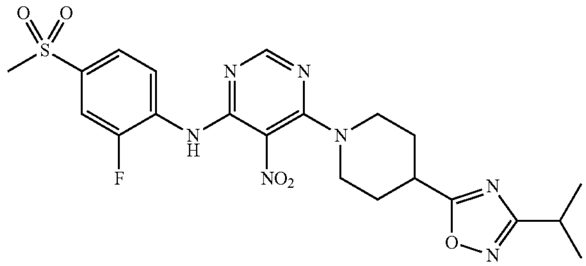 [SMILES: CC(C)c1noc(C2CCN(c3ncnc(Nc4ccc(S(C)(=O)=O)cc4F)c3[N+](=O)[O-])CC2)n1] | (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine |
| B112 | 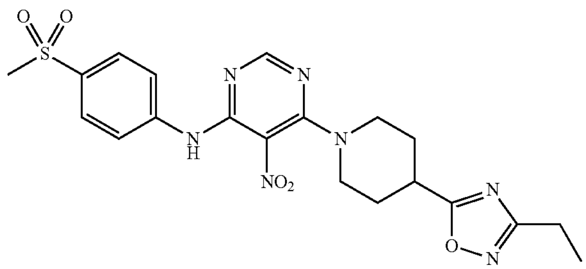 [SMILES: CCc1noc(C2CCN(c3ncnc(Nc4ccc(S(C)(=O)=O)cc4)c3[N+](=O)[O-])CC2)n1] | {6-[4-(3-Ethyl-[1,2,4]oxadiazol-5-yl)-piperidin-1-yl]-5-nitro-pyrimidin-4-yl}-(2-fluoro-4-methanesulfonyl-phenyl)-amine |
| B113 | 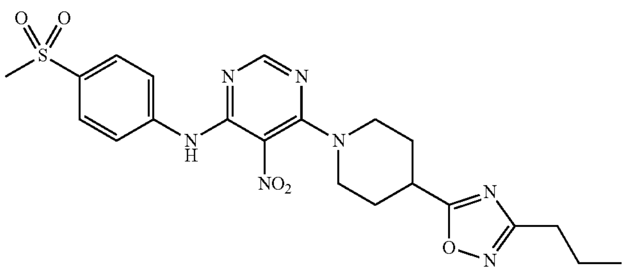 [SMILES: CCCc1noc(C2CCN(c3ncnc(Nc4ccc(S(C)(=O)=O)cc4)c3[N+](=O)[O-])CC2)n1] | (4-Methanesulfonyl-phenyl)-{5-nitro-6-[4-(3-propyl-[1,2,4]oxadiazol-5-yl)-piperidin-1-yl]-pyrimidin-4-yl}-amine |
| B114 | 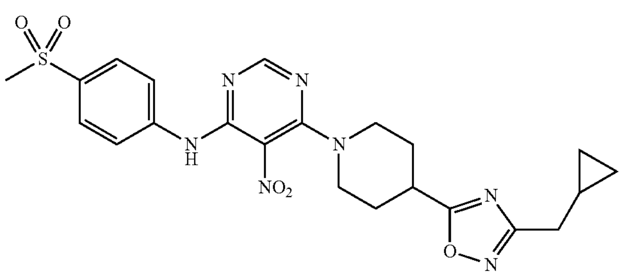 [SMILES: CS(=O)(=O)c1ccc(Nc2ncnc(N3CCC(c4nc(CC5CC5)no4)CC3)c2[N+](=O)[O-])cc1] | {6-[4-(3-Cyclopropylmethyl-[1,2,4]oxadiazol-5-yl)-piperidin-1-yl]-5-nitro-pyrimidin-4-yl}-(4-methanesulfonyl-phenyl)-amine |
| B115 | 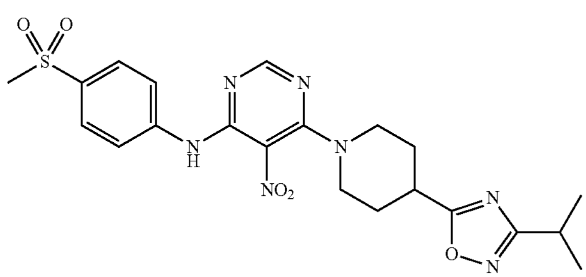 [SMILES: CC(C)c1noc(C2CCN(c3ncnc(Nc4ccc(S(C)(=O)=O)cc4)c3[N+](=O)[O-])CC2)n1] | {6-[4-(3-Isopropyl-[1,2,4]oxadiazol-5-yl)-piperidin-1-yl]-5-nitro-pyrimidin-4-yl}-(4-methanesulfonyl-phenyl)-amine |

TABLE B-continued

| Cmpd # | Structure | Chemical Name |
|---|---|---|
| B116 | 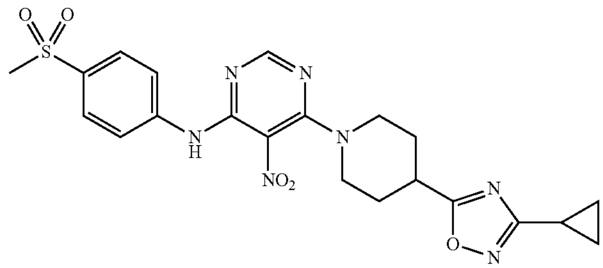 [SMILES: CS(=O)(=O)c1ccc(Nc2ncnc(N3CCC(c4nc(C5CC5)no4)CC3)c2[N+](=O)[O-])cc1] | {6-[4-(3-Cyclopropyl-[1,2,4]oxadiazol-5-yl)-piperidin-1-yl]-5-nitro-pyrimidin-4-yl}-(4-methanesulfonyl-phenyl)-amine |
| B117 | 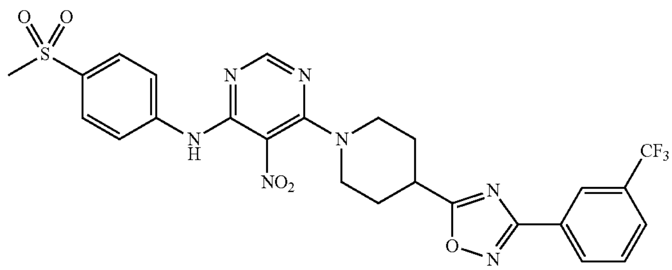 [SMILES: CS(=O)(=O)c1ccc(Nc2ncnc(N3CCC(c4nc(-c5cccc(C(F)(F)F)c5)no4)CC3)c2[N+](=O)[O-])cc1] | (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine |
| B118 | 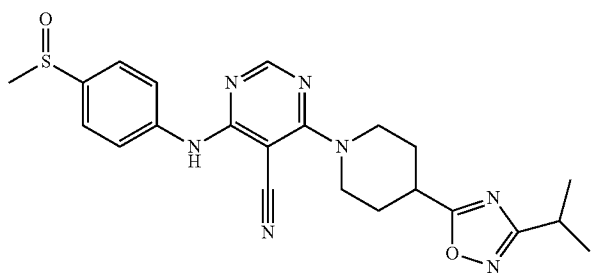 [SMILES: CC(C)c1noc(C2CCN(c3ncnc(Nc4ccc(S(C)=O)cc4)c3C#N)CC2)n1] | 4-[4-(3-Isopropyl-[1,2,4]oxadiazol-5-yl)-piperidin-1-yl]-6-(4-methanesulfinyl-phenylamino)-pyrimidine-5-carbonitrile |
| B119 | 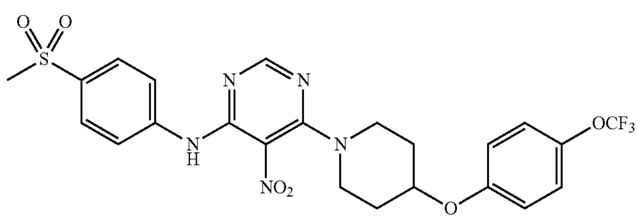 [SMILES: CS(=O)(=O)c1ccc(Nc2ncnc(N3CCC(Oc4ccc(OC(F)(F)F)cc4)CC3)c2[N+](=O)[O-])cc1] | (4-Methanesulfonyl-phenyl)-{5-nitro-6-[4-(4-trifluoromethoxy-phenoxy)-piperidin-1-yl]-pyrimidin-4-yl}-amine |
| B120 | 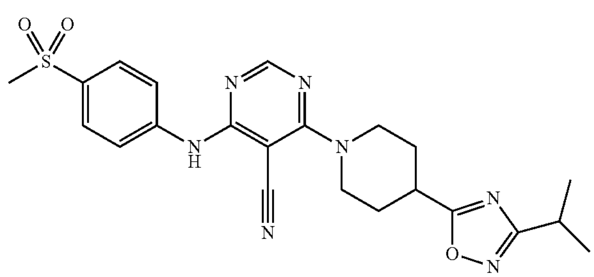 [SMILES: CC(C)c1noc(C2CCN(c3ncnc(Nc4ccc(S(C)(=O)=O)cc4)c3C#N)CC2)n1] | 4-[4-(3-Isopropyl-[1,2,4]oxadiazol-5-yl)-piperidin-1-yl]-6-(4-methanesulfonyl-phenylamino)-pyrimidine-5-carbonitrile |
| B121 | 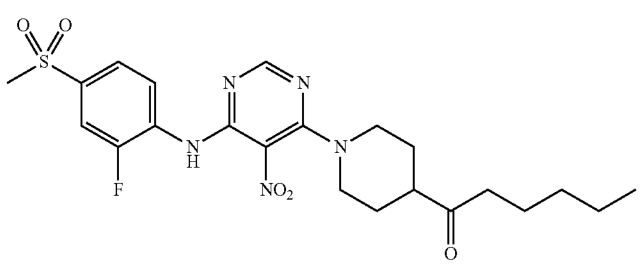 [SMILES: CCCCCC(=O)C1CCN(c2ncnc(Nc3ccc(S(C)(=O)=O)cc3F)c2[N+](=O)[O-])CC1] | 1-{1-[6-(2-Fluoro-4-methanesulfonyl-phenylamino)-5-nitro-pyrimidin-4-yl]-piperidin-4-yl}-hexan-1-one |

TABLE B-continued

| Cmpd # | Structure | Chemical Name |
|---|---|---|
| B122 | 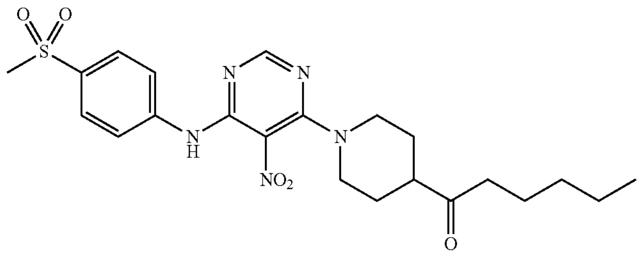 [SMILES: CCCCCC(=O)C1CCN(c2ncnc(Nc3ccc(S(C)(=O)=O)cc3)c2[N+](=O)[O-])CC1] | 1-{1-[6-(4-Methanesulfonyl-phenylamino)-5-nitro-pyrimidin-4-yl]-piperidin-4-yl}-hexan-1-one |
| B123 | 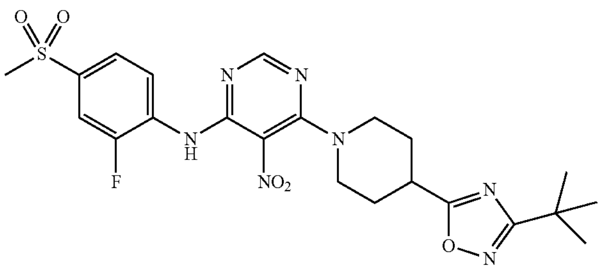 [SMILES: CC(C)(C)c1noc(C2CCN(c3ncnc(Nc4ccc(S(C)(=O)=O)cc4F)c3[N+](=O)[O-])CC2)n1] | {6-[4-(3-tert-Butyl-[1,2,4]oxadiazol-5-yl)-piperidin-1-yl]-5-nitro-pyrimidin-4-yl}-(2-fluoro-4-methanesulfonyl-phenyl)-amine |
| B124 | 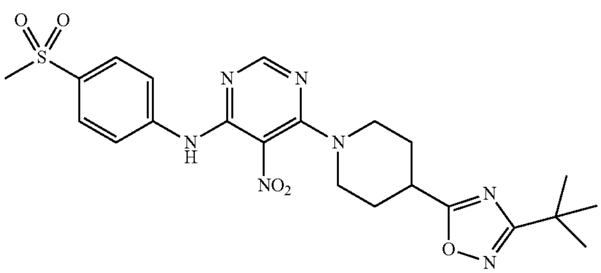 [SMILES: CC(C)(C)c1noc(C2CCN(c3ncnc(Nc4ccc(S(C)(=O)=O)cc4)c3[N+](=O)[O-])CC2)n1] | {6-[4-(3-tert-Butyl-[1,2,4]oxadiazol-5-yl)-piperidin-1-yl]-5-nitro-pyrimidin-4-yl}-(4-methanesulfonyl-phenyl)-amine |
| B125 | 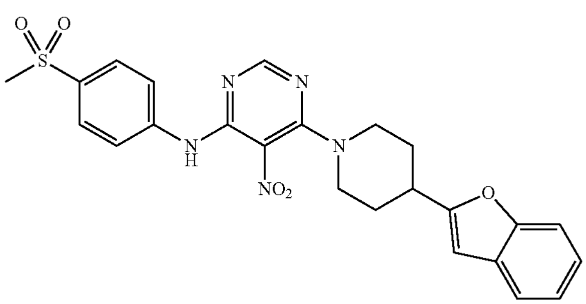 [SMILES: CS(=O)(=O)c1ccc(Nc2ncnc(N3CCC(c4cc5ccccc5o4)CC3)c2[N+](=O)[O-])cc1] | [6-(4-Benzofuran-2-yl-piperidin-1-yl)-5-nitro-pyrimidin-4-yl]-(4-methanesulfonyl-phenyl)-amine |
| B126 | 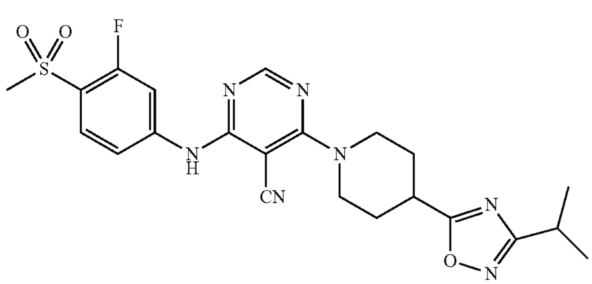 [SMILES: CC(C)c1noc(C2CCN(c3ncnc(Nc4ccc(S(C)(=O)=O)c(F)c4)c3C#N)CC2)n1] | 4-(3-Fluoro-4-methanesulfonyl-phenylamino)-6-[4-(3-isopropyl-[1,2,4]oxadiazol-5-yl)-piperidin-1-yl]-pyrimidine-5-carbonitrile |

TABLE B-continued

| Cmpd # | Structure | Chemical Name |
|---|---|---|
| B127 | 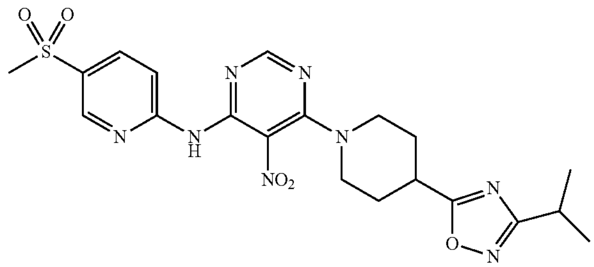 [SMILES: CC(C)c1noc(C2CCN(c3ncnc(Nc4ccc(S(C)(=O)=O)cn4)c3[N+](=O)[O-])CC2)n1] | {6-[4-(3-Isopropyl-[1,2,4]oxadiazol-5-yl)-piperidin-1-yl]-5-nitro-pyrimidin-4-yl}-(5-methanesulfonyl-pyridin-2-yl)-amine |
| B128 | 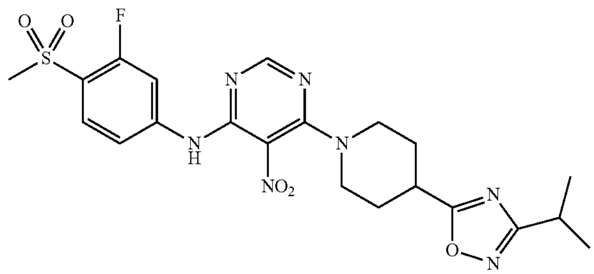 [SMILES: CC(C)c1noc(C2CCN(c3ncnc(Nc4ccc(S(C)(=O)=O)c(F)c4)c3[N+](=O)[O-])CC2)n1] | (3-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine |
| B129 | 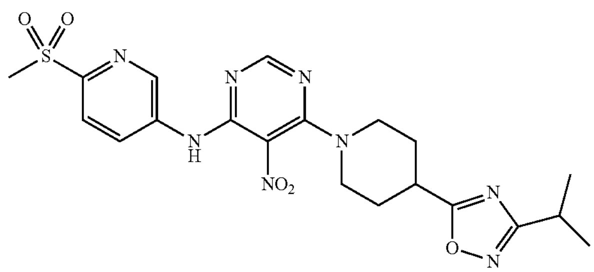 [SMILES: CC(C)c1noc(C2CCN(c3ncnc(Nc4ccc(S(C)(=O)=O)nc4)c3[N+](=O)[O-])CC2)n1] | {6-[4-(3-Isopropyl-[1,2,4]oxadiazol-5-yl)-piperidin-1-yl]-5-nitro-pyrimidin-4-yl}-(6-methanesulfonyl-pyridin-3-yl)-amine |
| B130 | 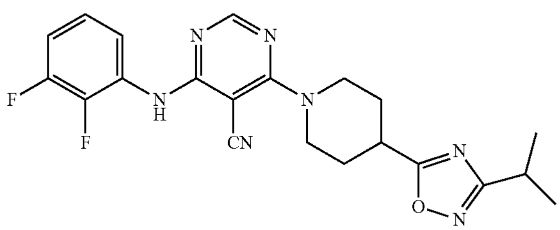 [SMILES: CC(C)c1noc(C2CCN(c3ncnc(Nc4cccc(F)c4F)c3C#N)CC2)n1] | 4-(2,3-Difluoro-phenylamino)-6-[4-(3-isopropyl-[1,2,4]oxadiazol-5-yl)-piperidin-1-yl]-pyrimidine-5-carbonitrile |
| B131 | 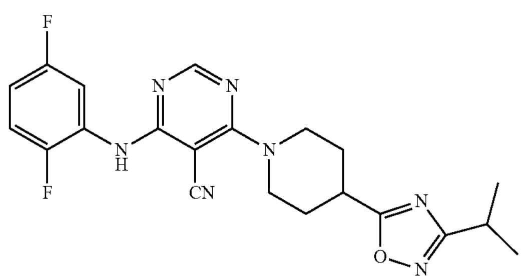 [SMILES: CC(C)c1noc(C2CCN(c3ncnc(Nc4cc(F)ccc4F)c3C#N)CC2)n1] | 4-(2,5-Difluoro-phenylamino)-6-[4-(3-isopropyl-[1,2,4]oxadiazol-5-yl)-piperidin-1-yl]-pyrimidine-5-carbonitrile |
| B132 | 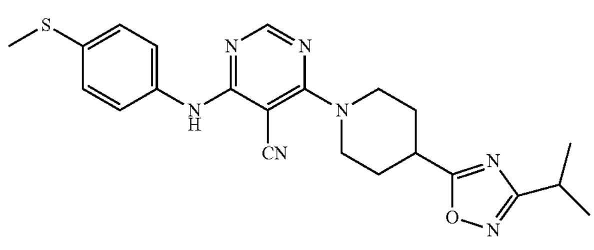 [SMILES: CSc1ccc(Nc2ncnc(N3CCC(c4nc(C(C)C)no4)CC3)c2C#N)cc1] | 4-[4-(3-Isopropyl-[1,2,4]oxadiazol-5-yl)-piperidin-1-yl]-6-(4-methylsulfanyl-phenylamino)-pyrimidine-5-carbonitrile |

TABLE B-continued

| Cmpd # | Structure | Chemical Name |
| --- | --- | --- |
| B133 | 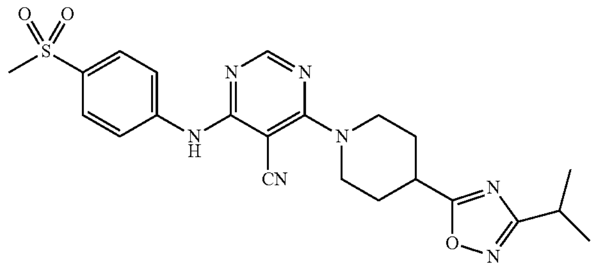 [SMILES: CC(C)c1noc(C2CCN(c3ncnc(Nc4ccc(S(C)(=O)=O)cc4)c3C#N)CC2)n1] | 4-[4-(3-Isopropyl-[1,2,4]oxadiazol-5-yl)-piperidin-1-yl]-6-(4-methanesulfonyl-phenylamino)-pyrimidine-5-carbonitrile |
| B134 | 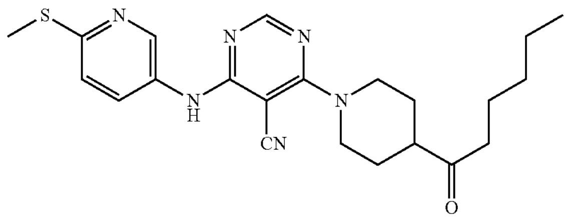 [SMILES: CCCCCC(=O)C1CCN(c2ncnc(Nc3ccc(SC)nc3)c2C#N)CC1] | 4-(4-Hexanoyl-piperidin-1-yl)-6-(6-methylsulfanyl-pyridin-3-ylamino)-pyrimidine-5-carbonitrile |
| B135 | 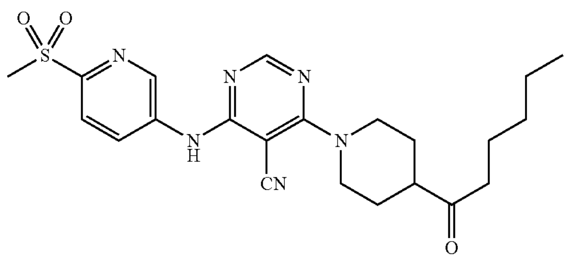 [SMILES: CCCCCC(=O)C1CCN(c2ncnc(Nc3ccc(S(C)(=O)=O)nc3)c2C#N)CC1] | 4-(4-Hexanoyl-piperidin-1-yl)-6-(6-methanesulfonyl-pyridin-3-ylamino)-pyrimidine-5-carbonitrile |
| B136 | 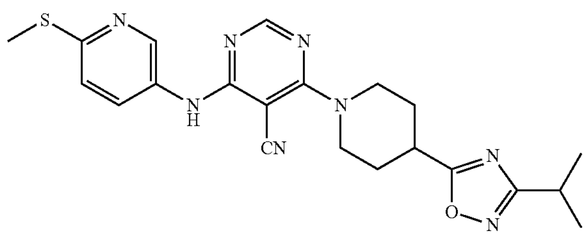 [SMILES: CSc1ccc(Nc2ncnc(N3CCC(c4nc(C(C)C)no4)CC3)c2C#N)cn1] | 4-[4-(3-Isopropyl-[1,2,4]oxadiazol-5-yl)-piperidin-1-yl]-6-(6-methylsulfanyl-pyridin-3-ylamino)-pyrimidine-5-carbonitrile |
| B137 | 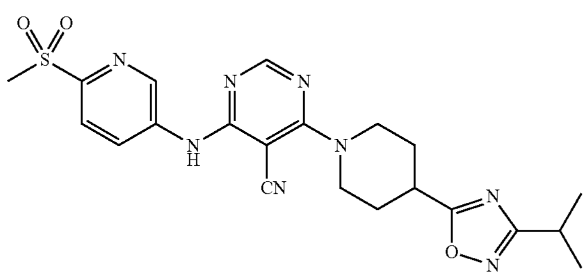 [SMILES: CC(C)c1noc(C2CCN(c3ncnc(Nc4ccc(S(C)(=O)=O)nc4)c3C#N)CC2)n1] | 4-[4-(3-Isopropyl-[1,2,4]oxadiazol-5-yl)-piperidin-1-yl]-6-(6-methanesulfonyl-pyridin-3-ylamino)-pyrimidine-5-carbonitrile |
| B138 | 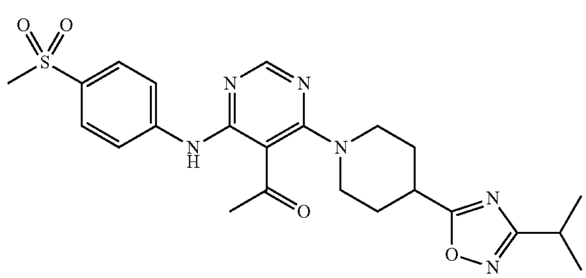 | 1-[4-[4-(3-Isopropyl-[1,2,4]oxadiazol-5-yl)-piperidin-1-yl]-6-(4-methanesulfonyl-phenylamino)-pyrimidin-5-yl]-ethanone |

TABLE B-continued

| Cmpd # | Structure | Chemical Name |
|---|---|---|
| B139 | 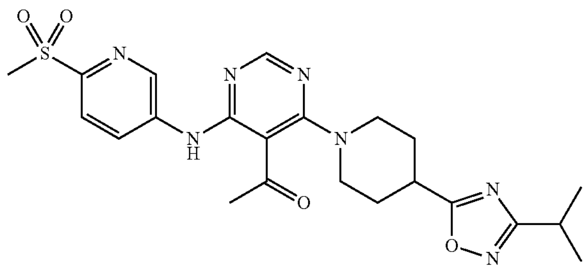 [SMILES: CC(=O)c1c(Nc2ccc(S(C)(=O)=O)nc2)ncnc1N1CCC(c2nc(C(C)C)no2)CC1] | 1-[4-[4-(3-Isopropyl-[1,2,4]oxadiazol-5-yl)-piperidin-1-yl]-6-(6-methanesulfonyl-pyridin-3-ylamino)-pyrimidin-5-yl]-ethanone |

TABLE C

| Cmpd # | Structure | Chemical Name |
|---|---|---|
| C1 | 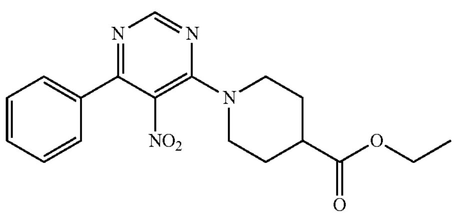 [SMILES: CCOC(=O)C1CCN(c2ncnc(-c3ccccc3)c2[N+](=O)[O-])CC1] | 1-(5-Nitro-6-phenyl-pyrimidin-4-yl)-piperidine-4-carboxylic acid ethyl ester |
| C2 | 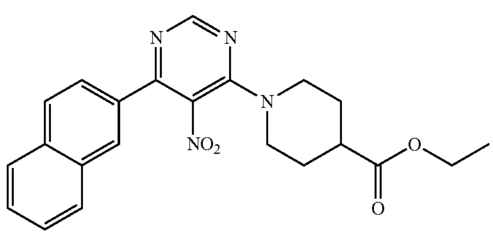 [SMILES: CCOC(=O)C1CCN(c2ncnc(-c3ccc4ccccc4c3)c2[N+](=O)[O-])CC1] | 1-(6-Naphthalen-2-yl-5-nitro-pyrimidin-4-yl)-piperidine-4-carboxylic acid ethyl ester |
| C3 | 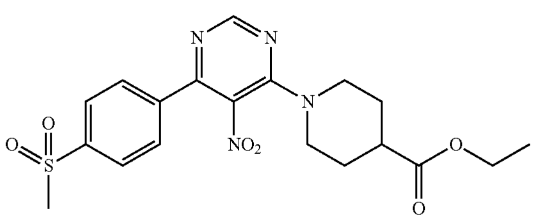 [SMILES: CCOC(=O)C1CCN(c2ncnc(-c3ccc(S(C)(=O)=O)cc3)c2[N+](=O)[O-])CC1] | 1-[6-(4-Methanesulfonyl-phenyl)-5-nitro-pyrimidin-4-yl]-piperidine-4-carboxylic acid ethyl ester |
| C4 | 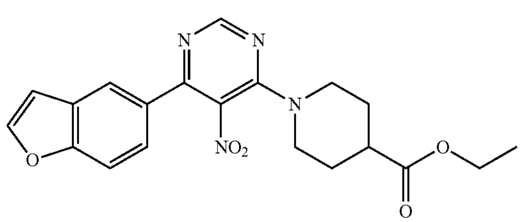 [SMILES: CCOC(=O)C1CCN(c2ncnc(-c3ccc4occc4c3)c2[N+](=O)[O-])CC1] | 1-(6-Benzofuran-5-yl-5-nitro-pyrimidin-4-yl)-piperidine-4-carboxylic acid ethyl ester |
| C5 | 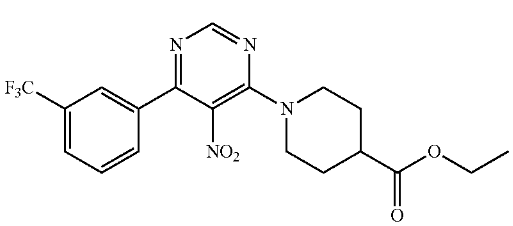 [SMILES: CCOC(=O)C1CCN(c2ncnc(-c3cccc(C(F)(F)F)c3)c2[N+](=O)[O-])CC1] | 1-[5-Nitro-6-(3-trifluoromethyl-phenyl)-pyrimidin-4-yl]-piperidine-4-carboxylic acid ethyl ester |

TABLE C-continued

| Cmpd # | Structure | Chemical Name |
|---|---|---|
| C6 | 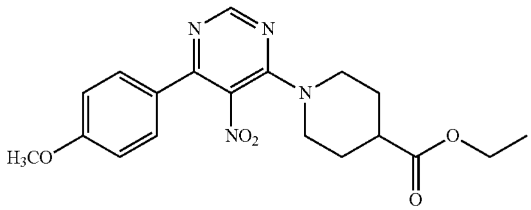 [SMILES: CCOC(=O)C1CCN(c2ncnc(-c3ccc(OC)cc3)c2[N+](=O)[O-])CC1] | 1-[6-(4-Methoxy-phenyl)-5-nitro-pyrimidin-4-yl]-piperidine-4-carboxylic acid ethyl ester |
| C7 | 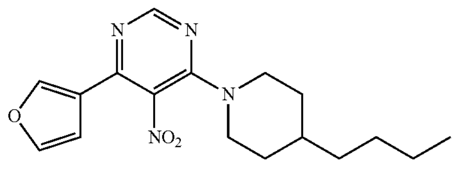 [SMILES: CCCCC1CCN(c2ncnc(-c3ccoc3)c2[N+](=O)[O-])CC1] | 4-(4-Butyl-piperidin-1-yl)-6-furan-3-yl-5-nitro-pyrimidine |
| C8 | 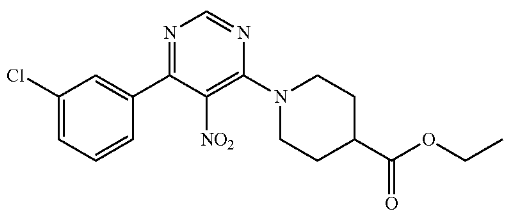 [SMILES: CCOC(=O)C1CCN(c2ncnc(-c3cccc(Cl)c3)c2[N+](=O)[O-])CC1] | 1-[6-(3-Chloro-phenyl)-5-nitro-pyrimidin-4-yl]-piperidine-4-carboxylic acid ethyl ester |
| C9 | 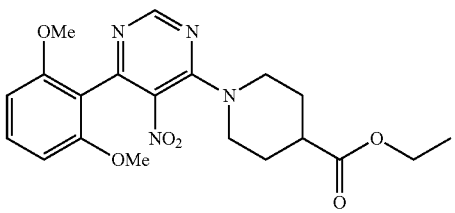 [SMILES: CCOC(=O)C1CCN(c2ncnc(-c3c(OC)cccc3OC)c2[N+](=O)[O-])CC1] | 1-[6-(2,6-Dimethoxy-phenyl)-5-nitro-pyrimidin-4-yl]-piperidine-4-carboxylic acid ethyl ester |
| C10 | 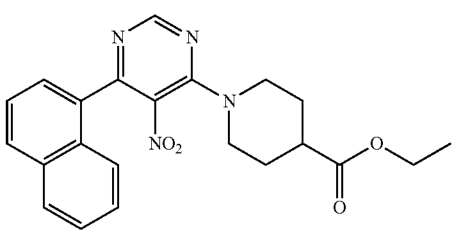 [SMILES: CCOC(=O)C1CCN(c2ncnc(-c3cccc4ccccc34)c2[N+](=O)[O-])CC1] | 1-(6-Naphthalen-1-yl-5-nitro-pyrimidin-4-yl)-piperidine-4-carboxylic acid ethyl ester |
| C11 | 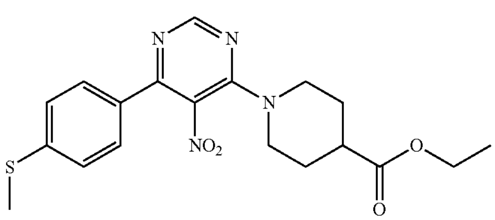 [SMILES: CCOC(=O)C1CCN(c2ncnc(-c3ccc(SC)cc3)c2[N+](=O)[O-])CC1] | 1-[6-(4-Methylsulfanyl-phenyl)-5-nitro-pyrimidin-4-yl]-piperidine-4-carboxylic acid ethyl ester |
| C12 | 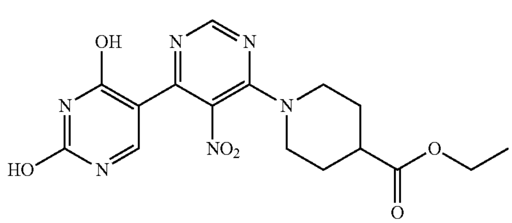 [SMILES: CCOC(=O)C1CCN(c2ncnc(-c3cnc(O)nc3O)c2[N+](=O)[O-])CC1] | 1-(2',4'-Dihydroxy-5-nitro-[4,5']bipyrimidinyl-6-yl)-piperidine-4-carboxylic acid ethyl ester |

TABLE C-continued

| Cmpd # | Structure | Chemical Name |
| --- | --- | --- |
| C13 | 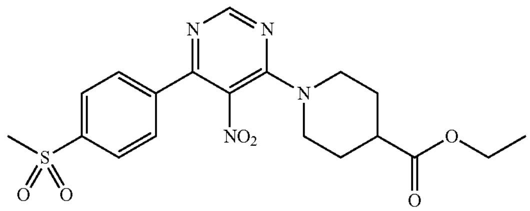 [SMILES: CCOC(=O)C1CCN(c2ncnc(-c3ccc(S(C)(=O)=O)cc3)c2[N+](=O)[O-])CC1] | 1-[6-(4-Methanesulfonyl-phenyl)-5-nitro-pyrimidin-4-yl]-piperidine-4-carboxylic acid ethyl ester |
| C14 | 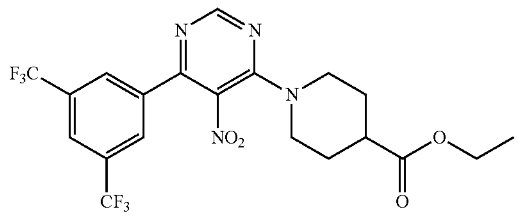 [SMILES: CCOC(=O)C1CCN(c2ncnc(-c3cc(C(F)(F)F)cc(C(F)(F)F)c3)c2[N+](=O)[O-])CC1] | 1-[6-(3,5-Bis-trifluoromethyl-phenyl)-5-nitro-pyrimidin-4-yl]-piperidine-4-carboxylic acid ethyl ester |
| C15 | 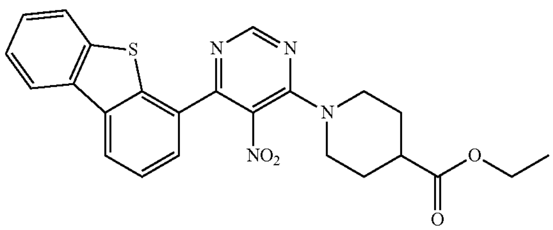 [SMILES: CCOC(=O)C1CCN(c2ncnc(-c3cccc4c3sc3ccccc34)c2[N+](=O)[O-])CC1] | 1-(6-Dibenzothiophen-4-yl-5-nitro-pyrimidin-4-yl)-piperidine-4-carboxylic acid ethyl ester |
| C16 | 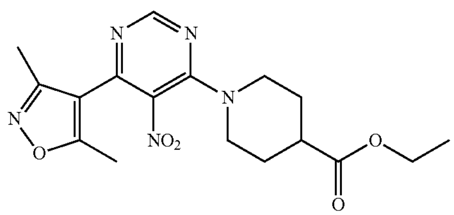 [SMILES: CCOC(=O)C1CCN(c2ncnc(-c3c(C)noc3C)c2[N+](=O)[O-])CC1] | 1-[6-(3,5-Dimethyl-isoxazol-4-yl)-5-nitro-pyrimidin-4-yl]-piperidine-4-carboxylic acid ethyl ester |
| C17 | 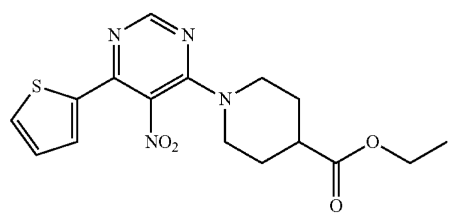 [SMILES: CCOC(=O)C1CCN(c2ncnc(-c3cccs3)c2[N+](=O)[O-])CC1] | 1-(5-Nitro-6-thiophen-2-yl-pyrimidin-4-yl)-piperidine-4-carboxylic acid ethyl ester |
| C18 | 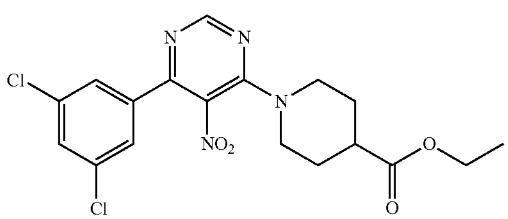 [SMILES: CCOC(=O)C1CCN(c2ncnc(-c3cc(Cl)cc(Cl)c3)c2[N+](=O)[O-])CC1] | 1-[6-(3,5-Dichloro-phenyl)-5-nitro-pyrimidin-4-yl]-piperidine-4-carboxylic acid ethyl ester |
| C19 | 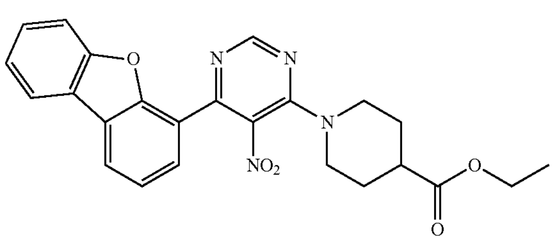 [SMILES: CCOC(=O)C1CCN(c2ncnc(-c3cccc4c3oc3ccccc34)c2[N+](=O)[O-])CC1] | 1-(6-Dibenzofuran-4-yl-5-nitro-pyrimidin-4-yl)-piperidine-4-carboxylic acid ethyl ester |

TABLE C-continued

| Cmpd # | Structure | Chemical Name |
| --- | --- | --- |
| C20 | 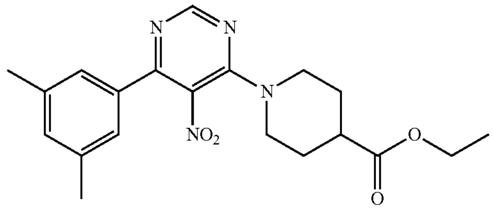 [SMILES: CCOC(=O)C1CCN(c2ncnc(-c3cc(C)cc(C)c3)c2[N+](=O)[O-])CC1] | 1-[6-(3,5-Dimethyl-phenyl)-5-nitro-pyrimidin-4-yl]-piperidine-4-carboxylic acid ethyl ester |
| C21 | 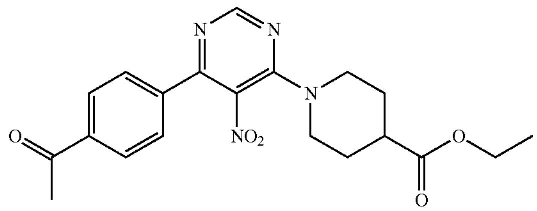 [SMILES: CCOC(=O)C1CCN(c2ncnc(-c3ccc(C(C)=O)cc3)c2[N+](=O)[O-])CC1] | 1-[6-(4-Acetyl-phenyl)-5-nitro-pyrimidin-4-yl]-piperidine-4-carboxylic acid ethyl ester |
| C22 | 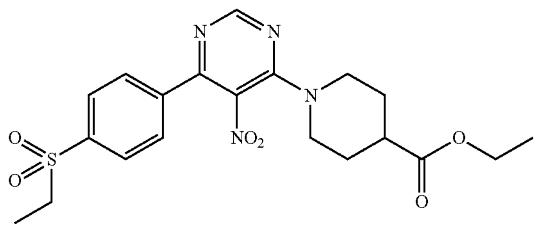 [SMILES: CCOC(=O)C1CCN(c2ncnc(-c3ccc(S(=O)(=O)CC)cc3)c2[N+](=O)[O-])CC1] | 1-[6-(4-Ethanesulfonyl-phenyl)-5-nitro-pyrimidin-4-yl]-piperidine-4-carboxylic acid ethyl ester |
| C23 | 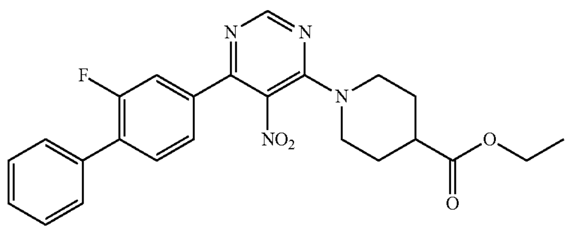 [SMILES: CCOC(=O)C1CCN(c2ncnc(-c3ccc(-c4ccccc4)c(F)c3)c2[N+](=O)[O-])CC1] | 1-[6-(2-Fluoro-biphenyl-4-yl)-5-nitro-pyrimidin-4-yl]-piperidine-4-carboxylic acid ethyl ester |
| C24 | 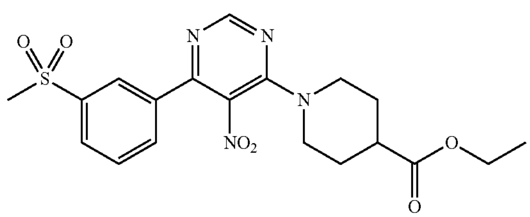 [SMILES: CCOC(=O)C1CCN(c2ncnc(-c3cccc(S(C)(=O)=O)c3)c2[N+](=O)[O-])CC1] | 1-[6-(3-Methanesulfonyl-phenyl)-5-nitro-pyrimidin-4-yl]-piperidine-4-carboxylic acid ethyl ester |
| C25 | 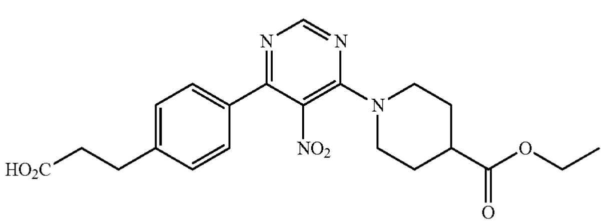 [SMILES: CCOC(=O)C1CCN(c2ncnc(-c3ccc(CCC(=O)O)cc3)c2[N+](=O)[O-])CC1] | 1-{6-[4-(2-Carboxy-ethyl)-phenyl]-5-nitro-pyrimidin-4-yl}-piperidine-4-carboxylic acid ethyl ester |
| C26 | 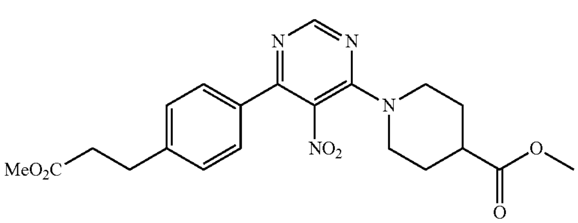 [SMILES: COC(=O)CCc1ccc(-c2ncnc(N3CCC(C(=O)OC)CC3)c2[N+](=O)[O-])cc1] | 1-{6-[4-(2-Methoxycarbonyl-ethyl)-phenyl]-5-nitro-pyrimidin-4-yl}-piperidine-4-carboxylic acid methyl ester |

TABLE C-continued

| Cmpd # | Structure | Chemical Name |
|---|---|---|
| C27 | 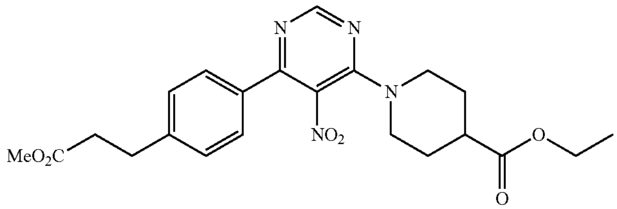 [SMILES: CCOC(=O)C1CCN(c2ncnc(-c3ccc(CCC(=O)OC)cc3)c2[N+](=O)[O-])CC1] | 1-{6-[4-(2-Methoxycarbonyl-ethyl)-phenyl]-5-nitro-pyrimidin-4-yl}-piperidine-4-carboxylic acid ethyl ester |

TABLE D

| Cmpd # | Structure | Chemical Name |
|---|---|---|
| D1 | 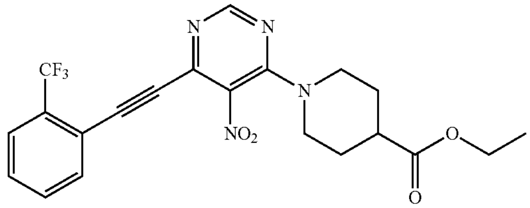 [SMILES: CCOC(=O)C1CCN(c2ncnc(C#Cc3ccccc3C(F)(F)F)c2[N+](=O)[O-])CC1] | 1-[5-Nitro-6-(2-trifluoromethyl-phenylethynyl)-pyrimidin-4-yl]-piperidine-4-carboxylic acid ethyl ester |
| D2 | 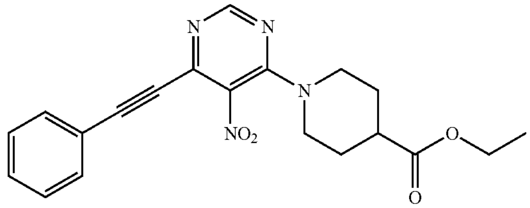 [SMILES: CCOC(=O)C1CCN(c2ncnc(C#Cc3ccccc3)c2[N+](=O)[O-])CC1] | 1-(5-Nitro-6-phenylethynyl-pyrimidin-4-yl)-piperidine-4-carboxylic acid ethyl ester |
| D3 | 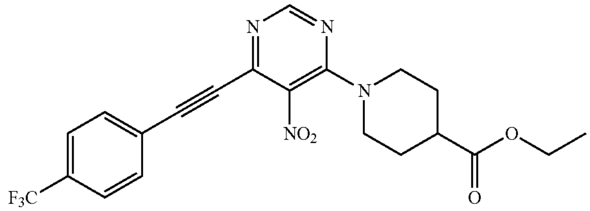 [SMILES: CCOC(=O)C1CCN(c2ncnc(C#Cc3ccc(C(F)(F)F)cc3)c2[N+](=O)[O-])CC1] | 1-[5-Nitro-6-(4-trifluoromethyl-phenylethynyl)-pyrimidin-4-yl]-piperidine-4-carboxylic acid ethyl ester |
| D4 | 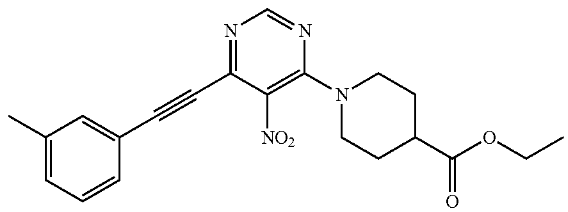 [SMILES: CCOC(=O)C1CCN(c2ncnc(C#Cc3cccc(C)c3)c2[N+](=O)[O-])CC1] | 1-(5-Nitro-6-m-tolylethynyl-pyrimidin-4-yl)-piperidine-4-carboxylic acid ethyl ester |
| D5 | 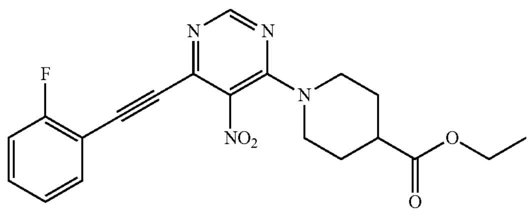 [SMILES: CCOC(=O)C1CCN(c2ncnc(C#Cc3ccccc3F)c2[N+](=O)[O-])CC1] | 1-[6-(2-Fluoro-phenylethynyl)-5-nitro-pyrimidin-4-yl]-piperidine-4-carboxylic acid ethyl ester |

TABLE D-continued

| Cmpd # | Structure | Chemical Name |
|---|---|---|
| D6 | 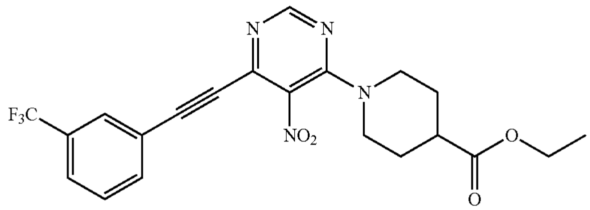 [SMILES: CCOC(=O)C1CCN(c2ncnc(C#Cc3cccc(C(F)(F)F)c3)c2[N+](=O)[O-])CC1] | 1-[5-Nitro-6-(3-trifluoromethyl-phenylethynyl)-pyrimidin-4-yl]-piperidine-4-carboxylic acid ethyl ester |

TABLE E

| Cmpd # | Structure | Chemical Name |
|---|---|---|
| E1 | 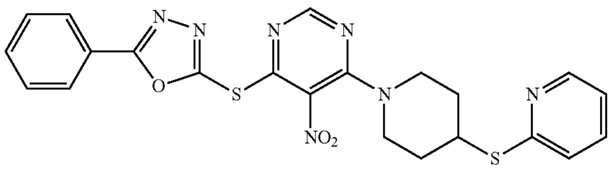 [SMILES: O=[N+]([O-])c1c(Sc2nnc(-c3ccccc3)o2)ncnc1N1CCC(Sc2ccccn2)CC1] | 5-Nitro-4-(5-phenyl-[1,3,4]oxadiazol-2-ylsulfanyl)-6-[4-(pyridin-2-ylsulfanyl)-piperidin-1-yl]-pyrimidine |

Some embodiments of the present invention include a pharmaceutical composition comprising at least one compound according to any of the compound embodiments disclosed herein and a pharmaceutically acceptable carrier.

Additionally, compounds of Formula (Ia) encompass all pharmaceutically acceptable solvates, particularly hydrates, thereof. The present invention also encompasses diastereomers as well as optical isomers, e.g. mixtures of enantiomers including racemic mixtures, as well as individual enantiomers and diastereomers, which arise as a consequence of structural asymmetry in certain compounds of Formula (Ia). Separation of the individual isomers or selective synthesis of the individual isomers is accomplished by application of various methods which are well known to practitioners in the art.

Indications

In addition to the foregoing beneficial uses for compounds of the present invention disclosed herein, compounds of the invention are useful in the prophylaxis or treatment of additional diseases. Without limitation, these include the following.

The most significant pathologies in Type II diabetes are impaired insulin signaling at its target tissues ("insulin resistance") and failure of the insulin-producing cells of the pancreas to secrete an appropriate degree of insulin in response to a hyperglycemic signal. Current therapies to treat the latter include inhibitors of the β-cell ATP-sensitive potassium channel to trigger the release of endogenous insulin stores, or administration of exogenous insulin. Neither of these achieves accurate normalization of blood glucose levels and both carry the risk of inducing hypoglycemia. For these reasons, there has been intense interest in the development of pharmaceuticals that function in a glucose-dependent action, i.e. potentiators of glucose signaling. Physiological signaling systems which function in this manner are well-characterized and include the gut peptides GLP1, GIP and PACAP. These hormones act via their cognate G-protein coupled receptor to stimulate the production of cAMP in pancreatic β-cells. The increased cAMP does not appear to result in stimulation of insulin release during the fasting or preprandial state. However, a series of biochemical targets of cAMP signaling, including the ATP-sensitive potassium channel, voltage-sensitive potassium channels and the exocytotic machinery, are modified in such a way that the insulin secretory response to a postprandial glucose stimulus is markedly enhanced. Accordingly, agonists of novel, similarly functioning, β-cell GPCRs, including RUP3, would also stimulate the release of endogenous insulin and consequently promote normoglycemia in Type II diabetes.

It is also established that increased cAMP, for example as a result of GLP1 stimulation, promotes β-cell proliferation, inhibits β-cell death and thus improves islet mass. This positive effect on β-cell mass is expected to be beneficial in both Type II diabetes, where insufficient insulin is produced, and Type I diabetes, where β-cells are destroyed by an inappropriate autoimmune response.

It is also well-established that metabolic diseases exert a negative influence on other physiological systems. Thus, there is often the codevelopment of multiple disease states (e.g. type I diabetes, type II diabetes, inadequate glucose tolerance, insulin resistance, hyperglycemia, hyperlipidemia, hypertriglyceridemia, hypercholesterolemia, dyslipidemia, obesity or cardiovascular disease in "Syndrome X") or secondary diseases which clearly occur secondary to diabetes (e.g. kidney disease, peripheral neuropathy). Thus, it is expected that effective treatment of the diabetic condition will in turn be of benefit to such interconnected disease states.

Some embodiments of the present invention include a method for prophylaxis or treatment of a metabolic disorder or complications thereof in an individual comprising administering to the individual a therapeutically effective amount of a compound of the present invention or a pharmaceutical composition thereof. In some embodiments, the metabolic disorder or complications thereof is type I, type II diabetes, inadequate glucose tolerance, insulin resistance, hyperglycemia, hyperlipidemia, hypertriglyceridemia, hypercholesterolemia, dyslipidemia syndrome X, or metabolic syndrome. In some embodiments, the metabolic disorder is type II diabetes. In some embodiments, the metabolic disorder is hyperglycemia. In some embodiments, the metabolic disorder is hyperlipidemia. In some embodiments, the metabolic disorder is hypertriglyceridemia. In some embodiments, the metabolic disorder is type I diabetes. In some embodiments, the metabolic disorder is dyslipidemia. In some embodiments, the metabolic disorder is syndrome X. In some embodiments, the individual is a mammal. In some embodiments, the mammal is a human.

Some embodiments of the present invention include a method of controlling or decreasing weight gain of an individual comprising administering to the individual a therapeutically effective amount of a compound of the present invention or pharmaceutical composition thereof. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

One aspect of the present invention pertains to a compound of Formula (Ia), as described herein, for use in a method of treatment of the human or animal body by therapy.

Some embodiments of the present invention include a method of modulating a RUP3 receptor comprising contacting the receptor with a compound of the present invention.

Some embodiments of the present invention include a method of modulating a RUP3 receptor in an individual comprising contacting the receptor with a compound of the present invention. In some embodiments, the compound is an agonist. In some embodiments, the compound is an inverse agonist.

Some embodiments of the present invention include a method of modulating a RUP3 receptor in an individual comprising contacting the receptor with a compound of the present invention wherein the modulation of the RUP3 receptor is prophylaxis or treatment of a metabolic disorder and complications thereof. In some embodiments, the metabolic disorder is type I, type II diabetes, inadequate glucose tolerance, insulin resistance, hyperglycemia, hyperlipidemia, hypertriglyceridemia, hypercholesterolemia, dyslipidemia syndrome X, or metabolic syndrome. In some embodiments, the metabolic disorder is type II diabetes. In some embodiments, the metabolic disorder is hyperglycemia. In some embodiments, the metabolic disorder is hyperlipidemia. In some embodiments, the metabolic disorder is hypertriglyceridemia. In some embodiments, the metabolic disorder is type I diabetes. In some embodiments, the metabolic disorder is dyslipidemia. In some embodiments, the metabolic disorder is syndrome X. In some embodiments, the individual is a mammal. In some embodiments, the mammal is a human.

Some embodiments of the present invention include a method of modulating a RUP3 receptor in an individual comprising contacting the receptor with a compound of the present invention wherein the modulation of the RUP3 receptor controls or reduces weight gain of the individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

Some embodiments of the present invention include the use of a compound of the present invention for production of a medicament for use in prophylaxis or treatment of a metabolic disorder. In some embodiments, the metabolic disorder is type II diabetes, inadequate glucose tolerance, insulin resistance, hyperglycemia, hyperlipidemia, hypertriglyceridemia, hypercholesterolemia, dyslipidemia syndrome X, or metabolic syndrome.

Some embodiments of the present invention include the use of a compound of the present invention for production of a medicament for use in controlling or decreasing weight gain in an individual. In some embodiments, the individual is a mammal. In some embodiments, the mammal is a human. In some embodiments, the human has a body mass index of about 18.5 to about 45. In some embodiments, the human has a body mass index of about 25 to about 45. In some embodiments, the human has a body mass index of about 30 to about 45. In some embodiments, the human has a body mass index of about 35 to about 45.

Compounds of the present invention are identified as an agonist or an inverse agonist using methods known to those skilled in art, such as an assay as described in Example 1. Accordingly, representative examples of compounds of the present invention that are agonists include the following: [6-(4-Benzenesulfonyl-piperidin-1-yl)-5-nitro-pyrimidin-4-yl}-(4-methanesulfonyl-phenyl)-amine; {4-[6-(4-Methanesulfonyl-phenylamino)-5-nitro-pyrimidin-4-yl]-piperazin-1-yl}-acetic acid ethyl ester; (2-Fluoro-phenyl)-{5-nitro-6-[4-(pyridin-2-ylsulfanyl)-piperidin-1-yl]-pyrimidin-4-yl}-amine; 1-[6-(4-Imidazol-1-yl-phenoxy)-5-nitro-pyrimidin-4-yl]-piperidine-4-carboxylic acid ethyl ester; 1-[5-Nitro-6-(4-[1,2,4]triazol-1-yl-phenoxy)-pyrimidin-4-yl]-piperidine-4-carboxylic acid ethyl ester; {6-[4-(4-Fluoro-phenoxy)-piperidin-1-yl]-5-nitro-pyrimidin-4-yl}-(4-methanesulfonyl-phenyl)-amine; {6-[4-(3-Isopropyl-[1,2,4]oxadiazol-5-yl)-piperidin-1-yl]-5-nitro-pyrimidin-4-yl}-(4-methanesulfonyl-phenyl)-amine; {6-[4-(3-Cyclopropyl-[1,2,4]oxadiazol-5-yl)-piperidin-1-yl]-5-nitro-pyrimidin-4-yl}-(4-methanesulfonyl-phenyl)-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(2-fluoro-phenyl)-amine; (2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine; {6-[4-(3-Ethyl-[1,2,4]oxadiazol-5-yl)-piperidin-1-yl]-5-nitro-pyrimidin-4-yl}-(2-fluoro-4-methanesulfonyl-phenyl)-amine; (4-Methanesulfonyl-phenyl)-[5-nitro-6-[4-(3-propyl-[1,2,4]oxadiazol-5-yl)-piperidin-1-yl]-pyrimidin-4-yl}-amine; 6-[4-(3-Cyclopropylmethyl-[1,2,4] oxadiazol-5-yl)-piperidin-1-yl]-5-nitro-pyrimidin-4-yl}-(4-methanesulfonyl-phenyl)-amine; (4-Methanesulfonyl-phenyl)-{5-nitro-6-[4-(pyridin-4-yloxy)-piperidin-1-yl]-pyrimidin-4-yl}-amine; (4-Methanesulfonyl-phenyl)-{5-nitro-6-[4-(pyrimidin-2-yloxy)-piperidin-1-yl]-pyrimidin-4-yl}-amine; 1-[6-(4-Carbamoylmethyl-phenoxy)-5-nitro-pyrimidin-4-yl]-piperidine-4-carboxylic acid ethyl ester; 1-{6-[4-(1,3-Dioxo-1,3-dihydro-isoindol-2-yl)-phenoxy]-5-nitro-pyrimidin-4-yl}-piperidine-4-carboxylic acid ethyl ester; 4'44-(2-Methoxycarbonyl-acetyl)-phenoxy]-3'-nitro-3,4,5,6-tetrahydro-2H-[1,2']bipyridinyl-4-carboxylic acid ethyl ester; {6-[4-(2-Methoxy-phenylsulfanyl)-piperidin-1-yl]-5-nitro-pyrimidin-4-yl}-(4-[1,2,4]triazol-1-yl-phenyl)-amine; 4'-(2-Amino-4-ethanesulfonyl-phenoxy)-3'-nitro-3,4,5,6-tetrahydro-2H-[1,2]bipyridinyl-4-carboxylic acid ethyl ester; 4'-(4-Imidazol-1-yl-phenoxy)-3'-nitro-3,4,5,6-tetrahydro-2H-[1,2]bipyridinyl-4-carboxylic acid ethyl ester; (4-Methoxy-2-{5-nitro-6-[4-(pyridin-2-ylsulfanyl)-piperidin-1-yl]-pyrimidin-4-yloxy}-phenyl)-phenyl-methanone; 4-{4-[6-(4-Cyclopropylmethoxymethyl-piperidin-1-yl)-5-nitro-pyrimidin-4-yloxy]-phenyl}-butan-2-one; 4-{4-[5-Nitro-6-(4-prop oxymethyl-piperidin-1-yl)-pyrimidin-4-yloxy]-phenyl}-butan-2-one; 4-{4-[6-(4-Butoxymethyl-piperidin-1-yl)-5-nitro-pyrimidin-4-yloxy]-phenyl}-butan-2-one; 4-{4-[6-(4-Isobutoxymethyl-piperidin-1-yl)-5-nitro-pyrimidin-4-yloxy]-phenyl}-butan-2-one; {1-[6-(Benzo[1,3]dioxol-5-ylamino)-5-nitro-pyrimidin-4-yl]-piperidin-4-yl}-(4-fluoro-phenyl)-methanone; (2,3-Difluoro-phenyl)-{5-nitro-6-[4-(pyridin-2-ylsulfanyl)-piperidin-1-yl]-pyrimidin-4-yl}-amine; (2,4-Difluoro-phenyl)-{5-nitro-6-[4-(pyridin-2-ylsulfanyl)-piperidin-1-yl]-pyrimidin-4-yl}-amine; 1-{2-Nitro-3-[4-(3-oxo-butyp-phenoxy]-phenyl}-piperidine-4-carboxylic acid ethyl ester; 1-[6-(4-Acetyl-phenoxy)-5-nitro-pyrimidin-4-yl]-piperidine-4-carboxylic acid ethyl ester; 3'-Nitro-2'44-(3-oxo-butyl)-phenoxy]-3,4,5,6-tetrahydro-2H-[1,4']bipyridinyl-4-carboxylic acid ethyl ester; 4-(4-{5-Nitro-6-[4-(pyridin-2-ylsulfanyl)-piperidin-1-yl]-pyrimidin-4-yloxy}-phenyl)-butan-2-one; 4-(4-{5-Nitro-6-[4-(2-trifluoromethyl-phenoxy)-piperidin-1-yl]-pyrimidin-4-yloxy}-phenyl)-butan-2-one; 4-(4-{6-[4-(3-Methyl-[1,2,4]oxadiazol-5-yl)-piperidin-1-yl]-5-nitro-pyrimidin-4-yloxy}-phenyl)-butan-2-one; 4-(2,4-Difluoro-phenoxy)-5-nitro-6-[4-(pyridin-2-ylsulfanyl)-piperidin-1-yl]-pyrimidine; 4-(4-{6-[4-(4-Fluoro-benzoyl)-piperidin-1-yl]-5-nitro-pyrimidin-4-yloxy}-phenyl)-butan-2-one; 4-(4-Methanesulfonyl-phenoxy)-5-nitro-6-[4-(pyridin-2-ylsulfanyl)-cyclohexyl]-pyrimidine; 4-(4-Methanesulfonyl-phenoxy)-5-nitro-6-[4-(pyridin-4-ylsulfanyl)-cyclohexyl]-pyrimidine; 4-(4-Methanesulfonyl-phenoxy)-5-nitro-6-(4-phenylsulfanyl-cyclohexyl)-pyrimidine; 1-{6-[(Benzo[1,3]dioxol-5-ylmethyl)-amino]-5-nitro-pyrimidin-4-yl}-piperidine-4-carboxylic acid ethyl ester; 1-{6-[4-(1,1-Dioxo-1$\lambda^6$-thiomorpholin-4-ylmethyl)-phenylamino]-5-nitro-pyrimidin-4-yl}-piperidine-4-carboxylic acid ethyl ester; 1-[6-(4-Methanesulfonyl-phenylamino)-5-nitro-pyrimidin-4-yl]-piperidine-4-carboxylic acid ethyl ester; 1-[6-(4-Dimethylsulfamoyl-phenylamino)-5-nitro-pyrimidin-4-yl]-piperidine-4-carboxylic acid ethyl ester; 1-[6-(3-Methoxy-phenylamino)-5-nitro-pyrimidin-4-yl]-piperidine-4-carboxylic acid ethyl ester; 1-[6-(2-Methoxy-phenylamino)-5-nitro-pyrimidin-4-yl]-piperidine-4-carboxylic acid ethyl ester; 1-[6-(4-Methanesulfonyl-phenoxy)-5-nitro-pyrimidin-4-yl]-piperidine-4-carboxylic acid ethyl ester; 1-[6-[4-(2-Methoxycarbonyl-acetyl)-phenoxy]-5-nitro-pyrimidin-4-yl]-piperidine-4-carboxylic acid ethyl ester; 1-[6-(2-Amino-4-ethanesulfonyl-phenoxy)-5-nitro-pyrimidin-4-yl]-piperidine-4-carboxylic acid ethyl ester; 1-[6-(2,5-Dimethoxy-phenylamino)-5-nitro-pyrimidin-4-yl]-piperidine-4-carboxylic acid ethyl ester; (4-{5-Nitro-6-[4-(pyridin-2-ylsulfanyl)-piperidin-1-yl]-pyrimidin-4-ylamino}-phenyl)-phenyl-methanone; 1-[6-(4-Cyclohexyl-phenylamino)-5-nitro-pyrimidin-4-yl]-piperidine-4-carboxylic acid ethyl ester; 1-[5-Nitro-6-(4-[1,2,4]triazol-1-yl-phenylamino)-pyrimidin-4-yl]-piperidine-4-carboxylic acid ethyl ester; 1-[5-Nitro-6-(4-trifluoromethanesulfonyl-phenylamino)-pyrimidin-4-yl]-piperidine-4-carboxylic acid ethyl ester; HS-Nitro-6-[4-[1,2,3]thiadiazol-4-yl-phenylamino)-pyrimidin-4-yl]-piperidine-4-carboxylic acid ethyl ester; [6-(4-Ethoxymethyl-piperidin-1-yl)-5-nitro-pyrimidin-4-yl}-(4-methanesulfonyl-phenyl)-amine; {5-Nitro-6-(4-propyl-piperidin-1-yl)-pyrimidin-4-yl}-(4-[1,2,4]triazol-1-yl-phenyl)-amine; {5-Nitro-6-[4-(pyridin-2-ylsulfanyl)-piperidin-1-yl]-pyrimidin-4-yl}-(4-1,2,4]triazol-1-yl-phenyl)-amine; (2-Fluoro-phenyl)-{6-[4-(3-methyl-[1,2,4]oxadiazol-5-yl)-piperidin-1-yl]-5-nitro-pyrimidin-4-yl}-amine; (4-Methanesulfonyl-phenyl)-{6-[4-(3-methyl-[1,2,4]oxadiazol-5-yl)-piperidin-1-yl]-5-nitro-pyrimidin-4-yl}-amine; {6-[4-(3-Methyl-1,2,4]oxadiazol-5-yl)-piperidin-1-yl]-5-nitro-pyrimidin-4-yl}-(4-[1,2,4]triazol-1-yl-phenyl)-amine; (4-Methanesulfonyl-phenyl)-{5-nitro-6-[4-(pyridin-2-ylsulfanyl)-piperidin-1-yl]-pyrimidin-4-yl}-amine; (3-Methoxy-phenyl)-{5-nitro-6-[4-(pyridin-2-ylsulfanyl)-piperidin-1-yl]-pyrimidin-4-yl}-amine; 1-[6-(Benzo[1,3]dioxol-5-ylamino)-5-nitro-pyrimidin-4-yl]-piperidine-4-carboxylic acid ethyl ester; 1-[6-(2-Fluoro-phenylamino)-5-nitro-pyrimidin-4-yl]-piperidine-4-carboxylic acid ethyl ester; 1-[6-(3-Fluoro-phenylamino)-5-nitro-pyrimidin-4-yl]-piperidine-4-carboxylic acid ethyl ester; 1-[6-(3,4-Dihydro-2H-benzo[b][1,4]dioxepin-7-ylamino)-5-nitro-pyrimidin-4-yl]-piperidine-4-carboxylic acid ethyl ester; 1-{6-[4-(Morpholine-4-sulfonyl)-phenylamino]-5-nitro-pyrimidin-4-yl}-piperidine-4-carboxylic acid ethyl ester; Benzo[1,3]dioxol-5-yl-[5-nitro-6-(4-propyl-piperidin-1-yl)-pyrimidin-4-yl]-amine; (4-Fluoro-phenyl)-{1-[5-nitro-6-(4-[1,2,4]triazol-1-methanone; [5-Nitro-6-(4-phenylsulfanyl-piperidin-1-yl)-pyrimidin-4-yl}-(4-[1,2,4]triazol-1-yl-phenyl)-amine; (4-Fluoro-phenyl)-{1-[6-(2-fluoro-phenylamino)-5-nitro-pyrimidin-4-yl]-piperidin-4-yl}-methanone; (4-Methanesulfonyl-phenyl)-[5-nitro-6-(4-phenylsulfanyl-piperidin-1-yl)-pyrimidin-4-yl]amine; (4-Methanesulfonyl-phenyl)-{5-nitro-6-[4-(pyridin-2-yloxy)-piperidin-1-yl]-pyrimidin-4-yl}-amine; (4-Methanesulfonyl-phenyl)-{5-nitro-6-[4-(pyridin-4-ylsulfanyl)-piperidin-1-yl]-pyrimidin-4-yl}-amine; (4-Methanesulfonyl-phenyl)-{6-[4-(4-methoxy-phenylsulfanyl)-piperidin-1-yl]-5-nitro-pyrimidin-4-yl}-amine; 2-Methoxy-phenyl)-{5-nitro-6-[4-(pyridin-2-ylsulfanyl)-piperidin-1-yl]-pyrimidin-4-yl}-amine; (4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine; {6-[4-(3-Ethyl-[1,2,4]oxadiazol-5-yl)-piperidin-1-yl]-5-nitro-pyrimidin-4-yl}-(4-methanesulfonyl-phenyl)-amine; (6-{4-[5-(4-Fluoro-phenyl)-[1,3,4]oxadiazol-2-yl]-piperidin-1-yl}-5-nitro-pyrimidin-4-yl)-(4-methanesulfonyl-phenyl)-amine; (4-Methanesulfonyl-phenyl)-[5-nitro-6-(4-pyridin-2-ylmethyl-piperidin-1-yl)-pyrimidin-4-yl]amine; 1-{6-[4-(2,5-Dioxo-imidazolidin-4-yl)-phenoxy]-5-nitro-pyrimidm-4-yl}-piperidine-4-carboxylic acid ethyl ester; 1-[5-Nitro-6-(4-propionyl-phenoxy)-pyrimidin-4-yl]-piperidine-4-carboxylic acid ethyl ester; 1-[5-Nitro-6-(4-[1,2,3]thiadiazol-4-yl-phenoxy)-pyrimidin-4-yl]-piperidine-4-carboxylic acid ethyl ester; 1-[6-[4-(3-oxo-butyl)-phenoxy]-5-(2,2,2-trifluoro-acetylamino)-pyrimidin-4-yl]-piperidine-4-carboxylic acid ethyl ester; 1-[6-(2-Benzoyl-5-methoxy-phenoxy)-5-nitro-pyrimidin-4-yl]-piperidine-4-carboxylic acid ethyl ester; 3'-Nitro-4'-[4-(3-oxo-butyl)-phenoxy]-3,4,5,6-tetrahydro-2H-[1,2']bipyridinyl-4-carboxylic acid ethyl ester; 1-[6-(4-Dimethyl sulfamoyl-phenylamino)-5-nitro-pyrimidin-4-yl]-piperidine-4-carboxylic acid ethyl ester; 1-{6-[4-(4,5-Dichloro-imidazol-1-yl)-phenylamino]-5-nitro-pyrimidin-4-yl}-piperidine-4-carboxylic acid ethyl ester; Benzo[1,3]dioxol-5-yl-{5-nitro-6-[4-(pyridin-2-ylsulfanyl)-piperidin-1-yl]-pyrimidin-4-yl}-amine; (4-Fluoro-phenyl)-{1-[6-(2-fluoro-phenyl amino)-5-nitro-pyrimidin-4-yl]-piperidin-4-yl}-methanone; (2,5-Difluoro-phenyl)-{5-nitro-6-[4-(pyridin-2-ylsulfanyl)-piperidin-1-yl]-pyrimidin-4-yl}-amine; 1-{5-Nitro-6-[4-(3- oxo-butyl)-phenoxy]-pyrimidin-4-yl}-piperidine-4-carboxylic acid ethyl ester; 4-[4-(3-Isopropyl-[1,2,4]oxadiazol-5-yl)-piperidin-1-yl]-6-(4-methanesulfonyl-phenoxy)-pyrimidine-5-carbonitrile; 5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine; 4-[4-(3-Isopropyl-[1,2,4]oxadiazol-5-yl)-piperidin-1-yl]-6-(4-methanesulfonyl-phenoxy)-pyrimidine-5-carbaldehyde; 5-[1,3]Dioxolan-2-yl-4-[4-(3-Isopropyl-[1,2,4]oxadiazol-5-yl)-piperidin-1-yl]-6-(4-[1,2,3]thiadiazol-4-yl-phenoxy)-pyrimidine; 444-(3-Isopropyl-[1,2,4]oxadiazol-5-yl)-piperidin-1-yl]-6-(4-[1,2,3]thiadiazol-4-yl-phenoxy)-pyrimidine-5-carbaldehyde; 4-[4-(3-Isopropyl-[1,2,4]oxadiazol-5-yl)-piperidin-1-yl]-6-(4-[1,2,3]thiadiazol-4-yl-phenoxy)-pyrimidine-5-carboxylic acid; [4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol; [4-[4-(3-Isopropyl-[1,2,4]oxadiazol-5-yl)-piperidin-1-yl]-6-(4-[1,2,3]thiadiazol-4-yl-phenoxy)-pyrimidin-5-yl-methyl]-dimethyl-amine; 4-[4-(3-Isopropyl-[1,2,4]oxadiazol-5-yl)-piperidin-1-yl]-6-(4-methylsulfanyl-phenylamino)-pyrimidine-5-carbonitrile; 4-[4-(3-Isopropyl-[1,2,4]oxadiazol-5-yl)-piperidin-1-yl]-6-(4-methanesulfinyl-phenylamino)-pyrimidine-5-carbonitrile; (4-Methanesulfonyl-phenyl)-{5-nitro-6-[4-(4-trifluoromethoxy-phenoxy)-piperidin-1-yl]-pyrimidin-4-yl}-amine; 4-[4-(3-Isopropyl-[1,2,4]oxadiazol-5-yl)-piperidin-1-yl]-6-(4-methanesulfonyl-phenylamino)-pyrimidine-5-carbonitrile; 1-{1-[6-(2-Fluoro-4-methanesulfonyl-phenylamino)-5-nitro-pyrimidin-4-yl]-piperidin-4-yl}-hexan-1-one; 1-{1-[6-(4-Methanesulfonyl-phenylamino)-5-nitro-pyrimidin-4-yl]-piperidin-4-yl}-hexan-1-one; {6-[4-(3-tert-Butyl-[1,2,4]oxadiazol-5-yl)-piperidin-1-yl]-5-nitro-pyrimidin-4-yl}-(2-fluoro-4-methanesulfonyl-phenyl)-amine; {614-(3-tert-Butyl-[1,2,4]oxadiazol-5-yl)-piperidin-1-yl]-5-nitro-pyrimidin-4-yl}-(4-methanesulfonyl-phenyl)-amine; [6-(4-Benzofuran-2-yl-piperidin-1-yl)-5-nitro-pyrimidin-4-yl]-(4-methanesulfonyl-phenyl)-amine and 5-Nitro-4-(5-phenyl-[1,3,4]oxadiazol-2-ylsulfanyl)-6-[4-(pyridin-2-ylsulfanyl)-piperidin-1-yl]-pyrimidine.

Representative examples of compounds of the present invention that are inverse agonists include the following:

1-{6-[4-(2-Carboxy-ethyl)-phenyl]-5-nitro-pyrimidin-4-yl]-piperidine-4-carboxylic acid ethyl ester; 1-{6-[4-(2-Methoxycarbonyl-ethyl)-phenyl]-5-nitro-pyrimidin-4-yl}-piperidine-4-carboxylic acid methyl ester; 1-{6-[4-(2-Methoxycarbonyl-ethyl)-phenyl]-5-nitro-pyrimidin-4-yl}-piperidine-4-carboxylic acid ethyl ester; 1-[5-Nitro-6-(2-trifluoromethyl-phenylethynyl)-pyrimidin-4-yl]-piperidine-4-carboxylic acid ethyl ester; 1-(5-Nitro-6-phenylethynyl-pyrimidin-4-yl)-piperidine-4-carboxylic acid ethyl ester; 1-[5-Nitro-6-(4-trifluoromethyl-phenylethynyl)-pyrimidin-4-yl]-piperidine-4-carboxylic acid ethyl ester; 1-(5-Nitro-6-m-tolylethynyl-pyrimidin-4-yl)-piperidine-4-carboxylic acid ethyl ester; 1-[6-(2-Methyl-5-trifluoromethyl-2H-pyrazol-3-yloxy)-5-nitro-pyrimidin-4-yl]-piperidine-4-carboxylic acid ethyl ester; 1-[6-(Benzo[1,2,5]oxadiazol-5-yloxy)-5-nitro-pyrimidin-4-yl]-piperidine-4-carboxylic acid ethyl ester; 1-[6-(2-Methyl-5-trifluoromethyl-2H-pyrazol-3-yloxy)-5-nitro-pyrimidin-4-yl]-piperidine-4-carboxylic acid methyl ester; 2,6-Dimethyl-4-[6-1-{6-[4-(5-Hydroxy-pyrimidin-2-yl)-phenoxy]-5-nitro-pyrimidin-4-yl]-piperidine-4-carboxylic acid ethyl ester; 1-[5-Nitro-6-(4-sulfo-phenoxy)-pyrimidin-4-yl]-piperidine-4-carboxylic acid ethyl ester; 1-[6-(4'-Methoxy-biphenyl-4-yloxy)-5-nitro-pyrimidin-4-yl]-piperidine-4-carboxylic acid ethyl ester; 4-(4,4-Difluoro-piperidin-1-yl)-6-(2-methyl-5-trifluoromethyl-2H-pyrazol-3-yloxy)-5-nitro-pyrimidine; 1-{5-Nitro-6-[4-(4-oxo-cyclohexyl)-phenoxy]-pyrimidin-4-yl}-piperidine-4-carboxylic acid ethyl ester; 1-{6-[4-(2-Hydroxy-ethyl)-phenoxy]-5-nitro-pyrimidin-4-yl]-piperidine-4-carboxylic acid ethyl ester; 1-[6-(2-Methyl-5-trifluoromethyl-2H-pyrazol-3-yloxy)-5-nitro-pyrimidin-4-yl]-piperidine-3-carboxylic acid ethyl ester; 1-[6-(2-Methyl-5-trifluoromethyl-2H-pyrazol-3-yloxy)-5-nitro-pyrimidin-4-yl]-piperidine-4-carboxylic acid ethylamide; 1-[6-(2-Methyl-5-phenyl-2H-pyrazol-3-yloxy)-5-nitro-pyrimidin-4-yl]-piperidine-4-carboxylic acid ethyl ester; 4-(2-Methyl-5-trifluoromethyl-2H-pyrazol-3-yloxy)-5-nitro-6-piperidin-1-yl-pyrimidine; 1-[5-Acetylamino-6-(2-methyl-5-trifluoromethyl-2H-pyrazol-3-yloxy)-pyrimidin-4-yl]-piperidine-4-carboxylic acid ethyl ester; 1-[5-Diacetylamino-6-(2-methyl-5-trifluoromethyl-2H-pyrazol-3-yloxy)-pyrimidin-4-yl]-piperidine-4-carboxylic acid ethyl ester; 1-[6-(2-Methyl-5-trifluoromethyl-2H-pyrazol-3-yloxy)-5-nitro-pyrimidin-4-yl]-piperidine-4-carboxylic acid; 1-{5-Nitro-6-[2-(2-trifluoromethyl-phenyl)-ethoxy]-pyrimidin-4-yl}-piperidine-4-carboxylic acid ethyl ester; 1-{5-Nitro-6-[2-(3-trifluoromethyl-phenyl)-ethoxy]-pyrimidin-4-yl}-piperidine-4-carboxylic acid ethyl ester; 1-[5-Di-(methanesulfonyl)amino-6-(2-methyl-5-trifluoromethyl-2H-pyrazol-3-yloxy)-pyrimidin-4-yl]-piperidine-4-carboxylic acid ethyl ester; 1-[5-Nitro-6-(3-trifluoromethyl-phenoxy)-pyrimidin-4-yl]-piperidine-4-carboxylic acid ethyl ester; 1-[5-Methyl-6-(2-methyl-5-trifluoromethyl-2H-pyrazol-3-yloxy)-pyrimidin-4-yl]-piperidine-4-carboxylic acid ethyl ester; 1-[5-Nitro-6-(2-trifluoromethyl-phenoxy)-pyrimidin-4-yl]-piperidine-4-carboxylic acid ethyl ester; 1-[5-Nitro-6-(4-trifluoromethyl-phenoxy)-pyrimidin-4-yl]-piperidine-4-carboxylic acid ethyl ester; 1-[6-(4-Fluoro-phenoxy)-5-nitro-pyrimidin-4-yl]-piperidine-4-carboxylic acid ethyl ester; 1-[6-(2,5-Dimethyl-2H-pyrazol-3-yloxy)-5-nitro-pyrimidin-4-yl]-piperidine-4-carboxylic acid ethyl ester; 1-[5-Nitro-6-(2-oxo-benzo[1,3]oxathiol-6-yloxy)-pyrimidin-4-yl]-piperidine-4-carboxylic acid ethyl ester; 1-[6-(9H-Carbazol-2-yloxy)-5-nitro-pyrimidin-4-yl]-piperidine-4-carboxylic acid ethyl ester; 1-[5-Nitro-6-(9-oxo-9H-fluoren-2-yloxy)-pyrimidin-4-yl]-piperidine-4-carboxylic acid ethyl ester; 1-{5-Amino-6-[4-(3-oxo-butyl)-phenoxy]-pyrimidin-4-yl}-piperidine-4-carboxylic acid ethyl ester; 1-{5-Amino-6-[4-(hydroxy-phenyl-methyl)-phenoxy]-pyrimidin-4-yl}-piperidine-4-carboxylic acid ethyl ester; 1-[6-(6-Chloro-pyridin-3-yloxy)-5-nitro-pyrimidin-4-yl]-piperidine-4-carboxylic acid ethyl ester; 1-[6-(Benzo[1,3]dioxol-5-yloxy)-5-nitro-pyrimidin-4-yl]-piperidine-4-carboxylic acid ethyl ester; 1-[6-(4-Benzyloxy-phenoxy)-5-nitro-pyrimidin-4-yl]-piperidine-4-carboxylic acid ethyl ester; 1-[6-(4-Bromo-phenoxy)-5-nitro-pyrimidin-4-yl]-piperidine-4-carboxylic acid ethyl ester; 1-[6-(4-Chloro-phenoxy)-5-nitro-pyrimidin-4-yl]-piperidine-4-carboxylic acid ethyl ester; 1-[6-(4-Carbamoyl-phenoxy)-5-nitro-pyrimidin-4-yl]-piperidine-4-carboxylic acid ethyl ester; 1-{6-[4-(2-Methoxy-ethyl)-phenoxy]-5-nitro-pyrimidin-4-yl}-piperidine-4-carboxylic acid ethyl ester; 1-[6-(4-Benzoyl-phenoxy)-5-nitro-pyrimidin-4-yl]-piperidine-4-carboxylic acid ethyl ester; 1-{6-[4-(4-Hydroxy-benzenesulfonyl)-phenoxy]-5-nitro-pyrimidin-4-yl}-piperidine-4-carboxylic acid ethyl ester; 1-[5-Amino-6-(2-methyl-5-trifluoromethyl-2H-pyrazol-3-yloxy)-pyrimidin-4-yl]-piperidine-4-carboxylic acid ethyl ester; 1-[6-(2-Methyl-5-trifluoromethyl-2H-pyrazol-3-yloxy)-5-(2,2,2-trifluoro-acetylamino)-pyrimidin-4-yl]-piperidine-4-carboxylic acid ethyl ester; Propionic acid 1-[2-amino-5-formyl-6-(2-methyl-5-trifluoromethyl-2H-pyrazol- 3-yloxy)-pyrimidin-4-yl]-piperidin-4-yl ester; 4-[6-(2-Methyl-5-trifluoromethyl-2H-pyrazol-3-yloxy)-5-nitro-pyrimidin-4-yl]-piperazine-1-carboxylic acid ethyl ester; 1-[6-(4'-Cyano-biphenyl-4-yloxy)-5-nitro-pyrimidin-4-yl]-piperidine-4-carboxylic acid ethyl ester; {4-[6-(4,4-Difluoro-piperidin-1-yl)-5-nitro-pyrimidin-4-yloxy]-phenyl}-phenyl-methanone; 3-{4-[6-(4,4-Difluoro-piperidin-1-yl)-5-nitro-pyrimidin-4-yloxy]-phenyl}-3-oxo-propionic acid methyl ester; 246-(4,4-Difluoro-piperidin-1-yl)-5-nitro-pyrimidin-4-yloxy]-5-ethanesulfonyl-phenylamine; 4-(4-Cyclopentyl-phenoxy)-6-(4,4-difluoro-piperidin-1-yl)-5-nitro-pyrimidine; 1-[6-(2,6-Dichloro-4-methanesulfonyl-phenoxy)-5-nitro-pyrimidin-4-yl]-piperidine-4-carboxylic acid ethyl ester; 1-{6-[4-(4-Chloro-benzoyl)-phenoxy]-5-nitro-pyrimidin-4-yl}-piperidine-4-carboxylic acid ethyl ester; 1-{6-[4-(4-Hydroxy-benzoyl)-phenoxy]-5-nitro-pyrimidin-4-yl}-piperidine-4-carboxylic acid ethyl ester; 1-[6-(4-Cyanomethyl-phenoxy)-5-nitro-pyrimidin-4-yl]-piperidine-4-carboxylic acid ethyl ester; (4-{6-[4-(2-Methanesulfonyl-ethyl)-piperazin-1-yl]-5-nitro-pyrimidin-4-yloxy}-phenyl)-phenyl-methanone; 4-(4-{6-[4-(2-Methanesulfonyl-ethyl)-piperazin-1-yl]-5-nitro-pyrimidin-4-yloxy]-phenyl)-butan-2-one; 3-(4-{6-[4-(2-Methanesulfonyl-ethyl)-piperazin-1-yl]-5-nitro-pyrimidin-4-yloxy]-phenyl)-3-oxo-propionic acid methyl ester; 4-(4-Methyl-piperidin-1-yl)-6-(2-methyl-5-trifluoromethyl-2H-pyrazol-3-yloxy)-5-nitro-pyrimidine; 4-(4-Bromo-piperidin-1-yl)-6-(2-methyl-5-trifluoromethyl-2H-pyrazol-3-yloxy)-5-nitro-pyrimidine; 4-(2-Methyl-5-trifluoromethyl-2H-pyrazol-3-yloxy)-5-nitro-6-(4-propyl-piperidin-1-yl)-pyrimidine; 1-[5-Nitro-6-(2-trifluoromethyl-benzyloxy)-pyrimidin-4-yl]-piperidine-4-carboxylic acid ethyl ester; 1-[5-Nitro-6-(3-trifluoromethyl-benzyloxy)-pyrimidin-4-yl]-piperidine-4-carboxylic acid ethyl ester; 1-[5-Nitro-6-(4-trifluoromethyl-benzyloxy)-pyrimidin-4-yl]-piperidine-4-carboxylic acid ethyl ester; 1-[5-Bromo-6-(2-methyl-5-trifluoromethyl-2H-pyrazol-3-yloxy)-pyrimidin-4-yl]-piperidine-4-carboxylic acid ethyl ester; 1-[6-(2-Methyl-5-trifluoromethyl-2H-pyrazol-3-yloxy)-5-nitro-pyrimidin-4-yl]-piperidine-4-carboxylic acid amide; 1-[5-Nitro-6-(2-oxo-2H-chromen-6-yloxy)-pyrimidin-4-yl]-piperidine-4-carboxylic acid ethyl ester; 1-[6-(3-Morpholin-4-yl-phenoxy)-5-nitro-pyrimidin-4-yl]-piperidine-4-carboxylic acid ethyl ester; 1-[5-Nitro-6-(4-trifluoromethylsulfanyl-phenoxy)-pyrimidin-4-yl]-piperidine-4-carboxylic acid ethyl ester; 1-[5-Nitro-6-(4-trifluoromethoxy-phenoxy)-pyrimidin-4-yl]-piperidine-4-carboxylic acid ethyl ester; 1-[6-(4-Benzoyl-phenoxy)-5-(2,2,2-trifluoro-acetylamino)-pyrimidin-4-yl]-piperidine-4-carboxylic acid ethyl ester; {4-[5-Nitro-6-(4-propyl-piperidin-1-yl)-pyrimidin-4-yloxy]-phenyl}-phenyl-methanone; {4-Methoxy-2-[5-nitro-6-(4-propyl-piperidin-1-yl)-pyrimidin-4-yloxy]-phenyl}-phenyl-methanone; 4-{4-[5-Nitro-6-(4-propyl-piperidin-1-yl)-pyrimidin-4-yloxy]-phenyl}-butan-2-one; 5-Nitro-4-(4-propyl-piperidin-1-yl)-6-(4-[1,2,3]thiadiazol-4-yl-phenoxy)-pyrimidine; 3-{4-[5-Nitro-6-(4-propyl-piperidin-1-yl)-pyrimidin-4-yloxy]-phenyl}-3-oxo-propionic acid methyl ester; 5-Ethanesulfonyl-2-[5-nitro-6-(4-propyl-piperidin-1-yl)-pyrimidin-4-yloxy]-phenylamine; Benzo[1,3]dioxol-5-yl-[5-nitro-6-(4-propyl-piperidin-1-yl)-pyrimidin-4-yl]-amine; 1-[6-(4-Difluoromethoxy-benzyloxy)-5-nitro-pyrimidin-4-yl]-piperidine-4-carboxylic acid ethyl ester; 1-[6-(3-Ethynyl-phenoxy)-5-nitro-pyrimidin-4-yl]-piperidine-4-carboxylic acid ethyl ester; 1-[6-(4-Chloro-2-fluoro-phenoxy)-5-nitro-pyrimidin-4-yl]-piperidine-4-carboxylic acid ethyl ester; 1-[6-(2,4-Difluoro-phenoxy)-5-nitro-pyrimidin-4-yl]-piperidine-4-carboxylic acid ethyl ester; 1-[6-(4-Bromo-2-fluoro-phenoxy)-5-nitro-pyrimidin-4-yl]-piperidine-4-carboxylic acid ethyl ester; 4-(3-Ethynyl-phenoxy)-5-nitro-6-(4-propyl-piperidin-1-yl)-pyrimidine; 4-(4-Chloro-2-fluoro-phenoxy)-5-nitro-6-(4-propyl-piperidin-1-yl)-pyrimidine; 4-(2,4-Difluoro-phenoxy)-5-nitro-6-(4-propyl-piperidin-1-yl)-pyrimidine; 1-[6-(3-Difluoromethoxy-benzyloxy)-5-nitro-pyrimidin-4-yl]-piperidine-4-carboxylic acid ethyl ester; 4-[4-(4-Methyl-benzyl)-piperidin-1-yl]-6-(2-methyl-5-trifluoromethyl-2H-pyrazol-3-yloxy)-5-nitro-pyrimidine; 4-(3-Methanesulfonyl-pyrrolidin-1-yl)-6-(2-methyl-5-trifluoromethyl-2H-pyrazol-3-yloxy)-5-nitro-pyrimidine; 4-(2-Methyl-5-trifluoromethyl-2H-pyrazol-3-yloxy)-5-nitro-6-[4-(2-trifluoromethyl-phenoxy)-piperidin-1-yl]-pyrimidine; 4-(2-Methyl-5-trifluoromethyl-2H-pyrazol-3-yloxy)-5-nitro-6-[4-(pyridin-2-ylsulfanyl)-piperidin-1-yl]-pyrimidine; 1-[6-(4-Cyclopentyl-phenoxy)-5-nitro-pyrimidin-4-yl]-piperidine-4-carboxylic acid ethyl ester; 1-[5-Nitro-6-(4-pyrrol-1-yl-phenoxy)-pyrimidin-4-yl]-piperidine-4-carboxylic acid ethyl ester; 4'-(4-Benzoyl-phenoxy)-3'-nitro-3,4,5,6-tetrahydro-2H-[1,2']bipyridinyl-4-carboxylic acid ethyl ester; 4-(2-Methyl-5-trifluoromethyl-2H-pyrazol-3-yloxy)-5-nitro-6-(4-trifluoromethyl-piperidin-1-yl)-pyrimidine; 4-(2-Methyl-5-trifluoromethyl-2H-pyrazol-3-yloxy)-5-nitro-6-(4-phenylsulfanyl-piperidin-1-yl)-pyrimidine; 4-(4-Bromo-2-fluoro-phenoxy)-5-nitro-6-(4-propyl-piperidin-1-yl)-pyrimidine; 4-[4-(3'-Nitro-4-propyl-3,4,5,6-tetrahydro-2H-[1,4]bipyridinyl-2'-yloxy)-phenyl]-butan-2-one; 2'-(4-Benzoyl-phenoxy)-3'-nitro-3,4,5,6-tetrahydro-2H-[1,4]bipyridinyl-4-carboxylic acid ethyl ester; (5-Nitro-6-piperidin-1-yl-pyrimidin-4-yl)-(3-trifluoromethyl-benzyl)-amine; 1-[5-Nitro-6-(2-trifluoromethyl-benzylamino)-pyrimidin-4-yl]-piperidine-4-carboxylic acid ethyl ester; 1-[5-Nitro-6-(4-trifluoromethyl-benzylamino)-pyrimidin-4-yl]-piperidine-4-carboxylic acid ethyl ester; 1-[5-Nitro-6-(3-trifluoromethyl-benzylamino)-pyrimidin-4-yl]-piperidine-4-carboxylic acid ethyl ester; (5-Nitro-6-piperidin-1-yl-pyrimidin-4-yl)-(2-trifluoromethyl-benzyl)-amine; [4-(3'-Nitro-4-propyl-3,4,5,6-tetrahydro-2H-[1,4]bipyridinyl-2'-yloxy)-phenyl]-phenyl-methanone; (4-{6-[4-(3-Methyl-[1,2,4]oxadiazol-5-yl)-piperidin-1-yl]-5-nitro-pyrimidin-4-yloxy]-phenyl)-phenyl-methanone; 1-{6-[4-(4-Fluoro-benzoyl)-phenoxy]-5-nitro-pyrimidin-4-yl}-piperidine-4-carboxylic acid ethyl ester; (4-Fluoro-phenyl)-{4-[5-nitro-6-(4-propyl-piperidin-1-yl)-pyrimidin-4-yloxy]-phenyl}-methanone; 4-[4-(3-Methyl-[1,2,4]oxadiazol-5-yl)-piperidin-1-yl]-6-(2-methyl-5-trifluoromethyl-2H-pyrazol-3-yloxy)-5-nitro-pyrimidine; 4-(4-Methoxymethyl-piperidin-1-yl)-6-(2-methyl-5-trifluoromethyl-2H-pyrazol-3-yloxy)-5-nitro-pyrimidine; 4-{4-[6-(4-Methoxymethyl-piperidin-1-yl)-5-nitro-pyrimidin-4-yloxy]-phenyl}-butan-2-one; 1-{5-Nitro-6-[3-(1,1,2,2-tetrafluoro-ethoxy)-phenylamino]-pyrimidin-4-yl}-piperidine-4-carboxylic acid ethyl ester; 1-(5-Nitro-6-phenyl-pyrimidin-4-yl)-piperidine-4-carboxylic acid ethyl ester; 1-(6-Naphthalen-2-yl-5-nitro-pyrimidin-4-yl)-piperidine-4-carboxylic acid ethyl ester; 4-[4-(2-Methoxy-ethyl)-piperidin-1-yl]-6-(2-methyl-5-trifluoromethyl-2H-pyrazol-3-yloxy)-5-nitro-pyrimidine; 4-{4-[6-(4-Ethoxymethyl-piperidin-1-yl)-5-nitro-pyrimidin-4-yloxy]-phenyl}-butan-2-one; 4-[4-(3'-Nitro-4-propyl-3,4,5,6-tetrahydro-2H[1,2']bipyridinyl-4'-yloxy)-phenyl]-butan-2-one; 3'-Nitro-4-propyl-4'-(4-[1,2,4]triazol-1-yl-phenoxy)-3,4,5,6-tetrahydro-2H-[1,2]bipyridinyl; 1-[3-(4-Benzoyl-phenoxy)-2-nitro-phenyl]-piperidine-4-carboxylic acid ethyl ester; {4-[6-(4-Ethoxy-piperidin-1-yl)-5-nitro-pyrimidin-4-yloxy]-phenyl}-(4-fluoro-phenyl)-methanone; 1-[6-(2-Methyl-5-trifluoromethyl-2H-pyrazol-3-yloxy)-5-nitro-pyrimidin-4-yl]-piperidin-4-ol; 2-{1-[6-(2-Methyl-5- trifluoromethyl-2H-pyrazol-3-yloxy)-5-nitro-pyrimidin-4-yl]-piperidin-4-yl}-ethanol; 3-{1-[6-(2-Methyl-5-trifluoromethyl-2H-pyrazol-3-yloxy)-5-nitro-pyrimidin-4-yl]-piperidin-4-yl}-propionic acid; (1-{6-[4-(4-Fluoro-benzoyl)-phenoxy]-5-nitro-pyrimidin-4-yl}-piperidin-4-yl)-(4-fluoro-phenyl)-methanone; 1-[5-Nitro-6-(4-trifluoromethylsulfanyl-phenoxy)-pyrimidin-4-yl]-piperidine-4-carboxylic acid ethyl ester; 1-[5-Nitro-6-(3,4,5-trimethoxy-benzylamino)-pyrimidin-4-yl]-piperidine-4-carboxylic acid ethyl ester; (5-Nitro-6-piperidin-1-yl-pyrimidin-4-yl)-(4-trifluoromethyl-benzyl)-amine; 1-[5-Amino-6-(3-trifluoromethyl-benzylamino)-pyrimidin-4-yl]-piperidine-4-carboxylic acid ethyl ester; 1-[5-Amino-6-(4-trifluoromethyl-benzylamino)-pyrimidin-4-yl]-piperidine-4-carboxylic acid ethyl ester; 1-[6-(4-Bromo-phenylamino)-5-nitro-pyrimidin-4-yl]-piperidine-4-carboxylic acid ethyl ester; 1-[5-Nitro-6-(4-trifluoromethyl-phenylamino)-pyrimidin-4-yl]-piperidine-4-carboxylic acid ethyl ester; 1-[6-(Methyl-phenyl-amino)-5-nitro-pyrimidin-4-yl]-piperidine-4-carboxylic acid ethyl ester; 1-[5-Nitro-6-(4-trifluoromethoxy-phenylamino)-pyrimidin-4-yl]-piperidine-4-carboxylic acid ethyl ester; 1-[6-(4-Fluoro-phenylamino)-5-nitro-pyrimidin-4-yl]-piperidine-4-carboxylic acid ethyl ester; 1-{6-[(2,3-Dihydro-benzo[1,4]dioxin-6-ylmethyl)-amino]-5-nitro-pyrimidin-4-yl]-piperidine-4-carboxylic acid ethyl ester; 1-{6-[(2,3-Dihydro-benzo[1,4]dioxin-2-ylmethyl)-amino]-5-nitro-pyrimidin-4-yl]-piperidine-4-carboxylic acid ethyl ester; 1-{6-[(2,3-Dihydro-benzofuran-5-ylmethyl)-amino]-5-nitro-pyrimidin-4-yl}-piperidine-4-carboxylic acid ethyl ester; 1-{6-[(6-Fluoro-4H-benzo[1,3]dioxin-8-ylmethyl)-amino]-5-nitro-pyrimidin-4-yl]-piperidine-4-carboxylic acid ethyl ester; 1-[6-(2,2-Difluoro-benzo[1,3]dioxol-4-ylamino)-5-nitro-pyrimidin-4-yl]-piperidine-4-carboxylic acid ethyl ester; 1-[6-(2,2-Difluoro-benzo[1,3]dioxol-5-ylamino)-5-nitro-pyrimidin-4-yl]-piperidine-4-carboxylic acid ethyl ester; 1-[6-(1,1-Dioxo-1H-1$\lambda^6$-benzo[b]thiophen-6-ylamino)-5-nitro-pyrimidin-4-yl]-piperidine-4-carboxylic acid ethyl ester; 1-{6-[(Furan-3-ylmethyl)-amino]-5-nitro-pyrimidin-4-yl]-piperidine-4-carboxylic acid ethyl ester; 1-{6-[2-(4-Methoxy-phenoxy)-ethylamino]-5-nitro-pyrimidin-4-yl]-piperidine-4-carboxylic acid ethyl ester; 1-{6-[2-(5-Methoxy-1H-indol-3-yl)-ethylamino]-5-nitro-pyrimidin-4-yl]-piperidine-4-carboxylic acid ethyl ester; (3,4-Dihydro-2H-benzo[b][1,4]dioxepin-7-yl)-[5-nitro-6-(4-propyl-piperidin-1-yl)-pyrimidin-4-yl]-amine; (3-Fluoro-phenyl)-[5-nitro-6-(4-propyl-piperidin-1-yl)-pyrimidin-4-yl]-amine; (3-Methoxy-phenyl)-[5-nitro-6-(4-propyl-piperidin-1-yl)-pyrimidin-4-yl]-amine; 1-{6-[(3-Fluoro-phenyl)-methyl-amino]-5-nitro-pyrimidin-4-yl]-piperidine-4-carboxylic acid ethyl ester; 1-[6-(4-Benzoyl-phenylamino)-5-nitro-pyrimidin-4-yl]-piperidine-4-carboxylic acid ethyl ester; 1-[6-(3,5-Bis-trifluoromethyl-phenylamino)-5-nitro-pyrimidin-4-yl]-piperidine-4-carboxylic acid ethyl ester; 1-[6-(3,5-Dimethoxy-benzylamino)-5-nitro-pyrimidin-4-yl]-piperidine-4-carboxylic acid ethyl ester; 1-[6-(4-Heptyl-phenylamino)-5-nitro-pyrimidin-4-yl]-piperidine-4-carboxylic acid ethyl ester; 2'-(4-Benzoyl-phenylamino)-3'-nitro-3,4,5,6-tetrahydro-2H-[1,4]bipyridinyl-4-carboxylic acid ethyl ester; 1-[5-Nitro-6-(3,4,5-trimethoxy-phenylamino)-pyrimidin-4-yl]-piperidine-4-carboxylic acid ethyl ester; 1-[5-Nitro-6-(4-pentyl-phenylamino)-pyrimidin-4-yl]-piperidine-4-carboxylic acid ethyl ester; 1-{6-[4-(3-Carboxy-propyl)-phenylamino]-5-nitro-pyrimidin-4-yl}-piperidine-4-carboxylic acid ethyl ester; [5-Nitro-6-(4-propyl-piperidin-1-yl)-pyrimidin-4-yl]-(3,4,5-trimethoxy-benzyl)-amine; (3,5-Dimethoxy-benzyl)-[5-nitro-6-(4-propyl-piperidin-1-yl)-pyrimidin-4-yl]-amine; (4-{5-Nitro-6-[4-(2-trifluoromethyl-phenoxy)-piperidin-1-yl]-pyrimidin-4-ylamino}-phenyl)-phenyl-methanone; 1-[6-(3,5-Difluoro-phenylamino)-5-nitro-pyrimidin-4-yl]-piperidine-4-carboxylic acid ethyl ester; 1-[6-(3,5-Dichloro-phenylamino)-5-nitro-pyrimidin-4-yl]-piperidine-4-carboxylic acid ethyl ester; 1-[6-(2-Bromo-4-trifluoromethoxy-phenylamino)-5-nitro-pyrimidin-4-yl]-piperidine-4-carboxylic acid ethyl ester; 1-{6-[(2-Fluoro-phenyl)-methyl-amino]-5-nitro-pyrimidin-4-yl}-piperidine-4-carboxylic acid ethyl ester; 1-[6-(Ethyl-phenyl-amino)-5-nitro-pyrimidin-4-yl]-piperidine-4-carboxylic acid ethyl ester; 1-{6-[(4-Chloro-phenyl)-methyl-amino]-5-nitro-pyrimidin-4-yl}-piperidine-4-carboxylic acid ethyl ester; 1-[6-(4-Difluoromethyl-benzylamino)-5-nitro-pyrimidin-4-34]-piperidine-4-carboxylic acid ethyl ester; 1-[6-(4-Cyano-phenylamino)-5-nitro-pyrimidin-4-yl]-piperidine-4-carboxylic acid ethyl ester; 1-[6-(3,5-Dimethoxy-phenylamino)-5-nitro-pyrimidin-4-yl]-piperidine-4-carboxylic acid ethyl ester; 1-[6-(4-sec-Butyl-phenylamino)-5-nitro-pyrimidin-4-yl]-piperidine-4-carboxylic acid ethyl ester; 1-{6-[4-(Cyano-phenyl-methyl)-phenylamino]-5-nitro-pyrimidin-4-yl}-piperidine-4-carboxylic acid ethyl ester; 1-{5-Nitro-6-[4-(4-trifluoromethyl-phenoxy)-phenylamino]-pyrimidm-4-yl}-piperidine-4-carboxylic acid ethyl ester; 1-[6-(2-Methyl-5-phenyl-2H-pyrazol-3-ylamino)-5-nitro-pyrimidin-4-yl]-piperidine-4-carboxylic acid ethyl ester; 1-[6-(4-Benzenesulfonyl-phenylamino)-5-nitro-pyrimidin-4-yl]-piperidine-4-carboxylic acid ethyl ester; 1-[5-Nitro-6-(2-trifluoromethyl-3H-benzoimidazol-5-ylamino)-pyrimidin-4-yl]-piperidine-4-carboxylic acid ethyl ester; 1-[6-(4-Methanesulfonyl-phenyl)-5-nitro-pyrimidin-4-yl]-piperidine-4-carboxylic acid ethyl ester; 1-(6-Benzofuran-5-yl-5-nitro-pyrimidin-4-yl)-piperidine-4-carboxylic acid ethyl ester; 1-[5-Nitro-6-(3-trifluoromethyl-phenyl)-pyrimidin-4-yl]-piperidine-4-carboxylic acid ethyl ester; 1-[6-(4-Methoxy-phenyl)-5-nitro-pyrimidin-4-yl]-piperidine-4-carboxylic acid ethyl ester; 4-(4-Butyl-piperidin-1-yl)-6-furan-3-yl-5-nitro-pyrimidine; 1-[6-(3-Chloro-phenyl)-5-nitro-pyrimidin-4-yl]-piperidine-4-carboxylic acid ethyl ester; 1-[6-(2,6-Dimethoxy-phenyl)-5-nitro-pyrimidin-4-yl]-piperidine-4-carboxylic acid ethyl ester; 1-(6-Naphthalen-1-yl-5-nitro-pyrimidin-4-yl)-piperidine-4-carboxylic acid ethyl ester; 1-[6-(4-Methylsulfanyl-phenyl)-5-nitro-pyrimidin-4-yl]-piperidine-4-carboxylic acid ethyl ester; 1-(2',4'-Dihydroxy-5-nitro-[4,5]bipyrimidinyl-6-yl)-piperidine-4-carboxylic acid ethyl ester; 1-[6-(4-Methanesulfonyl-phenyl)-5-nitro-pyrimidin-4-yl]-piperidine-4-carboxylic acid ethyl ester; 1-[6-(3,5-Bis-trifluoromethyl-phenyl)-5-nitro-pyrimidin-4-yl]-piperidine-4-carboxylic acid ethyl ester; 1-(6-Dibenzothiophen-4-yl-5-nitro-pyrimidin-4-yl)-piperidine-4-carboxylic acid ethyl ester; 4-(2,4-Difluoro-phenoxy)-6-(4-ethoxymethyl-piperidin-1-yl)-5-nitro-pyrimidine; 1-{4-[6-(4-Methoxymethyl-piperidin-1-yl)-5-nitro-pyrimidin-4-yloxy]-phenyl}-ethanone; 4-{4-[2-Nitro-3-(4-propyl-piperidin-1-yl)-phenoxy]-phenyl}-butan-2-one; 1-{4-[2-Nitro-3-(4-propyl-piperidin-1-yl)-phenoxy]-phenyl}-ethanone; {4-[2-Nitro-3-(4-propyl-piperidin-1-yl)-phenoxy]-phenyl}-phenyl-methanone; 3-{-4-[2-Nitro-3-(4-propyl-piperidin-1-yl)-phenoxy]-phenyl}-3-oxo-propionic acid methyl ester; (4-Fluoro-phenyl)-[4-(3'-nitro-4-propyl-3,4,5,6-tetrahydro-2H-[1,2']bipyridinyl-4'-yloxy)-phenyl]-methanone; 1-[6-(3,5-Dimethyl-isoxazol-4-yl)-5-nitro-pyrimidin-4-yl]-piperidine-4-carboxylic acid ethyl ester; 1-(5-Nitro-6-thiophen-2-yl-pyrimidin-4-yl)-piperidine-4-carboxylic acid ethyl ester; 1-[6-(3,5-Dichloro-phenyl)-5-nitro-pyrimidin-4-yl]-piperidine-4-carboxylic acid ethyl ester; 1-(6-Dibenzofuran-4-yl-5-nitro-pyrimidin-4-yl)-piperidine-4-carboxylic acid ethyl ester; 1-[6-(3,5-Dimethyl-phenyl)-5-nitro-pyrimidin-4-yl]-piperidine-4-carboxylic acid ethyl ester; 1-[6-(4-Acetyl-phenyl)-5-nitro-pyrimidin-4-yl]-piperidine-4-carboxylic acid ethyl ester; 1-[6-(4-Ethanesulfonyl-phenyl)-5-nitro-pyrimidin-4-yl]-piperidine-4-carboxylic acid ethyl ester; 1-[6-(2-Fluoro-biphenyl-4-yl)-5-nitro-pyrimidin-4-yl]-piperidine-4-carboxylic acid ethyl ester; 1-[6-(3-Methanesulfonyl-phenyl)-5-nitro-pyrimidin-4-yl]-piperidine-4-carboxylic acid ethyl ester; 1-[6-(2-Fluoro-phenylethynyl)-5-nitro-pyrimidin-4-yl]-piperidine-4-carboxylic acid ethyl ester and 1-[5-Nitro-6-(3-trifluoromethyl-phenylethynyl)-pyrimidin-4-yl]-piperidine-4-carboxylic acid ethyl ester.

Pharmaceutical Compositions

Some embodiments of the present invention include a method of producing a pharmaceutical composition comprising admixing at least one compound according to any of the compound embodiments disclosed herein and a pharmaceutically acceptable carrier.

A compound of the present invention can be formulated into pharmaceutical compositions using techniques well known to those in the art. Suitable pharmaceutically-acceptable carriers, outside those mentioned herein, are available to those in the art; for example, see Remington's Pharmaceutical Sciences, 16$^{th}$ Edition, 1980, Mack Publishing Co., (Oslo et al., eds.) and the most current version.

While it is possible that, for use in the prophylaxis or treatment, a compound of the invention may in an alternative use be administered as a raw or pure chemical, it is preferable however to present the compound or active ingredient as a pharmaceutical formulation or composition further comprising a pharmaceutically acceptable carrier.

The invention thus further provides pharmaceutical formulations comprising a compound of the invention or a pharmaceutically acceptable salt or derivative thereof together with one or more pharmaceutically acceptable carriers therefor and/or prophylactic ingredients. The carrier(s) must be "acceptable" in the sense of being compatible with the other ingredients of the formulation and not overly deleterious to the recipient thereof.

Pharmaceutical formulations include those suitable for oral, rectal, nasal, topical (including buccal and sub-lingual), vaginal or parenteral (including intramuscular, sub-cutaneous and intravenous) administration or in a form suitable for administration by inhalation or insufflation.

The compounds of the invention, together with a conventional adjuvant, carrier, or diluent, may thus be placed into the form of pharmaceutical formulations and unit dosages thereof, and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles, and such unit dosage forms may contain any suitable effective amount of the active ingredient commensurate with the intended daily dosage range to be employed.

For oral administration, the pharmaceutical composition may be in the form of for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

The dose when using the compounds of Formula (Ia) can vary within wide limits, and as is customary and is known to the physician, it is to be tailored to the individual conditions in each individual case. It depends, for example, on the nature and severity of the illness to be treated, on the condition of the patient, on the compound employed or on whether an acute or chronic disease state is treated or prophylaxis is conducted or on whether further active compounds are administered in addition to the compounds of the Formula (Ia). Representative doses of the present invention include, about 0.01 mg to about 1000 mg, about 0.01 to about 750 mg, about 0.01 to about 500 mg, 0.01 to about 250 mg, 0.01 mg to about 200 mg, about 0.01 mg to 150 mg, about 0.01 mg to about 100 mg, and about 0.01 mg to about 75 mg. Multiple doses may be administered during the day, especially when relatively large amounts are deemed to be needed, for example 2, 3 or 4, doses. If appropriate, depending on individual behavior and as appropriate from the patients physician or care-giver it may be necessary to deviate upward or downward from the daily dose.

The amount of active ingredient, or an active salt or derivative thereof; required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. Typically, animal models include, but are not limited to, the rodents diabetes models as described in Example 6, infra (other animal models have been reported by Reed and Scribner in Diabetes, Obesity and Metabolism, 1, 1999, 75-86). In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular compound employed, whether a drug delivery system is utilized, on whether an acute or chronic disease state is being treated or prophylaxis is conducted or on whether further active compounds are administered in addition to the compounds of the Formula (Ia) and as part of a drug combination. The dosage regimen for treating a disease condition with the compounds and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4, part administrations. If appropriate, depending on individual behavior, it may be necessary to deviate upward or downward from the daily dose indicated.

The compounds of the present invention can be administrated in a wide variety of oral and parenteral dosage forms. It will be obvious to those skilled in the art that the following dosage forms may comprise, as the active component, either a compound of the invention or a pharmaceutically acceptable salt of a compound of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories, and dispersible granules. A solid carrier can be one or more substances which may also act as diluents, flavouring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active compound. A representative amount in a powder or tablet may contain from 0.5 to about 90 percent of the active compound; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as carrier providing a capsule in which the active component, with or without carriers, is surrounded by a carrier, which is thus in association with it. Similarly, cachets and lozenges are included. Tablets, powders, capsules, pills, cachets, and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool, and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions, and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, pre-filled syringes, small volume infusion or in multi-dose containers with an added preservative. The pharmaceutical compositions may take such forms as suspensions, solutions, or emulsions in oily or aqueous vehicles, and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous solutions suitable for oral use can be prepared by dissolving the active component in water and adding suitable colorants, flavours, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

For topical administration to the epidermis the compounds according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the compounds of the Formula (Ia) or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the compounds of the Formula (Ia) as an aerosol can be prepared by processes well-known to the person skilled in the art. For their preparation, for example, solutions or dispersions of the compounds of the Formula (Ia) in water, water/alcohol mixtures or suitable saline solutions can be employed using customary additives, for example benzyl alcohol or other suitable preservatives, absorption enhancers for increasing the bioavailability, solubilizers, dispersants and others, and, if appropriate, customary propellants, for example include carbon dioxide, CFC's, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the compound will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the compound in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

The term "prodrug" refers to compounds that are rapidly transformed in vivo to yield the parent compound of the above formulae, for example, by hydrolysis in blood. A thorough discussion is provided in T. Higuchi and V. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987, both of which are hereby incorporated by reference.

Combination Therapy/Prophylaxis

While the compounds of the invention can be administered as the sole active pharmaceutical agent as described herein above, they can also be used in combination with one or more agents belonging to the class of drugs known as α-glucosidase inhibitors, aldose reductase inhibitors, biguanides, HMG-CoA reductase inhibitors, squalene synthesis inhibitors, fibrate compounds, LDL catabolism enhancers and angiotensin converting enzyme (ACE) inhibitors.

α-Glucosidase inhibitors belong to the class of drugs which competitively inhibit digestive enzymes such as α-amylase, maltase, α-dextrinase, sucrase, etc. in the pancreas and or small intesting. The reversible inhibition by α-glucosidase inhibitors retard, diminish or otherwise reduce blood glucose levels by delaying the digestion of starch and sugars. Some representative examples of α-glucosidase inhibitors include acarbose, N-(1,3-dihydroxy-2-propyl)valiolamine (generic name; voglibose), miglitol, and α-glucosidase inhibitors known in the art.

The class of aldose reductase inhibitors are drugs which inhibit the first-stage rate-limiting enzyme in the polyol pathway that prevent or arrest diabetic complications. In the hyperglycemic state of diabetes, the utilization of glucose in the polyol pathway is increased and the excess sorbitol accumulated intracellularly as a consequence acts as a tissue toxin and hence evokes the onset of complications such as diabetic neuropathy, retinopathy, and nephropathy. Examples of the aldose reductase inhibitors include tolurestat; epalrestat; 3,4-dihydro-2,8-diisopropyl-3-thioxo-2H-1,4-benzoxazine-4-acetic acid; 2,7-difluorospiro(9H-fluorene-9,4'-imidazolidine)-2',5'-dione (generic name: imirestat); 3-[(4-bromo-2-fluorophenyl)methy]-7-chloro-3,4-dihydro-2,4-dioxo-1 (2H)-quinazoline acetic acid (generic name: zenarestat); 6-fluoro-2,3-dihydro-2',5'-dioxo-spiro[4H-1-benzopyran-4, 4'-imidazolidine]-2-carboxamide (SNK-860); zopolrestat; sorbinil; and 1-[(3-bromo-2-benzofuranyl)sulfonyl]-2,4-imidazolidinedione (M-16209), and aldose reductase inhibitors known in the art.

The biguanides are a class of drugs that stimulate anaerobic glycolysis, increase the sensitivity to insulin in the peripheral tissues, inhibit glucose absorption from the intestine, suppress of hepatic gluconeogenesis, and inhibit fatty acid oxidation. Examples of biguanides include phenformin, metformin, buformin, and biguanides known in the art.

Statin compounds belong to a class of drugs that lower blood cholesterol levels by inhibiting hydroxymethylglutalyl CoA (HMG-CoA) reductase. HMG-CoA reductase is the rate-limiting enzyme in cholesterol biosynthesis. A statin that inhibits this reductase lowers serum LDL concentrations by upregulating the activity of LDL receptors and responsible for clearing LDL from the blood. Examples of the statin compounds include rosuvastatin, pravastatin and its sodium salt, simvastatin, lovastatin, atorvastatin, fluvastatin, cerivastatin, and HMG-CoA reductase inhibitors known in the art.

Squalene synthesis inhibitors belong to a class of drugs that lower blood cholesterol levels by inhibiting synthesis of squalene. Examples of the squalene synthesis inhibitors include (S)-α-[Bis[2,2-dimethyl-1-oxopropoxy)methoxy] phosphinyl]-3-phenoxybenzenebutanesulfonic acid, mono potassium salt (BMS-188494) and squalene synthesis inhibitors known in the art.

Fibrate compounds belong to a class of drugs that lower blood cholesterol levels by inhibiting synthesis and secretion of triglycerides in the liver and activating a lipoprotein lipase. Fibrates have been known to activate peroxisome proliferators-activated receptors and induce lipoprotein lipase expression. Examples of fibrate compounds include bezafibrate, beclobrate, binifibrate, ciplofibrate, clinofibrate, clofibrate, clofibric acid, etofibrate, fenofibrate, gemfibrozil, nicofibrate, pirifibrate, ronifibrate, simfibrate, theofibrate, and fibrates known in the art.

LDL (low-density lipoprotein) catabolism enhancers belong to a class of drugs that lower blood cholesterol levels by increasing the number of LDL (low-density lipoprotein) receptors, examples include LDL catabolism enhancers known in the art.

Angiotensin converting enzyme (ACE) inhibitors belong to the class of drugs that partially lower blood glucose levels as well as lowering blood pressure by inhibiting angiotensin converting enzymes. Examples of the angiotensin converting enzyme inhibitors include captopril, enalapril, alacepril, delapril; ramipril, lisinopril, imidapril, benazepril, ceronapril, cilazapril, enalaprilat, fosinopril, moveltopril, perindopril, quinapril, spirapril, temocapril, trandolapril, and angiotensin converting enzyme inhibitors known in the art.

Insulin secretion enhancers belong to the class of drugs having the property to promote secretion of insulin from pancreatic β cells. Examples of the insulin secretion enhancers include sulfonylureas (SU). The sulfonylureas (SU) are drugs which promote secretion of insulin from pancreatic β cells by transmitting signals of insulin secretion via SU receptors in the cell membranes. Examples of the sulfonylureas include tolbutamide; chlorpropamide; tolazamide; acetohexamide; 4-chloro-N-[(1-pyrrolidinylamino) carbonyl]-benzenesulfonamide (generic name: glycopyramide) or its ammonium salt; glibenclamide (glyburide); gliclazide; 1-butyl-3-metanilylurea; carbutamide; glibonuride; glipizide; gliquidone; glisoxepid; glybuthiazole; glibuzole; glyhexamide; glymidine; glypinamide; phenbutamide; tolcyclamide, glimepiride, and other insulin secretion enhancers known in the art. Other insulin secretion enhancers include N-[[4-(1-methylethyl)cyclohexyl)carbonyl]-D-phenylalanine (Nateglinide); calcium (2S)-2-benzyl-3-(cis-hexahydro-2-isoindolinylcarbonyl)propionate dihydrate (Mitiglinide, KAD-1229); and other insulin secretion enhancers known in the art.

Thiazolidinediones belong to the class of drugs more commoningly known as TZDs. Examples of thiazolidinediones include rosiglitazone, pioglitazone, and thiazolidinediones known in the art.

Some embodiments of the invention include, a pharmaceutical composition comprising a compound of Formula (Ia) or a pharmaceutically acceptable salt thereof in combination with at least one member selected from the group consisting of an α-glucosidase inhibitor, an aldose reductase inhibitor, a biguanide, a HMG-CoA reductase inhibitor, a squalene synthesis inhibitor, a fibrate compound, a LDL catabolism enhancer and an angiotensin converting enzyme inhibitor. In another embodiment, the pharmaceutical composition is a compound of Formula (Ia) or a pharmaceutically acceptable salt thereof in combination with a HMG-CoA reductase inhibitor. In still another embodiment, the HMG-CoA reductase inhibitor is selected from the group consisting of prevastatin, simvastatin, lovastatin, atorvastatin, fluvastatin and lipitor.

In accordance with the present invention, the combination can be used by mixing the respective active components either all together or independently with a physiologically acceptable carrier, excipient, binder, diluent, etc., as described herein above, and administering the mixture or mixtures either orally or non-orally as a pharmaceutical composition. When a compound or a mixture of compounds of Formula (Ia) are administered as a combination therapy or prophylaxis with another active compound the therapeutic agents can be formulated as a separate pharmaceutical compositions given at the same time or at different times, or the therapeutic agents can be given as a single composition.

Other Utility

Another object of the present invention relates to radiolabelled compounds of Formula (Ia) that would be useful not only in radio-imaging but also in assays, both in vitro and in vivo, for localizing and quantitating RUP3 in tissue samples, including human, and for identifying RUP3 ligands by inhibition binding of a radiolabelled compound. It is a further object of this invention to develop novel RUP3 assays of which comprise such radiolabelled compounds.

Suitable radionuclides that may be incorporated in compounds of the present invention include but are not limited to $^3H$ (also written as T), $^{11}C$, $^{14}C$, $^{18}F$, $^{125}I$, $^{82}Br$, $^{123}I$, $^{124}I$, $^{125}I$, $^{131}I$, $^{75}Br$, $^{76}Br$, $^{15}O$, $^{13}N$, $^{35}S$ and $^{77}Br$. The radionuclide that is incorporated in the instant radiolabelled compounds will depend on the specific application of that radiolabelled compound. Thus, for in vitro RUP3 labeling and competition assays, compounds that incorporate $^3H$, $^{14}C$, $^{125}I$, $^{131}I$, $^{35}S$ or $^{82}Br$ will generally be most useful. For radio-imaging applications $^{11}C$, $^{18}F$, $^{125}I$, $^{123}I$, $^{124}I$, $^{131}I$, $^{75}Br$, $^{76}Br$ or $^{77}Br$ will generally be most useful.

It is understood that a "radio-labelled" or "labelled compound" is a compound of Formula (Ia) that has incorporated at least one radionuclide; In some embodiments, the radionuclide is selected from the group consisting of $^3H$, $^{14}C$, $^{125}I$, $^{35}S$ and $^{82}Br$; In some embodiments, the radionuclide $^3H$ or $^{14}C$. Moreover, it should be understood that all of the atoms represented in the compounds of the invention can be either the most commonly occurring isotope of such atoms or the more scarce radio-isotope or nonradio-active isotope.

Synthetic methods for incorporating radio-isotopes into organic compounds including those applicable to those compounds of the invention are well known in the art and include incorporating activity levels of tritium into target molecules include: A. Catalytic Reduction with Tritium Gas—This procedure normally yields high specific activity products and requires halogenated or unsaturated precursors. B. Reduction with Sodium Borohydride [$^3H$]—This procedure is rather inexpensive and requires precursors containing reducible functional groups such as aldehydes, ketones, lactones, esters, and the like. C. Reduction with Lithium Aluminum Hydride [$^3H$]—This procedure offers products at almost theoretical specific activities. It also requires precursors containing reducible functional groups such as aldehydes, ketones, lactones, esters, and the like. D. Tritium Gas Exposure Labeling—This procedure involves exposing precursors containing exchangeable protons to tritium gas in the presence of a suitable catalyst. E. N-Methylation using Methyl Iodide [$^3H$]—This procedure is usually employed to prepare O-methyl or N-methyl ($^3H$) products by treating appropriate precursors with high specific activity methyl iodide ($^3H$). This method in general allows for high specific activity, such as about 80-87 Ci/mmol.

Synthetic methods for incorporating activity levels of $^{125}I$ into target molecules include: A. Sandmeyer and like reactions —This procedure transforms an aryl or heteroaryl amine into a diazonium salt, such as a tetrafluoroborate salt, and subsequently to $^{125}I$ labelled compound using Na$^{125}I$. A represented procedure was reported by Zhu, D.-G. and co-workers in *J. Org. Chem.* 2002, 67, 943-948. B. Ortho $^{125}I$odination of phenols—This procedure allows for the incorporation of $^{125}I$ at the ortho position of a phenol as reported by Collier, T. L. and co-workers in *J. Labelled Compd Radiopharm.* 1999, 42, S264-S266. C. Aryl and heteroaryl bromide exchange with $^{125}I$—This method is generally a two step process. The first step is the conversion of the aryl or heteroaryl bromide to the corresponding tri-alkyltin intermediate using for example, a Pd catalyzed reaction [i.e. Pd(Ph$_3$P)$_4$] or through an aryl or heteroaryl lithium, in the presence of a tri-alkyltinhalide or hexaalkylditin [e.g., (CH$_3$)$_3$SnSn(CH$_3$)$_3$]. A represented procedure was reported by Bas, M.-D. and co-workers in *J Labelled Compd Radiopharm.* 2001, 44, S280-S282.

A radiolabelled RUP3 compound as described herein can be used in a screening assay to identify/evaluate compounds. In general terms, a newly synthesized or identified compound (I.e., test compound) can be evaluated for its ability to reduce binding of the "radiolabelled compound of Formula (Ia)" to the RUP3 receptor. Accordingly, the ability of a test compound to compete with the "radio-labelled compound of Formula (Ia)" for the binding to the RUP3 receptor directly correlates to its binding affinity.

The labelled compounds of the present invention bind to the RUP3 receptor. In one embodiment the labelled compound has an $IC_{50}$ less than about 500 μM, in another embodiment the labelled compound has an $IC_{50}$ less than about 100 μM, in yet another embodiment the labelled compound has an $IC_{50}$ less than about 10 μM, in yet another embodiment the labelled compound has an $IC_{50}$ less than about 1 μM, and in still yet another embodiment the labelled inhibitor has an $IC_{50}$ less than about 0.1 μM.

Other uses of the disclosed receptors and methods will become apparent to those in the art based upon, inter alia, a review of this patent document.

This application claims priority benefit of U.S. Provisional Application No. 60/440,394, filed Jan. 14, 2003; U.S. Provisional Patent Application No. 60/449,829, filed Feb. 24, 2003, U.S. Provisional Patent Application No. 60/453,390, filed Mar. 6, 2003, and U.S. Non-Provisional Patent Application No. 60/470,875, filed May 14, 2003; wherein each are hereby incorporated by reference in their entirety.

The following examples are given to illustrate the invention and are not intended to be inclusive in any manner:

EXAMPLES

The compounds of the present invention and their syntheses are further illustrated by the following examples. The examples are provided to further define the invention without, however, limiting the invention to the specifics of these examples.

Example 1

96-well Cyclic AMP membrane assay for RUP3
Materials:
1) Adenlyl cyclase Activation Flashplate Assay kit from Perkin Elmer—96 wells (SMP004B) and $^{125}I$ tracer (NEX130) which comes with the kit. Keep in refrigerator, in a box, and do not expose the Flashplates to light.
2) Phosphocreatine—Sigma P-7936
3) Creatine Phosphokinase—Sigma C-3755
4) GTP—Sigma G-8877
5) ATP—Sigma A-2383
6) IBMX—Sigma I-7018
7) Hepes—1M solution in distilled water—Gibco #15630080
8) MgC12—Sigma M-1028—1M Solution
9) NaC1—Sigma—S6546—5M Solution
10) Bradford Protein Assay Kit—Biorad #5000001
11) Proclin 300—Sigma #4-8126
Binding Buffer—filter through 45-micron Nalgene filter and keep in refrigerator. All buffers and membranes should be kept cold (in ice bucket) while performing assay.
20 mM Hepes, pH7.4
1 mM MgCl2
100 mM NaCl
2× Regeneration Buffer (make in binding buffer):
20 mM Phosphocreatine (1.02 gm/200 ml binding buffer)
20 units Creatine phosphokinase (4 mg/200 ml)
20 uM GTP (make up 10.46 mg/ml in binding buffer and add 200 ul/200 ml)
0.2 mM ATP (22.04 mg/200 ml)
100 mM IBMX (44.4 mg IBMX dissolved in 1 ml 100% DMSO first and then add the entire amount to 200 ml of buffer).
Regeneration buffer can be aliquoted into 40-45 ml portions (in 50 ml sterile tubes) and kept frozen for up to 2 months. Simply put the tube in a beaker with room temperature water to thaw out the regeneration buffer on the day of the assay.

A. Assay procedure
1) Pipet 50 ul regeneration buffer in all 96 wells using Matrix 1250 8-channel pipettor.
2) Pipet 5 ul DMSO in columns 1 and columns 11 and 12.
3) Pipet 50 ul cAMP standards in columns 11 and 12 in this format: 50 pmole/well for row A, 25 pmole/well for row B, 12.5 μmol/well for row C, 5 picomol/well for row D, 2.5 pmole/well for row E, 1.25 pmole/well for row F, 0.5 pmole/well for row G, and 0 pmole/well (buffer only) for row H.
4) Pipet 5 ul compounds from each well of a compound dilution plate, for $IC_{50}$s, using the following dilution scheme:
   Well H: 400 uM compound (final concentration of compound in reaction mix =5/100×400 uM=20 uM
   Well G: 1:10 dilution of Well H (i.e. 5 ul compound from well H+45 ul 100% DMSO) (final concentration=2 uM)
   Well F: 1:10 dilution of well G (final concentration=0.2 uM)
   Well E: 1:10 dilution of well F (final concentration=0.02 uM)
   Well D: 1:10 dilution of well E (final concentration=0.002 uM)
   Well C: 1:10 dilution of well D (final concentration=0.0002 uM
   Well B: 1:10 dilution of well C (final concentration=0.00002 uM)
   Well A: 1:10 dilution of well B (final concentration=0.000002 uM)
   $IC_{50}$s or $EC_{50}$s are done in triplicate. One Flashplate can therefore be set up to handle 3 compounds. (i.e., columns 2, 3, and 4 are for compound #1, columns 5, 6, and 7 are for compound #2, and columns 8, 9, and 10 are for compound #3.)
5) Add 50 ul of RUP3 membranes to all wells in Columns 2 to 10. (Prior to the start of the assay, the frozen membrane pellets for both RUP3 and CMV (cells transfected with an expression plasmid containing no RUP3 sequences), are suspended in binding buffer, usually 1 ml binding buffer for 1 plate of membranes. The membranes are kept in ice all the time, and a polytron (Brinkmann polytron, model # PT-3100) is used (setting 6-7, for 15-20 seconds) to obtain a homogeneous membrane suspension.) Protein concentration is determined by Bradford protein assay kit using instructions given in the kit, using the standard supplied with the kit as a reference. The protein concentration of the membranes is adjusted with binding buffer, so that 50 ul membranes=15 ug protein (i.e. 0.3 mg/ml protein).
6) In column 1, Wells A, B, C, and D, add 50 ul RUP3 membranes. To wells E, F, G, and H, add 50 ul CMV membranes, (CMV membranes being of the same protein concentration as the RUP3 membranes).
7) Incubate 1 hour at room temperature with agitation on a rotating platform shaker. Cover with foil while shaking.
8) After 1 hour, add (to all 96 wells), 100 ul of the $^{12}I$ tracer in detection buffer supplied with the Flashplate kit plus proclin, made up in the following manner:
Pipet per 10 ml per Flashplate: 100 ml of detection buffer+ 1 ml $^{125}I$+0.2 ml of Proclin ( the proclin helps to stop the production of cAMP). Make a smaller quantity of detection buffer mix if you have fewer plates.
9) Shake the plates on a rotating platform shaker for 2 hours, covering the plates with lead sheeting.

10) Seal the plates with the plastic film sealers provided with the Flashplate kit.
11) Count the plates using a TRILUX 1450 Microbeta Counter. See the door of the counter to determine which counting protocol to use.
12) Data is analyzed on the Arena Database according to the RUP3 non-fusion, $IC_{50}$ $EC_{50}$ for 96-well cAMP membrane assay, and the compound numbers and the concentrations of compounds must be entered by the user.

B. Membrane Cyclase Criteria
   1) Signal to Noise:
      An acceptable signal-to-noise ratio for RUP3 can vary from 4 to 6. The raw cpms are approximately 1800 to 2500 for RUP3 and 3500-4500 for CMV. The cpm (or ultimately pmoles of cAMP/well) cannot be outside the standard curve, and should not approach well A of the standard curve (50 pmole/well) and well H (no cAMP). Generally, the pmoles of cAMP produced by RUP3 receptor are around 11 to 13 pmole/well (for 15 ug/well protein), and for CMV are between 2 to 3 pmole/well (for 15 ug protein/well).
   2) Standard curve:
      The slope should be linear and the error bars for duplicates should be very small. The receptor and CMV controls cannot be off scale of the standard curve, as described above. If the receptor controls are off the high end of the standard curve, i.e. 50 pmole/well or higher, one must repeat the experiment using less protein. However, such a case has not been observed with transiently transfected RUP3 membranes (10 ug DNA/15 cm plate, using 60 ul Lipofectamine, and preparing membranes after 24 hour of transfection.)
   3) The $IC_{50}$ or $EC_{50}$ curve should be at 100% (+ or −20%) of control RUP3 membranes at the top, and should go down to 0 (or up to 20%) at the bottom. The standard error of the triplicate determinations should be + or −10%.

C. Stimulation of cAMP in HIT-T15 cells
   HIT-T15 (ATCC CRL#1777) is an immortalized hamster insulin-producing cell line. These cells express RUP3 and therefore can be used to assess the ability of RUP3 ligands to stimulate or inhibit cAMP accumulation via its endogenously expressed receptor. In this assay, cells are grown to 80% confluence and then distributed into a 96-well Flashplate (50,000 cells/well) for detection of cAMP via a "cAMP Flashplate Assay" (NEN, Cat # SMP004). Briefly, cells are placed into anti-cAMP antibody-coated wells that contain either vehicle, the test ligand(s) at a concentration of interest, or 1 uM forskolin. The latter is a direct activator of adenylyl cyclase and serves as a positive control for stimulation of cAMP in HIT-T15 cells. All conditions are tested in triplicate. After a 1 hour incubation to allow for stimulation of cAMP, a Detection Mix containing $^{125}$I-cAMP is added to each well and the plate is allowed to incubate for another 1 hour. The wells are then aspirated to remove unbound $^{125}$I-cAMP. Bound $^{125}$I-cAMP is detected using a Wallac Microbeta Counter. The amount of cAMP in each sample is determined by comparison to a standard curve, obtained by placing known concentrations of cAMP in some wells on the plate.

D. Stimulation of insulin secretion in HIT-T15 cells
   It is known that stimulation of cAMP in HIT-T15 cells causes an increase in insulin secretion when the glucose concentration in the culture media is changed from 3 mM to 15 mM. Thus, RUP3 ligands can also be tested for their ability to stimulate glucose-dependent insulin secretion (GSIS) in HIT-T15 cells. In this assay, 30,000 cells/well in a 12-well plate are incubated in culture media containing 3 mM glucose and no serum for 2 hours. The media is then changed; wells receive media containing either 3 mM or 15 mM glucose, and in both cases the media contains either vehicle (DMSO) or RUP3 ligand at a concentration of interest. Some wells receive media containing 1 uM forskolin as a positive control. All conditions are tested in triplicate. Cells are incubated for 30 minutes, and the amount of insulin secreted into the media is determined by ELISA, using a kit from either Peninsula Laboratories (Cat #ELIS-7536) or Crystal Chem Inc, (Cat #90060).

E. Stimulation of insulin secretion in isolated rat islets
   As with HIT-T15 cells, it is known that stimulation of cAMP in isolated rat islets causes an increase in insulin secretion when the glucose concentration in the culture media is changed from 60 mg/dl to 300 mg/dl. RUP3 is an endogenously expressed GPCR in the insulin-producing cells of rat islets. Thus, RUP3 ligands can also be tested for their ability to stimulate GSIS in rat islet cultures. This assay is performed as follows:

A. Select 75-150 islet equivalents (IEQ) for each assay condition using a dissecting microscope. Incubate overnight in low-glucose culture medium. (Optional.)
   B. Divide the islets evenly into triplicate samples of 25-40 islet equivalents per sample. Transfer to 40 um mesh sterile cell strainers in wells of a 6-well plate with 5 ml of low (60 mg/dl) glucose Krebs-Ringers Buffer (KRB) assay medium.
   C. Incubate 30 minutes (1 hour if overnight step skipped) at 37° C. and 5% $CO_2$. Save the supernatants if a positive control for the RIA is desired.
   D. Move strainers with islets to new wells with 5 ml/well low glucose KRB. This is the second pre-incubation and serves to remove residual or carryover insulin from the culture medium. Incubate 30 minutes.
   E. Move strainers to next wells (Low 1) with 4 or 5 ml low glucose KRB. Incubate @37° C. for 30 minutes. Collect supernatants into low-binding polypropylene tubes pre-labelled for identification and keep cold.
   F. Move strainers to high glucose wells (300 mg/dl, which is equivalent to 16.7 mM). Incubate and collect supernatants as before. Rinse islets in their strainers in low-glucose to remove residual insulin. If the rinse if to be collected for analysis, use one rinse well for each condition (i.e. set of triplicates.)
   G. Move strainers to final wells with low-glucose assay medium (Low 2). Incubate and collect supernatants as before.
   H. Keeping cold, centrifuge supernatants at 1800 rpm for 5 minutes @ 4-8° C. to remove small islets/islet pieces that escape the 40 mm mesh. Remove all but lower 0.5-1 ml and distribute in duplicate to pre-labelled low-binding tubes. Freeze and store at <−20° C. until insulin concentrations can be determined.
   I. Insulin determinations are done as above, or by Linco Labs as a custom service, using their rat insulin RIA (Cat. # RI-13K).

Example 2

A. RT-PCR analysis of RUP3 expression in human tissues (FIG. 1A)

RT-PCR was applied to determine the tissue distribution of RUP3. Oligonucleotides used for PCR had the following sequences:

```
ZC47: 5'-CATTGCCGGGCTGTGGTTAGTGTC-3'
(forward primer), (SEQ ID NO: 3);

ZC48: 5'-GGCATAGATGAGTGGGTTGAGCAG-3'
(reverse primer), (SEQ ID NO: 4);
``` and the human multiple tissue cDNA panels (MTC, Clontech) were used as templates (1 ng cDNA per PCR amplification). Twenty-two (22) human tissues were analyzed. PCR was performed using Platinum PCR SuperMix (Life Technologies, Inc.; manufacture instructions were followed) in a 50 µl reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 466 base-pair DNA fragment representing RUP3 was specifically amplified from cDNA of pancreas origin. Low expression was also evident in subregions of brain.

B. cDNA Dot-Blot analysis of RUP3 expression in human tissues (FIG. 1B).

Results from RT-PCR analysis were further confirmed in cDNA dot-blot analysis. In this assay, a dot-blot membrane containing cDNA from 50 human tissues (Clontech) was hybridized with a $^{32}$P-radiolabelled DNA probe having sequences derived from human RUP3. Hybridization signals were seen in pancreas and fetal liver, suggesting these tissues express RUP3. No significant expression was detected in other tissues analyzed.

C. Analysis of RUP3 by RT-PCR with isolated human pancreatic islets of Langerhans (FIG. 1C).

Further analysis of RUP3 by RT-PCR with isolated human pancreatic islets of Langerhans showed robust expression of RUP3 in islet cells but not in control samples.

D. Analysis of RUP3 expression with cDNAs of rat origin by RT-PCR (FIG. 1D).

RUP3 expression was further analyzed with cDNAs of rat origin by RT-PCR technique. Tissue cDNAs used for this assay were obtained from Clontech except those for hypothalamus and islets, which were prepared in house. Concentrations of each cDNA sample were normalized via a control RT-PCR analysis of the house-keeping gene GAPDH before assaying for RUP3 expression. Oligonucleotides used for PCR had the following sequences:

```
rat RUP3 ("rRUP3") forward:
                              (SEQ ID NO: 5)
5'-CATGGGCCCTGCACCTTCTTTG-3';

rRUP3 reverse:
                              (SEQ ID NO: 6)
5'-GCTCCGGATGGCTGATGATAGTGA-3'.
```

PCR was performed using Platinum PCR SuperMix (Life Technologies, Inc.; manufacture instructions were followed) in a 50 ul reaction by the following sequences: step 1, 95° C. for 4 min; step 2, 95° C. for 1 min; step 3, 60° C. for 30 sec; step 4, 72° C. for 1 min; and step 5, 72° C. for 7 min. Steps 2 through 4 were repeated 35 times.

The resulting PCR reactions (15 µl) were loaded on a 1.5% agarose gel to analyze the RT-PCR products, and a specific 547 base-pair DNA fragment representing rat RUP3 was specifically amplified from cDNA of pancreas origin, revealing a similar expression profile with human. Of particular note, robust expression was seen in isolated islets and hypothalamus.

Example 3

Figure 2:
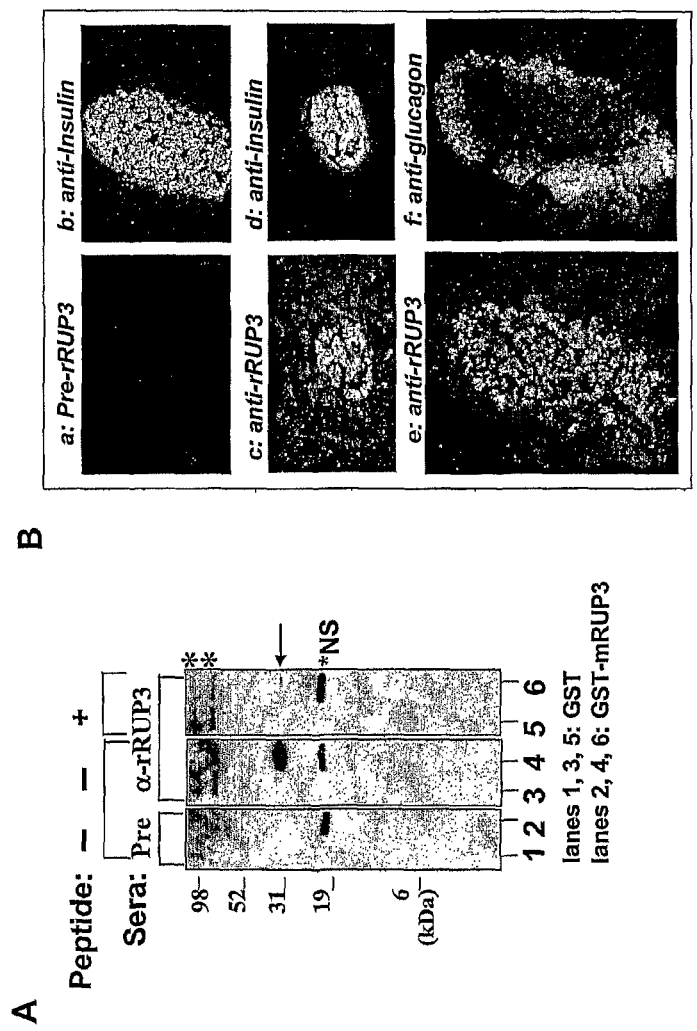
FIG. 2A shows a polyclonal anti-RUP3 antibody prepared in Rabbits.
FIG. 2B shows the expression of RUP3 in insulin-producing p cells of pancreatic islets.

RUP3 protein expression is restricted to β cell lineage of pancreatic islets (FIG. 2)

A. A polyclonal anti-RUP3 antibody was prepared in rabbits (FIG. 2A).

Rabbits were immunized with an antigenic peptide with sequence derived from rat RUP3 ("rRUP3"). The peptide sequence was RGPERTRESAYHIVTISHPELDG and shared 100% identity with mouse RUP3 in the corresponding region. A cysteine residue was incorporated at the N-terminal end of this antigenic peptide to facilitate KLH crosslinking before injecting into rabbits. The resulting antisera ("anti-rRUP3") and the corresponding preimmune sera ("pre-rRUP3") were tested for immune reactivity to mouse RUP3 in immunobloting assays (lanes 1 thought 4). In this assay, the GST-RUP3 fusion protein was readily recognized by the anti-rRUP3 antisera (lane 4), but not by the preimmune sera (lane 2). The immunoreactive signal could be efficiently eliminated when the immunoblotting assay was performed in the presence of excess antigenic peptide (lane 6).

B. RUP3 expression in insulin-producing β cells of pancreatic islets (FIG. 2B).

Rat pancreas was perfused with 4% paraformaldehyde (PFA) in PBS and embedded in OCT embedding medium. Ten micron sections were prepared, fixed on glass slides, and immunostained with either pre-rRUP3 (FIG. 2B, panel a) or with anti-rRUP3 antisera (FIG. 2B, panels c and e) followed by secondary staining with donkey anti-rabbit IgG conjugated to the fluorochrome Cy-3. Each section was also co-immunostained with a monoclonal anti-insulin antibody (Santa Cruz, FIG. 2B, panels b and d) in primary staining followed by a secondary staining with donkey anti-mouse IgG conjugated with FITC, or with a goat anti-glucagon antibody (Santa Cruz, FIG. 2B, panel f) and donkey anti-goat IgG coupled to FITC. Immunofluorescent signals were examined under a fluorescent microscope. RUP3 was found expressed in insulin producing cells (panels c and d), but not in glucagons producing cells (panels e and f). These data demonstrated that RUP3 is expressed in β cells but not in α cells of the rat pancreatic islets. Analogous results were obtained when mouse pancreatic sections were investigated for RUP3 expression.

Example 4

Figure 3:
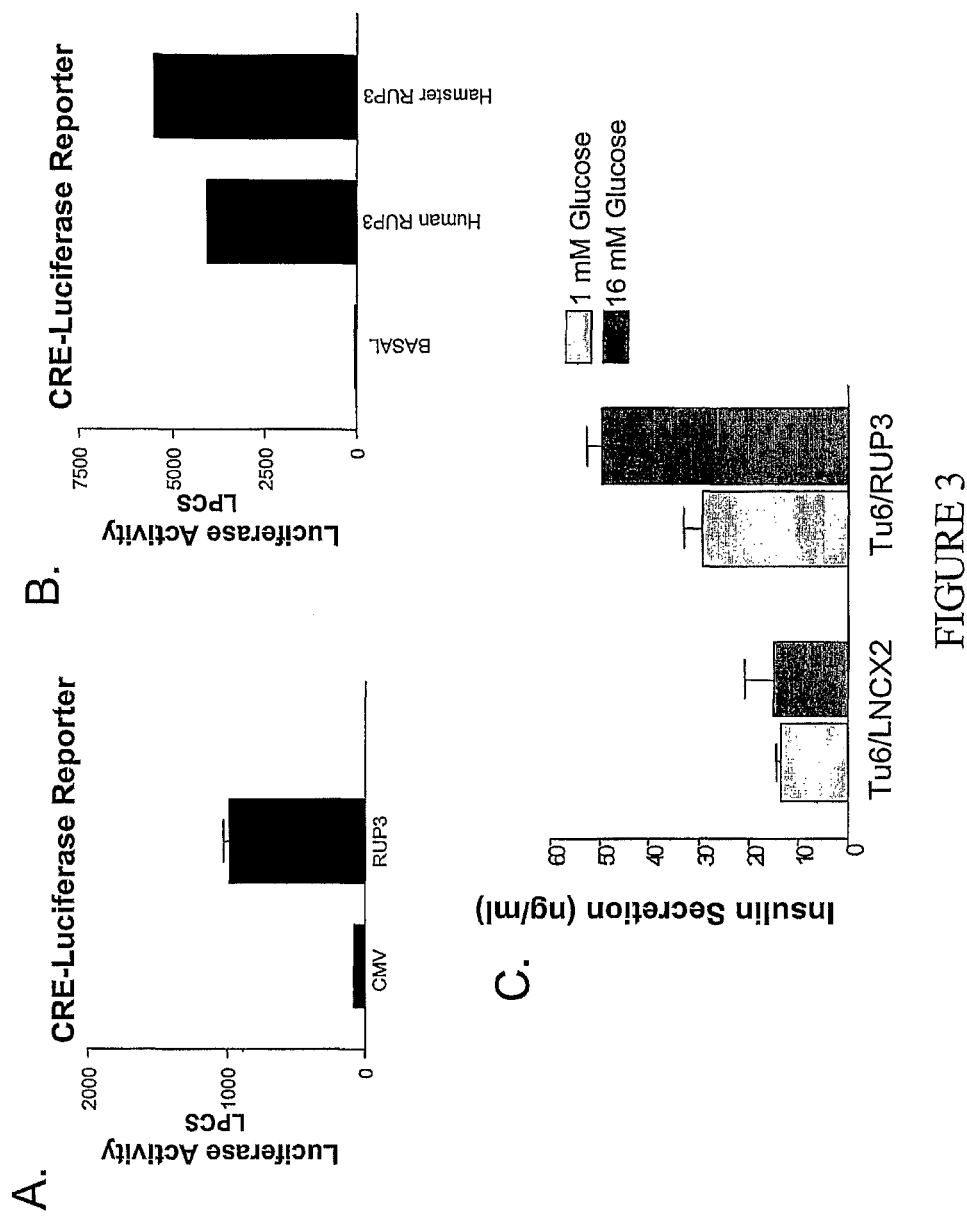
FIG. 3 shows functional activities of RUP3 In vitro.
Figure 4A:
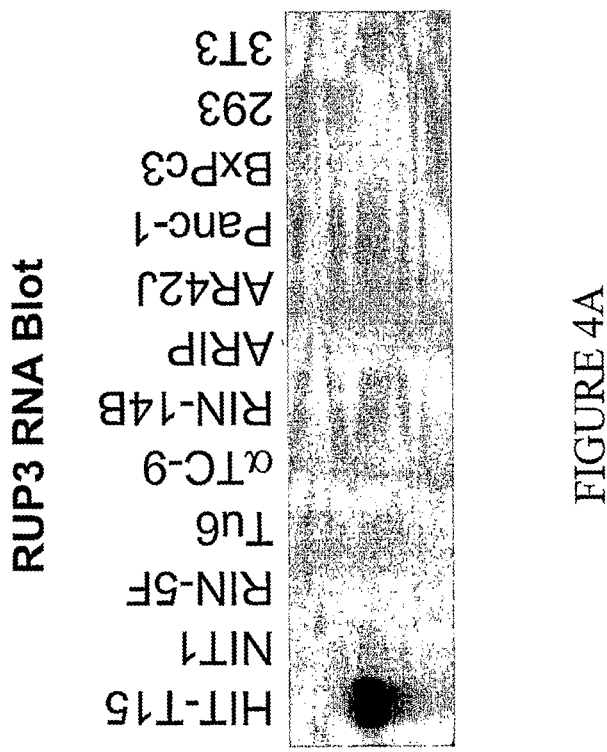
FIG. 4A shows a RUP3 RNA blot.
Figure 4B:
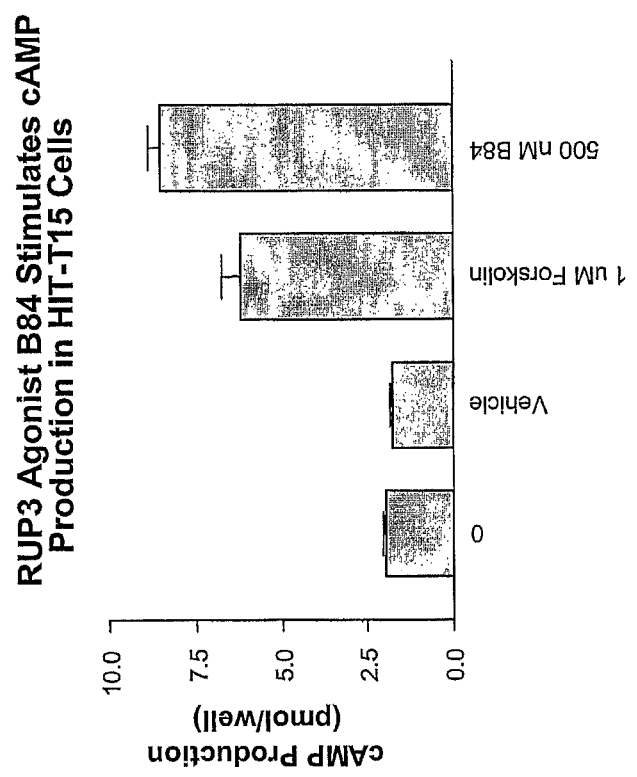
FIG. 4B shows RUP3 agonist, Compound B84, stimulates cAMP production in HIT cells, at a level comparable to that seen with the adenyl cyclase activator forskolin.
Figure 4C:
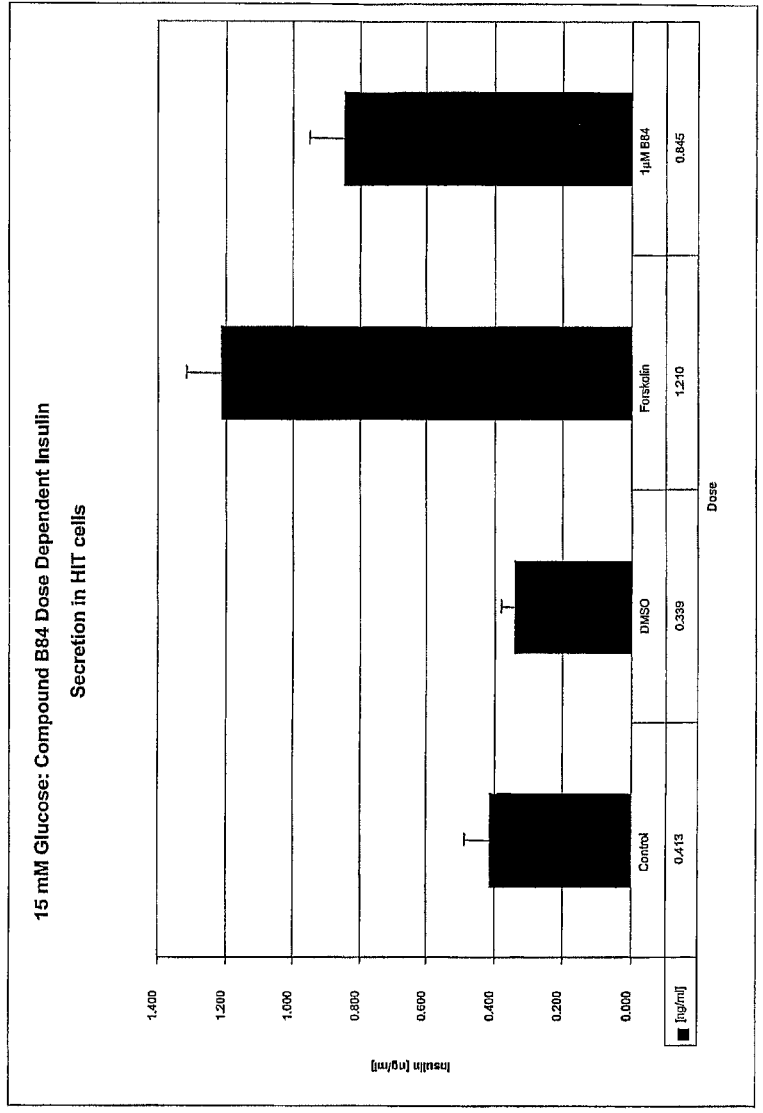
FIG. 4C shows RUP3 agonist, Compound B84, stimulates insulin secretion in HIT cells exposed to 15 mM glucose, at a level comparable to that seen with the adenylcyclase activator forskolin.
Figure 4D:
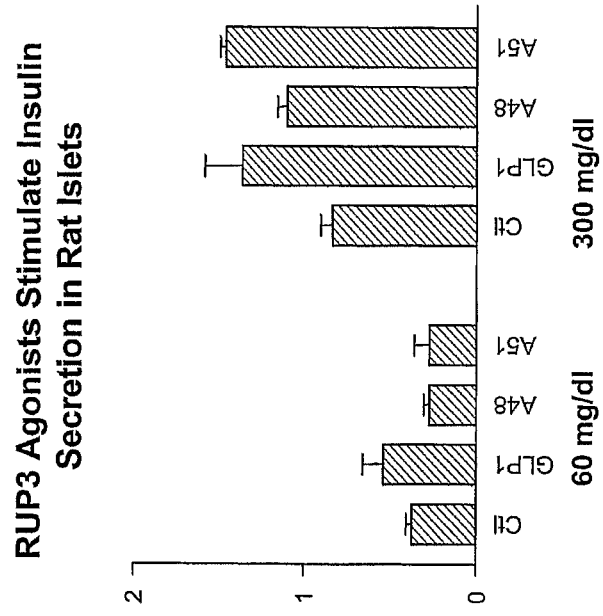
FIG. 4D shows two RUP3 compounds, Compounds A48 and A51 (at 10 uM concentration), and the enhanced glucose-dependent insulin release compared to control.

Functional Activities of RUP3 In Vitro (FIG. 3)

It was established that RUP3 stimulates the production of cAMP by cotransfection of 293 cells with: (1) a CRE-Luciferase reporter, wherein the ability to stimulate the production of firefly luciferase depends on increased cAMP in cells, and (2) an expression plasmid encoding the human form of RUP3 (FIG. 3A). Note that cells co-transfected with an expression plasmid containing no RUP3 sequences ("CMV" in FIG. 3A) produce very little luciferase activity, whereas cells transfected with an expression plasmid encoding RUP3 ("RUP3" in FIG. 3A) have at least a 10-fold increase in luciferase activity. This indicates that RUP3 stimulates the production of cAMP when introduced into 293 cells. This property of RUP3 is conserved across species, because hamster RUP3 stimulates luciferase activity when introduced into 293 cells in a manner analogous to that described for human RUP3 (FIG. 3B).

It is established that, when cAMP is increased in insulin-producing cells of the pancreas, these cells exhibit an enhanced ability to secrete insulin when glucose concentrations rise. To test whether RUP3 might impart enhanced glucose-dependent insulin release, retrovirus containing human RUP3 was used to generate Tu6 cells that express high levels of RUP3. Tu6 cells produce insulin, but do not express appreciable levels of RUP3 and do not normally exhibit an increase in insulin release when increased glucose is present in the culture media. As shown in FIG. 3C, Tu6 cells transduced with a control virus that contains no receptor are still able to produce insulin, but do not show an increase in insulin secretion when the concentration of glucose in the culture media is shifted from 1 mM to 16 mM. By contrast, Tu6 cells transduced with RUP3-containing retrovirus display significant glucose-dependent insulin secretion (FIG. 3C).

Example 5

Functional Activities of RUP3 Agonists In Vitro (FIG. 4)

To demonstrate that RUP3 agonists stimulate endogenously expressed RUP3 in insulin-producing cells, two in vitro models can be used. In the first of these, RUP3 agonists are used to stimulate HIT-T15 cells, which express RUP3 at significant levels, as indicated in the Northern blot shown in FIG. 4A. Moreover, these cells are known to exhibit enhanced glucose-dependent insulin release when intracellular cAMP concentrations are elevated. In the example shown in FIG. 4B, the RUP3 agonist Compound B84 stimulates cAMP production in HIT cells, at a level comparable to that seen with the adenyl cyclase activator forskolin. This indicates that Compound B84 is a very robust stimulator of cAMP in HIT-T15 cells. In the example shown in FIG. 4C, Compound B84 also stimulates insulin secretion in HIT cells exposed to 15 mM glucose, once again at a level comparable to that seen with the adenyl cyclase activator forskolin. This indicates that Compound B84 is a very robust potentiator of insulin secretion in HIT-T15 cells.

Isolated rat islets are the other in vitro model used to demonstrate the efficacy of RUP3 agonists. In this model, agents that induce cAMP are not expected to stimulate insulin secretion when glucose concentrations are low (e.g. 60 mg/di). However, when glucose concentrations are increased (e.g. to 300 mg/di), these agents are expected to enhance insulin secretion to levels above those seen with glucose alone. In the example shown in FIG. 4D, both RUP3 agonists (Compounds 48 and 51 at 10 uM concentration) enhanced glucose-dependent insulin release. Moreover, the level of enhancement was comparable to that seen with 25 nM GLP-1, a gut hormone known to act on islets in this manner.

Example 6

In Vivo effects of RUP3 agonists on glucose homeostasis in mice

Figure 5A:
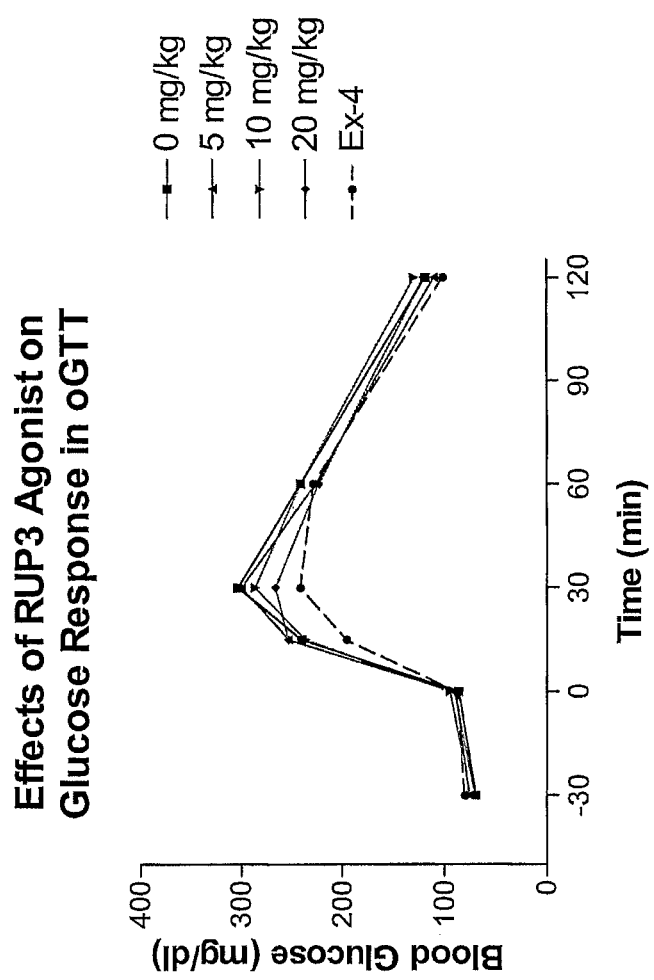
FIG. 5A shows the In vivo effects of a RUP3 agonist (Compound B70) on glucose homeostasis in mice and specifically the effect by a RUP3 agonist in a dose-dependent manner on the lowering of blood glucose after glucose challenge.

A. Oral Glucose tolerance test (oGTT) (FIG. 5A).

Male C57b1/6N mice at age of 8 weeks were fasted for 18 hours and randomly grouped (n=11) to receive a RUP3 agonist (Compound B70) at indicated doses, or with control extendin-4 (ex-4, 1 μg/kg), a GLP-1 peptide analog known to stimulate glucose-dependent insulin secretion. Compound B70 was delivered orally via a gavage needle (p.o. volume at 100 μl). Control Ex-4 was delivered intraperitoneally. Thirty minutes after administration of test compound and control ex-4, mice were administered orally with dextrose at 5 g/kg dose. Levels of blood glucose were determined at the indicated time points using Glucometer Elite XL (Bayer). FIG. 5A shows the mean glucose concentration averaged from eleven animals in each treatment group. These results demonstrated that the RUP3 agonist, Compound B70, lowered blood glucose in a dose-dependent manner in mice after challenged with glucose.

Figure 5B:
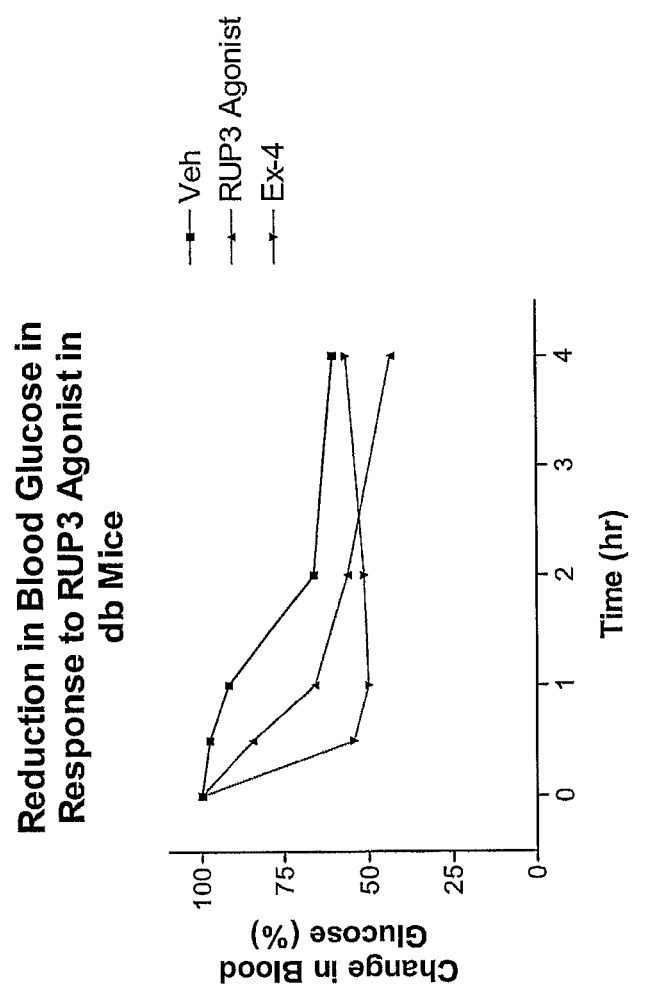
FIG. 5B shows the acute response of db mice to a RUP3 agonist and Ex-4.

B. Acute response of db mice to RUP3 agonist (FIG. 5B).

Male db mice (C57BL/KsOlahsd-Leprdb, diabetic, Harlan) at age of 10 weeks were randomly grouped (n=6) to receive vehicle (oral gavage), Compound B70 (60 mg/kg, oral gavage), or Ex-4 (1 μg/kg, intraperitoneally). After compound administration, food was removed and blood glucose levels were determined at indicated times as shown in FIG. 5B. Reduction in blood glucose at each time point was expressed as percentage of original glucose levels, averaged from six animals for each group. These animals had blood glucose levels (fed state) of 300-400 mg/dl, significantly higher than non-diabetic wild type animals. Treatment with Compound B70 or Ex-4 significantly reduced glucose levels compared to vehicle control as shown in FIG. 5B. These data demonstrated that the RUP3 agonist had efficacy in improving glucose homeostasis in diabetic animals.

Example 7

CRE-Luciferase Assay in 293 Cells 293 cells were plated in 96-well tissue culture plates at a concentration of 20,000 cells per well. The following day, the cells are transfected with a mixture of pCRE-Luc (Stratagene, Cat. #219076), the indicated expression plasmid, and pEGFP-N1 (Clontech, Cat. #6085-1) at a ratio of 5:1:0.25 using Lipofectamine Reagent (Invitrogen, Cat. #18324-020) according to the manufacturer's directions. pEGFP-N1 encodes a "green fluorescent protein" and was used as a control to determine that most cells were successfully transfected. After 24-48 hr, the cells were lysed in situ with 100 ul/well reconstituted Luclite buffer (Luclite Reporter Gene Assay Kit, Packard, Cat. #6016911), according to the manufacturer's directions. After a 10 minute incubation in the dark, luminescence was measured using a TRILUX 1450 Microbeta Counter (Wallac).

Example 8

Generation of Tu6/RUP3 Stable Lines

To produce Tu6 cells that express RUP3 at high levels, a retrovirus bearing an expression cassette for RUP3 was generated. Briefly, RUP3 coding sequence was cloned into the retroviral vector pLNCX2 (Clontech, Cat #6102-1). The amphotropic packaging cell line PT-67 (Clontech, K1060-D) was then transfected with either the parental vector pLNCX2 or pLNCX2/RUP3 using Lipofectamine and stable lines were established using guidelines provided by the PT-67 vendor. Retrovirus-containing supernatant was obtained by collecting media from the resultant stables according to the manufacturer's directions. Tu6 cells, in a 10 cm dish, were then infected with retrovirus by incubating in a solution of 1 ml viral supernatant/9 ml culture media containing 40 ug/ml polybrene for 24 hours. The medium was then changed to culture media containing 300 ug/ml G418. G418-resistant clones were ultimately created by virtue of the neomycin-resistance gene cassette present in the pLNCX2 vector, thus indicating the successful integration of retrovirus into the Tu6 genome. The expression of RUP3 in the Tu6/RUP3 G418-resistant colonies was confirmed by Northern blot.

Example 9

Insulin secretion, Tu6 Stables

To measure insulin secretion from rodent insulin-producing cell lines, cells were first cultured overnight in serum-free, glucose-deficient media. The following morning, the cells were then placed in the same media supplemented with either 1 mM or 16 mM glucose. After an incubation of 4 hours, the media was collected and analyzed for insulin content using a Rat Insulin Enzyme-Immunoassay (EIA) System (Amersham Pharmacia Biotech, Cat. # RPN 2567). Typically, the assay was performed using multiple dilutions of sample media in order to ensure that the sample measurements fell within the boundaries of the standard curve (generated using known amounts of insulin), as recommended by the manufacturer.

Example 10

RUP3 RNA Blot

To determine the expression of RUP3 in insulin-producing or non islet cells, the following cell lines were obtained and cultured according to guidelines provided by American Type Culture Collection or the indicated provider.

| Cell Line | Provider | Cat. # |
|---|---|---|
| HIT-T15 | American Type Culture Collection | CRL-1777 |
| NIT-1 | American Type Culture Collection | CRL-2055 |
| RIN-5F | American Type Culture Collection | CRL-2058 |
| Tu-6 | Ole Madsen, Hagedorn Res. Lab. | N/A |
| αTC-9 | American Type Culture Collection | CRL-2350 |
| RIN-14B | American Type Culture Collection | CRL-2059 |
| ARIP | American Type Culture Collection | CRL-1674 |
| AR42J | American Type Culture Collection | CRL-1492 |
| Panc-1 | American Type Culture Collection | CRL-1469 |
| BxPc-3 | American Type Culture Collection | CRL-1687 |
| 293 | Q-Biogene | AES0503 |
| NIH-3T3 | American Type Culture Collection | CRL-1658 |

Total RNA was isolated from each of these cell lines using TRIZOL (Invitrogen, Cat #15596-018), subjected to electrophoresis through an agarose/formaldehyde gel and an RNA blot was prepared using standard molecular biological techniques. A radiolabelled RUP3 probe, corresponding to the full-length coding sequence of RUP3, was prepared using a Prime-It II Random Primer Labeling Kit (Stratagene, Cat #300385). The denatured probe, 10 ml ExpressHyb solution (Clontech, Cat #8015-2) and the RNA blot were incubated in a hybridization oven, washed and exposed to film using standard molecular biology practices.

Example 11

Receptor Binding Assay

In addition to the methods described herein, another means for evaluating a test compound is by determining binding affinities to the RUP3 receptor. This type of assay generally requires a radiolabelled ligand to the RUP3 receptor. Absent the use of known ligands for the RUP3 receptor and radiolabels thereof, compounds of Formula (Ia) can be labelled with a radioisotope and used in an assay for evaluating the affinity of a test compound to the RUP3 receptor.

A radiolabelled RUP3 compound as described herein can be used in a screening assay to identify/evaluate compounds. In general terms, a newly synthesized or identified compound (I.e., test compound) can be evaluated for its ability to reduce binding of the "radiolabelled compound of Formula (Ia)" to the RUP3 receptor. Accordingly, the ability to compete with the "radio-labelled compound of Formula (Ia)" or Radiolabelled RUP3 Ligand for the binding to the RUP3 receptor directly correlates to its binding affinity of the test compound to the RUP3 receptor.

Assay Protocol for Determining Receptor Binding for RUP3:

A. RUP3 Receptor Preparation 293 cells (human kidney, ATCC), transiently transfected with 10 ug human RUP3 receptor and 60 ul Lipofectamine (per 15-cm dish), were grown in the dish for 24 hours (75% confluency) with a media change and removed with 10 ml/dish of Hepes-EDTA buffer (20 mM Hepes+10 mM EDTA, pH 7.4). The cells were then centrifuged in a Beckman Coulter centrifuge for 20 minutes, 17,000 rpm (JA-25.50 rotor). Subsequently, the pellet was resuspended in 20 mM Hepes+1 mM EDTA, pH 7.4 and homogenized with a 50-ml Dounce homogenizer and again centrifuged. After removing the supernatant, the pellets were stored at −80° C., until used in binding assay. When used in the assay, membranes were thawed on ice for 20 minutes and then 10 mL of incubation buffer (20 mM Hepes, 1 mM $MgCl_2$, 100 mM NaCl, pH 7.4) added. The membranes were then vortexed to resuspend the crude membrane pellet and homogenized with a Brinkmann PT-3100 Polytron homogenizer for 15 seconds at setting 6. The concentration of membrane protein was determined using the BRL Bradford protein assay.

B. Binding Assay

For total binding, a total volume of 50 ul of appropriately diluted membranes (diluted in assay buffer containing 50 mM Tris HCl (pH 7.4), 10 mM $MgCl_2$, and 1 mM EDTA; 5-50 ug protein) is added to 96-well polyproylene microtiter plates followed by addition of 100 ul of assay buffer and 50 ul of Radiolabelled RUP3 Ligand. For nonspecific binding, 50 ul of assay buffer is added instead of 100 ul and an additional 50 ul of 10 uM cold RUP3 is added before 50 ul of Radiolabelled RUP3 Ligand is added. Plates are then incubated at room temperature for 60-120 minutes. The binding reaction is terminated by filtering assay plates through a Microplate Devices GF/C Unifilter filtration plate with a Brandell 96-well plate harvestor followed by washing with cold 50 mM Tris HCl, pH 7.4 containing 0.9% NaCl. Then, the bottom of the filtration plate are sealed, 50 ul of Optiphase Supermix is added to each well, the top of the plates are sealed, and plates are counted in a Trilux MicroBeta scintillation counter. For compound competition studies, instead of adding 100 ul of assay buffer, 100 ul of appropriately diluted test compound is added to appropriate wells followed by addition of 50 ul of Radiolabelled RUP3 Ligand.

C. Calculations

The test compounds are initially assayed at 1 and 0.1 µM and then at a range of concentrations chosen such that the middle dose would cause about 50% inhibition of a Radio-RUP3 Ligand binding (i.e., $IC_{50}$). Specific binding in the absence of test compound ($B_O$) is the difference of total binding ($B_T$) minus non-specific binding (NSB) and similarly specific binding (in the presence of test compound) (B) is the difference of displacement binding ($B_D$) minus non-specific binding (NSB). $IC_{50}$ is determined from an inhibition response curve, logit-log plot of % BM° vs concentration of test compound.

K, is calculated by the Cheng and Prustoff transformation:

$$K_i = IC_{50}/(1+[L]/K_D)$$

where [L] is the concentration of a Radio-RUP3 Ligand used in the assay and $K_D$ is the dissociation constant of a Radio-RUP3 Ligand determined independently under the same binding conditions.

Chemistry

Syntheses of Compounds of The Present Invention

Example 12

Figure 6:
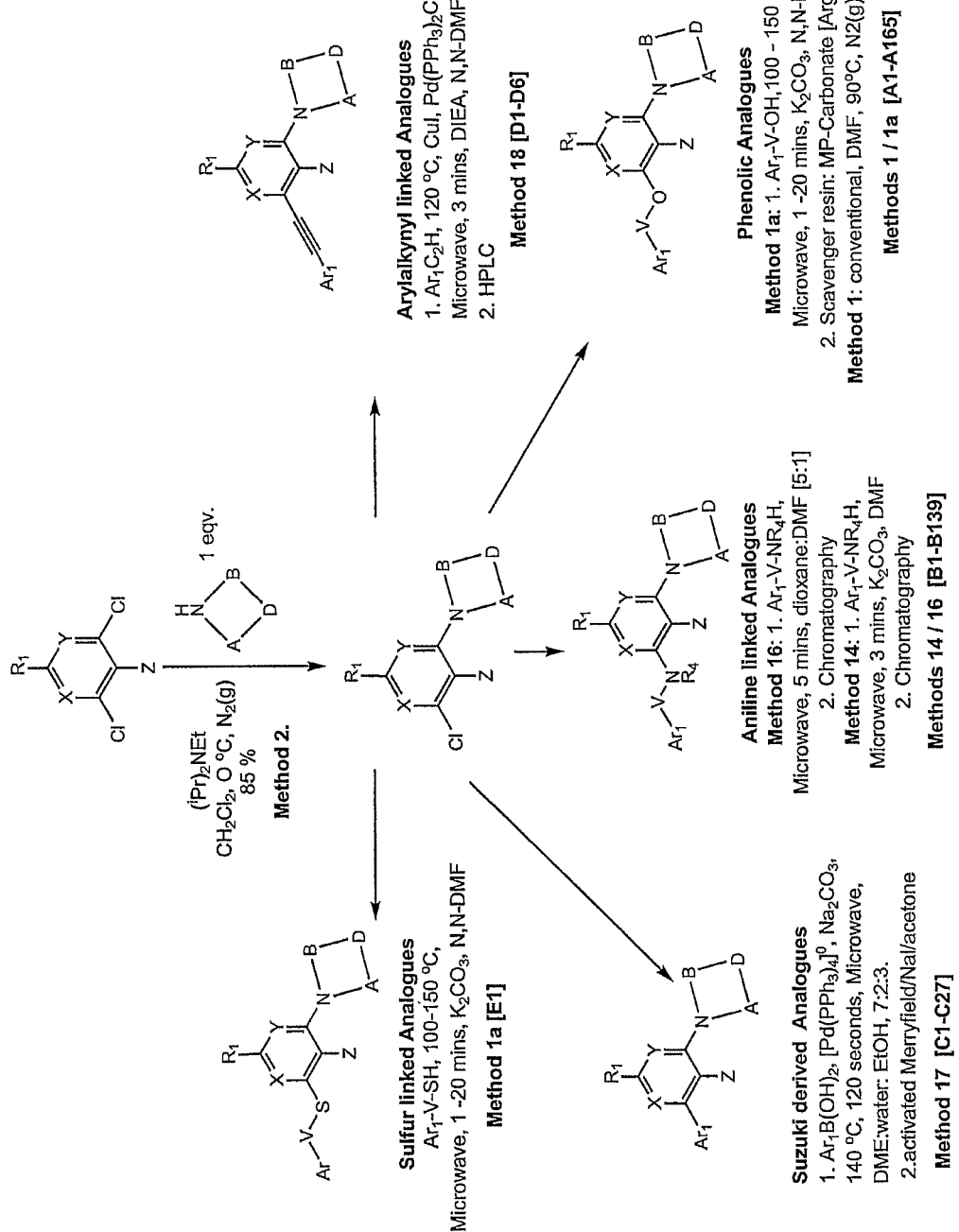
FIG. 6 shows a representative scheme for the syntheses of compounds of the present invention.

Illustrated syntheses for compounds of Formula (Ia) are shown in FIG. 6 where the symbols have the same definitions as used throughout this disclosure. The preparation of N-oxides is well know in the art, which include, but not limited to pyridines, pyrimidines and the like. For example, N-oxides can be prepared at normal or elevated pressure, in the presence of an oxidizing agent, such as, hydrogen peroxide, peracetic acid, perbenzoic, m-chloroperbenzoic acid (mCPBA), ozone, oxygen and the like, in the presence or absence of solvent, such as chloroform, dichlormethane, acetic acid, trifluoroacetic acid, and the like or mixtures thereof.

Chemistry: Proton nuclear magnetic resonance ($^1$H NMR) spectra were recorded on a Varian Mercury Vx-400 equipped with a 4 nucleus auto switchable probe and z-gradient or a Bruker Avance-400 equipped with a QNP (Quad Nucleus Probe) or a BBI (Broad Band Inverse) and z-gradient. Chemical shifts are given in parts per million (ppm) with the residual solvent signal used as reference. NMR abbreviations are used as follows: s=singlet, d=doublet, t=triplet, q=quartet, m=multiplet, br=broad. Microwave irradiations were carried out using the Smith Synthesizer (Personal Chemistry). Thin-layer chromatography (TLC) was performed on silica gel 60 $F_{254}$ (Merck), preparatory thin-layer chromatography (prep TLC) was preformed on PK6F silica gel 60 A 1 mm plates (Whatman), and column chromatography was carried out on a silica gel column using Kieselgel 60, 0.063-0.200 mm (Merck). Evaporation was done in vacuo on a Buchi rotary evaporator. Celite 545® was used during palladium filtrations.

LCMS specs: 1) PC: HPLC-pumps: LC-10AD VP, Shimadzu Inc.; HPLC system controller: SCL-10A VP, Shimadzu Inc; UV-Detector: SPD-10A VP, Shimadzu Inc; Autosampler: CTC HTS, PAL, Leap Scientific; Mass spectrometer: API 150EX with Turbo Ion Spray source, AB/MDS Sciex; Software: Analyst 1.2. 2) Mac: HPLC-pumps: LC-8A VP, Shimadzu Inc; HPLC system controller: SCL-10A VP, Shimadzu Inc.

UV-Detector: SPD-10A VP, Shimadzu Inc; Autosampler: 215 Liquid Handler, Gilson Inc; Mass spectrometer: API 150EX with Turbo Ion Spray source, AB/MDS Sciex Software: Masschrom 1.5.2.

Compound A1

1-[6-(4-Imidazol-1-yl-phenoxy)-5-nitro-pyrimidin-4-yl]-piperidine-4-carboxylic acid ethyl ester: General Method 1

A mixture of 1-(6-chloro-5-nitro-pyrimidin-4-yl)-piperidine-4-carboxylic acid ethyl ester (63 mg, 0.2 mmol), 4-imidazol-1-yl-phenol (42 mg, 0.26 mmol) and potassium carbonate (36 mg, 0.26 mmol, 1 equivalent) in anhydrous DMF (1 ml) was heated to 90° C. overnight. The resulting residue was purified by Flash Chromatography (hexanes:ethyl acetate=1:1) to give 1-[6-(4-Imidazol-1-yl-phenoxy)-5-nitro-pyrimidin-4-yl]-piperidine-4-carboxylic acid ethyl ester [A1] as a yellow solid (80 mg, 92%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 7.38-7.42 (m, 2H), 7.46 (t, 1H), 7.55-7.59 (m, 3H), 8.17 (s, 1H), 8.90-8.92 (m, 1H). Exact mass calculated for $C_{21}H_{22}N_6O_5$ 438.17, found 439.2 (MH$^+$).

The intermediate 1-(6-chloro-5-nitro-pyrimidin-4-yl)-piperidine-4-carboxylic acid ethyl ester was prepared by following general method 2.

General Method 2: Addition of Substituted Piperidines to Dichloro-5-Nitropyrimidine.

Compound 2,6-dichloro-5-nitropyrimidine (500 mg, 2.57 mmol) was dissolved in dichloromethane (40 ml) and cooled to 0° C. To this was added diisopropylethyl amine (0.54 ml, 3.08 mmol) followed by a solution of piperidine-4-ethyl-ester (3.69 mmol) in dichloromethane (5 ml) dropwise. The mixture was stirred at 0° C. for 1 hour and then concentrated in vacuo. Flash chromatography (hexanes:ethyl acetate=1:1) provided Compound A1a, 1-(6-chloro-5-nitro-pyrimidin-4-yl)-piperidine-4-carboxylic acid ethyl ester as a yellow solid (466 mg, 60%). $^1$HNMR (DMSO, 400 MHz) δ 1.57-1.63 (m, 2H), 1.91-1.95 (m, 2H), 2.72-2.74 (m, 1H), 3.17 (t, 2H), 3.60 (s, 3H), 3.84-3.89 (m, 2H), 8.46 (s, 1H). Exact mass calculated for $C_{11}H_{13}ClN_4O_4$ 300.06, found 301.2 (MH$^+$).

Compounds A2-A155 were prepared in an analogous manner as described for Compound A1, supra.

Compound A2

1-[6-(2-Methyl-5-trifluoromethyl-2H-pyrazol-3-yloxy)-5-nitro-pyrimidin-4-yl]-piperidine-4-carboxylic acid ethyl ester. General Method 3

4,6-dichloro-5-nitro pyrimidine (5.00 g, 25.7 mmol) and diisopropylethylamine (7.66 ml, 43.9 mmol) were dissolved in dichloromethane (17.0 ml). The mixture was stirred in an ice bath and 4-ethyl ester piperidine (3.33 ml, 43.9 mmol) dissolved in dichloromethane (17.0 ml) was added dropwise. The mixture was warmed to room temperature and after 30 min. the desired product was observed by LCMS m/z 315 (M+H$^+$). The solvent was removed under reduced pressure, the crude dissolved in dioxane (20 ml), sequentially, diisopropylethylamine (6.31 ml, 36.22 mmol) and 2-Methyl-5-trifluoromethyl-2H-3-hydroxypyrazole (3.60 g, 21.73 mmol) were added and the mixture was heated at 90° C. for 18 h. Work up yielded a crude red oil. Purification by Flash Chromatography (0-35% diethyl ether/hexane). Yield 58.47% yellow solid. $^1$H NMR 400MHz DMSO δ (ppm): 8.34 (s, 1H); 6.71 (s, 1H); 4.07 (m, 2H); 3.88 (d, 2H); 3.70 (s, 3H); 3.27 (m, 2H); 2.72 (m, 1H); 1.94 (m, 2H); 1.62 (m, 2H); 1.18 (t, 3H). LCMS (ESI) m/z 444.3 (M+H$^+$, 100%)

Compound A3

1-[6-(4-Methanesulfonyl-phenoxy)-5-nitro-pyrimidin-4-yl]-piperidine-4-carboxylic acid ethyl ester Following the general procedure [method 1]compound A3 was obtained as a yellow solid (52%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A4

1-[6-(Benzo[1,2,5]oxadiazol-5-yloxy)-5-nitro-pyrimidin-4-yl]-piperidine-4-carboxylic acid ethyl ester Following the general procedure, [method 1]compound A4 was obtained as a brown solid (65%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 7.22 (d, 1H), 7.60 (s, 1H), 7.82 (d, 1H), 8.16 (s, 1H). Exact mass calculated for C$_{18}$H$_{18}$N$_6$O$_6$ 414.13, found 415.3 (MH$^+$).

Compound A5

1-{6-[4-(2-Methoxycarbonyl-acetyl)-phenoxy]-5-nitro-pyrimidin-4-yl]-piperidine-4-carboxylic acid ethyl ester: [method 1]

Flash chromatography (hexanes:ethyl acetate=2:1) provided compound A5 as a yellow solid (250 mg, 65%). $^1$HNMR (CDCl$_3$, 400 MHz) δ 1.28 (t, 3H), 1.78-1.88 (m, 2H), 1.95-2.05 (m, 2H), 2.62-2.70 (m, 1H), 3.22 (t, 2H), 3.76 (s, 2H), 4.00 (s, 3H), 4.02-4.08 (m, 2H), 4.18 (q, 2H), 7.25 (d, 2H), 8.00 (d, 2H), 8.22 (s, 1H). Exact mass calculated for C$_{22}$H$_{24}$N$_4$O$_8$ 472.16, found 473.4 (MH$^+$).

Compound A6

1-[5-Amino-6-(2-methyl-5-trifluoromethyl-2,1-pyrazol-3-yloxy)-pyrimidin-4-yl]-piperidine-4-carboxylic acid ethyl ester: General Method 4

A2 (100 mg, 0.225 mmol) was dissolved in ethanol (8.0 ml), 5% Pd/C (0.1 mmol) was added to the reaction vessel with stirring. The mixture was purged with hydrogen and after 15 min the desired product A6 was observed by LCMS. Filtration followed by solvent removal under reduced pressure yielded a solid that was purified by filtration through a silica plug using 50% ethyl acetate/hexane as solvent. Yield 32.13%. $^1$H NMR 400 MHz DMSO δ (ppm): 8.34 (s, 1H); 6.71 (s, 1H); 4.07 (m, 2H); 3.88 (d, 2H); 3.70 (s, 2H); 3.30 (s, 3H); 3.23 (m, 2H); 2.72 (m, 1H); 1.95 (m, 2H); 1.62 (m, 2H); 1.17 (t, 3H). LCMS (ESI) m/z 415.3 (M$^+$H$^+$, 100%)

Compound A7

1-[6-(2-Methyl-5-trifluoromethyl-2H-pyrazol-3-yloxy)-5-(2,2,2-trifluoro-acetylamino)-pyrimidin-4-yl]-piperidine-4-carboxylic acid ethyl ester General Method 5:

A6 (50 mg, 0.12 mmol) and diisopropylamine (0.83 ml, 0.476 mmol) were dissolved in anhydrous dichloromethane (2.0 ml), and excess (CF$_3$CO)$_2$O was added dropwise at 0° C. Stirring at room temp. was maintained for 12 hours. Purification by RP-HPLC. Yield 46% white solid. $^1$H NMR 400 MHz DMSO δ (ppm): 8.36 (s, 1H); 6.73 (s, 1H); 4.06 (m, 2H); 3.89 (d, 2H); 3.72 (s, 3H); 3.23 (m, 2H); 2.73 (m, 1H); 1.97 (m, 2H); 1.62 (m, 2H); 1.17 (t, 3H).LCMS (ESI) m/z 511.3 (M$^+$H$^+$, 100%)

Compound A8

Propionic acid 1-[2-amino-5-formyl-6-(2-methyl-5-trifluoromethyl-2H-pyrazol-3-yloxy)-pyrimidin-4-yl]-piperidin-4-yl ester General Method 6:

4,6-dichloro-2-amino-5-formylpyrimidine (1.90 g, 9.89 mmol) and diisopropylethylamine (3.30 ml, 18.95 mmol) were dissolved in anhydrous 1,4-dioxane (25.0 ml). The mixture was stirred on an ice bath and 4-ethyl ester piperidine (1.46 ml, 9.47 mmol) dissolved in dioxane (25.0 ml) was added dropwise. The mixture attained room temperature and after 30 min. the desired product was observed by LCMS m/z 313 (M+H$^+$). The solvent was removed under reduced pressure, and the crude residue dissolved in dioxane (20 ml), to it were added diisopropylethylamine (6.31 ml, 36.22 mmol) and 2-Methyl-5-trifluoromethyl-2H-pyrazol-3-ol (3.95 g, 23.77 mmol). The mixture heated at 90° C. for 18 h. Aqueous work up yielded a pale orange solid. Recrystallization from ether and hexanes, followed by filtration of the solid yielded white crystals. Yield 50.28%, $^1$H NMR 400 MHz DMSO δ (ppm): 9.90 (s, 1H); 7.42 (d, 2H); 6.76 (s, 1H); 4.09 (m, 2H); 3.95 (d, 2H); 3.76 (s, 3H); 3.09 (m, 2H); 2.63 (m, 1H); 1.90 (m, 2H); 1.66 (m, 2H); 1.19 (t, 3H). LCMS (ESI) m/z 443 (M+H$^+$, 100%)

Compound A9

4-[6-(2-Methyl-5-trifluoromethyl-2H-pyrazol-3-yloxy)-5-nitro-pyrimidin-4-yl]-piperazine-1-carboxylic acid ethyl ester

[Method 3]. Purification by Flash Chromatography (5-30% ethyl acetate/hexane). Yield 33% yellow oil. $^1$H NMR 400 MHz DMSO δ (ppm): 8.38 (s, 1H); 6.71 (s, 1H); 4.04 (m, 2H); 3.88 (d, 2H); 3.70 (s, 3H); 3.54 (m, 2H); 3.42 (m, 2H); 3.29 (m, 2H) 1.18 (t, 3H). LCMS (ESI) m/z 446.2 (M$^+$H$^+$, 100%)

Compound A10

1-[6-(2-Methyl-5-trifluoromethyl-2H-pyrazol-3-yloxy)-5-nitro-pyrimidin-4-yl]-piperidine-4-carboxylic acid methyl ester

[Method 3]. Flash chromatography (hexanes:ethyl acetate=2:1) provided compound A10 as a yellow solid (173 mg, 30%). $^1$H NMR (CDCl$_3$, 400 MHz) δ 1.80-1.88 (m, 2H), 2.02-2.12 (m, 2H), 2.72-2.74 (m, 1H), 3.72 (s, 3H), 3.78 (s, 3H). 3.94-4.06 (m, 2H), 6.49 (s, 1H), 8.25 (s, 1H). Exact mass calculated for C$_{16}$H$_{17}$F$_3$N$_6$O$_5$ 430.12, found 431.4 (MH$^{30}$).

Compound A11

2,6-Dimethyl-4-[6-(2-methyl-5-trifluoromethyl-2H-pyrazol-3-yloxy)-5-nitro-pyrimidin-4-yl]-morpholine

[Method 3]. Purification by Flash Chromatography (0-30% ethyl acetate/hexane). Yield 57% yellow oil. $^1$H NMR 400 MHz DMSO δ (ppm): 8.37 (s, 1H); 6.71 (s, 1H); 3.83 (m, 2H); 3.72 (s, 3H); 3.62 (m, 2H); 2.81 (m, 2H); 1.12 (t, 6H). LCMS (ESI) m/z 403 (M$^+$H$^+$, 100%)

Compound A12

1-[6-(2-Methyl-5-trifluoromethyl-2H-pyrazol-3-yloxy)-5-nitro-pyrimidin-4-yl]-piperidine-3-carboxylic acid ethyl ester

[Method 3]. Purification by Flash Chromatography (0-50% ethyl acetate/hexane). Yield 50% yellow oil. $^1$H NMR 400 MHz DMSO δ (ppm): 8.36 (s, 1H); 6.72 (s, 1H); 4.08 (m, 2H); 3.98 (m, 2H); 3.72 (s, 3H); 3.58 (m, 1H); 3.45 (m, 1H);

2.69 (m, 1H); 1.99 (m, 1H); 1.76 (m, 2H); 1.57 (m, 1H); 1.17 (t, 3H). LCMS (ESI) m/z 445 (M+H+, 100%)

Compound A13

1-[6-(2-Methyl-5-trifluoromethyl-2H-pyrazol-3-yloxy)-5-nitro-pyrimidin-4-yl]-piperidine-4-carboxylic acid ethylamide

[Method 1]. Purification by HPLC. Yield 16%. $^1$H NMR 400 MHz CDCl$_3$ δ (ppm): 8.17 (s, 1H); 6.43 (s, 1H); 4.06 (m, 2H); 3.72 (s, 3H); 3.12 (m, 2H); 2.58 (m, 3H); 1.88 (m, 4H). LCMS (ESI) m/z 416.1 (M+H+, 100%)

Compound A14

1-[6-(2-Methyl-5-phenyl-2H-pyrazol-3-yloxy)-5-nitro-pyrimidin-4-yl]-piperidine-4-carboxylic acid ethyl ester

[Method 1]. The product was purified by column chromatography on silica (Biotage) using hexane/ethyl acetate (7:3). $^1$H NMR 400 MHz CDCl$_3$ δ (ppm): 8.23 (s, 1H, pyrimidine); 7.78 (d, 2H), 7.40-7.35 (dd, 2H), 6.50 (s, 1H), 4.20 (q, 2H), 4.10-4.00 (m, 2H), 3.78 (s, 3H), 3.30-3.20 (m, 2H), 2.70-2.60 (m, 1H), 2.10-2.00 (m, 2H), 2.95-2.80 (m, 2H), 1.30 (t, 3H). LCMS (ESI) for C$_{22}$H$_{24}$N$_6$O$_5$: m/z 453.2 (M+H+, 100%)

Compound A15

4-(2-Methyl-5-trifluoromethyl-2H-pyrazol-3-yloxy)-5-nitro-6-piperidin-1-yl-pyrimidine

[Method 3]. The product was purified by Preparatory TLC using hexane/ethyl acetate (7:3). $^1$H NMR 400 MHz CDCl$_3$ δ (ppm): 8.20 (s,1H, pyrimidine); 6.45 (s, 1H); 3.80 (s, 3H, CH$_3$), 3.60-3.50 (m, 4H); 1.75-1.60 (m, 5H). LCMS (ESI) for C$_{14}$H$_{15}$F$_3$N$_6$O$_3$: m/z 373 (M+H$^{30}$, 100%)

Compound A16

1-[5-Nitro-6-(2-trifluoromethyl-benzyloxy)-pyrimidin-4-yl]-piperidine-4-carboxylic acid ethyl ester; General Method 7

1-(6-chloro-5-nitropyrimidine-4-yl)-piperidine-4-carboxylic acid ethyl ester 1 (0.22 g, 0.63 mmol) and 2-(trifluoromethanol) benzyl alcohol (0.11 g, 1.26 mmol) were dissolved in DMF at room temperature. Sodium hydride (30 mg, 1.26 mmol) was added and the mixture was stirred at 40° C. for 30 minutes. Diluted the mixture with 10% aq. HCl, and extracted twice with EtOAc. The combined organic extracts were washed with water and brine, dried over anhydrous Na$_2$SO$_4$, and concentrated in vacuo. The residue was purified by preparatory LCMS. $^1$H NMR, 400 MHz, CDCl$_3$, δ (ppm): 8.20 (s, 1H); 7.63 (t, 2H); 7.55 (t, 1H); 7.39 (t, 1H); 5.63 (s, 2H); 4.13 (q, 2H); 3.95 (d, 2H); 3.14 (t, 2H); 2.54 (m, 1H); 1.98 (m, 2H); 1.79 (m, 2H); 1.24 (t, 3H). LCMS (ESI) for C$_{20}$H$_{21}$F$_3$N$_4$O$_5$: m/z 454 (M+H+, 100%)

Compound A17

1-[5-Nitro-6-(3-trifluoromethyl-benzyloxy)-pyrimidin-4-yl]-piperidine-4-carboxylic acid ethyl ester

[Method 7]. The residue was purified by preparatory TLC using hexane/ethyl acetate (3/1, v/v). $^1$H NMR, 400 MHz, CDCl$_3$, δ (ppm): 8.22 (s, 1H); 7.66 (s, 1H); 7.58 (t, 2H); 7.49 (t, 1H); 5.52 (s, 2H); 4.15 (q, 2H); 3.62 (m, 2H); 3.15 (t, 2H); 2.60 (m, 1H); 2.00 (m, 2H); 1.80 (m, 2H); 1.27 (t, 3H). LCMS (ESI) for C$_{21}$H$_{23}$F$_3$N$_4$O$_5$: m/z 469 (M+H+, 100%)

Compound A18

1-[5-Nitro-6-(4-trifluoromethyl-benzyloxy)-pyrimidin-4-yl]-piperidine-4-carboxylic acid ethyl ester

[Method 7.]. The residue was purified by preparatory TLC using hexane/ethyl acetate (3/1, v/v). $^1$H NMR, 400 MHz, CDCl$_3$, δ (ppm): 8.20(s, 1H); 7.62(d, 2H); 7.52(d, 2H); 5.52 (s, 2H); 4.11(q, 2H); 3.96(m, 2H); 3.15(t, 2H); 2.58(m, 1H); 2.01(m, 2H); 1.81(m, 2H); 1.25(t, 3H). LCMS (ESI) for C$_{20}$H$_{21}$F$_3$N$_4$O$_5$: m/z 454 (M+H+, 100%)

Compound A19

1-[5-Bromo-6-(2-methyl-5-trifluoromethyl-2H-pyrazol-3-yloxy)-pyrimidin-4-yl]-piperidine-4-carboxylic acid ethyl ester; General Method 8

A mixture of 1-[6-(2-methyl-5-trifluoromethyl-2H-pyrazol-3-yloxy)-pyrimidin-4-yl]-piperidine-4-carboxylic acid ethyl ester (150 mg, 0.37 mmol) and NBS (65 mg, 0.37 mmol) in DMF (3 ml) was stirred at 60° C. for 2 days. The mixture was quenched with sodium thiosulfate, and extracted with ethyl acetate. The combined organic layer was dried with anhydrous sodium sulfate and concentrated in vacuo. Flash chromatography (hexanes:ethyl acetate=3:1) provided compound A19 as a white solid (100 mg, 57%). $^1$HNMR (CDCl$_3$, 400 MHz) δ 1.28 (t, 3H), 1.78-1.88 (m, 2H), 1.95-2.05 (m, 2H), 2.57-2.62 (m, 1H), 3.17 (t, 2H), 3.81 (s, 3H), 4.18 (q, 2H), 4.22-4.33 (m, 2H), 6.41 (s,1H), 8.22 (s, 1H). Exact mass calculated for C$_{17}$H$_{19}$BrF$_3$N$_5$O$_3$ 477.06, found 478.0 (MH+).

Compound A20

1-[5-Acetylamino-6-(2-methyl-5-trifluoromethyl-2H-pyrazol-3-yloxy)-pyrimidin-4-yl]-piperidine-4-carboxylic acid ethyl ester and Compound A21 1-[5-Diacetylamino-6-(2-methyl-5-trifluoromethyl-2H-pyrazol-3-yloxy)-pyrimidin-4-yl]-piperidine-4-carboxylic acid ethyl ester General Method 9:

A mixture of compound A6 (100 mg, 0.24 mmol) and acetic anhydride (0.1 ml, 1 mmol) in pyridine (5 ml) was heated to 60° C. for three days. The mixture was concentrated in vacuo. Flash chromatography (hexanes:ethyl acetate=1:1) provided compound A20a (7 mg, 7%) and A20b (40 mg, 34%) both as a yellow oil. Compound A20a $^1$HNMR (CDCl$_3$, 400 MHz) δ 1.33 (t, 3H), 1.77-1.85 (m, 2H), 1.95-2.05 (m, 2H), 2.22 (s, 3H), 2.55-2.62 (m, 1H), 3.16 (t, 2H), 3.76 (s, 3H), 4.06-4.22 (m, 4H), 6.24 (s, 1H), 6.50 (s, 1H), 8.22 (s, 1H). Exact mass calculated for C$_{19}$H$_{24}$F$_3$N$_6$O$_4$ 456.17, found 457.2 (MH+). Compound A20b NMR (CDCl$_3$, 400 MHz) δ 1.25 (t, 3H), 1.77-1.85 (m, 2H), 1.95-2.05 (m, 2H), 2.37 (s, 6H), 2.55-2.62 (m, 1H), 3.18 (t, 2H), 3.66 (s, 3H), 4.06-4.22 (m, 4H), 6.24 (s, 1H), 6.31 (s, 1H), 8.25 (s, 1H). Exact mass calculated for C$_{21}$H$_{25}$F$_3$N$_6$O$_5$ 498.18, found 499.4 (M+H+).

Compound A22

1-[6-(2-Methyl-5-trifluoromethyl-2,1-pyrazol-3-yloxy)-5-nitro-pyrimidin-4-yl]-piperidine-4-carboxylic acid

[Method 3]. Purification of part of the crude by HPLC. Yield 8.58% yellow solid. $^1$H NMR 400 MHz DMSO δ (ppm): 8.33 (s, 1H); 6.71 (s, 1H); 3.88 (m, 2H); 3.70 (s, 3H); 3.22 (m, 2H); 2.63 (m, 1H); 1.93 (m, 2H); 1.59 (m, 2H). LCMS (ESI) m/z 417 (M+H$^+$, 100%)

Compound A23

1-{5-Nitro-6-[2-(2-trifluoromethyl-phenyl)-ethoxy]-pyrimidin-4-yl}-piperidine-4-carboxylic acid ethyl ester

[Method 7]. The residue was purified by preparatory TLC using hexane/ethyl acetate (9/1,v/v). $^1$H NMR, 400 MHz, CDCl$_3$, δ (ppm): 8.63 (s, 1H); 7.45 (m, 4H); 4.16 (q, 2H); 4.03 (m, 2H); 3.89 (t, 2H); 3.08 (t, 2H); 3.20 (t, 2H); 2.55 (m, 1H); 2.03 (m, 2H); 1.80 (m, 2H); 1.28 (t, 3H). LCMS (ESI) for C$_{21}$H$_{23}$F$_3$N$_4$O$_5$: m/z 468 (M+H$^+$, 100%)

Compound A24

1-{5-Nitro-6-[2-(3-trifluoromethyl-phenyl)-ethoxy]-pyrimidin-4-yl}-piperidine-4-carboxylic acid ethyl ester

[Method 7]. The residue was purified by preparatory TLC using hexane/ethyl acetate (9/1, v/v). $^1$H NMR, 400 MHz, CDCl$_3$, δ (ppm): 8.63 (s, 1H); 7.45 (m, 4H); 4.16 (q, 2H); 4.03 (m, 2H); 3.89 (t, 2H); 3.08 (t, 2H); 3.20 (t, 2H); 2.55 (m, 1H); 2.03 (m, 2H); 1.80 (m, 2H); 1.28 (t, 3H). LCMS (ESI) for C$_{21}$H$_{23}$F$_3$N$_4$O$_5$: m/z 468 (M+H$^+$, 100%)

Compound A25

1-[5-Di-(methanesulfonyl)amino-6-(2-methyl-5-trifluoromethyl-2H-pyrazol-3-yloxy)-pyrimidin-4-yl]-piperidine-4-carboxylic acid ethyl ester; General Method 10

Compound A6 (150 mg, 0.36 mmol) was dissolved in dichloromethane (5 ml). To this was added DIEA (0.125 ml) and methane sulfonic anhydride (94 mg, 0.54 mmol). The mixture was stirred at room temperature for 24 hours, quenched with water and extracted with dichloromethane. The combined organic layer was dried in vacuo and purified by HPLC to give compound A25 as a yellow solid (24 mg, 12%). $^1$HNMR (CDCl$_3$, 400 MHz) δ 1.28 (t, 3H), 1.80-1.95 (m, 2H), 2.05-2.15 (m, 2H), 2.60-2.68 (m, 1H), 3.38 (t, 2H), 3.50 (s, 6H), 3.79 (s, 3H), 4.17 (q, 2H), 4.44-4.55 (m, 2H), 6.24 (s, 1H), 8.22 (s, 1H). Exact mass calculated for C$_{19}$E$_{25}$F$_3$N$_6$O$_5$S$_2$ 570.12, found 571.3 (MH$^+$).

Compound A26

1-[5-Nitro-6-(3-trifluoromethyl-phenoxy)-pyrimidin-4-yl]-piperidine-4-carboxylic acid ethyl ester

[Method 1]. The residue was purified by column chromatography (Biotage) using 10% hexane/ethyl acetate. $^1$H NMR, 400 MHz, CDCl$_3$, δ (ppm): 8.16 (s, 1H); 7.53 (m, 2H); 7.41 (s, 1H); 7.02 (d, 1H); 4.16 (q, 2H); 4.01 (m, 1H); 3.21 (t, 2H); 2.97 (s, 9H); 2.90 (s, 9H); 2.63 (m, 1H); 2.02 (m, 2H); 1.85 (m, 4H); 1.27 (t, 3H). LCMS (ESI) for C$_{19}$H$_{19}$F$_3$N$_4$O$_5$: m/z 440 (M+H$^+$, 100%)

Compound A27

1-[5-Methyl-6-(2-methyl-5-trifluoromethyl-2H-pyrazol-3-yloxy)-pyrimidin-4-yl]-piperidine-4-carboxylic acid ethyl ester; General Method 11

A mixture of A19 (100 mg, 0.21 mmol), methyl boronic acid (25 mg, 0.42 mmol), dichlorobis(triphenylphosphine) palladium (II) (15 mg, 0.021 mmol) and potassium carbonate (87 mg, 0.62 mmol) in dry DMF (5 ml) was heated to 100° C. under nitrogen overnight. The mixture was cooled to room temperature, quenched with water and extracted with ethyl acetate. The combined organic layer was dried with anhydrous sodium sulfate and concentrated in vacuo. Flash chromatography (hexanes:ethyl acetate=3:1) provided compound A27 as an oil (20 mg, 23%). $^1$HNMR (CDCl$_3$, 400 MHz) δ 1.28 (t, 3H), 1.82-1.94 (m, 2H), 1.97-2.05 (m, 2H), 2.23 (s, 3H), 2.57-2.62 (m, 1H), 3.02 (t, 2H), 3.77 (s, 3H), 3.82-3.88 (m, 2H), 4.18 (q, 2H), 6.34 (s, 1H), 8.22 (s, 1H). Exact mass calculated for C$_{18}$H$_{22}$F$_3$N$_5$O$_3$ 413.17, found 414.4 (MH$^+$).

Compound A28

1-[5-Nitro-6-(2-trifluoromethyl-phenoxy)-pyrimidin-4-yl]-piperidine-4-carboxylic acid ethyl ester

[Method 1]. The residue was purified by column chromatography (Biotage) using 10% hexane/ethyl acetate. Yield 74%. $^1$H NMR, 400 MHz, CDCl$_3$, δ (ppm): 8.14 (s, 1H); 7.70 (d, 1H); 7.62 (t, 1H); 7.38 (t, 1H); 7.26 (d, 1H); 4.17 (q, 2H); 4.03 (m, 2H); 3.23 (t, 2H); 2.63 (m, 1H); 2.04 (m, 2H); 1.85 (m,2H); 1.28 (t, 3H). LCMS (ESI) for C$_{19}$H$_{19}$F$_3$N$_4$O$_5$: m/z 440 (M+H$^+$, 100%)

Compound A29

1-{1-[5-Nitro-6-(4-trifluoromethyl-phenoxy)-pyrimidin-4-yl]-piperidin-4-carboxylic acid ethyl ester

[Method 1]. The residue was purified by column chromatography (Biotage) using 10% hexane/ethyl acetate. Yield 58%. $^1$H NMR, 400 MHz, CDCl$_3$, δ (ppm): 8.01 (s, 1H); 7.47 (d, 2H); 6.93 (d, 2H); 4.16 (q, 2H); 4.05 (m, 2H); 3.23 (t, 2H); 2.66 (m, 1H); 2.09 (m, 2H); 1.93 (m, 2H); 1.28 (t, 3H). LCMS (ESI) for C$_{19}$H$_{191}$F$_3$N$_4$O$_5$: m/z 440 (M+H$^+$, 100%)

Compound A30

1-[6-(4-Fluoro-phenoxy)-5-nitro-pyrimidin-4-yl]-piperidine-4-carboxylic acid ethyl ester

[Method 1]. Yield 0.016 g, 16%. Yellow solid. $^1$H NMR 400 MHz CDCl$_3$ δ (ppm): 8.17 (s, 1H); 7.10 (m, 4H); 4.18 (q, 2H); 4.03 (m, 2H); 3.22 (m, 2H); 2.63 (m 1H); 2.03 (m, 2H); 1.84 (m, 2H); 1.29 (m, 3H). LCMS (ESI) m/z 391 (M+H$^+$, 100%)

Compound A31

1-[6-(2,5-Dimethyl-2H-pyrazol-3-yloxy)-5-nitro-pyrimidin-4-yl]-piperidine-4-carboxylic acid ethyl ester

[Method 3]. The product was purified by column chromatography on silica (Biotage) using hexane/ethyl acetate (7:3).

¹H NMR 400 MHz CDCl₃ δ (ppm): 8.23 (s, 1H, pyrimidine); 5.97 (s, 1H), 4.20 (q, 2H), 4.10-4.00 (m,2H), 3.50 (s,3H), 3.30-3.20 (m, 2H), 2.70-2.60 (m, 1H), 2.10 (s, 3H), 2.00 (m,2H), 1.95-1.90 (m, 2H), 1.30 (t, 3H). LCMS (ESI) for $C_{17}H_{22}N_6O_5$: m/z 391.3 (M+H⁺, 100%)

Compound A32

1-[6-(4-Bromo-phenoxy)-5-nitro-pyrimidin-4-yl]-piperidine-4-carboxylic acid ethyl ester

[Method 1]. The solvent was removed in vacuo and the residue purified by preparatory thin layer chromatography [SiO₂; EtOAc/hexane; 50:50]. Yield 0.010 g, 9%. Yellow solid. ¹H NMR 400 MHz CDCl₃ δ (ppm): 8.17 (s, 1H); 7.52 (d, 2H); 7.03 (d, 2H); 4.17 (q, 2H); 4.02 (m, 2H); 3.22 (m, 2H); 2.63 (m, 1H); 2.03 (m, 2H); 1.84 (m, 2H); 1.29 (m, 3H) LCMS (ESI) m/z 452, 453 (M+H⁺, 100%)

Compound A33

1-[6-(4-Chloro-phenoxy)-5-nitro-pyrimidin-4-yl]-piperidine-4-carboxylic acid ethyl ester

[Method 1]. Yield 0.009 g, 9%. Yellow solid. ¹H NMR 400 MHz CDCl₃ δ (ppm): 8.17 (s, 1H); 7.37 (d, 2H); 7.08 (d, 2H); 4.17 (m, 2H); 4.03 (m, 2H); 3.22 (m, 2H); 2.64 (m, 1H); 2.03 (m, 2H); 1.84 (m, 2H); 1.29 (m, 3H). LCMS (ESI) m/z 407 (M+H⁺, 100%)

Compound A34

1-[6-(4-Carbamoyl-phenoxy)-5-nitro-pyrimidin-4-yl]-piperidine-4-carboxylic acid ethyl ester General Method 1a:
A mixture of compound 7 (63 mg, 0.2 mmol), 4-hydroxy-benzene carboxamide (35 mg, 0.26 mmol) and potassium carbonate (36 mg, 0.26 mmol) in DMF (1 ml) was heated in microwave for 2 minutes at 80° C. Following the general procedure, compound A34 was obtained as a yellow solid (65%). ¹HNMR (CDCl₃, 400 MHz) δ 1.19 (t, 3H), 1.70-1.80 (m, 2H), 1.98-2.03 (m, 2H), 2.65-2.80 (m, 1H), 3.22 (t, 2H), 3.82-3.96 (m, 2H), 4.07 (q, 2H), 7.25 (d, 2H), 7.40 (s, 1H), 7.92 (d, 2H), 8.00 (s, 1H), 8.20 (s, 1H). Exact mass calculated for $C_{19}H_{21}N_5O_6$ 415.15, found 416.2 (MH⁺).

Compound A35

1-{6-[4-(2-Methoxy-ethyl)-phenoxy]-5-nitro-pyrimidin-4-yl}-piperidine-4-carboxylic acid ethyl ester

[Method 1a]. Following the general procedure, compound A35 was obtained as a yellow solid (71%). ¹HNMR (CDCl₃, 400 MHz) δ 1.28 (t, 3H), 1.70-1.80 (m, 2H), 1.98-2.03 (m, 2H), 2.65-2.75 (m, 1H), 2.94 (t, 2H), 3.22 (t, 2H), 3.37 (s, 3H), 3.62 (t, 2H), 3.96-4.03 (m, 2H), 4.15 (q, 2H), 7.05 (d, 2H), 7.25 (d, 2H), 8.17 (s, 1H). Exact mass calculated for $C_{21}H_{26}N_4O_6$ 430.19, found 431.4 (MH⁺).

Compound A36

1-[6-(4-Cyclopentyl-phenoxy)-5-nitro-pyrimidin-4-yl]-piperidine-4-carboxylic acid ethyl ester

[Method 1a]. Following the general procedure, compound A36 was obtained as a yellow solid (58%). ¹HNMR (CDCl₃, 400 MHz) δ 1.28 (t, 3H), 1.58-1.92 (m, 8H), 1.98-2.15 (m, 4H), 2.65-2.75 (m, 1H), 3.00 (quintet, 1H), 3.22 (t, 2H), 3.96-4.03 (m, 2H), 4.15 (q, 2H), 7.04 (d, 2H), 7.25 (d, 2H), 8.18 (s, 1H). Exact mass calculated for $C_{23}H_{28}N_4O_5$ 440.21, found 4-[1.2 (MH⁺).

Compound A37

1-[5-Nitro-6-(4-pyrrol-1-yl-phenoxy)-pyrimidin-4-yl]-piperidine-4-carboxylic acid ethyl ester

[Method 1a]. Following the general procedure, compound A37 was obtained as a yellow solid (77%). ¹HNMR (CDCl₃, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 6.36 (d, 2H), 7.04 (d, 2H), 7.19 (d, 2H), 7.40 (d, 2H), 8.18 (s, 1H). Exact mass calculated for $C_{22}H_{23}N_5O_5$ 437.17, found 438.2 (MH⁺).

Compound A38

1-[6-(4-Benzoyl-phenoxy)-5-nitro-pyrimidin-4-yl]-piperidine-4-carboxylic acid ethyl ester

[Method 1a]. Following the general procedure, compound A38 was obtained as a yellow solid (70%). ¹HNMR (CDCl₃, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 7.24-7.28 (m, 2H), 7.46-7.51 (m, 2H), 7.58-7.62 (m, 1H), 7.78-7.82 (m, 2H), 7.87-7.90 (m, 2H), 8.21 (s, 1H). Exact mass calculated for $C_{25}H_{24}N_4O_6$ 476.17, found 477.2 (MH⁺).

Compound A39

1-{6-[4-(4-Hydroxy-benzenesulfonyl)-phenoxy]-5-nitro-pyrimidin-4-yl}-piperidine-4-carboxylic acid ethyl ester

[Method 1a]. Following the general procedure, compound A39 was obtained as a yellow solid (51%). ¹HNMR (CDCl₃, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 6.82 (d, 2H), 7.25 (d, 2H), 7.78 (d, 2H), 7.96 (d, 2H), 8.13 (s, 1H). Exact mass calculated for $C_{24}H_{24}N_4O_8S$ 528.13, found 529.2 (MH⁺).

Compound A40

1-[6-(4'-Cyano-biphenyl-4-yloxy)-5-nitro-pyrimidin-4-yl]-piperidine-4-carboxylic acid ethyl ester

[Method 1a]. Following the general procedure, compound A40 was obtained as a yellow solid. ¹HNMR (CDCl₃, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 7.24-7.26 (m, 2H), 7.61-7.78 (m, 6H), 8.19 (s, 1H). Exact mass calculated for $C_{25}H_{23}N_5O_5$ 473.17, found 473.3 (MH⁺).

Compound A41

1-[6-(2-Amino-4-ethanesulfonyl-phenoxy)-5-nitro-pyrimidin-4-yl]-piperidine-4-carboxylic acid ethyl ester

[Method 1a]. Following the general procedure, compound A41 was obtained as a yellow solid. ¹HNMR (CDCl₃, 400

MHz) δ 1.28 (t, 3H), 1.80-1.96 (m, 2H), 2.00-2.08 (m, 2H), 2.65-2.75 (m, 1H), 3.14 (q, 2H), 3.40 (t, 2H), 3.96-4.03 (m, 2H), 4.18 (q, 2H), 7.18 (d, 2H), 7.68 (d, 1H), 7.72 (d, 1H), 8.06 (s, 1H), 10.35 (s, 2H). Exact mass calculated for $C_{20}H_{25}N_5O_7S$ 479.15, found 480.0 (MH$^+$).

Compound A42

1-{6-[4-(5-Hydroxy-pyrimidin-2-yl)-phenoxy]-5-nitro-pyrimidin-4-yl}-piperidine-4-carboxylic acid ethyl ester

[Method 1a]. Following the general procedure, compound A42 was obtained as a yellow solid. $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.14 (q, 2H), 3.40 (t, 2H), 3.96-4.03 (m, 2H), 4.18 (q, 2H), 7.36 (d, 2H), 8.20 (s, 1H), 8.38 (d, 2H), 8.77 (s, 2H). Exact mass calculated for $C_{22}H_{22}N_6O_6$ 466.16, found 467.2 (MH$^+$).

Compound A43

1-[5-Nitro-6-(4-sulfo-phenoxy)-pyrimidin-4-yl]-piperidine-4-carboxylic acid ethyl ester

[Method 1a]. Following the general procedure, compound A43 was obtained as a yellow solid. $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.14 (q, 2H), 3.40 (t, 2H), 3.70-3.82 (m, 2H), 4.05 (q, 2H), 7.12 (d, 2H), 7.60 (d, 2H), 8.20 (s, 1H). Exact mass calculated for $C_{18}H_{19}N_4O_8SNa$ 474.08, found 475 (M+H$^+$).

Compound A44

1-[5-Nitro-6-(4-1,2,4]triazol-1-yl-phenoxy)-pyrimidin-4-yl]-piperidine-4-carboxylic acid ethyl ester

[Method 1a]. Following the general procedure, compound A44 was obtained as a yellow solid. $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 7.33 (d, 2H), 7.73 (d, 2H), 8.17 (s, 2H), 8.69 (s, 1H). Exact mass calculated for $C_{20}H_{21}N_7O_5$ 439.16, found 440.4 (MH$^+$).

Compound A45

1-[6-(4-Carbamoylmethyl-phenoxy)-5-nitro-pyrimidin-4-yl]-piperidine-4-carboxylic acid ethyl ester

[Method 1a]. Following the general procedure, compound A45 was obtained as a yellow solid. $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.60 (s, 2H), 3.96-4.03 (m, 2H), 4.15 (q, 2H), 7.17 (d, 2H), 7.38 (d, 2H), 8.17 (s, 1H). Exact mass calculated for $C_{20}H_{23}N_5O_6$ 429.16, found 430.3 (MH$^+$).

Compound A46

1-{6-[4-(1,3-Dioxo-1,3-dihydro-isoindol-2-yl)-phenoxy]-5-nitro-pyrimidin-4-yl}-piperidine-4-carboxylic acid ethyl ester

[Method 1a]. Following the general procedure, compound a46 was obtained as a yellow solid. $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.60 (s, 2H), 3.96-4.03 (m, 2H), 4.15 (q, 2H), 7.26-7.29 (m, 2H), 7.52-7.55 (m, 2H), 7.82 (dd, 2H), 7.94 (dd, 2H), 8.19 (s, 1H). Exact mass calculated for $C_{26}H_{23}N_5O_7$ 517.16, found 518.3 (MH$^+$).

Compound A47

1-[6-(4'-Methoxy-biphenyl-4-yloxy)-5-nitro-pyrimidin-4-yl]-piperidine-4-carboxylic acid ethyl ester

[Method 1a]. Following the general procedure, compound A47 was obtained as a yellow solid. $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.60 (s, 2H), 3.85 (s, 3H), 3.96-4.03 (m, 2H), 4.15 (q, 2H), 6.96 (d, 2H), 7.17 (d, 2H), 7.54 (d, 2H), 7.60 (d, 2H), 8.17 (s, 1H). Exact mass calculated for $C_{25}H_{26}N_4O_6$ 478.19, found 479.2 (MH$^+$).

Compound A48

1-{6-[4-(2,5-Dioxo-imidazolidin-4-yl)-phenoxy]-5-nitro-pyrimidin-4-yl}-piperidine-4-carboxylic acid ethyl ester

[Method 1a]. Following the general procedure, compound A48 was obtained as a yellow solid. $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.60 (s, 2H), 3.96-4.03 (m, 2H), 4.15 (q, 2H), 5.16 (s, 1H), 5.30 (s, 1H), 5.60 (s, 1H), 7.26 (d, 2H), 7.43 (d, 2H), 8.16 (s, 1H). Exact mass calculated for $C_{21}H_{22}N_6O_7$ 470.15, found 471.1 (MH$^+$).

Compound A49

4-(4,4-Difluoro-piperidin-1-yl)-6-(2-methyl-5-trifluoromethyl-2H-pyrazol-3-yloxy)-5-nitro-pyrimidine

[Method 2 Followed by Method 3]. Purification by HPLC yielded a yellow solid. Yield 54.71%. $^1$H NMR 400 MHz CDCl$_3$ δ (ppm): 8.29 (s, 1H); 6.52 (s, 1H); 3.80 (s, 3H); 3.71 (m, 2H); 2.11 (m, 2H); 2.01 (m, 4H). LCMS (ESI) m/z 409.2 (M$^+$H$^{30}$, 100%)

Compound A50

1-{5-Nitro-6-[4-(4-oxo-cyclohexyl)-phenoxy]-pyrimidin-4-yl}-piperidine-4-carboxylic acid ethyl ester

[Method 1a]. Following the general procedure, compound A50 was obtained as a yellow solid (45%). $^1$HNMR (CDCl$_3$, 400 MHz) δ 1.28 (t, 3H), 1.80-2.05 (m, 6H), 2.21-2.24 (m, 2H), 2.52-2.56 (m, 2H), 2.65-2.75 (m, 1H), 3.22 (t, 2H), 3.60 (s, 2H), 3.96-4.03 (m, 2H), 4.15 (q, 2H), 7.10 (d, 2H), 7.26 (d, 2H), 8.17 (s, 1H). Exact mass calculated for $C_{24}H_{283}N_4O_6$ 468.2, found 469.2 (MH$^+$).

Compound A51

1-{5-Nitro-6-[4-(3-oxo-butyl)-phenoxy]-pyrimidin-4-yl}-piperidine-4-carboxylic acid ethyl ester

[Method 1a]. Following the general procedure, compound A51 was obtained as a yellow solid (61%). $^1$HNMR (CDCl$_3$, 400 MHz) δ 1.28 (t, 3H), 1.80-1.96 (m, 2H), 2.00-2.08 (m, 2H), 2.16 (s, 3H), 2.65-2.75 (m, 1H), 2.72-2.78 (m, 2H), 2.82-2.90 (m, 2H), 3.22 (t, 2H), 3.60 (s, 2H), 3.96-4.03 (m, 2H), 4.15 (q, 2H), 7.02 (d, 2H), 7.22 (d, 2H), 8.17 (s, 1H). Exact mass calculated for $C_{22}H_{26}N_4O_6$ 442.19, found 443.0 (MH$^+$).

Compound A52

1-[5-Nitro-6-(4-propionyl-phenoxy)-pyrimidin-4-yl]-piperidine-4-carboxylic acid ethyl ester

[Method 1a]. Following the general procedure, compound A52 was obtained as a yellow solid (70%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.01 (q, 2H), 3.22 (t, 2H), 3.96-4.03 (m, 2H), 4.15 (q, 2H), 7.21 (d, 2H), 8.02 (d, 2H), 8.17 (s, 2H). Exact mass calculated for $C_{21}H_{24}N_4O_6$ 428.17, found 429.3 (MH$^+$).

Compound A53

1-[5-Nitro-6-(4-[1,2,3]thiadiazol-4-yl-phenoxy)-pyrimidin-4-yl]-piperidine-4-carboxylic acid ethyl ester

[Method 1a]. Following the general procedure, compound A53 was obtained as a yellow solid (57%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.22 (t, 2H), 3.96-4.03 (m, 2H), 4.15 (q, 2H), 7.28 (d, 2H), 8.10 (d, 2H), 8.19 (s, 1H), 8.64 (s, 1H). Exact mass calculated for $C_{20}H_{20}N_6O_5S$ 456.12, found 457.2 (MH$^+$).

Compound A54

1-{6-[4-(2-Hydroxy-ethyl)-phenoxy]-5-nitro-pyrimidin-4-yl}-piperidine-4-carboxylic acid ethyl ester

[Method 1a]. Following the general procedure, compound A54 was obtained as a yellow solid. $^1$HNMR (CDCl$_3$, 400 MHz) δ 1.28 (t, 3H), 1.80-1.96 (m, 2H), 2.00-2.08 (m, 2H), 2.65-2.75 (m, 1H), 2.88 (t, 2H), 3.05 (t, 0.5H), 3.22 (t, 2H), 3.87 (t, 2H), 3.96-4.03 (m, 2H), 4.15 (q, 2H), 4.55 (t, 0.5H), 7.07 (d, 2H), 7.22 (d, 2H), 8.15 (s, 1H). Exact mass calculated for $C_{20}H_{24}N_4O_6$ 416.17, found 417.3 (MH$^+$).

Compound A55

{4-[6-(4,4-Difluoro-piperidin-1-yl)-5-nitro-pyrimidin-4-yloxy]-phenyl}-phenyl-methanone

General Procedure 2 Followed by Method 1A. Flash column chromatography [Hexane:Ethyl Acetate=1:1]provided the intermediate as a yellow oil (444 mg, 84%). $^1$H NMR 400 MHz CDCl$_3$ δ(ppm): 8.40 (s, 1H); 3.70(sb, 4H); 2.1(t, 4H). Exact mass calculated for $C_9H_9ClF_2N_4O_2$ 278.04, LCMS (ESI) m/z 279.3(M+H$^+$, 100%).

[Method 1a]. HPLC provided compound A55 as yellow solid (26 mg, 59%). $^1$H NMR 400 MHz CDCl$_3$ δ(ppm): 8.25(s,1H); 7.90(dd,2H); 7.80(dd, 2H); 7.61(td, 1H); 7.50(td, 2H); 7.26(d,2H); 3.75 (sb, 4H); 2.15(qu,4H). Exact mass calculated for $C_{22}H_{18}F_2N_4O_4$ 440.13, LCMS (ESI) m/z 4-[1.3 (M+H$^+$, 100%).

Compound A56

3-{4-[6-(4,4-Difluoro-piperidin-1-yl)-5-nitro-pyrimidin-4-yloxy]-phenyl}-3-oxo-propionic acid methyl ester

[Method 1a]. HPLC provided compound A56 as yellow solid (10 mg, 24%).
$^1$H NMR 400 MHz CDCl$_3$ δ(ppm): 8.21(s,1H); 8.04(d, 2H); 7.24(d, 2H); 4.01(s, 2H); 3.75 (sb, 4H); 2.15(q,4H); 2.00(sb,3H). Exact mass calculated for $C_{19}H_{18}F_2N_4O_6$ 436.12, LCMS (ESI) m/z 437.3 (M+H$^+$, 100%).

Compound A57

2-[6-(4,4-Difluoro-piperidin-1-yl)-5-nitro-pyrimidin-4-yloxy]-5-ethanesulfonyl-phenylamine

[Method 1a]. HPLC provided compound A57 as yellow oil (31 mg, 70%). $^1$H NMR 400 MHz CDCl$_3$ δ (ppm): 10.35 (s,1H); 8.18 (s,1H); 7.85 (s,1H); 7.63 (d, 11-1); 7.19 (d, 1H); 3.78 (s, 4H); 3.16 (q, 2H); 2.20 (q,4H); 1.21 (sb,3H). Exact mass calculated for $C_{17}H_{19}F_2N_5O_5S$ 443.11, LCMS (ESI) m/z 444.3 (M+H$^+$, 100%).

Compound A58

4-(4-Cyclopentyl-phenoxy)-6-(4,4-difluoro-piperidin-1-yl)-5-nitro-pyrimidine

[Method 1a]. HPLC provided compound A58 as yellow solid (20 mg, 50%). $^1$H NMR 400 MHz CDCl$_3$ δ(ppm): 8.21 (s,1H); 7.25 (d,2H); 7.06 (d, 2H); 3.70 (s, 4H); 3.03 (q,1H); 2.10 (sb, 4 h); 1.80 (d,2H); 1.71 (t,2H); 1.60 (sb, 4H). Exact mass calculated for $C_{20}H_{22}F_2N_4O_3$ 404.17, LCMS (ESI) m/z 405.2 (M+H$^+$, 100%).

Compound A59

1-[6-(2,6-Dichloro-4-methanesulfonyl-phenoxy)-5-nitro-pyrimidin-4-yl]-piperidine-4-carboxylic acid ethyl ester

[Method 1a]. Following the general procedure, compound A59 was obtained as a yellow solid (52%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A60

1-{6-[4-(4-Chloro-benzoyl)-phenoxy]-5-nitro-pyrimidin-4-yl}-piperidine-4-carboxylic acid ethyl ester

[Method 1a]. Following the general procedure, compound A60 was obtained as a yellow solid (52%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A61

1-{6-[4-(4-Hydroxy-benzoyl)-phenoxy]-5-nitro-pyrimidin-4-yl}-piperidine-4-carboxylic acid ethyl ester

[Method 1a]. Following the general procedure, compound A61 was obtained as a yellow solid (52%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A62

1-{6-[4-Cyanomethyl-phenoxy)-5-nitro-pyrimidin-4-yl]-piperidine-4-carboxylic acid ethyl ester

[Method 1a]. Following the general procedure, compound A62 was obtained as a yellow solid (52%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A63

(4-{6-[4-(2-Methanesulfonyl-ethyl)-piperazin-1-yl]-5-nitro-pyrimidin-4-yloxy}-phenyl)-phenyl-methanone General Procedure 2 followed by method 1a. Flash column chromatography [Methanol: Dichloromethane=1:9]provided the intermediate monochloro compound as red oil (124 mg, 35%). Exact mass calculated for $C_{11}H_{16}ClN_5O_4S$ 349.06, LCMS (ESI) m/z 350.1 (M+H$^+$, 100%). [method 1a]. Flash column chromatography [Hexane:Ethyl Acetate=2:1 then Methanol: Dichloromethane=1:9]provided compound A63 as yellow oil (7 mg, 14%). $^1$H NMR 400 MHz CDCl$_3$ δ(ppm): 8.13 (d,2H); 7.91 (d,2H); 7.80 (d, 2H); 7.60 (d, 1H); 7.50 (d, 2H); 7.21 (t, 1H); 4.03 (m, 2H); 3.71 (db, 6H); 3.31 (sb, 2H); 3.08 (s,3H); 3.00 (s,2H). Exact mass calculated for $C_{24}H_{25}N_5O_6S$ 511.15, LCMS (ESI) m/z 512.1 (M+H$^+$, 100%).

Compound A64

4-(4-{6-[4-(2-Methanesulfonyl-ethyl)-piperazin-1-yl]-5-nitro-pyrimidin-4-yloxy}-phenyl)-butan-2-one

[Method 1a]. Flash column chromatography [Hexane: Ethyl Acetate=2:1 then Methanol: Dichloromethane=1:9] provided compound A64 as yellow oil (6 mg, 13%). $^1$H NMR 400 MHz CDCl$_3$ δ(ppm): 8.20 (s,1H); 7.21 (d,2H); 7.05 (d, 2H); 3.63 (s, 4H); 3.20 (d, 2H); 3.03 (s,3H); 2.90 (m, 4H); 2.80 (t, 2H); 2.61 (sb, 4H); 2.18 (s, 3H). Exact mass calculated for $C_{21}H_{27}N_5O_6S$ 477.17, LCMS (ESI) m/z 478.1 (M+H$^+$, 100%).

Compound A65

3-(4-{6-[4-(2-Methanesulfonyl-ethyl)-piperazin-1-yl]-5-nitro-pyrimidin-4-yloxy}-phenyl)-3-oxo-propionic acid methyl ester

[Method 1a]. Flash column chromatography [Hexane: Ethyl Acetate=2:1 then Methanol: Dichloromethane=1:9] provided compound A65 as yellow oil (7 mg, 14%). $^1$H NMR 400 MHz CDCl$_3$ δ(ppm): 8.20 (s,1H); 8.02 (d, 2H); 7.26 (d,2H); 4.01 (d, 2H); 3.73 (s, 7H); 3.10 (sb, 5H). Exact mass calculated for $C_{21}H_{25}N_5O_8S$ 507.14, LCMS (ESI) m/z 508.2 (M+H$^+$, 100%).

Compound A66

4-(4-Methyl-piperidin-1-yl)-6-(2-methyl-5-trifluoromethyl-2H-pyrazol-3-yloxy)-5-nitro-pyrimidine

[Method 2 followed by general method 3]. Purification by HPLC yielded A66 as a yellow solid. Yield: 18%. $^1$H NMR 400 MHz CDCl$_3$ δ (ppm): 8.10 (s, 1H); 6.36 (s, 1H); 3.95 (d, 2H); 3.65 (s, 3H); 2.93 (m, 2H); 1.62 (m, 3H); 1.14 (m, 2H); 0.85 (m, 3H). LCMS (ESI) m/z 387 (M$^+$H$^+$, 100%)

Compound A67

4-(4-Bromo-piperidin-1-yl)-6-(2-methyl-5-trifluoromethyl-2H-pyrazol-3-yloxy)-5-nitro-pyrimidine

[Method 2 Followed by General Method 3]. Final purification by HPLC yielded an orange solid. Yield 22%. $^1$H NMR 400 MHz CDCl$_3$ δ (ppm): 8.31 (s, 1H); 6.51 (s, 1H); 4.41 (m, 1H); 3.84 (m, 2H); 3.81 (s, 3H); 3.66 (m, 2H); 2.17 (m, 2H); 1.98 (m, 2H). LCMS (ESI) m/z 453 (M$^+$H$^+$, 100%)

Compound A68

4-(2-Methyl-5-trifluoromethyl-2H-pyrazol-3-yloxy)-5-nitro-6-(4-propyl-piperidin-1-yl)-pyrimidine

[Method 1a]. provided compound A68 as yellow solid (501 mg, 55% yield). $^1$H NMR 400 MHz CDCl$_3$ δ (ppm): 8.25 (s, 1H); 6.51 (s, 1H); 4.13 (dt, 2H); 3.80 (s, 3H); 3.07 (td, 2H); 1.82 (d, 2H); 1.63-1.56 (m, 1H); 1.40-1.22 (m, 6H); 0.93 (t, 3H). Exact mass calculated for $C_{17}H_{21}F_3N_6O_3$ 414.16, LCMS (ESI) m/z 415.3 (M+H$^+$, 100%).

Compound A69

1-[6-(2-Methyl-5-trifluoromethyl-2H-pyrazol-3-yloxy)-5-nitro-pyrimidin-4-yl]-piperidine-4-carboxylic acid amide

[Method 3]. Purification by HPLC yielded a yellow solid. Yield 16%. $^1$H NMR 400 MHz CDCl$_3$ δ (ppm): 8.17 (s, 1H); 6.43 (s, 1H); 4.06 (m, 2H); 3.72 (s, 3H); 3.12 (m, 2H); 2.58 (m, 3H); 1.88 (m, 4H). LCMS (ESI) m/z 416.1 (M+H$^+$, 100%)

Compound A70

1-[5-Nitro-6-(2-oxo-2H-chromen-6-yloxy)-pyrimidin-4-yl]-piperidine-4-carboxylic acid ethyl ester

[Method 1a]. Following the general procedure, compound A70 was obtained as a yellow solid (43%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 6.38 (d, 1H), 7.02 (d, 1H), 7.10 (s, 1H), 7.42 (d, 1H), 7.63 (d, 1H), 8.13 (s, 1H). Exact mass calculated for $C_{21}H_{20}N_4O_7$ 440.13, found 4-[1.3 (MH$^+$).

Compound A71

1-[5-Nitro-6-(2-oxo-benzo[1,3]oxathiol-6-yloxy)-pyrimidin-4-yl]-piperidine-4-carboxylic acid ethyl ester

[Method 1a]. Following the general procedure, compound A71 was obtained as a yellow solid (34%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 7.02 (d, 1H), 7.15 (s, 1H), 7.40 (d, 1H), 8.14 (s, 1H). Exact mass calculated for $C_{19}H_{18}N_4O_7S$ 446.09, found 447.0 (MH$^+$).

Compound A72

1-[6-(9H-Carbazol-2-yloxy)-5-nitro-pyrimidin-4-yl]-piperidine-4-carboxylic acid ethyl ester

[Method 1a]. Following the general procedure, compound A72 was obtained as a yellow solid (89%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 6.90 (d, 1H), 7.00 (d, 1H), 7.03-7.08 (m, 1H), 7.30-7.36 (m, 2H), 7.78-7.82 (m, 2H), 8.12 (s, 1H), 8.26 (s, 1H). Exact mass calculated for $C_{24}H_{23}N_5O_5$ 461.17, found 462.3 (MH$^+$).

Compound A73

1-[5-Nitro-6-(9-oxo-9H-fluoren-2-yloxy)-pyrimidin-4-yl]-piperidine-4-carboxylic acid ethyl ester

[Method 1a]. Following the general procedure, compound A73 was obtained as a yellow solid (84%). $^1$HNMR (CDCl$_3$, 400 MHz) d 1.28 (t, 3H), 1.80-1.96 (m, 2H), 2.00-2.08 (m, 2H), 2.65-2.75 (m, 1H), 4.02-4.05(m, 2H), 4.14 (q, 2H), 7.20-7.25 (m, 3H), 7.40-7.60 (m, 4H), 8.16 (s, 1H). Exact mass calculated for $C_{25}H_{22}N_4O_6$ 474.15, found 475.1 (MH$^{30}$).

Compound A74

1-{5-Amino-6-[4-(3-oxo-butyl)-phenoxy]-pyrimidin-4-yl}-piperidine-4-carboxylic acid ethyl ester General method 12:
A51 (348 mg, 0.786 mmol) was dissolved in ethyl acetate (10 mL), palladium on activated carbon (10 wt-degussa type) was added and the mixture purged with H$_2$. The reaction was monitored by LCMS and after completion the crude was filtered through celite and activated carbon. Purification by HPLC afforded Compound A74 as a light yellow oil. Yield: 26%. $^1$H NMR 400 MHz CDCl$_3$ δ (ppm): 8.14(s, 1H); 7.26 (d, 2H); 7.05 (d, 2H); 6.38 (s, 2H); 4.19 (m, 2H); 3.88 (d, 2H); 3.17 (m, 2H); 2.94 (m, 2H); 2.81 (m, 2H); 2.63 (m, 1H); 2.18 (s, 3H); 2.14 (d, 2H); 1.91 (m, 2H); 1.30 (t, 3H). LCMS (ESI) m/z 413.4 (M$^+$H$^+$, 100%).

Compound A75

1-[6-[4-(3-oxo-butyl)-phenoxy]-5-(2,2,2-trifluoro-acetylamino)-pyrimidin-4-yl]-piperidine-4-carboxylic acid ethyl ester General Method 13:
A74 (61 mg, 0,148 mmol) and diisopropylethylamine (84 ml, 0.484 mmol) were dissolved in dichloromethane and trifluoroacetic anhydride (0.51 ml, 0.363 mmol) was added. The mixture was stirred at room temperature for 3 hours and LCMS indicated the desired product. Purification by HPLC yielded light yellow oil. Yield 72.97%. $^1$H NMR 400 MHz CDCl$_3$ δ (ppm): 8.21 (s, 1H); 8.14 (s, 1H); 7.20 (d, 2H); 7.00 (d, 2H); 4.15 (m, 4H); 3.13 (m, 2H); 2.89 (m, 2H); 2.77 (m, 2H); 2.57 (m, 2H); 2.15 (s, 3H); 1.99 (m, 2H); 1.77 (m, 2H); 1.26 (t, 3H). LCMS (ESI) m/z 509.2 (M$^+$H$^+$, 100%)

Compound A76

1-{5-Amino-6-[4-(hydroxy-phenyl-methyl)-phenoxy]-pyrimidin-4-yl}-piperidine-4-carboxylic acid ethyl ester

[Method 12]. Purification by HPLC yielded oil. Yield 8%. $^1$H NMR 400 MHz CDCl$_3$ δ (ppm): 8.05 (s, 1H); 7.38 (m, 8H); 7.12 (d, 2H); 5.86 (s, 1H); 4.18 (m, 2H); 3.99 (s, 2H); 3.80 (d, 2H); 2.94 (m, 2H); 2.55 (m, 1H); 2.09 (m, 2H); 1.88 (m, 2H); 1.29 (t, 3H). LCMS (ESI) m/z 449.3 (M$^+$H$^+$, 100%)

Compound A77

1-[6-(2-Benzoyl-5-methoxy-phenoxy)-5-nitro-pyrimidin-4-yl]-piperidine-4-carboxylic acid ethyl ester

[Method 1a]. Following the general procedure, compound A77 was obtained as a yellow solid (52%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 3.35-4.05 (m, 16H), 4.15 (q, 2H), 7.55-7.58 (m, 2H), 7.62-7.66 (m, 1H), 7.88-7.92 (m, 2H), 7.95 (s, 1H). Exact mass calculated for $C_{24}H_{32}N_6O_6S$ 532.21, found 533.3 (MH$^+$).

Compound A78

1-[6-(6-Chloro-pyridin-3-yloxy)-5-nitro-pyrimidin-4-yl]-piperidine-4-carboxylic acid ethyl ester

[Method 1a]. HPLC provided compound A78 as yellow solid (63 mg, 61%). $^1$H NMR 400 MHz CDCl$_3$ δ (ppm): 8.20 (d, 1H); 8.08 (s, 1H); 7.43 (dd, 1H); 7.30 (d, 1H); 4.09 (q, 2H); 3.95 (dt, 2H); 3.15 (td, 2H); 2.55 (m, 1H); 1.95 (dt, 2H); 1.77 (td, 2H); 1.19 (t, 3H). Exact mass calculated for $C_{17}H_{18}ClN_5O_5$ 407.10, LCMS (ESI) m/z 408.3 (M+H$^+$, 100%).

Compound A79

1-[6-(Benzo[1,3]dioxol-5-yloxy)-5-nitro-pyrimidin-4-yl]-piperidine-4-carboxylic acid ethyl ester

[Method 1a]. Following the general procedure, compound A79 was obtained as an oil (46%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 6.00 (s, 2H), 6.57 (d, 1H), 6.60 (s, 1H), 6.80 (d, 1H), 8.16 (s, 1H). Exact mass calculated for $C_{19}H_{20}N_4O_7$ 416.13, found 417.0 (MH$^+$).

Compound A80

1-[6-(4-Benzyloxy-phenoxy)-5-nitro-pyrimidin-4-yl]-piperidine-4-carboxylic acid ethyl ester

[Method 1a]. Following the general procedure, compound A80 was obtained as a yellow solid (25%). $^1$HNMR (CDCl$_3$, 400 MHz) d 1.28 (t, 3H), 1.80-1.96 (m, 2H), 2.00-2.08 (m, 2H), 2.65-2.75 (m, 1H), 4.02-4.05 (m, 2H), 4.14 (q, 2H), 5.04 (s, 2H), 6.94-7.05 (m, 4H), 7.27-7.41 (m, 5H), 8.19 (s, 1H). Exact mass calculated for $C_{25}H_{26}N_4O_6$ 478.19, found 479.1 (MH$^+$).

Compound A81

1-[6-(3-Morpholin-4-yl-phenoxy)-5-nitro-pyrimidin-4-yl]-piperidine-4-carboxylic acid ethyl ester

[Method 1a]. Following the general procedure, compound A81 was obtained as an oil (84%). $^1$HNMR (CDCl$_3$, 400 MHz δ 1.28 (t, 3H), 1.80-1.96 (m, 2H), 2.00-2.08 (m, 2H), 2.65-2.75 (m, 1H), 3.20-3.35 (m, 6H), 3.82-3.84 (m, 2H), 3.98-4.05(m, 2H), 4.14 (q, 2H), 6.75-6.80 (m, 2H), 6.95-6.99 (m, 1H), 7.32-7.38 (m, 1H), 8.17 (s, 1H). Exact mass calculated for C$_{22}$H$_{27}$N$_5$O$_6$ 457.20, found 458.3 (MH$^+$).

Compound A82

1-[5-Nitro-6-(4-trifluoromethylsulfanyl-phenoxy)-pyrimidin-4-yl]-piperidine-4-carboxylic acid ethyl ester

[Method 1a]. Following the general procedure, compound A82 was obtained as a yellow solid (32%). $^1$HNMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 7.26 (d, 2H), 7.68 (d, 2H), 8.17 (s, 1H). Exact mass calculated for C$_{19}$H$_{19}$F$_3$N$_4$O$_5$S 472.1, found 473.1 (MH$^+$).

Compound A83

1-[5-Nitro-6-(4-trifluoromethoxy-phenoxy)-pyrimidin-4-yl]-piperidine-4-carboxylic acid ethyl ester

[Method 1a]. Following the general procedure, compound A83 was obtained as a yellow solid (79%). $^1$H NMR (CDCl$_3$, 400 MHz) δ 1.28 (t, 3H), 1.80-1.96 (m, 2H), 2.00-2.08 (m, 2H), 2.65-2.75 (m, 1H), 4.02-4.05 (m, 2H), 4.14 (q, 2H), 7.18 (d, 2H), 7.26 (d, 2H), 8.17 (s, 1H). Exact mass calculated for C$_{19}$H$_{19}$F$_3$N$_4$O$_6$ 456.13, found 457.1 (MH$^+$).

Compound A84

1-[6-(4-Benzoyl-phenoxy)-5-(2,2,2-trifluoro-acetylamino)-pyrimidin-4-yl]-piperidine-4-carboxylic acid ethyl ester

[Method 13]. Purification by HPLC. $^1$H NMR 400 MHz CDCl$_3$ δ (ppm): 8.20 (s, 1H); 7.97 (s, 1H); 7.79 (d, 2H); 7.72 (d, 2H); 7.52 (m, 1H); 7.41 (m, 2H); 7.13 (d, 2H); 4.09 (m, 4H); 3.11 (m, 2H); 2.53 (m, 1H); 1.94 (m, 2H); 1.72 (m, 2H); 1.19 (t, 3H). LCMS (ESI) m/z 543.5 (M+H$^+$, 100%)

Compound A85

{4-[5-Nitro-6-(4-propyl-piperidin-1-yl)-pyrimidin-4-yloxy]-phenyl}-phenyl-methanone General Procedure 2 followed by method 3

Intermediate: $^1$H NMR 400 MHz CDCl$_3$ δ(ppm): 8.26(s, 1H); 4.035(d, 2H); 2.94(td, 2H); 1.73(dt, 2H); 1.50 (m, 1H); 1.27 (m, 2H); 1.18 (m, 2H); 1.12 (dd, 2H); 0.84(t, 3H). Exact mass calculated for C$_{12}$H$_{17}$ClN$_4$O$_2$ 284.10, LCMS (ESI) m/z 285.0(M+H$^+$, 100%).

[Method 1]. HPLC provided compound A85 as yellow oil (77 mg, 69% yield). $^1$H NMR 400 MHz CDCl$_3$ δ (ppm): 8.01(s, 1H); 7.71 (dd,2H); 7.62 (dd,2H); 7.41 (tt,1H); 7.30 (dt,2H); 7.07 (dt,3H); 3.92 (d, 2H); 2.86 (td,2H); 1.62 (dd, 2H); 1.39 (m, 1H); 1.14 (dt, 2H); 1.06 (t,2H); 1.06 (q, 2H); 0.72 (t,3H). Exact mass calculated for C$_{25}$H$_{26}$N$_4$O$_4$ 446.20, LCMS (ESI) m/z 447.2 (M+H$^+$, 100%).

Compound A86

{4-Methoxy-2-[5-nitro-6-(4-propyl-piperidin-1-yl)-pyrimidin-4-yloxy]-phenyl}-phenyl-methanone

[Method 1]. HPLC provided compound A86 as orange oil (67 mg, 57% yield).
$^1$H NMR 400 MHz CDCl$_3$ δ(ppm): 7.88 (s, 1H); 7.50 (dd,2H); 7.40 (s,1H); 7.37 (tt,1H); 7.30 (t,1H); 7.22 (t,2H); 6.71 (dd,1H); 6.625 (d, 1H); 3.81 (d, 2H); 3.71 (s,3H); 2.81 (td,2H); 1.58 (dd, 2H); 1.36 (m, 1H); 1.16 (dt, 2H); 1.06 (td,2H); 1.01 (dd, 2H); 0.73 (t,3H). Exact mass calculated for C$_{26}$H$_{28}$N$_4$O$_5$ 476.21, LCMS (ESI) m/z 476.9(M+H$^+$, 100%).

Compound A87

4-{4-[5-Nitro-6-(4-propyl-piperidin-1-yl)-pyrimidin-4-yloxy]-phenyl}-butan-2-one

[Method 1]. HPLC provided compound A87 as yellow solid (62 mg, 59% yield). $^1$H NMR 400 MHz CDCl$_3$ δ(ppm): 8.08 (s, 1H); 7.13 (d,2H); 6.95 (d,2H); 4.00 (d, 2H); 2.96 (td,2H); 2.82 (t,2H); 2.69 (t, 2H); 2.07 (s, 3H); 1.71 (dd, 2H); 1.48 (m, 1H); 1.27 (m, 2H); 1.17 (m, 4H); 0.83 (t,3H). Exact mass calculated for C$_{22}$H$_{28}$N$_4$O$_4$ 412.21, LCMS (ESI) m/z 413.4 (M+H$^+$, 100%).

Compound A88

5-Nitro-4-(4-propyl-piperidin-1-yl)-6-(4-[1,2,3]thiadiazol-4-yl-phenoxy)-pyrimidine

[Method 1]. HPLC provided compound A88 as yellow solid (61 mg, 56% yield). $^1$H NMR 400 MHz CDCl$_3$ δ (ppm): 8.56 (s, 1H); 8.11 (s, 1H); 8.02 (d, 2H); 7.22 (d,2H); 4.03 (d, 2H); 2.96 (td,2H); 1.73 (dd, 2H); 1.48 (m, 1H); 1.27 (m, 2H); 1.2 (m, 4H); 0.84 (t,3H). Exact mass calculated for C$_{20}$H$_{22}$N$_6$O$_3$S 426.15, LCMS (ESI) m/z 427.1 (M+H$^+$, 100%).

Compound A89

3-{4-[5-Nitro-6-(4-propyl-piperidin-1-yl)-pyrimidin-4-yloxyl]-phenyl}-3-oxo-propionic acid methyl ester

[Method 1]. HPLC provided compound A89 and A89a [enol] as yellow solid (12 mg, 4 mg, 18% yield). $^1$H NMR 400 MHz CDCl$_3$ δ (ppm): A89: 8.08 (s, 1H); 7.94 (d, 2H); 7.18 (d, 2H); 4.02 (d, 2H); 3.92 (s,2H); 3.68 (s,3H); 2.96 (td,2H); 1.72 (dd, 2H); 1.50 (m, 1H); 1.26 (m, 2H); 1.17 (m, 4H); 0.83 (t,3H). A89a: 8.08(s, 1H); 7.94(d, 2H); 7.75(dd, 2H); 7.12 (dd, 2H); 5.57(s, 1H); 4.02 (d, 2H); 3.73 (s,3H); 2.96 (t,2H); 1.72 (d, 2H); 1.51(m, 1H); 1.26 (m, 2H); 1.18 (m, 4H); 0.83 (t,3H). Exact mass calculated for C$_{22}$H$_{26}$N$_4$O$_6$ 442.19, LCMS (ESI) m/z 443.3(M+H$^+$, 100%).

Compound A90

5-Ethanesulfonyl-2-[5-nitro-6-(4-propyl-piperidin-1-yl)-pyrimidin-4-yloxy]-phenylamine

[Method 1]. HPLC provided compound A92 as yellow solid (60 mg, 53% yield). $^1$H NMR 400 MHz CDCl$_3$ δ (ppm): 10.2 (s, 1H); 7.97 (s, 1H); 7.63 (d, 1H); 7.61 (s, 1H); 7.11 (d, 1H); 3.13 (td, 2H); 3.04 (q, 2H); 1.81 (d, 2H); 1.59 (m, 1H); 1.28 (m, 2H); 1.2 (m, 4H); 0.84 (t, 3H). Exact mass calculated for $C_{20}H_{27}N_5O_5S$ 449.17, LCMS (ESI) m/z 450.3 (M+H⁺, 100%).

Compound A91

4-[4-(3-Isopropyl-[1,2,4]oxadiazol-5-yl]-piperidin-1-yl]-6-(4-methanesulfonyl-phenoxy)-pyrimidine-5-carbonitrile 4,6-Dichloro-pyrimidine-5-carbonitrile (254 mg, 1.47 mmol) was dissolved in DMF (3 mL). $K_2CO_3$ (203 mg, 1.47 mmol) and phenoxy methyl sulfone (253 mg, 1.47 mmol) were added to the solution at 0° C. The reaction was stirred for 30 min. The completion of the reaction was judged with TLC (EtOAc: Hex=1:1, $R_f$=0.82). After the completion of the reaction, were added the oxodiimidazol (340 mg, 1.47 mmol) and $K_2CO_3$ (406 mg, 2.94 mmol) to the reaction at 0° C. The reaction was warmed to rt and stirred for 30 min. The reaction was heated to 40° C. and maintained for 1 h. The reaction was cooled to rt, poured in to $H_2O$ (50 mL) and extracted with EtOAc (50 mL, two times). The EtOAc was dried over $MgSO_2$ and concentrated under vacuum. The crude product was purified over $SiO_2$ (EtOAc:Hex=1:1, $R_f$=0.39) to afford the desired compound (523 mg; 76.1%). ¹H-NMR (DMSO-$d_6$): 8.32 (1H, s), 8.02 (2H, J=4.3 Hz, d), 8.00 (2H, J=4.3 Hz, d), 4.68 (2H, m), 3.50 (2H, m), 3.32 (1H, m), 3.44 (3H, s), 3.05 (1H, m), 2.22 (2H, m), 1.83 (2H, J=17 Hz, d), 1.25 (6H, J=7 Hz, d) ppm. LCMS: 469.4, 384.9, 357.2.

The starting material, 4,6-Dichloro-pyrimidine-5-carbonitrile, used in the preparation of Compound A91 was prepared in the following manner: To a solution of 5-fomyl-4,6-dichloropyrimidine (3.6 g, 20.3 mmol) in EtOAc (50 ml), was added a solution of $NH_2OH\cdot HCl$ (1.41 g, 20.3 mmol) in $H_2O$ (30 ml) followed by AcONa (1.67 g, 20.3 mmol) at rt. After stirring for 2 h, the reaction was washed with $H_2O$ (50 ml, two times) and dried over $MgSO_4$. The EtOAc was concentrated under vacuum to afford the crude iminohydroxy compound (3.51 g, 90.2%). The crude compound was used for next step without further purification. The iminohydroxy compound (3.51 g, 18.3 mmol) was dissolved in $SOCl_2$ (20 ml) at 0° C. and stirred for 30 min. The reaction was warmed to rt and maintained for 3 h. The reaction was poured into $H_2O$ (100 g) portionwise and stirred for 30 min. The precipitate was filtered, washed with $H_2O$ (100 mL) and dried under vacuum to afford 4,6-Dichloro-pyrimidine-5-carbonitrile (2.99 g, 91%). ¹H-NMR (DMSO-$d_6$): 8.53 ppm; LCMS: not detectable.

Compound A92

1-[6-(4-Difluoromethoxy-benzyloxy)-5-nitro-pyrimidin-4-yl]-piperidine-4-carboxylic acid ethyl ester

[Method 7]. The residue was purified by preparatory LCMS. ¹H NMR, 400 MHz, CDCl₃, δ (ppm): 8.19 (s, 1H); 7.38 (d, 2H); 7.08 (d, 2H); 6.47 (m, 1H); 5.43 (s, 2H); 4.12 (q, 2H); 3.93 (m, 2H); 3.12 (m, 2H); 2.56 (m, 1H); 1.96 (m, 2H); 1.76 (m 2H); 1.23 (t, 3H). LCMS (ESI) for $C_{20}H_{22}F_2N_4O_6$: m/z 452 (M+H⁺, 100%).

Compound A93

1-[6-(3-Difluoromethoxy-benzyloxy)-5-nitro-pyrimidin-4-yl]-piperidine-4-carboxylic acid ethyl ester

[Method 7]. The residue was purified by preparatory LCMS. ¹HNMR, 400 MHz, CDCl₃, δ (ppm): 8.16 (s, 1H); 7.29 (t, 1H); 7.17 (d, 1H); 7.11 (s, 1H); 7.00 (d, 1H); 6.45 (m, 1H); 5.40 (s, 2H); 4.08 (q, 2H); 3.89 (m, 2H); 3.08 (m, 2H); 2.52 (m, 1H); 1.92 (m, 2H); 1.74 (m 2H); 1.19 (t, 3H). LCMS (ESI) for $C_{20}H_{22}F_2N_4O_6$: m/z 452 (M+H⁺, 100%).

Compound A94

2-{1-[6-(2-Methyl-5-trifluoromethyl-2H-pyrazol-3-yloxy)-5-nitro-pyrimidin-4-yl]-piperidin-4-yl}-ethanol

[Methods 2 Followed by 3]. Purification by HPLC yielded brownish oil. Yield 21%. ¹H NMR 400 MHz CDCl₃ δ (ppm): 8.50 (s, 1H); 6.76 (s, 1H); 4.37 (d, 2H); 4.04 (s, 3H); 3.99 (m, 2H); 3.33 (t, 2H); 1.82 (m, 8H). LCMS (ESI) m/z 417 (M+H⁺, 100%)

Compound A95

3-{1-[6-(2-Methyl-5-trifluoromethyl-2H-pyrazol-3-yloxy)-5-nitro-pyrimidin-4-yl]-piperidin-4-yl}-propionic acid

[Method 2 Followed by 3]. Purification by HPLC yielded brownish solid. Yield 21%. ¹H NMR 400 MHz CDCl₃ δ (ppm): 8.20 (s, 1H); 6.45 (s, 1H); 4.07 (d, 2H); 3.74 (s, 3H); 3.01 (m, 2H); 2.33 (m, 2H); 2.19 (m, 2H); 1.58 (m, 4H); 1.28 (m, 4H). LCMS (ESI) m/z 459 (M+H⁺, 100%)

Compound A96

4-[4-(4-Methyl-benzyl)-piperidin-1-yl]-6-(2-methyl-5-trifluoromethyl-2H-pyrazol-3-yloxy)-5-nitro-pyrimidine

[Method 2 followed by 3]. Purification by Flash Chromatography yielded an yellow oil. Yield 29%. ¹H NMR 400 MHz CDCl₃ δ (ppm): 8.25 (s, 1H); 7.11 (m, 2H); 7.04 (m, 2H); 6.51 (s, 1H); 4.12 (m, 2H); 3.79 (s, 3H); 3.03 (t, 2H); 2.57 (d, 2H); 2.34 (s, 3H); 1.83 (m, 3H); 1.33 (m, 2H). LCMS (ESI) m/z 477 (M+H⁺, 100%)

Compound A97

4-(3-Methanesulfonyl-pyrrolidin-1-yl)-6-(2-methyl-5-trifluoromethyl-2H-pyrazol-3-yloxy)-5-nitro-pyrimidine

[Methods 2 and 3].Purification by HPLC yielded brownish oil. Yield 30%. LCMS (ESI) m/z 438 (M+H⁺, 100%)

Compound A98

4-(2-Methyl-5-trifluoromethyl-2H-pyrazol-3-yloxy)-5-nitro-6-[4-(2-trifluoromethyl-phenoxy)-piperidin-1-yl]-pyrimidine

[Methods 2 and 3]. Purification by HPLC yielded orange solid. Yield 77%. ¹H NMR 400 MHz CDCl₃ δ (ppm): 8.29 (s, 1H); 7.1 (d, 1H); 7.51 (t, 1H); 7.02 (m, 2H); 6.54 (s, 1H); 3.82 (m, 7H); 2.09 (m, 5H). LCMS (ESI) m/z 533.1 (M+H⁺, 100%)

Compound A99

4-(2-Methyl-5-trifluoromethyl-2H-pyrazol-3-yloxy)-5-nitro-6-[4-(pyridin-2-ylsulfanyl)-piperidin-1-yl]-pyrimidine

[Methods 2 and 3]. Purification by HPLC yielded A99 as a brown oil. Yield 12%. $^1$H NMR 400 MHz CDCl$_3$ δ (ppm): 8.31 (s, 1H); 6.54 (s, 1H); 4.22 (d, 2H); 3.82 (s, 3H); 3.12 (m, 2H); 2.40 (m, 1H); 2.03 (m, 2H); 1.72 (m, 2H). LCMS (ESI) m/z 482.1 (M+H$^+$, 100%)

Compound A100

4'-(4-Benzoyl-phenoxy)-3'-nitro-3,4,5,6-tetrahydro-2H-[1,2']bipyridinyl-4-carboxylic acid ethyl ester

[Method 1a]. Purification by HPLC provided compound A100 as yellow solid (43 mg, 41%). $^1$H NMR 400 MHz CDCl$_3$ δ(ppm): 7.84 (d, 1H); 7.81 (s, 2H); 7.73 (d, 2H); 7.52 (t, 1H); 7.41 (q,2H); 7.17 (d, 2H); 6.57 (d, 1H); 4.10 (q, 2H); 3.48 (dt,2H); 3.03 (td, 2H); 2.50 (m, 5H); 1.96 (dd, 2H); 1.81 (td, 2H); 1.21 (t, 3H). Exact mass calculated for C$_{26}$H$_{25}$N$_3$O$_6$ 475.17 LCMS (ESI) m/z 476.0 (M+H$^+$, 100%).

Compound A101

3'-Nitro-4-[4-(3-oxo-butyl)-phenoxy]-3,4,5,6-tetrahydro-2H-[1,2]bipyridinyl-4-carboxylic acid ethyl ester

[Method 1]. Purification by HPLC provided compound A101 as yellow oil (49 mg, 49%). $^1$H NMR 400 MHz CDCl$_3$ δ(ppm): 7.89 (d,1H); 7.21 (d, 2H); 7.05 (d, 2H); 6.60 (d, 1H); 4.19 (q,2H); 3.56 (dt, 2H); 3.12 (td, 2H); 2.91 (t, 2H); 2.78 (t,2H); 2.59 (t, 1H); 2.17 (s, 3H); 2.04 (dd, 2H); 1.89 (m, 2H); 1.30 (t, 3H). Exact mass calculated for C$_{23}$H$_{27}$N$_3$O$_6$ 4-[1.19 LCMS (ESI) m/z 442.5 (M+H$^+$, 100%).

Compound A102

4'-[4-(2-Methoxycarbonyl-acetyl)-phenoxy]-3'-nitro-3,4,5,6-tetrahydro-2H-[1,2]bipyridinyl-4-carboxylic acid ethyl ester

[Method 1a]. HPLC provided compound A102 as yellow solid (28 mg, 27%). $^1$H NMR 400 MHz CDCl$_3$ δ (ppm): 8.03 (d, 2H); 7.92 (d, 1H); 7.24 (d, 2H); 6.65 (d, 1H); 4.19 (q, 2H); 3.57 (dd, 2H); 3.12 (td, 2H); 2.62 (s, 3H); 2.59 (m, 1H); 2.05 (dd, 2H); 1.90 (m, 2H); 1.30 (t, 3H). Exact mass calculated for C$_{23}$H$_{25}$N$_3$O$_8$ 471.16 LCMS (ESI) m/z 472.4 (M+H$^+$, 100%).

Compound A103

4'-(2-Amino-4-ethanesulfonyl-phenoxy)-3'-nitro-3,4,5,6-tetrahydro-2H-[1,2]bipyridinyl-4-carboxylic acid ethyl ester

[Method 1a]. HPLC provided compound A103 as brown solid (61 mg, 57%). $^1$H NMR 400 MHz CDCl$_3$ δ(ppm): 9.83 (s,1H); 7.97 (d, 1H); 7.45 (dd, 1H); 7.10 (d, 1H); 6.76 (d, 1H); 4.10 (q,2H); 3.45 (d, 2H); 3.16 (m, 4H); 2.69 (m, 1H); 1.93 (d,2H); 1.69 (t, 2H); 1.18 (t,3H); 1.12 (t, 3H). Exact mass calculated for C$_{21}$H$_{26}$N$_4$O$_7$S 478.15 LCMS (ESI) m/z 479.2 (M+H$^+$, 100%).

Compound A104

4'-(4-Imidazol-1-yl-phenoxy)-3'-nitro-3,4,5,6-tetrahydro-2H-[1,2]bipyridinyl-4-carboxylic acid ethyl ester

[Method 1a]. HPLC provided compound A104 as brown oil (64 mg, 65%). $^1$HNMR 400 MHz CDCl$_3$ δ (ppm): 8.85 (s, 1H); 7.90 (d, 1H); 7.57 (d, 1H); 7.53 (dd,2H); 7.45 (d, 1H); 7.41 (dd, 2H); 4.20 (q, 2H); 3.56 (d, 2H); 3.13 (td, 2H); 2.60 (m, 1H); 2.06 (dd, 2H); 1.90 (td, 2H); 1.30 (t, 3H). Exact mass calculated for C$_{22}$H$_{23}$N$_5$O$_5$ 437.17 LCMS (ESI) m/z 438.3 (M+H$^+$, 100%).

Compound A105

4-(2-Methyl-5-trifluoromethyl-2H-pyrazol-3-yloxy)-5-nitro-6-(4-trifluoromethyl-piperidin-1-yl)-pyrimidine

[Method 2 followed by 3]. Purification by HPLC yielded orange oil. Yield 41%. $^1$H NMR 400 MHz CDCl$_3$ δ (ppm): 8.31 (s, 1H); 6.54 (s, 1H); 4.22 (d, 2H); 3.82 (s, 3H); 3.12 (m, 2H); 2.40 (m, 1H); 2.03 (m, 2H); 1.72 (m, 2H). LCMS (ESI) m/z 481.1 (M$^+$H$^+$, 100%)

Compound A106

4-(2-Methyl-5-trifluoromethyl-2H-pyrazol-3-yloxy)-5-nitro-6-(4-phenylsulfanyl-piperidin-1-yl)-pyrimidine

[Method 3]. Purification by HPLC yielded A106 as an orange solid. Yield 55%. $^1$H NMR 400 MHz CDCl$_3$ δ (ppm): 8.28 (s, 1H); 7.47 (m, 2H); 7.34 (m, 2H); 6.53 (s, 1H); 4.03 (d, 2H); 3.82 (s, 3H); 3.42 (m, 1H); 3.33 (m, 2H); 2.09 (m, 3H); 1.74 (m, 2H). LCMS (ESI) m/z 481.1 (M+H$^+$, 100%)

Compound A107

1-[6-(3-Ethynyl-phenoxy)-5-nitro-pyrimidin-4-yl]-piperidine-4-carboxylic acid ethyl ester

[Method 1a]. Purification by semi preparatory HPLC afforded the pure product in 50%. $^1$H NMR, 400 MHz, CDCl$_3$, δ (ppm): 8.12 (s, 1H); 7.30 (m, 2H); 7.19 (s, 1H); 7.06 (m, 1H); 4.10 (q, 2H); 3.95 (m, 2H); 3.14 (m, 2H); 3.03 (s, 1H); 2.56 (m, 1H); 1.95 (m, 2H); 1.76 (m, 2H); 1.20 (t, 3H). LCMS (ESI) for C$_{20}$H$_{20}$N$_4$O$_5$: m/z 396 (M+H$^+$, 100%).

Compound A108

1-[6-(4-Chloro-2-fluoro-phenoxy)-5-nitro-pyrimidin-4-yl]-piperidine-4-carboxylic acid ethyl ester

[Method 1a]. Purified by semi preparatory HPLC afforded the pure product in 42%. $^1$H NMR, 400 MHz, CDCl$_3$, δ (ppm): 8.00 (s, 1H); 7.06 (m, 3H); 4.02 (q, 2H); 3.86 (m, 2H); 3.07 (m, 2H); 2.48 (m, 1H); 1.87 (m, 2H); 1.69 (m, 2H); 1.12 (t, 3H). LCMS (ESI) for C$_{18}$H$_{18}$ClFN$_4$O$_5$: m/z 424 (M+H$^+$, 100%).

Compound A109

1-[6-(2,4-Difluoro-phenoxy)-5-nitro-pyrimidin-4-yl]-piperidine-4-carboxylic acid ethyl ester

[Method 1a]. purified by semi preparatory HPLC afforded the pure product in 34%. $^1$H NMR, 400 MHz, CDCl$_3$, δ

(ppm): 8.14 (s, 1H); 7.15 (m, 1H); 6.89 (m, 2H); 4.14 (q, 2H); 3.98 (m, 2H); 3.19 (m, 2H); 2.60 (m, 1H); 2.00 (m, 2H); 1.82 (m, 2H); 1.24 (t, 3H). LCMS (ESI) for $C_{18}H_{18}F_2N_4O_5$: m/z 408 (M+H$^+$, 100%).

Compound A110

1-[6-(4-Bromo-2-fluoro-phenoxy)-5-nitro-pyrimidin-4-yl]-piperidine-4-carboxylic acid ethyl ester

[Method 1a]. purified by semi preparatory HPLC afforded the pure product in 41%. $^1$H NMR, 400 MHz, CDCl$_3$, δ (ppm): 8.07 (s, 1H); 7.26(m, 2H); 7.02 (t, 1H); 4.09(q, 2H); 3.94 (m, 2H); 3.14 (m, 2H); 2.55 (m, 1H); 1.95 (m, 2H); 1.76 (m, 2H); 1.19 (t, 3H). LCMS (ESI) for $C_{18}H_{18}BrFN_4O_5$: m/z 468 (M+H$^+$, 100%).

Compound A111

4-(3-Ethynyl-phenoxy)-5-nitro-6-(4-propyl-piperidin-1-yl)-pyrimidine

[Method 1a]. purified by semi preparatory HPLC afforded the pure product in 28%. $^1$H NMR, 400 MHz, CDCl$_3$, δ (ppm): 8.07 (s, 1H); 7.28 (m, 2H); 7.19 (m, 1H); 7.05 (m, 1H); 4.00 (m, 2H); 3.01 (s, 1H); 2.93 (m, 2H); 1.71 (m, 2H); 1.48 (m, 1H); 1.28 (m, 2H); 1.16 (m, 4H); 0.83 (t, 3H). LCMS (ESI) for $C_{20}H_{22}N_4O_3$: m/z 366 (M+H$^+$, 100%).

Compound A112

4-(4-Chloro-2-fluoro-phenoxy)-5-nitro-6-(4-propyl-piperidin-1-yl)-pyrimidine

[Method 1a]. Purified by semi preparatory HPLC afforded the pure product in 39%. $^1$H NMR, 400 MHz, CDCl$_3$, δ (ppm): 8.04 (s, 1H); 7.13 (m, 3H); 4.01 (m, 2H); 2.94 (m, 2H); 1.71 (m, 2H); 1.49 (m, 1H); 1.28 (m, 2H); 1.16 (m, 4H); 0.82 (t, 3H). LCMS (ESI) for $C_{18}H_{20}ClFN_4O_3$: m/z 394 (M+H$^+$, 100%).

Compound A113

4-(2,4-Difluoro-phenoxy)-5-nitro-6-(4-propyl-piperidin-1-yl)-pyrimidine

[Method 1a]. purified by semi preparatory HPLC afforded the pure product in 54%. $^1$H NMR, 400 MHz, CDCl$_3$, δ (ppm): 8.04 (s, 1H); 7.10 (m, 1H); 6.85 (m, 2H); 4.00 (m, 2H); 2.94 (m, 2H); 1.71 (m, 2H); 1.49 (m, 1H); 1.28 (m, 2H); 1.16 (m, 4H); 0.82 (t, 3H).LCMS (ESI) for $C_{18}H_{20}F_2N_4O_3$: m/z 378(M+H$^+$, 100%).

Compound A114

4-(4-Bromo-2-fluoro-phenoxy)-5-nitro-6-(4-propyl-piperidin-1-yl)-pyrimidine

[Method 1a]. purified by semi preparatory HPLC afforded the pure product in 62%. $^1$H NMR, 400 MHz, CDCl$_3$, δ (ppm): 8.15 (s, 1H); 7.35 (m, 2H); 7.12 (t, 2H); 4.10 (m, 2H); 3.10 (m, 2H); 1.81 (m, 2H); 1.59 (m, 1H); 1.36 (m, 2H); 1.26 (m, 4H); 0.93 (t, 3H). LCMS (ESI) for $C_{18}H_{20}BrFN_4O_3$: m/z 438 (M+H$^+$, 100%).

Compound A115

3'-Nitro-2'-[4-(3-oxo-butyl)-phenoxy]-3,4,5,6-tetrahydro-2H-[1,4]bipyridinyl-4-carboxylic acid ethyl ester General Procedure 2:
Intermediate monochloro as a yellow oil (128 mg, 80% yield).Exact mass calculated for $C_{15}H_{13}ClN_2O_4$ 320.06, LCMS (ESI) m/z 320.8 (M+H$^+$, 100%). [method 1a]. HPLC provided compound A119 as yellow oil (44 mg, 50%). $^1$H NMR 400 MHz CDCl$_3$ δ(ppm): 8.30 (d,1H); 7.42 (d, 2H); 7.18 (d, 2H); 6.40 (d, 1H); 4.34 (q, 2H); 3.95 (dt, 2H); 3.36 (td, 2H); 3.10(t, 2H); 2.96 (t, 2H); 2.74 (m, 1H); 2.34 (s, 3H); 2.20 (dt, 2H); 2.05 (td, 2H); 1.44 (t, 3H). Exact mass calculated for $C_{23}H_{27}N_3O_6$ 4-[1.19 LCMS (ESI) m/z 442.3 (M+H$^+$, 100%).

Compound A116

4-[4-(3'-Nitro-4-propyl-3,4,5,6-tetrahydro-2H-[1,4']bipyridinyl-2'-yloxy)-phenyl]-butan-2-one

[Method 1a]. HPLC provided compound A116 as yellow oil (34 mg, 32%). $^1$H NMR 400 MHz CDCl$_3$ δ(ppm): 8.09 (d, 1H); 7.24 (d, 2H); 7.00 (d, 2H); 6.15 (d, 1H); 3.80 (d, 2H); 3.06 (td, 2H); 2.91 (t,2H); 2.77 (t, 2H); 1.77 (d, 2H); 1.51 (m, 1H); 1.36-1.22 (m, 6H); 0.8 (t,3H). Exact mass calculated for $C_{23}H_{29}N_3O_4$ 411.22 LCMS (ESI) m/z 412.4 (M+H$^+$, 100%).

Compound A117

2'-(4-Benzoyl-phenoxy)-3'-nitro-3,4,5,6-tetrahydro-2H-[1,4']bipyridinyl-4-carboxylic acid ethyl ester

[Method 1a]. HPLC provided compound A117 as yellow oil (37 mg, 39%). $^1$H NMR 400 MHz CDCl$_3$ δ(ppm): 8.24 (d, 1H); 7.97 (d, 2H); 7.86 (d, 2H); 7.68 (t, 1H); 7.57(t, 2H); 7.27 (d, 2H); 6.36 (d, 1H); 4.23 (q, 2H); 3.87 (dt, 2H); 3.23 (td, 2H); 2.66-2.60 (m, 1H); 2.08 (dt, 2H); 1.92 (td, 2H); 1.33 (t, 3H). Exact mass calculated for $C_{26}H_{25}N_3O_6$ 475.17 LCMS (ESI) m/z 476.2(M+H$^+$, 100%).

Compound A118

4-(4-{5-Nitro-6-[4-(pyridin-2-ylsulfanyl)-piperidin-1-yl]-pyrimidin-4-yloxy}-phenyl)-butan-2-one

[Method 1a]. The crude was dissolved in dichloromethane and purified by preparative TLC. [SiO$_2$; 20/80 EtOAc/hexanes]. Yield 37 mg, 48%. Yellow solid. $^1$H-NMR (400 MHz, CDCl$_3$) δ (ppm) 8.36 (d, 1H); 8.11 (s, 1H); 7.42 (ddd, 1H); 7.11 (m, 3H); 6.95 (m, 3H); 4.12 (heptet, 1H); 3.94 (tt, 2H); 3.33 (m, 2H); 2.84 (m, 2H); 2.70 (m, 2H); 2.15 (m, 2H); 2.08 (s, 3H); 1.75 (m, 2H). LCMS (ESI), m/z 480 (M+H$^+$, 100%)

Compound A119

[4-(3'-Nitro-4-propyl-3,4,5,6-tetrahydro-2H-[1,4] bipyridinyl-2'-yloxy)-phenyl]-phenyl-methanone General Procedure 2: Intermediate monochloro as a yellow oil (142 mg, 80% yield). Exact mass calculated for $C_{18}H_{11}ClN_2O_4$ 354.04, LCMS (ESI) m/z 355.2 (M+H$^+$, 100%). [method 1a]. HPLC provided compound A119 as yellow solid (26 mg, 29%). $^1$H NMR 400 MHz CDCl$_3$ δ(ppm): 8.33 (d, 1H); 8.07 (d, 2H); 7.94 (d, 2H); 7.77 (m, 1H); 7.65 (t, 2H); 7.37 (d, 2H); 6.44 (d, 1H); 3.96 (d, 2H); 3.28 (td, 2H); 1.95 (d, 2H); 1.71-1.65 (m, 1H); 1.51-1.38 (m, 6H); 1.1 (t,3H). Exact mass calculated for C$_{26}$H$_{27}$N$_3$O$_4$ 445.20 LCMS (ESI) m/z 446.0 (M+H$^+$, 100%).

Compound A120

4-(4-{5-Nitro-6-[4-(2-trifluoromethyl-phenoxy)-piperidin-1-yl]-pyrimidin-4-yloxy}-phenyl)-butan-2-one

[Method 2 followed by method 1]. Yield 0.173 g, 83%. Yellow solid. $^1$H NMR 400 MHz CDCl$_3$ δ(ppm): 8.30 (s, 1H); 7.53 (m, 1H); 7.42 (m, 1H); 6.93 (m, 2H); 4.75 (m, 1H); 3.77 (m, 2H); 3.56 (m, 2H); 1.95 (m, 4H). LCMS (ESI) m/z 403 (M+H$^+$, 100%)

[Method 1a]. Compound A120 purified through a silica plug [SiO$_2$; EtOAc/hexane; 20:80]. Yield 0.067 g, 85%. Yellow oil. $^1$H NMR 400 MHz CDCl$_3$ δ (ppm): 8.12 (s, 1H); 7.53 (m, 1H); 7.42 (m, 1H); 7.15 (m, 2H); 6.97 (m, 4H); 3.72 (m, 2H); 3.60 (m, 2H); 2.82 (m, 2H); 2.70 (m, 3H); 2.08 (m, 4H); 1.97 (m, 4H). LCMS (ESI) m/z 531 (M+H$^+$, 100%)

Compound A121

4-(4-{6-[4-(3-Methyl-[1,2,4]oxadiazol-5-yl)-piperidin-1-yl]-5-nitro-pyrimidin-4-yloxy}-phenyl)-butan-2-one

[Method 1]. Purification by HPLC. Yield 52%. Yellow solid. $^1$H NMR 400 MHz CDCl$_3$ δ (ppm): 8.11 (s, 1H); 7.17 (d, 2H); 6.98 (d, 2H); 4.06 (d, 2H); 3.23 (t, 2H); 3.12 (d, 2H); 3.00 (m, 2H); 2.85 (t, 2H); 2.72 (t, 2H); 2.10 (s, 3H); 1.81 (m, 4H); 1.28 (m, 2H); 0.84 (t, 6H). LCMS (ESI) m/z 453 (M+H$^+$, 100%)

[Method 1a]. Purification by HPLC yielded a yellow solid. Yield 62%. $^1$H NMR 400 MHz CDCl$_3$ δ (ppm): 8.13 (s, 1H); 7.15 (d, 2H); 6.98 (d, 2H); 4.02 (d, 2H); 3.22 (m, 3H); 2.83 (t, 2H); 2.70 (t, 2H); 2.33 (s, 3H); 2.10 (m, 5H); 1.04 (m, 2H). LCMS (ESI) m/z 453.2 (M+H$^+$, 100%)

Compound A122

(4-{6-[4-(3-Methyl-[1,2,4]oxadiazol-5-yl)-piperidin-1-yl]-5-nitro-pyrimidin-4-yloxy}-phenyl)-phenyl-methanone Purification by HPLC yielded yellow solid. Yield 68%. $^1$H NMR 400 MHz CDCl$_3$ δ (ppm): 8.04 (s, 1H); 7.71 (d, 2H); 7.61 (d, 2H); 7.41 (m, 1H); 7.30 (m, 2H); 7.08 (m, 2H); 3.92 (d, 2H); 3.13 (m, 3H); 2.21 (s, 3H); 2.02 (m, 2H); 1.83 (m, 2H). LCMS (ESI) m/z 487.1 (M+H$^+$, 100%)

Compound A123

1-{6-[4-(4-Fluoro-benzoyl)-phenoxy]-5-nitro-pyrimidin-4-yl}-piperidine-4-carboxylic acid ethyl ester

[Method 1]. HPLC provided compound A123 as yellow solid (85 mg, 86% yield). $^1$H NMR 400 MHz CDCl$_3$ δ (ppm): 8.13 (s, 1H); 7.79 (d, 2H); 7.76 (d, 2H); 7.20 (d, 2H); 7.10 (d,2H); 4.09 (q, 2H); 3.96 (dt,2H); 3.15 (td, 2H); 2.59-2.52 (m, 1H); 1.96 (dt, 2H); 1.77 (td, 2H); 1.19 (t, 3H). Exact mass calculated for C$_{25}$H$_{23}$FN$_4$O$_6$ 494.16, LCMS (ESI) m/z 495.1 (M+H$^+$, 100%).

Compound A124

(4-Fluoro-phenyl)-{4-[5-nitro-6-(4-propyl-piperidin-1-yl)-pyrimidin-4-yloxy]-phenyl}-methanone

[Method 1]. HPLC provided compound A124 as yellow solid (69 mg, 84% yield). $^1$H NMR 400 MHz CDCl$_3$ δ(ppm): 8.10 (s, 1H); 7.78 (d, 2H); 7.76 (d, 2H); 7.19 (d, 2H); 7.09 (tt, 2H); 4.03 (d, 2H); 2.96 (td, 2H); 1.73 (dd, 2H); 1.51(m, 1H); 1.37 (m, 2H); 1.21 (m, 2H); 1.15(m, 2H); 0.83 (t, 3H). Exact mass calculated for C$_{25}$H$_{25}$FN$_4$O$_4$ 464.19, LCMS (ESI) m/z 465.2 (M+H$^+$, 100%).

Compound A125

4-[4-(3-Methyl-[1,2,4]oxadiazol-5-yl)-piperidin-1-yl]-6-(2-methyl-5-trifluoromethyl-2H-pyrazol-3-yloxy)-5-nitro-pyrimidine

[Method 3]. Purification by HPLC yielded yellow oil. Yield 38%. $^1$H NMR 400 MHz CDCl$_3$ δ (ppm): 8.16 (s, 1H); 6.38 (s, 1H); 3.98 (d, 2H); 3.65 (s, 3H); 3.21 (m, 3H); 2.26 (s, 3H); 2.08 (m, 2H); 1.89 (m, 2H). LCMS (ESI) m/z 417 (M+H$^+$, 100%)

Compound A126

4-(4-Methoxymethyl-piperidin-1-yl)-6-(2-methyl-5-trifluoromethyl-2H-pyrazol-3-yloxy)-5-nitro-pyrimidine

[Method 3]. Purification by HPLC yielded A126 as a yellow oil. Yield 21%. $^1$H NMR 400 MHz CDCl$_3$ δ (ppm): 8.05 (s, 1H); 6.30 (s, 1H); 3.93 (d, 2H); 3.59 (s, 3H); 3.15 (s, 3H); 3.07 (m, 2H); 2.89 (m, 2H); 1.69 (m, 3H); 1.15 (m, 2H). LCMS (ESI) m/z 417 (M+H$^+$, 100%)

Compound A127

4-{4-[6-(4-Methoxymethyl-piperidin-1-yl)-5-nitro-pyrimidin-4-yloxy]-phenyl}-butan-2-one

[Method 1a]. Purification by HPLC yielded A127 as a yellow solid. Yield 19%. $^1$H NMR 400 MHz CDCl$_3$ δ (ppm): 8.04 (s, 1H); 7.07 (d, 2H); 6.91 (d, 2H); 3.98 (d, 2H); 3.22 (s, 3H); 3.14 (d, 2H); 2.92 (m, 2H); 2.76 (m, 2H); 2.64 (m, 2H); 2.02 (s, 3H); 1.74 (m, 3H); 1.20 (m, 2H). LCMS (ESI) m/z 414.45 (M+H$^+$, 100%)

Compound A128

4-[4-(2-Methoxy-ethyl)-piperidin-1-yl]-6-(2-methyl-5-trifluoromethyl-2H-pyrazol-3-yloxy)-5-nitro-pyrimidine

[Method 2 Followed by 1a]. Purification by HPLC yielded orange solid. Yield 41%. $^1$H NMR 400 MHz CDCl$_3$ δ (ppm): 8.11 (s, 1H); 6.36 (s, 1H); 3.97 (d, 2H); 3.65 (s, 3H); 3.33 (m, 2H); 3.22 (s, 3H); 2.93 (m, 2H); 1.69 (m, 3H); 1.43 (m, 2H); 1.16 (m, 2H). LCMS (ESI) m/z 431.1 (M+H$^+$, 100%)

Compound A129

4-{4-[6-(4-Ethoxymethyl-piperidin-1-yl)-5-nitro-pyrimidin-4-yloxy]-phenyl}-butan-2-one

[Method 1a]. A129 was purified by HPLC. $^1$H NMR 400 MHz CDCl$_3$ δ (ppm): 8.00 (s, 1H), 7.10 (d, 2H), 6.80 (d, 2H), 3.90 (m, 2H), 3.30 (q, 2H), 3.15 (d, 2H), 2.90 (m, 2H), 2.70 (t, 2H), 2.60 (t, 2H), 2.00 (s, 3H) 1.70 (m, 3H), 1.20 (m, 2H), 1.00 (t, 2H). LCMS (ESI) for C$_{22}$H$_{28}$N$_4$O$_5$: m/z 429.0 (M+H$^+$, 100%)

Compound A130

4-(2,4-Difluoro-phenoxy)-5-nitro-6-[4-(pyridin-2-ylsulfanyl)-piperidin-1-yl]-pyrimidine

[Method 1a]. A130 was purified by semi preparatory HPLC afforded the pure product in 73%. $^1$H NMR, 400 MHz, CDCl$_3$, δ (ppm): 8.67 (d, 1H); 8.10(s, 1H); 7.80 (t, 1H); 7.42 (d, 1H); 7.31(t, 1H); 7.11 (m, 1H); 6.88 (m, 2H); 4.12 (m, 1H); 3.99 (m, 2H); 3.29 (m, 2H); 2.14 (m, 2H); 1.76 (m, 2H). LCMS (ESI) for C$_{20}$H$_{17}$F$_2$N$_5$O$_3$S: m/z 445 (M+H$^+$, 100%).

Compound A131

(4-Methoxy-2-{5-nitro-6-[4-(pyridin-2-ylsulfanyl)-piperidin-1-yl]-pyrimidin-4-yloxy}-phenyl)-phenyl-methanone

[Method 1a]. Purified by semi preparatory LCMS afforded the pure product in 38%. $^1$H NMR, 400 MHz, CDCl$_3$, δ (ppm): 8.55 (d, 1H); 7.98 (s, 1H); 7.62 (m, 3H); 7.46 (m, 2H); 7.31 (m, 3H); 7.15 (m, 1H); 6.80 (m, 1H); 6.72 (d, 1H); 4.05 (m, 1H); 3.86 (m, 2H); 3.82 (s, 3H, —OCH$_3$); 3.22 (m, 2H); 2.09 (m, 2H); 1.70 (m, 2H). LCMS (ESI) for C$_{28}$H$_{25}$N$_5$O$_5$S: m/z 543 (M+H$^+$, 100%).

Compound A132

4-(2,4-Difluoro-phenoxy)-6-(4-ethoxymethyl-piperidin-1-yl)-5-nitro-pyrimidine

[Method 1]. crude product was purified by HPLC to afford yellow oil (35.4 mg, 27%). $^1$H NMR 400 MHz CDCl$_3$ S (ppm): 8.20 (s, 1H), 7.20 (m, 1H), 6.80 (d, 2H), 7.00-6.90 (m, 2H), 4.10 (m, 2H), 3.50 (d, 2H), 3.10 (m, 2H), 2.00 (m, 1H), 1.90 (m, 2H), 1.40 (m, 2H), 1.20 (t, 3H). LCMS (ESI) for C$_{18}$H$_{20}$FN$_4$O$_4$: m/z 395.1 (M+H$^+$, 100%)

Compound A133

4-{4-[6-(4-Cyclopropylmethoxymethyl-piperidin-1-yl)-5-nitro-pyrimidin-4-yloxy]-phenyl}-butan-2-one

[Method 2 followed by method 1a]. Purification by HPLC yielded yellow solid. Yield 53%. $^1$H NMR 400 MHz CDCl$_3$ S (ppm): 7.97 (s, 1H); 7.02 (d, 2H); 6.84 (d, 2H); 3.92 (d, 2H); 3.13 (m, 2H); 3.07 (m, 2H); 2.86 (m, 2H); 2.71 (m, 21-1); 2.57 (m, 2H); 1.56 (s, 3H); 1.70 (m, 3H); 1.13 (m, 2H); 0.85 (m, 1H); 0.34 (m, 2H); 0.01 (m, 2H). LCMS (ESI) m/z 455.2 (M+H$^+$, 100%)

Compound A134

4-{4-[5-Nitro-6-(4-propoxymethyl-piperidin-1-yl)-pyrimidin-4-yloxy]-phenyl}-butan-2-one

[Method 2 Followed by 1a]. Purification by HPLC yielded yellow solid. Yield 22%. $^1$H NMR 400 MHz CDCl$_3$ S (ppm): 8.03 (s, 1H); 7.08 (d, 2H); 6.90 (d, 2H); 3.98 (d, 2H); 3.24 (t, 2H); 3.16 (d, 2H); 2.92 (m, 2H); 2.76 (m, 2H); 2.63 (m, 2H); 2.01 (s, 3H); 1.74 (m, 3H); 1.45 (m, 2H); 1.19 (m, 2H); 0.78 (t, 3H). LCMS (ESI) m/z 443.3 (M+H$^+$, 100%)

Compound A135

1-{4-[6-(4-Methoxymethyl-piperidin-1-yl)-5-nitro-pyrimidin-4-yloxy]-phenyl}-ethanone

[Method 1a]. Yield 12%. $^1$H NMR 400 MHz CDCl$_3$ δ (ppm): 8.03 (s, 1H); 7.89 (d, 2H); 7.10 (d, 2H); 3.99 (d, 2H); 3.21 (t, 3H); 3.13 (m, 2H); 2.93 (m, 2H); 2.47 (s, 3H); 1.75 (m, 3H); 1.19 (m, 2H). LCMS (ESI) m/z 387 (M$^+$H$^+$, 100%)

Compound A136

4-{4-[2-Nitro-3-(4-propyl-piperidin-1-yl)-phenoxy]-phenyl}-butan-2-one

Following general procedure 1, compound A136 was obtained as a yellow oil (70%). $^1$HNMR (CDCl$_3$, 400 MHz) δ 0.70 (t, 3H), 1.04-1.17 (m, 7H), 1.53(d, 2H), 1.97 (s, 3H), 2.54-2.70 (m, 6H), 3.10(d, 2H), 6.36 (d, 2H), 6.69 (d, 1H), 6.77 (d, 2H), 6.96 (d, 2H), 7.04(t, 1H). Exact mass calculated for C$_{24}$H$_{30}$N$_2$O$_4$ 410.22, found 411.2 (MH$^+$).

Compound A137

1-{4-[2-Nitro-3-(4-propyl-piperidin-1-yl)-phenoxy]-phenyl}-ethanone

Following the general procedure 1, compound A137 was obtained as a yellow solid (11%) $^1$HNMR (CDCl$_3$, 400 MHz) δ 0.82 (t, 3H), 1.17-1.28 (m, 7H), 1.64 (d, 2H), 2.50 (s, 3H), 2.67 (t, 2H), 3.20 (d, 2H), 6.58 (d, 1H), 6.89 (d, 1H), 6.98 (d, 2H), 7.24 (t, 1H), 7.88 (d, 2H). Exact mass calculated for C$_{22}$H$_{26}$N$_2$O$_4$ 382.19, found 383.3 (MH$^+$).

Compound A138

{4-[2-Nitro-3-(4-propyl-piperidin-1-yl)-phenoxy]-phenyl}-phenyl-methanone

The intermediate monofluoro was made by method 2. It was obtained as a yellow solid (88% yield). $^1$HNMR (CDCl$_3$, 400 MHz) δ 0.88 (t, 3H), 1.24-1.33 (m, 7H), 1.71 (m, 2H), 2.74 (t, 2H), 3.23 (d, 2H), 6.77(t, 1H), 6.87 (d, 1H), 7.30 (d, 1H). Exact mass calculated for C$_{14}$H$_{19}$FN$_2$O$_2$ 266.14, found 297.0 (MH$^+$).

Following the general procedure 2, compound A138 was obtained as a yellow oil (72%). $^1$HNMR (CDCl$_3$, 400 MHz) δ 0.75 (t, 3H), 1.10-1.24 (m, 7H), 1.59-1.62 (m, 2H), 2.67 (t, 2H), 3.20 (d, 2H), 6.59 (d, 1H), 6.88 (d, 1H), 6.95 (d, 2H), 7.21 (t, 1H), 7.34 (t, 2H), 7.44 (t, 1H), 7.63 (d, 2H), 7.68 (d, 2H). Exact mass calculated for $C_{27}H_{28}N_2O_4$ 444.20, found 445.1(MH$^+$).

Compound A139

3-{4-[2-Nitro-3-(4-propyl-piperidin-1-yl)-phenoxy]-phenyl}-3-oxo-propionic acid methyl ester

[Method 1]. Following the general procedure, compound A139 was obtained as a yellow solid (6%). $^1$HNMR (CDCl$_3$, 400 MHz) δ 0.71 (t, 3H), 0.99-1.16 (m, 7H), 1.54 (m, 2H), 2.33-2.35 (m, 2H), 2.62 (m, 2H), 3.68 (s, 3H), 6.74 (d, 1H), 6.96 (d, 2H), 7.06 (d, 1H), 7.37 (t, 1H), 7.83(d, 2H). Exact mass calculated for $C_{24}H_{28}N_2O_6$ 440.19, found 399.2 (MH$^+$).

Compound A140

4-{4-[6-(4-Butoxymethyl-piperidin-1-yl)-5-nitro-pyrimidin-4-yloxy]-phenyl}-butan-2-one

[Method 1a]. Purification by HPLC yielded yellow oil. Yield 41%. $^1$H NMR 400 MHz CDCl$_3$ δ (ppm): 8.03 (s, 1H); 7.08 (d, 2H); 6.89 (d, 2H); 3.97 (d, 2H); 3.27 (t, 2H); 3.16 (d, 2H); 2.90 (m, 2H); 2.76 (t, 2H); 2.63 (t, 2H); 2.02 (s, 3H); 1.74 (m, 1H); 1.70 (d, 2H); 1.41 (m, 2H); 1.22 (m, 4H); 0.78 (t, 3H). LCMS (ESI) m/z 457 (M$^+$H$^+$, 100%)

Compound A141

4-{4-[6-(4-Isobutoxymethyl-piperidin-1-yl)-5-nitro-pyrimidin-4-yloxy]-phenyl}-butan-2-one

[Method 1a]. Purification by HPLC yielded yellow oil. Yield 45%. $^1$H NMR 400 MHz CDCl$_3$ δ (ppm): 8.11 (s, 1H); 7.17 (d, 2H); 6.98 (d, 2H); 4.06 (d, 2H); 3.23 (t, 2H); 3.12 (d, 2H); 3.00 (m, 2H); 2.85 (t, 2H); 2.72 (t, 2H); 2.10 (s, 3H); 1.81 (m, 4H); 1.28 (m, 2H); 0.84 (t, 6H). LCMS (ESI) m/z 457 (M$^+$H$^+$, 100%)

Compound A142

(4-Fluoro-phenyl)-[4-(3'-nitro-4-propyl-3,4,5,6-tetrahydro-2H-[1,2']bipyridinyl-4'-yloxy)-phenyl]-methanone General Procedure 2 provided the monochloro intermediate as yellow crystal (484 mg, 66% yield). $^1$H NMR 400 MHz CDCl$_3$ δ (ppm): 8.21(d, 1H); 6.91 (d, 1H); 3.62(d, 2H); 3.09 (td, 2H); 1.89 (d, 2H); 1.61 (m, 1H); 1.50-1.34 (m, 6H); 1.03 (t, 3H). Exact mass calculated for $C_{13}H_{18}ClN_3O_2$ 283.11, LCMS (ESI) m/z 284.3 (M+H$^+$, 100%).
[Method 1a]. HPLC provided compound A142 as tan solid (34 mg, 37% yield). $^1$H NMR 400 MHz CDCl$_3$ δ (ppm): 7.83 (d, 1H); 7.78 (d, 2H); 7.75 (d, 2H); 7.15 (d, 2H); 7.11 (d, 2H); 6.58 (d, 1H); 3.51 (d, 2H); 2.97 (td, 2H); 1.73 (dd, 2H); 1.49-1.42 (m, 1H); 1.31-1.17 (m, 6H); 0.84 (t, 3H). Exact mass calculated for $C_{26}H_{26}FN_3O_4$ 463.19, LCMS (ESI) m/z 464.0 (M+H$^+$, 100%).

Compound A143

4-[4-(3'-Nitro-4-propyl-3,4,5,6-tetrahydro-2H-[1,2]bipyridinyl-4'-yloxy)-phenyl]-butan-2-one

[Method 1a]. HPLC provided compound A143 as yellow solid (57 mg, 70% yield). $^1$H NMR 400 MHz CDCl$_3$ δ(ppm): 7.75 (d, 1H); 7.11 (d, 2H); 6.95 (d, 2H); 6.46 (d, 2H); 3.46 (d, 2H); 2.90 (td, 2H); 2.81 (t, 2H); 2.68(t, 2H); 2.07 (s, 3H); 1.69 (m, 2H); 1.43-1.38 (m, 1H); 1.29-1.16 (m, 6H); 0.83 (t, 3H). Exact mass calculated for $C_{23}H_{29}N_3O_4$ 411.22, LCMS (ESI) m/z 412.0 (M+H$^{30}$, 100%).

Compound A144

3'-Nitro-4-propyl-4'-(4-[1,2,4]triazol-1-yl-phenoxy)-3,4,5,6-tetrahydro-2H-[1,2']bipyridinyl

[Method 1a]. HPLC provided compound A144 as yellow solid (46 mg, 56% yield). $^1$H NMR 400 MHz CDCl$_3$ δ(ppm): 8.62(s, 1H); 8.08 (s, 1H); 7.72(d, 1H); 7.58 (d, 2H); 7.18 (d, 2H); 6.49 (d, 1H); 3.43(d, 2H); 2.89 (td, 2H); 1.66 (d, 2H); 1.42-1.35 (m, 1H); 1.25-1.11 (m, 6H); 0.79 (t, 3H). Exact mass calculated for $C_{21}H_{24}N_6O_3$ 408.19, LCMS (ESI) m/z 409.0 (M+H$^+$, 100%).

Compound A145

1-{2-Nitro-3-[4-(3-oxo-butyl)-phenoxy]-phenyl}-piperidine-4-carboxylic acid ethyl ester The intermediate monofluoro was made by method 2. It was obtained as a yellow solid (90% yield). $^1$HNMR (CDCl$_3$, 400 MHz) δ 1.20 (t, 3H), 1.77-1.93 (m, 4H), 2.35 (m, 1H), 2.73-2.79 (t, 2H), 3.18-3.22 (m, 2H), 4.08 (q, 2H), 6.77-6.86 (m, 2H), 7.25-7.31 (m, 1H). Exact mass calculated for $C_{14}H_{17}FN_2O_4$ 296.12, found 297.2. Following general procedure 1, compound A145 was obtained as a yellow oil (61%). $^1$HNMR (CDCl$_3$, 400 MHz) δ 1.19 (t, 3H), 1.77-1.83 (m, 2H), 1.88-1.92(m, 2H), 2.07(s, 3H), 2.30-2.33 (m, 1H), 2.66-2.82(m, 6H), 3.18-3.22(m, 2H), 4.07 (q, 2H), 6.50 (d, 1H), 6.79 (d, 1H), 6.88(d, 2H), 7.08(d, 2H), 7.16(t,1H). Exact mass calculated for $C_{24}H_{28}N_2O_6$ 440.19, found 4-[1.1 (MH$^+$).

Compound A146

1-[3-(4-Benzoyl-phenoxy)-2-nitro-phenyl]-piperidine-4-carboxylic acid ethyl ester

[Method 2]. Intermediate was obtained as a yellow solid (90% yield). $^1$HNMR (CDCl$_3$, 400 MHz) δ 1.20 (t, 3H), 1.77-1.93 (m, 4H), 2.35 (m, 1H), 2.73-2.79 (t, 2H), 3.18-3.22 (m, 2H), 4.08 (q, 2H), 6.77-6.86 (m, 2H), 7.25-7.31 (m, 1H). Exact mass calculated for $C_{14}H_{17}FN_2O_4$ 296.12, found 297.2 (MH$^+$). Following the general procedure 1, compound A146 was obtained as a yellow solid (44%). $^1$HNMR (CDCl$_3$, 400 MHz) δ 1.20 (t, 3H), 1.80-1.91 (m, 4H), 2.37(m, 1H), 2.74-2.81(m, 2H), 3.22-3.25 (m, 2H), 4.10 (q, 2H), 6.68(d, 1H), 6.93 (d, 1H), 7.02 (d, 2H), 7.29 (t, 1H), 7.42(t, 1H), 7.52 (d, 1H), 7.70(d, 2H), 7.76(d, 2H). Exact mass calculated for $C_{27}H_{26}N_2O_6$ 474.18, found 475.2 (MH$^+$).

Compound A147

{4-[6-(4-Ethoxy-piperidin-1-yl)-5-nitro-pyrimidin-4-yloxy]phenyl}-(4-fluoro-phenyl)-methanone

[Method 1a]. Purification by HPLC. Yield 24%. $^1$H NMR 400 MHz CDCl$_3$ δ (ppm): 8.03 (s, 1H); 7.66 (m, 4H); 7.07 (m, 2H); 6.98 (m, 2H); 3.65 (m, 2H); 3.48 (m, 1H); 3.39 (q, 2H); 3.25 (m, 2H); 1.77 (m, 2H); 1.56 (m, 2H); 1.06 (t, 3H). LCMS (ESI) m/z 467 (M$^+$H$^+$, 100%)

Compound A148

1-[6-(2-Methyl-5-trifluoromethyl-2H-pyrazol-3-yloxy)-5-nitro-pyrimidin-4-yl]-piperidin-4-ol

[Method 3]. Purification by HPLC. Yield 35% yellow oil. $^1$H NMR 400 MHz DMSO (ppm): 8.26 (s, 1H); 6.67 (s, 1H); 4.82 (s, 1H); 3.75 (m, 2H); 3.68 (s, 3H); 3.31 (m, 2H); 1.76 (m, 2H); 1.41 (m, 2H). LCMS (ESI) m/z 389 (M$^+$H$^+$, 100%)

Compound A149

1-[6-(4-Acetyl-phenoxy)-5-nitro-pyrimidin-4-yl]-piperidine-4-carboxylic acid ethyl ester

[Method 1a]. The mixture was purified by HPLC to give compound A149 as a yellow solid (57 mg, 70%). $^1$HNMR (CDCl$_3$, 400 MHz) δ 1.28 (t, 3H), 1.80-1.90 (m, 2H), 1.98-2.03 (m, 2H), 2.62 (s, 3H), 3.22 (t, 2H), 3.97-4.03 (m, 2H), 4.17 (q, 2H), 7.25 (d, 2H), 8.02 (d, 2H), 8.17 (s, 1H). Exact mass calculated for C$_{20}$H$_{22}$N$_4$O$_6$ 414.15, found 415.2 (MH$^+$).

Compound A150

(1-{6-[4-(4-Fluoro-benzoyl)-phenoxy]-5-nitro-pyrimidin-4-yl]-piperidin-4-yl)-(4-fluoro-phenyl)-methanone

[Method 1a]. Purification by HPLC. Yield 40% of a yellow solid as TFA salt. $^1$H NMR 400 MHz CDCl$_3$ δ (ppm): 10.0 (s, 1H); 8.19 (s, 1H); 8.01 (m, 2H); 7.91 (m, 2H); 7.76 (m, 4H); 7.19 (m, 2H); 7.09 (m, 4H); 4.06 (d, 2H); 3.52 (m, 1H); 3.25 (m, 2H); 1.88 (m, 4H). LCMS (ESI) m/z 545.4 (M$^+$H$^+$, 100%)

Compound A151

4-(4-{6-[4-(4-Fluoro-benzoyl)-piperidin-1-yl]-5-nitro-pyrimidin-4-yloxy}-phenyl)-butan-2-one

[Method 1a]. Purification by HPLC yielded yellow solid. Yield 62%. $^1$H NMR 400 MHz CDCl$_3$ δ (ppm): 8.25 (s, 1H); 8.04 (m, 2H); 7.26 (m, 4H); 7.10 (d, 2H); 4.19 (m, 2H); 3.61 (m, 1H); 3.35 (m, 2H); 2.96(t; 2H); 2.83 (t, 2H); 2.21 (s, 3H); 2.00 (m, 4H). LCMS (ESI) m/z 493.4 (M$^+$H$^+$, 100%)

Compound A152

4-(4-Methanesulfonyl-phenoxy)-5-nitro-6-[4-(pyridin-2-ylsulfanyl)-cyclohexyl]-pyrimidine

[Method 1a]. The crude was dissolved in DMF and purified by HPLC. Yellow solid. Yield 66 mg, 72%. $^1$H-NMR (400 MHz, CDCl$_3$) δ(ppm): 8.43 (m, 1H); 8.12 (s, 1H); 7.94 (tt, 2H); 7.49 (ddd, 1H); 7.28 (tt, 2H), 7.15 (m, 1H); 7.01 (m, 1H); 4.10 (heptet, 1H); 3.96 (tt, 2H); 3.34 (m, 2H); 3.00 (s, 3H); 2.15 (m, 2H); 1.75 (m, 2H). LCMS (ESI), m/z 488 (M+H+, 100%)

Compound A153

4-(4-Methanesulfonyl-phenoxy)-5-nitro-6-[4-(pyridin-4-ylsulfanyl)-cyclohexyl]-pyrimidine

[Method 1a]. The crude was dissolved in dichloromethane and purified by HPLC. Yellow solid. Yield 85 mg, 87%. $^1$H-NMR (400 MHz, CDCl$_3$) δ(ppm): 8.41 (m, 2H); 8.10(s, 1H); 7.94 (m, 2H); 7.79 (m, 2H); 7.33 (m, 2H); 4.02 (m, 3H); 3.37 (m, 2H); 3.06 (s, 3H); 2.20 (m, 2H); 1.78 (m, 2H). LCMS (ESI), m/z 488 (M+H$^+$, 100%)

Compound A154

4-(4-Methanesulfonyl-phenoxy)-5-nitro-6-(4-phenyl-sulfanyl-cyclohexyl)-pyrimidine

[Method 1a]. The crude was dissolved in dichloromethane and purified by HPLC. Yellow solid. Yield 80 mg, 83%. $^1$H-NMR (400 MHz, CDCl$_3$) δ(ppm): 7.97 (s, 1H); 7.78 (m, 2H); 7.21 (m, 2H); 7.15 (m, 3H); 7.08 (m, 2H); 3.80 (m, 2H); 3.16 (heptet, 1H); 3.06 (m, 2H); 2.86 (s, 3H); 1.87 (m, 2H); 1.50 (m, 2H). LCMS (ESI), m/z 487 (M+H$^+$, 100%)

Compound A155

1-[5-Nitro-6-(4-trifluoromethylsulfanyl-phenoxy)-pyrimidin-4-yl]-piperidine-4-carboxylic acid ethyl ester

[Method 1a]. yellow solid (92%). $^1$H NMR (CDCl$_3$, 400 MHz) δ 1.28 (t, 3H), 1.79 (m, 2H), 1.98 (m, 2H), 2.58 (m, 1H), 3.18 (t, 2H), 3.85 (m, 2H), 4.10 (q, 2H), 7.58 (d, 2H), 7.67 (d, 1H), 8.09 (s, 1H), 10.13 (s, 1H). Exact mass calculated for C$_{19}$H$_{20}$F$_3$N$_5$O$_4$S 471.45, found 472.1 (MH$^+$).

Compound A156

5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine Using the method described herein Compound A156 was prepared. The crude mixture was purified by flash chromatography, eluted with 50% ethyl acetate/hexane to afford Compound A156 (316.5 mg, 67.8%). $^1$H NMR 400 MHz CDCl$_3$ δ (ppm): 8.24 (s, 1H), 7.93 (d, 2H), 7.26(d, 2H), 5.95(s, 1H), 4.10 (m, 2H), 3.96 (m, 2H), 3.17 (q, 1H), 3.02 (s, 3H), 2.14 (m, 2H), 1.95 (m, 2H), 1.28 (d, 6H). LCMS (ESI) for C$_{24}$H$_{29}$N$_5$O$_6$S: m/z 516.3 (M+H$^+$, 100%)

Compound A157

4-[4-(3-Isopropyl-[1,2,4]oxadiazol-5-371)-piperidin-1-yl]-6-(4-methanesulfonyl-phenoxy)-pyrimidine-5-carbaldehyde Compound A156 was hydrolyzed using HCl aq in a mixture of acetone/acetonitrile to give Compound A157 (30.0 mg, 93.72%); $^1$H NMR 400 MHz CDCl$_3$ δ (ppm): 10.3(s, 1H), 8.17 (s, 1H), 7.96 (d, 2H), 7.32(d, 2H), 4.12 (m, 2H), 3.30 (m, 2H), 3.22 (m, 1H), 3.00(s, 3H), 3.00 (q, 1H), 2.06 (m, 2H), 2.00 (m, 2H), 1.27 (d, 6H). LCMS (ESI) for C$_{22}$H$_{25}$N$_5$O$_5$S: m/z 472.2 (M+H$^+$, 100%).

Compound A158

5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine White solid, $^1$H NMR 400 MHz CDCl$_3$ δ (ppm): 8.62 (s, 1H), 8.31(s, 1H), 8.08(d, 2H), 7.28(d, 2H), 6.06(s, 1H), 4.24 (m, 2H), 4.13 (m, 2H), 4.04 (m, 2H), 3.23 (m, 2H), 3.07(q, 1H), 2.20 (m, 2H), 2.02 (m, 2H), 1.33 (d, 6H). LCMS (ESI) for C$_{25}$H$_{27}$N$_7$O$_4$S: m/z 522.3 (M+H$^+$, 100%).

The intermediate 4-chloro-5-[1,3]dioxolan-2-yl-6-(4-[1,2,3]thiadiazol-4-yl-phenoxy)-pyrimidine was prepared using the following method: Phosphorus Oxychloride (200 mL, 2184.8 mmol) was added drop wise (additional funnel) in DMF at 0° C., and stirred for 1 hour, treated with 4,6 dihydroxypyridimidine (50.0 g, 446.1 mmol) and stirred for half hour at room temperature. The heterogeneous mixture was refluxed for 3 hours. The volatiles were removed at reduce pressure, and the residue was poured in ice water and extract with chloroform and diethylether, wash with sodium bicarbonate and concentrate under high vacuum. The resulting mixture was purified on silica ($CH_2Cl_2$) to afford 4,6-dichloro-pyrimidine-5-carbaldehyde as a yellow solid (54.0 g). $^1$H NMR 400 MHz $CDCl_3$ δ (ppm): 10.3 (s, 1H, aldehyde), 8.7 (s, 1H, pyrimidine).

Compound 4,6-Dichloro-pyrimidine-5-carbaldehyde (8.6 g, 0.049 mmol), anhydrous ethylene glycol (8.2 ml) and p-Toluene-sulfonic acid (150 mg) were mixture in benzene (200 mL) and heated under reflux for 3 hours. Concentrate under high vacuum, worked up with chloroform, water, sodium bicarbonate and sodium chloride, concentrate. The reaction mixture was purified on silica ($CH_2Cl_2$) to give 4,6-Dichloro-5-[1,3]dioxolan-2-yl-pyrimidine (8.86 g, 82.5%). $^1$H NMR 400 MHz $CDCl_3$ δ (ppm): 8.8 (s, 1H), 6.3 (s, 1H), 4.3 (m, 2H,), 4.1(m, 2H).

To a mixture of 4,6-dichloro-5-[1,3]dioxolan-2-yl-pyrimidine (100.0 mg, 0.45 mmol) and added Potassium Carbonate (80.62 mg, 0.45 mmol) in DMF (5 mL) cooled to 0° C. was added a solution of 4-[1,2,3]-thiadiazol-4-yl-phenol (DMF) drop wise. The resulting mixture was stirred at room temperature for 30 minutes to give 4-chloro-5-[1,3]dioxolan-2-yl-6-(4-[1,2,3]thiadiazol-4-yl-phenoxy)-pyrimidine. LCMS (ESI) for $C_{15}H_{11}ClN_4O_3S$: m/z 362.9 (M+H$^+$, 100%).

Compound A159

4-[4-(3-Isopropyl-[1,2,4]oxadiazol-5-yl)-piperidin-1-yl]-6-(4-[1,2,3]thiadiazol-4-yl-phenoxy)-pyrimidine-5-carbaldehyde White solid (18.01 mg, 25.9%); $^1$H NMR 400 MHz $CDCl_3$ δ (ppm): 10.7(s, 1H), 8.67 (s, 1H), 8.26(s, 1H), 8.14(d, 2H), 7.34(d, 2H), 4.19 (m, 2H), 3.40 (m, 2H), 3.26 (m, 1H), 3.07(q, 1H), 2.20 (m, 2H), 2.02 (m, 2H), 1.33 (d, 6H). LCMS (ESI) for $C_{23}H_{23}N_7O_3S$: m/z 478.2 (M+H$^+$, 100%).

Compound A160

4-[4-(3-Isopropyl-[1,2,4]oxadiazol-5-yl)-piperidin-1-yl]-6-(4-[1,2,3]thiadiazol-4-yl-phenoxy)-pyrimidine-5-carboxylic acid White solid (3.8 mg, 13.63%); NMR 400 MHz MeOD δ (ppm): 9.23 (s, 1H), 8.13(d, 2H) 8.06(s, 1H), 7.29(d, 2H), 4.61 (m, 2H), 3.30 (m, 2H), 3.05(q, 1H), 2.15 (m, 2H), 1.97 (m, 2H), 1.32 (d, 6H); LCMS (ESI) for $C_{23}H_{23}N_7O_4S$: m/z 494.3 (M+H$^+$, 100%).

Compound A161

[4-[4-(3-Isopropyl-[1,2,4]oxadiazol-5-yl)-piperidin-1-yl]-6-(4-1,2,3]thiadiazol-4-yl-phenoxy)-pyrimidin-5-yl]-methanol Yellow solid (17.5 mg, 85.03%); $^1$H NMR 400 MHz $CDCl_3$ δ (ppm): 8.63 (s, 1H), 8.31(s, 1H), 8.11(d, 2H), 7.27(d, 2H), 4.77 (s, 2H), 4.23 (m, 2H), 3.28 (m, 2H), 3.28 (m, 1H), 3.07(q, 1H), 2.21 (m, 2H), 2.03 (m, 2H), 1.34 (d, 6H); LCMS (ESI) for $C_{23}H_{25}N_7O_3S$: m/z 480.3 (M+H$^+$, 100%)

Compound A162

[4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine White solid, (4.2 mg, 15.83%), LCMS (ESI) for $C_{25}H_{30}N_8O_2S$: m/z 507.3 (M+H$^+$, 100%).

Compound A163

4-[4-(3-tert-Butyl-[1,2,4]oxa diazol-5-yl)-piperidin-1-yl]-6-(6-methanesulfonyl-pyridin-3-yloxy)-5-nitro-pyrimidine Compound A163 was prepared using the general procedure for the addition of amine to pyrimidine; yellow solid (82 mg, 81%). $^1$H NMR 400 MHz $CDCl_3$ δ(ppm): 8.60(s, 1H); 8.19(s, 1H); 8.18(d,1H); 7.79(d,1H); 4.12(db,2H); 3.39-3.29 (m,3H); 3.26(s,3H); 2.22(db,2H); 2.06-2.02(m,2H); 1.36(s, 9H).Exact mass calculated for $C_{21}H_{25}N_7O_6S$ 503.16, LCMS (ESI) m/z 504.2(M+H$^+$, 100%).

Compound A164

4-[4-(3-Isopropyl-[1,2,4]oxadiazol-5-yl)-piperidin-1-yl]-6-(4-methanesulfonyl-phenoxy)-2-methyl-pyrimidine-5-carbonitrile To a solution of 4-chloro-6-(4-methanesulfonyl-phenoxy)-2-methyl-pyrimidine-5-carbonitrile (80.0 mg, 0.25 mmol) and 4-(3-isopropyl-[1,2,4]oxadiazol-5-yl)-piperidine (107.1 mg, 0.50 mmol) in DMF (1 mL) was added potassium carbonate (68.3 mg, 0.50 mmol) and the resulting mixture was left stirring for 2 hours at room temperature. Worked up with ethyl acetate, sodium bicarbonate, dried with magnesium sulfate and evaporated. The crude product was crystallized with ethyl acetate/hexane over night and filtered off to afford Compound A164 as a yellow solid (30.6 mg). LCMS (ESI) for $C_{23}H_{26}N_6O_4S$: m/z 483.3 (M+H$^+$, 100%), $^1$H NMR 400 MHz $CDCl_3$ δ (ppm): 8.00 (d, 2H), 7.38 (d, 2H), 4.82 (m, 2H), 3.45 (m, 2H), 3.31 (m, 1H), 3.10 (s, 3H), 3.08 (m, 1H), 2.35 (s, 3H), 2.24(m, 2H), 2.03 (m, 2H), 1.34(d, 6H).

Compound A165

1-[4-[4-(3-Isopropyl-[1,2,4]oxadiazol-5-yl)-piperidin-1-yl]-6-(4-methanesulfonyl-phenoxy)-pyrimidin-5-yl]-ethanone To a solution of 1-[4-chloro-6-(4-methanesulfonyl-phenoxy)-pyrimidin-5-yl]-ethanone (0.21 mmol, 70 mg) and 4-(3-isopropyl-[1,2,4]oxadiazol-5-yl)-piperidine (0.21 mmol, 49 mg) in N,N-dimethyl formamide (500 uL) was added potassium carbonate (0.21 mmol, 29 mg). The mixture was microwaved at 100° C. for 150 seconds. Its progress was monitored by thin layer chromatography and LCMS. The reaction was treated with water and the desired compound was extracted in ethyl acetate. Organic layer was evaporated in vacuo. Purification by HPLC provided Compound A165 as a white solid (20 mg, 20%). $^1$H-NMR (400 MHz, $CDCl_3$) δ(ppm): 8.24 (s, 1H); 8.01 (d, 2H); 7.32 (d, 2H); 4.02 (m, 2H);

3.22 (m, 3H); 3.10 (m, 1H); 3.08 (s, 3H); 2.69 (s, 3H); 2.18 (m, 2H); 2.02 (m, 2H); 1.35 (d, 6H). LCMS (ESI), m/z 486.3 (M+H+, 100%).

Example 13

Syntheses of Compounds of the Present Invention

Compound B1

1-{6-[(Benzo[1,3]dioxol-5-ylmethyl)-amino]-5-nitro-pyrimidin-4-yl}-piperidine-4-carboxylic acid ethyl ester; General Method 14

Starting material, {6-chloro-5-nitro-pyrimidin-4-yl}-piperidine-4-carboxylic acid ethyl ester was prepared by general method 2. A mixture of 6-chloro-5-nitro-pyrimidin-4-yl}-piperidine-4-carboxylic acid ethyl ester (63 mg, 0.2 mmol), amine (1.1 eqv, 33 mg, 0.22 mmol) and potassium carbonate (1.1 eqv, 31 mg, 0.22 mmol) in DMF (1 ml) was stirred at 100° C. for 3 minutes in Smith microwave Synthesiser. HPLC purification afforded compound B1 as yellow oil (59 mg, 54%). $^1$H NMR 400 MHz CDCl$_3$ δ (ppm): 8.58 (s, 1H); 8.01 (s, 1H); 6.63 (d, 2H); 6.61 (s, 1H); 5.79 (s, 2H); 4.51 (d, 2H); 3.99 (q, 2H) 3.70 (dt, 2H); 3.10 (td, 2H); 2.48 (m, 1H); 1.88 (dt, 2H); 1.70 (td, 2H); 1.09 (t, 3H). Exact mass calculated for $C_{20}H_{23}N_5O_6$ 429.16, LCMS (ESI) m/z 430.0 (M+H$^+$, 100%).

Compound B2

1-[5-Nitro-6-(3,4,5-trimethoxy-benzylamino)-pyrimidin-4-yl]-piperidine-4-carboxylic acid ethyl ester

[Method 14]. Filtered the reaction mixture and the filtrate was purified by semi preparatory HPLC afforded the pure product in 28% yield. $^1$H NMR, 400 MHz, CDCl$_3$, δ (ppm): 8.71 (m, 1H); 8.07 (s, 1H); 7.10 (s, 2H); 6.42 (s, 2H); 4.56 (d, 2H); 4.02 (q, 2H); 3.71 (s, 6H); 3.69 (s, 3H); 3.16 (m, 2H); 2.52 (m, 1H); 1.91 (m, 2H); 1.74 (m, 2H); 1.12 (t, 3H). LCMS (ESI) for $C_{22}H_{29}N_5O_7$: m/z 475 (M+H$^{30}$, 100%).

Compound B3

(5-Nitro-6-piperidin-1-yl-pyrimidin-4-yl)-(3-trifluoromethyl-benzyl)-amine

[Method 14]. The product was purified by Preparatory TLC using hexane/ethyl acetate (9:1). $^1$H NMR 400 MHz CDCl$_3$ δ (ppm): 8.65 (s); 8.05 (s, 1H, pyrimidine); 7.65 (d, 1H); 7.50 (m, 2H); 7.40 (d, 1H); 5.00(s, 2H); 3.50 (m, 4H), 1.80 (s, NH); 1.75-1.60 (m, 5H)

Compound B4

1-[5-Nitro-6-(2-trifluoromethyl-benzylamino)-pyrimidin-4-yl]-piperidine-4-carboxylic acid ethyl ester

[Method 14]. The residue was filtered through a silica plug [SiO$_2$; EtOAc/hexane; 50:50]and solvent removed in vacuo. Yield 0.143 g, 50%. Yellow oil. $^1$H NMR 400 MHz CDCl$_3$ δ(ppm): 8.63 (m, 1H); 8.07 (s, 1H); 7.68 (m, 1H); 7.53 (m, 2H); 7.40 (m, 1H); 5.01 (m, 2H); 4.17 (m, 2H); 3.89 (m, 2H); 3.21 (m, 2H); 2.63 (m, 1H); 2.03 (m, 2H); 1.85 (m, 2H); 1.28 (m, 3H). LCMS (ESI) m/z 390 (M+H$^+$, 100%)

Compound B5

1-[5-Nitro-6-(4-trifluoromethyl-benzylamino)-pyrimidin-4-yl]-piperidine-4-carboxylic acid ethyl ester

[Method 14]. Solvent was removed in vacuo and residue was purified by preparatory TLC. [SiO$_2$; EtOAc/hexane; 10:90]. Yield 0.227 g, 73%. Yellow oil. $^1$H NMR 400 MHz CDCl$_3$ δ(ppm): 8.69 (m, 1H); 8.06 (s, 1H); 7.60 (d, 2H); 7.45 (d, 2H); 4.87 (m, 2H); 4.17 (m, 2H); 3.90 (m, 2H); 3.22 (m, 2H); 2.64 (m, 1H); 2.03 (m, 2H); 1.85 (m, 2H); 1.28 (m, 3H)

Compound B6

1-[5-Nitro-6-(3-trifluoromethyl-benzylamino)-pyrimidin-4-yl]-piperidine-4-carboxylic acid ethyl ester

[Method 14]. Solvent was removed in vacuo and residue was purified by preparatory TLC. [SiO$_2$; EtOAc/hexane; 10:90. Yield 0.177 g, 65%. Yellow solid. $^1$H NMR 400 MHz CDCl$_3$ δ(ppm): 8.69 (m, 1H); 8.06 (s, 1H); 7.61 (m, 1H); 7.54 (m, 2H); 7.48 (m, 1H); 4.87 (m, 2H); 4.17 (m, 2H); 3.90 (m, 2H); 3.22 (m, 2H); 2.64 (m, 1H); 2.03 (m, 2H); 1.85 (m, 2H); 1.28 (m, 3H)

Compound B7

(5-Nitro-6-piperidin-1-yl-pyrimidin-4-yl)-(2-trifluoromethyl-benzyl)-amine

[Method 14]. The product was purified by Preparatory TLC using hexane/ethyl acetate (9:1). $^1$H NMR 400 MHz CDCl$_3$ δ (ppm): 8.65 (s); 8.05 (s, 1H, pyrimidine); 7.65 (d, 1H); 7.50 (m, 2H); 7.40 (d, 1H); 5.00(s, 2H); 3.50 (m, 4H,), 1.80 (s, NH),1.75-1.60 (m, 5H)

Compound B8

(5-Nitro-6-piperidin-1-yl-pyrimidin-4-yl)-(4-trifluoromethyl-benzyl)-amine;

The product was purified by Preparatory TLC using hexane/ethyl acetate/dichloromethane (8:1:1). $^1$H NMR 400 MHz CDCl$_3$ δ (ppm): 9.05 (s); 8.05 (s, 1H, pyrimidine); 7.70 (d, 2H); 7.50 (d, 2H); 4.90 (s, 2H); 3.40 (m, 4H,), 1.75-1.60 (.m, 6H).

Compound B9

1-[5-Amino-6-(3-trifluoromethyl-benzylamino)-pyrimidin-4-yl]-piperidine-4-carboxylic acid ethyl ester; General Method 15

Di-substituted-5-nitropyrimidine (180 mg, 0.4 mmol) was dissolved in ethyl acetate (5 mL) and flushed with N$_2$ gas. Palladium catalyst [5%, Pd/C] was added and hydrogen gas was introduced into the mixture. The reaction mixture was stirred for 4 hours at room temperature. The reaction mixture was filtered through Celite and the solvent was removed under vacuo. Yield 0.158 g, 94%. White solid. $^1$H NMR 400 MHz CDCl$_3$ δ(ppm): 8.69 (m, 1H); 8.06 (s, 1H); 7.61 (m, 1H); 7.54 (m, 2H); 7.48 (m, 1H); 4.87 (m, 2H); 4.17 (m, 2H);

3.90 (m, 2H); 3.22 (m, 2H); 2.64 (m, 1H); 2.03 (m, 2H); 1.85 (m, 2H); 1.28 (m, 3H). LCMS (ESI) m/z 424 (M+H$^+$, 100%)

Compound B10

1-[5-Amino-6-(4-trifluoromethyl-benzylamino)-pyrimidin-4-yl]-piperidine-4-carboxylic acid ethyl ester

[Method 15]. Yield 0.121 g, 72%. White solid. $^1$H NMR 400 MHz CDCl$_3$ δ(ppm): 8.13 (s, 1H); 7.58 (d, 2H); 7.46 (d, 2H); 4.75 (m, 2H); 4.17 (m, 2H); 3.43 (m, 2H); 2.86 (m, 2H); 2.49 (m, 1H); 2.05 (m, 2H); 1.86 (m, 2H); 1.29 (m, 3H). LCMS (ESI) m/z 424 (M+H$^+$, 100%)

Compound B11

1-[6-(4-Bromo-phenylamino)-5-nitro-pyrimidin-4-yl]-piperidine-4-carboxylic acid ethyl ester; General Method 16

[6-chloro-5-nitro-pyrimidin-4-yl]-piperidine-4-carboxylic acid ethyl ester (415 mg, 1.32 mmol) and 4-bromoaniline (309 mg, 1.80 mmol) were dissolved in anhydrous 1,4-dioxane (0.5-1 ml) and irradiated in a sealed microwave reaction tube at 250° C. for 300 seconds. The reaction mixture was passed through a silica plug [SiO$_2$; EtOAc/hexane; 20:80]. Yield 0.070 g, 12%. Yellow solid. $^1$H NMR 400 MHz CDCl$_3$ δ(ppm): 9.98 (s, 1H); 8.03 (s, 1H); 7.41 (m, 2H); 7.17 (m, 2H); 4.09 (m, 2H); 3.83 (m, 2H); 3.16 (m, 2H); 2.77 (m, 1H); 1.97 (m, 2H); 1.78 (m, 2H); 1.20 (m, 3H). LCMS (ESI) m/z 451, 452 (M+H$^+$, 100%)

Compound B12

1-[5-Nitro-6-(4-trifluoromethyl-phenylamino)-pyrimidin-4-yl]-piperidine-4-carboxylic acid ethyl ester

[Method 16]. Yield 0.010 g, 14%. Yellow solid. $^1$H NMR 400 MHz CDCl$_3$ δ (ppm): 10.11 (s, 1H); 8.07 (s, 1H); 7.69 (d, 2H); 7.54 (d, 2H); 4.09 (m, 2H); 3.84 (m, 2H); 3.17 (m, 2H); 2.58 (m, 1H); 1.97 (m, 2H); 1.79 (m, 21-1); 1.20 (m, 3H). LCMS (ESI) m/z 440 (M+H$^+$, 100%)

Compound B13

1-[6-(Methyl-phenyl-amino)-5-nitro-pyrimidin-4-yl]-piperidine-4-carboxylic acid ethyl ester

[Method 16]. Yield 0.062 g, 93%. Yellow solid. $^1$H NMR 400 MHz CDCl$_3$ δ(ppm): 8.09 (s, 1H); 7.33 (m, 2H); 7.17 (m, 3H); 4.14 (m, 2H); 3.92 (m, 2H); 3.54 (s, 3H); 3.19 (m, 2H); 2.58 (m, 1H); 1.99 (m, 2H); 1.83 (m, 2H); 1.26 (m, 3H). LCMS (ESI) m/z 386 (M+H$^+$, 100%)

Compound B14

1-[5-Nitro-6-(4-trifluoromethoxy-phenylamino)-pyrimidin-4-yl]-piperidine-4-carboxylic acid ethyl ester

[Method 16]. Yield 0.066 g, 92%. Yellow solid. $^1$H NMR 400 MHz CDCl$_3$ δ(ppm): 10.09 (s, 1H); 8.11 (s, 1H); 7.63 (d, 2H); 7.22 (d, 2H); 4.17 (m, 2H); 3.91 (m, 2H); 3.25 (m, 2H); 2.66 (m, 1H); 2.05 (m, 2H); 1.86 (m, 2H); 1.28 (m, 3H). LCMS (ESI) m/z 456 (M+H$^+$, 100%)

Compound B15

1-[6-(4-Fluoro-phenylamino)-5-nitro-pyrimidin-4-yl]-piperidine-4-carboxylic acid ethyl ester

[Method 16]. Yield 0.071 g, 100%. Yellow solid. $^1$H NMR 400 MHz CDCl$_3$ δ(ppm): 10.01 (s, 1H); 8.08 (s, 1H); 7.50 (m, 2H); 7.06 (m, 2H); 4.16 (m, 2H); 3.90 (m, 2H); 3.23 (m, 2H); 2.65 (m, 1H); 2.03 (m, 2H); 1.86 (m, 2H); 1.27 (m, 3H). LCMS (ESI) m/z 390 (M+H$^+$, 100%)

Compound B16

1-[6-(3,5-Difluoro-phenylamino)-5-nitro-pyrimidin-4-yl]-piperidine-4-carboxylic acid ethyl ester

[Method 16]. Yield 0.066 g, 89%. Yellow solid. $^1$H NMR 400 MHz CDCl$_3$ δ(ppm): 10.13 (s, 1H); 8.15 (s, 1H); 7.29 (m, 2H); 6.60 (m, 1H); 4.16 (m, 2H); 3.90 (m, 2H); 3.22 (m, 2H); 2.64 (m, 1H); 2.03 (m, 2H); 1.84 (m, 2H); 1.27 (m, 3H). LCMS (ESI) m/z 408 (M+H$^+$, 100%)

Compound B17

1-[6-(3,5-Dichloro-phenylamino)-5-nitro-pyrimidin-4-yl]-piperidine-4-carboxylic acid ethyl ester

[Method 16]. Yield 0.023 g, 33%. Yellow solid. $^1$H NMR 400 MHz CDCl$_3$ δ(ppm): 10.08 (s, 1H); 8.16 (s, 1H); 7.62 (m, 2H); 7.15 (m, 1H); 4.17 (m, 2H); 3.91 (m, 2H); 3.23 (m, 2H); 2.66 (m, 1H); 2.05 (m, 2H); 1.85 (m, 2H); 1.28 (m, 3H). LCMS (ESI) m/z 440 (M+H$^+$, 100%)

Compound B18

1-[6-(Benzo[1,3]dioxol-5-ylamino)-5-nitro-pyrimidin-4-yl]-piperidine-4-carboxylic acid ethyl ester

[Method 16]. The solvent was removed in vacuo and the residue purified by preparatory TLC [SiO2; EtOAc/hexane; 20:80]. Yield 0.063 g, 70%. Orange oil. $^1$H NMR 400 MHz CDCl$_3$ δ(ppm): 9.96 (s, 1H); 8.09 (s, 1H); 7.17 (s, 1H); 6.81 (m, 2H); 5.98 (s, 2H); 4.16 (q, 21-1); 3.91 (m, 2H); 3.24 (m, 2H); 2.64 (m, 1H); 2.04 (m, 2H); 1.86 (m, 2H); 1.27 (m, 3H). LCMS (ESI) m/z 416 (M+H$^+$, 100%)

Compound B19

1-[6-(2-Bromo-4-trifluoromethoxy-phenylamino)-5-nitro-pyrimidin-4-yl]-piperidine-4-carboxylic acid ethyl ester

[Method 16]. The reaction mixture was passed through a silica plug [SiO2; EtOAc/hexane; 10:90]. Yield 0.020 g, 24%. Yellow solid. $^1$H NMR 400 MHz CDCl$_3$ δ(ppm): 10.21 (s, 1H); 8.28 (m, 1H); 8.06 (s, 1H); 7.42 (m, 1H); 7.17 (m, 1H); 4.09 (m, 2H); 3.85 (m, 3.85); 3.18 (m, 2H); 2.55 (m, 1H); 1.98 (m, 2H); 1.79 (m, 2H); 1.20 (m, 3H). LCMS (ESI) m/z 535, 536 (M+H$^+$, 100%)

Compound B20

1-[6-(2-Fluoro-phenylamino)-5-nitro-pyrimidin-4-yl]-piperidine-4-carboxylic acid ethyl ester

[Method 16]. The solvent was removed in vacuo and the residue was purified by preparatory TLC [SiO$_2$; EtOAc/hexane; 20:80]. Yield 0.016 g, 22%. Yellow oil. $^1$H NMR 400 MHz CDCl$_3$ δ(ppm): 10.11 (s, 1H); 8.16 (m, 2H); 7.15 (m, 3H); 4.16 (m, 2H); 3.92 (m, 2H); 3.25 (m, 2H); 2.65 (m, 1H); 2.03 (m, 2H); 1.86 (m, 2H); 1.28 (m, 3H). LCMS (ESI) m/z 390 (M+H$^+$, 100%)

Compound B21

1-[6-(3-Fluoro-phenylamino)-5-nitro-pyrimidin-4-yl]-piperidine-4-carboxylic acid ethyl ester

[Method 16]. The reaction mixture was passed through a silica plug [SiO2; EtOAc/hexane; 20:80]. Yield 0.034 g, 43%. Yellow solid. $^1$H NMR 400 MHz CDCl$_3$ δ(ppm): 10.12 (s, 1H); 8.14 (s, 1H); 7.63 (m, 1H); 7.31 (m, 1H); 7.23 (m, 1H); 6.87 (m, 1H); 4.17 (m, 2H); 3.91 (m, 2H); 3.24 (m, 2H); 2.65 (m, 1H); 2.05 (m, 2H); 1.86 (m, 2H); 1.28 (m, 3H). LCMS (ESI) m/z 390 (M+H$^+$, 100%)

Compound B22

1-{6-[(2-Fluoro-phenyl)-methyl-amino]-5-nitro-pyrimidin-4-yl}-piperidine-4-carboxylic acid ethyl ester

[Method 16]. purified by preparatory TLC [SiO2; EtOAc/hexane; 20:80]. Yield 0.018 g, 23%. Yellow oil. $^1$H NMR 400 MHz CDCl$_3$ δ(ppm): 8.09 (s, 1H); 7.14 (m, 2H); 7.03 (m, 2H); 4.15 (m, 2H); 3.93 (m, 2H); 3.51 (s, 3H); 3.20 (m, 2H); 2.60 (m, 1H); 2.00 (m, 2H); 1.83 (m, 2H); 1.27 (m, 3H). LCMS (ESI) m/z 404 (M+H$^+$, 100%)

Compound B23

1-[6-(Ethyl-phenyl-amino)-5-nitro-pyrimidin-4-yl]-piperidine-4-carboxylic acid ethyl ester

[Method 16]. The solvent was removed in vacuo and the residue purified by preparatory TLC [SiO$_2$; EtOAc/hexane; 20:80]. Yield 0.008 g, 8%. Yellow oil. $^1$H NMR 400 MHz CDCl$_3$ δ(ppm): 8.13 (s, 1H); 7.32 (m, 2H); 7.20 (m, 2H); 7.12 (m, 1H); 4.14 (m, 4H); 3.86 (m, 2H); 3.14 (m, 5H); 2.57 (m, 1H); 1.98 (m, 2H); 1.83 (m, 2H); 1.24 (m, 4H). LCMS (ESI) m/z 400 (M+H$^+$, 100%)

Compound B24

1-{6-[(4-Chloro-phenyl)-methyl-amino]-5-nitro-pyrimidin-4-yl}-piperidine-4-carboxylic acid ethyl ester

[Method 16]. The solvent was removed in vacuo and the residue purified by preparatory TLC [SiO$_2$; EtOAc/hexane; 20:80]. Yield 0.008 g, 8%. Yellow oil. $^1$H NMR 400 MHz CDCl$_3$ δ(ppm): 8.10 (s, 1H); 7.29 (d, 2H); 7.10 (d, 2H); 4.15 (m, 2H); 3.93 (m, 2H); 3.52 (s, 3H); 3.21 (m, 2H); 2.56 (m, 1H); 2.01 (m, 2H); 1.85 (m, 2H); 1.26 (m, 3H). LCMS (ESI) m/z 420 (M+H$^+$, 100%)

Compound B25

1-[6-(4-Difluoromethyl-benzylamino)-5-nitro-pyrimidin-4-yl]-piperidine-4-carboxylic acid ethyl ester

[Method 14]. HPLC provided compound B25 as yellow oil (58 mg, 64%). $^1$H NMR 400 MHz CDCl$_3$ δ (ppm): 8.48 (s, 1H); 8.13 (s, 1H); 7.27 (d, 2H); 7.05 (d, 2H); 4.72 (d, 2H); 4.10 (q, 2H); 3.80 (dt, 2H); 3.25 (td, 2H); 2.60 (m, 1H); 2.00 (dt, 2H); 1.84 (td, 2H); 1.19 (t, 3H). Exact mass calculated for C$_{20}$H$_{23}$F$_2$N$_5$O$_5$ 451.17, LCMS (ESI) m/z 452.1 (M+H$^+$, 100%).

Compound B26

1-{6-[(2,3-Dihydro-benzo[1,4]dioxin-6-ylmethyl)-amino]-5-nitro-pyrimidin-4-yl}-piperidine-4-carboxylic acid ethyl ester

[Method 14]. HPLC provided compound B26 as yellow solid (62 mg, 56%). $^1$H NMR 400 MHz CDCl$_3$ δ (ppm): 8.86 (s, 1H); 8.28 (s, 1H); 6.95 (d, 1H); 6.93 (s, 1H); 6.89 (d, 1H); 4.75 (d, 2H); 4.25 (q, 2H); 3.96 (dt, 4H); 3.87 (dt, 2H); 3.38 (td, 2H); 2.75 (m, 1H); 2.15 (dt, 2H); 1.98 (td, 2H); 1.35 (t, 3H). Exact mass calculated for C$_{21}$H$_{25}$N$_5$O$_6$ 443.18, LCMS (ESI) m/z 444.6 (M+H$^+$, 100%).

Compound B27

1-{6-[(2,3-Dihydro-benzo[1,4]dioxin-2-ylmethyl)-amino]-5-nitro-pyrimidin-4-yl}-piperidine-4-carboxylic acid ethyl ester

[Method 14]. HPLC provided compound B27 as yellow solid (62 mg, 56%). $^1$H NMR 400 MHz CDCl$_3$ δ(ppm): 8.86 (s, 1H); 8.28 (s, 1H); 6.95 (d, 1H); 6.93 (s, 1H); 6.89 (d, 1H); 4.75 (d, 2H); 4.25 (q, 2H); 3.96 (dt, 4H); 3.87 (dt, 2H); 3.38 (td, 2H); 2.75 (m, 1H); 2.15 (dt, 2H); 1.98 (td, 2H); 1.35 (t, 3H). Exact mass calculated for C$_{21}$H$_{25}$N$_5$O$_6$ 443.18, LCMS (ESI) m/z 444.6 (M+H$^+$, 100%).

Compound B28

1-{6-[(2,3-Dihydro-benzofuran-5-ylmethyl)-amino]-5-nitro-pyrimidin-4-yl}-piperidine-4-carboxylic acid ethyl ester

[Method 14]. HPLC provided compound B28 as yellow solid (62 mg, 57%). $^1$H NMR 400 MHz CDCl$_3$ δ(ppm): 8.47(s, 1H); 8.02(s, 1H); 7.12(s, 1H); 7.02(d, 1H); 6.68(d, 1H); 4.62(d, 2H); 4.50(t, 2H); 4.09(q, 2H); 3.81(dt, 2H); 3.15(d, 2H); 3.12(t, 2H); 2.55(m, 1H); 1.95(dt, 2H); 1.77(td, 2H); 1.19(t, 3H). Exact mass calculated for C$_{21}$H$_{25}$N$_5$O$_5$ 427.19, LCMS (ESI) m/z 428.1(M+H$^+$, 100%).

Compound B29

1-{6-[(6-Fluoro-4H-benzo[1,3]dioxin-8-ylmethyl)-amino]-5-nitro-pyrimidin-4-yl}-piperidine-4-carboxylic acid ethyl ester

[Method 14]. HPLC provided compound B29 as yellow solid (77 mg, 67%). $^1$H NMR 400 MHz CDCl$_3$ δ(ppm): 8.92 (s, 1H); 8.09 (s, 1H); 6.88 (dd, 1H); 6.58 (dd, 1H); 5.22 (s, 2H); 4.80 (s, 2H); 4.68 (d, 2H); 4.09 (q, 2H); 3.80 (d, 2H); 3.19 (td, 2H); 2.57 (m, 1H); 1.96 (dt, 2H); 1.79 (td, 2H); 1.19 (t, 3H). Exact mass calculated for C$_{21}$H$_{24}$ FN$_5$O$_6$ 461.17, LCMS (ESI) m/z 462.3 (M+H$^+$, 100%).

Compound B30

1-[6-(3,4-Dihydro-2H-benzo[b][1,4]dioxepin-7-ylamino)-5-nitro-pyrimidin-4-yl]-piperidine-4-carboxylic acid ethyl ester

[Method 16]. The solvent was removed in vacuo and residue purified by preparatory TLC [SiO$_2$; EtOAc/hexane;

20:80]. Yield 0.069 g, 71%. Yellow oil. $^1$H NMR 400 MHz CDCl$_3$ δ(ppm): 9.96 (s, 1H); 8.09 (s, 1H); 7.24 (m, 1H); 7.04 (m, 1H); 6.95 (m, 1H); 4.22 (m, 6H); 3.90 (m, 2H); 3.22 (m, 2H); 2.63 (m, 1H); 2.19 (m, 2H); 2.03 (m, 2H); 1.85 (m, 2H); 1.26 (m, 3H). LCMS (ESI) m/z 444 (M+H$^+$, 100%)

Compound B31

1-{6-[4-(Morpholine-4-sulfonyl)-phenylamino]-5-nitro-pyrimidin-4-yl}-piperidine-4-carboxylic acid ethyl ester

[Method 16]. The solvent was removed in vacuo and the residue purified by preparatory TLC [SiO$_2$; EtOAc/hexane; 20:80]. Yield 0.030 g, 29%. Yellow oil. $^1$H NMR 400 MHz CDCl$_3$ δ (ppm): 10.29 (s, 1H); 8.19 (s, 1H); 7.89 (d, 2H); 7.74 (d, 2H); 4.17 (m, 21-1); 3.91 (m, 2H); 3.75 (m, 3.75); 3.27 (m, 2H); 3.02 (m, 6H); 2.66 (m, 1H); 2.07 (m, 2H); 1.87 (m, 2H); 1.28 (m, 4H). LCMS (ESI) m/z 521 (M+H$^+$, 100%)

Compound B32

1-[6-(2,2-Difluoro-benzo[1,3]dioxol-4-ylamino)-5-nitro-pyrimidin-4-yl]-piperidine-4-carboxylic acid ethyl ester

[Method 16]. purified by preparatory TLC [SiO$_2$; EtOAc/hexane; 20:80]. Yield 0.069 g, 74%. Yellow solid. $^1$H NMR 400 MHz CDCl$_3$ δ (ppm): 10.06 (s, 1H); 8.10 (s, 1H); 7.61 (s, 1H); 7.25 (s, 1H); 7.04 (m, 2H); 4.17 (m, 2H); 3.91 (m, 2H); 3.25 (m, 2H); 2.65 (m, 1H); 2.05 (m, 2H); 1.87 (m. 2H); 1.28 (m, 3H). LCMS (ESI) m/z 452 (M+H$^+$, 100%)

Compound B33

1-[6-(2,2-Difluoro-benzo[1,3]dioxol-5-ylamino)-5-nitro-pyrimidin-4-yl]-piperidine-4-carboxylic acid ethyl ester

[Method 16]. Preparatory TLC [SiO2; EtOAc/hexane; 20:80]. Yield 0.048 g, 50%. Yellow solid. $^1$H NMR 400 MHz CDCl$_3$ δ(ppm): 9.87 (s, 1H); 8.13 (s, 1H); 7.67 (m, 1H); 7.25 (s, 1H); 7.09 (m, 1H); 6.92 (m, 1H); 4.17 (m, 2H); 3.92 (m, 2H); 3.26 (m, 2H); 2.66 (m, 1H); 2.06 (m, 2H); 1.88 (m, 2H); 1.58 (m, 2H); 1.28 (m, 3H). LCMS (ESI) m/z 452 (M+H$^+$, 100%)

Compound B34

1-[6-(1,1-Dioxo-1H-1λ$^6$-benzo[b]thiophen-6-ylamino)-5-nitro-pyrimidin-4-yl]-piperidine-4-carboxylic acid ethyl ester

[Method 16]. preparatory TLC [SiO2; EtOAc/hexane; 20:80]. Yield 0.021 g, 22%. Yellow solid. $^1$H NMR 400 MHz CDCl$_3$ δ (ppm): 10.23 (s, 1H); 8.35 (m, 1H); 8.07 (s, 1H); 7.51 (m, 1H); 7.21 (m, 1H); 7.08 (m, 1H); 6.57 (m, 1H); 4.05 (q, 2H); 3.79 (m, 2H); 3.13 (m, 2H); 2.53 (m, 1H); 1.93 (m, 2H); 1.74 (m, 2H); 1.15 (m, 3H). LCMS (ESI) m/z 460 (M+H$^+$, 100%)

Compound B35

1-{6-[(Furan-3-ylmethyl)-amino]-5-nitro-pyrimidin-4-yl}-piperidine-4-carboxylic acid ethyl ester

[Method 14]. HPLC provided compound B35 as yellow solid (46 mg, 61%). $^1$HNMR 400 MHz CDCl$_3$ δ(ppm): 8.71 (s, 1H); 8.16(s, 1H); 7.44 (s, 1H); 7.37(d, 1H); 6.35(d, 1H); 4.59(d, 2H); 4.11(q, 2H); 3.82(dt, 2H); 3.26(td, 2H); 2.61(m, 1H); 2.00(dt, 2H); 1.84(td, 2H); 1.20(t, 3H). Exact mass calculated for C$_{17}$H$_{21}$N$_5$O$_5$ 375.15, LCMS (ESI) m/z 376.1 (M+H$^+$, 100%).

Compound B36

1-{6-[2-(4-Methoxy-phenoxy)-ethylamino]-5-nitro-pyrimidin-4-yl}-piperidine-4-carboxylic acid ethyl ester

[Method 14]. HPLC provided compound B36 as yellow solid (77 mg, 69%). $^1$H NMR 400 MHz CDCl$_3$ δ (ppm): 9.22 (s, 1H); 8.26 (s, 1H); 6.90 (d,2H); 6.87 (d, 2H); 4.20 (t,2H); 4.19 (t,2H); 4.04 (q, 2H); 3.93 (dt,2H); 3.79 (s,3H); 3.39 (td, 2H); 2.72 (m, 1H); 2.11 (dt, 2H); 1.94 (td,2H); 1.30 (t, 3H). Exact mass calculated for C$_{21}$H$_{27}$N$_5$O$_6$ 445.20, LCMS (ESI) m/z 446.2 (M+H$^+$, 100%).

Compound B37

1-{6-[2-(5-Methoxy-1H-indol-3-yl)-ethylamino]-5-nitro-pyrimidin-4-yl}-piperidine-4-carboxylic acid ethyl ester

[Method 14]. HPLC provided compound B37 as yellow solid (63 mg, 54%). $^1$H NMR 400 MHz CDCl$_3$ δ (ppm): 8.47 (s, 1H); 8.04 (s, 1H); 7.91 (s, 1H); 7.19 (d, 1H); 7.01 (dd, 2H); 6.80 (dd, 1H); 4.08 (q, 2H); 3.84 (dt, 2H); 3.78 (s, 3H); 3.13 (td, 2H); 3.03 (t, 2H); 2.54 (m, 5H); 1.94 (dt, 2H); 1.76 (td, 2H); 1.18 (t, 3H). Exact mass calculated for C$_{23}$H$_{28}$N$_6$O$_5$ 468.21 (ESI) m/z 469.2, 100%).

Compound B38

(3,4-Dihydro-2H-benzo[b][1,4]dioxepin-7-yl)-[5-nitro-6-(4-propyl-piperidin-1-yl)-pyrimidin-4-yl]-amine

[Method 16]. preparatory TLC [SiO$_2$; EtOAc/hexane; 20:80]. Yield 0.003 g, 3%. Yellow oil. $^1$H NMR 400 MHz CDCl$_3$ δ(ppm): 9.78 (s, 1H); 7.87 (s, 1H); 6.85 (m, 1H); 6.74 (m, 1H); 4.00 (m, 4H); 3.71 (m, 2H); 2.86 (m, 2H); 1.97 (m, 2H); 1.58 (m, 2H); 1.12 (m, 2H); 1.03 (m, 6H); 0.69 (m, 3H). LCMS (ESI) m/z 414 (M+H$^+$, 100%)

Compound B39

(3-Fluoro-phenyl)-[5-nitro-6-(4-propyl-piperidin-1-yl)-pyrimidin-4-yl]-amine

[Method 16]. The solvent was removed in vacuo and the residue purified by preparatory TLC [SiO$_2$; EtOAc/hexane; 20:80]. Yield 0.007 g, 9%. Yellow oil. $^1$H NMR 400 MHz CDCl$_3$ δ(ppm): 10.11 (s, 1H); 8.08 (s, 1H); 7.59 (m, 1H); 7.26 (m, 1H); 7.20 (m, 1H); 6.82 (m, 1H); 3.90 (m, 2H); 3.04 (m, 2H); 1.76 (m, 2H); 1.56 (m, 1H); 1.29 (m, 2H); 1.20 (m, 4H); 0.86 (m, 3H). LCMS (ESI) m/z 360 (M+H$^+$, 100%)

Compound B40

(3-Methoxy-phenyl)-5-nitro-6-(4-propyl-piperidin-1-yl)-pyrimidin-4-yl]-amine

[Method 16]. The solvent was removed in vacuo and the residue purified by preparatory TLC [SiO$_2$; EtOAc/hexane;

20:80]. Yield 0.002 g, 2%. Yellow oil. $^1$H NMR 400 MHz CDCl$_3$ δ(ppm): 10.04 (s, 1H); 8.04 (s, 1H); 7.21 (m, 2H); 7.04 (m, 1H); 6.67 (m, 1H); 3.87 (m, 2H); 3.75 (s, 3H); 3.02 (m, 2H); 1.74 (m, 2H); 1.49 (m, 1H); 1.27 (m, 2H); 1.19 (m, 4H); 0.84 (m, 3H). LCMS (ESI) m/z 404 (M+H$^+$, 100%)

Compound B41

1-{6-[(3-Fluoro-phenyl)-methyl-amino]-5-nitro-pyrimidin-4-yl}-piperidine-4-carboxylic acid ethyl ester

[Method 16]. The solvent was removed in vacuo and the residue purified by preparatory TLC [SiO$_2$; EtOAc/hexane; 20:80]. Yield 0.023 g, 30%. Light brown oil. $^1$H NMR 400 MHz CDCl$_3$ δ(ppm): 8.13 (s, 1H); 7.26 (m, 1H); 6.88 (m, 3H); 4.13 (q, 2H); 3.91 (m, 2H); 3.53 (s, 3H); 3.19 (m, 2H); 2.58 (m, 1H); 1.99 (m, 2H); 1.81 (m, 2H); 1.24 (m, 3H). LCMS (ESI) m/z 404 (M+H$^+$, 100%)

Compound B42

1-[6-(4-Benzoyl-phenylamino)-5-nitro-pyrimidin-4-yl]-piperidine-4-carboxylic acid ethyl ester

[Method 16]. The solvent was removed in vacuo and the residue purified by preparatory TLC [SiO$_2$; EtOAc/hexane; 20:80]. Yield 0.059 g, 65%. Light yellow solid. $^1$H NMR 400 MHz CDCl$_3$ δ (ppm): 10.31 (s, 1H); 8.21 (s, 1H); 7.89 (m, 2H); 7.82 (m, 4H); 7.61 (m, 1H); 7.50 (m, 2H); 4.19 (q, 2H); 3.94 (m, 2H); 3.27 (m, 2H); 2.67 (m, 1H); 2.08 (m, 2H); 1.89 (m, 2H); 1.29 (m, 3H). LCMS (ESI) m/z 476 (M+H$^+$, 100%)

Compound B43

1-{6-[4-(1,1-Dioxo-1λ$^6$-thiomorpholin-4-ylmethyl)-phenylamino]-5-nitro-pyrimidin-4-yl}-piperidine-4-carboxylic acid ethyl ester

[Method 16]. The solvent was removed in vacuo and the residue purified by preparatory TLC [SiO$_2$; EtOAc/hexane; 50:50]. Yield 0.055 g, 56%. Yellow oil. $^1$H NMR 400 MHz CDCl$_3$ δ(ppm): 10.09 (s, 1H); 8.11 (s, 1H); 7.55 (d, 2H); 7.31 (d, 2H); 5.29 (s, 1H); 4.15 (m, 2H); 3.89 (m, 2H); 3.63 (m, 2H); 3.22 (m, 2H); 3.01 (m, 6H); 2.64 (m, 1H); 2.03 (m, 2H); 1.84 (m, 2H); 1.25 (m, 4H). LCMS (ESI) m/z 519 (M+H$^+$, 100%)

Compound B44

1-[6-(4-Methanesulfonyl-phenylamino)-5-nitro-pyrimidin-4-yl]-piperidine-4-carboxylic acid ethyl ester

[Method 16]. The solvent was removed in vacuo and the residue purified by preparatory TLC [SiO$_2$; EtOAc/hexane; 50:50]. Yield 0.032 g, 37%. Yellow solid. $^1$H NMR 400 MHz CDCl$_3$ δ (ppm): 10.21 (s, 1H); 8.11 (s, 1H); 7.83 (m, 4H); 4.09 (m, 2H); 3.84 (m, 2H); 3.18 (m, 2H); 2.99 (s, 3H); 2.59 (m, 1H); 1.98 (m, 2H); 1.79 (m, 2H); 1.20 (m, 3H). LCMS (ESI) m/z 450 (M+H$^+$, 100%)

Compound B45

1-[6-(4-Dimethylsulfamoyl-phenylamino)-5-nitro-pyrimidin-4-yl]-piperidine-4-carboxylic acid ethyl ester

[Method 16]. The solvent was removed in vacuo and the residue purified by preparatory TLC [SiO$_2$; EtOAc/hexane; 40:60]. Yield 0.060 g, 57%. Yellow solid. $^1$H NMR 400 MHz CDCl$_3$ δ(ppm): 10.20 (s, 1H); 8.10 (s, 1H); 7.79 (d, 2H); 7.68 (d, 2H); 4.09 (q, 2H); 3.84 (m, 2H); 3.18 (m, 2H); 2.64 (s, 6H); 2.57 (m, 1H); 1.98 (m, 2H); 1.79 (m, 2H); 1.20 (m, 3H). LCMS (ESI) m/z 479 (M+H$^+$, 100%)

Compound B46

1-[6-(3-Methoxy-phenylamino)-5-nitro-pyrimidin-4-yl]-piperidine-4-carboxylic acid ethyl ester

[Method 16]. purified by preparatory TLC. [SiO$_2$; 2:3 EtOAc/hexanes]. Yield 75 mg, 84%. Yellow solid. $^1$H-NMR (400 MHz, CDCl$_3$) δ(ppm): 10.15 (s, 1H); 8.16 (s, 1H); 7.24 (m, 2H); 7.11 (m, 1H); 6.88 (m, 1H); 4.10 (q, 2H); 3.92 (m, 2H); 3.82 (s, 1H); 3.17 (m, 2H); 2.62 (heptet, 1H); 2.09 (m, 2H); 1.95 (m, 2H); 1.25 (t, 3H). LCMS (ESI), m/z 401 (M+H$^+$, 100%)

Compound B47

1-[6-(2-Methoxy-phenylamino)-5-nitro-pyrimidin-4-yl]-piperidine-4-carboxylic acid ethyl ester

[Method 16]. purified by preparatory TLC. [SiO$_2$; 15/85 EtOAc/hexanes]. Yield 56 mg, 63%. Yellow solid. $^1$H-NMR (400 MHz, CDCl$_3$) δ(ppm): 10.57 (s, 1H); 8.41 (m, 1H); 8.18 (s, 1H); 7.15 (m, 1H); 7.0 (m, 1H); 4.21 (q, 2H); 3.92 (m, 5H); 3.25 (m, 2H); 2.63 (m, 2H); 2.08 (m, 2H); 1.88 (m, 21-1); 1.24 (m, 3H). LCMS (ESI), m/z 401 (M+H$^+$, 100%)

Compound B48

1-[6-(3,5-Bis-trifluoromethyl-phenylamino)-5-nitro-pyrimidin-4-yl]-piperidine-4-carboxylic acid ethyl ester

[Method 16]. Purified by flash chromatography. [Silica Gel 60; 20/80 EtOAc/hexanes]. Yield 89 mg, 80%. Yellow solid. $^1$H-NMR (400 MHz, CDCl$_3$) δ(ppm): 10.23 (s, 1H); 8.20 (m, 3H); 7.65 (s, 1H); 4.20 (m, 2H); 3.92 (m, 2H); 3.15 (m, 2H); 2.68 (heptet, 1H); 2.10 (m, 2H); 1.94 (m, 2H); 1.30 (t, 3H). LCMS (ESI), m/z 507 (M+H$^+$, 100%)

Compound B49

1-[6-(2,5-Dimethoxy-phenylamino)-5-nitro-pyrimidin-4-yl]-piperidine-4-carboxylic acid ethyl ester

[Method 16]. purified by preparatory TLC. [SiO$_2$; 20/80 EtOAc/hexanes]. Yield 61 mg, 64%. Orange solid. $^1$H-NMR (400 MHz, CDCl$_3$) δ(ppm): 10.61 (s, 1H); 8.24 (s, 1H); 8.17 (s, 1H); 6.84 (d, 1H); 6.62 (dd, 1H); 4.17(q, 2H); 3.92 (m, 5H); 3.80 (s, 3H); 3.23 (m, 2H); 2.63 (heptet, 1H); 2.10 (m, 2H); 1.84 (m, 2H); 1.25 (t, 3H). LCMS (ESI), m/z 431 (M+H$^+$, 100%)

Compound B50

1-[6-(3,5-Dimethoxy-benzylamino)-5-nitro-pyrimidin-4-yl]-piperidine-4-carboxylic acid ethyl ester

[Method 14]. Semi preparatory HPLC afforded the pure product in 28%. $^1$H NMR, 400 MHz, CDCl$_3$, δ (ppm): 8.85 (m, 1H); 8.32 (s, 1H); 7.50 (s, 1H); 6.73 (d, 2H); 6.63 (t, 1H); 4.96 (d, 2H); 4.40 (q, 2H); 4.13 (m, 2H); 4.03 (s, 6H); 3.45 (m, 2H); 2.86 (m, 1H); 2.26 (m, 2H); 2.08 (m, 2H); 1.50 (t, 3H). LCMS (ESI) for $C_{22}H_{29}N_5O_7$: m/z 475 (M+H$^+$, 100%).

Compound B51

[5-Nitro-6-(4-propyl-piperidin-1-yl)-pyrimidin-4-yl}-(3,4,5-trimethoxy-benzyl)-amine

[Method 14]. semi preparative HPLC afforded the pure product in 16%. $^1$H NMR, 400 MHz, CDCl$_3$, δ (ppm): 8.81 (m, 1H); 8.05(s, 1H); 7.07 (s, 1H); 6.39 (s, 2H); 4.53 (d, 2H); 3.76 (m, 1H); 3.67 (s, 6H); 3.66 (s, 3H); 3.01 (m, 2H); 1.68 (d, 2H); 1.12 (m, 6H); 0.72 (t, 3H). LCMS (ESI) for $C_{22}H_{31}N_5O_5$: m/z 445 (M+H$^+$, 100%).

Compound B52

(3,5-Dimethoxy-benzyl)[5-nitro-6-(4-propyl-piperidin-1-yl)-pyrimidin-4-yl]-amine

[Method 14]. Semi preparative HPLC afforded the pure product in 20%. $^1$H NMR, 400 MHz, CDCl$_3$, δ (ppm): 8.66 (m, 1H); 8.11 (s, 1H); 7.30 (s, 1H); 6.54 (d, 2H); 6.43 (t, 1H); 4.76 (d, 2H); 3.96 (m, 1H); 3.83 (s, 6H); 3.12 (m, 2H); 1.84 (m, 2H); 1.38 (m 2H); 1.30 (m 4H); 0.95 (t, 3H). LCMS (ESI) for $C_{21}H_{29}N_5O_4$: m/z 415 (M+H$^+$, 100%).

Compound B53

(4-[5-Nitro-6-[4-(pyridin-2-ylsulfanyl)-piperidin-1-yl]-pyrimidin-4-ylamino}-phenyl)-phenyl-methanone

[Method 16]. purified by preparative TLC. [SiO$_2$; 30/70 EtOAc/hexanes].Yield 42 mg, 51%. Yellow solid. $^1$H-NMR (400 MHz, CDCl$_3$) δ(ppm): 10.3 (s, 1H); 8.44 (d, 1H); 8.20 (s, 1H); 7.87 (m, 2H); 7.81 (m, 4H); 7.59 (m, 1H); 7.50 (m, 3H); 7.18 (d, 1H); 7.01 (d, 1H); 4.22 (heptet, 1H); 3.92 (m, 2H); 3.45 (dt, 2H); 2.26 (m, 2H); 1.86 (m, 2H). LCMS (ESI), m/z 513 (M+H+, 100%)

Compound B54

(4-{5-Nitro-6-[4-(2-trifluoromethyl-phenoxy)-piperidin-1-yl]-pyrimidin-4-ylamino}-phenyl)-phenyl-methanone

[Method 16]. residue purified by preparatory TLC [SiO$_2$; EtOAc/hexane; 20:80]. Yield 0.057 g, 68%. Yellow solid. $^1$H NMR 400 MHz CDCl$_3$ δ (ppm): 10.24 (s, 1H); 8.13 (s, 1H); 7.80 (m, 2H); 7.74 (m, 4H); 7.52 (m, 2H); 7.42 (m, 4H); 6.95 (m, 2H); 4.78 (m, 1H); 3.64 (m, 4H); 2.02 (m, 4H). LCMS (ESI) m/z 564 (M+H$^+$, 100%)

Compound B55

1-[6-(4-Cyano-phenylamino)-5-nitro-pyrimidin-4-yl]-piperidine-4-carboxylic acid ethyl ester

[Method 16]. residue purified by preparatory TLC [SiO$_2$; EtOAc/hexane; 20:80]. Yield 0.035 g, 40%. Yellow solid. $^1$H NMR 400 MHz CDCl$_3$ δ(ppm): 10.19 (s, 1H); 8.10 (s, 1H); 7.76 (d, 2H); 7.58 (d, 2H); 4.09 (q, 2H); 3.83 (m, 2H); 3.17 (m, 2H); 2.58 (m, 1H); 1.97 (m, 2H); 1.78 (m, 2H); 1.19 (m, 3H) LCMS (ESI) m/z 397 (M+H$^+$, 100%)

Compound B56

1-[6-(3,5-Dimethoxy-phenylamino)-5-nitro-pyrimidin-4-yl]-piperidine-4-carboxylic acid ethyl ester

[Method 16]. residue purified by preparatory TLC [SiO$_2$; EtOAc/hexane; 20:80]. Yield 0.070 g, 73%. Orange solid. $^1$H NMR. 400 MHz CDCl$_3$ δ (ppm): 9.84 (s, 1H); 7.91 (s, 1H); 6.60 (d, 2H); 6.10 (t, 1H); 3.954 (q, 2H); 3.69 (m, 2H); 3.58 (s, 6H); 3.01 (m, 2H); 2.42 (m, 1H); 1.82 (m, 2H); 1.63 (m, 2H); 1.05 (m, 3H). LCMS (ESI) m/z 432 (M+H$^+$, 100%)

Compound B57

1-[6-(4-sec-Butyl-phenylamino)-5-nitro-pyrimidin-4-yl]-piperidine-4-carboxylic acid ethyl ester

[Method 16]. residue purified by preparatory TLC [SiO$_2$; EtOAc/hexane; 20:80]. Yield 0.088 g, 93%. Orange oil. $^1$H NMR 400 MHz CDCl$_3$ δ(ppm): 10.10 (s, 1H); 8.14 (s, 1H); 7.50 (d, 2H); 7.21 (d, 2H); 4.19 (q, 2H); 3.94 (m, 2H); 3.26 (m, 2H); 2.63 (m, 2H); 2.06 (m, 2H); 1.87 (m, 2H); 1.61 (m, 2H); 1.27 (m, 6H); 0.86 (m, 3H). LCMS (ESI) m/z 428 (M+H$^+$, 100%)

Compound B58

1-[6-(4-Heptyl-phenylamino)-5-nitro-pyrimidin-4-yl]-piperidine-4-carboxylic acid ethyl ester

[Method 16]. residue purified by preparatory TLC [SiO$_2$; EtOAc/hexane; 20:80]. Yield 0.092 g, 89%. Orange oil. $^1$H NMR 400 MHz CDCl$_3$ δ(ppm): 10.05 (s, 1H); 8.09 (s, 1H); 7.43 (d, 2H); 7.18 (d, 2H); 4.16 (q, 2H); 3.90 (m, 2H); 3.22 (m, 2H), 2.60 (m, 3H); 2.02 (m, 2H); 1.84 (m, 2H); 1.27 (m, 13H); 0.87 (m, 3H). LCMS (ESI) m/z 470 (M+H$^+$, 100%)

Compound B59

2'-(4-Benzoyl-phenylamino)-3'-nitro-3,4,5,6-tetrahydro-2H-[1,4']bipyridinyl-4-carboxylic acid ethyl ester. General Method 17.

A mixture of 2,4-dichloro-3-nitro-pyridine (77 mg, 0.4 mmol), 4-benzoyl-aniline (1.0 eqv, 7 9 mg, 0.4 mmol) and potassium carbonate (1.4 eqv, 78 mg, 0.56 mmol) in DMF (1 ml) was stirred in a sealed vessel at 150° C. for 30 mins under microwave irradiation. HPLC provided intermediate compound 2-[4-benzoyl-anilino]-4-dichloro-3-nitro-pyridine as brown solid (58 mg, 41% yield). Exact mass calculated for $C_{18}H_{12}ClN_3O_3$ 353.06, LCMS (ESI) m/z 353.6 (M+H$^+$, 100%).

[Method 14]. RP-HPLC provided compound B59 as orange solid (26 mg, 27% yield). $^1$H NMR 400 MHz CDCl$_3$ δ (ppm): 9.55 (s, 1H); 7.89 (d, 3H); 7.74 (d, 2H); 7.57 (t, 1H); 7.46 (t, 2H); 7.32 (d, 2H); 6.50 (d, 1H); 4.12 (q, 2H); 3.63 (d, 2H); 3.26 (t, 2H); 2.63-2.58 (m, 1H); 2.04(d, 2H); 1.94 (td, 2H); 1.21(t, 3H). Exact mass calculated for $C_{26}H_{26}N_4O_5$ 474.19, LCMS (ESI) m/z 475.3 (M+H$^+$, 100%).

Compound B60

1-[5-Nitro-6-(3,4,5-trimethoxy-phenylamino)-pyrimidin-4-yl]-piperidine-4-carboxylic acid ethyl ester

[Method 16]. purified by preparatory TLC. [SiO$_2$; 30/70 EtOAc/hexanes].Yield 42 mg, 41%. Orange oil. $^1$H-NMR (400 MHz, CDCl$_3$) δ(ppm): 9.97 (s, 1H); 8.05 (s, 1H); 6.77 (s, 2H); 4.08 (q, 2H); 3.81 (m, 11H); 3.17 (t, 2H); 2.58 (heptet, 1H); 1.97 (t, 2H); 1.78 (q, 2H); 1.19 (t, 3H). LCMS (ESI), m/z 462 (M+H+, 100%)

Compound B61

1-[5-Nitro-6-(4-pentyl-phenylamino)-pyrimidin-4-yl]-piperidine-4-carboxylic acid ethyl ester

[Method 16]. purified by preparatory TLC. [SiO$_2$; 20/80 EtOAc/hexanes]. Yield 79 mg, 81%. Yellow oil. $^1$H-NMR (400 MHz, CDCl$_3$) δ(ppm): 9.99 (s, 1H); 8.00 (s, 1H); 7.38 (d, 2H); 7.12 (d, 2H); 4.09 (q, 2H); 3.83 (m, 2H); 3.15 (m, 2H); 2.55 (m, 3H); 1.95 (m, 2H); 1.79 (m, 2H); 1.53 (m, 2H); 1.24 (m, 7H); 0.81 (t, 3H). LCMS (ESI), m/z 442 (M+H$^+$, 100%)

Compound B62

1-{6-[4-(3-Carboxy-propyl)-phenylamino]-5-nitro-pyrimidin-4-yl}-piperidine-4-carboxylic acid ethyl ester

[Method 16]. purified by preparatory TLC. [SiO$_2$; 30/70 EtOAc/hexanes]. Yield 67 mg, 67%. Yellow solid. $^1$H-NMR (400 MHz, CDCl$_3$) δ (ppm): 10.08 (s, 1H); 8.13 (s, 1H); 7.49 (d, 2H); 7.22 (d, 2H); 4.18 (q, 2H); 3.92 (m, 2H); 3.25 (m, 2H); 2.68 (m, 3H); 2.40 (t, 2H); 2.06 (m, 2H); 1.96 (m, 2H); 1.88 (m, 2H); 1.27 (t, 3H). LCMS (ESI), m/z 458 (M+H$^+$, 100%)

Compound B63

1-{6-[4-(Cyano-phenyl-methyl)-phenylamino]-5-nitro-pyrimidin-4-yl}-piperidine-4-carboxylic acid ethyl ester

[Method 16]. Dry crude B63 was purified by Biotage Horizon 2 [12+M column; 30/70 EtOAc/hexanes]. Yield 93 mg, 87%. Yellow film. $^1$H-NMR (400 MHz, CDCl$_3$) δ(ppm): 10.13 (s, 1H); 8.13 (s, 1H); 7.64 (tt, 2H); 7.36 (m, 7H); 5.31 (s, 1H); 4.17 (q, 2H); 3.92 (m, 2H); 3.25 (m, 2H); 2.66 (heptet, 1H); 2.06 (m, 2H); 1.88 (m, 2H); 1.28 (t, 3H). LCMS (ESI), m/z 486 (M+H$^+$, 100%)

Compound B64

1-[6-(4-Cyclohexyl-phenylamino)-5-nitro-pyrimidin-4-yl]-piperidine-4-carboxylic acid ethyl ester

[Method 16]. Crude B64 was purified by preparatory TLC [SiO2; 20/80 EtOAc/hexanes]. Yield 55 mg, 55%. Yellow solid. $^1$H-NMR (400 MHz, CDCl$_3$) δ(ppm): 9.99 (s, 1H); 8.04 (s, 1H); 7.38 (tt, 2H); 7.16 (m, 2H); 4.09 (m, 2H); 3.84 (m, 2H); 3.16 (m, 2H); 2.56 (heptet, 1H); 2.43 (m, 1H); 1.95 (m, 2H); 1.79 (m, 8H); 1.31 (m, 2H), 1.20 (t, 5H). LCMS (ESI), m/z 453 (M+H$^+$, 100%)

Compound B65

1-[5-Nitro-6-(4-[1,2,4]triazol-1-yl-phenylamino)-pyrimidin-4-yl]-piperidine-4-carboxylic acid ethyl ester

[Method 16]. Crude B65 was purified by flash chromatography [Silica Gel 60; 30/70 EtOAc/hexanes]. Yield 53 mg, 55%. Yellow solid. $^1$H-NMR (400 MHz, CDCl$_3$) δ(ppm): 10.42 (s, 1H); 8.56 (s, 1H); 8.15 (s, 1H); 8.11 (s, 1H); 7.79 (tt, 2H); 7.71 (tt, 2H); 4.17 (q, 2H); 3.93 (m, 2H); 3.26 (m, 2H); 2.66 (heptet, 1H); 2.05 (m, 2H); 1.87 (m, 2H); 1.27 (m, 3H). LCMS (ESI), m/z 438 (M+H$^+$, 100%)

Compound B66

1-[5-Nitro-6-(4-trifluoromethanesulfonyl-phenylamino)-pyrimidin-4-yl]-piperidine-4-carboxylic acid ethyl ester

[Method 16]. Purified by flash chromatography [Silica Gel 60; 30/70 EtOAc/hexanes]. Yield 34 mg, 31%. Yellow solid. (400 MHz, CDCl$_3$) δ(ppm): 10.72 (s, 1H); 8.16 (s, 1H); 7.98 (m, 4H); 4.10 (q, 2H); 3.85 (m, 2H); 3.20 (m, 2H); 2.60 (heptet, 1H); 1.99 (m, 2H); 1.81 (m, 2H); 1.19 (m, 3H). LCMS (ESI), m/z 503 (M+H$^+$, 100%)

Compound B67

1-[5-Nitro-6-(4-[1,2,3]thiadiazol-4-yl-phenylamino)-pyrimidin-4-yl]-piperidine-4-carboxylic acid ethyl ester

[Method 16]. purified by flash chromatography [Silica Gel 60; 30/70 EtOAc/hexanes]. Yield 39 mg, 39%. Yellow solid. $^1$H-NMR (400 MHz, CDCl$_3$) δ(ppm): 10.48 (s, 1H); 8.65 (s, 1H); 8.18 (s, 1H); 8.08 (ft, 2H); 7.80 (tt, 2H); 4.16 (q, 2H); 3.94 (m, 2H); 3.26 (m, 2H); 2.66 (heptet, 1H); 2.06 (m, 2H); 1.89 (m, 2H); 1.28 (t, 3H).

Compound B68

[6-(4-Ethoxymethyl-piperidin-1-yl)-5-nitro-pyrimidin-4-yl}-(4-methanesulfonyl-phenyl)-amine

[Method 16]. purified by HPLC [Semi-Prep]. Yield 13 mg, 17%. Yellow solid. $^1$H-NMR (400 MHz, CDCl$_3$) δ(ppm): 10.13 (s, 1H); 7.99 (s, 1H); 7.73 (m, 4H); 3.79 (m, 2H); 3.3 (q, 2H); 3.11 (d, 2H); 2.95 (m, 2H); 2.86 (s, 3H); 1.77 (m, 3H); 1.18 (m, 2H); 1.02 (m, 3H). LCMS (ESI), m/z 436 (M+H$^+$, 100%)

Compound B69

[5-Nitro-6-(4-propyl-piperidin-1-yl)-pyrimidin-4-yl}-(4-[1,2,4]triazol-1-yl-phenyl)-amine

[Method 16]. purified by preparatory TLC [SiO$_2$; 50/50 EtOAc/hexanes]. Yield 27 mg, 27%. Yellow solid. $^1$H-NMR (400 MHz, CDCl$_3$) δ(ppm): 10.17 (s, 1H); 8.47 (s, 1H); 8.07 (s, 1H); 8.04 (s, 1H); 7.73 (tt, 2H); 7.63 (tt, 2H); 3.89 (m, 2H); 3.05 (m, 2H); 1.76 (m, 2H); 1.40 (m, 1H); 1.24 (m, 6H); 0.85 (t, 3H). LCMS (ESI), m/z 408 (M+H$^+$, 100%)

Compound B70

{5-Nitro-6-[4-(pyridin-2-ylsulfanyl)-piperidin-1-yl]-pyrimidin-4-yl}-(4-[1,2,4]triazol-1-yl-phenyl)-amine

[Method 16]. The crude was purified by HPLC. Yield 52 mg, 55%. Yellow solid. $^1$H-NMR (400 MHz, CDCl$_3$) δ(ppm): 10.18 (s, 1H); 8.47 (s, 1H); 8.37 (m, 1H); 8.09 (s, 1H); 8.04 (s, 1H); 7.72 (tt, 2H); 7.63 (tt, 2H); 7.43 (ddd, 1H); 7.12 (ft, 1H); 6.94 (m, 1H); 4.15 (heptet, 1H); 3.85 (m, 2H); 3.37 (m, 2H); 2.19 (m, 2H); 1.79 (m, 2H). LCMS (ESI), m/z 476 (M+H$^+$, 100%)

Compound B71

(2-Fluoro-phenyl)-{6-[4-(3-methyl-[1,2,4]oxadiazol-5-yl)-piperidin-1-yl]-5-nitro-pyrimidin-4-yl}-amine

[Method 16]. Purified by HPLC. Yield 33 mg, 38%. Yellow solid. $^1$H-NMR (400 MHz, CDCl$_3$) δ(ppm): 10.01 (s, 1H); 8.09 (s, 1H); 7.63 (t, 1H); 7.28 (m, 1H); 7.16 (m, 2H); 3.98 (m, 2H); 3.41 (m, 2H); 3.33 (heptet, 1H); 2.36 (s, 3H); 2.23 (m, 2H); 2.05 (m, 2H). LCMS (ESI), m/z 399 (M+H$^+$, 100%)

Compound B72

(4-Methanesulfonyl-phenyl)-{6-[4-(3-methyl-[1,2,4]oxadiazol-5-yl)-piperidin-1-yl]-5-nitro-pyrimidin-4-yl}-amine

[Method 16]. yellow solid. Yield 15.2%. $^1$H NMR 400 MHz CDCl$_3$ δ (ppm): 10.5 (s, 1H); 8.49 (s, 11-1); 8.2 (dd, 4H); 4.26 (d, 2H); 3.64 (m, 2H); 3.60 (m, 1H); 3.33 (s, 3H); 2.67 (s, 3H); 2.5 (d, 2H); 2.33 (m, 2H). LCMS (ESI) m/z 460.2 (M$^+$H$^+$, 100%)

Compound B73

{6-[4-(3-Methyl-[1,2,4]oxadiazol-5-yl)-piperidin-1-yl]-5-nitro-pyrimidin-4-yl}-(4-[1,2,4]triazol-1-yl-phenyl)-amine

[Method 16]. yellow solid. Yield 11%. 400 MHz CDCl$_3$ δ (ppm): 10 (s, 1H); 8.41 (s, 1H); 8.02 (s, 1H); 7.97 (s, 1H); 7.64 (d, 2H); 7.55 (d, 2H); 3.84 (d, 2H); 3.24 (m, 2H); 3.20 (m, 1H); 2.25 (s, 3H); 2.09 (d, 2H); 1.90 (m, 2H). LCMS (ESI) m/z 449.2 (M$^+$H$^+$, 100%)

Compound B74

1-{5-Nitro-6-[4-(4-trifluoromethyl-phenoxy)-phenylamino]-pyrimidin-4-yl}-piperidine-4-carboxylic acid ethyl ester

[Method 16]. residue purified by preparatory TLC [SiO2; EtOAc/hexane; 20:80]Yield 0.057 g, 56%. Yellow solid. $^1$H NMR 400 MHz CDCL$_3$ δ (ppm): 10.23 (s, 1H); 8.25 (s, 1H); 7.72 (m, 4H); 7.20 (m, 4H); 4.30 (q, 2H); 4.05 (m, 2H); 3.37 (m, 2H); 2.78 (m, 1H); 2.18 (m, 2H); 2.00 (m, 2H); 1.40 (m, 3H). LCMS (ESI) m/z 532 (M+H$^+$, 100%)

Compound B75

{6-[4-(3-Ethyl-[1,2,4]oxadiazol-5-yl)-piperidin-1-yl]-5-nitro-pyrimidin-4-yl}-(2-fluoro-phenyl)-amine

[Method 16]. The desired product was observed by LCMS m/z 414 (M+H$^+$). Purification by RP-HPLC. Yield 69%. $^1$H NMR 400 MHz CDCl$_3$ δ (ppm): 10.00 (s, 1H); 8.11 (s, 1H); 8.09 (m, 1); 7.12 (m, 3H); 3.97 (d, 2H); 3.29 (m, 2H); 3.26 (m, 1H); 2.69 (m, 2H); 2.18 (m, 2H); 2.06 (m, 2H); 1.29 (t, 3H). LCMS (ESI) m/z 414 (M+H$^+$, 100%)

Compound B76

{6-[4-(2-Methoxy-phenylsulfanyl)-piperidin-1-yl]-5-nitro-pyrimidin-4-yl}-(4-[1,2,4]triazol-1-yl-phenyl)-amine

[Method 16]. Yield 43%. Yellow solid. $^1$H NMR 400 MHz CDCl$_3$ δ (ppm): 9.98 (s, 1H); 8.33 (s, 1H); 7.91 (d, 2H); 7.57 (d, 2H); 7.47 (d, 2H); 7.20 (m, 1H); 7.09 (m, 2H); 6.70 (m, 2H); 3.69 (s, 3H); 3.33 (m, 1H); 3.10 (m, 2H); 1.85 (m, 2H); 1.51 (m, 4H). LCMS (ESI) m/z 505 (M+H$^+$, 100%)

Compound B77

(4-Methanesulfonyl-phenyl)-{5-nitro-6-[4-(pyridin-2-ylsulfanyl)-piperidin-1-yl]-pyrimidin-4-yl}-amine Crude B77 was purified by flash chromatography [Silica gel 60; 50/50 EtOAc/hexanes]. Yield 49 mg, 50%. Yellow solid. $^1$H-NMR (400 MHz, CDCl$_3$) δ(ppm): 10.25 (s, 1H); 8.13 (s, 1H); 7.85 (m, 4H); 7.64 (tt, 1H); 7.43 (m, 1H); 7.11 (d, 1H); 6.95 (m, 1H); 4.15 (m, 1H); 3.85 (m, 2H); 3.38 (m, 2H); 2.99 (s, 3H); 2.19 (m, 2H); 1.79 (m, 2H). LCMS (ESI), m/z 487 (M+H$^+$, 100%)

Compound B78

(3-Methoxy-phenyl)-{5-nitro-6-[4-(pyridin-2-ylsulfanyl)-piperidin-1-yl]-pyrimidin-4-yl}-amine

[Method 16]. The crude mixture was purified by preparatory TLC [SiO$_2$; 20/80 EtOAc/hexanes].

Yield 70 mg, 87%. Yellow solid. $^1$H-NMR (400 MHz, CDCl$_3$) δ(ppm): 10.25 (s, 1H); 8.55 (m, 1H); 8.25 (s, 1H); 7.60 (ddd, 1H); 7.40 (m, 2H); 7.38 (s, 1H); 7.29 (d, 1H); 7.22 (d, 1H); 7.12 (m, 1H); 4.33 (heptet, 1H); 4.01 (m, 2H); 3.94 (s, 3H); 3.54 (m, 2H); 2.36 (m, 2H); 1.98 (m, 2H). LCMS (ESI), m/z 439 (M+H$^+$, 100%)

Compound B79

Benzo[1,3]dioxol-5-yl-[5-nitro-6-(4-propyl-piperidin-1-yl)-pyrimidin-4-yl]-amine

[Method 16]. Residue purified by preparatory TLC [SiO$_2$; EtOAc/hexane; 20:80]. Yield 0.005 g, 6%. Yellow oil. $^1$H NMR 400 MHz CDCl$_3$ δ(ppm): 9.92 (s, 1H); 8.01 (s, 1H); 7.13 (m, 1H); 6.78 (m, 1H); 6.72 (m, 1H); 5.92 (s, 2H); 3.87 (m, 2H); 3.02 (m, 2H); 1.74 (m, 2H); 1.48 (m, 1H); 1.27 (m, 2H); 1.18 (m, 4H); 0.84 (m, 3H). LCMS (ESI) m/z 386 (M+H$^+$, 100%)

Compound B80

(4-Fluoro-phenyl)-{1-[5-nitro-6-(4-[1,2,4]triazol-1-yl-phenylamino)-pyrimidin-4-yl]-piperidin-4-yl}-methanone Purification by HPLC. Yield 56%. yellow solid TFA salt. $^1$H NMR 400 MHz CDCl$_3$ δ (ppm): 11.61 (s, 3H); 10.3 (s, 1H); 9.18 (s, 1H); 8.39 (s, 1H); 8.18 (s, 1H); 8.01 (m, 2H); 7.84 (d, 2H); 7.74 (d, 2H); 7.19 (t, 2H); 4.07 (d, 2H); 3.67 (m, 1H); 3.47 (m, 2H); 2.05 (m, 4H). LCMS (ESI) m/z 489.4 (M$^+$H$^+$, 100%)

Compound B81

[5-Nitro-6-(4-phenylsulfanyl-piperidin-1-yl)-pyrimidin-4-yl]-(4-[1,2,4]triazol-1-yl-phenyl)-amine

[Method 16]. product precipitated from the crude as a yellow solid. It was filtered and washed with hexane. Yield 36%. $^1$H NMR 400 MHz CDCl$_3$ δ (ppm): 10.17 (s, 1H); 8.57 (s, 1H); 8.10 (d, 2H); 7.76 (d, 2H); 7.66 (d, 2H); 7.42 (m, 2H);

7.29 (m, 3H); 3.89 (m, 2H); 3.39 (m, 1H); 3.27 (m, 2H); 2.06 (m; 2H); 1.71 (m, 2H). LCMS (ESI) m/z 475.3 (M⁺H⁺, 100%)

Compound B82

(4-Fluoro-phenyl)-{1-[6-(2-fluoro-phenylamino)-5-nitro-pyrimidin-4-yl]-piperidin-4-yl}-methanone

[Method 16]. Purification by HPLC. Yield 17%. red oil. ¹H NMR 400 MHz CDCl₃ δ (ppm): 9.92 (s, 1H); 7.96 (s, 1H); 7.79 (m, 2H); 7.46 (m, 1H); 7.17 (m, 1H); 7.02 (m, 4H); 3.86 (d, 2H); 3.46 (m, 1H); 3.31 (m, 2H); 1.86 (m, 4H). LCMS (ESI) m/z 440.4 (M⁺H⁺, 100%)

Compound B83

1-[6-(2-Methyl-5-phenyl-2H-pyrazol-3-ylamino)-5-nitro-pyrimidin-4-yl]-piperidine-4-carboxylic acid ethyl ester

[Method 16]. Purification by HPLC yielded orange solid. Yield 30%. ¹H NMR 400 MHz CDCl₃ δ (ppm), 8.34 (s, 1H); 7.90 (m, 2H); 7.68 (d, 3H); 7.04 (s, 1H); 4.32 (m, 2H); 4.11 (s, 3H); 4.06 (m, 2H); 3.44 (m, 2H); 2.83 (m, 1H); 2.22 (m, 2H); 2.04 (m, 2H); 1.41 (t, 3H). LCMS (ESI) m/z 452 (M⁺H⁺, 100%)

Compound B84

(4-Methanesulfonyl-phenyl)-[5-nitro-6-(4-phenylsulfanyl-piperidin-1-yl)-pyrimidin-4-yl]-amine

[Method 16]. Purification by HPLC yielded yellow solid. Yield 9%. ¹H NMR 400 MHz CDCl₃ δ (ppm): 10.0 (s, 1H); 8.00 (s, 1H); 7.75 (d, 2H); 7.68 (d, 2H); 7.26 (m, 2H); 7.14 (m, 3H); 3.73 (d, 2H); 3.22 (m, 1H); 3.13 (m, 2H); 2.87 (s, 3H); 1.91 (m, 2H); 1.55 (m, 2H). LCMS (ESI) m/z 486 (M⁺H⁺, 100%)

Compound B85

(4-Methanesulfonyl-phenyl)-{5-nitro-6-[4-(pyridin-2-yloxy)-piperidin-1-yl]-pyrimidin-4-yl}-amine

[Method 16]. as yellow solid (68 mg, 72%). ¹H NMR 400 MHz CDCl₃ δ(ppm): 10.2 (s, 1H); 8.13 (s, 1H); 8.12 (d, 1H); 7.87 (d, 2H); 7.83 (d, 2H); 7.60 (t, 1H); 6.87 (t, 1H); 6.73 (d, 1H); 5.29 (m,1H); 3.76-3.70 (m,2H); 3.56-3.51 (m,2H); 2.99 (s,3H); 2.10-2.05 (m, 2H); 1.95-1.90 (m,2H). Exact mass calculated for C₂₁H₂₂N₆O₅S 470.14, LCMS (ESI) m/z 471.4 (M+H⁺, 100%).

Compound B86

{6-[4-(4-Fluoro-phenoxy)-piperidin-1-yl]-5-nitro-pyrimidin-4-yl}-(4-methanesulfonyl-phenyl)-amine

[Method 16]. afforded compound B86 as yellow solid (58 mg, 60%). ¹H NMR 400 MHz CDCl₃ δ(ppm): 10.2 (s, 1H); 8.13 (s, 1H); 7.87 (d, 2H); 7.81 (d, 2H); 6.92(m, 2H); 6.82 (m, 2H); 4.50 (m, 1H); 3.71-3.65 (m,2H); 3.54-3.51 (m,2H); 2.99 (s,3H); 1.99-1.91 (m 2H). Exact mass calculated for C₂₂H₂₂FN₅O₅S 487.13, LCMS (ESI) m/z 488.3(M+H⁺, 100%).

Compound B87

(4-Methanesulfonyl-phenyl)-{5-nitro-6-[4-(pyridin-4-yloxy)-piperidin-1-yl]-pyrimidin-4-yl}-amine Method 16 afforded compound B87 as yellow solid (56 mg, 60%). ¹H NMR 400 MHz CDCl₃ δ(ppm): 10.2(s, 1H); 8.68 (d, 2H); 8.17(s, 1H); 7.88 (d, 2H); 7.83(d, 2H); 7.26 (d, 2H); 4.96 (m,1H); 3.76-3.69 (m,2H); 3.62-3.57 (m,2H); 3.00 (s,3H); 2.21-2.15 (m 2H); 2.03-1.99 (m,2H). Exact mass calculated for C₂₁H₂₂N₆O₅S 470.14, LCMS (ESI) m/z 471.2 (M+H⁺, 100%).

Compound B88

(4-Methanesulfonyl-phenyl)-{5-nitro-6-[4-(pyrimidin-2-yloxy)-piperidin-1-yl]-pyrimidin-4-yl}-amine Method 16 afforded compound B88 as a yellow solid (69 mg, 73%). ¹H NMR 400 MHz CDCl₃ δ(ppm): 10.2 (s, 1H); 8.52 (d, 2H); 8.14 (s,1H); 7.88 (d, 2H); 7.83 (d, 2H); 6.96(t, 1H); 5.34 (m, 1H); 3.79-3.72 (m,2H); 3.58-3.52 (m,2H); 2.99 (s,3H); 2.14-2.08 (m 2H); 2.02-1.93 (m,2H). Exact mass calculated for C₂₀H₂₁N₇O₅S 471.13, LCMS (ESI) m/z 472.0 (M+H⁺, 100%).

Compound B89

(4-Methanesulfonyl-phenyl)-{5-nitro-6-[4-(pyridin-4-ylsulfanyl)-piperidin-1-yl]pyrimidin-4-yl}-amine Method 16 afforded compound B89 as a yellow solid (52 mg, 54%). ¹H NMR 400 MHz CDCl₃ δ(ppm): 10.1(s, 1H); 8.56(d, 2H); 8.17(s, 1H); 7.89 (d, 2H); 7.83(d, 2H); 7.53(d, 2H); 3.92-3.89(m,2H); 3.84(m,1H); 3.44-3.38(m,2H); 3.00 (s,3H); 2.26-2.22(m 2H); 1.94-1.88 (m,2H). Exact mass calculated for C₂₁H₂₂N₆O₄S₂ 486.11, LCMS (ESI) m/z 487.2 (M+H⁺, 100%).

Compound B90

(4-Methanesulfonyl-phenyl)-{6-[4-(4-methoxy-phenylsulfanyl)-piperidin-1-yl]-5-nitro-pyrimidin-4-yl}-amine Method 16 afforded compound B90 as a as yellow solid (50 mg, 49%). ¹H NMR 400 MHz CDCl₃ δ(ppm): 10.2(s, 1H); 8.11(s, 1H); 7.87 (d, 2H); 7.80(d, 2H); 7.34(d, 2H); 6.79(d, 2H); 3.86-3.83(m,2H); 3.74(s,3H); 3.22-3.12(m,3H); 2.99(s, 3H); 1.99-1.95(m 2H); 1.66-1.57(m,2H). Exact mass calculated for C₂₃H₂₅N₅O₅S₂ 515.13, LCMS (ESI) m/z 516.1(M+H⁺, 100%).

Compound B91

[6-(4-Benzenesulfonyl-piperidin-1-yl)-5-nitro-pyrimidin-4-yl]-(4-methanesulfonyl-phenyl)-amine Method 16 afforded compound B91a as yellow solid (51 mg, 50%). ¹H NMR 400 MHz CDCl₃ δ(ppm): 10.2(s, 1H); 8.12(s, 1H); 7.87 (d, 2H); 7.81(d,2H); 7.79(d, 2H); 7.64(t, 1H); 7.53(t,1H); 4.01(m,2H); 3.17(m,1H); 3.08-3.04 (m,2H);

2.99(s,3H); 2.08-2.04(m 2H); 1.82-1.78(m,2H). Exact mass calculated for $C_{22}H_{23}N_5O_6S_2$ 517.11, LCMS (ESI) m/z 518.3 (M+H$^+$, 100%).

Compound B92

{4-[6-(4-Methanesulfonyl-phenylamino)-5-nitropyrimidin-4-yl]-piperazin-1-yl}-acetic acid ethyl ester

[Method 16]. afforded compound B92 as a yellow solid (45 mg, 48%). $^1$H NMR 400 MHz CDCl$_3$ δ (ppm): 10.2(s, 1H); 8.18(s, 1H); 7.88 (d, 2H); 7.81 (d, 2H); 4.21(q, 2H); 3.86-3.83 (m, 6H); 3.46-3.43 (m, 4H); 3.00 (s, 3H); 1.23 (t, 3H). Exact mass calculated for $C_{19}H_{24}N_6O_6S$ 464.15, LCMS (ESI) m/z 465.3 (M+H$^+$, 100%).

Compound B93

(2-Fluoro-phenyl)-{5-nitro-6-[4-(pyridin-2-ylsulfanyl)-cyclohexyl]-pyrimidin-4-yl}-amine

[Method 16]. The crude was dissolved in dichloromethane and purified by preparative TLC. [SiO$_2$; 15/85 EtOAc/hexanes].Yellow solid. Yield 7 mg, 10%. $^1$H-NMR (400 MHz, CDCl$_3$) δ(ppm): 10.07 (s, 1H); 8.37 (d, 1H); 8.13 (m, 1H); 8.08 (s, 1H); 7.43 (ddd, 1H); 7.07 (m, 4H); 6.94 (m, 1H); 4.15 (heptet, 1H); 3.85 (m, 2H); 3.36 (m, 2H); 2.18 (m, 2H); 1.79 (m, 2H). LCMS (ESI), m/z 427 (M+H$^+$, 100%)

Compound B94

(2-Methoxy-phenyl)-{5-nitro-6-[4-(pyridin-2-ylsulfanyl)-cyclohexyl]-pyrimidin-4-yl}-amine

[Method 16]. purified by preparative TLC. [SiO2; 15/85 EtOAc/hexanes].Yellow solid. Yield 42 mg, 56%. (400 MHz, CDCl$_3$) δ(ppm): 10.51 (s, 1H); 8.36 (d, 2H); 8.10 (s, 1H); 7.42 (ddd, 1H); 7.10 (d, 1H); 7.03 (ddd, 1H); 6.87 (d, 1H); 4.14 (heptet, 1H); 3.85 (m, 5H); 3.35 (m, 2H); 2.17 (m, 2H); 1.78 (m, 2H). LCMS (ESI), m/z 438 (M+H+, 100%)

Compound B95

(4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine Following the general procedure 16, compound B95 was obtained as a yellow solid (61%). (CDCl$_3$, 400 MHz) δ 2.06-2.10 (m, 2H), 2.23-2.27 (m, 2H), 2.99 (s, 3H), 3.31-3.38 (m, 3H), 3.96-3.99 (m, 2H), 7.55 (t, 1H), 7.70 (d, 1H), 7.86 (dd, 4H), 8.16 (s, 1H), 8.20 (d, 1H), 8.28 (s, 1H), 10.2 (s, 1H). Exact mass calculated for $C_{25}H_{22}F_3N_7O_5S$ 589.1, found 590.4 (MH$^+$).

Compound B96

{6-[4-(3-Ethyl-[1,2,4]oxadiazol-5-yl)-piperidin-1-yl]-5-nitro-pyrimidin-4-yl}-(4-methanesulfonyl-phenyl)-amine Following the general procedure 16, compound B96 was obtained as a yellow solid (31%). $^1$H NMR (CDCl$_3$, 400 MHz) δ 1.25 (t, 3H), 2.06-2.10 (m, 2H), 2.23-2.27 (m, 2H), 2.70 (q, 2H), 2.99 (s, 3H), 3.31-3.38 (m, 3H), 3.96-3.99 (m, 2H), 7.84 (dd, 4H), 8.14 (s, 1H), 10.2 (s, 1H). Exact mass calculated for $C_{20}H_{23}N_7O_5S$ 473.1, found 474.2 (MH$^+$).

Compound B97

(6-{4-[5-(4-Fluoro-phenyl)-[1,3,4]oxadiazol-2-yl]-piperidin-1-yl}-5-nitro-pyrimidin-4-yl)-(4-methanesulfonyl-phenyl)-amine Following the general procedure 16, compound B97 was obtained as a yellow solid (93%). $^1$H NMR (CDCl$_3$, 400 MHz) δ 2.06-2.10 (m, 2H), 2.23-2.27 (m, 2H), 2.99 (s, 3H), 3.31-3.38 (m, 3H), 3.96-3.99 (m, 2H), 7.24 (dd, 2H), 7.96 (dd, 4H), 8.04-8.08 (m, 2H), 8.25 (s, 1H), 10.3 (s, 1H). Exact mass calculated for $C_{24}H_{22}FN_7O_5S$ 539.14, found 540.3 (MH$^+$).

Compound B98

(4-Methanesulfonyl-phenyl)-[5-nitro-6-(4-pyridin-2-ylmethyl-piperidin-1-yl)-pyrimidin-4-yl]-amine Following the general procedure 16, Compound B98 was obtained as a yellow solid (95%). $^1$HNMR (CDCl$_3$, 400 MHz) δ 1.36-1.47 (m, 2H), 1.69-1.72 (m, 2H), 2.12-2.18 (m, 1H), 2.99 (s, 3H), 3.00-3.05 (m, 2H), 3.91-3.94 (m, 2H), 7.52 (d, 1H), 7.65 (dt, 1H), 7.85 (dd, 4H), 8.11 (s, 1H), 8.17 (dt, 1H), 8.82 (d, 1H), 10.2 (s, 1H). Exact mass calculated for $C_{22}H_{24}N_6O_4S$ 468.1, found 469.4 (MH$^+$).

Compound B99

4-[4-(3-Isopropyl-[1,2,4]oxadiazol-5-yl)-piperidin-1-yl]-6-(4-methylsulfanyl-phenylamino)-pyrimidine-5-carbonitrile Following the general procedure, Compound B99 was prepared. $^1$H-NMR (DMSO-d$_6$): 9.38 (1H, s), 8.21 (1H, s), 7.47 (2H, J=4.3 Hz, d), 7.23 (2H, J=4.3 Hz, d), 4.50 (2H, m), 3.35 (2H, m), 3.02 (1H, m), 2.51 (3H, s), 2.18 (2H, m), 1.79 (2H, m) 1.83 (6H, J=7 Hz, d) ppm. LCMS: 436.3, 351.9, 324.4, 270.2.

Compound B100

1-{6-[4-(4,5-Dichloro-imidazol-1-yl)-phenylamino]-5-nitro-pyrimidin-4-yl}-piperidine-4-carboxylic acid ethyl ester

[Method 16]. yellow solid (40 mg, 49%). (CDCl$_3$, 400 MHz) δ 1.28 (t, 3H), 1.87 (m, 2H), 2.06 (m, 2H), 2.66 (m, 1H), 3.26 (t, 2H), 3.93 (m, 2H), 4.17 (q, 2H), 7.37 (m, 2H), 7.54 (s, 1H), 7.82 (m, 2H), 8.17 (s, 1H), 10.23 (s, 1H). Exact mass calculated for $C_{21}H_2Cl_2N_7O_4$ 506.34, found 506.2 (MH$^+$).

Compound B101

Benzo[1,3]dioxol-5-yl-{5-nitro-6-[4-(pyridin-2-ylsulfanyl)-piperidin-1-yl]-pyrimidin-4-yl}-amine

[Method 16]. orange solid (9 mg, 14%). $^1$HNMR (CDCl$_3$, 400 MHz) δ 1.78 (m, 2H), 2.17 (m, 2H), 3.35 (m, 2H), 3.83 (m, 2H), 4.14 (m, 1H), 5.92 (m, 2H), 6.75 (m, 2H), 6.94 (m, 1H), 7.11 (m, 1H), 7.19 (m, 1H), 7.42 (m, 1H), 8.02 (s, 1H), 8.36 (m, 1H), 9.91 (s, 1H). Exact mass calculated for $C_{24}H_{24}N_4O_8S$ 452.49, found 453.2 (MH$^+$).

Compound B102

(4-Fluoro-phenyl)-{1-[6-(2-fluoro-phenylamino)-5-nitro-pyrimidin-4-yl]-piperidin-4-yl}-methanone

[Method 16]. yellow solid (16 mg, 44%). $^1$HNMR (CDCl$_3$, 400 MHz) δ 1.89 (m, 4H), 3.26 (m, 2H), 3.51 (m, 1H), 3.96 (m, 2H), 7.10 (m, 5H), 7.92 (m, 2H), 8.08 (s, 1H), 8.13 (m, 1H), 10.06 (s, 1H). Exact mass calculated for C$_{24}$H$_{24}$N$_4$O$_8$S 439.41, found 440.3 (MH$^+$).

Compound B103

{1-[6-(Benzo[1,3]dioxol-5-ylamino)-5-nitro-pyrimidin-4-yl]-piperidin-4-yl}-(4-fluoro-phenyl)-methanone

[Method 16]. orange solid (20 mg, 53%). $^1$HNMR (CDCl$_3$, 400 MHz) δ 1.89 (m, 4H), 3.26 (m, 2H), 3.51 (m, 1H), 3.96 (m, 2H), 5.92 (s, 2H), 6.76 (m, 2H), 7.10 (m, 3H), 7.92 (m, 2H), 8.03 (s, 1H), 9.91 (s, 1H). Exact mass calculated for C$_{23}$H$_{20}$FN$_5$O$_5$ 465.43, found 466.3 (MH$^+$).

Compound B104

(2,3-Difluoro-phenyl)-{5-nitro-6-[4-(pyridin-2-ylsulfanyl)-piperidin-1-yl]-pyrimidin-4-yl}-amine

[Method 16]. yellow solid (5 mg, 8%), $^1$HNMR (CDCl$_3$, 400 MHz) δ 1.78 (m, 2H), 2.17 (m, 2H), 3.35 (m, 2H), 3.83 (m, 2H), 4.14 (m, 1H), 6.94 (m, 2H), 7.03 (m, 1H), 7.10 (m, 1H), 7.42 (m, 1H), 7.89 (m, 1H), 8.08 (s, 1H), 8.37 (m, 1H), 10.05 (s, 1H). Exact mass calculated for C$_{20}$H$_{18}$F$_2$N$_6$O$_2$S 444.46, found 444.9 (M+H$^+$).

Compound B105

(2,4-Difluoro-phenyl)-{5-nitro-6-[4-(pyridin-2-ylsulfanyl)-piperidin-1-yl]-pyrimidin-4-yl}-amine

[Method 16]. yellow solid (12 mg, 19%). $^1$HNMR (CDCl$_3$, 400 MHz) δ 1.78 (m, 2H), 2.17 (m, 2H), 3.35 (m, 2H), 3.83 (m, 2H), 4.14 (m, 1H), 6.85 (m, 2H), 6.93 (m, 1H), 7.10 (m, 1H), 7.42 (m, 1H), 7.89 (m, 1H), 8.05 (s, 1H), 8.37 (m, 1H), 9.91 (s, 1H). Exact mass calculated for C$_{20}$H$_{18}$F$_2$N$_6$O$_2$S 444.46, found 445.4 (M+H$^+$).

Compound B106

(2,5-Difluoro-phenyl)-{5-nitro-6-[4-(pyridin-2-ylsulfanyl)-piperidin-1-yl]-pyrimidin-4-yl}-amine

[Method 16]. yellow solid (3 mg, 5%). $^1$HNMR (CDCl$_3$, 400 MHz) δ 1.78 (m, 2H), 2.17 (m, 2H), 3.35 (m, 2H), 3.83 (m, 2H), 4.14 (m, 1H), 6.73 (m, 1H), 6.93 (m, 1H), 7.03 (m, 1H), 7.11 (m, 1H), 7.42 (m, 1H), 8.13 (s, 1H), 8.25 (m, 1H), 8.37 (m, 1H), 10.25 (s, 1H). Exact mass calculated for C$_{20}$H$_{18}$F$_2$N$_6$O$_2$S 444.46, found 445.3 (M+H$^+$).

Compound B107

1-[6-(4-Benzenesulfonyl-phenylamino)-5-nitro-pyrimidin-4-yl]-piperidine-4-carboxylic acid ethyl ester

[Method 16]. yellow solid (32 mg, 39%). $^1$HNMR (CDCl$_3$, 400 MHz) δ 1.22 (t, 3H), 1.80 (m, 2H), 2.00 (m, 2H), 2.60 (m, 1H), 3.20 (t, 2H), 3.85 (m, 2H), 4.12 (q, 2H), 7.48 (m, 3H), 7.78 (d, 2H), 7.90 (m, 4H), 8.11 (s, 1H), 10.19 (s, 1H). Exact mass calculated for C$_{24}$H$_{25}$N$_5$O$_6$S 511.55, found 512.3 (MH$^+$).

Compound B108

1-[5-Nitro-6-(2-trifluoromethyl-3H-benzoimidazol-5-ylamino)-pyrimidin-4-yl]-piperidine-4-carboxylic acid ethyl ester

[Method 16]. yellow solid (11 mg, 14%). $^1$HNMR (CDCl$_3$, 400 MHz) δ 1.40 (t, 3H), 2.00 (m, 2H), 2.18 (m, 2H), 2.79 (m, 1H), 3.39 (t, 2H), 4.06 (m, 2H), 4.30 (q, 2H), 7.43 (m, 1H), 7.65 (m, 1H), 7.95 (m, 1H), 8.26 (m, 2H), 10.40 (s, 1H). Exact mass calculated for C$_{20}$H$_{20}$F$_3$N$_7$O$_4$ 479.41, found 480.3 (MH$^+$).

Compound B109

1-{5-Nitro-6-[3-(1,1,2,2-tetrafluoro-ethoxy)-phenylamino]-pyrimidin-4-yl}-piperidine-4-carboxylic acid ethyl ester

[Method 16]. yellow solid (65 mg, 84%). $^1$HNMR (CDCl$_3$, 400 MHz) δ 1.36 (t, 3H), 1.96 (m, 2H), 2.14 (m, 2H), 2.74 (m, 1H), 3.34 (m, 2H), 4.01 (m, 2H), 4.26 (q, 2H), 6.02 (m, 1H), 7.14 (m, 1H), 7.47 (m, 1H), 7.56 (m, 1H), 7.77 (m, 1H), 8.24 (s, 1H), 10.23 (s, 1H). Exact mass calculated for C$_{20}$H$_{21}$F$_4$N$_5$O$_5$ 487.40, found 488.2 (MH$^+$).

Compound B110

{6-[4-(4-Iodo-phenoxy)-piperidin-1-yl]-5-nitro-pyrimidin-4-yl}-(4-methanesulfonyl-phenyl)-amine Yellow solid; yield 82.6%. $^1$H NMR 400 MHz CDCl$_3$ δ (ppm): 10.2 (s, 1H); 8.13 (s, 1H); 7.86 (m, 4H); 7.50 (m, 2H); 6.64 (m, 2H); 4.55 (m, 1H); 3.65 (m, 2H); 3.55 (m, 2H); 2.98 (s, 3H); 1.96 (m, 4H). LCMS (ESI) m/z 596 (MH$^+$, 100%).

Compound B111

(2-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine Following the general procedure, Compound B111 was obtained as a yellow solid (38%). $^1$H NMR 400 MHz CDCl$_3$ δ 10.3(s, 1H); 8.74(t, 1H); 8.17(s, 1H); 7.70 (d, 1H); 7.67(d, 1H); 3.95-3.92(m, 2H); 3.33-3.27(m, 2H); 3.29-3.23(m, 1H); 3.00(s, 3H); 3.03-2.96(m, 1H); 2.19-2.11 (m, 2H); 2.03-1.96 (m, 2H); 1.26(d, 6H). Exact mass calculated for C$_{21}$H$_{24}$FN$_7$O$_5$S 505.15, LCMS (ESI) m/z 506.2(M+H$^+$, 100%).

Compound B112

{6-[4-(3-Ethyl-[1,2,4]oxadiazol-5-yl)-piperidin-1-yl]-5-nitro-pyrimidin-4-yl}-(2-fluoro-4-methanesulfonyl-phenyl)-amine Following the general procedure, Compound B112 was obtained as a yellow solid (31%). $^1$HNMR (CDCl$_3$, 400 MHz) δ 1.25 (t, 3H), 2.06-2.10 (m, 2H), 2.23-2.27 (m, 2H), 2.70 (q, 2H), 2.99 (s, 3H), 3.31-3.38 (m, 3H), 3.96-3.99 (m, 2H), 7.84 (dd, 4H), 8.14 (s, 1H), 10.2 (s, 1H). Exact mass calculated for C$_{20}$H$_{23}$N$_7$O$_5$S 473.1, found 474.2 (MH$^+$).

Compound B113

(4-Methanesulfonyl-phenyl)-{5-nitro-6-[4-(3-propyl-[1,2,4]oxadiazol-5-yl)-piperidin-1-yl]-pyrimidin-4-yl]-amine Following the general procedure, Compound B113 was obtained as a yellow solid (44%). $^1$H NMR 400 MHz CDCl$_3$ δ 10.2(s, 1H); 8.13(s, 1H); 7.87 (d, 2H); 7.83(d, 2H); 3.92(m, 2H); 3.32-3.29(m, 2H); 3.26-3.23(m, 1H); 2.99(s, 3H); 2.62 (t, 2H); 2.19-2.15(m, 2H); 2.01-1.95(m, 2H); 1.69(se, 2H); 0.91(t, 3H). Exact mass calculated for $C_{21}H_{25}N_7O_5S$ 487.16, LCMS (ESI) m/z 488.2 (M+H$^+$, 100%).

Compound B114

{6-[4-(3-Cyclopropylmethyl-[1,2,4]oxadiazol-5-yl)-piperidin-1-yl]-5-nitro-pyrimidin-4-yl}-(4-methanesulfonyl-phenyl)-amine Following the general procedure, Compound B114 was obtained as a yellow solid (45%). $^1$H NMR 400 MHz CDCl$_3$ δ 10.2(s, 1H); 8.15(s, 1H); 7.87 (d, 2H); 7.78(d, 2H); 3.95(m, 2H); 3.34-3.30(m, 2H); 3.30-3.27(m, 1H); 3.00(s, 3H); 2.57 (d, 2H); 2.21-2.17(m, 2H); 2.04-1.96(m, 2H); 1.06-1.02(m, 1H); 0.53-0.48 (m, 2H); 0.25-0.16(m, 2H). Exact mass calculated for $C_{22}H_{25}N_2O_5S$ 499.16, LCMS (ESI) m/z 500.5 (M+H$^+$, 100%).

Compound B115

{6-[4-(3-Isopropyl-[1,2,4]oxadiazol-5-yl)-piperidin-1-yl]-5-nitro-pyrimidin-4-yl}-(4-methanesulfonyl-phenyl)-amine Following the general procedure, Compound B115 was obtained as a yellow solid (76%). $^1$H NMR 400 MHz CDCl$_3$ δ 10.2 (s, 1H); 8.14 (s, 1H); 7.85 (dd, 4H); 3.92 (d, 2H); 127 (m, 3H); 3.0 (s, 3H); 2.14 (m, 2H); 1.99 (m, 2H); 1.25 (d, 6H). LCMS (ESI) m/z 488 (M$^+$H$^+$, 100%)

Compound B116

{6-[4-(3-Cyclopropyl-[1,2,4]oxadiazol-5-yl)-piperidin-1-yl]-5-nitro-pyrimidin-4-yl}-(4-methanesulfonyl-phenyl)-amine Following the general procedure, Compound B116 was obtained as a yellow solid (83.6%). $^1$H NMR 400 MHz CDCl$_3$ δ10.2 (s, 1H); 8.14 (s, 1H); 7.86 (dd, 4H); 3.90 (d, 2H); 3.30 (m, 2H); 3.27 (m, 1H); 3.00 (s, 3H); 2.13 (m, 2H); 1.98 (m, 3H); 0.97 (m, 4H). LCMS m/z 486 (MH$^+$, 100%)

Compound B117

(4-Methanesulfonyl-phenyl)-(5-nitro-6-{4-[3-(3-trifluoromethyl-phenyl)-[1,2,4]oxadiazol-5-yl]-piperidin-1-yl}-pyrimidin-4-yl)-amine Following the general procedure, Compound B117 was obtained as a yellow solid (61%). $^1$HNMR (CDCl$_3$, 400 MHz) δ 2.06-2.10 (m, 2H), 2.23-2.27 (m, 2H), 2.99 (s, 3H), 3.31-3.38 (m, 3H), 3.96-3.99 (m, 2H), 7.55 (t, 1H), 7.70 (d, 1H), 7.86 (dd, 4H), 8.16 (s, 1H), 8.20 (d, 1H), 8.28 (s, 1H), 10.2 (s, 1H). Exact mass calculated for $C_{25}H_{22}F_3N_7O_5S$ 589.1, found 590.4 (MH$^+$).

Compound B118

4-[4-(3-Isopropyl-[1,2,4]oxadiazol-5-yl)-piperidin-1-yl]-6-(4-methanesulfinyl-phenylamino)-pyrimidine-5-carbonitrile Compound B99 was selectively oxidized using mCPBA to give Compound B118 as the sulfoxide. $^1$H-NMR (DMSO-d$_6$): 9.65 (1H, s), 8.26 (1H, s), 7.75 (2H, m), 7.63 (2H, m), 4.52 (2H, m), 3.45 (1H, m), 3.32 (2H, m), 3.04 (1H, m), 2.73 (3H, s), 2.18 (2H, m), 1.79 (2H, m) 1.18 (6H, J=7 Hz, d) ppm. LCMS: 468.4, 384.1, 356.2, 302.1.

Compound B119

(4-Methanesulfonyl-phenyl)-{5-nitro-6-[4-(4-trifluoromethoxy-phenoxy)-piperidin-1-yl]pyrimidin-4-yl}-amine A mixture of compound (6-chloro-5-nitro-pyrimidin-4-yl)-(4-methanesulfonyl-phenyl)-amine (400 mg, 1.22 mmol), 4-(4-trifluoromethoxy-phenoxy)-piperidine (399 mg, 1.34 mmol) and potassium carbonate (336 mg, 2.44 mmol) in DMF (8 ml) was heated in an oil bath at 60° C. for 2 hours. The crude mixture was cooled to 0° C. and quenched with water. The solid was filtered off, rinsed with water and dried in vacuum oven to give product B119 as a yellow solid (604 mg, 90%). $^1$HNMR (CDCl$_3$, 400 MHz) d 2.01-2.08 (m, 4H), 3.06 (s, 3H), 3.64-3.66 (m, 2H), 3.73-3.75 (m, 2H), 4.62-4.66 (m, 1H), 6.93 (d, 2H), 7.17 (d, 2H), 7.93 (dd, 4H), 8.21 (s, 1H), 10.2 (s, 1H). Exact mass calculated for $C_{23}H_{22}F_3N_5O_6S$ 553.1, found 554.3 (MH$^+$).

Compound B120

4-[4-(3-Isopropyl-[1,2,4]oxadiazol-5-yl)-piperidin-1-yl]-6-(4-methanesulfonyl-phenylamino)-pyrimidine-5-carbonitrile Compound B99 was oxidized using mCPBA to give Compound B120 as the sulfone. $^1$H NMR (DMSO-d$_6$): 9.86 (1H, s), 8.34 (1H, s), 7.93~7.84 (4H, m), 4.54 (2H, m), 3.50~3.39 (3H, m), 3.21 (3H, s) 3.05 (1H, m), 2.21 (2H, m), 1.83 (2H, m) 1.27 (6H, J=7 Hz, d) ppm. LCMS: 452.1, 437.2, 368.1, 340.0.

Compound B121

1-{1-[6-(2-Fluoro-4-methanesulfonyl-phenylamino)-5-nitro-pyrimidin-4-yl]-piperidin-4-yl}-hexan-1-one The general procedure for the addition of Amine to pyrimidine afforded Compound 121; $^1$H NMR, 400 MHz, CDCl$_3$, δ (ppm): 10.48(s, NH); 8.84(s, 1H); 8.23(s, 1H); 7.75(m, 2H); 3.98(m, 2H); 3.22(m, 2H); 3.06 (s, CH$_3$); 2.69(m, 1H); 2.48 (m, 2H); 1.99(m, 2H); 1.77(m, 2H), 1.59(m, 2H), 1.29(m, 4H), 0.89(t, 3H); LCMS (ESI) for $C_{22}H_{28}FN_5O_5S$: m/z 493 (M+H$^+$, 100%).

Compound B122

1-{1-[6-(4-Methanesulfonyl-phenylamino)-5-nitro-pyrimidin-4-yl]-piperidin-4-yl}-hexan-1-one The general procedure for the addition of Amine to pyrimidine afforded Compound 122; $^1$H NMR, 400 MHz, CDCl$_3$, δ (ppm): 10.2(s, NH); 8.20(s, 1H); 7.92(m, 4H); 3.98(m, 2H); 3.22(m, 2H); 3.06 (s, CH$_3$); 2.69(m, 1H); 2.48(m, 2H); 1.99

(m, 2H); 1.77(m, 2H), 1.59(m, 2H), 1.29(m, 4H), 0.89(t, 3H); LCMS (ESI) for $C_{22}H_{29}N_5O_5S$: m/z 476 (M+H$^+$, 100%).

Compound B123

{6-[4-(3-tert-Butyl-[1,2,4]oxadiazol-5-yl)-piperidin-1-yl]-5-nitro-pyrimidin-4-yl}-(2-fluoro-4-methanesulfonyl-phenyl)-amine The general procedure for the addition of Amine to pyrimidine afforded Compound B123 as yellow oil (40 mg, 51%). $^1$H NMR 400 MHz CDCl$_3$ d(ppm): 10.4(s,NH); 8.83(t, 1H); 8.25(s, 1H); 7.76 (t, 2H); 4.01(d,2H); 3.41-3.34(m, 2H); 3.32-3.28(m, 1H); 3.08(s,3H); 2.27-2.22 (m, 2H); 2.11-2.04(m, 2H); 3.36(s, 9H). Exact mass calculated for:
$C_{23}H_{27}FN_6O_5S$ 518.17, LCMS (ESI) m/z 520.4 (M+H$^+$, 100%).

Compound B124

{6-[4-(3-tert-Butyl-[1,2,4]oxadiazol-5-yl)-piperidin-1-yl]-5-nitro-pyrimidin-4-yl}-(4-methanesulfonyl-phenyl)-amine The general procedure for the addition of amine to pyrimidine afforded Compound 124 as a yellow solid, yield 90%; $^1$H NMR 400 MHz CDCl$_3$ δ (ppm): 10.2 (s, 1H); 8.23 (s, 1H); 7.97 (d, 2H); 7.76 (d, 2H); 4.02 (d, 2H); 3.44 (m, 3H); 3.2 (s, 3H); 2.27 (m, 2H); 2.03 (m, 2H); 1.37 (s, 9H); LCMS (ESI) m/z 502 (M$^+$H$^+$, 100%)

Compound B125

[6-(4-Benzofuran-2-yl-piperidin-1-yl)-5-nitro-pyrimidin-4-yl]-(4-methanesulfonyl-phenyl)-amine The general procedure for the addition of amine to pyrimidine afforded Compound B125 as a yellow solid (82 mg, 91%). $^1$H NMR (CDCl$_3$, 400 MHz) δ 1.00 (s, 1H), 1.54 (m, 2H), 1.93 (m, 2H), 2.97 (s, 3H), 3.09 (m, 2H), 3.74 (m, 2H), 6.42 (s, 1H), 6.98 (m, 3H), 7.27 (d, 1H), 7.32 (d, 1H), 7.66 (m, 4H), 7.97 (s, 1H). Exact mass calculated for $C_{20}H_{21}F_2N_7O_3$ 493.53, found 494.4 (M+H$^+$).

Compound B126

4-(3-Fluoro-4-methanesulfonyl-phenylamino)-6-[4-(3-isopropyl-[1,2,4]oxadiazol-5-yl)-piperidin-1-yl]-pyrimidine-5-carbonitrile Compound B126 was obtained as a solid (90%). $^1$HNMR (CDCl$_3$, 400 MHz) δ 1.34 (d, 6H), 2.01-2.08 (m, 2H), 2.23-2.27 (m, 2H), 3.06 (heptet, 1H), 3.22 (s, 3H), 3.30-3.34 (m, 1H), 3.46-3.50 (m, 2H), 4.70-4.77 (m, 2H), 7.33 (dd, 1H), 7.40 (s, 1H), 7.90 (t, 1H), 8.08 (dd, 1H), 8.38 (s, 1H). Exact mass calculated for $C_{22}H_{24}FN_7O_3S$ 485.2, found 486.3 (MH$^+$).

Compound B127

{6-[4-(3-Isopropyl-[1,2,4]oxadiazol-5-yl)-piperidin-1-yl]-5-nitro-pyrimidin-4-yl}-(5-methanesulfonyl-pyridin-2-yl)-amine Compound B127 was prepared by the general procedure for the addition of pyridinylsulfone to pyrimidine to give a solid (4 mg, 4%). $^1$H NMR 400 MHz CDCl$_3$ δ(ppm): 10.5(s, NH); 8.86(s,1H); 8.74(d, 1H); 8.29(s,1H); 8.20(d, 1H); 4.02-3.99(m,2H); 3.40-3.28(m, 3H); 3.11(s,3H); 3.11-3.06(m, 1H); 2.26-2.22(m, 2H); 2.09-2.03(m, 2H); 1.33(d, 6H). Exact mass calculated for $C_{20}H_{24}N_8O_5S$ 488.16, LCMS (ESI) m/z 489.3 (M+H$^+$, 100%).

Compound B128

(3-Fluoro-4-methanesulfonyl-phenyl)-{6-[4-(3-isopropyl-[1,2,4]oxadiazol-5-yl)-piperidin-1-yl]-5-nitro-pyrimidin-4-yl}-amine Compound B128 was prepared using the general procedure for the oxidation of a sulfide to sulfone; yellow solid (9 mg, 36%). $^1$H NMR 400 MHz CDCl$_3$ δ(ppm): 10.3(s,NH); 8.25(s, 1H); 8.13(d, 1H); 7.92(t,1H); 7.40(d,1H); 4.00(db, 2H); 3.41-3.29(m,3H); 3.23(s,3H); 3.10-3.07(m, 1H); 2.26-2.24(m,2H); 2.10-2.02(m,2H); 1.34(d,6H). Exact mass calculated for $C_{21}H_{24}FN_7O_5S$ 505.15, LCMS (ESI) m/z 506.3 (M+H$^+$, 100%).

Compound B129

{6-[4-(3-Isopropyl-[1,2,4]oxadiazol-5-yl)-piperidin-1-yl]-5-nitro-pyrimidin-4-yl}-(6-methanesulfonyl-pyridin-3-yl)-amine Compound B129 was prepared using the general procedure for the oxidation of a sulfide to sulfone; yellow solid (6 mg, 67%). $^1$H NMR 400 MHz CDCl$_3$ δ(ppm): 10.3(s,NH); 8.93(s, 1H); 8.52(d, 1H); 8.22(s,1H); 8.10(d,1H); 4.00(db, 2H); 3.41-3.31(m,3H); 3.23(s,3H); 3.08(qu, 1H); 2.27-2.23 (m,2H); 2.10-2.04(m,2H); 1.33(d,6H).Exact mass calculated for $C_{20}H_{24}N_3O_5S$ 488.16, LCMS (ESI) m/z 489.2 (M+H$^+$, 100%).

Compound B130

4-(2,3-Difluoro-phenylamino)-6-[4-(3-isopropyl-[1,2,4]oxadiazol-5-yl)-piperidin-1-yl]-pyrimidine-5-carbonitrile To a solution of 4,6-dichloro-pyrimidine-5-carbonitrile (254 mg, 1.47 mmol) and 2,3-difluoroaniline (190 mg, 1.47 mmol) in DMF (3 mL) at 0° C. was added K$_2$CO$_3$ (203 mg, 1.47 mmol). The completion of the reaction was monitored by TLC (EtOAc:Hex 1:1, R$_f$=0.90). After the completion of the reaction, 4-(3-isopropyl-[1,2,4]oxadiazol-5-yl)-piperidine (340 mg, 1.47 mmol) and K$_2$CO$_3$ (406 mg, 2.94 mmol) were added at 0° C. The reaction was warmed to rt and stirred for 30 min. The reaction was heated to 40° C. and maintained for 1 h. The reaction was cooled to rt, poured in to H$_2$O (50 mL) and extracted with EtOAc (50 mL, two times). The EtOAc was dried over MgSO$_2$ and concentrated under vacuum. The crude product was purified over SiO$_2$ (EtOAc:Hex=1:1, R$_f$=0.49) to afford Compound B130 (501 mg; 76.7%). $^1$H-NMR (DMSO-d$_6$): 9.60 (1H, s), 8.28 (1H, s), 7.45~7.29 (3H, m), 4.64 (2H, m), 3.59~3.52 (4H, m), 3.41~3.49 (2H, m), 2.29~2.25 (2H, b), 1.96~1.86 (2H, m), 1.39 (6H, d) ppm. LCMS: 426.43.

Compound B131

4-(2,5-Difluoro-phenylamino)-6-[4-(3-isopropyl-[1,2,4]oxadiazol-5-yl)-piperidin-1-yl]-pyrimidine-5-carbonitrile To a solution of 4,6-Dichloro-pyrimidine-5-carbonitrile (254 mg, 1.47 mmol) and 2,5-difluoroaniline (190 mg, 1.47 mmol) in DMF (3 mL) at 0° C. was added K₂CO₃ (203 mg, 1.47 mmol) The completion of the reaction was monitored by TLC (EtOAc:Hex=1:1, R$_f$=0.90). After the reaction was complete, 4-(3-isopropyl-[1,2,4]oxadiazol-5-yl)-piperidine (340 mg, 1.47 mmol) and K₂CO₃ (406 mg, 2.94 mmol) were added at 0° C. The reaction was warmed to rt and stirred for 30 min. The reaction was heated to 40° C. and maintained for 1 h. The reaction was cooled to rt, poured in to H₂O (50 mL) and extracted with EtOAc (50 mL, two times). The EtOAc was dried over MgSO₂ and concentrated under vacuum. The crude product was purified over SiO₂ (EtOAc:Hex=1:1, R$_f$=0.44) to afford the desired Compound B131 (465 mg; 71.1%). ¹H-NMR (DMSO-d₆): 9.32 (1H, s), 8.19 (1H, s), 7.40-7.08 (3H, m), 4.54 (2H, m), 3.48-3.32 (4H, m), 3.07-3.01 (2H, m), 2.18-2.14 (2H, b), 1.96-1.86 (2H, m), 1.27 (6H, d) ppm. LCMS: 426.43.

Compound B132

4-[4-(3-Isopropyl-[1,2,4]oxadiazol-5-yl)-piperidin-1-yl]-6-(4-methylsulfanyl-phenylamino)-pyrimidine-5-carbonitrile Compound B132 was prepared by the general procedure for the addition of amine to pyrimidine as described herein using 4-chloro-6-(4-methylsulfanyl-phenylamino)-pyrimidine-5-carbonitrile and 4-(3-isopropyl-[1,2,4]oxadiazol-5-yl)-piperidine. ¹H-NMR (DMSO-d6): 9.38 (1H, s), 8.21 (1H, s), 7.47 (2H, J=4.3 Hz, d), 7.23 (2H, J=4.3 Hz, d), 4.50 (2H, m), 3.35 (2H, m), 3.02 (1H, m), 2.51 (3H, s), 2.18 (2H, m), 1.79 (2H, m) 1.83 (6H, J=7 Hz, d) ppm. LCMS: 436.3, 351.9, 324.4, 270.2.

Intermediate 4-chloro-6-(4-methylsulfanyl-phenylamino)-pyrimidine-5-carbonitrile was prepared in a similar manner as described herein using 4,6-dichloro-pyrimidine-5-carbonitrile and 4-methylsulfanyl-phenylamine. ¹H-NMR (DMSO-d6): 10.22 (1H, s), 8.53 (1H, s) 7.43 (2H, m), 7.40 (2H, m), 2.49 (3H, s) ppm. LCMS: 277.0, 234.0, 149.0.

Compound B133

4-[4-(3-Isopropyl-[1,2,4]oxadiazol-5-yl)-piperidin-1-yl]-6-(4-methanesulfonyl-phenylamino)-pyrimidine-5-carbonitrile To a solution of 4-[4-(3-isopropyl-[1,2,4]oxadiazol-5-yl]-piperidin-1-yl]-6-(4-methylsulfanyl-phenylamino)-pyrimidine-5-carbonitrile (200 mg, 0.46 mmol) in dichloromethane (5 mL) at 0° C. was added 216 mg of m-CPBA (0.94 mmol). The reaction was stirred for 10 min and warmed to room temperature. The reaction was maintained for 2 h at the same temperature and the completion of the reaction was judged by TLC. The reaction was concentrated under vacuum and purified over SiO₂ (ethyl acetate/Hex=1/1m R$_f$=0.69) to afford Compound B133 (167 mg, 80%). ¹H-NMR (DMSO-d6): 9.86 (1H, s), 8.34 (1H, s), 7.93~7.84 (4H, m), 4.54 (2H, m), 3.50~3.39 (3H, m), 3.21 (3H, s) 3.05 (1H, m), 2.21 (2H, m), 1.83 (2H, m) 1.27 (6H, J=7 Hz, d) ppm. LCMS: 452.1, 437.2, 368.1, 340.0.

Compound B134

4-(4-Hexanoyl-piperidin-1-yl)-6-(6-methylsulfanyl-pyridin-3-ylamino)-pyrimidine-5-carbonitrile 4-Chloro-6-(4-methylsulfanyl-phenylamino)-pyrimidine-5-carbonitrile (150.00 mg, 0.54 mmol) in DMF (2 ml) was mixture with Potassium Carbonate (82.1 mg, 0.59 mmol), added 1-piperidin-4-yl-hexan-1-one hydrochloride (237.4 mg, 1.08 mmol) in DMF (1 ml) and left stirring at room temperature for 1 hour. Reaction was worked up with ethyl acetate, sodium bicarbonate, dried with magnesium sulfate, filtered and concentrate under high vacuum to afford a lithe yellow solid as product. Compound was recrystallized using hexane in ethyl acetate to afford Compound B134 (157 mg). LCMS (ESI) for C₂₂H₂₈N₆OS: m/z 425.4 (M+H⁺, 100%). ¹H NMR 400 MHz CDCl₃ δ (ppm): 8.72 (d, 1H), 8.40 (s, 1H), 7.97 (q, 1H), 7.21 (s,1H,NH), 4.92 (m, 2H), 3.42 (m, 2H), 2.86 (m, 1H), 2.75 (s, 3H), 2.65 (t, 2H), 2.15 (m, 2H), 1.77 (m, 2H), 1.50(m, 2H), 1.50 (m, 2H), 1.07 (t, 3H).

Compound B135

4-(4-Hexanoyl-piperidin-1-yl)-6-(6-methanesulfonyl-pyridin-3-ylamino)-pyrimidine-5-carbonitrile 4-(4-Hexanoyl-piperidin-1-yl)-6-(6-methylsulfanyl-pyridin-3-ylamino)-pyrimidine-5-carbonitrile (100 mg, 0.236 mmol) in chloroform was mixture with mCPBA (122.0 mg, 0.71 mmol) at 0 C under stirring, left reaction warmed up to room temperature and reacted for an additional 12 hours. Worked up with water (pH=10 using ammonium hydroxide as base), chloroform, sodium bicarbonate, dried with magnesium sulfate, concentrate under high vacuum and crystallized using hexane and ethyl acetate to afford Compound B135 as a solid (90 mg, 84%). LCMS (ESI) for C₂₂H₂₈N₆O₃S: m/z 457.2 (M+H⁺, 100%). ¹H NMR 400 MHz CDCl₃ δ (ppm): 8.87 (d, 1H), 8.46 (q, 1H), 8.32 (s, 1H), 8.07(d, 1H), 7.42 (s, 1H, NH), 4.74 (m, 2H), 3.48 (m, 2H), 3.21(s, 3H), 2.70 (m, 1H), 2.48 (t, 2H), 1.98 (m, 2H), 1.58 (m, 2H), 1.27(m, 2H), 1.27 (m, 2H), 0.89 (t, 3H).

Compound B136

4-[4-(3-Isopropyl-[1,2,4]oxadiazol-5-yl)-piperidin-1-yl]-6-(6-methylsulfanyl-pyridin-3-ylamino)-pyrimidine-5-carbonitrile 4-Chloro-6-(6-methylsulfanyl-pyridin-3-ylamino)-pyrimidine-5-carbonitrile (80.00 mg, 0.29 mmol) in DMF (2 ml) was mixture with Potassium Carbonate (79.62 mg, 0.58 mmol), added 4-(3-isopropyl-[1,2,4]oxadiazol-5-yl)-piperidine hydrochloride (237.4 mg, 1.08 or 1.02 mmol) in DMF (1 ml) and left stirring at room temperature for 1 hour. Reaction was worked up with ethyl acetate, sodium bicarbonate, dried with magnesium sulfate, filtered and concentrate under high vacuum. Compound was recrystallized using hexane in ethyl acetate to afford Compound B136. ¹H NMR 400 MHz DMSO δ (ppm): 9.48 (s,1H), 8.55 (d, 1H), 8.35 (s, 1H), 8.19 (s, 1H), 7.77 (d, 1H), 7.26 (d, 1H), 4.52(m, 2H), 3.48 (m, 1H), 3.37 (m, 2H), 3.32 (s, 3H), 3.04 (m, 1H), 2.14 (m, 2H), 1.75 (m, 2H), 1.33 (d, 6H).

Compound B137

4-[4-(3-Isopropyl-[1,2,4]oxadiazol-5-yl)-piperidin-1-yl]-6-(6-methanesulfonyl-pyridin-3-ylamino)-pyrimidine-5-carbonitrile 4-[4-(3-Isopropyl-[1,2,4]oxadiazol-5-yl)-piperidin-1-yl]-6-(6-methylsulfanyl-pyridin-3-ylamino)-pyrimidine-5-carbonitrile (26.0 mg, 0.06 mmol) in chloroform was mixture with mCPBA (41.1 mg, 0.24 mmol) at 0 C under stirring, left reaction warmed up to room temperature and reacted for an additional 12 hours. Worked up with water (pH=10 using ammonium hydroxide as base), chloroform, sodium bicarbonate, dried with magnesium sulfate, concentrate under high vacuum and crystallized using hexane and ethyl acetate to afford Compound B137 as a solid (7.5 mg). $^1$H NMR 400 MHz DMSO δ (ppm): 8.88 (d, 1H), 8.55 (d, 1H), 8.35 (s, 1H), 8.08 (d, 1H), 7.44 (s, 1H), 4.72 (m, 2H), 3.48 (m, 1H), 3.30 (m, 1H), 3.22 (s, 3H), 3.08 (m, 1H), 2.23 (m, 2H), 2.03 (m, 2H), 1.33 (d, 6H).

Compound B138

1-[4-[4-(3-Isopropyl-[1,2,4]oxadiazol-5-yl)-piperidin-1-yl]-6-(4-methanesulfonyl-phenylamino)-pyrimidin-5-yl]-ethanone To a solution of 1-[4-Chloro-6-(4-methanesulfonyl-phenylamino)-pyrimidin-5-yl]-ethanone (0.21 mmol, 70 mg) and 4-(3-isopropyl-[1,2,4]oxadiazol-5-yl)-piperidine hydrochloride (0.21 mmol, 49 mg) in N,N-dimethyl formamide (500 uL) was added potassium carbonate (0.21 mmol, 29 mg). The resulting mixture was microwaved at 100° C. for 150 seconds. Its progress was monitored by thin layer chromatography and LCMS. The reaction was treated with water and the desired compound was extracted in ethyl acetate. Organic layer was evaporated in vacuo. Purification by HPLC provided Compound B138 as a white solid (15 mg, 15%). $^1$H-NMR (400 MHz, CDCl$_3$) δ(ppm): 10.85 (s, 1H); 8.32 (s, 1H); 7.92 (s, 4H); 4.07 (m, 2H); 3.40 (m, 2H); 3.29 (h, 1H); 3.09 (m, 1H); 3.07 (s, 3H); 2.47 (s, 3H); 2.18 (m, 2H); 2.03 (m, 2H); 1.33 (d, 6H). LCMS (ESI), m/z 485.3 (M+H+, 100%).

Compound B139

1-[4-[4-(3-Isopropyl-[1,2,4]oxadiazol-5-yl)-piperidin-1-yl]-6-(6-methanesulfonyl-pyridin-3-ylamino)-pyrimidin-5-yl]-ethanone To a solution of 1-[4-chloro-6-(6-methanesulfonyl-pyridin-3-ylamino)-pyrimidin-5-yl]-ethanone (0.21 mmol, 70 mg) and 4-(3-isopropyl-[1,2,4]oxadiazol-5-yl)-piperidine hydrochloride (0.21 mmol, 49 mg) in N,N-dimethyl formamide (500 uL) was added potassium carbonate (0.21 mmol, 29 mg). The mixture was microwaved at 100° C. for 150 seconds. Its progress was monitored by thin layer chromatography and LCMS. The reaction was treated with water and the desired compound was extracted in ethyl acetate. Organic layer was evaporated in vacuo. Purification by HPLC provided Compound B139 as a white solid (31 mg, 31%). $^1$H-NMR (400 MHz, CDCl$_3$) δ(ppm): 10.9 (s, 1H); 8.90 (d, 1H); 8.58 (d, 1H); 8.32 (s, 1H); 8.05 (d, 1H); 4.09 (m, 2H); 3.41 (m, 2H); 3.29 (h, 1H); 3.23 (s, 3H); 3.09 (h, 1H); 2.48 (s, 3H), 2.18 (m, 2H), 2.02 (m, 2H), 1.35 (d, 6H) LCMS (ESI), m/z 486.3 (M+H+, 100%).

Example 14

Syntheses of Compounds of the Present Invention

Compound C1

1-(5-Nitro-6-phenyl-pyrimidin-4-yl)-piperidine-4-carboxylic acid ethyl ester

General Method 17. A mixture of 1-(6-chloro-5-nitropyrimidine-4-yl)-piperidine-4-carboxylic acid ethyl ester (0.157 g, 0.49 mmol), phenyl boronic acid (62.1 mg, 0.50 mmol), tetrakistriphenylphosphinepalladium(0) (11.6 mg), 2M Na$_2$CO$_3$ (375 µL), DME/H$_2$O/ethanol (7/3/2) (1239 µL) was heated in a microwave tube at 140° C. for 120 s in a microwave reactor. The reaction mixture was cooled and filtered and the filtrate was partitioned between ethyl acetate and water. The organic layer was washed with 1N NaOH (2×) and brine, dried (Na$_2$CO$_3$) and evaporated. Flash column chromatography (Biotage, silica, 20% EtOAc/hexane) afforded the desired product C1 in 47% yield. $^1$HNMR, 400 MHz, CDCl$_3$, δ (ppm): 8.63(s, 1H); 7.45(m, 5H); 4.16(q, 2H); 4.07 (m, 2H); 3.20(t, 2H); 2.62(m, 1H); 2.03(m, 2H); 1.84(m, 2H); 1.28(t, 3H). LCMS (ESI) for C$_{18}$H$_{20}$N$_4$O$_4$: m/z 356 (M+H+, 100%)

Compound C2

1-(6-Naphthalen-2-yl-5-nitro-pyrimidin-4-yl)-piperidine-4-carboxylic acid ethyl ester

[Method 17]. Purification of the crude product by HPLC afforded the pure product. $^1$H NMR, 400 MHz, CDCl$_3$, δ (ppm): 8.62(s, 1H); 7.93(s, 1H); 7.80 (m, 3H); 7.50(m, 3H); 4.10(q, 2H); 3.99(m, 2H); 3.16 (t, 2H); 2.58(m, 1H); 1.98 (m, 2H); 1.21(t, 3H). LCMS (ESI) for C$_{22}$H$_{22}$N$_4$O$_4$: m/z 406 (M+H+, 100%)

Compound C3

1-[6-(4-Methanesulfonyl-phenyl)-5-nitro-pyrimidin-4-yl]-piperidine-4-carboxylic acid ethyl ester

[Method 17]. Purification of the crude product by preparatory LCMS afforded the pure product in 7%. $^1$H NMR, 400 MHz, CDCl$_3$, δ (ppm): 8.66(s, 1H); 8.02(d, 1H); 7.66(d, 1H); 4.18(q, 2H); 4.05(m, 2H); 3.27(t, 2H); 3.09(s, 3H); 2.66(m, 1H); 2.06(m, 2H); 1.88(m, 2H); 1.28(t, 3H). LCMS (ESI) for C$_{19}$H$_{22}$N$_4$O$_6$S: m/z 434 (M+H+, 100%)

Compound C4

1-(6-Benzofuran-5-yl-5-nitro-pyrimidin-4-yl)-piperidine-4-carboxylic acid ethyl ester

[Method 17]. Flash column chromatography (Biotage, silica, 20% EtOAc/hexane) afforded the product in 61% yield. $^1$H NMR, 400 MHz, CDCl$_3$, δ (ppm): 8.63(s, 1H); 7.66(d, 1H); 7.57(s, 1H); 7.54(d, 1H); 7.39(t, 1H); 7.28(t, 114); 4.15(m, 4H); 3.22(t, 2H); 2.63(m, 1H); 2.04(m, 2H); 1.85(m, 2H); 1.28(t, 3H). LCMS (ESI) for C$_{22}$H$_{20}$N$_4$O$_5$: m/z 396 (M+H+, 100%)

Compound C5

1-[5-Nitro-6-(3-trifluoromethyl-phenyl]-pyrimidin-4-yl}-piperidine-4-carboxylic acid ethyl ester

[Method 17]. Purification of the crude product by HPLC afforded the pure product in 11%. $^1$H NMR, 400 MHz, CDCl$_3$, δ (ppm): 8.65 (s, 1H); 7.46 (q, 1H); 4.18 (q, 2H); 4.05 (m, 2H); 3.24 (m, 3H); 2.65 (m, 1H); 2.05 (m, 2H); 1.86 (m, 2H); 1.27 (t, 3H). LCMS (ESI) for C$_{19}$H$_{22}$N$_4$O$_4$: m/z 370 (M+H+, 100%)

Compound C6

1-[6-(4-Methoxy-phenyl)-5-nitro-pyrimidin-4-yl]-piperidine-4-carboxylic acid ethyl ester

[Method 17]. Flash column chromatography (Biotage, silica, 20% EtOAc/hexane) afforded the product in 24% yield. ¹H NMR, 400 MHz, CDCl₃, δ (ppm): 8.60(s, 1H); 7.47(d, 1H); 6.94(, 2H); 4.15(q, 2H); 4.03(m, 2H); 3.84(s, 2H); 3.17(m, 2H); 2.61(m, 1H); 1.96(m, 2H); 1.83(m, 2H); 1.27(t, 3H). LCMS (ESI) for $C_{19}H_{22}N_4O_5$: m/z 386 (M+H⁺, 100%)

Compound C7

4-(4-Butyl-piperidin-1-yl)-6-furan-3-yl-5-nitro-pyrimidine

[Method 17]. Flash column chromatography (Biotage, silica, 20% EtOAc/hexane) afforded the product in 35% yield. ¹H NMR, 400 MHz, CDCl₃, δ (ppm): 8.55(s, 1H); 7.97(s, 1H); 7.46(s, 1H); 6.73(s, 2H); 4.16(q, 2H); 3.18 (m, 2H); 2.61(m, 1H); 2.01(m, 2H); 1.83(m, 2H); 1.27(t, 3H). LCMS (ESI) for $C_{16}H_{18}N_4O_5$: m/z 346 (M+H⁺, 100%)

Compound C8

1-[6-(3-Chloro-phenyl)-5-nitro-pyrimidin-4-yl]-piperidine-4-carboxylic acid ethyl ester

[Method 17]. Purification of the crude product by HPLC afforded the pure product in 14%. ¹H NMR, 400 MHz, CDCl₃, δ (ppm): 8.67(s, 1H); 7.47(m, 1H); 7.38(t, 1H); 7.32 (m, 1H); 4.18(q, 2H); 4.05 (m, 2H); 3.28 (t, 2H); 2.67(m, 1H); 2.07(m, 2H); 1.88(m, 2H); 1.28(t, 3H). LCMS (ESI) for $C_{18}H_{19}ClN_4O_4$: m/z 390 (M+H⁺, 100%)

Compound C9

1-[6-(2,6-Dimethoxy-phenyl)-5-nitro-pyrimidin-4-yl]-piperidine-4-carboxylic acid ethyl ester

[Method 17].Purification of the crude product by HPLC afforded the pure product in 28%. ¹H NMR, 400 MHz, CDCl₃, δ (ppm): 8.79(s, 1H); 7.95(s, 3H); 7.40(t, 1H); 6.59(d, 2H); 4.18(q, 2H); 4.07 (m, 2H); 3.74 (s, 6H); 3.38 (t, 2H); 2.70(m, 1H); 2.10(m, 2H); 1.95(m, 2H); 1.28(t, 3H). LCMS (ESI) for $C_{18}H_{19}ClN_4O_4$: m/z 390 (M+H⁺, 100%)

Compound C10

1-(6-Naphthalen-1-yl-5-nitro-pyrimidin-4-yl)-piperidine-4-carboxylic acid ethyl ester

[Method 17]. The reaction mixture was filtered through Celite and activated carbon and purified by preparatory LCMS. 400 MHz CDCl₃ δ(ppm): 8.75 (s, 1H); 7.96 (m, 1H); 7.90 (m, 2H); 7.51 (m, 3H); 7.40 (m, 1H); 4.19 (m, 2H); 4.11 (m, 2H); 3.31 (m, 2H); 2.68 (m, 1H); 2.08 (m, 2H); 1.91 (m, 2H); 1.29 (m, 3H). LCMS (ESI) m/z 407 (M+H⁺, 100%)

Compound C11

1-[6-(4-Methylsulfanyl-phenyl)-5-nitro-pyrimidin-4-yl]-piperidine-4-carboxylic acid ethyl ester

[Method 17].The reaction mixture was filtered through Celite and activated carbon and purified by preparatory LCMS. ¹H NMR 400 MHz CDCl₃ χ(ppm): 8.68 (s, 1H); 7.41 (m, 2H); 7.28 (m, 2H); 4.18 (m, 2H); 4.07 (m, 2H); 3.27 (m, 2H); 2.66 (m, 1H); 2.52 (s, 3H); 2.03 (m, 2H); 1.85 (m, 2H); 1.29 (m, 3H). LCMS (ESI) m/z 403 (M+H⁺, 100%)

Compound C12

1-(2',4'-Dihydroxy-5-nitro-[4,5']bipyrimidinyl-6-yl)-piperidine-4-carboxylic acid ethyl ester;

[Method 17]. The reaction mixture was filtered through Celite and activated carbon and purified by HPLC w/TFA. Yield 0.015 g, 11%. Yellow solid. ¹H NMR 400 MHz CDCl₃ δ(ppm): 8.48, 7.33 (s, 1H); 8.02 (s, 1H); 4.07 (m, 2H); 3.86 (m, 2H); 3.13 (m, 2H); 2.65 (s, 2H); 2.55 (m, 1H); 1.93 (m, 2H); 1.74 (m, 2H); 1.18 (m, 3H). LCMS (ESI) m/z 391 (M+H⁺, 100%)

Compound C13

1-[6-(4-Methanesulfonyl-phenyl)-5-nitro-pyrimidin-4-yl]-piperidine-4-carboxylic acid ethyl ester

[Method 17]Yield: 6 mg (4%). ¹H NMR, 400 MHz, CDCl₃, δ (ppm): 8.66(s, 1H); 8.02(d, 1H); 7.66(d, 1H); 4.18 (q, 2H); 4.05(m, 2H); 3.27(t, 2H); 3.09(s, 3H); 2.66(m, 1H); 2.06(m, 2H); 1.88(m, 2H); 1.28(t, 3H). LCMS (ESI) for $C_{19}H_{22}N_4O_6S$: m/z 434 (M+H⁺, 100%)

Compound C14

1-[6-(3,5-Bis-trifluoromethyl-phenyl)-5-nitro-pyrimidin-4-yl]-piperidine-4-carboxylic acid ethyl ester

[Method 17]. Purification of the crude product by preparatory LCMS afforded the pure product in 23%. ¹H NMR, 400 MHz, CDCl₃, δ (ppm): 8.64(s, 1H); 7.96(s, 3H); 4.18(q, 2H); 4.05(m, 2H); 3.25(t, 2H); 2.65(m, 1H); 2.05(m, 2H); 1.85(m, 4H); 1.28(t, 3H). LCMS (ESI) for $C_{20}H_{18}F_6N_4O_4$: m/z 492 (M+H⁺, 100%)

Compound C15

1-(6-Dibenzothiophen-4-yl-5-nitro-pyrimidin-4-yl)-piperidine-4-carboxylic acid ethyl ester

[Method 17]. Purification of the crude product by preparatory LCMS afforded the pure product in 24%. ¹H NMR, 400 MHz, CDCl₃, δ (ppm): 8.72(s, 1H); 8.20(d, 1H); 8.12 (m, 1H); 7.76 (m, 1H); 7.45(m, 4H); 7.37(m, 1H); 4.14(q, 2H); 4.05(m, 2H); 3.27(t, 2H); 2.64(m, 1H); 2.03(m, 2H); 1.86(m, 2H); 1.25(t, 3H). LCMS (ESI) for $C_{24}H_{22}N_4O_4S$: m/z 462 (M+H⁺, 100%)

Compound C16

1-[6-(3,5-Dimethyl-isoxazol-4-yl)-5-nitro-pyrimidin-4-yl]-piperidine-4-carboxylic acid ethyl ester

[Method 17]. Purification of the crude product by preparatory LCMS afforded the pure product in 12%. 400 MHz, CDCl₃, δ (ppm): 8.64(s, 1H); 4.18(q, 2H); 4.05(m, 2H); 3.25 (t, 2H); 2.66(m, 1H); 2.35(s, 3H); 2.21(s, 3H); 2.05(m, 2H); 1.86(m, 2H); 1.28(t, 3H). LCMS (ESI) for $C_{17}H_{21}N_5O_5$: m/z 375 (M+H⁺, 100%)

Compound C17

1-(5-Nitro-6-thiophen-2-yl-pyrimidin-4-yl)-piperidine-4-carboxylic acid ethyl ester

[Method 17]. Purification of the crude product by preparatory LCMS afforded the pure product in 23%. ¹HNMR, 400

MHz, CDCl₃, δ (ppm): 8.56(s, 1H); 7.58(d, 1H); 7.47(d, 11-1); 7.10(t, 1H); 4.17(q, 2H); 4.09(d, 2H); 3.21(t, 2H); 2.62(m, 1H); 2.03(m, 2H); 1.85(m, 2H); 1.28(t, 3H). LCMS (ESI) for $C_{16}H_{18}N_4O_4S$: m/z 362 (M+H⁺, 100%)

Compound C18

1-[6-(3,5-Dichloro-phenyl)-5-nitro-pyrimidin-4-yl]-piperidine-4-carboxylic acid ethyl ester

[Method 17]. Purification of the crude product by preparatory LCMS afforded the pure product in 7%. 400 MHz, CDCl₃, δ (ppm): 8.59(s, 1H); 7.44(s, 1H); 7.30(s, 2H); 7.23(s, 1H); 4.14(q, 2H); 4.00(m, 2H); 3.21(m, 2H); 2.61(m, 1H); 2.02(m, 2H); 1.81(m, 2H); 1.25(t, 3H). LCMS (ESI) for $C_{16}H_{18}N_4O_4S$: m/z 362 (M+H⁺, 100%)

Compound C19

1-(6-Dibenzofuran-4-yl-5-nitro-pyrimidin-4-yl)-piperidine-4-carboxylic acid ethyl ester

[Method 17]. Purification of the crude product by preparatory LCMS afforded the pure product in 17%. ¹HNMR, 400 MHz, CDCl₃, δ (ppm): 8.77(s, 1H); 8.07(d, 1H); 7.96(d, 1H); 7.45(m, 4H); 7.36(t, 1H); 4.18(q, 21-1); 4.08(m, 2H); 3.31(t, 2H); 2.69(m, 1H); 2.07(m, 2H); 1.92(m, 2H); 1.29(t, 3H). LCMS (ESI) for $C_{24}H_{22}N_4O_5$: m/z 446 (M+H⁺, 100%)

Compound C20

1-[6-(3,5-Dimethyl-phenyl)-5-nitro-pyrimidin-4-yl]-piperidine-4-carboxylic acid ethyl ester

[Method 17]. Purification of the crude product by preparatory LCMS afforded the pure product in 23%. ¹H NMR, 400 MHz, CDCl₃, δ (ppm): 8.46(s, 1H); 6.93(s, 3H); 4.02(q, 2H); 3.89(m, 2H); 3.05(m, 2H); 2.47(m, 1H); 2.20(s, 6H); 1.88(m, 2H); 1.70(m, 4H); 1.18(t, 3H). LCMS (ESI) for $C_{18}H_{18}ClN_4O_4$: m/z 384 (M+H⁺, 100%)

Compound C21

1-[6-(4-Acetyl-phenyl)-5-nitro-pyrimidin-4-yl]-piperidine-4-carboxylic acid ethyl ester Filtered the reaction mixture and the filtrate was purified by semi preparatory HPLC afforded the pure product in 21%. ¹H NMR, 400 MHz, CDCl₃, δ (ppm): 8.63(s, 1H); 8.00(d, 2H); 7.57(d, 2H); 4.16(q, 2H); 4.03(m, 2H); 3.22(m, 2H); 2.64(s, 3H); 2.03(m, 2H); 1.85(m, 4H); 1.27(t, 3H). LCMS (ESI) for $C_{20}H_{22}N_4O_5$: m/z 398 (M+H⁺, 100%)

Compound C22

1-[6-(4-Ethanesulfonyl-phenyl)-5-nitro-pyrimidin-4-yl]-piperidine-4-carboxylic acid ethyl ester

[Method 17]. Purification of the crude product by preparatory TLC using 20% EtOAc/hexane afforded the pure product in 21%. ¹H NMR, 400 MHz, CDCl₃, δ (ppm): 8.63(s, 1H); 7.97(d, 2H); 7.67(d, 2H); 4.18(q, 2H); 3.22(m, 2H); 3.12(m, 3H); 2.65(m, 1H); 2.04(m, 2H); 1.85(m, 2H); 1.28(t, 3H). LCMS (ESI) for $C_{20}H_{24}N_4O_6S$: m/z 448 (M+H⁺, 100%)

Compound C23

1-[6-(2-Fluoro-biphenyl-4-yl)-5-nitro-pyrimidin-4-yl]-piperidine-4-carboxylic acid ethyl ester

[Method 17]. purified by semi preparatory HPLC afforded the pure product in 14%. ¹H NMR, 400 MHz, CDCl₃, δ (ppm): 8.54(s, 1H); 7.35(m, 8H); 4.07(q, 2H); 3.96(m, 2H); 3.13(t, 2H); 2.53(m, 1H); 1.95(m, 2H); 1.77(m, 2H); 1.19(t, 3H). LCMS (ESI) for $C_{20}H_{22}N_4O_5$: m/z 398 (M+H⁺, 100%)

Compound C24

1-[6-(3-Methanesulfonyl-phenyl)-5-nitro-pyrimidin-4-yl]-piperidine-4-carboxylic acid ethyl ester

[Method 17]. Purification of the crude product by flash column chromatography (Biotage, silica, 20% EtOAc/hexane) afforded the pure product in 5%. 400 MHz, CDCl₃, δ (ppm): 8.67(s, 1H); 8.07(m, 2H); 7.69(m, 2H); 4.18(q, 2H); 4.09(m, 2H); 3.29(t, 2H); 3.08(s, 3H); 2.71(m, 1H); 2.06(m, 2H); 1.87(m, 2H); 1.27(t, 3H). LCMS (ESI) for $C_{19}H_{22}N_4O_6S$: m/z 434 (M+H⁺, 100%)

Compound C25

1-{6-[4-(2-Carboxy-ethyl)-phenyl]-5-nitro-pyrimidin-4-yl}-piperidine-4-carboxylic acid ethyl ester

[Method 17]. C25 was purified by preparatory HPLC afforded the pure product in 24%. ¹H NMR, 400 MHz, CDCl₃, δ (ppm): 8.52(s, 1H); 7.33(d, 2H); 7.17(d, 2H); 4.07 (m, 2H); 3.94(m, 2H); 3.10(t, 2H); 2.94(t, 2H); 2.64(t, 2H); 2.52(m, 1H); 1.40(t, 3H). LCMS (ESI) for $C_{21}H_{24}N_4O_6$: m/z 428 (M+H⁺, 100%)

Compound C26

1-{6-[4-(2-Methoxycarbonyl-ethyl)-phenyl]-5-nitro-pyrimidin-4-yl}-piperidine-4-carboxylic acid methyl ester

[Method 17]. Purification of the residue by column chromatography (silica, 20% EtOAc/hexane) afforded the pure product in 14%. ¹HNMR, 400 MHz, CDCl₃, δ (ppm): 8.55(s, 1H); 7.36(d, 2H); 7.19(d, 2H); 3.95(m, 2H); 3.64(s, 3H); 3.60(s, 3H); 3.11(m, 2H); 2.92(t, 2H); 2.57(t, 2H); 2.54(m, 1H); 1.95(m, 2H); 1.76(m, 2H). LCMS (ESI) for $C_{21}H_{24}N_4O_6$: m/z 428 (M+H⁺, 100%).

Compound C27

1-{6-[4-(2-Methoxycarbonyl-ethyl)-phenyl]-5-nitro-pyrimidin-4-yl}-piperidine-4-carboxylic acid ethyl ester

[Method 17]. Purification of the residue by preparatory TLC (silica, 20% EtOAc/hexane) afforded the pure product in 16%. ¹H NMR, 400 MHz, CDCl₃, δ (ppm): 8.55(s, 1H); 7.35(d, 2H); 7.19(d, 2H); 4.09(q, 2H); 3.96(m, 2H); 3.60(s, 3H); 3.11(m, 2H); 2.92(t, 2H); 2.57(t, 2H); 1.94(s, 3H); 1.77(m, 2H); 1.19(t, 3H). LCMS (ESI) for $C_{22}H_{26}N_4O_6$: m/z 442 (M+H⁺, 100%).

Example 15

Syntheses of Compounds of the Present Invention

Compound D1

1-[5-Nitro-6-(2-trifluoromethyl-phenylethynyl)-pyrimidin-4-yl]-piperidine-4-carboxylic acid ethyl ester. General Method 18

1-{6-chloro-5-nitro-pyrimidin-4-yl}-piperidine-4-carboxylic acid ethyl ester (100 mg, 0.317 mmol), Pd(PPh$_3$)$_2$Cl$_2$ (12 mg, 0.017 mmol) and copper(I)iodide (5 mg, 0.026 mmol) were dissolved in diisopropylethylamine and stirred for 2 min. o-ethynyl-trifluoromethylbenzene (100 ul, 0.072 mmol) was added and the mixture stirred under N$_2$ at 70° C. for 18 hours. The yellow suspension turned black. After cooling to room temperature, the reaction mixture was diluted with chloroform (12 ml), passed through a celite plug and concentrated under vacuo. Purification by Flash Chromatography (0-30% Ethyl acetate/Hexanes) gave Compound D1. Yield 35%. $^1$H NMR 400 MHz CDCl$_3$ δ (ppm): 8.58 (s, 1H); 7.78 (d, 1H); 7.71 (d, 1H); 7.56 (m, 2H); 4.16 (m, 2H); 4.01 (d, 2H); 3.21 (m, 2H); 2.63 (m, 1H); 2.03 (m, 2H); 1.84 (m, 2H); 1.26 (t, 3H). LCMS (ESI) m/z 449 (M$^+$H$^+$, 100%)

Compound D2

1-(5-Nitro-6-phenylethynyl-pyrimidin-4-yl)-piperidine-4-carboxylic acid ethyl ester

[Method 18]. Purification by HPLC yielded red oil. Yield 9%. $^1$H NMR 400 MHz CDCl$_3$ δ (ppm): 8.49 (s, 1H); 7.54 (d, 2H); 7.32 (d, 3H); 4.11 (m, 2H); 3.95 (d, 2H); 3.20 (m, 2H); 2.58 (m, 1H); 2.01 (m, 2H); 1.80 (m, 2H); 1.21 (t, 3H). LCMS (ESI) m/z 381 (M+H$^+$, 100%)

Compound D3

1-[5-Nitro-6-(4-trifluoromethyl-phenylethynyl)-pyrimidin-4-yl]-piperidine-4-carboxylic acid ethyl ester

[Method 18]. Purification by HPLC. Yield 30% brown solid. $^1$H NMR 400 MHz CDCl$_3$ δ (ppm): 8.55 (s, 1H); 7.7 (d, 2H); 7.65 (d, 2H); 4.17 (m, 2H); 4.00 (d, 2H); 3.24 (m, 2H); 2.64 (m, 1H); 1.96 (m, 4H); 1.28 (t, 3H). LCMS (ESI) m/z 449 (M+H$^+$, 100%)

Compound D4

1-(5-Nitro-6-m-tolylethynyl-pyrimidin-4-yl)-piperidine-4-carboxylic acid ethyl ester;

Purification by HPLC. Yield 60% brown solid. $^1$H NMR 400 MHz CDCl$_3$ δ (ppm): 8.55 (s, 1H); 7.44 (d, 2H); 7.27 (d, 2H); 4.18 (m, 2H); 4.00 (d, 2H); 3.24 (m, 2H); 2.64 (m, 1H); 2.37 (s, 3H); 2.04 (m, 2H); 1.87 (m, 2H); 1.28 (t, 3H). LCMS (ESI) m/z 395 (M+H$^+$, 100%)

Compound D5

1-[6-(2-Fluoro-phenylethynyl)-5-nitro-pyrimidin-4-yl]-piperidine-4-carboxylic acid ethyl ester $^1$H NMR 400 MHz CDCl$_3$ δ (ppm): 8.58 (s, 1H); 7.78 (d, 1H); 7.71 (d, 1H); 7.56 (m, 2H); 4.16 (m, 2H); 4.01 (d, 2H); 3.21 (m, 2H); 2.63 (m, 1H); 2.03 (m, 2H); 1.84 (m, 2H); 1.26 (t, 3H). LCMS (ESI) m/z 449 (M+H$^+$, 100%)

Compound D6

1-[5-Nitro-6-(3-trifluoromethyl-phenylethynyl)-pyrimidin-4-yl]-piperidine-4-carboxylic acid ethyl ester

[Method 18]. Purification by Flash Chromatography (20-30% Ethyl acetate/Hexanes). Yield 42%. $^1$H NMR 400 MHz CDCl$_3$ δ (ppm): 8.55 (s, 1H); 7.87 (s, 1H); 7.78 (d, 1H); 7.68 (d, 1H); 7.55 (m, 1H); 4.19 (m, 2H); 4.00 (d, 2H); 3.23 (m, 2H); 2.65 (m, 1]-1); 2.04 (m, 2H); 1.86 (m, 2H); 1.27 (t, 3H). LCMS (ESI) m/z 449 (M$^+$H$^+$, 100%)

Example 16

Syntheses of Compounds of the Present Invention

5-Nitro-4-(5-phenyl-[1,3,4]oxadiazol-2-ylsulfanyl)-6-[4-(pyridin-2-ylsulfanyl)-piperidin-1-yl]-pyrimidine

Compound E1

[Method 16]. yellow solid (56 mg, 80%). $^1$HNMR (CDCl$_3$, 400 MHz) δ 1.61 (m, 2H), 2.02 (m, 2H), 3.22 (m, 2H), 3.69 (m, 2H), 3.98 (m, 2H), 6.87 (m, 1H), 6.94 (m, 1H), 7.30 (m, 4H), 7.72 (m, 2H), 7.89 (m, 1H), 8.20 (m, 1H). Exact mass calculated for C$_{22}$H$_{19}$N$_7$O$_3$S$_2$ 493.56, found 494.5 (MH$^+$).

The compounds in the above examples were screened in the Membrane Cyclase Assay. Representative compounds are shown in the table below:

| Compound | RUP3 (IC$_{50}$) Membrane Cyclase (μM) |
|---|---|
| A124 | 0.241 |
| B70 | 0.129 |
| B84 | 0.050 |

The other compounds in the Examples showed IC$_{50}$ activities in the membrane cyclase assay less than about 500 μM.

Those skilled in the art will recognize that various modifications, additions, substitutions, and variations to the illustrative examples set forth herein can be made without departing from the spirit of the invention and are, therefore, considered within the scope of the invention. All documents referenced above, including, but not limited to, printed publications, and provisional and regular patent applications, are incorporated herein by reference in their entirety.

---

We claim:

1. A method for treatment of a metabolic disorder in an individual, wherein the metabolic disorder is type II diabetes, inadequate glucose tolerance, insulin resistance, hyperglycemia, hyperlipidemia, hypertriglyceridemia, hypercholesterolemia, dyslipidemia, syndrome X, metabolic synderome or obesity, the method comprising administering to the individual a therapeutically effective amount of a compound according of Formula (Ia):

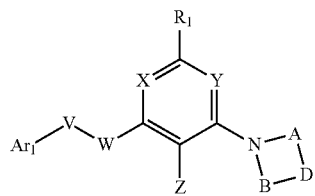

(Ia)

or a pharmaceutically acceptable salt, hydrate or solvate thereof, wherein:

A and B are independently $C_{1-3}$ alkylene optionally substituted with 1 to 4 methyl groups;

D is $CR_2R_3$ or $N-R_2$;

V is absent;

W is $NR_4$ or O;

X is N;

Y is N;

Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1 or 2 groups selected from the group consisting of $C_{2-4}$ dialkylamino, hydroxy, and halogen; or Z is selected from the group consisting of nitro, amino, formyl, $NHC(O)CF_3$, Br, $NHC(O)CH_3$, $N(C(O)CH_3)_2$, $N(S(O)_2CH_3)_2$, $CH_3$, [1,3]dioxolan-2-yl, $CH_2OH$, $CH_2N(CH_3)_2$, and $C(O)CH_3$; or Z is a group of Formula (A):

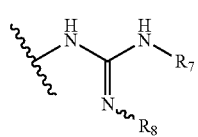

(A)

wherein:

$R_7$ is H, $C_{1-8}$ alkyl or $C_{3-6}$ cycloalkyl; and $R_8$ is H, nitro or nitrile;

$Ar_1$ is aryl or heteroaryl wherein each is optionally substituted with $R_9$-$R_{13}$;

wherein the heteroaryl of $Ar_1$ is selected from the group consisting of pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline, 1H-imidazolyl, [1,2,4]triazolyl, [1,2,3]triazolyl, pyrrolyl, pyrazolyl, 1H-pyrazolyl, imidazolyl, oxazolyl, [1,3,4]oxadiazolyl, [1,3,4]thiadiazolyl, [1,2,4]oxadiazolyl, [1,2,4]thiadiazolyl, tetrazolyl, 1,3-dioxo-1,3-dihydro-isoindolyl, and [1,2,3]thiadiazol-4-yl;

$R_1$ is selected from the group consisting of H, $C_{1-4}$ alkoxy, $C_{1-8}$ alkyl, $C_{2-6}$ alkynyl, amino, $C_{3-6}$ cycloalkyl, and $C_{1-4}$ haloalkyl;

$R_2$ is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, $C_{3-6}$-cycloalkyl, $C_{1-4}$ haloalkoxy, $C_{1-4}$ haloalkyl, halogen, hydroxyl, $CH_2OCH_2$-cyclopropyl, $CH_2OCH_2$-cyclobutyl, $CH_2OCH_2$-cyclopentyl, $CH_2OCH_2$-cyclohexyl, $CH_2OCH_2CH_2$-cyclopropyl, $CH_2OCH_2CH_2$-cyclobutyl, $CH_2OCH_2CH_2$-cyclopentyl, $CH_2OCH_2CH_2$-cyclohexyl, $CH_2CH_2OCH_2$-cyclopropyl, $CH_2CH_2OCH_2$-cyclobutyl, $CH_2CH_2OCH_2$-cyclopentyl, $CH_2CH_2OCH_2$-cyclohexyl, $CH_2CH_2OCH_2CH_2$-cyclopropyl, $CH_2CH_2OCH_2CH_2$-cyclobutyl, $CH_2CH_2OCH_2CH_2$-cyclopentyl, and $CH_2CH_2OCH_2CH_2$-cyclohexyl; or $R_2$ is $C_{1-8}$ alkyl or heteroaryl, each optionally substituted with 1 to 5 substituents selected from the group consisting of $C_{1-5}$ acyloxy, $C_{1-4}$ alkoxy, $C_{1-8}$ alkyl, $C_{1-4}$ alkylsulfonyl, carbo-$C_{1-6}$-alkoxy, carboxamide, carboxy, $C_{3-6}$-cycloalkyl, $C_{3-6}$-cycloalkyl-$C_{1-3}$-alkylene, $C_{3-6}$-cycloalkyl-$C_{1-3}$-heteroalkylene, and hydroxyl; or $R_2$ is $C_{1-8}$ alkyl, heteroaryl or phenyl each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$-$Ar_3$ wherein $Ar_2$ and $Ar_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

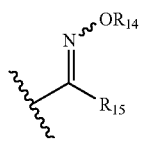

(B)

wherein:
$R_{14}$ is $C_{1-8}$ alkyl or $C_{3-6}$ cycloalkyl; and $R_{15}$ is F, Cl, Br or CN; or $R_2$ is a group of Formula (C):

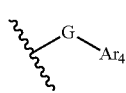

(C)

wherein:
G is C=O, $CR_{16}R_{17}$, O, S, S(O), or $S(O)_2$;
wherein
$R_{16}$ and $R_{17}$ are independently H or $C_{1-8}$ alkyl; and
$Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$ alkoxy, carboxamide, carboxy, cyano, $C_{3-6}$-cycloalkyl, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy, halogen or hydroxyl;
$R_4$ is H or $C_{1-8}$ alkyl;
$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, $C_{2-6}$ dialkylsulfonamide, halogen, $C_{1-4}$ haloalkoxy, $C_{1-4}$ haloalkyl, haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (D):

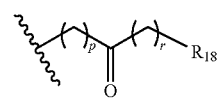

(D)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{10}$-$R_{13}$ are independently selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or
two adjacent $R_{10}$-$R_{11}$ groups together with $Ar_1$ form a 5, 6 or 7 membered cycloalkyl, cycloalkenyl or heterocyclic group wherein the 5, 6 or 7 membered group is optionally substituted with halogen.

2. The method according to claim 1, wherein A and B are both ethylene and wherein A and B are optionally substituted with 1 to 4 methyl groups.

3. The method according to claim 1, wherein Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1, or 2 groups selected from the group consisting of $C_{2-4}$ dialkylmino, hydroxy, and halogen.

4. The method according to claim 1, wherein D is $CR_2R_3$.

5. The method according to claim 1, wherein $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$- heteroalkylene, C<sub>2-8</sub> dialkylamino, C<sub>2-6</sub> dialkylcarboxamide, C<sub>1-4</sub> dialkylthiocarboxamide, C<sub>2-6</sub> dialkylsulfonamide, C<sub>1-4</sub> alkylthioureyl, C<sub>1-4</sub> haloalkoxy, C<sub>1-4</sub> haloalkyl, C<sub>1-4</sub> haloalkylsulfinyl, C<sub>1-4</sub> haloalkylsulfonyl, C<sub>1-4</sub> haloalkyl, C<sub>1-4</sub> haloalkylthio, halogen, heterocyclic, hydroxyl, hydroxylamino and nitro.

6. The method according to claim 1, wherein the compound is a compound of the following formula:

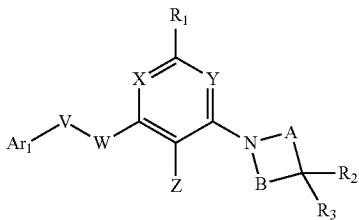

or a pharmaceutically acceptable salt, hydrate or solvate thereof, wherein:
wherein R<sub>2</sub> is a 5-membered heteroaryl optionally substituted with 1 to 4 substituents selected from the group consisting of C<sub>1-5</sub> acyl, C<sub>1-5</sub> acyloxy, C<sub>1-4</sub> alkoxy, C<sub>1-8</sub> alkyl, C<sub>1-4</sub> alkylamino, C<sub>1-4</sub> alkylcarboxamide, C<sub>1-4</sub> alkylthiocarboxamide, C<sub>1-4</sub> alkylsulfonamide, C<sub>1-4</sub> alkylsulfinyl, C<sub>1-4</sub> alkylsulfonyl, C<sub>1-4</sub> alkylthio, C<sub>1-4</sub> alkylthioureyl, C<sub>1-4</sub> alkylureyl, amino, carbo-C<sub>1-6</sub>-alkoxy, carboxamide, carboxy, cyano, C<sub>3-6</sub>-cycloalkyl-C<sub>1-3</sub>-heteroalkylene, C<sub>2-8</sub> dialkylamino, C<sub>2-6</sub> dialkylcarboxamide, C<sub>1-4</sub> dialkylthiocarboxamide, C<sub>2-6</sub> dialkylsulfonamide, C<sub>1-4</sub> alkylthioureyl, C<sub>1-4</sub> haloalkoxy, C<sub>1-4</sub> haloalkyl, C<sub>1-4</sub> haloalkylsulfinyl, C<sub>1-4</sub> haloalkylsulfonyl, C<sub>1-4</sub> haloalkyl, C<sub>1-4</sub> haloalkylthio, halogen, heterocyclic, hydroxyl, hydroxylamino and nitro; and
R<sub>3</sub> is hydrogen or C<sub>1-4</sub> alkyl.

7. The method according to claim 6, wherein R<sub>2</sub> is a 5-membered heteroaryl optionally substituted with 1 or 2 substituents selected from the group consisting of C<sub>1-8</sub> alkyl, C<sub>1-4</sub> haloalkyl and halogen; and
R<sub>3</sub> is hydrogen.

8. The method according to claim 1, wherein the compound is:

1-[6-(4-Imidazol-1-yl-phenoxy)-5-nitro-pyrimidin-4-yl]-piperidine-4-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid ethyl ester;
1-[6-(4-Methanesulfonyl-phenoxy)-5-nitro-pyrimidin-4-yl]-piperidine-4-carboxylic acid ethyl ester;
1-{6-[4-(2-Methoxycarbonyl-acetyl)-phenoxy]-5-nitro-pyrimidin-4-yl}-piperidine-4-carboxylic acid ethyl ester;
1-[5-Amino-6-(2-methyl-5-trifluoromethyl-2H-pyrazol-3-yloxy)-pyrimidin-4-yl]-piperidine-4-carboxylic acid ethyl ester;
1-[6-(2-Methyl-5-trifluoromethyl-2H-pyrazol-3-yloxy)-5-(2,2,2-trifluoro-acetylamino)-pyrimidin-4-yl]-piperidine-4-carboxylic acid ethyl ester;
Propionic acid 1-[2-amino-5-formyl-6-(2-methyl-5-trifluoromethyl-2H-pyrazol-3-yloxy)-pyrimidin-4-yl]-piperidin-4-yl ester;
4-[6-(2-Methyl-5-trifluoromethyl-2H-pyrazol-3-yloxy)-5-nitro-pyrimidin-4-yl]-piperazine-1-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid methyl ester;
1-[6-(2-Methyl-5-trifluoromethyl-2H-pyrazol-3-yloxy)-5-nitro-pyrimidin-4-yl]-(piperidine-3-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid ethylamide;
1-[6-(2-Methyl-5-phenyl-2H-pyrazol-3-yloxy)-5-nitro-pyrimidin-4-yl]-piperidine-4-carboxylic acid ethyl ester;
1-[5-Bromo-6-(2-methyl-5-trifluoromethyl-2H-pyrazol-3-yloxy)-pyrimidin-4-yl]-piperidine-4-carboxylic acid ethyl ester;
1-[5-Acetylamino-6-(2-methyl-5-trifluoromethyl-2H-pyrazol-3-yloxy)-pyrimidin-4-yl]-piperidine-4-carboxylic acid ethyl ester;
1-[5-Diacetylamino-6-(2-methyl-5-trifluoromethyl-2H-pyrazol-3-yloxy)-pyrimidin-4-yl]-piperidine-4-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid;
1-[5-Di-(methanesulfonyl)amino-6-(2-methyl-5-trifluoromethyl-2H-pyrazol-3-yloxy)-pyrimidin-4-yl]-piperidine-4-carboxylic acid ethyl ester;
1-[5-Nitro-6-(3-trifluoromethyl-phenoxy)-pyrimidin-4-yl]-piperidine-4-carboxylic acid ethyl ester;
1-[5-Methyl-6-(2-methyl-5-trifluoromethyl-2H-pyrazol-3-yloxy)-pyrimidin-4-yl]-piperidine-4-carboxylic acid ethyl ester;
1-[5-Nitro-6-(2-trifluoromethyl-phenoxy)-pyrimidin-4-yl]-piperidine-4-carboxylic acid ethyl ester;
1-[5-Nitro-6-(4-trifluoromethyl-phenoxy)-pyrimidin-4-yl]-piperidine-4-carboxylic acid ethyl ester;
1-[6-(4-Fluoro-phenoxy)-5-nitro-pyrimidin-4-yl]-piperidine-4-carboxylic acid ethyl ester;
1-[6-(2,5-Dimethyl-2H-pyrazol-3-yloxy)-5-nitro-pyrimidin-4-yl]-piperidine-4-carboxylic acid ethyl ester;
1-[6-(4-Bromo-phenoxy)-5-nitro-pyrimidin-4-yl]-piperidine-4-carboxylic acid ethyl ester;
1-[6-(4-Chloro-phenoxy)-5-nitro-pyrimidin-4-yl]-piperidine-4-carboxylic acid ethyl ester;
1-[6-(4-Carbamoyl-phenoxy)-5-nitro-pyrimidin-4-yl]-piperidine-4-carboxylic acid ethyl ester;
1-{6-[4-(2-Methoxy-ethyl)-phenoxy]-5-nitro-pyrimidin-4-yl}-piperidine-4-carboxylic acid ethyl ester;
1-[6-(4-Cyclopentyl-phenoxy)-5-nitro-pyrimidin-4-yl]-piperidine-4-carboxylic acid ethyl ester;
1-[5-Nitro-6-(4-pyrrol-1-yl-phenoxy)-pyrimidin-4-yl]-piperidine-4-carboxylic acid ethyl ester;
1-[6-(4-Benzoyl-phenoxy)-5-nitro-pyrimidin-4-yl]-piperidine-4-carboxylic acid ethyl ester;
1-{6-[4-(4-Hydroxy-benzenesulfonyl)-phenoxy]-5-nitro-pyrimidin-4-yl}-piperidine-4-carboxylic acid ethyl ester;
1-[6-(4'-Cyano-biphenyl-4-yloxy)-5-nitro-pyrimidin-4-yl]-piperidine-4-carboxylic acid ethyl ester;
1-[6-(2-Amino-4-ethanesulfonyl-phenoxy)-5-nitro-pyrimidin-4-yl]-piperidine-4-carboxylic acid ethyl ester;
1-{6-[4-(5-Hydroxy-pyrimidin-2-yl)-phenoxy]-5-nitro-pyrimidin-4-yl}-piperidine-4-carboxylic acid ethyl ester;
1-[5-Nitro-6-(4-sulfo-phenoxy)-pyrimidin-4-yl]-piperidine-4-carboxylic acid ethyl ester;
1-[5-Nitro-6-(4-[1,2,4]triazol-1-yl-phenoxy)-pyrimidin-4-yl]-piperidine-4-carboxylic acid ethyl ester;

1-[6-(4-Carbamoylmethyl-phenoxy)-5-nitro-pyrimidin-4-yl]-piperidine-4-carboxylic acid ethyl ester;
1-{6-[4-(1,3-Dioxo-1,3-dihydro-isoindol-2-yl)-phenoxy]-5-nitro-pyrimidin-4-yl}-piperidine-4-carboxylic acid ethyl ester;
1-[6-(4'-Methoxy-biphenyl-4-yloxy)-5-nitro-pyrimidin-4-yl]-piperidine-4-carboxylic acid ethyl ester;
1-{6-[4-(2,5-Dioxo-imidazolidin-4-yl)-phenoxy]-5-nitro-pyrimidin-4-yl}-piperidine-4-carboxylic acid ethyl ester;
4-(4,4-Difluoro-piperidin-1-yl)-6-(2-methyl-5-trifluoromethyl-2H-pyrazol-3-yloxy)-5-nitro-pyrimidine;
1-{5-Nitro-6-[4-(4-oxo-cyclohexyl)-phenoxy]-pyrimidin-4-yl}-piperidine-4-carboxylic acid ethyl ester;
1-{5-Nitro-6-[4-(3-oxo-butyl)-phenoxy]-pyrimidin-4-yl}-piperidine-4-carboxylic acid ethyl ester;
1-[5-Nitro-6-(4-propionyl-phenoxy)-pyrimidin-4-yl]-piperidine-4-carboxylic acid ethyl ester;
1-[5-Nitro-6-(4-[1,2,3]thiadiazol-4-yl-phenoxy)-pyrimidin-4-yl]-piperidine-4-carboxylic acid ethyl ester;
1-{6-[4-(2-Hydroxy-ethyl)-phenoxy]-5-nitro-pyrimidin-4-yl}-piperidine-4-carboxylic acid ethyl ester;
{4-[6-(4,4-Difluoro-piperidin-1-yl)-5-nitro-pyrimidin-4-yloxy]-phenyl}-phenyl-methanone;
3-{4-[6-(4,4-Difluoro-piperidin-1-yl)-5-nitro-pyrimidin-4-yloxy]-phenyl}-3-oxo-propionic acid methyl ester;
2-[6-(4,4-Difluoro-piperidin-1-yl)-5-nitro-pyrimidin-4-yloxy]-5-ethanesulfonyl-phenylamine;
4-(4-Cyclopentyl-phenoxy)-6-(4,4-difluoro-piperidin-1-yl)-5-nitro-pyrimidine;
1-[6-(2,6-Dichloro-4-methanesulfonyl-phenoxy)-5-nitro-pyrimidin-4-yl]-piperidine-4-carboxylic acid ethyl ester;
1-{6-[4-(4-Chloro-benzoyl)-phenoxy]-5-nitro-pyrimidin-4-yl}-piperidine-4-carboxylic acid ethyl ester;
1-{6-[4-(4-Hydroxy-benzoyl)-phenoxy]-5-nitro-pyrimidin-4-yl}-piperidine-4-carboxylic acid ethyl ester;
1-[6-(4-Cyanomethyl-phenoxy)-5-nitro-pyrimidin-4-yl]-piperidine-4-carboxylic acid ethyl ester;
(4-{6-[4-(2-Methanesulfonyl-ethyl)-piperazin-1-yl]-5-nitro-pyrimidin-4-yloxy}-phenyl)-phenyl-methanone;
4-(4-{6-[4-(2-Methanesulfonyl-ethyl)-piperazin-1-yl]-5-nitro-pyrimidin-4-yloxy}-phenyl)-butan-2-one;
3-(4-{6-[4-(2-Methanesulfonyl-ethyl)-piperazin-1-yl]-5-nitro-pyrimidin-4-yloxy}-phenyl)-3-oxo-propionic acid methyl ester;
4-(4-Methyl-piperidin-1-yl)-6-(2-methyl-5-trifluoromethyl-2H-pyrazol-3-yloxy)-5-nitro-pyrimidine;
4-(4-Bromo-piperidin-1-yl)-6-(2-methyl-5-trifluoromethyl-2H-pyrazol-3-yloxy)-5-nitro-pyrimidine;
4-(2-Methyl-5-trifluoromethyl-2H-pyrazol-3-yloxy)-5-nitro-6-(4-propyl-piperidin-1-yl)-pyrimidine;
1-[6-(2-Methyl-5-trifluoromethyl-2H-pyrazol-3-yloxy)-5-nitro-pyrimidin-4-yl]-(piperidine-4-carboxylic acid amide;
1-[5-Nitro-6-(2-oxo-2H-chromen-6-yloxy)-pyrimidin-4-yl]-piperidine-4-carboxylic acid ethyl ester;
1-[5-Nitro-6-(9-oxo-9H-fluoren-2-yloxy)-pyrimidin-4-yl]-piperidine-4-carboxylic acid ethyl ester;
1-{5-Amino-6-[4-(3-oxo-butyl)-phenoxy]-pyrimidin-4-yl}-piperidine-4-carboxylic acid ethyl ester;
1-[6-[4-(3-oxo-butyl)-phenoxy]-5-(2,2,2-trifluoro-acetylamino)-pyrimidin-4-yl]-piperidine-4-carboxylic acid ethyl ester;
1-{5-Amino-6-[4-(hydroxy-phenyl-methyl)-phenoxy]-pyrimidin-4-yl}-piperidine-4-carboxylic acid ethyl ester;
1-[6-(2-Benzoyl-5-methoxy-phenoxy)-5-nitro-pyrimidin-4-yl]-piperidine-4-carboxylic acid ethyl ester;
1-[6-(6-Chloro-pyridin-3-yloxy)-5-nitro-pyrimidin-4-yl]-piperidine-4-carboxylic acid ethyl ester;
1-[6-(Benzo[1,3]dioxol-5-yloxy)-5-nitro-pyrimidin-4-yl]-piperidine-4-carboxylic acid ethyl ester;
1-[6-(4-Benzyloxy-phenoxy)-5-nitro-pyrimidin-4-yl]-piperidine-4-carboxylic acid ethyl ester;
1-[6-(3-Morpholin-4-yl-phenoxy)-5-nitro-pyrimidin-4-yl]-piperidine-4-carboxylic acid ethyl ester;
1-[5-Nitro-6-(4-trifluoromethylsulfanyl-phenoxy)-pyrimidin-4-yl]-piperidine-4-carboxylic acid ethyl ester;
1-[5-Nitro-6-(4-trifluoromethoxy-phenoxy)-pyrimidin-4-yl]-piperidine-4-carboxylic acid ethyl ester;
1-[6-(4-Benzoyl-phenoxy)-5-(2,2,2-trifluoro-acetylamino)-pyrimidin-4-yl]-piperidine-4-carboxylic acid ethyl ester;
{4-[5-Nitro-6-(4-propyl-piperidin-1-yl)-pyrimidin-4-yloxy]-phenyl}-phenyl-methanone;
{4-Methoxy-2-[5-nitro-6-(4-propyl-piperidin-1-yl)-pyrimidin-4-yloxy]-phenyl}-phenyl-methanone;
4-{4-[5-Nitro-6-(4-propyl-piperidin-1-yl)-pyrimidin-4-yloxy]-phenyl}-butan-2-one;
5-Nitro-4-(4-propyl-piperidin-1-yl)-6-(4-[1,2,3]thiadiazol-4-yl-phenoxy)-pyrimidine;
3-{4-[5-Nitro-6-(4-propyl-piperidin-1-yl)-pyrimidin-4-yloxy]-phenyl}-3-oxo-propionic acid methyl ester;
5-Ethanesulfonyl-2-[5-nitro-6-(4-propyl-piperidin-1-yl)-pyrimidin-4-yloxy]-phenylamine;
2-{1-[6-(2-Methyl-5-trifluoromethyl-2H-pyrazol-3-yloxy)-5-nitro-pyrimidin-4-yl]-piperidin-4-yl}-ethanol;
3-{1-[6-(2-Methyl-5-trifluoromethyl-2H-pyrazol-3-yloxy)-5-nitro-pyrimidin-4-yl]-piperidin-4-yl}-propionic acid;
4-[4-(4-Methyl-benzyl)-piperidin-1-yl]-6-(2-methyl-5-trifluoromethyl-2H-pyrazol-3-yloxy)-5-nitro-pyrimidine;
4-(3-Methanesulfonyl-pyrrolidin-1-yl)-6-(2-methyl-5-trifluoromethyl-2H-pyrazol-3-yloxy)-5-nitro-pyrimidine;
4-(2-Methyl-5-trifluoromethyl-2H-pyrazol-3-yloxy)-5-nitro-6-[4-(2-trifluoromethyl-phenoxy)-piperidin-1-yl]-pyrimidine;
4-(2-Methyl-5-trifluoromethyl-2H-pyrazol-3-yloxy)-5-nitro-6-[4-(pyridin-2-ylsulfanyl)-piperidin-1-yl]-pyrimidine;
4-(2-Methyl-5-trifluoromethyl-2H-pyrazol-3-yloxy)-5-nitro-6-(4-trifluoromethyl-piperidin-1-yl)-pyrimidine;
4-(2-Methyl-5-trifluoromethyl-2H-pyrazol-3-yloxy)-5-nitro-6-(4-phenylsulfanyl-piperidin-1-yl)-pyrimidine;
1-[6-(3-Ethynyl-phenoxy)-5-nitro-pyrimidin-4-yl]-piperidine-4-carboxylic acid ethyl ester;
1-[6-(4-Chloro-2-fluoro-phenoxy)-5-nitro-pyrimidin-4-yl]-piperidine-4-carboxylic acid ethyl ester;
1-[6-(2,4-Difluoro-phenoxy)-5-nitro-pyrimidin-4-yl]-piperidine-4-carboxylic acid ethyl ester;
1-[6-(4-Bromo-2-fluoro-phenoxy)-5-nitro-pyrimidin-4-yl]-piperidine-4-carboxylic acid ethyl ester;
4-(3-Ethynyl-phenoxy)-5-nitro-6-(4-propyl-piperidin-1-yl)-pyrimidine;
4-(4-Chloro-2-fluoro-phenoxy)-5-nitro-6-(4-propyl-piperidin-1-yl)-pyrimidine;
4-(2,4-Difluoro-phenoxy)-5-nitro-6-(4-propyl-piperidin-1-yl)-pyrimidine;
4-(4-Bromo-2-fluoro-phenoxy)-5-nitro-6-(4-propyl-piperidin-1-yl)-pyrimidine;

4-(4-{5-Nitro-6-[4-(pyridin-2-ylsulfanyl)-piperidin-1-yl] pyrimidin-4-yloxy}-phenyl)-butan-2-one;
4-(4-{5-Nitro-6-[4-(2-trifluoromethyl-phenoxy)-piperidin-1-yl]-pyrimidin-4-yloxy}-phenyl)-butan-2-one;
4-(4-{6-[4-(3-Methyl-[1,2,4]oxadiazol-5-yl)-piperidin-1-yl]-5-nitro-pyrimidin-4-yloxy}-phenyl)-butan-2-one;
(4-{6-[4-(3-Methyl-[1,2,4]oxadiazol-5-yl)-piperidin-1-yl]-5-nitro-pyrimidin-4yloxy}-phenyl)-phenyl-methanone;
1-{6-[4-(4-Fluoro-benzoyl)-phenoxy]-5-nitro-pyrimidin-4-yl}-piperidine-4-carboxylic acid ethyl ester;
(4-Fluoro-phenyl)-{-4-[5-nitro-6-(4-propyl-piperidin-1-yl)-pyrimidin-4-yloxy]-phenyl}-methanone;
4-[4-(3-Methyl-[1,2,4]oxadiazol-5-yl)-piperidin-1-yl]-6-(2-methyl-5-trifluoromethyl-2H-pyrazol-3-yloxy)-5-nitro-pyrimidine;
4-(4-Methoxymethyl-piperidin-1-yl)-6-(2-methyl-5-trifluoromethyl-2H-pyrazol-3-yloxy)-5-nitro-pyrimidine;
4-{4-[6-(4-Methoxymethyl-piperidin-1-yl)-5-nitro-pyrimidin-4-yloxy]-phenyl}-butan-2-one;
4-[4-(2-Methoxy-ethyl)-piperidin-1-yl]-6-(2-methyl-5-trifluoromethyl-2H-pyrazol-3-yloxy)-5-nitro-pyrimidine;
4-{4-[6-(4-Ethoxymethyl-piperidin-1-yl)-5-nitro-pyrimidin-4-yloxy]-phenyl}-butan-2-one;
4-(2,4-Difluoro-phenoxy)-5-nitro-6-[4-(pyridin-2-ylsulfanyl)-piperidin-1-yl]-pyrimidine;
(4-Methoxy-2-{5-nitro-6-[4-(pyridin-2-ylsulfanyl)-piperidin-1-yl]-pyrimidin-4-yloxy}-phenyl)-phenyl-methanone;
4-(2,4-Difluoro-phenoxy)-6-(4-ethoxymethyl-piperidin-1-yl)-5-nitro-pyrimidine;
4-{4-[6-(4-Cyclopropylmethoxymethyl-piperidin-1-yl)-5-nitro-pyrimidin-4-yloxy]-phenyl}-butan-2-one;
4-{4-[5-Nitro-6-(4-propoxymethyl-piperidin-1-yl)-pyrimidin-4-yloxy]-phenyl}-butan-2-one;
1-{4-[6-(4-Methoxymethyl-piperidin-1-yl)-5-nitro-pyrimidin-4-yloxy]-phenyl}-ethanone;
4-{4-[6-(4-Butoxymethyl-piperidin-1-yl)-5-nitro-pyrimidin-4-yloxy]-phenyl}-butan-2-one;
4-{4-[6-(4-Isobutoxymethyl-piperidin-1-yl)-5-nitro-pyrimidin-4-yloxy]-phenyl}-butan-2-one;
{4-[6-(4-Ethoxy-piperidin-1-yl)-5-nitro-pyrimidin-4-yloxy]-phenyl}-(4-fluoro-phenyl)-methanone;
1-[6-(2-Methyl-5-trifluoromethyl-2H-pyrazol-3-yloxy)-5-nitro-pyrimidin-4-yl]-piperidin-4-ol;
1-[6-(4-Acetyl-phenoxy)-5-nitro-pyrimidin-4-yl]-piperidine-4-carboxylic acid ethyl ester;
(1-{6-[4-(4-Fluoro-benzoyl)-phenoxy]-5-nitro-pyrimidin-4-yl}-piperidin-4-yl)-(4fluoro-phenyl)-methanone;
4-(4-{6-[4-(4-Fluoro-benzoyl)-piperidin-1-yl]-5-nitro-pyrimidin-4-yloxy}-phenyl)-butan-2-one;
4-(4-Methanesulfonyl-phenoxy)-5-nitro-6-[4-(pyridm-2-ylsulfanyl)-piperidin-1-yl]-pyrimidine;
4-(4-Methanesulfonyl-phenoxy)-5-nitro-6-[4-(pyridin-4-ylsulfanyl)-piperidin-1yl]-pyrimidine;
4-[4-(3-Isopropyl-[1,2,4]oxadiazol-5-yl)-piperidin-1-yl]-6-(4-methanesulfonyl-phenoxy)-pyrimidine-5-carbonitrile;
1-[5-Nitro-6-(4-trifluoromethylsulfanyl-phenoxy)-pyrimidin-4-yl]-piperidine-4-carboxylic acid ethyl ester;
5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine;
4-[4-(3-Isopropyl-[1,2,4]oxadiazol-5-yl)-piperidin-1-yl]-6-(4-methanesulfonyl-phenoxy)-pyrimidine-5-carbaldehyde;
5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine;
4-[4-(3-Isopropyl-[1,2,4]oxadiazol-5yl]-6-(4-[1,2,3]thiadiazol-4-yl-phenoxy)-pyrimidine-5-carbaldehyde;
[4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol;
[4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine;
4-(4-Methanesulfonyl-phenoxy)-5-nitro-6-(4-phenylsulfanyl-piperidin-1-yl)-pyrimidine;
4-[4-(3-tert-Butyl-[1,2,4]oxadiazol-5-yl)-piperidin-1-yl]-6-(6-methanesulfonyl-pyridin-3-yloxy)-5-nitro-pyrimidine;
4-[4-(3-Isopropyl-[1,2,4]oxadiazol-5-yl)-piperidin-1-yl]-6-(4-methanesulfonyl-phenoxy)-2-methyl-pyrimidine-5-carbonitrile; or
1[4-[4-(3-Isopropyl-[1,2,4]oxadiazol-5-yl)-piperidin-1-yl]-6-(4-methanesulfonyl-phenoxy)-pyrimidin-5-yl]-ethanone;

or a pharmaceutically acceptable salt, hydrate or solvate of such a compound.

9. The method according to claim 1, wherein the metabolic disorder is type II diabetes.

10. The method according to claim 6, wherein the metabolic disorder is type II diabetes.

11. The method according to claim 7, wherein the metabolic disorder is type II diabetes.

12. The method according to claim 1, wherein the metabolic disorder is obesity.

13. A method for controlling or decreasing weight gain of an individual comprising administering to the individual a therapeutically effective amount of a compound of Formula (Ia):

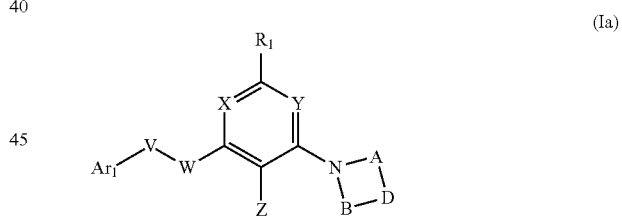

or a pharmaceutically acceptable salt, hydrate or solvate thereof, wherein:

A and B are independently $C_{1-3}$ alkylene optionally substituted with 1 to 4 methyl groups;

D is $CR_2R_3$ or $N$—$R_2$;

V is absent;

W is $NR_4$ or O;

X is N;

Y is N;

Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1 or 2 groups selected from the group consisting of $C_{2-4}$ dialkylamino, hydroxy, and halogen; or Z is selected from the group consisting of nitro, amino, formyl, $NHC(O)CF_3$, Br, $NHC(O)CH_3$, $N(C(O)CH_3)_2$, N(S(O)$_2$CH$_3$)$_2$, CH$_3$, [1,3]dioxolan-2-yl, CH$_2$OH, CH$_2$N(CH$_3$)$_2$, and C(O)CH$_3$; or Z is a group of Formula (A):

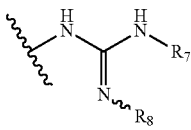

(A)

wherein:
R$_7$ is H, C$_{1-8}$ alkyl or C$_{3-6}$ cycloalkyl; and
R$_8$ is H, nitro or nitrile;

Ar$_1$ is aryl or heteroaryl wherein each is optionally substituted with R$_9$-R$_{13}$;
wherein the heteroaryl of Ar$_1$ is selected from the group consisting of pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline, 1H-imidazolyl, [1,2,4]triazolyl, [1,2,3]triazolyl, pyrrolyl, pyrazolyl, 1H-pyrazolyl, imidazolyl, oxazolyl, [1,3,4]oxadiazolyl, [1,3,4]thiadiazolyl, [1,2,4]oxadiazolyl, [1,2,4]thiadiazolyl, tetrazolyl, 1,3-dioxo-1,3-dihydro-isoindolyl, and [1,2,3]thiadiazol-4-yl;

R$_1$ is selected from the group consisting of H, C$_{1-4}$ alkoxy, C$_{1-8}$ alkyl, C$_{2-6}$ alkynyl, amino, C$_{3-6}$ cycloalkyl, and C$_{1-4}$ haloalkyl;

R$_2$ is selected from the group consisting of C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfinyl, C$_{1-4}$ alkylsulfonyl, C$_{1-4}$ alkylthio, amino, carbo-C$_{1-6}$-alkoxy, carboxamide, carboxy, C$_{3-6}$-cycloalkyl, C$_{1-4}$ haloalkoxy, C$_{1-4}$ haloalkyl, halogen, hydroxyl, CH$_2$OCH$_2$-cyclopropyl, CH$_2$OCH$_2$-cyclobutyl, CH$_2$OCH$_2$-cyclopentyl, CH$_2$OCH$_2$-cyclohexyl, CH$_2$OCH$_2$CH$_2$-cyclopropyl, CH$_2$OCH$_2$CH$_2$-cyclobutyl, CH$_2$OCH$_2$CH$_2$-cyclopentyl, CH$_2$OCH$_2$CH$_2$-cyclohexyl, CH$_2$CH$_2$OCH$_2$-cyclopropyl, CH$_2$CH$_2$OCH$_2$-cyclobutyl, CH$_2$CH$_2$OCH$_2$-cyclopentyl, CH$_2$CH$_2$OCH$_2$-cyclohexyl, CH$_2$CH$_2$OCH$_2$CH$_2$-cyclopropyl, CH$_2$CH$_2$OCH$_2$CH$_2$-cyclobutyl, CH$_2$CH$_2$OCH$_2$CH$_2$-cyclopentyl, and CH$_2$CH$_2$OCH$_2$CH$_2$-cyclohexyl; or R$_2$ is C$_{1-8}$ alkyl or heteroaryl, each optionally substituted with 1 to 5 substituents selected from the group consisting of C$_{1-5}$ acyloxy, C$_{1-4}$ alkoxy, C$_{1-8}$ alkyl, C$_{1-4}$ alkylsulfonyl, carbo-C$_{1-6}$-alkoxy, carboxamide, carboxy, C$_{3-6}$-cycloalkyl, C$_{3-6}$-cycloalkyl-C$_{1-3}$-alkylene, C$_{3-6}$-cycloalkyl-C$_{1-3}$-heteroalkylene, and hydroxyl; or R$_2$ is C$_{1-8}$ alkyl, heteroaryl or phenyl each optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylamino, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl -C$_{1-3}$-heteroalkylene, C$_{2-8}$ dialkylamino, C$_{2-6}$ dialkylcarboxamide, C$_{1-4}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heterocyclic, hydroxyl, hydroxylamino and nitro; or R$_2$ is —Ar$_2$-Ar$_3$ wherein Ar$_2$ and Ar$_3$ are independently aryl or heteroaryl each optionally substituted with 1 to 5 substituents selected from the group consisting of H, C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfinyl, C$_{1-4}$ alkylsulfonyl, C$_{1-4}$ alkylthio, amino, carbo-C$_{1-6}$-alkoxy, carboxamide, carboxy, cyano, C$_{3-6}$-cycloalkyl, C$_{2-6}$ dialkylcarboxamide, C$_{1-4}$ haloalkoxy, C$_{1-4}$ haloalkyl, halogen, hydroxyl and nitro; or R$_2$ is a group of Formula (B):

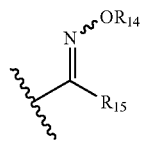

(B)

wherein:
R$_{14}$ is C$_{1-8}$ alkyl or C$_{3-6}$ cycloalkyl; and R$_{15}$ is F, Cl, Br or CN; or R$_2$ is a group of Formula (C):

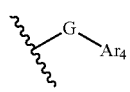

(C)

wherein:
G is C=O, CR$_{16}$R$_{17}$, O, S, S(O), or S(O)$_2$;
wherein
R$_{16}$ and R$_{17}$ are independently H or C$_{1-8}$ alkyl; and
Ar$_4$ is phenyl or heteroaryl optionally substituted with 1 to 5 substituents selected from the group consisting of C$_{1-5}$ acyl, C$_{1-5}$ acyloxy, C$_{1-4}$ alkoxy, C$_{1-8}$ alkyl, C$_{1-4}$ alkylcarboxamide, C$_{1-4}$ alkylthiocarboxamide, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylthioureyl, C$_{1-4}$ alkylureyl, amino, carbo-C$_{1-6}$-alkoxy, carboxamide, carboxy, cyano, C$_{3-6}$-cycloalkyl, C$_{2-6}$ dialkylcarboxamide, C$_{1-4}$ dialkylthiocarboxamide, C$_{2-6}$ dialkylsulfonamide, C$_{1-4}$ alkylthioureyl, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkyl, C$_{1-4}$ haloalkylthio, halogen, heteroaryl, hydroxyl, hydroxylamino and nitro;

R$_3$ is H, C$_{1-8}$ alkyl, C$_{1-4}$ alkoxy, halogen or hydroxyl;
R$_4$ is H or C$_{1-8}$ alkyl;
R$_9$ is selected from the group consisting of C$_{1-5}$ acyl, C$_{1-5}$ acyloxy, C$_{2-6}$ alkenyl, C$_{1-4}$ alkoxy, C$_{1-8}$ alkyl, C$_{1-4}$ alkylamino, C$_{1-4}$ alkylcarboxamide, C$_{2-6}$ alkynyl, C$_{1-4}$ alkylsulfonamide, C$_{1-4}$ alkylsulfinyl, C$_{1-4}$ alkylsulfonyl, C$_{1-4}$ alkylthio, C$_{1-4}$ alkylureyl, amino, arylsulfonyl, carbo-C$_{1-6}$-alkoxy, carboxamide, carboxy, cyano, C$_{3-6}$ cycloalkyl, C$_{2-6}$ dialkylamino, C$_{2-6}$ dialkylcarboxamide, C$_{2-6}$ dialkylsulfonamide, halogen, C$_{1-4}$ haloalkoxy, C$_{1-4}$ haloalkyl, C$_{1-4}$ haloalkylsulfinyl, C$_{1-4}$ haloalkylsulfonyl, C$_{1-4}$ haloalkylthio, heterocyclic, heterocyclicsulfonyl, heteroaryl, hydroxyl, nitro, C$_{4-7}$ oxo-cycloalkyl, phenoxy, phenyl, sulfonamide and sulfonic acid, and wherein C$_{1-5}$ acyl, C$_{1-4}$ alkoxy, C$_{1-8}$ alkyl, C$_{1-4}$ alkylsulfonamide, alkylsulfonyl, arylsulfonyl, heteroaryl, phenoxy and phenyl are each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (D):

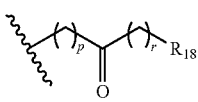

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{10}$-$R_{13}$ are independently selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or two adjacent $R_{10}$-$R_{11}$ groups together with $Ar_1$ form a 5, 6 or 7 membered cycloalkyl, cycloalkenyl or heterocyclic group wherein the 5, 6 or 7 membered group is optionally substituted with halogen.

14. The method according to claim 13, wherein A and B are both ethylene and wherein A and B are optionally substituted with 1 to 4 methyl groups.

15. The method according to claim 13, wherein Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1, or 2 groups selected from the group consisting of $C_{2-4}$ dialkylmino, hydroxy, and halogen.

16. The method according to claim 13, wherein D is $CR_2R_3$.

17. The method according to claim 13, wherein $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro.

18. The method according to claim 13, wherein the compound is a compound of the following formula:

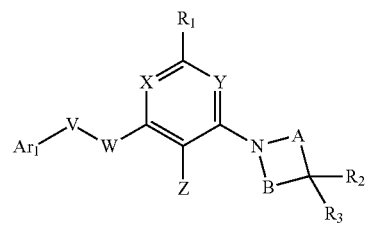

or a pharmaceutically acceptable salt, hydrate or solvate thereof, wherein:
wherein $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; and $R_3$ is hydrogen or $C_{1-4}$ alkyl.

19. The method according to claim 18, wherein $R_2$ is a 5-membered heteroaryl optionally substituted with 1 or 2 substituents selected from the group consisting of $C_{1-8}$ alkyl, $C_{1-4}$ haloalkyl and halogen; and
$R_3$ is hydrogen.

20. The method according to claim 13, wherein the compound is:
1-[6-(4-Imidazol-1-yl-phenoxy)-5-nitro-pyrimidin-4-yl]-piperidine-4-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid ethyl ester;
1-[6-(4-Methanesulfonyl-phenoxy)-5-nitro-pyrimidin-4-yl]-piperidine-4-carboxylic acid ethyl ester;
1-{6-[4-(2-Methoxycarbonyl-acetyl)-phenoxy]-5-nitro-pyrimidin-4-yl}-piperidine-4-carboxylic acid ethyl ester;
1-[5-Amino-6-(2-methyl-5-trifluoromethyl-2H-pyrazol-3-yloxy)-pyrimidin-4-yl]-piperidine-4-carboxylic acid ethyl ester;
1-[6-(2-Methyl-5-trifluoromethyl-2H-pyrazol-3-yloxy)-5-(2,2,2-trifluoro-acetylamino)-pyrimidin-4-yl]-piperidine-4-carboxylic acid ethyl ester;
Propionic acid 1-[2-amino-5-formyl-6-(2-methyl-5-trifluoromethyl-2H-pyrazol-3-yloxy)-pyrimidin-4-yl]-piperidin-4-yl ester;
4-[6-(2-Methyl-5-trifluoromethyl-2H-pyrazol-3-yloxy)-5-nitro-pyrimidin-4-yl]-piperazine-1-carboxylic acid ethyl ester;

1-[6-(2-Methyl-5-trifluoromethyl-2H-pyrazol-3-yloxy)-5-nitro-pyrimidin-4-yl]-piperidine-4-carboxylic acid methyl ester;
1-[6-(2-Methyl-5-trifluoromethyl-2H-pyrazol-3-yloxy)-5-nitro-pyrimidin-4-yl]-piperidine-3-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid ethylamide;
1-[6-(2-Methyl-5-phenyl-2H-pyrazol-3-yloxy)-5-nitro-pyrimidin-4-yl]-piperidine-4-carboxylic acid ethyl ester;
1-[5-Bromo-6-(2-methyl-5-trifluoromethyl-2H-pyrazol-3-yloxy)-pyrimidin-4-yl]-piperidine-4-carboxylic acid ethyl ester;
1-[5-Acetylamino-6-(2-methyl-5-trifluoromethyl-2H-pyrazol-3-yloxy)-pyrimidin-4-yl]-piperidine-4-carboxylic acid ethyl ester;
1-[5-Diacetylamino-6-(2-methyl-5-trifluoromethyl-2H-pyrazol-3-yloxy)-pyrimidin-4-yl]-piperidine-4-carboxylic acid ethyl ester;
1-[6-(2-Methyl-5-trifluoromethyl-2H-pyrazol-3-yloxy)-5-nitro-pyrimidin-4-yl]-piperidine-4-carboxylic acid;
1-[5-Di-(methanesulfonyl)amino-6-(2-methyl-5-trifluoromethyl-2H-pyrazol-3-yloxy)-pyrimidin-4-yl]-piperidine-4-carboxylic acid ethyl ester;
1-[5-Nitro-6-(3-trifluoromethyl-phenoxy)-pyrimidin-4-yl]-piperidine-4-carboxylic acid ethyl ester;
1-[5-Methyl-6-(2-methyl-5-trifluoromethyl-2H-pyrazol-3-yloxy)-pyrimidin-4-yl]-piperidine-4-carboxylic acid ethyl ester;
1-[5-Nitro-6-(2-trifluoromethyl-phenoxy)-pyrimidin-4-yl]-piperidine-4-carboxylic acid ethyl ester;
1-[5-Nitro-6-(4-trifluoromethyl-phenoxy)-pyrimidin-4-yl]-piperidine-4-carboxylic acid ethyl ester;
1-[6-(4-Fluoro-phenoxy)-5-nitro-pyrimidin-4-yl]-piperidine-4-carboxylic Acid ethyl ester;
1-[6-(2,5-Dimethyl-2H-pyrazol-3-yloxy)-5-nitro-pyrimidin-4-yl]-piperidine-4-carboxylic acid ethyl ester;
1-[6-(4-Bromo-phenoxy)-5-nitro-pyrimidin-4-yl]-piperidine-4-carboxylic Acid ethyl ester;
1-[6-(4-Chloro-phenoxy)-5-nitro-pyrimidin-4-yl]-piperidine-4-carboxylic acid ethyl ester;
1-[6-(4-Carbamoyl-phenoxy)-5-nitro-pyrimidin-4-yl]-piperidine-4-carboxylic acid ethyl ester;
1-{6-[4-(2-Methoxy-ethyl)-phenoxy]-5-nitro-pyrimidin-4-yl}-piperidine-4-carboxylic acid ethyl ester;
1-[6-(4-Cyclopentyl-phenoxy)-5-nitro-pyrimidin-4-yl]-piperidine-4-carboxylic acid ethyl ester;
1-[5-Nitro-6-(4-pyrrol-1-yl-phenoxy)-pyrimidin-4-yl]-piperidine-4-carboxylic acid ethyl ester;
1-[6-(4-Benzoyl-phenoxy)-5-nitro-pyrimidin-4-yl]-piperidine-4-carboxylic acid ethyl ester;
1-{6-[4-(4-Hydroxy-benzenesulfonyl)-phenoxy]-5-nitro-pyrimidin-4-yl}-piperidine-4-carboxylic acid ethyl ester;
1-[6-(4'-Cyano-biphenyl-4-yloxy)-5-nitro-pyrimidin-4-yl]-piperidine-4-carboxylic acid ethyl ester;
1-[6-(2-Amino-4-ethanesulfonyl-phenoxy)-5-nitro-pyrimidin-4-yl]-piperidine-4-carboxylic acid ethyl ester;
1-{6-[4-(5-Hydroxy-pyrimidin-2-yl)-phenoxy]-5-nitro-pyrimidin-4-yl}-piperidine-4-carboxylic acid ethyl ester;
1-[5-Nitro-6-(4-sulfo-phenoxy)-pyrimidin-4-yl]-piperidine-4-carboxylic acid ethyl ester;
1-[5-Nitro-6-(4-[1,2,4]triazol-1-yl-phenoxy)-pyrimidin-4-yl]-piperidine-4-carboxylic acid ethyl ester;
1-[6-(4-Carbamoylmethyl-phenoxy)-5-nitro-pyrimidin-4-yl]-piperidine-4-carboxylic acid ethyl ester;
1-{6-[4-(1,3-Dioxo-1,3-dihydro-isoindol-2-yl)-phenoxy]-5-nitro-pyrimidin-4-yl}-piperidine-4-carboxylic acid ethyl ester;
1-[6-(4'-Methoxy-biphenyl-4-yloxy)-5-nitro-pyrimidin-4-yl]-piperidine-4-carboxylic acid ethyl ester;
1-{6-[4-(2,5-Dioxo-imidazolidin-4-yl)-phenoxy]-5-nitro-pyrimidin-4-yl}-piperidine-4-carboxylic acid ethyl ester;
4-(4,4-Difluoro-piperidin-1-yl)-6-(2-methyl-5-trifluoromethyl-2H-pyrazol-3-yloxy)-5-nitro-pyrimidine;
1-{5-Nitro-6-[4-(4-oxo-cyclohexyl)-phenoxy]-pyrimidin-4-yl}-piperidine-4-carboxylic acid ethyl ester;
1-{5-Nitro-6-[4-(3-oxo-butyl)-phenoxy]-pyrimidin-4-yl}-piperidine-4-carboxylic acid ethyl ester;
1-[5-Nitro-6-(4-propionyl-phenoxy)-pyrimidin-4-yl]-piperidine-4-carboxylic acid ethyl ester;
1-[5-Nitro-6-(4-[1,2,3]thiadiazol-4-yl-phenoxy)-pyrimidin-4-yl]-piperidine-4-carboxylic acid ethyl ester;
1-{6-[4-(2-Hydroxy-ethyl)-phenoxy]-5-nitro-pyrimidin-4-yl}-piperidine-4-carboxylic acid ethyl ester;
{4-[6-(4,4-Difluoro-piperidin-1-yl)-5-nitro-pyrimidin-4-yloxy]-phenyl}-phenyl-methanone;
3-{4-[6-(4,4-Difluoro-piperidin-1-yl)-5-nitro-pyrimidin-4-yloxy]-phenyl}-3-oxo-propionic acid methyl ester;
2-[6-(4,4-Difluoro-piperidin-1-yl)-5-nitro-pyrimidin-4-yloxy]-5-ethanesulfonyl-phenylamine;
4-(4-Cyclopentyl-phenoxy)-6-(4,4-difluoro-piperidin-1-yl)-5-nitro-pyrimidine;
1-[6-(2,6-Dichloro-4-methanesulfonyl-phenoxy)-5-nitro-pyrimidin-4-yl]-piperidine-4-carboxylic acid ethyl ester;
1-{6-[4-(4-Chloro-benzoyl)-phenoxy]-5-nitro-pyrimidin-4-yl}-piperidine-4-carboxylic acid ethyl ester;
1-{6-[4-(4-Hydroxy-benzoyl)-phenoxy]-5-nitro-pyrimidin-4-yl}-piperidine-4-carboxylic acid ethyl ester;
1-[6-(4-Cyanomethyl-phenoxy)-5-nitro-pyrimidin-4-yl]-piperidine-4-carboxylic acid ethyl ester;
(4-{6-[4-(2-Methanesulfonyl-ethyl)-piperazin-1-yl]-5-nitro-pyrimidin-4-yloxy}-phenyl)-phenyl-methanone;
4-(4-{6-[4-(2-Methanesulfonyl-ethyl)-piperazin-1-yl]-5-nitro-pyrimidin-4-yloxy}-phenyl)-butan-2-one;
3-(4-{6-[4-(2-Methanesulfonyl-ethyl)-piperazin-1-yl]-5-nitro-pyrimidin-4-yloxy}-phenyl)-3-oxo-propionic acid methyl ester;
4-(4-Methyl-piperidin-1-yl)-6-(2-methyl-5-trifluoromethyl-2H-pyrazol-3-yloxy)-5-nitro-pyrimidine;
4-(4-Bromo-piperidin-1-yl)-6-(2-methyl-5-trifluoromethyl-2H-pyrazol-3-yloxy)-5-nitro-pyrimidine;
4-(2-Methyl-5-trifluoromethyl-2H-pyrazol-3-yloxy)-5-nitro-6-(4-propyl-piperidin-1-yl)-pyrimidine;
1-[6-(2-Methyl-5-trifluoromethyl-2H-pyrazol-3-yloxy)-5-nitro-pyrimidin-4-yl]-piperidine-4-carboxylic acid amide;
1-[5-Nitro-6-(2-oxo-2H-chromen-6-yloxy)-pyrimidin-4-yl]-piperidine-4-carboxylic acid ethyl ester;
1-[5-Nitro-6-(9-oxo-9H-fluoren-2-yloxy)-pyrimidin-4-yl]-piperidine-4-carboxylic acid ethyl ester;
1-{5-Amino-6-[4-(3-oxo-butyl)-phenoxy]-pyrimidin-4-yl}-piperidine-4-carboxylic acid ethyl ester;
1-[6-[4-(3-Oxo-butyl)-phenoxy]-5-(2,2,2-trifluoro-acetylamino)-pyrimidin-4-yl]-piperidine-4-carboxylic acid ethyl ester;
1-{5-Amino-6-[4-(hydroxy-phenyl-methyl)-phenoxy]-pyrimidin-4-yl}-piperidine-4-carboxylic acid ethyl ester;

1-[6-(2-Benzoyl-5-methoxy-phenoxy)-5-nitro-pyrimidin-4-yl]-piperidine-4-carboxylic acid ethyl ester;
1-[6-(6-Chloro-pyridin-3-yloxy)-5-nitro-pyrimidin-4-yl]-piperidine-4-carboxylic acid ethyl ester;
1-[6-(Benzo[1,3]dioxol-5-yloxy)-5-nitro-pyrimidin-4-yl]-piperidine-4-carboxylic acid ethyl ester;
1-[6-(4-Benzyloxy-phenoxy)-5-nitro-pyrimidin-4-yl]-piperidine-4-carboxylic acid ethyl ester;
1-[6-(3-Morpholin-4-yl-phenoxy)-5-nitro-pyrimidin-4-yl]-piperidine-4-carboxylic acid ethyl ester;
1-[5-Nitro-6-(4-trifluoromethylsulfanyl-phenoxy)-pyrimidin-4-yl]-piperidine-4-carboxylic acid ethyl ester;
1-[5-Nitro-6-(4-trifluoromethoxy-phenoxy)-pyrimidin-4-yl]-piperidine-4-carboxylic acid ethyl ester;
1-[6-(4-Benzoyl-phenoxy)-5-(2,2,2-trifluoro-acetylamino)-pyrimidin-4-yl]-piperidine-4-carboxylic acid ethyl ester;
{4-[5-Nitro-6-(4-propyl-piperidin-1-yl)-pyrimidin-4-yloxy]-phenyl}-phenyl-methanone;
{4-Methoxy-2-[5-nitro-6-(4-propyl-piperidin-1-yl)-pyrimidin-4-yloxy]-phenyl}-phenyl-methanone;
4-{4-[5-Nitro-6-(4-propyl-piperidin-1-yl)-pyrimidin-4-yloxy]-phenyl}-butan-2-one;
5-Nitro-4-(4-propyl-piperidin-1-yl)-6-(4-[1,2,3]thiadiazol-4-yl-phenoxy)-pyrimidine;
3-{4-[5-Nitro-6-(4-propyl-piperidin-1-yl)-pyrimidin-4-yloxy]-phenyl}-3-oxo-propionic acid methyl ester;
5-Ethanesulfonyl-2-[5-nitro-6-(4-propyl-piperidin-1-yl)-pyrimidin-4-yloxy]-phenylamine;
2-{1-[6-(2-Methyl-5-trifluoromethyl-2H-pyrazol-3-yloxy)-5-nitro-pyrimidin-4-yl]-piperidin-4-yl}-ethanol;
3-{1-[6-(2-Methyl-5-trifluoromethyl-2H-pyrazol-3-yloxy)-5-nitro-pyrimidin-4-yl]-piperidin-4-yl}-propionic acid;
4-[4-(4-Methyl-benzyl)-piperidin-1-yl]-6-(2-methyl-5-trifluoromethyl-2H-pyrazol-3-yloxy)-5-nitro-pyrimidine;
4-(3-Methanesulfonyl-pyrrolidin-1-yl)-6-(2-methyl-5-trifluoromethyl-2H-pyrazol-3-yloxy)-5-nitro-pyrimidine;
4-(2-Methyl-5-trifluoromethyl-2H-pyrazol-3-yloxy)-5-nitro-6-[4-(2-trifluoromethyl-phenoxy)-piperidin-1-yl]-pyrimidine;
4-(2-Methyl-5-trifluoromethyl-2H-pyrazol-3-yloxy)-5-nitro-6-[4-(pyridin-2-ylsulfanyl)-piperidin-1-yl]-pyrimidine;
4-(2-Methyl-5-trifluoromethyl-2H-pyrazol-3-yloxy)-5-nitro-6-(4-trifluoromethyl-piperidin-1-yl)-pyrimidine;
4-(2-Methyl-5-trifluoromethyl-2H-pyrazol-3-yloxy)-5-nitro-6-(4-phenylsulfanyl-piperidin-1-yl)-pyrimidine;
1-[6-(3-Ethynyl-phenoxy)-5-nitro-pyrimidin-4-yl]-piperidine-4-carboxylic acid ethyl ester;
1-[6-(4-Chloro-2-fluoro-phenoxy)-5-nitro-pyrimidin-4-yl]-piperidine-4-carboxylic acid ethyl ester;
1-[6-(2,4-Difluoro-phenoxy)-5-nitro-pyrimidin-4-yl]-piperidine-4-carboxylic acid ethyl ester;
1-[6-(4-Bromo-2-fluoro-phenoxy)-5-nitro-pyrimidin-4-yl]-piperidine-4-carboxylic acid ethyl ester;
4-(3-Ethynyl-phenoxy)-5-nitro-6-(4-propyl-piperidin-1-yl)-pyrimidine;
4-(4-Chloro-2-fluoro-phenoxy)-5-nitro-6-(4-propyl-piperidin-1-yl)-pyrimidine;
4-(2,4-Difluoro-phenoxy)-5-nitro-6-(4-propyl-piperidin-1-yl)-pyrimidine;
4-(4-Bromo-2-fluoro-phenoxy)-5-nitro-6-(4-propyl-piperidin-1-yl)-pyrimidine;
4-(4-{5-Nitro-6-[4-(pyridin-2-ylsulfanyl)-piperidin-1-yl]-pyrimidin-4-yloxy}-phenyl)-butan-2-one;
4-(4-{5-Nitro-6-[4-(2-trifluoromethyl-phenoxy)-piperidin-1-yl]-pyrimidin-4-yloxy}-phenyl)-butan-2-one;
4-(4-{6-[4-(3-Methyl-[1,2,4]oxadiazol-5-yl)-piperidin-1-yl]-5-nitro-pyrimidin-4-yloxy}-phenyl)-butan-2-one;
(4-{6-[4-(3-Methyl-[1,2,4]oxadiazol-5-yl)-piperidin-1-yl]-5-nitro-pyrimidin-4-yloxy}-phenyl)-phenyl-methanone;
1-{6-[4-(4-Fluoro-benzoyl)-phenoxy]-5-nitro-pyrimidin-4-yl}-piperidine-4-carboxylic acid ethyl ester;
(4-Fluoro-phenyl)-{4-[5-nitro-6-(4-propyl-piperidin-1-yl)-pyrimidin-4-yloxy]-phenyl}-methanone;
4-[4-(3-Methyl-[1,2,4]oxadiazol-5-yl)-piperidin-1-yl]-6-(2-methyl-5-trifluoromethyl-2H-pyrazol-3-yloxy)-5-nitro-pyrimidine;
4-(4-Methoxymethyl-piperidin-1-yl)-6-(2-methyl-5-trifluoromethyl-2H-pyrazol-3-yloxy)-5-nitro-pyrimidine;
4-{4-[6-(4-Methoxymethyl-piperidin-1-yl)-5-nitro-pyrimidin-4-yloxy]-phenyl}-butan-2-one;
4-[4-(2-Methoxy-ethyl)-piperidin-1-yl]-6-(2-methyl-5-trifluoromethyl-2H-pyrazol-3-yloxy)-5-nitro-pyrimidine;
4-{4-[6-(4-Ethoxymethyl-piperidin-1-yl)-5-nitro-pyrimidin-4-yloxy]-phenyl}-butan-2-one;
4-(2,4-Difluoro-phenoxy)-5-nitro-6-[4-(pyridin-2-ylsulfanyl)-piperidin-1-yl]-pyrimidine;
(4-Methoxy-2-{5-nitro-6-[4-(pyridin-2-ylsulfanyl)-piperidin-1-yl]-pyrimidin-4-yloxy}-phenyl)-phenyl-methanone;
4-(2,4-Difluoro-phenoxy)-6-(4-ethoxymethyl-piperidin-1-yl)-5-nitro-pyrimidine;
4-{4-[6-(4-Cyclopropylmethoxymethyl-piperidin-1-yl)-5-nitro-pyrimidin-4-yloxy]-phenyl}-butan-2-one;
4-{4-[5-Nitro-6-(4-propoxymethyl-piperidin-1-yl)-pyrimidin-4-yloxy]-phenyl}-butan-2-one;
1-{4-[6-(4-Methoxymethyl-piperidin-1-yl)-5-nitro-pyrimidin-4-yloxy]-phenyl}-ethanone;
4-{4-[6-(4-Butoxymethyl-piperidin-1-yl)-5-nitro-pyrimidin-4-yloxy]-phenyl}-butan-2-one;
4-{4-[6-(4-Isobutoxymethyl-piperidin-1-yl)-5-nitro-pyrimidin-4-yloxy]-phenyl}-butan-2-one;
{4-[6-(4-Ethoxy-piperidin-1-yl)-5-nitro-pyrimidin-4-yloxy]-phenyl}-(4-fluoro-phenyl)-methanone;
1-[6-(2-Methyl-5-trifluoromethyl-2H-pyrazol-3-yloxy)-5-nitro-pyrimidin-4-yl]-piperidin-4-ol;
1-[6-(4-Acetyl-phenoxy)-5-nitro-pyrimidin-4-yl]-piperidine-4-carboxylic acid ethyl ester;
(1-{6-[4-(4-Fluoro-benzoyl)-phenoxy]-5-nitro-pyrimidin-4-yl}-piperidin-4-yl)-(4-fluoro-phenyl)-methanone;
4-(4-{6-[4-(4-Fluoro-benzoyl)-piperidin-1-yl]-5-nitro-pyrimidin-4-yloxy}-phenyl)-butan-2-one;
4-(4-Methanesulfonyl-phenoxy)-5-nitro-6-[4-(pyridin-2-ylsulfanyl)-piperidin-1-yl]-pyrimidine;
4-(4-Methanesulfonyl-phenoxy)-5-nitro-6-[4-(pyridin-4-ylsulfanyl)-piperidin-1-yl]pyrimidine;
4-[4-(3-Isopropyl-[1,2,4]oxadiazol-5-yl)-piperidin-1-yl]-6-(4-methanesulfonyl-phenoxy)-pyrimidine-5-carbonitrile;
1-[5-Nitro-6-(4-trifluoromethylsulfanyl-phenoxy)-pyrimidin-4-yl]-piperidine-4-carboxylic acid ethyl ester;
5-[1,3]Dioxolan-2-yl-4-[4-(3-isopropyl-[1,2,4]oxadiazol-5-yl)-piperidin-1-yl]-6-(4-methanesulfonyl-phenoxy)-pyrimidine;

4-[4-(3-Isopropyl-[1,2,4]oxadiazol-5-yl)-piperidin-1-yl]-6-(4-methanesulfonyl-phenoxy)-pyrimidine-5-carbaldehyde;

5-[1,3]Dioxolan-2-yl-4-[4-(3-isopropyl-[1,2,4]oxadiazol-5-yl)-piperidin-1-yl]-6-(4-[1,2,3]thiadiazol-4-yl-phenoxy)-pyrimidine;

4-[4-(3-Isopropyl-[1,2,4]oxadiazol-5-yl)-piperidin-1-yl]-6-(4-[1,2,3]thiadiazol-4-yl-phenoxy)-pyrimidine-5-carbaldehyde;

[4-[4-(3-Isopropyl-[1,2,4]oxadiazol-5-yl)-piperidin-1-yl]-6-(4-[1,2,3]thiadiazol-4-yl-phenoxy)-pyrimidin-5-yl]-methanol;

[4-[4-(3-Isopropyl-[1,2,4]oxadiazol-5-yl)-piperidin-1-yl]-6-(4-[1,2,3]thiadiazol-4-yl-phenoxy)-pyrimidin-5-ylmethyl]-dimethyl-amine;

4-(4-Methanesulfonyl-phenoxy)-5-nitro-6-(4-phenylsulfanyl-piperidin-1-yl)-pyrimidine;

4-[4-(3-tert-Butyl-[1,2,4]oxadiazol-5-yl)-piperidin-1-yl]-6-(6-methanesulfonyl-pyridin-3-yloxy)-5-nitro-pyrimidine;

4-[4-(3-Isopropyl-[1,2,4]oxadiazol-5-yl)-piperidin-1-yl]-6-(4-methanesulfonyl-phenoxy)-2-methyl-pyrimidine-5-carbonitrile; or 1-[4-[4-(3-Isopropyl-[1,2,4]oxadiazol-5-yl)-piperidin-1-yl]-6-(4-methanesulfonyl-phenoxy)-pyrimidin-5-yl]-ethanone;

or a pharmaceutically acceptable salt, hydrate or solvate of such a compound.

21. A method for treatment of a metabolic disorder in an individual, wherein the metabolic disorder is type II diabetes, inadequate glucose tolerance, insulin resistance, hyperglycemia, hyperlipidemia, hypertriglyceridemia, hypercholesterolemia, dyslipidemia, syndrome X, metabolic syndrome or obesity, the method comprising administering to the individual a pharmaceutical composition comprising a pharmaceutically acceptable carrier and a therapeutically effective amount of a compound of Formula (Ia):

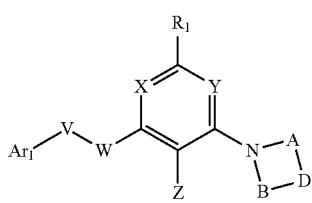

(Ia)

or a pharmaceutically acceptable salt, hydrate or solvate thereof, wherein:

A and B are each independently $C_{1-3}$ alkylene optionally substituted with 1 to 4 methyl groups;

D is $CR_2R_3$ or $N-R_2$;

V is absent;

W is $NR_4$ or O;

X is N;

Y is N;

Z is selected from the group consisting of $C_{1-5}$ acyl, $C_{1-8}$ alkyl, $C_{1-4}$ alkylcarboxamide, amino, cyano, $C_{4-8}$ diacylamino, $C_{2-6}$ dialkylsulfonamide, formyl, halogen, heterocyclic, and nitro wherein $C_{1-8}$ alkyl and $C_{1-5}$ acyl are each optionally substituted with 1 or 2 groups selected from the group consisting of $C_{2-4}$ dialkylamino, hydroxy, and halogen; or Z is selected from the group consisting of nitro, amino, formyl, $NHC(O)CF_3$, Br, $NHC(O)CH_3$, $N(C(O)CH_3)_2$, $N(S(O)_2CH_3)_2$, $CH_3$, [1,3]dioxolan-2-yl, $CH_2OH$, $CH_2N(CH_3)_2$, and $C(O)CH_3$; or Z is a group of Formula (A):

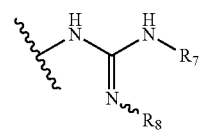

(A)

wherein:

$R_7$ is H, $C_{1-8}$ alkyl or $C_{3-6}$ cycloalkyl; and $R_8$ is H, nitro or nitrile;

$Ar_1$ is aryl or heteroaryl wherein each is optionally substituted with $R_9$-$R_{13}$;

wherein the heteroaryl of $Ar_1$ is selected from the group consisting of pyridyl, benzofuranyl, pyrazinyl, pyridazinyl, pyrimidinyl, triazinyl, quinoline, benzoxazole, benzothiazole, 1H-benzimidazole, isoquinoline, quinazoline, quinoxaline, 1H-imidazolyl, [1,2,4]triazolyl, [1,2,3]triazolyl, pyrrolyl, pyrazolyl, 1H-pyrazolyl, imidazolyl, oxazolyl, [1,3,4]oxadiazolyl, [1,3,4]thiadiazolyl, [1,2,4]oxadiazolyl, [1,2,4]thiadiazolyl, tetrazolyl, 1,3-dioxo-1,3-dihydro-isoindolyl, and [1,2,3]thiadiazol-4-yl;

$R_1$ is selected from the group consisting of H, $C_{1-4}$ alkoxy, $C_{1-8}$ alkyl, $C_{2-6}$ alkynyl, amino, $C_{3-6}$ cycloalkyl, and $C_{1-4}$ haloalkyl;

$R_2$ is selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, $C_{3-6}$-cycloalkyl, $C_{1-4}$ haloalkoxy, $C_{1-4}$ haloalkyl, halogen, hydroxyl, $CH_2OCH_2$-cyclopropyl, $CH_2OCH_2$-cyclobutyl, $CH_2OCH_2$-cyclopentyl, $CH_2OCH_2$-cyclohexyl, $CH_2OCH_2CH_2$-cyclopropyl, $CH_2OCH_2CH_2$-cyclobutyl, $CH_2OCH_2CH_2$-cyclopentyl, $CH_2OCH_2CH_2$-cyclohexyl, $CH_2CH_2OCH_2$-cyclopropyl, $CH_2CH_2OCH_2$-cyclobutyl, $CH_2CH_2OCH_2$-cyclopentyl, $CH_2CH_2OCH_2$-cyclohexyl, $CH_2CH_2OCH_2CH_2$-cyclopropyl, $CH_2CH_2OCH_2CH_2$-cyclobutyl, $CH_2CH_2OCH_2CH_2$-cyclopentyl, and $CH_2CH_2OCH_2CH_2$-cyclohexyl; or $R_2$ is $C_{1-8}$ alkyl or heteroaryl, each optionally substituted with 1 to 5 substituents selected from the group consisting of $C_{1-5}$ acyloxy, $C_{1-4}$ alkoxy, $C_{1-8}$ alkyl, $C_{1-4}$ alkylsulfonyl, carbo-$C_{1-6}$-alkoxy, carboxamide, carboxy, $C_{3-6}$-cycloalkyl, $C_{3-6}$-cycloalkyl-$C_{1-3}$-alkylene, $C_{3-6}$-cycloalkyl-$C_{1-3}$-heteroalkylene, and hydroxyl; or $R_2$ is $C_{1-8}$ alkyl, heteroaryl or phenyl each optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; or $R_2$ is —$Ar_2$-$Ar_3$ wherein $Ar_2$ and $Ar_3$ are independently aryl or heteroaryl each optionally substituted with 1 to 5 substituents selected from the group consisting of H, $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfinyl, $C_{1-4}$ alkylsulfonyl, $C_{1-4}$ alkylthio, amino, carbo-$C_{1-6}$-alkoxy, carboxamide, carboxy, cyano, $C_{3-6}$-cycloalkyl, $C_{2-6}$ dialkylcarboxamide, $C_{1-4}$ haloalkoxy, $C_{1-4}$ haloalkyl, halogen, hydroxyl and nitro; or $R_2$ is a group of Formula (B):

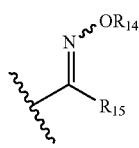

(B)

wherein:
$R_{14}$ is $C_{1-8}$ alkyl or $C_{3-6}$ cycloalkyl; and $R_{15}$ is F, Cl, Br or CN; or $R_2$ is a group of Formula (C):

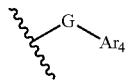

(C)

wherein:
G is C=O, $CR_{16}R_{17}$, O, S, S(O), or $S(O)_2$;
wherein
$R_{16}$ and $R_{17}$ are independently H or $C_{1-8}$ alkyl; and
$Ar_4$ is phenyl or heteroaryl optionally substituted with 1 to 5 substituents selected from the group consisting of $C_{1-5}$ acyl, $C_{1-5}$ acyloxy, $C_{1-4}$ alkoxy, $C_{1-8}$ alkyl, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$-alkoxy, carboxamide, carboxy, cyano, $C_{3-6}$-cycloalkyl, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heteroaryl, hydroxyl, hydroxylamino and nitro;

$R_3$ is H, $C_{1-8}$ alkyl, $C_{1-4}$ alkoxy, halogen or hydroxyl;
$R_4$ is H or $C_{1-8}$ alkyl;
$R_9$ is selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylamino, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, amino, arylsulfonyl, carbo-$C_{1-6}$-alkoxy, carboxamide, carboxy, cyano, $C_{3-6}$ cycloalkyl, $C_{2-6}$ dialkylamino, $C_{2-6}$ dialkylcarboxamide, $C_{2-6}$ dialkylsulfonamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heterocyclic, heterocyclicsulfonyl, heteroaryl, hydroxyl, nitro, $C_{4-7}$ oxo-cycloalkyl, phenoxy, phenyl, sulfonamide and sulfonic acid, and wherein $C_{1-5}$ acyl, $C_{1-4}$ alkoxy, $C_{1-8}$ alkyl, $C_{1-4}$ alkylsulfonamide, alkylsulfonyl, arylsulfonyl, heteroaryl, phenoxy and phenyl are each optionally substituted with 1 to 5 substituents selected independently from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, heteroaryl, heterocyclic, hydroxyl, nitro and phenyl; or $R_9$ is a group of Formula (D):

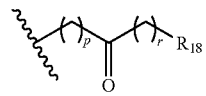

(D)

wherein:
"p" and "r" are independently 0, 1, 2 or 3; and
$R_{18}$ is H, $C_{1-5}$ acyl, $C_{2-6}$ alkenyl, $C_{1-8}$ alkyl, $C_{1-4}$ alkylcarboxamide, $C_{2-6}$ alkynyl, $C_{1-4}$ alkylsulfonamide, carbo-$C_{1-6}$-alkoxy, carboxamide, carboxy, cyano, $C_{3-6}$ cycloalkyl, $C_{2-6}$ dialkylcarboxamide, halogen, heteroaryl or phenyl, and wherein the heteroaryl and phenyl are each optionally substituted with 1 to 5 substituents selected independently from the group consisting of $C_{1-4}$ alkoxy, amino, $C_{1-4}$ alkylamino, $C_{2-6}$ alkynyl, $C_{2-8}$ dialkylamino, halogen, $C_{1-4}$ haloalkoxy, $C_{1-4}$ haloalkyl and hydroxyl; and $R_{10}$-$R_{13}$ are independently selected from the group consisting of $C_{1-5}$ acyl, $C_{1-5}$ acyloxy, $C_{2-6}$ alkenyl, $C_{1-4}$ alkoxy, $C_{1-8}$ alkyl, $C_{1-4}$ alkylcarboxamide, $C_{2-6}$ alkynyl, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylureyl, carbo-$C_{1-6}$-alkoxy, carboxamide, carboxy, cyano, $C_{3-6}$ cycloalkyl, $C_{2-6}$ dialkylcarboxamide, halogen, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkylthio, hydroxyl and nitro; or
two adjacent $R_{10}$-$R_{11}$ groups together with $Ar_1$ form a 5, 6 or 7 membered cycloalkyl, cycloalkenyl or heterocyclic group wherein the 5, 6 or 7 membered group is optionally substituted with halogen.

22. The method according to claim 21, wherein the compound is a compound of the following formula:

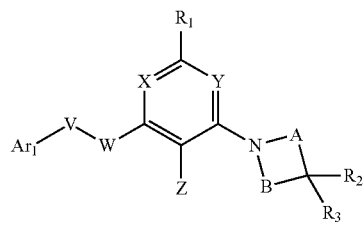

or a pharmaceutically acceptable salt, hydrate or solvate thereof, wherein:
wherein $R_2$ is a 5-membered heteroaryl optionally substituted with 1 to 4 substituents selected from the group consisting of $C_{1-5}$ acyl, $C_{1-5}$ acyloxy, $C_{1-4}$ alkoxy, $C_{1-8}$ alkyl, $C_{1-4}$ alkylamino, $C_{1-4}$ alkylcarboxamide, $C_{1-4}$ alkylthiocarboxamide, $C_{1-4}$ alkylsulfonamide, $C_{1-4}$ alkylsulfinyl, $C_{1-4}$ alkylsulfonyl, $C_{1-4}$ alkylthio, $C_{1-4}$ alkylthioureyl, $C_{1-4}$ alkylureyl, amino, carbo-$C_{1-6}$- alkoxy, carboxamide, carboxy, cyano, $C_{3-6}$-cycloalkyl-$C_{1-3}$-heteroalkylene, $C_{2-8}$ dialkylamino, $C_{2-6}$ dialkylcarboxamide, $C_{1-4}$ dialkylthiocarboxamide, $C_{2-6}$ dialkylsulfonamide, $C_{1-4}$ alkylthioureyl, $C_{1-4}$ haloalkoxy, $C_{1-4}$ haloalkyl, $C_{1-4}$ haloalkylsulfinyl, $C_{1-4}$ haloalkylsulfonyl, $C_{1-4}$ haloalkyl, $C_{1-4}$ haloalkylthio, halogen, heterocyclic, hydroxyl, hydroxylamino and nitro; and $R_3$ is hydrogen or $C_{1-4}$ alkyl.

23. The method according to claim 22, wherein $R_2$ is a 5-membered heteroaryl optionally substituted with 1 or 2 substituents selected from the group consisting of $C_{1-8}$ alkyl, $C_{1-4}$ haloalkyl and halogen; and $R_3$ is hydrogen.

24. The method according to claim 22, wherein the metabolic disorder is type II diabetes.

25. The method according to claim 23, wherein the metabolic disorder is type II diabetes.

26. The method according to claim 1, wherein the metabolic disorder is inadequate glucose tolerance.

27. The method according to claim 21, wherein the metabolic disorder is inadequate glucose tolerance.

28. The method according to claim 1, wherein the metabolic disorder is insulin resistance.

29. The method according to claim 21, wherein the metabolic disorder is insulin resistance.

30. The method according to claim 1, wherein the metabolic disorder is hyperglycemia.

31. The method according to claim 21, wherein the metabolic disorder is hyperglycemia.

32. The method according to claim 1, wherein the metabolic disorder is hyperlipidemia, hypertriglyceridemia, hypercholesterolemia or dyslipidemia.

33. The method according to claim 21, wherein the metabolic disorder is hyperlipidemia, hypertriglyceridemia, hypercholesterolemia or dyslipidemia.

34. The method according to claim 1, wherein the metabolic disorder is obesity.

35. The method according to claim 21, wherein the metabolic disorder is obesity.

36. The method according to claim 1, wherein the metabolic disorder is metabolic syndrome.

37. The method according to claim 21, wherein the metabolic disorder is metabolic syndrome.

* * * * *